United States Patent
Gruber

(10) Patent No.: US 10,954,271 B2
(45) Date of Patent: Mar. 23, 2021

(54) ANTI-MICROBIAL PEPTIDES

(71) Applicant: TENSIVE CONTROLS, INC., Columbia, MO (US)

(72) Inventor: Kenneth Allen Gruber, Columbia, MO (US)

(73) Assignee: Tensive Controls, Inc., Columbia, MO (US)

( * ) Notice: Subject to any disclaimer, the term of this patent is extended or adjusted under 35 U.S.C. 154(b) by 0 days.

(21) Appl. No.: 16/418,127

(22) Filed: May 21, 2019

(65) Prior Publication Data

US 2020/0109171 A1 Apr. 9, 2020

Related U.S. Application Data

(63) Continuation of application No. 15/511,669, filed as application No. PCT/US2015/050847 on Sep. 18, 2015, now Pat. No. 10,351,599.

(60) Provisional application No. 62/052,719, filed on Sep. 18, 2014.

(51) Int. Cl.
  *C07K 7/08* (2006.01)
  *C07K 7/06* (2006.01)
  *A61K 38/00* (2006.01)

(52) U.S. Cl.
  CPC .............. *C07K 7/08* (2013.01); *C07K 7/06* (2013.01); *A61K 38/00* (2013.01)

(58) Field of Classification Search
  None
  See application file for complete search history.

(56) References Cited

U.S. PATENT DOCUMENTS

| | | | |
|---|---|---|---|
| 4,938,763 | A | 7/1990 | Dunn et al. |
| 5,693,608 | A | 12/1997 | Bechgaard et al. |
| 5,908,825 | A | 6/1999 | Fasano et al. |
| 5,977,070 | A | 11/1999 | Piazza et al. |
| 6,432,438 | B1 | 8/2002 | Shukla et al. |
| 6,673,767 | B1 | 1/2004 | Brodbeck et al. |
| 7,563,764 | B2 | 7/2009 | Lu et al. |
| 8,513,381 | B2 | 8/2013 | Catania et al. |
| 8,541,545 | B2 | 9/2013 | Gruber et al. |
| 9,346,865 | B2 | 5/2016 | Hodges |
| 9,534,018 | B2 | 1/2017 | Gruber et al. |
| 10,351,599 | B2 * | 7/2019 | Gruber ............... C07K 7/08 |

FOREIGN PATENT DOCUMENTS

| | | |
|---|---|---|
| WO | WO 2008/022444 | 2/2008 |
| WO | WO 2011/026015 | 3/2011 |
| WO | WO 2013/138340 A1 | 9/2013 |

OTHER PUBLICATIONS

Anderson et al., Trends in Ecology & Evolution 13(11): 444-449 (1998).
Balse-Srinivasan et al., "Structure-Activity Relationships of Novel Cyclic r-MSH/A-MSH Hybrid Analogues That Lead to Potent and Selective Ligands for the Human MC3R and Human MCSR," J. Med. Chem., 46(17):3728-3733 (2003).
Balse-Srinivasan. P., et al., "Structure-Activity Relationships of c-MSH Analogues at the Human Melanocortin MC3, MC4, and MC5 Receptors. Discovery of Highly Selective hMC3R, hMC4R, and hMC5R Analogues," J. Med. Chem, 46(26):4965-4973 (2003).
Barysheva et al., "Application of Unstable Gfp Variants to the Kinetic Study of Legionella Pneumophila lcm Gene Expression During Infection" Microbiology 154(4): 1015-1025 (2008).
Bednarek et al., "Potent and Selective Peptide Agonists of a-Melanotropin Action at Human Melanocortin Receptor 4: Their Synthesis and Biological Evaluation in Vitro/," Biochem Biophys. Res. Com., 286(3):641-645 (2001).
Bhatt, U. and Just, G., "Synthesis of a Novel Thyrotropin Releasing Hormone (TRH) Analog Incorporating a Piperazin-2-one Ring," Helvetica Chimica Acta, 83:722-727 (2000).
"Natural and synthetic cathelicidin peptides with anti-microbial and anti-biofilm activity against *Staphylococcus aureus*," BMC Microbiology 11:114 (2001).
Brandsch, "Transport of L-proline, L-proline-containing peptides and related drugs at mammalian epithelial cell membranes" Amino Acids 31(2): 119-136 (2006).
Brandsch et al., "Pharmaceutical and pharmacological importance of peptide transporters", J. Pharm. Pharmacol. 60(5): 543-58 (2008).
Brogden, "Antimicrobial peptides: pore formers or metabolic inhibitors in bacteria" Nature Reviews Microbiology 3(3): 238-250 (2005).
Burmolle M, et al., "Enhanced biofilm formation and increased resistance to antimicrobial agents and bacterial invasion are caused by synergistic interactions in multispecies biofilms." Applied and Environmental Microbiology, 72(6):3916-23, (2006).
USPTO; "Biotechnology", Manual of Patent Examining Procedure, (MPEP) 9th Edition, Chapter 2400 (2015).
Church, "Livestock Feeds and Feeding", O&B Books, Inc., Corvallis Oreg. (1984).
Dathe M, et al., "Cyclization Increases the Antimicrobial Activity and Selectivity of Arginine- and Tryptophan-Containing Hexapeptides", Biochemistry. 43(28):9140-50, (2004).
De la Fuente-Nunez, C, et al., "Broad-Spectrum Anti-biofilm Peptide That Targets a Cellular Stress Response" 10(5):e1004152, (2014).

(Continued)

*Primary Examiner* — Sergio Coffa
(74) *Attorney, Agent, or Firm* — Womble Bond Dickinson (US) LLP

(57) ABSTRACT

Described herein are anti-microbial peptides having enhanced activity and transport.

7 Claims, 5 Drawing Sheets

Specification includes a Sequence Listing.

(56) References Cited

OTHER PUBLICATIONS

Dean, S.N., et al., "Natural and synthetic cathelicidin peptides with anti-microbial and anti-biofilm activity against *Staphylococcus aureus*" BMC microbiology. 11:114, (2011).
Ensminger, O., et al.; "Feeds and Nutrition Digest", The Ensminger Publishing Company, California, USA (1978).
Fernandez-Lopez, et al., "Antibacterial agents based on the cyclic D,L-a-peptide architecture," Nature 412(6845): 452-455 (2001).
O'Toole, G.A., "Microtiter dish biofilm formation assay." J Vis Exp (47), Figure 5, (2011).
Fox, "Antimicrobial peptides stage a comeback," Nature Biotechnology 31(5): 379-382 (2013).
Hancock, "Cationic peptides: effectors in innate immunity and novel antimicrobials," The Lancet Infectious Diseases 1(3): 156-164 (2001).
Hess et al., "Effect of Structural and Conformation Modifications, Including Backbone Cyclization, of Hydrophilic Hexapeptides on Their Intestinal Permeability and Enzymatic Stability," J. Med. Chem. 50: 6201-6211 (2007).
Hicks et al., "Antimicrobial Peptides containing Unnatural Amino Acid exhibit potent bactericidal activity against ESKAPE Pathogens," Bioorganic & Medicinal Chemistry 21(1): 205-214 (2013).
Giacomini, K.M., et al. "Membrane transporters in drug development," Nat. Rev. Drug Discov. 9(3): 215-236 (2010).
Kavarana et al., "Novel Cyclic Templates of r-MSH Give Highly Selective and Potent Antagonists/Agonists for Human Melanocortin-3/4 Receptors," J. Med. Chem. 45(12): 2644-2650 (2002).
Lipinski et al., "Experimental and computational approaches to estimate solubility and permeability in drug discovery and development settings," Adv. Drug Deliv. Rev. 46(1-3): 3-26 (2001).
Liu, Z., et al., "Length effects in antimicrobial peptides of the (RW)n series." Antimicrob. Agents Chemother, 51(2): p. 597-603, Fig 6 (2007).
Ojha, A. and G.F. Hatfull, "The role of iron in *Mycobacterium smegmatis* biofilm formation: the exochelin siderophore is essential in limiting iron conditions for biofilm formation but not for planktonic growth," Mol Microbiol, 66(2): p. 468-83 (2007).
MacBain, "Pelleting Animal Feed," American Feed Manufacturers Association, Arlington, Va. (1974).
Mayorov et al., "Development of Cyclic y-Msh Analogues With Selective hMC3R Agonist and hMC3R/hMC5R Antagonist Activities," J. Med. Chem. 49: 1946-1952 (2006).
Merrifield, "Solid Phase Synthesis," Angew Chem. 24: 799-810 (1985).
Rosey et al., "Lactose metabolism by *Staphylococcus aureu*: characterization of lacABCD, the structural genes of the tagatose 6-phosphate pathway," Journal of Bacteriology 173(19): 5992-5998 (1991).
Oskouian et al., Repression and Catabolite Repression of the Lactose Operon of *Staphylococcus aureusaloumal* of Bacteriology 172(7): 3804-3812 (1990).
Safarinejad, M, "Evaluation of the Safety and Efficacy of Bremelanotide, a Melanocortin Receptor Agonist, in Female Subjects with Arousal Disorder: A Double-Blind Placebo-Controlled, Fixed Dose, Randomized Study", J. Sex Med. 5(4): 887-897 (2008).
Sanchez, C.J., Jr. et al. "Biofilm formation by clinical isolates and the implications in chronic infections," BMC Infectious Diseases 13: 47 (2013).
Strom, MB, et al., "Antimicrobial Activity of Short Arginine- and Tryptophan-rich Peptides", Journal of Peptide Science 8(8):431-7.
Grant, G. A.; "Synthetic Peptides: A User's Guide," W.H. Freeman & Co., New York (1992).
Hruby et al., "Synthetic Peptides: A User's Guide, supra"; Biochem. J. 268(2): 49-262 (1990).
Teixido et al., "Exploratory neuropharmacological evaluation of a conformationally constrained thyrotropin-releasing hormone analogue," Brain Res Bull, 73(1-3): 103107 (2007).
Thiemermann et al., "FMRF-amide and L-Arg-L-Phe increase blood pressure and heart rate in the anaesthetised rat by central stimulation of the sympathetic nervous system," Biochem Biophys Res Commun. 175(1): 318-324 (1991).
Gruber et al., "ACTH-(4-10) Through Gamma-Msh: Evidence for a New Class of Central Autonomic Nervous System-Regulating Peptides," Am J Physiol. 257(4 Pt 2): R681-694 (1989).
Toniolo, "Confomationally restricted peptides through short-range cyclizations " Int. J. Peptide Protein Res. 35: 287-300 (1990).
Torrent et al., "Exploring New Biological Functions of Amyloids: Bacteria Cell Agglutination Mediated by Host Protein Aggregation", PLoS Pathogens 8(11): e1003005 (2012).
Tugyi et al., "Partial D-amino acid substitution: Improved enzymatic stability and preserved Ab recognition of a MUC2 epitope peptide," Proc. Natl. Acad. Sci USA 102(2): 413-418 (2005).
Van Acker H, et al., "Molecular mechanisms of antimicrobial tolerance and resistance in bacterial and fungal biofilms." Trends in microbiology. 22(6):326-33, PMID 24598086 (2014).
Sutton G et al., "A derivative of the melanocortin receptor antagonist SHU9119," National Institute of HealthPublic Access, Peptides. 29(1):104-111, Jan. 2008.
Grieco, P., et al. "Novel [alpha]-MSH Peptide Analogues with Broad Spectrum Antimicrobial Activity", PLOS ONE, vol. 8, No. 4, Apr. 23, 2013, p. e61614.
Carotenuto, A. et al.,"Structure-function relationships and conformational properties of alpha-MSH(6-13) analogues with candidacidal activity", Chemical Biology & Drug Des, Blackwell Publishing TD., Oxford, GB, vol. 69, No. 1, Jan. 1, 2007, pp. 68-74.
Tahsina, S. et al., "Characterization of cell membrane parameters of clinical isolates of *Staphylococcus aureus* with varied susceptibility to alpha-melanocyte stimulating hormone", Peptides, vol. 37, No. 2, Oct. 1, 2012, pp. 334-339.
De la Fuente-Nunez, C., et al., "Inhibition of Bacterial Biofilm Formation and Swarming Motility by a Small Synthetic Cationic Peptide", Antimicrobial Agents and Chemotherapy, vol. 56, No. 5, May 1, 2012, pp. 2696-2704.

\* cited by examiner

A.

B.

C.

D.

E.

ANTI-MICROBIAL PEPTIDES

CROSS-REFERENCE TO RELATED APPLICATIONS

This application is a continuation of International App. No. PCT/US2015/050847; filed Sep. 18, 2015, which International Application was published by the International Bureau in English on Mar. 24, 2016, and claims priority to U.S. Provisional Application No. 62/052,719, filed Sep. 19, 2014, each of which is incorporated by reference in their entirety and for all purposes.

TECHNICAL FIELD

Described herein are anti-microbial peptides having enhanced activity and transport.

SEQUENCE LISTING SUBMITTED VIA EFS-WEB

The entire content of the following electronic submission of the sequence listing via the USPTO EFS-WEB server, as authorized and set forth in MPEP § 1730 II.B.2(a), is incorporated herein by reference in its entirety for all purposes. The sequence listing is within the electronically filed text file that is identified as follows:
File Name: 1030USPCT_sequence_listing.txt
Date of Creation: Mar. 21, 2019
Size (bytes): 7,429

BACKGROUND

The evolution of new strains of multi drug resistant bacteria is an emerging problem. Currently, there is a lack of a concerted effort among major pharmaceutical companies for addressing this problem. Highlighting this aspect is the small number of U.S. Food and Drug Administration (FDA) approved antibiotics. For example, only Teflaro® (ceftaroline fosamil) has been approved by the FDA since 2010. Moreover, anti-biotic resistant gram-negative bacteria in hospital acquired infections are increasingly becoming problematic with dwindling supplies of antibiotics that are efficacious against these pathogens. These antibiotic resistant bacterial infections in immunocompromised/sick patients further complicate the therapy of other underlying diseases. Thus, new strategies for the development of anti-bacterial drugs and methods of treatment are needed.

Accordingly, a paradigm shift in how the scientific community thinks about developing new anti-bacterial therapeutics may be underway. Fox, *Nature Biotechnology* 31(5): 379-382 (2013). This shift is into the potential use and therapeutic potential of anti-microbial peptides (AMPs). AMPs are molecules naturally found in microorganisms to mammals that comprise short peptides of about 15 amino acids to about 50 amino acids. The product is ribosomally synthesized and often post-translationally modified. This synthesis is in contrast to other natural peptide based antibiotics, such as vancomycin, which are formed by enzymatic cleavage. Fox, *Nature Biotechnology* 31(5): 379-382 (2013).

Anti-microbial peptides serve as a major component of the innate immunity and complement cell-mediated immune responses. The mechanism of action of most anti-microbial peptides depends on the target cellular surface. The principle anti-microbial activity of most AMPs has been proposed by the so called "carpet model," wherein the amino acid composition, amphipathicity, and positive charge allow the peptides to electrostatically interact and insert into the mostly negatively charged microbial cell membranes, resulting in pore formation and cell death. Other modes of action include the inhibition of cell wall synthesis, autolysin activation, and the inhibition of DNA, RNA, and protein synthesis. The specificity of AMPs to microbes is due to mammalian and plant cell membranes having no net charge, which limits AMP interaction. Furthermore, acquired resistance to AMPs appears to be low as only a moderate increase in AMP resistance was observed after more than ten passages. Hancock, *The Lancet Infectious Diseases* 1(3): 156-164 (2001).

Additional problems emerging in the treatment of infectious diseases is biofilms. Sanchez et al., *BMC Infectious Diseases* 13: 47 (2013); Dean et al., *BMC Microbiology* 11: 114 (2011). Bacteria and fungi can assume a planktonic or free swimming phenotype, or they can exist as part of a colony (i.e., attached to a surface) or a biofilm. A colony of bacteria in a biofilm are surrounded by an exopolysaccharide matrix for protection, making them notoriously difficult to eradicate. Biofilms are found in 60-80% of chronic hospital-associated infections. Van Acker et al., *Trends in Microbiology* 22(6): 326-333 (2014). There are endogenous anti-biofilm peptides, Dean et al., *BMC Microbiology* 11: 114 (2011); de la Fuente-Nunez et al., *PLoS Pathogens* 10(5): e1004152 (2014), and while these peptides are similar to AMPs, not all of them are anti-microbial. These anti-biofilm peptides are potentially useful as topical agents for bacterial infections with a biofilm component, but in their natural form, they are not amenable for the treatment of systemic infections. Dean et al., *BMC Microbiology* 11: 114 (2011).

AMPs have principally been generated or discovered from naturally occurring AMPs. For example, U.S. Pat. No. 7,550,558 describes a method of using phage display to identify new anti-microbial peptides. Using the methods of this invention, the identified and most efficacious peptide had a high level of similarity to naturally occurring indolicidin and tritrpticin AMPs, which are known to have high levels of in vivo toxicity. While this AMP is potentially useful, no in vivo safety testing or efficacy was provided. U.S. Pat. No. 7,452,864 describes the use of a natural peptide cathelicidin LL-37 for topical wound regeneration promoted by its anti-microbial activity. Further examples of naturally derived peptides that have promising in vitro results are described by U.S. Pat. Nos. 7,531,509 and 7,504,380. However, anti-microbial peptides based on native peptide sequences are often subject to in vivo proteolysis or degradation, preventing in vivo efficacy. Fox, *Nature Biotechnology* 31(5): 379-382 (2013).

Thus, despite the promise of AMPs, many concerns remain, including toxicity, oral availability, and in vivo stability. Many peptides lack activity against gram-negative bacterial pathogens. Fox, *Nature Biotechnology* 31(5): 379-382 (2013). AMPs can have toxic effects from their hemolytic activity. Furthermore, naturally occurring small AMP-like melanocortin peptides have been shown to have potent cardiovascular side-effects from the presence of "RFamide" sequences (Arg-Phe or conservative substitutions) near the C-terminus of these peptides. Thiemermann et al., *Biochem Biophys Res Commun.* 175(1): 318-324 (1991); Gruber et al., *Am J Physiol.* 257(4 Pt 2): R681-694 (1989). U.S. Pat. No. 8,541,545 describes the elimination of RFamide effects in a similar class of small melanocortin peptides leading to decreased cardiovascular side effects. However, no concerted effort has been made in the prior art to eliminate potential RFamide effects in AMPs.

Thus, described herein, are rationally designed AMPs with efficacy against both gram negative and gram positive bacteria. The AMPs described herein further have modifications to overcome previous limitations of AMPs, which include decreased proteolysis, reduced hemolysis, and increased in vivo safety. Further, described herein are AMPs having both anti-biofilm and anti-microbial activity in a single molecule. Additionally, contemplated herein, are methods of use of the described AMPs.

SUMMARY

Described herein are anti-microbial peptide having enhanced anti-microbial activity and transport. Some anti-microbial peptides described herein have a metabolically stable C-terminal extension to minimize or abolish side effects, and potentiate therapeutic activity for use in the treatment of various pathological conditions. Also described herein are structural modifications to anti-microbial peptides that enhance the therapeutic activity of overlapping pharmacophores for use in the treatment of various pathological conditions, and allow regulation of drug active transport through the gastrointestinal tract (oral activity) and drug access or the prevention of access to the central nervous system (transport through the blood-brain-barrier).

One embodiment described herein is a non-naturally occurring anti-microbial peptide comprising at least three or more amino acid or amino acid analog residues, wherein at least one of the three or more residues comprises: (a) at least one or more natural, synthetic, or chemically modified cationic amino acid residues; (b) at least one, synthetic, or chemically modified anionic amino acid residue; (c) at least one or more natural, synthetic, or chemically modified aromatic residues; or (d) a combination of natural, synthetic, or chemically modified amino acid residues thereof. In one aspect, the length of the peptide is from about 3 residues to about 17 residues. In another aspect, the peptide is stabilized. In another aspect, the N-terminus of the non-naturally occurring anti-microbial peptide is stabilized. In another aspect, stabilization comprises the addition of between 1 and 3 natural or artificial stabilizing residues. In another aspect, the N-terminal stabilizing residues comprise: D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-norleucine, L-norleucine, D-isoleucine, L-isoleucine, β-isoleucine, or a piperazin-2-one ring. In another aspect, the N-terminus is acylated. In another aspect, the C-terminus of the non-naturally occurring anti-microbial peptide is stabilized. In another aspect, the stabilization comprises the addition of between 1 and 3 natural or artificial stabilizing residues. In one aspect, the C-terminal stabilizing residues comprise: D-threonine, L-threonine, D-proline, L-proline, β-homo proline, D-alanine, L-alanine, D-valine, L-valine, β-valine, 3-methyl-β-valine, D-leucine, L-leucine, β-leucine, D-norleucine, L-norleucine, D-norleucine, L-norleucine, D-isoleucine, L-isoleucine, β-isoleucine, D-phenylalanine, L-phenylalanine, or a piperazin-2-one ring. In another aspect, the C-terminus is amidated. In another aspect, the C-terminal stabilization also increases the specificity of the anti-microbial peptide to target gram-negative bacteria. In another aspect, the C-terminal stabilization increases the specificity of the anti-microbial peptide to target gram-positive bacteria. In one aspect, the C-terminal stabilizing residues comprise: D-Pro-D-Val; D-Val-D-Pro; β-Val-β-Pro; β-Pro-3-Val; 3-methyl-β-Val-β-Pro; D-Pro-D-Ala; D-Ala-D-Pro; β-Pro-β-Ala; β-Ala-β-Pro; D-Pro-D-Leu; D-Leu-D-Pro; β-Pro-β-Leu; β-Leu-β-Pro; D-Val-D-Ala; D-Ala-D-Val; β-Val-β-Ala; β-Ala-β-Val; 3-methyl-β-Val-β-Ala; D-Val-D-Leu; D-Leu-D-Val; β-Val-β-Leu; β-Leu-β-Val; 3-methyl-3-Val-β-Leu; D-Phe-D-Val; or D-Val-D-Phe. In another aspect, the C-terminus is amidated. In another aspect, the non-naturally occurring anti-microbial peptide is cyclized. In another aspect, the non-naturally occurring anti-microbial peptide is cyclized through a lactam linkage. In another aspect, the non-naturally occurring anti-microbial peptide is cyclized between a positive and negative residue.

In another embodiment described herein, an anti-biofilm peptide is covalently linked to the anti-microbial peptide. In one aspect, the anti-biofilm peptide is covalently linked to the N-terminus of the anti-microbial peptide. In another aspect, the anti-biofilm peptide is covalently linked to the C-terminus of the anti-microbial peptide. In another aspect, the anti-biofilm peptide is covalently linked to the anti-microbial peptide through at least one linker. In another aspect, the anti-biofilm peptide comprises between 1 and 12 natural, synthetic, or chemically modified residues.

In another embodiment described herein, the anti-biofilm peptide comprises the sequence according to Formula IV: $B^1$-$B^2$-$B^3$-$B^4$-$B^5$-$B^6$-$B^7$-$B^8$-$B^9$-$B^{10}$-$B^{11}$-$B^{12}$, wherein: each residue corresponding to positions $B^1$, $B^3$, $B^4$, $B^5$, $B^6$, $B^7$, or $B^9$ comprises any hydrophobic non-aromatic natural, synthetic, or chemically modified amino acid; each residue corresponding to positions $B^2$, $B^8$, $B^{11}$, or $B^{12}$ comprises any natural, synthetic, or chemically modified positive amino acid; and each residue corresponding to position $B^{10}$ comprises any natural, synthetic, or chemically modified aromatic amino acid. In one aspect, the anti-biofilm peptide comprises the sequence $B^1$-$B^2$-$B^3$-$B^4$-$B^5$-$B^6$-$B^7$-$B^8$. In another aspect, the anti-biofilm peptide comprises the sequence $B^7$-$B^8$-$B^9$-$B^{10}$-$B^{11}$-$B^{12}$. In another aspect, the anti-biofilm peptide comprises the sequence $B^1$-$B^2$-$B^3$-$B^4$-$B^5$-$B^6$. In another aspect, the anti-biofilm peptide comprises the sequence $B^1$-$B^2$-$B^3$-$B^4$-$B^5$-$B^6$-$B^7$.

In another embodiment described herein, the anti-biofilm peptide comprises the sequence according to Formula IV: $B^1$-$B^2$-$B^3$-$B^4$-$B^5$-$B^6$-$B^7$-$B^8$-$B^9$-$B^{10}$-$B^{11}$, wherein: each residue corresponding to positions $B^1$, $B^2$, $B^4$, $B^5$, $B^8$, $B^9$, or $B^{11}$ comprises any natural, synthetic, or chemically modified positive amino acid; each residue corresponding to positions $B^3$, $B^6$, or $B^7$ comprises any natural, synthetic, or chemically modified aromatic amino acid; and each residue corresponding to position $B^{10}$ comprises any hydrophobic non-aromatic natural, synthetic, or chemically modified amino acid. In one aspect, the anti-biofilm peptide comprises the sequence $B^1$-$B^2$-$B^3$-$B^4$-$B^5$-$B^6$-$B^7$. In another aspect, the anti-biofilm peptide comprises the sequence $B^6$-$B^7$-$B^8$-$B^9$-$B^{10}$-$B^{11}$. In another aspect, the anti-biofilm peptide comprises the sequence $B^1$-$B^2$-$B^3$-$B^4$-$B^5$-$B^6$-$B^7$-$B^8$-$B^9$. In another aspect, the anti-biofilm peptide comprises the sequence $B^4$-$B^5$-$B^6$-$B^7$-$B^8$-$B^9$-$B^{10}$. In another aspect, the anti-biofilm peptide is covalently linked to the N-terminus or C-terminus of the anti-microbial peptide. In another aspect, the anti-microbial peptide is stabilized by the addition of between 1 and 3 natural or artificial stabilizing residues to the anti-biofilm peptide. In another aspect, the stabilizing residues comprise: D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-norleucine, L-norleucine, D-norleucine, L-norleucine, D-isoleucine, L-isoleucine, β-isoleucine, or a piperazin-2-one ring. In another aspect, the anti-biofilm peptide is methylated.

Another embodiment described herein is a non-naturally occurring anti-microbial peptide comprising the sequence according to Formula I: $X^1$-$X^2$-$X^3$-$R^1$-$R^2$-[$R^3$-$R^4$-$R^5$-$R^6$-$R^7$-

$R^8$-$R^9$-$R^{10}$-$R^{11}$-$R^{12}$-$R^{13}$-$R^{14}$-$R^{15}$-$R^{16}$-$R^{17}$]$Y^1$-$Y^2$-$Y^3$, wherein: $X^1$, $X^2$, and $X^3$ represent optional N-terminal residues; $R^1$ to $R^{17}$ represent residues of the anti-microbial peptide; $Y^1$, $Y^2$, and $Y^3$ represent optional degradation-resistant C-terminal residues. In one aspect, $R^1$ to $R^{17}$ is further represented by formula II: $P_{0-2}$-|-[N-|-(U)$_{0-1}$-|-(P|A)$_{1-3}$-|-(U)$_{0-1}$-|-(P|A)$_{0-3}$-|-(U)$_{0-1}$-|-(P|A)$_{0-3}$-|-(U)$_{0-1}$-|-(P|A)$_{0-3}$-P], wherein: "N" is any natural, synthetic, or chemically modified negative residue; "U" is any natural, synthetic, or chemically modified polar uncharged residue or a hydrophobic non-aromatic natural, synthetic, or chemically modified residue; "P" is any natural, synthetic, or chemically modified proline residue or any natural, synthetic, or chemically modified positive residue; "A" is any natural, synthetic, or chemically modified aromatic residue. In another aspect, the length of the peptide is from about 3 residues to about 17 residues. In another aspect, the peptide is stabilized. In another aspect, the N-terminus of the non-naturally occurring anti-microbial peptide is stabilized. In another aspect, the stabilization comprises the addition of between 1 and 3 natural or artificial stabilizing residues. In another aspect, the N-terminal stabilizing residues comprise: D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-norleucine, L-norleucine, D-isoleucine, L-isoleucine, β-isoleucine, or a piperazin-2-one ring. In another aspect, the N-terminus is acylated. In another aspect, the C-terminus of the non-naturally occurring anti-microbial peptide is stabilized. In another aspect, the stabilization comprises the addition of between 1 and 3 natural or artificial stabilizing residues. In another aspect, the C-terminal stabilizing residues comprise: D-threonine, L-threonine, D-proline, L-proline, β-homo proline, D-alanine, L-alanine, D-valine, L-valine, 3-methyl-3-valine, D-leucine, L-leucine, β-leucine, D-norleucine, L-norleucine, D-isoleucine, L-isoleucine, β-isoleucine, D-phenylalanine, L-phenylalanine, or a piperazin-2-one ring. In another aspect, the C-terminus is amidated. In another aspect, the C-terminal stabilization also increases the specificity of the anti-microbial peptide to target gram-negative bacteria. In another aspect, the C-terminal stabilization increases the specificity of the anti-microbial peptide to target gram-positive bacteria. In another aspect, the C-terminal stabilizing residues comprise: D-Pro-D-Val; D-Val-D-Pro; β-Val-β-Pro; β-Pro-β-Val; β-methyl-β-Val-β-Pro; D-Pro-D-Ala; D-Ala-D-Pro; β-Pro-β-Ala; β-Ala-β-Pro; D-Pro-D-Leu; D-Leu-D-Pro; β-Pro-β-Leu; β-Leu-β-Pro; D-Val-D-Ala; D-Ala-D-Val; β-Val-β-Ala; β-Ala-β-Val; 3-methyl-β-Val-β-Ala; D-Val-D-Leu; D-Leu-D-Val; β-Val-β-Leu; β-Leu-β-Val; 3-methyl-β-Val-β-Leu; D-Phe-D-Val; or D-Val-D-Phe. In another aspect, the C-terminus is amidated. In another aspect, the non-naturally occurring anti-microbial peptide is cyclized. In another aspect, the non-naturally occurring anti-microbial peptide is cyclized through a lactam linkage. In another aspect, the non-naturally occurring anti-microbial peptide is cyclized between a positive and negative residue.

Another embodiment described herein is a non-naturally occurring anti-microbial peptide, wherein an anti-biofilm peptide is covalently linked to the anti-microbial peptide. In one aspect, the anti-biofilm peptide is covalently linked to the N-terminus of the anti-microbial peptide. In another aspect, the anti-biofilm peptide is covalently linked to the C-terminus of the anti-microbial peptide. In another aspect, the anti-biofilm peptide is covalently linked to the anti-microbial peptide through at least one linker. In another aspect, the anti-biofilm peptide comprises between 1 and 12 natural, synthetic, or chemically modified residues.

In another embodiment described herein, the anti-biofilm peptide comprises the sequence according to Formula IV: $B^1$-$B^2$-$B^3$-$B^4$-$B^5$-$B^6$-$B^7$-$B^8$-$B^9$-$B^{10}$-$B^{11}$-$B^{12}$, wherein: each residue corresponding to positions $B^1$, $B^3$, $B^4$, $B^5$, $B^6$, $B^7$, or $B^9$ comprises any hydrophobic non-aromatic natural, synthetic, or chemically modified amino acid; each residue corresponding to positions $B^2$, $B^8$, $B^{11}$, or $8^{12}$ comprises any natural, synthetic, or chemically modified positive amino acid; and each residue corresponding to position $B^{10}$ comprises any natural, synthetic, or chemically modified aromatic amino acid. In one aspect, the anti-biofilm peptide comprises the sequence $B^1$-$B^2$-$B^3$-$B^4$-$B^5$-$B^6$-$B^7$-$B^8$. In another aspect, the anti-biofilm peptide comprises the sequence $B^7$-$B^8$-$B^9$-$B^{10}$-$B^{11}$-$B^{12}$. In another aspect, the anti-biofilm peptide comprises the sequence $B^1$-$B^2$-$B^3$-$B^4$-$B^5$-$B^6$. In another aspect, the anti-biofilm peptide comprises the sequence $B^1$-$B^2$-$B^3$-$B^4$-$B^5$-$B^6$-$B^7$. In another aspect, the anti-biofilm peptide comprises the sequence according to Formula IV: $B^1$-$B^2$-$B^3$-$B^4$-$B^5$-$B^6$-$B^7$-$B^8$-$B^9$-$B^{10}$-$B^{11}$, wherein: each residue corresponding to positions $B^1$, $B^2$, $B^4$, $B^5$, $B^8$, $B^9$, or comprises any natural, synthetic, or chemically modified positive amino acid; each residue corresponding to positions $B^3$, $B^6$, or $B^7$ comprises any natural, synthetic, or chemically modified aromatic amino acid; and each residue corresponding to position $B^{10}$ comprises any hydrophobic non-aromatic natural, synthetic, or chemically modified amino acid. In another aspect, the anti-biofilm peptide comprises the sequence $B^1$-$B^2$-$B^3$-$B^4$-$B^5$-$B^6$-$B^7$. In another aspect, the anti-biofilm peptide comprises the sequence $B^6$-$B^7$-$B^8$-$B^9$-$B^{10}$-$B^{11}$. In another aspect, the anti-biofilm peptide comprises the sequence $B^1$-$B^2$-$B^3$-$B^4$-$B^5$-$B^6$-$B^7$-$B^8$-$B^9$. In another aspect, the anti-biofilm peptide comprises the sequence $B^4$-$B^5$-$B^6$-$B^7$-$B^8$-$B^9$-$B^{10}$. In another aspect, the anti-biofilm peptide is covalently linked to the N-terminus or C-terminus of the anti-microbial peptide. In another aspect, the anti-microbial peptide is stabilized by the addition of between 1 and 3 natural or artificial stabilizing residues to the anti-biofilm peptide. In another aspect, the stabilizing residues comprise: D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-norleucine, L-norleucine, D-isoleucine, L-isoleucine, β-isoleucine, or a piperazin-2-one ring. In another aspect, the anti-biofilm peptide is methylated.

Another embodiment described herein is a non-naturally occurring anti-microbial peptide comprising the sequence according to Formula I: $X^1$ $R^2$ [$R^3$ $R^4$ $R^5$ $R^6$ $R^7$ $R^8$ $R^9$ $R^{10}$ $R^{11}$ $R^{12}$ $R^{13}$ $R^{14}$ $R^{15}$ $R^{16}$ $R^{17}$]$Y^1$ $Y^2$, wherein: $X^1$ is norleucine and $Y^1$ $Y^2$ is D-Pro-D-Val, D-Val-D-Pro, D-Phe-D-Val or D-Val-D-Phe, wherein $R^1$ to $R^{17}$ represent residues of the anti-microbial peptide and $R^1$ to $R^{17}$ is further represented by formula II: $P_{0-2}$-|-[N-|-(U)$_{0-1}$-|-(P|A)$_{1-3}$-|-(U)$_{0-1}$-|-(P|A)$_{0-3}$-|-(U)$_{0-1}$-|-(P|A)$_{0-3}$-|-(U)$_{0-1}$-|-(P|A)$_{0-3}$-P], wherein: "N" is aspartic acid; "U" glutamine or leucine; "P" is proline, histidine, lysine, or arginine; "A" is noralanine, 2'-naphthylalanine, tryptophan, tyrosine, or phenylalanine; and wherein an anti-biofilm peptide is optionally covalently attached to the N-terminus of the antimicrobial peptide of formula I and formula II. In one aspect, the length of the peptide is from about 3 residues to about 17 residues. In another aspect, $X^1$ and $Y^1$ $Y^2$ increase the stability of the non-naturally occurring anti-microbial peptide. In another aspect, the N-terminus is acylated. In another aspect, the C-terminus is amidated. In another aspect, $Y^1$ $Y^2$ increases the specificity of the anti-microbial peptide to target gram-negative bacteria. In another aspect, $Y^1$ $Y^2$ increases the specificity of the anti-microbial peptide to target gram-positive bacteria. In another aspect, the non-naturally occurring anti-microbial peptide is cyclized through a lactam linkage between a positive and negative residue. In another aspect, an anti-biofilm peptide comprising between 1 and 12 natural, synthetic, or chemically modified residues is covalently linked to the anti-microbial peptide.

In another embodiment described herein, an anti-biofilm peptide comprises the sequence according to Formula IV: $B^1-B^2-B^3-Ba-B^5-B^6-B^7-B^8-B^9-B^{10}-B^{11}-B^{12}$, wherein: each residue corresponding to positions $B^1$, $B^3$, $B^4$, $B^5$, $B^6$, $B^2$, or $B^9$ is alanine, valine, or isoleucine; each residue corresponding to positions $B^2$, $B^8$, $B^{11}$, or $B^{12}$ is arginine, histidine, or lysine; and each residue corresponding to position $B^{10}$ is noralanine, 2'-naphthylalanine, tryptophan, tyrosine, or phenylalanine. In one aspect, the anti-biofilm peptide comprises the sequence $B^1-B^2-B^3-B^4-B^5-B^6-B^7-B^8$. In another aspect, the anti-biofilm peptide comprises the sequence $B^7-B^8-B^9-B^{10}-B^{11}-B^{12}$. In another aspect, the anti-biofilm peptide comprises the sequence $B^1-B^2-B^3-B^4-B^5-B^6$. In another aspect, the anti-biofilm peptide comprises the sequence $B^1-B^2-B^3-B^4-B^5-B^6-B^2$. In another aspect, the anti-biofilm peptide comprises the sequence according to Formula IV: $B^1-B^2-B^3-B^4-B^5-B^6-B^7-B^8-B^9-B^{10}-B^{11}$, wherein: each residue corresponding to positions $B^1$, $B^2$, $B^4$, $B^5$, $B^8$, $B^9$, or $B^{11}$ is arginine, histidine, or lysine; each residue corresponding to positions $B^3$, $B^6$, or $B^7$ is noralanine, 2'-naphthylalanine, tryptophan, tyrosine, or phenylalanine; and each residue corresponding to position $B^{10}$ is alanine, valine, or isoleucine. In another aspect, the anti-biofilm peptide comprises the sequence $B^1-B^2-B^3-B^4-B^5-B^6-B^7$. In another aspect, the anti-biofilm peptide comprises the sequence $B^6-B^2-B^8-B^9-B^{10}-B^{11}$. In another aspect, the anti-biofilm peptide comprises the sequence $B^1-B^2-B^3-B^4-B^5-B^6-B^7-B^8-B^9$. In another aspect, the anti-biofilm peptide comprises the sequence $B^4-B^5-B^6-B^7-B^8-B^9-B^{10}$. In another aspect, the anti-biofilm peptide is methylated.

Another embodiment described herein is a non-naturally occurring anti-microbial peptide comprising any one of SEQ NOs: 1-4296. In one aspect, the length of the peptide is from about 3 residues to about 17 residues. In another aspect, the peptide is stabilized.

In one aspect, the N-terminus of the non-naturally occurring anti-microbial peptide is stabilized. In another aspect, the stabilization comprises the addition of between 1 and 3 natural or artificial stabilizing residues. In another aspect, the N-terminal stabilizing residues comprise: D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-norleucine, L-norleucine, D-isoleucine, L-isoleucine, β-isoleucine, or a piperazin-2-one ring. In another aspect, the N-terminus is acylated. In another aspect, the C-terminus of the non-naturally occurring anti-microbial peptide is stabilized. In another aspect, the stabilization comprises the addition of between 1 and 3 natural or artificial stabilizing residues. In another aspect, the C-terminal stabilizing residues comprise: D-threonine, L-threonine, D-proline, L-proline, β-homo proline, D-alanine, L-alanine, D-valine, L-valine, β-valine, 3-methyl-β-valine, D-leucine, L-leucine, β-leucine, D-norleucine, L-norleucine, D-isoleucine, L-isoleucine, β-isoleucine, D-phenylalanine, L-phenylalanine, or a piperazin-2-one ring. In another aspect, the C-terminus is amidated. In another aspect, the C-terminal stabilization also increases the specificity of the anti-microbial peptide to target gram-negative bacteria. In another aspect, the C-terminal stabilization increases the specificity of the anti-microbial peptide to target gram-positive bacteria. In another aspect, the C-terminal stabilizing residues comprise: D-Pro-D-Val; D-Val-D-Pro; β-Val-β-Pro; β-Pro-β-Val; 3-methyl-β-Val-β-Pro; D-Pro-D-Ala; D-Ala-D-Pro; β-Pro-β-Ala; β-Ala-β-Pro; D-Pro-D-Leu; D-Leu-D-Pro; β-Pro-β-Leu; β-Leu-β-Pro; D-Val-D-Ala; D-Ala-D-Val; β-Val-β-Ala; β-Ala-β-Val; 3-methyl-β-Val-β-Ala; D-Val-D-Leu; D-Leu-D-Val; β-Val-β-Leu; β-Leu-β-Val; 3-methyl-β-Val-β-Leu; D-Phe-D-Val; or D-Val-D-Phe. In another aspect, the C-terminus is amidated. In another aspect, the non-naturally occurring anti-microbial peptide is cyclized. In another aspect, the non-naturally occurring anti-microbial peptide is cyclized through a lactam linkage. In another aspect, the non-naturally occurring anti-microbial peptide is cyclized between a positive and negative residue. In another aspect, an anti-biofilm peptide is covalently linked to the anti-microbial peptide. In another aspect, the anti-biofilm peptide is covalently linked to the N-terminus of the anti-microbial peptide. In another aspect, the anti-biofilm peptide is covalently linked to the C-terminus of the anti-microbial peptide. In another aspect, the anti-biofilm peptide is covalently linked to the anti-microbial peptide through at least one linker. In another aspect, the anti-biofilm peptide comprises between 1 and 12 natural, synthetic, or chemically modified residues.

In one embodiment described herein, the anti-biofilm peptide comprises the sequence according to Formula IV: $B^1-B^2-B^3-B^4-B^5-B^6-B^7-B^8-B^9-B^{10}-B^{11}-B^{12}$, wherein: each residue corresponding to positions $B^1$, $B^3$, $B^4$, $B^5$, $B^6$, $B^7$, or $B^9$ comprises any hydrophobic non-aromatic natural, synthetic, or chemically modified amino acid; each residue corresponding to positions $B^2$, $B^8$, $B^{11}$, or $B^{12}$ comprises any natural, synthetic, or chemically modified positive amino acid; and each residue corresponding to position $B^{10}$ comprises any natural, synthetic, or chemically modified aromatic amino acid. In one aspect, the anti-biofilm peptide comprises the sequence $B^1-B^2-B^3-B^4-B^5-B^6-B^7-B^8$. In another aspect, the anti-biofilm peptide comprises the sequence $B^7-B^8-B^9-B^{10}-B^{11}B^{12}$. In another aspect, the anti-biofilm peptide comprises the sequence $B^1-B^2-B^3-B^4-B^5-B^6$. In another aspect, the anti-biofilm peptide comprises the sequence $B^1-B^2-B^3-B^4-B^5-B^6-B^7$.

In another embodiment described herein, the anti-biofilm peptide comprises the sequence according to Formula IV: $B^1-B^2-B^3-B^4-B^5-B^6-B^7-B^8-B^9-B^{10}-B^{11}$, wherein: each residue corresponding to positions $B^1$, $B^2$, $B^4$, $B^5$, $B^8$, $B^9$, or $B^{11}$ comprises any natural, synthetic, or chemically modified positive amino acid; each residue corresponding to positions $B^3$, $B^6$, or $B^7$ comprises any natural, synthetic, or chemically modified aromatic amino acid; and each residue corresponding to position $B^{10}$ comprises any hydrophobic non-aromatic natural, synthetic, or chemically modified amino acid. In another aspect, the anti-biofilm peptide comprises residues $B^1$ $B^2$ $B^3$ $B^4$ $B^5$ $B^6$ $B^7$. In another aspect, the anti-biofilm peptide comprises residues $B^6$ $B^7$ $B^8$ $B^9$ $B^{10}$ $B^{11}$. In another aspect, the anti-biofilm peptide comprises residues $B^1$ $B^2$ $B^3$ $B^4$ $B^5$ $B^6$ $B^7$ $B^8$ $B^9$. In another aspect, the anti-biofilm peptide comprises residues $B^4$ $B^5$ $B^6$ $B^7$ $B^8$ $B^9$ $B^{10}$. In another aspect, the anti-biofilm peptide is covalently linked to the N-terminus or C-terminus of the anti-microbial peptide. In another aspect, the anti-microbial peptide is stabilized by the addition of between 1 and 3 natural or artificial stabilizing residues to the anti-biofilm peptide. In another aspect, the stabilizing residues comprise: D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-norleucine, L-norleucine, D-isoleucine, L-isoleucine, β-isoleucine, or a piperazin-2-one ring. In another aspect, the anti-biofilm peptide is methylated.

Another embodiment described herein is a method for changing the physiology of a microbe using any of the non-naturally occurring anti-microbial peptide described herein. In another aspect, the changing the physiology of a microbe comprises reducing the growth rate, inhibiting DNA synthesis, inhibiting protein synthesis, inhibiting structural stability, reducing cell-membrane integrity, inhibiting cell wall synthesis, reducing viability, or causing death. In another aspect, the microbe comprises a pathogenic organism. In another aspect, the pathogenic organism comprises a fungi, bacteria, virus, unicellular organism, bacterial colony, or biofilm. In another aspect, the anti-microbial peptides are used in a laboratory setting. In another aspect, the anti-microbial peptide is used as a scientific tool. In another aspect, the anti-microbial peptides are used in a hospital setting. In another aspect, the anti-microbial peptides are used as an animal feed additive.

Another embodiment described herein is a method for treating, ameliorating the symptoms of, or delaying the onset of a medical condition by administering to a subject in need thereof any of the anti-microbial peptides described herein. In one aspect, the medical condition comprises a microbial infection. In another aspect, the anti-microbial peptide reduces the growth rate, reduces the viability, or causes death of a microbe, thereby treating, ameliorating the symptoms of, or delaying the onset of a microbial infection. In another aspect, the anti-microbial peptide is administered to a subject comprising: intravenous (IV), subcutaneous (SC), intramuscular (IM), intraperitoneal (IP), intracerebroventricular (ICV), oral, topical, or nasal or a combination thereof the routes of administration.

DETAILED DESCRIPTION

Figure 1:
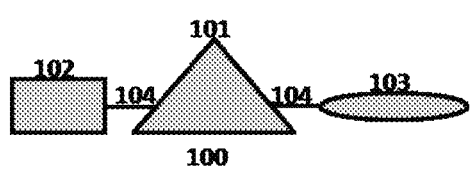
FIG. 1. Representative schematic of anti-microbial peptides described herein.
Figure 1:
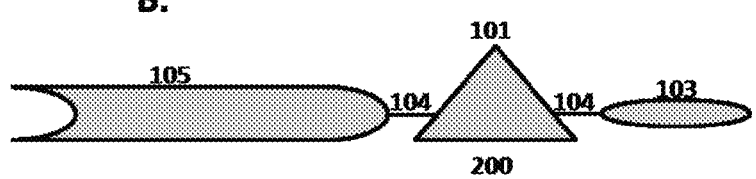
Figure 1:
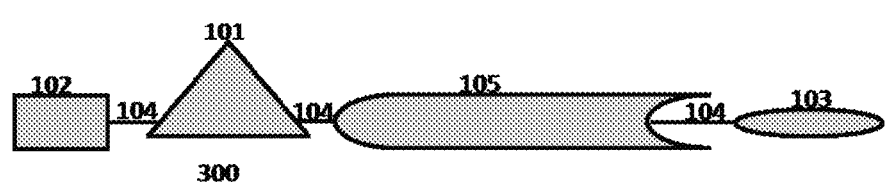
Figure 1:
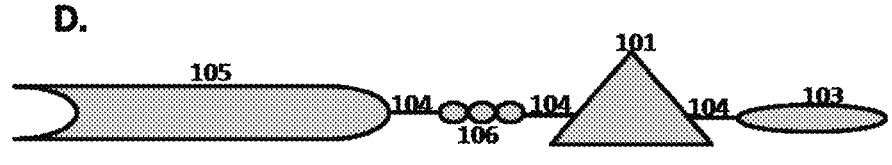
Figure 1:
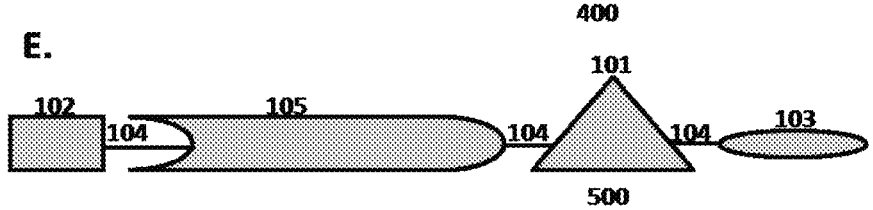

Short therapeutic peptides often need to be stabilized against enzymatic degradation, necessitating protective groups, modifications, or additional residues. These therapeutic peptides must also be able to exhibit trans-epithelial transport, in order to have oral activity (gastrointestinal transport) and in some applications blood-brain barrier transport. According to the "Rule of Five," a molecular mass greater than 500 g/mol is one of the "violations" that prevent drug paracellular transport. Lipinski et al., *Adv. Drug Deliv. Rev.* 46(1-3): 3-26 (2001). Thus according to Lipinski's Rule, most, if not all, peptide or peptide mimetic pharmacophores would be unable to exhibit paracellular movement through the gastrointestinal tract or blood-brain-barrier. A potential way to surmount this problem is to use an active transport mechanism for trans-epithelial movement of a peptide drug. Active transport carriers for di- and tri-peptides have been described, and these transported peptides could serve as carriers for small cyclic peptides or non-peptide drugs. Brandsch, *Amino Acids* 31(2): 119-136 (2006); Brandsch et al., *J. Pharm. Pharmacol.* 60(5): 543-58 (2008). Alternatively, organic anionic transport polypeptides have been implicated in transporting cyclic cationic peptides. International Transporter Consortium, *Nat. Rev. Drug Discov.* 9(3): 215-236 (2010).

In one aspect described herein, non-naturally occurring short peptides are provided that comprise an anti-microbial peptide coupled to a degradation resistant N- and/or C-terminal di or tri-peptide extension and in some aspects further coupled to an anti-biofilm peptide. One or both of the extensions contain a pharmacophore that enables active transport by di- or tri-peptide transport systems, conferring oral activity and/or blood-brain-barrier transport.

One aspect described herein, is a non-naturally occurring anti-microbial peptide that comprises an anti-microbial peptide coupled to a degradation resistant N- and/or C-terminal di or tri-peptide extension. The stabilizing effects of the extension(s) are designed to maximize the activity of the pharmacophores with therapeutically desirable activity.

Another aspect described herein is a non-naturally occurring anti-microbial peptide that comprises an anti-microbial peptide coupled to a degradation resistant N- and/or C-terminal di- or tri-peptide extension. The structure of the anti-microbial peptide and the peptide extension are designed to prevent a specific type of trans-epithelial transport. This analog would have utility when an orally active (i.e., having gastrointestinal transport) or when active only at peripheral sites of action (e.g., not within the central nervous system).

Another aspect described herein is a composition comprising a non-naturally occurring anti-microbial peptide coupled to a degradation-resistant N- and/or C-terminal extension to suppress exposure and effects of overlapping pharmacophores, and potentiate therapeutic activity. The degradation-resistant extension is at least one amino acid, at least one modified amino acid, a peptide mimetic (non-amino acid small molecule), or combinations thereof. A degradation-resistant N- and/or C-terminal extension is one selected to resist degradation under physiological conditions, thereby allowing the anti-microbial peptide to enhance at least one anti-microbial effect while exhibiting minimized or abolished side effects and potentiated therapeutic activity when acutely or chronically administered to a human or mammal.

Described herein are peptides comprising non-naturally occurring anti-microbial peptide comprising degradation-resistant N-terminal and/or C-terminal extensions.

A naturally occurring "anti-microbial peptide" is a small naturally occurring peptide that has a naturally occurring genomically-encoded peptide sequence that is ribosomally synthesized, which forms a secondary structure and acts on or targets microbes. Often, this targeting reduces microbial growth rate; inhibits DNA, RNA, or protein synthesis; reduces structural or membrane stability, inhibits cell wall synthesis, reduces viability, or causes microbial death.

A "non-naturally occurring anti-microbial peptide" is a non-naturally occurring man-made peptide, peptide mimetic, or pharmacophore that is not derived from any natural genomic sequences or any other natural source, which forms a secondary structure and acts on or targets microbes. In some aspects, non-naturally occurring anti-microbial peptides can be synthesized using peptide synthesis technology known in the art; or it can be artificially expressed as a recombinant protein encoded by an expression vector and purified from a host through methods known in the art.

A peptide or amino acid "mimetic" is a non-amino acid molecule that mimics a peptide (a chain of amino acids) or one amino acid residue.

A "pharmacophore" is the minimum set of amino acid residues necessary to achieve a physiological effect. An anti-microbial physiological effect comprises any change to the normal functions of any microbe.

A "microbe" is a microscopic organism that can be a single cell or a multicellular organism. As used herein, a microbe comprises all classes of bacteria, archaea, protozoa, and fungi.

"Side effects" refer to any unwanted biological activity that occurs in conjunction with a therapeutic anti-microbial effect.

"Substantial degradation" refers to the degradation of the N-terminal extension, the C-terminal extension, both N- and C-terminal degradation or degradation to other regions of the anti-microbial peptide by physiological enzymes and other factors, in such a manner or to a degree that side effects appear. According to one aspect, an anti-microbial peptide having a C-terminal extension that resists substantial degradation is one where no more than 50% of the administered peptide causes side effects and/or displays a low half-life. In some aspects, no more than 25% of the administered peptide causes side effects and/or displays a low half-life. More preferably, in some aspects, less than 10% of the administered peptide causes side effects and/or displays a low half-life, as compared to an anti-microbial peptide that lacks a C-terminal extension.

A "pharmaceutical composition" includes anti-microbial peptides described herein, or a pharmaceutically acceptable salt thereof, and a pharmaceutically acceptable carrier. The carrier may be a liquid formulation, for example, a buffered, isotonic, aqueous solution. Pharmaceutically acceptable carriers also can include excipients, such as diluents, carriers and the like, and additives, such as stabilizing agents, preservatives, solubilizing agents, buffers and the like.

The terms "bind," "binding," "complex," and "complexing," refer to all types of physical and chemical binding, reactions, complexing, attraction, chelating and the like.

The symbol between residues in the peptide formulas described herein represented by a "-" symbol (hyphen) corresponds to contiguously linked amino acid residues. In some aspects, this linkage is through an amide bond between the contiguous residues.

The "peptides" described herein can be (a) naturally-occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides.

By employing chemical synthesis, a useful means of production, it is possible to introduce various amino acids which do not naturally occur along the chain, modify the N- or C-terminus, and the like, thereby providing for improved stability and formulation, resistance to protease degradation, and the like.

The term "peptide" as used herein includes any structure comprised of two or more amino acids, including chemical modifications and derivatives of amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" also includes dimers or multimers of peptides. A "manufactured" peptide includes a peptide produced by chemical synthesis, recombinant DNA technology, biochemical, or enzymatic fragmentation of larger molecules, combinations of the foregoing or, in general, made by any other method. The term "peptide" includes peptides containing a variable number of amino acid residues, optionally with non-amino acid residue groups at the N- and C-termini, such groups including acyl, acetyl, alkenyl, alkyl, N-alkyl, amine, or amide groups, among others.

"Amino acids" are molecules containing an amine group, a carboxylic acid group, and a side-chain that is specific to each amino acid. The key elements of an amino acid are carbon, hydrogen, oxygen, and nitrogen and have the generic formula $H_2N-CHR-COOH$, wherein R represents a side chain group. The various α-amino acids differ in the side-chain moiety that is attached to the α-carbon.

The phrase "amino acid side chain moiety" used herein, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs, or structures designed to mimic amino acids, and the like. For example, the side chain moiety of any amino acid disclosed herein is included within the definition. A "derivative" of an amino acid side chain moiety is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties.

The "amino acids" used herein, and the term as used in the specification and claims, include the known naturally occurring protein amino acids, which are referred to by both their common three letter abbreviation and single letter abbreviation. See generally *Synthetic Peptides: A User's Guide*, G. A. Grant, editor, W.H. Freeman & Co., New York (1992), the teachings of which are incorporated herein by reference, including the text and table set forth at pages 11-24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, supra; Hruby et al., *Biochem. J.* 268(2): 49-262 (1990); and Toniolo, *Int. J. Peptide Protein Res.* 35: 287-300 (1990); the teachings of all of which are incorporated herein by reference.

In the peptides described herein, conventional amino acid residues have their conventional meaning as given in Chapter 2400, of the USPTO *Manual of Patent Examining Procedure*, (MPEP) 9th Ed. Thus, "Ala" is alanine; "Arg" is arginine; "Asn" is asparagine; "Asp" is aspartic acid; "Cys" is cysteine; "Gln" is glutamine; "Glu" is glutamic acid; "His" is histidine; "Ile" is isoleucine; "Leu" is leucine; "Lys" is lysine; "Met" is methionine; "Phe" is phenylalanine; "Pro" is proline; "Ser" is serine; Thr is threonine; "Trp" is tryptophan; "Tyr" is tryosine; and "Val" is valine. Unless otherwise indicated, all amino acids abbreviations represent either isomer, i.e., the L-isomer or the D-isomer. Thus, for example, "L-Phe" is L-phenylalanine; "D-Phe" is D-phenylalanine; "D-/L-Phe" is either D-phenylalanine or L-phenylalanine; "Phe" is also either D-phenylalanine or L-phenylalanine, and so on. Non-standard amino acids are "Nle" is norleucine; "Nal" is noralanine; "D-Nal" is D-noralanine; D-Nal(2') is D-2'-naphthylalanine; and so on.

An alpha ($\alpha$)-amino acid has the generic formula $H_2N-C_aHR-COOH$, where R is a side chain moiety and the amino group is attached to the carbon atom immediately adjacent to the carboxylate group (i.e., the $\alpha$-carbon). Other types of amino acid exist when the amino group is attached to a different carbon atom. For example, beta ($\beta$)-amino acids, the carbon atom to which the amino group is attached is separated from the carboxylate group by one carbon atom, $C_\beta$. For example, $\alpha$-alanine has the formula $H_2N-C_\alpha H(CH_3)-COOH$. In contrast, $\beta$-alanine has the general formula $H_2N-C_\beta H_2-C_\alpha H_2-COOH$ (i.e., 3-aminopropanoic acid).

When $\beta$-amino acids are incorporated into peptides, two main types of $\beta$-peptides exist: those with the side chain residue, R, on the carbon next to the amine are called $\beta^3$ peptides and those with the side chain residue on the carbon next to the carbonyl group are called $\beta^2$ amino acids. As a non-limiting example, "$\beta$-valine" can refer to:

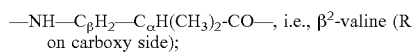
—NH—$C_\beta H_2$—$C_\alpha H(CH_3)_2$—CO—, i.e., $\beta^2$-valine (R on carboxy side);

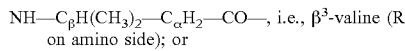
NH—$C_\beta H(CH_3)_2$—$C_\alpha H_2$—CO—, i.e., $\beta^3$-valine (R on amino side); or

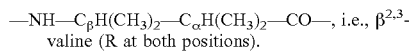
—NH—$C_\beta H(CH_3)_2$—$C_\alpha H(CH_3)_2$—CO—, i.e., $\beta^{2,3}$-valine (R at both positions).

Gamma ($\gamma$)-amino acids are amino acids with the carbon atom to which the amino group attaches is separated from the carboxylate moiety by two carbon atoms. For example, $\gamma$-amino butyric acid has the formula, $H_2N-C_\gamma H_2-C_\beta H_2-C_\alpha H_2-COOH$.

For additional modified and unusual amino acids, see MPEP § 2422, particularly Table 4 at 2400-24. Additionally, "Ac" indicates N-acetyl and "cyclo" refers to a cyclic structure, which is also shown in the literature as "c" or referred to as a "lactam." "NH$_2$" indicates an amine group, typically added on the C-terminus of a polypeptide. Accordingly, as used herein, an —NH$_2$ moiety on the C-terminus of a peptide indicates an amide, i.e., —CO—NH$_2$. In addition, the following abbreviations are used herein: Harg is Homo arginine; Hlys is Homo lysine; Nal(2') is D-(2'-naphthyl) alanine.

Additional abbreviations are used as follows: tBu is tert-butyl; Hyp(BzI) is benzyl-L-hydroxy-proline; Mamb is 3-aminomethyl-benzoic acid; glutaric acid linker is CO—(CH$_2$)$_3$—CO; Pen is L-Penicillamine; Aib is 2-Aminoisobutyric acid; Tic is 1,2,3,4-Tetrahydroisoquinoline-3-carboxylic Acid; Aba is 4-amino-1,2,4,5-tetra-hydro-2-benzazepin-3-one; Pip is piperidine-2-carboxylic acid; Nip is piperidine-3-carboxylic acid; Tic is tetrahydroquinoline-3-carboxylic acid; Bipisbiphenylalanine; Phg is $\alpha$-Phenyl-glycine; Sar is Sarcosine; Azt is 3'-azido-3'-deoxythymidine; Oic is Octohydroindole-2-carboxylic acid.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monovalent or bicyclic aromatic hydrocarbon radical of 6-to-12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group CH$_3$CO—, referred to herein as "Ac."

A peptide or aliphatic moiety is "acylated" when an alkyl or substituted alkyl group as defined above is bonded through one or more carbonyl {—(C=O)—} groups. A peptide is most usually acylated at the N-terminus.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen, and sulfur. Five- or six-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine, and thienopyridine.

An "amine" includes compounds that contain an amine group (—NH$_2$).

An "amide" includes compounds that have a trivalent nitrogen attached to a carbonyl group (i.e., —CO—NH$_2$), such as for example methylamide, ethylamide, propylamide, and the like. A peptide is most usually amidated at the C-terminus by the addition of an amine (—NH$_2$) moiety to the C-terminal carboxyl group.

An "imine" includes compounds that have a carbon-nitrogen double bond, with the nitrogen also attached to a hydrogen (NH=CH—R).

An "imide" includes compounds containing an imido group (—OC—NH—CO—).

A "nitrile" includes compounds that are carboxylic acid derivatives and contain a (—CN) group bound to an organic group.

The term "halogen" is intended to include the halogen atoms fluorine, chlorine, bromine and iodine, and groups including one or more halogen atoms, such as —$CF_3$ and the like.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions encompass any composition made by admixing a peptide and a pharmaceutically acceptable carrier.

Amino acids, including stereoisomers and modifications of naturally occurring amino acids, protein amino acids, non-protein amino acids, post-translationally modified amino acids, enzymatically synthesized amino acids, derivatized amino acids, constructs, or structures designed to mimic amino acids (peptide mimetics), and the like, including all of the foregoing, are sometimes referred to herein as "residues."

"Cachexia" refers to a state of general ill health and malnutrition. It is often associated with and induced by malignant cancer, cystic fibrosis, or AIDS, and is characterized by loss of appetite, loss of body mass, especially lean body mass, and muscle wasting.

"Anorexia" refers simply to a loss of appetite, whether brought on by medical, physiological, or psychological factors. Anorexia is often closely associated with, and generally contributes to, cachexia seen in patients with advanced cancers and other conditions.

Anti-Microbial Peptides

Non-naturally occurring peptide having a melanocortin pharmacophore (SEQ NOs: 205-212) were surprisingly found to have anti-microbial activity. Thus, described further herein are non-naturally occurring peptides having anti-microbial activity represented by the formulas, and amino acid sequences described herein.

A non-naturally occurring anti-microbial peptide sequence is represented by Formula I, as shown, and comprises an anti-microbial peptide coupled to a degradation-resistant C-terminal extension and an optional N-terminal extension:

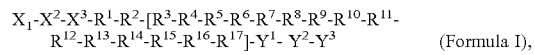
(Formula I), wherein $X^1$, $X^2$, and $X^3$ represent optional stabilizing N-terminal residues or an amino acid residue mimetic; $R^1$ to $R^{17}$ represent residues of the anti-microbial peptide; and $Y^1$, $Y^2$, and $Y^3$ represent degradation-resistant C-terminal residues or an amino acid residue mimetic; brackets indicate residues that are cyclized in some aspects.

In one aspect, the anti-microbial peptide is represented by Formula I above, and residues $R^1$ to $R^{17}$ represent the anti-microbial peptide comprising synthetic amino acid residues, chemically modified amino acid residues, or amino acid residues in natural form as either an L or D isomer. In one aspect, the anti-microbial peptide is represented by Formula I above, and residues $R^1$ to $R^{17}$ represent the anti-microbial peptide comprising but not limited to (o-Phe) Phe R5, 3-diamino-propionic acid, Aba, acetylated cysteine, acetylated norleucine, alanine, arginine, aspartic acid, Azt, Bip, CO-cis-CH=CH—CO, cysteine, D-Nal(2'), D-phenylalanine, D-proline, D-tryptophan, glutamic acid, glutaric acid, glycine, histidine, histidine methylated at positions 1 or 3, homoarginine, Hyp(Bzl), l-Nal(2'), 1-phenylalanine, 1-proline, 1-tryptophan, lysine, Mamb, methylated D-phenylalanine, n-hexanoyl group, Nip, norleucine, n-pentanoyl group, Oic, o-pthalic acid, ornithine, pCl-D-Phe, Phg, Pip, proline, Sar, succinic acid, tButGly, Tic, tyrosine, and β-alanine.

Collectively, residues $R^1$ to $R^{17}$ (i.e., $R^1 R^2 R^3 R^4 R^5 R^6 R^7 R^8 R^9 R^{10} R^{11} R^{12} R^{13} R^{14} R^{15} R^{16} R^{17}$) can be one of many known anti-microbial peptides, wherein each of the residues is independently an amino acid or peptide mimetic. In some aspects, the anti-microbial peptides have between 3 and 15 residues (e.g., $R^1$ to $R^3$ and $R^1$ to $R^{15}$). In some aspects, the anti-microbial peptides have 3, or 4, or 5, or 6, or 7, or 8, or 9, or 10, or 11, or 12, or 13, or 14, or 15 residues (e.g., $R^1$ to $R^3$, $R^1$ to $R^4$, $R^1$ to $R^5$, $R^1$ to $R^6$, $R^1$ to $R^7$, $R^1$ to $R^8$, $R^1$ to $R^9$, $R^1$ to $R^{10}$, $R^1$ to $R^{11}$, $R^1$ to $R^{12}$, $R^1$ to $R^{13}$, $R^1$ to $R^{14}$, or $R^1$ to $R^{15}$). The individual anti-microbial peptide residues $R^1$ to $R^{17}$ (e.g., $R^1$ to $R^3$, $R^1$ to $R^4$, $R^1$ to $R^5$, $R^1$ to $R^6$, $R^1$ to $R^7$, $R^1$ to $R^8$, $R^1$ to $R^9$, $R^1$ to $R^{10}$, $R^1$ to $R^{11}$, $R^1$ to $R^{12}$, $R^1$ to $R^{13}$, $R^1$ to $R^{14}$, or $R^1$ to $R^{15}$, $R^1$ to $R^{16}$, or $R^1$ to $R^{17}$) are further represented by Formula II below:

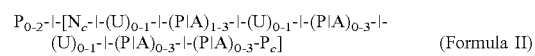
(Formula II)

wherein $R^1$-$R^{17}$ are represented by "P", "U", "N", and "A"; and "N" represents any negative residue; the "c" indicates cyclization between "c" labelled residues; "U" represents any polar uncharged residue (e.g., glutamine; Gln) or a hydrophobic non-aromatic residue (e.g., leucine; Leu); "P" represents any positive residue (e.g., histidine; His, lysine; Lys or arginine; Arg) or proline (Pro), "A" represents any aromatic residue (e.g., noralanine; Nal, 2'-naphthylalanine; Nal(2'), tryptophan; Trp, tyrosine; Tyr, or Phe; F); the symbol "|" indicates the presence of amide bond between an alternative residue or residues; the number of sequential residues is indicated in the adjacent numerical subscript (a 0 indicates no residue is present, a 1 indicates one residue is present with an amide bond with the adjacent residues, a 2 indicates two residues present with an amide bond with the adjacent residues, a 3 indicates three residues present with an amide bond with the adjacent residues). The alternative residues (number 0-3 or 1-3) according to Formula II can further be in any order or number (1-3 residues) as specified (e.g., P-P-P, P-P, P, A-A-A, A-A, A, P-A-A, P-P-A, P-A, A-P-P, A-A-P, A-P, P-A-P, OR A-P-A)

In another aspect, the anti-microbial peptide is represented by Formula III comprising an anti-microbial peptide coupled to a degradation-resistant C-terminal extension and an optional N-terminal extension:

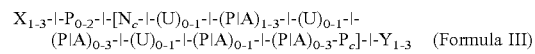
(Formula III)

wherein $X_{1-3}$ represents optional stabilizing N-terminal residues or an amino acid residue mimetic; wherein the individual residues of the antimicrobial peptide are represented by "P", "U", "N", and "A" and "N" and "N" represents any negative residue; the "$·_c$" indicates cyclization between "$·_c$" labelled residues; "U" represents any polar uncharged residue (e.g., glutamine; Gln) or a hydrophobic non-aromatic residue (e.g., leucine; Leu); "P" represents any positive residue (e.g., histidine; His, lysine; Lys or arginine; Arg) or proline (Pro), "A" represents any aromatic residue (e.g., noralanine; Nal, 2'-naphthylalanine; Nal(2'), tryptophan; Trp, tyrosine; Tyr, or Phe; F); the symbol "i" indicates the presence of amide bond between an alternative residue or residues; the number of sequential residues is indicated in the adjacent numerical subscript (a 0 indicates no residue is present, a 1 indicates one residue is present with an amide bond with the adjacent residues, a 2 indicates two residues present with an amide bond with the adjacent residues, a 3 indicates three residues present with an amide bond with the adjacent residues). The alternative residues (number 0-3 or 1-3) according to Formula II can further be in any order or number (1-3 residues) as specified (e.g., P-P-P, P-P, P, A-A-A, A-A, A, P-A-A, P-P-A, P-A, A-P-P, A-A-P, A-P, P-A-P, OR A-P-A); and $Y_{1-3}$ represent degradation-resistant C-terminal residues or an amino acid residue mimetic.

In another aspect, the anti-microbial peptide represented by Formula I, Formula II, or Formula III is provided, wherein at least one D-phenylalanine residue, or all D-phenylalanine residues are halogenated (e.g., fluorine or chlorine).

N-Terminal Extensions

In one aspect, an N-terminal extension is coupled to the anti-microbial peptide. The N-terminal extension is represented as $X^1 X^2 X^3$ in Formula I, wherein:

$X^1$ is selected from the group consisting of D-threonine, L-threonine, D-proline, L-proline, β-homo proline, D-alanine, L-alanine, 3-alanine, D-valine, L-valine, β-valine, 3-methyl-β-valine, D-leucine, L-leucine, β-leucine, D-norleucine, L-norleucine, D-isoleucine, L-isoleucine, β-isoleucine, and a piperazin-2-one ring;

$X^2$ is absent or is selected from the group consisting of D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-norleucine, L-norleucine, D-isoleucine, L-isoleucine, β-isoleucine, and a piperazin-2-one ring; and $X^3$ is absent or is selected from the group consisting of D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-norleucine, L-norleucine, D-isoleucine, L-isoleucine, β-isoleucine, and a piperazin-2-one ring.

In another aspect, an N-terminal extension is represented as $X_{1-3}$ in Formula III, wherein:

$X_{1-3}$ is between 1 and 3 residues selected from the group consisting of D-threonine, L-threonine, D-proline, L-proline, β-homo proline, D-alanine, L-alanine, β-alanine, D-valine, L-valine, β-valine, 3-methyl-β-valine, D-leucine, L-leucine, β-leucine, D-norleucine, L-norleucine, D-isoleucine, L-isoleucine, β-isoleucine, and a piperazin-2-one ring;

In another aspect, an anti-microbial peptide represented by Formula I or Formula II containing any of the above N-terminal Extensions, $X^1$, $X^2$, or $X^3$ may be modified on the N-terminus by acylation ($CH_3$—CO—).

C-Terminal Extensions

To the anti-microbial peptide of Formula I, or to the anti-microbial peptide of Formula III, a C-terminal extension is provided in order to confer degradation-resistance of the C-terminal extension to prevent exposure of the RFamide sequence, and to potentially confer trans-epithelial transport. International Patent Application Nos. WO 2013/138340 A1 and WO 2011/026015 A3 are incorporated by reference herein for their teachings thereof.

In one aspect the C-terminal extension is represented by $Y^1 Y^2 Y^3$ of Formula I, wherein $Y^1$ is absent or is selected from the group consisting of D-threonine, L-threonine, D-proline, L-proline, β-homo proline, D-alanine, L-alanine, D-valine, L-valine, β-valine, 3-methyl-3-valine, D-leucine, L-leucine, β-leucine, D-isoleucine, L-isoleucine, β-isoleucine, D-phenylalanine, L-phenylalanine, or a piperazin-2-one ring;

$Y^2$ is absent or is D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, D-phenylalanine, L-phenylalanine, or a piperazin-2-one ring; and $Y^3$ is absent or is D-cysteine, L-cysteine, D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, D-phenylalanine, L-phenylalanine, or a piperazin-2-one ring.

In another aspect, the C-terminal extension is represented by $Y_{1-3}$ of Formula III, wherein $Y_{1-3}$ is between 1 and 3 residues selected from the group consisting of D-threonine, L-threonine, D-proline, L-proline, β-homo proline, D-alanine, L-alanine, D-valine, L-valine, β-valine, 3-methyl-β-valine, D-leucine, L-leucine, β-leucine, D-isoleucine, L-isoleucine, β-isoleucine, D-phenylalanine, L-phenylalanine, or a piperazin-2-one ring.

In one aspect, the C-terminal extension has a conformation that chronically inhibits degradation from carboxy peptidases. Examples of a C-terminal extension that chronically inhibit degradation include the di- and tri-peptides: D-Pro-D-Pro; D-Thr-D-Pro; and D-Thr-D-Pro-D-Thr as described in Tugyi et al., *Proc. Natl. Acad. Sci USA* 102(2): 413-418 (2005). Other examples of C-terminal extensions that inhibit C-terminal degradation are D-Pro-D-Val; D-Val-D-Pro; β-Val-β-Pro; β-Pro-β-Val; 3-methyl-β-Val-β-Pro; D-Pro-D-Ala; D-Ala-D-Pro; β-Pro-β-Ala; β-Ala-β-Pro; D-Pro-D-Leu; D-Leu-D-Pro; β-Pro-β-Leu; β-Leu-β-Pro; D-Val-D-Ala; D-Ala-D-Val; β-Val-β-Ala; β-Ala-β-Val; 3-methyl-β-Val-β-Ala; D-Val-D-Leu; D-Leu-D-Val; β-Val-β-Leu; β-Leu-β-Val; 3-methyl-β-Val-β-Leu; D-Phe-D-Val; D-Val-D-Phe; and others.

In one aspect, the C-terminal extension unexpectedly changes the specificity of the anti-microbial peptide to invert its specificity between gram-positive and gram-negative bacteria. In another aspect, the C-terminal extension changes the specificity of the anti-microbial peptide to increase its anti-microbial activity against gram-negative bacteria, wherein there is a concomitant decrease in anti-microbial activity to gram-positive bacteria. In another aspect, the C-terminal extension changes the specificity of the anti-microbial peptide to increase its anti-microbial activity against gram-positive bacteria, wherein there is a concomitant decrease in anti-microbial activity to gram-negative bacteria.

In one aspect, the presence of D-Phe-D-Val or D-Val-D-Phe in the C-terminal extension of the anti-microbial peptide increases its specificity for gram-negative bacteria. In another aspect, the presence of D-Pro-D-Val or D-Val-D-Pro in the C-terminal extension of the anti-microbial peptide increases its specificity for gram-positive bacteria.

In some aspects, the anti-microbial activity is detectable by bacterial cell agglutination (cell-clumping). Agglutination is a common mode of action for the natural antimicrobial peptides which leads to increased phagocytosis and bacterial cell clearance by macrophages. Torrent et al., *PLoS Pathogens* 8(11): e1003005 (2012). In other aspects, the anti-microbial peptides described herein have anti-microbial activity ascribed to other intracellular modes of action, and many have been reported to transverse the cytoplasmic membrane. Accordingly, the anti-microbial peptides are capable of interfering with numerous bacterial processes by inhibiting DNA synthesis, RNA synthesis, protein synthesis, and cell wall synthesis In addition, the anti-microbial peptides described herein can inhibit septum formation process during bacterial cell division, leading to elongation and filamentation of bacterial cells. Brogden, *Nature Reviews Microbiology* 3(3): 238-250 (2005).

In another aspect, an anti-microbial peptide represented by Formula I or Formula III containing any of the above C-terminal Extensions, $Y^1$, $Y^2$, or $Y^3$ may be modified on the C-terminus by adding an amine group (—NH$_2$) to form an amide (i.e., —CO—NH$_2$).

In another aspect, a proline mimetic (piperazin-2-one ring) is substituted for D-Pro. In one approach, a proline mimetic is synthesized as described in Teixido et al., *Brain Res Bull*, 2007, 73(1-3): 103-107. The piperazin-2-one ring is also discussed in Bhatt and Just, *Helvetica Chimica Acta* 83: 722-727 (2000). For the replacement of proline with a piperazin-2-one ring, an ethylene bridge is incorporated between the nitrogen molecules of two adjacent α-amino groups. This produces a six-membered ring, containing two nitrogen and four carbon atoms, a structure that is similar to a proline ring (albeit six-membered) between the two adjacent amino acid residue functional groups.

The C-terminal extension of the anti-microbial peptide is resistant to substantial degradation prior to the peptide being cleared from the bloodstream in the human or animal body. A C-terminal extension is of sufficient stability such that the anti-microbial peptide does not cause cardiovascular effects, or has minimized cardiovascular effects when administered to a human or animal. As stability of peptides, amino acids, and small molecules varies widely, anti-microbial peptide described herein have variable length C-terminal extensions in the extracellular physiological environment. The C-terminal extension is of sufficient stability (e.g., length, steric structure) such that any degradation in the body prior to clearance from the bloodstream will not re-expose the cardiovascular (RFamide) pharmacophore to achieve the effect.

Cyclization of the Anti-Microbial Peptide Comprising Formula I

Cyclized anti-microbial peptides have shown improved efficacy and stability. See Balse-Srinivasan et al., *J. Med. Chem.* 46(17): 3728-3733 (2003) and Bednarek et al., *Biochem. Biophys. Res. Corn.* 286(3): 641-645 (2001); Kavarana et al., *J. Med. Chem.* 45(12): 2644-2650 (2002). In one aspect, the non-naturally occurring anti-microbial peptide represented by Formula I is cyclized. The following represents a non-limiting list of examples of how the anti-microbial peptide represented by Formula I can be cyclized:

In Formula I, disulfide bond between an amino terminal anti-microbial peptide residue ($R_n$; e.g., $R^1$ $R^2$ $R^3$ $R^4$) and a carboxy terminal anti-microbial peptide residue ($R_c$, e.g., $R^9$, $R^{10}$ $R^{11}$ $R^{12}$ $R^{13}$ $R^{14}$ $R^{15}$ $R^{16}$, $R^{17}$%) the exact number and location of which is dependent upon the number of residues of the anti-microbial peptide; or $Y^1$, when a $R_n$ is cysteine and $R_c$ or $Y^1$ is cysteine as described in Balse-Srinivasan et al., *J. Med. Chem.* 46(23): 4965-4973 (2003). When $Y^1$ is cysteine, $Y^2$ is not absent, but is selected from the group consisting of D-threonine, L-threonine, D-proline, L-proline and a piperazin-2-one ring.

A lactam bridge between an amino terminal anti-microbial peptide residue ($R_n$; e.g., $R^1$ $R^2$ $R^3$ $R^4$) and a carboxy terminal anti-microbial peptide residue ($R_c$, e.g., $R^9$, $R^{10}$ $R^{11}$ $R^{12}$ $R^{13}$ $R^{14}$ $R^{15}$ $R^{16}$ $R^{17}$), the exact number and location of which is dependent upon the number of residues of the anti-microbial peptide, when $R_n$ is norleucine and $R_c$ is glutamic acid, as described in Mayorov et al. *J. Med. Chem.* 49: 1946-1952 (2006) and Bednarek et al., *Biochem. Biophys. Res. Corn.* 286(3): 641-645 (2001).

A side-chain lactam bridge between an amino terminal anti-microbial peptide residue ($R_n$; e.g., $R^1$ $R^2$ $R^3$ $R_4$) and a carboxy terminal anti-microbial peptide residue ($R_c$, e.g., $R^9$, $R^{10}$ $R^{11}$ $R^{12}$ $R^{13}$ $R^{14}$ $R^{15}$ $R^{16}$, $R^{17}$) the exact number and location of which is dependent upon the number of residues of the anti-microbial peptide, when $R_n$ is glutamic acid or aspartic acid and $R_c$ is lysine, as described in Bednarek et al., *Biochem. Biophys. Res. Corn.* 286(3): 641-645 (2001).

A lactam bridge between an amino terminal anti-microbial peptide residue ($R_n$; e.g., $R^1$ $R^2$ $R^3$ $R^4$) and a carboxy terminal anti-microbial peptide residue ($R_c$, e.g., $R^9$, $R^{10}$ $R^{11}$ $R^{12}$ $R^{13}$ $R^{14}$ $R^{15}$ $R^{16}$ $R^{17}$), the exact number and location of which is dependent upon the number of residues of the anti-microbial peptide, when $R_n$ is succinic acid or o-pthalic acid and $R_c$ is lysine, as described in Bednarek et al., *Biochem. Biophys. Res. Corn.* 286(3): 641-645 (2001) and Kavarana et al., *J. Med. Chem.* 45(12): 2644-2650 (2002).

A lactam bridge between an amino terminal anti-microbial peptide residue ($R_n$; e.g., $R^1$ $R^2$ $R^3$ $R^4$) and a carboxy terminal anti-microbial peptide residue ($R_c$, e.g., $R^9$, $R^{10}$ $R^{11}$ $R^{12}$ $R^{13}$ $R^{14}$ $R^{15}R^{16}$ $R^{17}$) the exact number and location of which is dependent upon the number of residues of the anti-microbial peptide $R^2$ or $R^3$ and $R^7$, when $R_n$ is succinic acid and $R_c$ is 2,3-diamino-propionic acid as described in Bednarek et al., *Biochem. Biophys. Res. Corn.* 286(3): 641-645 (2001).

A "backbone" cyclized peptide is formed by covalent bond formation between the C- and/or N-terminus of a linear peptide of interest. An example of this is described in the bonding of two amide nitrogens via a bridge consisting of alkyl groups and an amide, as described by Hess et al., *J. Med. Chem.* 50: 6201-6211 (2007).

Amino Acids—Isomers and Non-Standard Amino Acids

In one aspect, the amino acid residues, as provided herein for the non-naturally occurring anti-microbial peptide described herein, can be either D- or L-amino acids or can be substituted with their non-standard, isomeric counterparts. For example, α-amino acids can be substituted with β-amino acids, and L-amino acids can be substituted with D-amino acids. An amino acid disclosed herein that is not designated as a D- or L-isomer, can be either isomer. All amino acids are α-amino acids, unless specifically indicated as β-amino acids. A β-amino acid can be either a β$^2$-amino acid or a β$^3$-amino acid, or both β$^2$ and β$^3$ in some cases, unless a specific designation is provided. In other aspects, the amino acid can be an amino acid analog, or a synthetic, or chemically modified amino acid.

Cyclization of the Anti-Microbial Peptide of Formula II or Formula III

In one aspect, the non-naturally occurring anti-microbial peptide represented by Formula II is cyclized. The anti-microbial peptide represented by Formula II or III can be cyclized through a lactam side chain between an amino terminal anti-microbial peptide residue ($R_n$; e.g., $R^1$ $R^2$ $R^3$ $R^4$) and a carboxy terminal anti-microbial peptide residue ($R_c$, e.g., $R^9$, $R^1$ $R^{11}$ $R^{12}$ $R^{13}$ $R^{14}$ $R^{15}$ $R^{16}$, $R^{17}$), the exact number and location of which is dependent upon the number of residues of the anti-microbial peptide, when $R_n$ is aspartic acid and $R_c$ is lysine, as described. See Bednarek et al., *Biochem. Biophys. Res. Corn.* 286(3): 641-645 (2001) and Mayorov et al., *J. Med. Chem.* 49: 1946-1952 (2006).

Anti-Biofilm Peptide Extensions

In some embodiments, the anti-microbial peptides described herein are used in conjunction with a peptide having anti-biofilm activity. In some aspects, the anti-microbial peptides described herein are covalently linked to an anti-biofilm peptide. Biofilms are growths of microorganisms on a surface embedded in an extracellular polymeric substance. Typically, biofilms are formed through quorum sensing and cell-cell communication in response to a myriad of extracellular cues, including nutrient stress and exposure to low doses of antibiotics. These aspects of biofilm formation make them particularly problematic in hospitals resulting in the generation of antibiotic resistant bacterial strains.

Suitable anti-biofilm peptides described herein are cationic peptides that are able to disrupt, reduce, or reverse biofilm formation and growth. In some aspects, the anti-biofilm peptides described herein also possess anti-microbial activity. This secondary anti-microbial activity of the anti-biofilm peptides stems from the presence of duplicate and triplet cationic residues with in the primary peptide sequence. In some aspects, the anti-biofilm peptides described herein only possess anti-biofilm activity and no anti-microbial activity.

In some aspects, the anti-biofilm peptide is represented by Formula IV, as shown below:

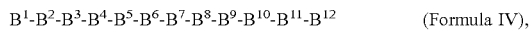

$$B^1\text{-}B^2\text{-}B^3\text{-}B^4\text{-}B^5\text{-}B^6\text{-}B^7\text{-}B^8\text{-}B^9\text{-}B^{10}\text{-}B^{11}\text{-}B^{12} \quad \text{(Formula IV)},$$

wherein each residue corresponding to positions $B^1$, $B^3$, $B^4$, $B^5$, $B^6$, $B^7$, or $B^9$ is any hydrophobic non-aromatic natural or synthetic amino acid (e.g., alanine (Ala), valine (Val), isoleucine (Ile); each residue corresponding to positions $B^2$, $B^8$, $B^{11}$, or $B^{12}$ is any positive natural or synthetic amino acid (e.g., arginine (Arg), histidine (His), lysine (Lys); residue corresponding to position $B^{10}$ is any natural or synthetic aromatic amino acid (e.g., noralanine, 2'-naphthylalanine, tryptophan (Trp), tyrosine (Tyr), or phenylalanine (F). In some aspects, the positive residue for the anti-biofilm peptide described herein is selected to be arginine (Arg). In some aspects, the anti-biofilm peptide described herein comprises the sequence corresponding to positions $B^1\text{-}B^2\text{-}B^3\text{-}B^4\text{-}B^5\text{-}B^6\text{-}B^7\text{-}B^8$ according to Formula IV. In some aspects, the anti-biofilm peptide described herein comprises the sequence corresponding to positions $B^7\text{-}B^8\text{-}B^9\text{-}B^{10}\text{-}B^{11}\text{-}B^{12}$ according to Formula IV. In some aspects, the anti-biofilm peptide described herein comprises the sequence corresponding to positions B $B^1\text{-}B^2\text{-}B^3\text{-}B^4\text{-}B^5\text{-}B^6$ according to Formula IV. In some aspects, the anti-biofilm peptide described herein comprises the sequence corresponding to positions $B^1\text{-}B^2\text{-}B^3\text{-}B^4\text{-}B^5\text{-}B^6\text{-}B^7$ according to Formula IV.

In some aspects, the anti-biofilm peptide is represented by Formula V, as shown below:

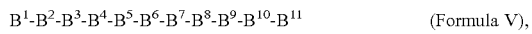

$$B^1\text{-}B^2\text{-}B^3\text{-}B^4\text{-}B^5\text{-}B^6\text{-}B^7\text{-}B^8\text{-}B^9\text{-}B^{10}\text{-}B^{11} \quad \text{(Formula V)},$$

wherein residue corresponding to position $B^{10}$ is any hydrophobic non-aromatic natural or synthetic amino acid (e.g., alanine (Ala), valine (Val), isoleucine (Ile); each residue corresponding to positions $B^1$ $B^2$ $B^4$ $B^5$ $B^8$ $B^9$ $B^{11}$ is any positive natural or synthetic amino acid (e.g., arginine (Arg), histidine (His), lysine (Lys); each residue corresponding to positions $B^3$ $B^6$ $B^7$ is any natural or synthetic aromatic amino acid (e.g., noralanine, 2'-naphthylalanine, tryptophan (Trp), tyrosine (Tyr), or phenylalanine (F). In some aspects, the positive residue for the anti-biofilm peptide described herein is selected to be arginine (Arg). In some aspects, the anti-biofilm peptide described herein comprises the sequence $B^1\text{-}B^2\text{-}B^3\text{-}B^4\text{-}B^5\text{-}B^6\text{-}B^7$ according to Formula V. In some aspects, the anti-biofilm peptide described herein comprises the sequence $B^6\text{-}B^7\text{-}B^8\text{-}B^9\text{-}B^{10}\text{-}B^{11}$ according to Formula V. In some aspects, the anti-biofilm peptide described herein comprises the sequence $B^1\text{-}B^2\text{-}B^3\text{-}B^4\text{-}B^5\text{-}B^6\text{-}B^7\text{-}B^8\text{-}B^9$ according to Formula V. In some aspects, the anti-biofilm peptide described herein comprises residues $B^4\text{-}B^5\text{-}B^6\text{-}B^7\text{-}B^8\text{-}B^9\text{-}B^{10}$ according to Formula V.

In some aspects, the anti-biofilm peptides described herein are linked to an anti-microbial peptide described herein to generate a fusion protein of consisting of an anti-microbial peptide fused to an antimicrobial peptide. In some aspects, the linkage is directly to the amino terminal amino acid of the anti-microbial peptides described herein. In some aspects, the linkage is directly to the carboxy terminal amino acid of the anti-microbial peptides described herein. In some aspects, the linkage is indirectly coupled through linking amino acids between the anti-microbial peptide and anti-biofilm peptides. The anti-biofilm can be on the carboxy terminus or amino terminus of the anti-microbial peptide through indirect coupling with linking amino acids.

In some aspects, the amino acids of the anti-biofilm are modified to prevent cyclization with the anti-microbial peptide during cyclization methods described herein. In some aspects, cyclization of the anti-biofilm peptides described herein with the anti-microbial peptides described herein is prevented by substituting residues that do not form a lactam bridge (e.g., substitution of Arg for Lys). In some aspects, the cyclization of the anti-biofilm peptides described herein with the anti-microbial peptides described herein is prevented by chemically modifying one or more amino terminal amino acids of the anti-microbial peptides described herein. In some aspects, the cyclization of the anti-biofilm peptides described herein with the anti-microbial peptides described herein is prevented by chemically methylating (e.g., adding a CH3 moiety) to one of the amino terminal amino acids of the anti-microbial peptides described herein.

In some aspects, the fusion of the anti-biofilm peptide to an anti-microbial peptide is represented by Formula VI, as shown below:

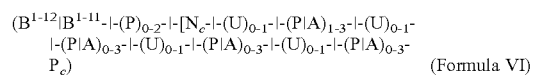

$$(B^{1\text{-}12}|B^{1\text{-}11}\text{-}|\text{-}(P)_{0\text{-}2}\text{-}|\text{-}[N_c\text{-}|\text{-}(U)_{0\text{-}1}\text{-}|\text{-}(P|A)_{1\text{-}3}\text{-}|\text{-}(U)_{0\text{-}1}\text{-}$$
$$|\text{-}(P|A)_{0\text{-}3}\text{-}|\text{-}(U)_{0\text{-}1}\text{-}|\text{-}(P|A)_{0\text{-}3}\text{-}|\text{-}(U)_{0\text{-}1}\text{-}|\text{-}(P|A)_{0\text{-}3}\text{-}$$
$$P_c) \quad \text{(Formula VI)}$$

wherein $B^{1\text{-}12}$ and $B^{1\text{-}11}$ correspond to the anti-biofilm peptide residues of Formula IV and Formula V, respectively; and "P", "U", "N", and "A" represent residues $R^1$ to $R^{17}$ (of Formula I) of the anti-microbial peptide; wherein "N" represents any negative residue; the "$_c$" indicates cyclization between "$_c$" labelled residues; "U" represents any polar uncharged residue (e.g., glutamine; Gln) or a hydrophobic non-aromatic residue (e.g., leucine; Leu); "P" represents any positive residue (e.g., histidine; His, lysine; Lys or arginine; Arg) or proline (Pro), "A" represents any aromatic residue (e.g., noralanine; Nal, 2'-naphthylalanine; Nal(2'), tryptophan; Trp, tyrosine; Tyr, or Phe; F); the symbol "|" indicates the presence of amide bond between an alternative residue or residues; the number of sequential residues is indicated in the adjacent numerical subscript (a 0 indicates no residue is present, a 1 indicates one residue is present with an amide bond with the adjacent residues, a 2 indicates two residues present with an amide bond with the adjacent residues, a 3 indicates three residues present with an amide bond with the adjacent residues). The alternative residues (number 0-3 or 1-3) according to Formula II can further be in any order or number (1-3 residues) as specified (e.g., P-P-P, P-P, P, A-A-A, A-A, A, P-A-A, P-P-A, P-A, A-P-P, A-A-P, A-P, P-A-P, OR A-P-A).

One of ordinary skill in the art would recognize that modifications can be made to the fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

As indicated above, in various embodiments a peptide linker/spacer is used to join the one or more targeting moieties to one or more effector(s). In various embodiments the peptide linker is relatively short, typically less than about 10 amino acids, preferably less than about 8 amino acids and more preferably about 3 to about 5 amino acids. Suitable illustrative linkers include, but are not limited to comprise: Ala-Ala-Ala, Gly-Gly-Gly, Ser-Gly-Gly, Gly-Gly-Ser-Gly-Gly-Ser (SEQ ID NO.: 22), Ser-Ala-Thr, Pro-Trp-Pro, Pro-Ser-Pro-Ser-Pro (SEQ ID NO.: 23), Ala-Ser-Ala, Ala-Ser-Ala-Ser-Ala (SEQ ID NO.: 24), Pro-Ser-Pro-Ser-Pro (SEQ ID NO.: 25), Lys-Lys-Lys-Lys (SEQ ID NO.: 26), Arg-Arg-Arg-Arg (SEQ ID NO.: 27), (Gly4-Ser)$_3$ (SEQ ID NO.: 28), Gly-Gly-Gly-Gly (SEQ ID NO.: 29), Gly-Gly-Gly-Gly-Ser (SEQ ID NO.: 30), (Gly-Gly-Gly-Gly-Ser)$_2$ (SEQ ID NO.: 31), (Gly-Gly-Gly-Gly-Ser)$_4$ (SEQ ID NO.: 32), (Gly-Gly-Gly-Gly-Ser)$_5$ (SEQ ID NO.: 33), (Gly-Gly-Gly-Gly-Ser)$_6$ (SEQ ID NO.: 34), 2-nitrobenzene or O-nitrobenzyl, Nitropyridyl disulfide, Dioleoylphosphatidylethanolamine (DOPE), S-acetylmercaptosuccinic acid, 1,4,7,10-tetraazacyclododecane-1,4,7,10-tetracetic acid (DOTA), β-glucuronide and β-glucuronide variants, Poly(alkylacrylic acid), Benzene-based linkers (for example: 2,5-Bis(hexyloxy)-1,4-bis[2,5-bis(hexyloxy)-4-formyl-phenylenevinylene]benzene) and like molecules, Disulfide linkages, Carbon nanotubes, Hydrazone and hydrazone variant linkers, alkane or alkene groups of any chain length, One or more DNA or RNA nucleotides, including polyamine and polycarboxyl-containing variants, Inulin, sucrose, glucose, or other single, di or polysaccharides, Linoleic acid or other polyunsaturated fatty acids, variants of any of the above linkers containing halogen or thiol groups, or any combination thereof.

In some aspects described herein, the anti-microbial peptides have a structure as indicated in FIG. 1. In one aspect, the anti-microbial peptide (100) is depicted by FIG. 1A. An amino-terminal protective group, as described herein (102) is covalently linked by an amide bond (104) to a cyclized anti-microbial pharmacophore (101) as described herein, which is further linked by an amide bond (104) to a carboxy-terminal protective group, as described herein (103). In another aspect, the anti-microbial peptide structure (200) is depicted by FIG. 1B. An amino terminal anti-biofilm peptide as described herein (105) is covalently linked by an amide (104) bond to a cyclized anti-microbial pharmacophore (101) as described herein, which is further linked by an amide bond (104) to a carboxy-terminal protective group, as described herein (103). In another aspect, the anti-microbial peptide structure (300) is depicted by FIG. 1C. An amino-terminal protective group, as described herein (102) is covalently linked by an amide bond (104) to a cyclized anti-microbial pharmacophore (101) as described herein, which is further linked by an amide bond (104) to a carboxy-terminal anti-biofilm peptide as described herein (105), which is further linked to a carboxy-terminal protective group, as described herein (103). In another aspect, the anti-microbial peptide structure (400) is depicted by FIG. 11). An amino terminal anti-biofilm peptide as described herein (105) is covalently linked by an amide (104) bond to amino acid linkers as described herein, which are covalently linked by an amide bond (104) both to each adjacent linking amino acid and to a cyclized anti-microbial pharmacophore (101) as described herein, which is further linked by an amide bond (104) to a carboxy-terminal protective group, as described herein (103). In another aspect, the anti-microbial peptide structure (500) is depicted by FIG. 1E. An amino-terminal protective group, as described herein (102) is covalently linked by an amide bond (104) to anti-biofilm peptide as described herein (105), which is covalently linked by an amide (104) bond to a cyclized anti-microbial pharmacophore (101) as described herein, which is further linked by an amide bond (104) to a carboxy-terminal protective group, as described herein (103).

Peptide Synthesis

The anti-microbial peptides, anti-biofilm peptides and fusion proteins thereof, described herein may be readily synthesized by any known conventional procedure for the formation of a peptide linkage between amino acids. Such conventional procedures include, for example, any solution phase procedure permitting a condensation between the free alpha amino group of an amino acid or residue thereof having the carboxyl group or other reactive groups protected and the free primary carboxyl group of another amino acid or residue thereof having the amino group or other reactive groups protected. In an exemplary procedure, the peptides described herein may be synthesized by solid-phase synthesis and purified according to methods known in the art. Any of a number of well-known procedures utilizing a variety of resins and reagents may be used to prepare the peptides described herein.

The process for synthesizing the peptides may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide. The resulting peptide is then cyclized to yield a cyclic peptide.

Solid phase peptide synthesis methods are well known and practiced in the art. In such methods, the synthesis of peptides can be carried out by sequentially incorporating the desired amino acid residues one at a time into the growing peptide chain according to the general principles of solid phase methods. These methods are disclosed in numerous references, including Merrifield, *Angew Chem.* 24: 799-810 (1985) and Barany et al., The Peptides, *Analysis, Synthesis and Biology*, Vol. 2, Gross E. and Meienhofer J., Eds. Academic Press, 1-284 (1980).

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting for solid phase synthesis methods and solution phase synthesis methods groups are known to those having ordinary skill in the art.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Fmoc is useful for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf) and Boc. Pmc is a useful protecting group for Arg.

Solid phase synthesis is commenced from the C-terminal end of the peptide by coupling a protected alpha amino acid to a suitable resin. Such starting material is prepared by attaching an alpha amino-protected amino acid by an ester linkage to a p-benzyloxybenzyl alcohol (Wang) resin or a 2-chlorotrityl chloride resin, by an amide bond between an Fmoc-Linker, such as p-[(R, S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Methods for N-terminus modification, such as acetylation, and for C-terminus modification, such as amidation, are known in the art. Similarly, methods for modifying side chains of amino acids are well known to those skilled in the art of peptide synthesis. The choice of modifications made to reactive groups present on the peptide will be determined, in part, by the characteristics that are desired in the peptide.

The peptide can be cyclized prior to cleavage from the peptide resin. For cyclization through reactive side chain moieties, the desired side chains are deprotected, and the peptide suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino) phosphoniumhexafluorophosphate (BOP), benzotriazole-1-yl-oxy-tris(pyrrolidino)phosphoniumhexafluorophosp-hate (PyBOP), 2-(7-aza-1H-benzotriazol-1-yl)-1,1,3,3-tetramethyluronium tetrafluoroborate (TATU), 2-(2-oxo-1 (2H)-pyridyl)-1,1,3,3-tetramethyluronium tetrafluoroborate (TPTU) or N,N'-dicyclohexylcarbodiimide/1-hydroxybenzotriazole (DCCI/HOBt). Coupling is convention initiated by use of a suitable base, such as N,N-diisopropylethylamine (DIPEA), sym-collidine or N-methylmorpholine (NMM).

Following cleavage of peptides from the solid phase following their synthesis, the peptide can be purified by any number of methods, such as reverse phase high performance liquid chromatography (RP-HPLC), using a suitable column, such as a $C_{18}$ column. Other methods of separation or purification, such as methods based on the size or charge of the peptide, can also be employed. Once purified, the peptide can be characterized by any number of methods, such as high performance liquid chromatograph (HPLC), amino acid analysis, mass spectrometry, and the like.

Formulation

The anti-microbial peptides disclosed herein can be used for both medical applications, animal husbandry, veterinary applications, or used in research laboratory settings as a research tool or a diagnostic tool. Typically, the product is used in humans, but may also be used in other mammals. The term "patient" is intended to denote a mammalian individual, and is so used throughout the specification and in the claims. The primary application can involve human patients, but may be applied to laboratory, farm, zoo, wildlife, pet, sport, or other animals.

In general, the anti-microbial peptide described herein may be synthesized by solid-phase synthesis and purified according to methods known in the art. Any of a number of procedures utilizing a variety of resins and reagents may be used to prepare the peptides described herein.

Salt Forms of Peptides

The anti-microbial peptide peptides described herein may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Exemplary salts are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the peptides described herein are basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the peptides described herein are prepared in a suitable solvent from the peptide and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the peptides described herein include an acidic moiety, suitable pharmaceutically acceptable salts may include alkali metal salts, such as sodium or potassium salts, or alkaline earth metal salts, such as calcium or magnesium salts.

Pharmaceutical Compositions

Also described herein are pharmaceutical composition that includes an anti-microbial peptide analog peptide and a pharmaceutically acceptable carrier. The carrier may be a liquid formulation, and can be a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The peptides described herein may be formulated or compounded into pharmaceutical compositions that include at least one peptide together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride, and sodium citrate. For injection or other liquid administration formulations, water containing at least one or more buffering constituents is useful, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide described herein over a period of time.

In general, the actual quantity of peptides administered to a patient will vary between fairly wide ranges depending on the mode of administration, the formulation used, and the response desired.

In practical use, the peptides as disclosed herein can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, ophthalmic, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or nonaqueous techniques. The amount of active peptide in such therapeutically useful compositions is such that an effective dosage will be obtained. In another advantageous dosage unit form, sublingual constructs may be employed, such as sheets, wafers, tablets or the like. The active peptides can also be administered intranasally as, for example, by liquid drops or spray.

The tablets, pills, capsules, and the like may also contain a binder such as gum tragacanth, acacia, cornstarch, or gelatin; excipients such as dicalcium phosphate; a disintegrating agent such as cornstarch, potato starch, or alginic acid; a lubricant such as magnesium stearate; and a sweetening agent such as sucrose, lactose, or saccharin. When a dosage unit form is a capsule, it may contain, in addition to materials of the above type, a liquid carrier such as a polyethylene glycol, a lipid or lipophilic oil, or combination thereof.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl, and propylparabens as preservatives, dyes, and flavorings such as cherry or orange flavor.

Peptides may also be administered parenterally. Solutions or suspensions of these active peptides can be prepared in water suitably mixed with a surfactant such as hydroxypropylcellulose. Dispersions can also be prepared in glycerol, liquid polyethylene glycols and mixtures thereof in oils. These preparations may optionally contain a preservative to prevent the growth of microorganisms.

The pharmaceutical peptides suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

Peptides as disclosed herein may be therapeutically applied by means of nasal administration. "Nasal administration" indicates any form of intranasal administration of any of the peptides described herein. The peptides may be in an aqueous solution, such as a solution including saline, citrate or other common excipients or preservatives. The peptides may also be in a dry or powder formulation.

Alternatively, peptides may be administered directly into the lung. Intrapulmonary administration may be performed by means of a metered dose inhaler, a device allowing self-administration of a metered bolus of a peptide when actuated by a patient during inspiration.

The peptides may be formulated with any of a variety of agents that increase effective nasal or ocular absorption of drugs. These agents should increase nasal absorption without unacceptable damage to the mucosal membrane. U.S. Pat. Nos. 5,693,608; 5,977,070; and 5,908,825, among others, teach a number of pharmaceutical compositions that may be employed, and are incorporated by reference for these teachings.

If in an aqueous solution, peptides may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that the peptide may be in a dried and particulate form. For example, the particles can be between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro milling, spray drying and a quick freeze aerosol followed by lyophilization. With micro-particles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Exemplary devices include dry powder inhalers, designed to form a cloud or aerosol of fine powder with a particle size that is typically less than about 6.0 µm.

Microparticle size, including mean size distribution, may be controlled by means of the method of making. For micro milling, the size of the milling head, speed of the rotor, time of processing and the like control the microparticle size. For spray drying, the nozzle size, flow rate, dryer heat, and the like control the microparticle size. For making by means of quick freeze aerosol followed by lyophilization, the nozzle size, flow rate, concentration of aerosolized solution and the like control the microparticle size. These parameters and others may be employed to control the microparticle size.

The peptides described herein may be therapeutically administered by means of an injection, typically a deep intramuscular injection, such as in the gluteal or deltoid muscle, of a time-release injectable formulation. A peptide may be formulated with a polyethylene glycol, such as polyethylene glycol 3350, and optionally one or more additional excipients and preservatives, including but not limited to excipients such as salts, polysorbate 80, sodium hydroxide, or hydrochloric acid to adjust pH, and the like. A peptide may also be formulated with a poly(ortho ester), which may be an auto-catalyzed poly(ortho ester) with any of a variable percentage of lactic acid in the polymeric backbone, and optionally one or more additional excipients. A poly(D,L-lactide-co-glycolide) polymer (PLGA polymer) may be employed, such as a PLGA polymer with a hydrophilic end group, such as PLGA RG502H from Boehringer Ingelheim, Inc. (Ingelheim, Germany). Such formulations may be made, for example, by combining a peptide in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which may also be adhesive polymers, may be employed in a time-release injectable formulation. The teachings of U.S. Pat. Nos. 4,938,763; 6,432,438; and 6,673,767, and the biodegradable polymers and methods of formulation disclosed therein, are incorporated here by reference. The formulation may be such that an injection is required on a weekly, monthly, or other periodic basis, depending on the concentration and amount of cyclic peptide, the biodegradation rate of the polymer, and other factors known to those of skill in the art.

Routes of Administration

In various aspects, the anti-microbial peptides described herein can be administered using any means known in the art, including orally, rectally, vaginally, ocularly, intranasally, topically, parenterally, or by injection. If administered by injection, the peptide injection may be intravenous (IV), subcutaneous (SC), intramuscular (IM), intraperitoneal (IP), intracerebroventricular (ICV), or other means known in the art. The peptides described herein may be formulated by any means known in the art, including but not limited to formulation as tablets, capsules, caplets, suspensions, powders, lyophilized preparations, suppositories, pessaries, ocular drops, skin patches, orally soluble formulations, enteric formulations, solutions sprays, aerosols and the like, and may be mixed and formulated with buffers, binders, excipients, stabilizers, lubricants, oils, adjuvants, anti-oxidants and other agents known in the art. In general, any route of administration by which the peptides are introduced across an epidermal layer of cells may be employed. Administration includes topical delivery. Administration includes delivery across the blood brain barrier. Administration includes delivery through mucous membranes, buccal administration, ophthalmic administration, oral administration, dermal administration, inhalation administration, nasal administration, urethral administration, vaginal administration, rectal administration, and the like.

Therapeutically Effective Amount

In general, the actual quantity of an anti-microbial peptide administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a peptide or pharmaceutical composition that is sufficient to therapeutically alleviate feeding disorder in a patient, or to prevent or delay onset or recurrence of the feeding disorder, or for the management of the feeding disorder in patients with diseases or syndromes associated with cachexia, including secondary to immune disorders and cancer.

In general, the anti-microbial peptides described herein are highly active. For example, the anti-microbial peptide can be administered at about 0.001 nmol, 0.005 nmol, 0.01 nmol, 0.02 nmol, 0.05 nmol, 0.1 nmol, 0.25 nmol, 0.5 nmol, 1 nmol, 2.5 nmol, 5 nmol, 10 nmol, 20 nmol, 25 nmol, 50 nmol, 100 nmol, 250 nmol, 500 nmol, or 1000 nmol, or even more, depending on the specific peptide selected, the desired therapeutic response, the route of administration, the formulation and other factors known to those of skill in the art.

In other aspects, the compositions are useful for topical administration can be, e.g., creams, lotions, mouthwashes, nasal or ocular drops or aerosol.

In some aspects, an effective dose of the peptide is at least about 0.001 nmol, 0.005 nmol, 0.01 nmol, 0.02 nmol, 0.03 nmol, 0.04 nmol, 0.05 nmol, 0.06 nmol, 0.07 nmol, 0.08 nmol, 0.09 nmol, 0.1 nmol, 0.2 nmol, 0.3 nmol, 0.4 nmol, 0.5 nmol, 0.6 nmol, 0.7 nmol, 0.8 nmol, 0.9 nmol, 1.0 nmol, 1.1 nmol, 1.2 nmol, 1.3 nmol, 1.4 nmol, 1.5 nmol, 1.6 nmol, 1.7 nmol, 1.8 nmol, 1.9 nmol, 2 nmol, 3 nmol, 4 nmol, 5 nmol, 6 nmol, 7 nmol, 8 nmol, 9 nmol, 10 nmol, 11 nmol, 12 nmol, 13 nmol, 14 nmol, 15 nmol, 16 nmol, 17 nmol, 18 nmol, 19 nmol, 20 nmol, 21 nmol, 22 nmol, 23 nmol, 24 nmol, 25 nmol, 26 nmol, 27 nmol, 28 nmol, 29 nmol, 30 nmol, 31 nmol, 32 nmol, 33 nmol, 34 nmol, 35 nmol, 36 nmol, 37 nmol, 38 nmol, 39 nmol, 40 nmol, 41 nmol, 42 nmol, 43 nmol, 44 nmol, 45 nmol, 46 nmol, 47 nmol, 48 nmol, 49 nmol, 50 nmol, 51 nmol, 52 nmol, 53 nmol, 54 nmol, 55 nmol, 56 nmol, 57 nmol, 58 nmol, 59 nmol, 60 nmol, 61 nmol, 62 nmol, 63 nmol, 64 nmol, 65 nmol, 66 nmol, 67 nmol, 68 nmol, 69 nmol, 70 nmol, 61 nmol, 72 nmol, 73 nmol, 74 nmol, 75 nmol, 76 nmol, 77 nmol, 78 nmol, 79 nmol, 80 nmol, 81 nmol, 82 nmol, 83 nmol, 84 nmol, 85 nmol, 86 nmol, 87 nmol, 88 nmol, 89 nmol, 90 nmol, 91 nmol, 92 nmol, 93 nmol, 94 nmol, 95 nmol, 96 nmol, 97 nmol, 98 nmol, 99 nmol, 100 nmol, 110 nmol, 120 nmol, 130 nmol, 140 nmol, 150 nmol, 160 nmol, 170 nmol, 180 nmol, 190 nmol, 200 nmol, 210 nmol, 220 nmol, 230 nmol, 240 nmol, 250 nmol, 260 nmol, 270 nmol, 280 nmol, 290 nmol, 300 nmol, 310 nmol, 320 nmol, 330 nmol, 340 nmol, 350 nmol, 360 nmol, 370 nmol, 380 nmol, 390 nmol, 400 nmol, 410 nmol, 420 nmol, 430 nmol, 440 nmol, 450 nmol, 460 nmol, 470 nmol, 480 nmol, 490 nmol, 500 nmol, 510 nmol, 520 nmol, 530 nmol, 540 nmol, 550 nmol, 660 nmol, 770 nmol, 880 nmol, 990 nmol, 600 nmol, 610 nmol, 620 nmol, 630 nmol, 640 nmol, 650 nmol, 660 nmol, 670 nmol, 680 nmol, 690 nmol, 700 nmol, 710 nmol, 720 nmol, 730 nmol, 740 nmol, 750 nmol, 760 nmol, 770 nmol, 780 nmol, 790 nmol, 800 nmol, 810 nmol, 820 nmol, 830 nmol, 840 nmol, 850 nmol, 860 nmol, 870 nmol, 880 nmol, 890 nmol, 900 nmol, 910 nmol, 920 nmol, 930 nmol, 940 nmol, 950 nmol, 960 nmol, 970 nmol, 980 nmol, 990 nmol, 1000 nmol, or in some aspects, even more.

In some aspects an effective dose of the peptide is at least about 0.001 mg, 0.005 mg, 0.1 mg, 0.2 mg, 0.3 mg, 0.4 mg, 0.5 mg, 6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 61 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 600 mg, 610 mg, 620 mg, 630 mg, 640 mg, 650 mg, 660 mg, 670 mg, 680 mg, 690 mg, 700 mg, 710 mg, 720 mg, 730 mg, 740 mg, 750 mg, 760 mg, 770 mg, 780 mg, 790 mg, 800 mg, 810 mg, 820 mg, 830 mg, 840 mg, 850 mg, 860 mg, 870 mg, 880 mg, 890 mg, 900 mg, 910 mg, 920 mg, 930 mg, 940 mg, 950 mg, 960 mg, 970 mg, 980 mg, 990 mg, 1000 mg, or in some aspects, even more.

In some aspects of the methods described herein, at least one individual dose of the peptide is no more than about 1000 nmol, 990 nmol, 980 nmol, 970 nmol, 960 nmol, 950 nmol, 940 nmol, 930 nmol, 920 nmol, 910 nmol, 900 nmol, 890 nmol, 880 nmol, 870 nmol, 860 nmol, 850 nmol, 840 nmol, 830 nmol, 820 nmol, 810 nmol, 800 nmol, 790 nmol, 780 nmol, 770 nmol, 760 nmol, 750 nmol, 740 nmol, 730 nmol, 720 nmol, 710 nmol, 700 nmol, 690 nmol, 680 nmol, 670 nmol, 660 nmol, 650 nmol, 640 nmol, 630 nmol, 620 nmol, 610 nmol, 600 nmol, 590 nmol, 580 nmol, 570 nmol, 560 nmol, 550 nmol, 540 nmol, 530 nmol, 520 nmol, 510 nmol, 500 nmol, 490 nmol, 480 nmol, 470 nmol, 460 nmol, 450 nmol, 440 nmol, 430 nmol, 420 nmol, 410 nmol, 400 nmol, 390 nmol, 380 nmol, 370 nmol, 360 nmol, 350 nmol, 340 nmol, 330 nmol, 320 nmol, 310 nmol, 300 nmol, 290 nmol, 280 nmol, 270 nmol, 260 nmol, 250 nmol, 240 nmol, 230 nmol, 220 nmol, 210 nmol, 200 nmol, 190 nmol, 180 nmol, 170 nmol, 160 nmol, 150 nmol, 140 nmol, 130 nmol, 120 nmol, 110 nmol, 100 nmol, 99 nmol, 98 nmol, 97 nmol, 96 nmol, 95 nmol, 94 nmol, 93 nmol, 92 nmol, 91 nmol, 90 nmol, 89 nmol, 88 nmol, 87 nmol, 86 nmol, 85 nmol, 84 nmol, 83 nmol, 82 nmol, 81 nmol, 80 nmol, 79 nmol, 78 nmol, 77 nmol, 76 nmol, 75 nmol, 74 nmol, 73 nmol, 72 nmol, 71 nmol, 70 nmol, 69 nmol, 68 nmol, 67 nmol, 66 nmol, 65 nmol, 64 nmol, 63 nmol, 62 nmol, 61 nmol, 60 nmol, 59 nmol, 58 nmol, 57 nmol, 56 nmol, 95 nmol, 54 nmol, 53 nmol, 52 nmol, 51 nmol, 50 nmol, 49 nmol, 48 nmol, 47 nmol, 46 nmol, 45 nmol, 44 nmol, 43 nmol, 42 nmol, 41 nmol, 40 nmol, 39 nmol, 38 nmol, 37 nmol, 36 nmol, 35 nmol, 34 nmol, 33 nmol, 32 nmol, 31 nmol, 30 nmol, 29 nmol, 28 nmol, 27 nmol, 26 nmol, 25 nmol, 24 nmol, 23 nmol, 22 nmol, 21 nmol, 20 nmol, 19 nmol, 18 nmol, 17 nmol, 16 nmol, 15 nmol, 94 nmol, 13 nmol, 12 nmol, 11 nmol, 10 nmol, 9 nmol, 8 nmol, 7 nmol, 6, nmol, 5 nmol, 4 nmol, 3 nmol, 2 nmol, 1 nmol, 0.9 nmol, 0.8 nmol, 0.7 nmol, 0.6 nmol, 0.5 nmol, 0.4 nmol, 0.3 nmol, 0.2 nmol, 0.1 nmol, 0.05 nmol, 0.01 nmol, 0.005 nmol, 0.001 nmol, and even, in some aspects, less than about 0.001 nmol.

In some aspects of the methods described herein, at least one individual dose of the peptide is no more than about 1000 mg, 990 mg, 980 mg, 970 mg, 960 mg, 950 mg, 940 mg, 930 mg, 920 mg, 910 mg, 900 mg, 890 mg, 880 mg, 870 mg, 860 mg, 850 mg, 840 mg, 830 mg, 820 mg, 810 mg, 800 mg, 790 mg, 780 mg, 770 mg, 760 mg, 750 mg, 740 mg, 730 mg, 720 mg, 710 mg, 700 mg, 690 mg, 680 mg, 670 mg, 660 mg, 650 mg, 640 mg, 630 mg, 620 mg, 610 mg, 600 mg, 590 mg, 580 mg, 570 mg, 560 mg, 550 mg, 540 mg, 530 mg, 520 mg, 510 mg, 500 mg, 490 mg, 480 mg, 470 mg, 460 mg, 450 mg, 440 mg, 430 mg, 420 mg, 410 mg, 400 mg, 390 mg, 380 mg, 370 mg, 360 mg, 350 mg, 340 mg, 330 mg, 320 mg, 310 mg, 300 mg, 290 mg, 280 mg, 270 mg, 260 mg, 250 mg, 240 mg, 230 mg, 220 mg, 210 mg, 200 mg, 190 mg, 180 mg, 170 mg, 160 mg, 150 mg, 140 mg, 130 mg, 120 mg, 110 mg, 100 mg, 99 mg, 98 mg, 97 mg, 96 mg, 95 mg, 94 mg, 93 mg, 92 mg, 91 mg, 90 mg, 89 mg, 88 mg, 87 mg, 86 mg, 85 mg, 84 mg, 83 mg, 82 mg, 81 mg, 80 mg, 79 mg, 78 mg, 77 mg, 76 mg, 75 mg, 74 mg, 73 mg, 72 mg, 71 mg, 70 mg, 69 mg, 68 mg, 67 mg, 66 mg, 65 mg, 64 mg, 63 mg, 62 mg, 61 mg, 60 mg, 59 mg, 58 mg, 57 mg, 56 mg, 95 mg, 54 mg, 53 mg, 52 mg, 51 mg, 50 mg, 49 mg, 48 mg, 47 mg, 46 mg, 45 mg, 44 mg, 43 mg, 42 mg, 41 mg, 40 mg, 39 mg, 38 mg, 37 mg, 36 mg, 35 mg, 34 mg, 33 mg, 32 mg, 31 mg, 30 mg, 29 mg, 28 mg, 27 mg, 26 mg, 25 mg, 24 mg, 23 mg, 22 mg, 21 mg, 20 mg, 19 mg, 18 mg, 17 mg, 16 mg, 15 mg, 94 mg, 13 mg, 12 mg, 11 mg, 10 mg, 9 mg, 8 mg, 7 mg, 6, mg, 5 mg, 4 mg, 3 mg, 2 mg, 1 mg, 0.9 mg, 0.8 mg, 0.7 mg, 0.6 mg, 0.5 mg, 0.4 mg, 0.3 mg, 0.2 mg, 0.1 mg, 0.05 mg, 0.01 mg, 0.005 mg, 0.001 mg, and in some aspects, even less.

In some aspects of the methods described herein, an effective dose of the peptide is at least about 0.001 mg/kg body weight to about 10 mg/kg body weight per day.

In some aspects described herein, an effective dose of the peptide is at least about 0.001 mg/kg, 0.005 mg/kg, 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 2.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10.0 mg/kg of body weight per day, or in some aspects, even more.

In some aspects, the peptide is administered by a clinician. In other aspects, the peptide is self-administered. For example, the peptide may be administered in the morning, in the afternoon, or periodically throughout the day. The dose size may be adjusted to account for the frequency and timing of administration of the peptide, and that the daily dosage may, to some degree, be determined by the subject or a clinician based on estimated need, on the delivery system used, and on the presence or absence of other risk factors (e.g., hereditary risk factors or other environmental risk factors such as occupational risk factors and/or exposure to air pollution).

In some aspects, it may be desirable to place an upper limit on single doses and/or daily dosage. Administration devices that limit or modulate self-administration of pulmonary administered pharmaceuticals and other substances in order to prevent possible overdose by the subject are known in the art.

In some aspects of the methods described herein, the peptide may be administered several times a month, several times a week, once each day, or even several times a day. Typically, a therapeutically effective dose is administered once each day. As a non-limiting example, an effective dose may be administered in one or more sessions, such as one portion of a dose is administered in the morning and the remaining portion of a dose is administered in the afternoon.

Dose frequency may be from once daily, twice daily, three times daily, or four times daily, to twice daily, four times daily, six times daily, eight times daily, ten times daily or more than ten times per day. In some aspects, the dose frequency is from once daily to ten times daily, once daily to five times daily, twice daily, or once daily. Frequency of administration may be determined and adjusted over the course of care, and is generally, but not necessarily, based on symptoms and clinical findings.

Therapeutic Uses of Anti-Microbial Peptides

In some aspects, described herein, the anti-microbial peptides described herein useful for preventing weight loss (e.g., through anti-cachexia activity), while further inhibiting infection.

In some aspects, the anti-microbial peptides are useful for the treatment, prophylaxis, or amelioration of any disease or condition, wherein an individual or subject has an altered immune response (e.g., any immunodeficiency, microbial infection, immunosuppresive therapy, or a reduced immune system), or needs to gain body mass or weight from Cachexia. In one aspect, the anti-microbial peptides are useful for the treatment, prophylaxis, or amelioration opportunistic infections stemming from the presence of a primary humoral immune deficiency, multiple myeloma, chronic lymphoid leukemia, human immunodeficiency virus infection (HIV), acquired immunodeficiency syndrome (AIDS), bone marrow transplantation, any solid organ allograft/transplantation, the chronic use of steroids, the chronic or acute use of immunosuppressive regimens (e.g., from a solid organ allograft/transplantation), cancer chemotherapy, lymphoma, glucocorticoid therapy, chronic granulomatous disease, a splenectomy, trauma, sickle cell anema, a congenital deficiency in the complement system.

In some aspects, the anti-microbial peptides are useful for the treatment, prophylaxis, or amelioration of a hospital acquired infection. In one aspect, the anti-microbial peptides are useful in emergency and severe situations and are suitable for the I.V. administration of a patient or subject (e.g., a human) in need thereof.

In some aspects, the anti-microbial peptides described herein are useful for the treatment of a bacterial infection. In some aspects, the anti-microbial peptides described herein are useful for the treatment of a fungal infection. In some aspects, the anti-microbial peptides described herein are useful for the treatment of sepsis stemming from a bacterial infection. In some aspects, the anti-microbial peptides described herein, are useful for the treatment of a gram-negative bacterial infection. In some aspects, the anti-microbial peptides described herein are useful for the treatment of a gram positive bacterial infection. Exemplary non-limiting examples of sepsis-causing microorganisms that can be treated in accordance with the present invention include, but are not limited to, those that cause infections in the lung, abdomen, bloodstream, skin, soft tissue, infections associated with intravascular devices, and respiratory infections. Examples of other pathogenic microorganisms that can be treated include, but are not limited to, Gram-negative bacteria such as *Bacteroides, Fusobacterium, Escherichia, Klebsiella, Salmonella, Shigella, Proteus, Pseudomonas, Vibrio, Legionella, Haemophilus, Bordetella, Brucella, Campylobacter, Neisseria, Branhamella*; Gram-positive bacteria such as *Streptococcus, Staphylococcus, Peptococcus, Bacillus, Listeria, Clostridium, Propionibacteria*; organisms that stain poorly or not at all with Gram's stain such as Mycobacteria, *Treponema, Leptospira, Borrelia, Mycoplasma, Chlamydia, Rickettsia* and *Coxiella*; and fungi such as *Candida, Aspergillosis, Blastomycosis, Coccidioidomycosis, Cryptococcosis, Histoplasmosis, Paracoccidioidomycosis, Sporotrichosis, Zygomycosis.*

Combination Therapies

In some aspects, the peptides described herein may be used in combination with other drugs or agents, particularly in the treatment of cachexia. These other drugs and agents may include agents that induce weight gain, including corticosteroids and progestational agents. Peptides may be used in combination with a therapeutically effective amount of a second weight gain pharmaceutical agent.

Methods for the treatment of cachexia are described herein. The methods include the step of administering to the patient having or at risk of having cachexia a therapeutically effective amount of a peptide in combination with a therapeutically effective amount of another compound that is useful in the treatment of cachexia. The second compound useful for the treatment of cachexia are selected from but not limited to the group consisting of ADP-ribose-polymerase inhibitors, ADP-ribose-transferase inhibitors, NADase inhibitors, nicotinamide benzamide, theophylline, thymine and analogs thereof; omega-3 fatty acids such as alpha-linolenic acid, stearidonic acid, eicosapentaenoic acid (EPA), docosapentaenoic acid, docosahexaenoic acid or mixtures thereof; branched-chain amino acids valine, leucine, isoleucine or mixtures thereof, with or without reduced levels of tryptophan and 5-hydroxytryptophan; antioxidants selected from the group comprising beta-carotene, vitamin C, vitamin E, selenium, or mixtures thereof; L-glutamine, vitamin A, vitamin C, vitamin E, and selenium; quinine derivatives including 3,5,6-trimethyl-2-(3-pyridyl)methyl-1, 4-benzoquinone hydrochloride; interleukin 2; benzaldehyde; 4,6-O-benzylidene-D-glucose; friedelan-3-one; hydrazine sulfate; medroxyprogesterone acetate; beta 2-adrenoceptor agonists; corticosteroids such as dexamethasone; Vitor™; Pro-Stat™; megestrol acetate (Megace™); dronabinol (Marinol™); magestrol acetate (Megace™); thalidomide (Thalidomid™); fluoxymesterone (Halotestin™); pentoxifylline (Trental™); cyproheptadine (Periactin™); metoclopramide (Reglan™); total parenteral nutrition; or other MC4-R antagonists. A second compound useful for the treatment of cachexia is somatropin (Serostim™), an injectable form of human growth hormone.

In some aspects, the anti-microbial peptides described herein are used alone or in combination with another agent for treating, reducing the symptoms of, or onset of an infection in a subject. In some aspects, the anti-microbial peptides described herein are used alone or in combination with another agent for treating, reducing the symptoms of, or onset of an opportunistic infection a subject. In some aspects, the anti-microbial peptides described herein are used alone or in combination with another agent for treating, reducing the symptoms of, or onset of a hospital acquired infection. In some aspects, the anti-microbial peptides described herein are used alone or in combination with another agent that decreases the efficiency of the immune system (e.g., immunosuppressive therapy, steroids, or anti-cancer therapeutics). In some aspects, the anti-microbial peptides described herein are used alone or in combination with another agent for the treatment of a symptom of an underlying condition or ailment (e.g., pain medications, anti-tussives, expectorants, anti-proliferatives, or a combination thereof).

In some aspects, the anti-microbial agents used in combination with the anti-microbial peptides described herein include other anti-microbial agents. Exemplary non-limiting examples of other anti-microbial agents include antibacterial drugs including beta-lactam compounds, such as penicillin, methicillin, nafcillin, oxacillin, cloxacillin, dicloxacillin, ampicillin, ticarcillin, amoxicillin, carbenicillin, and piperacillin; cephalosporins and cephamycins such as cefadroxil, cefazolin, cephalexin, cephalothin, cephapirin, cephradine, cefaclor, cefamandole, cefonicid, cefuroxime, cefprozil, loracarbef, ceforanide, cefoxitin, cefmetazole, cefotetan, cefoperazone, cefotaxime, ceftazidine, ceftizoxime, ceftriaxone, cefixime, cefpodoxime, proxetil, cefdinir, cefditoren, pivoxil, ceftibuten, moxalactam, and cefepime; other beta-lactam drugs such as aztreonam, clavulanic acid, sulbactam, tazobactam, ertapenem, imipenem, and meropenem; other cell wall membrane active agents such as vancomycin, teicoplanin, daptomycin, fosfomycin, bacitracin, and cycloserine; tetracyclines such as tetracycline, chlortetracycline, oxytetracycline, demeclocycline, methacycline, doxycycline, minocycline, and tigecycline; macrolides such as erythromycin, clarithromycin, azithromycin, and telithromycin; aminoglycosides such as streptomycin, neomycin, kanamycin, amikacin, gentamicin, tobramycin, sisomicin, and netilmicin; sulfonamides such as sulfacytine, sulfisoxazole, sulfamethizole, sulfadiazine, sulfamethoxazole, sulfapyridine, and sulfadoxine; fluoroquinolones such as ciprofloxacin, enoxacin, gatifloxacin, gemifloxacin, levofloxacin, lomefloxacin, moxifloxacin, norfloxacin, and ofloxacin; antimycobacterial drugs such as isoniazid, rifampin, rifabutin, rifapentine, pyrazinamide, ethambutol, ethionamide, capreomycin, clofazimine, and dapsone; and miscellaneous antimicrobials such as colistimethate sodium, methenamine hippurate, methenamine mandelate, metronidazole, mupirocin, nitrofurantoin, polymyxin B, clindamycin, chloramphenicol, quinupristin-dalfopristin, linezolid, spectinomycin, trimethoprim, pyrimethamine, and trimethoprim-sulfamethoxazole.

In some aspects, the anti-microbial agents used in combination with the anti-microbial peptides described herein include antifungal agents. Non-limiting examples of antifungal agents include anidulafungin, amphotericin B, butoconazole, butenafine, caspofungin, clotrimazole, econazole, fluconazole, flucytosine griseofulvin, itraconazole, ketoconazole, miconazole, micafungin, naftifine, natamycin, nystatin, oxiconazole, sulconazole, terbinafine, terconazole, tioconazole, tolnaftate, and/or voriconazole.

In some aspects, the anti-microbial agents used in combination with the anti-microbial peptides described herein include oxidizing chemicals suitable to disrupt or destroy cell membranes. For example, some oxidizing chemicals may withdraw electrons from a cell membrane causing it to, for example, become destabilized. Destroying the integrity of cell membranes of, for example, a pathogen may lead to cell death.

In some aspects, the anti-microbial agents used in combination with the anti-microbial peptides described herein include antiseptics and disinfectants. Non-limiting examples of antiseptics and disinfectants include acetic acid, acrisorcin, aluminum acetate, alcohols (e.g., ethanol, isopropanol, benzyl alcohol, phenylethyl alcohol), aldehydes (e.g., formaldehyde, glutaraldehyde), benzoic acid, boric acid, butylparaben, chlorhexidine gluconate, chlorine sodium hypochlorite, hexachlorophene, iodine, povidone-iodine, phenols, oxidizing agents (e.g., hydrogen peroxide), parabens (e.g., butylparaben, ethylparaben, methylparaben, propylparaben), phenylmercuric acetate, phenylmercuric nitrate, potassium permanganate, propylene oxide, pyrithione zinc, and quaternary ammonium (e.g., benzalkonium chloride, cetylpyridinum chloride, benzethonium chloride), nitrofurazone, selenium sulfide, silver nitrate, and silver sulfadiazine.

In some aspects, the anti-microbial agents used in combination with the anti-microbial peptides described herein include antiseptics and disinfectants incorporated into a substrate, or non-fouling polymer at a surface (e.g., a coating of a medical device or catheter) to enhance antimicrobial activity at the surface or be released to provide antimicrobial activity in a desired location. Suitable agents include silver metals, silver salts such as silver sulfadiazine, silver oxide, silver carbonate, silver acetate, silver alginate, silver azide, silver citrate, silver lactate, silver nitrate, silver sulfate, silver chloride, silver thiocyanate, silver-sodium-hydrogen-zirconium phosphate, silver sulfadiazine, silver cyclohexanediacetic acid and disilver 2,5-dichloro-3,6-dihydroxy-2,5-cyclohexadiene-1,4-dione, among others, a bismuth salt such as bismuth nitrate, bismuth citrate or bismuth salicylate among others, a zinc salt, a cerium salt, triclosan, combinations of chlorhexidine free base and chlorhexidine acetate, benzalkonium chloride, citrate, povidoneiodine, parachlorometaxylene, gramicidin, polymixin, norfloxacin, tobramycin, sulfamylon, polyhexamethylene biguanide, alexidine, iodine, rifampicin, miconazole, bacitracin, and minocycline, ciprofloxacin, clindamycin, erythromycin, gentamycin, tetracycline and vancomycin. Additional biguanide compounds which may be used and include poly(hexamethylene biguanide) hydrochloride and chiorhexidine compounds. Chlorhexidine is the term denoting the chemical compound 1,6 bis(N-5-p-chlorophenyl-N1-biguanido)hexane). Chlorhexidine compounds include chiorhexidine free base ("CHX") as well as chlorhexidine salts, such as chlorhexidine diphosphanilate, chlorhexidine digluconate ("CHG"), chlorhexidine diacetate ("CHA"), chlorhexidine dihydrochloride, chlorhexidine dichloride, chlorhexidine dihydroiodide, chlorhexidine diperchlorate, chlorhexidine dinitrate, chiorhexidine sulfate, chiorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chiorhexidine malonate, chlorhexidine succinate, chlorhexidine malate, chlorhexidine tartrate, chlorhexidine dimonoglycolate, chlorhexidine mono-diglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chiorhexidine dimandelate, chiorhexidine di-isophthalate, chiorhexidine di-2-hydroxynapthoate, and chiorhexidine embonate.

In some aspects, the anti-microbial agents used in combination with the anti-microbial peptides described herein can be further combined with antipyretics, analgesics and antiphlogistics (such as indometacin, acetylsalicylic acid, diclofenac sodium, ketoprofen, ibuprofen, mefenamic acid, azulene, phenacetin, isopropyl antipyrine, acetaminophen, bendazac, phenylbutazone, flufenamic acid, acetylsalicylic acid (aspirin), paracetamol, phenazone, sodium salicylate, salicylamide, sazapyrine, and etodolac) opioid analgesics (such as buprenorphine, dextromoramide, dextropropoxyphene, fentanyl, alfentanil, sufentanil, hydromorphone, methadone, morphine, oxycodone, papavereturn, pentazocine, pethidine, phenoperidine, codeine dihydrocodeine) non-selective COX inhibitors such as salicylic acid derivatives, aspirin, sodium salicylate, choline magnesium trisalicylate, salsalate, diflunisal, sulfasalazine and olsalazine). Para-aminophenol derivatives such as acetaminophen. Indole and indene acetic acids such as indomethacin and sulindac. Heteroaryl acetic acids such as tolmetin, diclofenac and ketorolac. Arylpropionic acids such as ibuprofen, naproxen, flurbiprofen, ketoprofen, fenoprofen and oxaprozin. Anthranilic acids (fenamates) such as mefenamic acid and meloxicam. Enolic acids such as the oxicams (piroxicam, meloxicam). Alkanones such as nabumetone. Selective COX-2 Inhibitors (such as diaryl-substituted furanones such as rofecoxib; diaryl-substituted pyrazoles such as celecoxib; indole acetic acids such as etodolac and sulfonanilides such as nimesulide).

In some aspects, the anti-microbial agents used in combination with the anti-microbial peptides described herein can be further combined with examples of anti-inflammatory steroids (such as cortisone, hydrocortisone, prednisone, dexamethasone, methylprednisolone, triamcinolone, beclomethasone, flunisolide, fluticasone proprionate, triamcinolone acetonide, budesonide, loteprednol etabonate, mometasone, aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone and their derivatives); antiulcer drugs (such as ecabet sodium, enprostil, sulpiride, cetraxate hydrochloride, gefarnate, irsogladine maleate, cimetidine, ranitidine hydrochloride, famotidine, nizatidine and roxatidine acetate hydrochloride); coronary vasodilators (such as nifedipine, isosorbide dinitrate, diltiazem hydrochloride, trapidil, dipyridamole, dilazep hydrochloride, verapamil, nicardipine, nicardipine hydrochloride and verapamil hydrochloride); or peripheral vasodilators (such as ifenprodil tartrate, cinepazide maleate, cyclandelate, cinnarizine and pentoxyphylline).

In some aspects, the anti-microbial agents used in combination with the anti-microbial peptides described herein can be further combined with synthetic antimicrobials (such as nalidixic acid, piromidic acid, pipemidic acid trihydrate, enoxacin, cinoxacin, of loxacin, norfloxacin, ciprofloxacin hydrochloride and sulfamethoxazole-trimethoprim); antiviral agents (such as acyclovir, ganciclovir, acyclovir prodrugs, famciclovir, zidovudine, didanosine, stavudine, lamivudine, zalcitabine, saquinavir, indinavir, ritonavir, n-docosanol, tromantadine and idoxuridine).

In some aspects, the anti-microbial agents used in combination with the anti-microbial peptides described herein can be further combined with antitussives (such as tipepidine hibenzate, methylephedrine hydrochloride, codeine phosphate, tranilast, dextromethorphan hydrobromide, dimemorfan phosphate, clobutinol hydrochloride, fominoben hydrochloride, benproperine phosphate, eprazinone hydrochloride, clofedanol hydrochloride, ephedrine hydrochloride, noscapine, pentoxyverine citrate, oxeladin citrate and isoaminyl citrate); expectorants (such as bromhexine hydrochloride, carbocysteine, ethyl cysteine hydrochloride and methylcysteine hydrochloride); bronchodilators (such as theophylline, aminophylline, sodium cromoglicate, procaterol hydrochloride, trimetoquinol hydrochloride, diprophylline, salbutamol sulfate, clorprenaline hydrochloride, formoterol fumarate, orciprenaline sulfate, pirbuterol hydrochloride, hexoprenaline sulfate, bitolterol mesilate, clenbuterol hydrochloride, terbutaline sulfate, malbuterol hydrochloride, fenoterol hydrobromide and methoxyphenamine hydrochloride), cardiotonics (such as dopamine hydrochloride, dobutamine hydrochloride, docarpamine, denopamine, caffeine, digoxin, digitoxin and ubidecarenone); antihistamines (such as chlorpheniramine maleate, clemastine fumarate, mequitazine, alimemazine tartrate, cyproheptadine hydrochloride and bepotastine besilate).

In some aspects, the anti-microbial agents used in combination with the anti-microbial peptides described herein can be further combined with antineoplastic/antiangiogenic (such as acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene hcl, bleomycin sulfate, busulfan, buthionine sulfoximine, BWA 773U82, BW 502U83.HCl, BW 7U85 mesylate, caracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrozole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydroxyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of Bacillus calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

In some aspects, the anti-microbial agents used in combination with the anti-microbial peptides described herein can be further combined with immunosuppressant agents (such as cyclosporine A, mycophenolic acid, tacrolimus, rapamycin, rapamycin analogues, azathioprine, recombinant or monoclonal antibodies to interleukins, T-cells, B-cells and/or their receptors).

In some aspects, the anti-microbial agents used in combination with the anti-microbial peptides described herein can be further combined with antiproliferative agents (such as paclitaxel, actinomycin D, rapamycin, tacrolimus, everolimus, dexamethasone and rapamycin analogues).

In some aspects, the anti-microbial agents used in combination with the anti-microbial peptides described herein can be further combined with local anaesthetics (such as benzocaine, bupivacaine, amethocaine, lignocaine, lidocaine, cocaine, cinchocaine, dibucaine, mepivacaine, prilocaine, etidocaine, veratridine (specific c-fiber blocker) and procaine).

In some aspects, the anti-microbial agents used in combination with the anti-microbial peptides described herein can be further combined with antifungals (such as amorolfine, isoconazole, clotrimazole, econazole, miconazole, nystatin, terbinafine, bifonazole, amphotericin, griseo fluvin, ketoconazole, fluconazole and flucytosine, salicylic acid, fezatione, ticlatone, tolnaftate, triacetin, zinc, pyrithione and sodium pyrithione).

In some aspects, the anti-microbial agents used in combination with the anti-microbial peptides described herein can be further combined with agents/chemicals that block microbial attachment to target cells and/or inhibits entry of infectious pathogens (e.g., sulphated and sulfonated polymers such as PC-515 (carrageenan), Pro-2000, and Dextrin 2 Sulphate); agents which change the condition of the tissue to make it hostile to the pathogen (such as substances which alter mucosal pH (e.g., Buffer Gel and Acidform).

In some aspects, the anti-microbial agents used in combination with the anti-microbial peptides described herein can be further combined with antiretroviral agents (e.g., PMPA gel) that prevent retroviruses from replicating in the cells.

In some aspects, the anti-microbial agents used in combination with the anti-microbial peptides described herein can be further combined with agents that treat or prevent an allergic or immune response and/or cellular proliferation (such as various cytokine inhibitors such as humanized anti-cytokine antibodies, anti-cytokine receptor antibodies, recombinant antagonists, or soluble receptors; various leukotriene modifiers such as zafirlukast, montelukast and zileuton; immunoglobulin E (IgE) inhibitors such as Omalizumab (an anti-IgE monoclonal antibody) and secretory leukocyte protease inhibitor) and SYK Kinase inhibitors).

In some aspects, the anti-microbial agents used in combination with the anti-microbial peptides described herein can be further combined with antibodies and antibody fragments (such as, but are not limited to, therapeutic antibodies include trastuzumab, alemtuzumab, gemtuzumab, rituximab, ibritumomab, tositumomab, edrecolomab, cetuximab, bevacizumab, Ranibizumab, satumomab, pertuzumab, and daclizumab).

In some aspects, the anti-microbial agents used in combination with the anti-microbial peptides described herein can be further combined with steroids (such as glucocorticoids, estrogens and androgens. By way of example, steroids can include dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolone hexacetonide, triamcinolone diacetate, methylprednisolone, methylprednisolone acetate, methylprednisolone sodium succinate, flunisolide, beclomethasone dipropionate, betamethasone sodium phosphate, betamethasone, vetamethasone disodium phosphate, vetamethasone sodium phosphate, betamethasone acetate, betamethasone disodium phosphate, chloroprednisone acetate, corticosterone, desoxycorticosterone, desoxycorticosterone acetate, desoxycorticosterone pivalate, desoximethasone, estradiol, fluorocortisone, fluorocortisone acetate, dichlorisone acetate, fluorohydrocortisone, fluorometholone, fluprednisolone, paramethasone, paramethasone acetate, androsterone, fluoxymesterone, aldosterone, methandrostenolone, methylandrostenediol, methyl testosterone, norethandrolone, testosterone, testosterone enanthate, testosterone propionate, equilenin, equilin, estradiol benzoate, estradiol dipropionate, estriol, estrone, estrone benzoate, acetoxypregnenolone, anagestone acetate, chlormadinone acetate, fluorogestone acetate, hydroxymethylprogesterone, hydroxymethylprogesterone acetate, hydroxyprogesterone, hydroxyprogesterone acetate, hydroxyprogesterone caproate, melengestrol acetate, norethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, hydrocortisone sodium succinate, methylprednisolone sodium succinate, prednisolone phosphate sodium, triamcinolone acetonide, hydroxydione sodium, spironolactone, oxandrolone, oxymetholone, prometholone, testosterone cypionate, testosterone phenylacetate, estradiol cypionate, and norethynodrel, analogs thereof, or combinations thereof).

Additives in Animal Foodstuff

In some aspects described herein, the antimicrobial peptides may be used as animal feed stock additives. In this way, animal feeds will contain one or more of an anti-microbial peptide in an amount effective to increase weight gain and/or feed conversion while also preventing infection by a pathogenic organism. The anti-microbial peptides described herein are not structurally similar to clinically used antibiotics for the treatment of human infection and do not lead to increased antibiotic resistance, thus, representing a new a needed method for controlling microbial growth in animals, while reducing the development of multi-resistant antibiotic bacterial strains from antibiotic use in animals. Hancock, *The Lancet Infectious Diseases* 1(3): 156-164 (2001).

The animal feeds are generally formulated to provide nutrients in accordance with industry standards. The feeds may be formulated from a variety of different feed ingredients, which are chosen according to market price and availability. Accordingly, some components of the feed may change over time. For discussions on animal feed formulations and NRC guidelines, see *Church, Livestock Feeds and Feeding*, O&B Books, Inc., Corvallis Oreg. (1984) and *Feeds and Nutrition Digest*, Ensminger, Oldfield and Heineman eds., Ensminger Publishing Corporation, Clovis, Calif. (1990), each of which is incorporated herein by reference.

Animal feeds are traditionally balanced based upon protein and energy requirements, and then adjusted if needed to meet the other requirements, which will vary for the different stages of growth and maintenance of the animal. Growing young animals will require higher protein feeds, while finishing animals close to market will require higher energy, high carbohydrate, feeds. For example, typical hog pre-starter, starter and grower-finisher feeds will generally contain about 20-24% protein, 18-20% protein, and 13-17% protein respectively. In some feeding situations, care must be taken to provide the appropriate amino acids as well as overall protein content. For example, hogs fed large amounts of corn must have adequate lysine made available in the feed. In most animal diets, energy requirements are met by starches in cereal grains. Energy requirements may also be met by addition of fat to the feed. Animal feeds containing the anti-microbial peptides as described herein may also be formulated for any animal including dogs, cats, poultry, fish, and cattle, hogs, horses, goats, sheep, among others.

Other ingredients may be added to the animal feed in addition to the anti-microbial peptides described herein, as needed to promote the health and growth of the animal. The ingredients include, without limitation, sugars, complex carbohydrates, amino acids (e.g., arginine, histidine, isoleucine, leucine, lysine, methionine, phenylalanine, threonine, tryptophan, valine, tyrosine, alanine, aspartic acid, sodium glutamate, glycine, proline, serine, and cysteine, among others), vitamins (e.g., thiamine, riboflavin, pyridoxine, niacin, niacinamide, inositol, choline chloride, calcium pantothenate, biotin, folic acid, ascorbic acid, and vitamins A, B, K, D, E, among others), minerals, protein (e.g., meat meal, fish meal, liquid or powdered egg, fish solubles, whey protein concentrate), oils (e.g., soybean oil), cornstarch, calcium, inorganic phosphate, copper sulfate, and sodium chloride. Any medicament ingredients known in the art may also be added to the animal feed, including, without limitation, antibiotics and hormones. For vitamin, mineral and antibiotic supplementation of animal feeds see Church, *Livestock Feeds and Feeding*, O&B Books, Inc., Corvallis Oreg. (1984).

Any animal feed blend known in the art can be used in accordance with the present invention, including, without limitation, forages, such as orchard grass, timothy, tall fescue, ryegrass, alfalfa, sainfoin, clovers, and vetches, grain feeds, such as corn, wheat, barley sorghum, triticale, rye, canola, and soya beans, crop residues, cereal grains, legume by-products, and other agricultural by-products. In situations where the resulting feed is to be processed or preserved, the feed may be treated with oxidatively transformed carotenoid or a component thereof before processing or preservation. Desirably, the animal feed of the invention includes rapeseed meal, cottonseed meal, soybean meal, or cornmeal.

Processing may include drying, ensiling, chopping, pelleting, cubing, baling, rolling, tempering, grinding, cracking, popping, extruding, micronizing, roasting, flaking, cooking, and/or exploding. For example, pelleted feed is created by first mixing feed components and then compacting and extruding the feed components through a die with heat and pressure. Animal feeds of the invention can be pelleted as described in, for example, MacBain, Pelleting Animal Feed, American Feed Manufacturers Association, Arlington, Va. (1974) incorporated herein by reference for its teachings thereof.

In some aspects, the one or more antimicrobial peptides supplemented in feed stock decreases acetate and methane production, increases propionate, enhances nitrogen efficiency, improves the digestion of dry matter in ruminants, and improves feeding efficiency. In some aspects, the antimicrobial peptides increase weight gain by its anti-cachexia effects described herein, and increases in feed conversions. In some aspects, weight gain in animals provided with feedstock supplemented with the one or more antimicrobial peptides is increased from about 2% to about 50%, including all integers within the specified range. In some aspects, food consumption by animals provided with feedstock supplemented with the one or more antimicrobial peptides is decreased from about 2% to about 25%, including all integers within the specified range. In some aspects, growth rate of animals provided with feedstock supplemented with the one or more antimicrobial peptides is increased from about 2% to about 25%, including all integers within the specified range.

In some aspects, one or more of the antimicrobial peptides described herein are supplemented with an antibiotic in a feed stock as described herein. In some aspects, one or more of the antimicrobial peptides described herein are supplemented with an ionophore or non-ionophore antibiotic, a phosphoglycolipid antibiotic, or other naturally occurring anti-microbial peptide, or a combination thereof in an animal feed stock. Exemplary non-limiting compounds safe for use in animal feed stocks include bambermycins, lasalocid sodium, monensin sodium, salinomycin, virginiamycin, and zinc bacitracin. In some aspects, the antimicrobial peptides described herein are supplemented in combination with about 6 ppm to about 100 ppm of another antibiotic or antimicrobial.

In some aspects, the use of the anti-microbial peptides described herein synergizes with an antibiotic. In this aspect, there is a reduction in the total amount of antibiotic and anti-microbial peptide required in the feed stock, thereby reducing feedstock cost.

In some aspects, the selection of one or more antimicrobial peptides modifies the growth rate of gram-negative or gram-positive bacteria selectively. The animal gut is made-up of a complex mixture of bacteria and protozoa. Gram negative bacteria are generally considered beneficial since they contribute to the break-down of cellulose into compounds beneficial for animal growth and energy. Gram positive bacteria and protozoa are generally not beneficial since their digestive byproducts are not beneficial to the animal. The gram positive organisms that need to be controlled include *Ruminococcus albus, R. flavefaciens* and *Butyrivibrio fibrisolvens*. Controlling these micro-organisms has the beneficial effect of decreasing fermentation thus allowing more energy nutrients to go to the animal. Controlling the bacterium *Methanobacterium ruminantium* reduces the conversion of $H_2$ to methane gas. Controlling the various species of Streptococci and Lactobacilli also reduce the undesirable use of $H_2$ and allows more to be used in the desirable formation of propionate. Proprionate is largely responsible for animal growth. Isotricha and Entodini are two protozoa which commonly infect the rumin that can also take away energy and nutrients from the farm animal.

In some aspects, the selection of one or more antimicrobial peptides, as described herein decreases the growth of gram-positive bacteria, while not affective the growth of gram-negative bacteria. In some aspects, the selection of one or more antimicrobial peptides, as described herein decreases the growth of gram-negative bacteria, while not affective the growth of gram-positive bacteria. In some aspects, the selection of one or more antimicrobial peptides, as described herein decreases the growth of gram-negative bacteria and gram-positive bacteria.

In some aspects, the anti-microbial peptides, as described herein are useful in foodstuffs and can be in the form of a health bar, preferably supplied in foil or other types of wrappers, as is commonly seen in most food markets, convenience stores, and health food stores. Typically, such health bars are commonly made by a machine extrusion process that extrudes the mixed ingredients into the desired size and shape bar, which is then conveyed to automatic wrapping machinery. Health bars may be baked, rather than extruded.

In some aspects, the anti-microbial peptides, as described herein are useful in other foodstuffs. Exemplary non-limiting foodstuffs may also be extruded, baked, rolled, pressed, cut or otherwise formed into bars or baked goods, such as cookies, brownies, cakes, or muffins. In the manufacturing process for bars that are extruded, ingredients such as glycerine, lecithin, vegetable and other oils (such as sunflower oil) are used in part to help bind ingredients together so as to help form a uniformly shaped bar in the extrusion machinery. Such known processes can be used to produce the health bars and baked goods of the present invention.

In some aspects, the anti-microbial peptides can be in the form of a ready-to-drink beverage, requiring no addition of water and/or mixing with water or other liquids, or a powder or a liquid concentrate that is mixed with water, fruit juice, fruit and/or other flavored drinks, and/or fruit drink concentrates to make, for example, a flavored beverage, or with milk to make a drink having a character similar to that of a milk-shake.

In some aspects, the anti-microbial peptides can be in the form of a therapeutic nutraceutical used for the treatment, reduction in symptoms of, or therapy of a subject. The nutraceutical may be in the form of a tablet or capsule described herein, a ready-to-drink beverage or other liquid, a powder or a liquid concentrate that is mixed with water.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of the claimed embodiments. All of the various embodiments, aspects, and options disclosed herein can be combined in all variations. The scope of the compositions and methods described herein include all actual or potential combinations of embodiments, aspects, options, examples, and preferences herein described. All patents and publications cited herein are entirely incorporated by reference herein for the specific teachings thereof.

EXAMPLES

Example 1

Solution NMR Studies of a Representative Anti-microbial Peptide.

Figure 2:
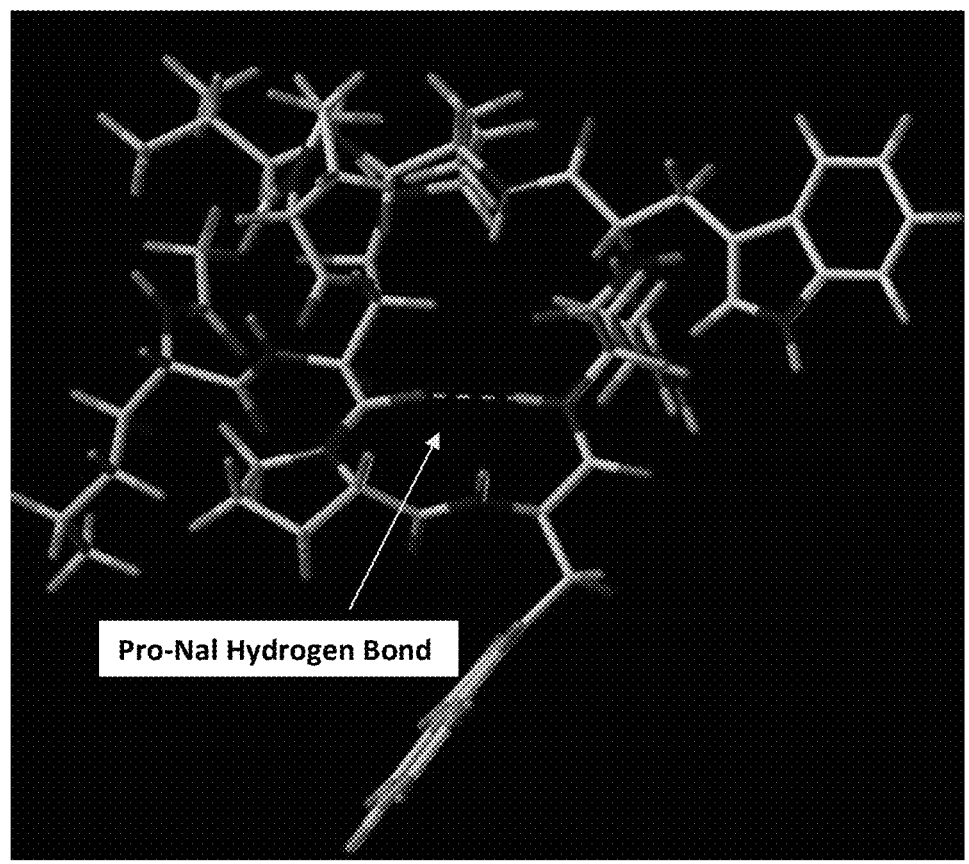
FIG. 2. NMR Imaging of anti-microbial peptide TCAM207 (SEQ NO: 209) (also referenced as TCMCB07).

To understand the importance of the structure of the anti-microbial peptides described herein we performed solution NMR on a representative peptide TCAM207 Ac-Nle-c[Asp-Pro-D-Nal(2')-Arg-Trp-Lys]-D-Val-D-Pro-NH$_2$ (SEQ NO: 209). While initial studies could assign spatial coordinates to the ring, interference from α-hydrogens obscured assignment of the amino acid residue's side-chains. To suppress interference, we replaced the α-hydrogens with deuterium; repeatedly dissolving the peptide in heavy water, followed by lyophilization. The result was an NMR image shown in FIG. 2 where spatial assignment of both ring and side-chains were possible. Computer analysis of the coordinates suggested that the ring is stabilized in a β2 conformation by a hydrogen bond between the adjacent Pro and Nal residues (dashed yellow line in the lower half of the ring). Thus, analysis of products from our platform technology shows the importance of both the C-terminal di-peptide sequence and the secondary structure of the lactam ring for oral activity and blood brain barrier transport.

Example 2

Cationic-Aromatic Peptide Safety in a Large Animal Model

Figure 3:
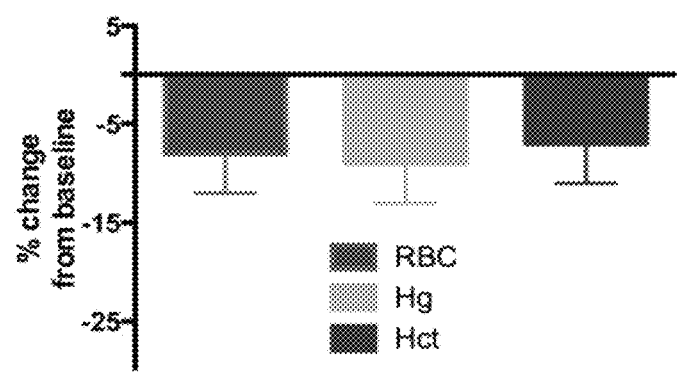
FIG. 3. In vivo safety profiling of anti-microbial peptide TCAM207 (SEQ NO: 209) in a large animal canine model.

We further conducted a preliminary study in a large animal canine model to assess cardiovascular and hematologic safety and clearance of the peptide TCAM207 (SEQ NO: 209) from plasma over a multiple day dosing. Male and female purpose bred beagles were randomized to treatment and instrumented with Holter 9 lead electrocardiograph (ECG) jackets and non-invasive oscillographic paw blood pressure monitoring (emkaPAC 4G telemetry). ECG and BP signals were sampled at 500 Hz using GLP compliant software (IOX, EMKA). ECG signals were saved continuously and blood pressure determined hourly. Blood samples were taken before and after 14 days of SC or oral drug administration for complete chemistry panel and CBC analysis. Samples were taken 1, 2, 4, 8, 12, and 24 hours after drug administration on days 1 and 5 for assay of plasma IIP to assess PK profile. After a 1-2 week washout, dogs were randomized to the other arm of the study. FIG. 3 shows the change in red blood cell (RBC) count, hemoglobin (Hg), and hematocrit (Hct) produced by 5 days of 5× therapeutic dose of TCMCB07 in normal beagles (n=4). While there were slight (statistically insignificant) decreases in all parameters, no RBC casts were noted. These small attributes decreases in the blood parameters are likely attributable to the amount of blood drawn during this PK study.

Example 2

Blood concentration of orally-administered Anti-microbial peptide TCAM207 (SEQ NO: 209) in Canines.

Figure 4:
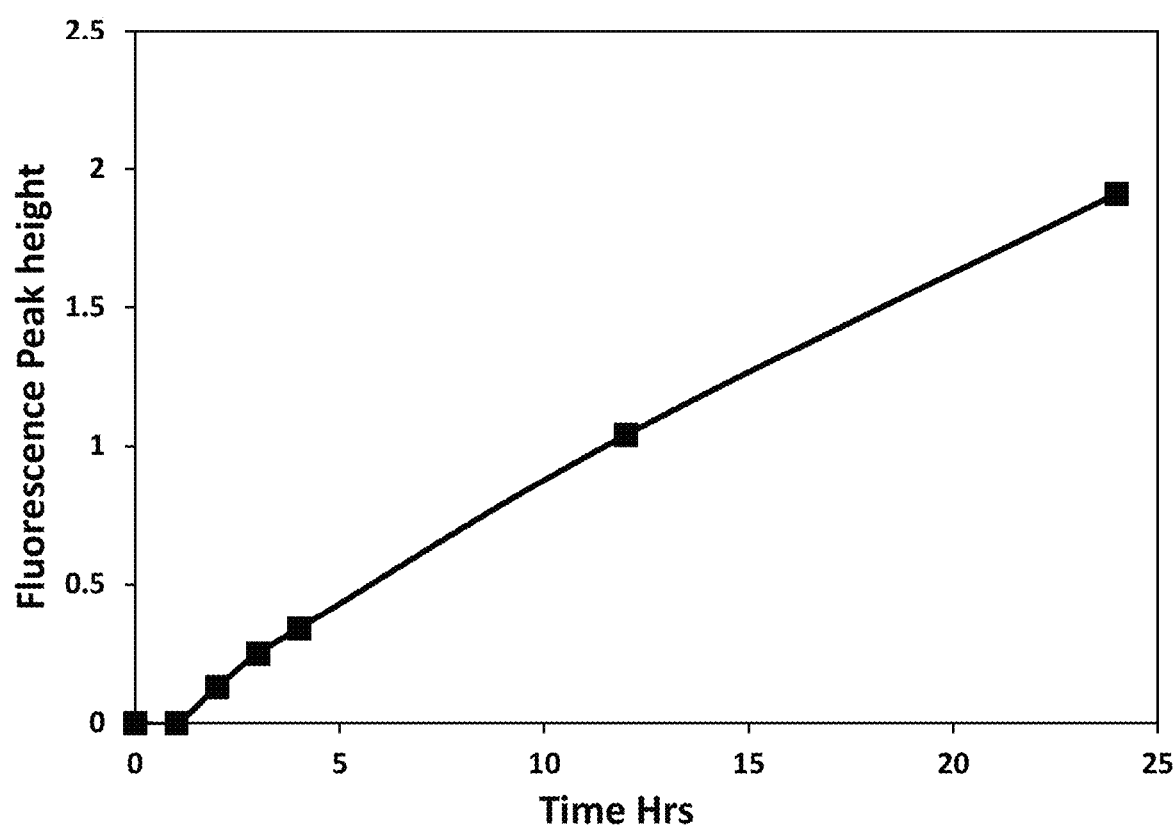
FIG. 4. Blood plasma concentration of orally administered anti-microbial peptide TCAM207 (SEQ NO: 209) in canines.

The concentration of anti-microbial peptide TCAM207 (SEQ NO: 209) was subsequently tested in canines (beagles) to determine stability of the peptides orally. As shown in FIG. 4, peptides were stable and remained in the plasma for up to 24 hrs.

Example 3

Selective Anti-microbial Activity of the Anti-microbial peptides to Gram-positive or Gram-negative Bacteria.

An emerging problem in the treatment of infectious diseases is biofilms (Sanchez C J, Jr., et al. Biofilm formation by clinical isolates and the implications in chronic infections. BMC infectious diseases. 2013; 13:47. PMCID: 3568419, PMID 23356488; and Dean S N, et al., Natural and synthetic cathelicidin peptides with anti-microbial and anti-biofilm activity against *Staphylococcus aureus*. BMC microbiology. 2011; 11:114. PMCID: 3397408, PMID 21605457). Bacteria and fungi can assume a planktonic or free swimming phenotype, or they can exist as part of a colony (typically attached to a surface): a biofilm. A colony of bacteria in a biofilm are surrounded by an exopolysaccharide matrix for protection. Biofilms are found in 60-80% of chronic hospital-associated infections: A biofilm allows infections to "escape" virtually any therapeutic agent (Van Acker H, et al., Molecular mechanisms of antimicrobial tolerance and resistance in bacterial and fungal biofilms. Trends in microbiology. 2014; 22(6):326-33, PMID 24598086). There is evidence that development of antibiotic-resistant strains of bacteria enhances biofilm production (Burmolle M, et al., Enhanced biofilm formation and increased resistance to antimicrobial agents and bacterial invasion are caused by synergistic interactions in multispecies biofilms. Applied and environmental microbiology. 2006; 72(6):3916-23. PMCID: 1489630, PMID 16751497).

Because there are both antimicrobial peptides (Dathe M, et al., Biochemistry. 2004; 43(28):9140-50, PMID 15248771; and Strom M B, et al., Journal of peptide science: an official publication of the European Peptide Society. 2002; 8(8):431-7, PMID 12212806) and antibiofilm peptides (Dean S N, et al., BMC microbiology. 2011; 11:114. PMCID: 3397408, PMID 21605457; and de la Fuente-Nunez C, et al., 2014; 10(5):e1004152. PMCID: 4031209, PMID 24852171), we developed a hybrid peptide that combines the activities of both these classes of peptides: an anti-biofilm/anti-microbial peptide, AB01: Ac-FRIRVRV-c[Asp-RR-dNal(21-FWR-Lys]-dVal-dPro-CONH$_2$.

Further, a set of the anti-microbial peptides described herein were tested for their anti-microbial activity on both Gram-positive and Gram-negative bacteria. All five of the tested anti-microbial peptides demonstrated substantial observable cell agglutination effects and non-membrane activity as outlined in Table 1. Unexpectedly, it was further observed that the C-terminal residues (denoted by bold font) selectively target gram-negative or gram-positive bacteria, as indicated.

TABLE 1

Optimization selective anti-microbial activity of peptide TCAM207 (SEQ NO: 209):
Ac-Nle$^1$c[Asp$^2$-Pro$^3$-D-Nal(2')$^4$-Arg$^5$-Trp$^6$-Lys$^7$]-D-Val$^8$-D-Pro$^9$-NH$_2$

| Amino Acid Addition/Substitution$^\#$ | IC$_{50}$, *E. coli*; μg/mL | IC50 *B. subtilis* μg/mL | Membrane Disruption? | Non-Membrane Activity? |
| --- | --- | --- | --- | --- |
| Asp$^2$-Arg-Pro$^3$ & D-Nal(2')$^6$ (Opt 1) | 5.3 | 0.7 | Yes, and Agglutination | Septum inhibition, protein aggregation |
| Asp$^2$-Arg-Pro$^3$ & D-Nal(2')$^6$-Arg-Lys$^7$ (Opt 2) | 2.6 | 0.7 | Yes, and Agglutination | Septum inhibition, protein aggregation |
| Asp$^2$-Arg-Pro$^3$ & D-Phe$^8$-dVal$^9$ (Opt 3) | 0.7 | 10.4 | Yes, and Agglutination | None observed |
| Asp$^2$-Arg-Pro$^3$ & Phe$^8$-Val$^9$ (Opt 4) | 0.7 | 10.4 | Yes, and Agglutination | Septum inhibition, protein aggregation |
| Asp$^2$-Arg-Pro$^3$ & Val$^8$-Phe$^9$ (Opt 5) | 1.3 | 20.8 | Yes, and Agglutination | Altered cell division, nonspecific |
| Melittin (Control) | 0.7 | 20.8 | Yes | None observed |

Exemplary, non-limiting representations of hybrid peptides having anti-microbial, anti-biofilm, or anti-microbial and anti-biofilm activity from the embodiments and aspects described herein are shown in Table 1 above.

A hybrid peptide was produced that combines an AMP (anti-microbial peptide) with an anti-biofilm peptide that also has anti-microbial activity. To this construct, a newly discovered series of C-terminal di-peptides was added that direct AMP anti-microbial activity to either Gram-positive or Gram-negative organisms. This produced a peptide with a micro molar MIC (anti-microbial activity) against planktonic bacteria, and the ability to disrupt bacterial adhesion in a biofilm. Concerns regarding potential hemolytic actions of AMPs were addressed in a 28-day canine administration study, showing no effects on hematocrit, RBC count, or reticulocytosis at 3× the dose required for μM blood levels.

Table 1 shows the first series of AMPs. Core sequences were cyclized to enhance druggability and anti-microbial activity. Multiple cationic residues increased binding to anionic membrane and intracellular structures. Naphthylalanine (Nal) and proline are residues that also enhanced anti-microbial activity. The C-terminal di-peptides in these AMPs were used for their ability to enhance oral activity in peptides. It was discovered that they also directed relative anti-microbial activity towards either Gram-positive or negative organisms (Table 1 and FIG. 5). These AMPs appear to have multiple mechanisms of action (Table 1), potentially mediated by specific binding to the bacterial membrane, and their intracellular accumulation (data not shown). In essence, these AMPs are a form of combination therapy.

Table 1 depicts a series of derivatives of an orally active AMP. Anti-microbial activity is reported as the concentration needed to inhibit 50% of bacterial division (ICso, a standard used in the AMP field). Opt 1 & Opt 2 have a Val-Pro C-terminal di-peptide and are relatively specific for *B. subtilis*, a Gram-positive organism. In contrast, Opt 3-5 have a Phe for Pro substitution in the C-terminal di-peptide, which produces relatively specificity for Gram-negative organisms (e.g. *E. coli*). Melittin is a cationic-hydrophobic AMP that served as anti-microbial positive control. Agglutination, an attribute assisting in the clearance of bacterial cells during infection, was assessed via microscopy, and was present with all five AMPs.

A second series of cationic-aromatic AMPs was designed, and linked (via the N-terminus) to linear anti-biofilm peptides. This created a hybrid anti-biofilm/AMP (AB01), with a Gram-positive specific C-terminal di-peptide (dVal-dPro). A model Gram positive organism that rapidly forms biofilms (*M. smegmatis*; Ojha, A. and G. F. Hatfull, The role of iron in *Mycobacterium smegmatis* biofilm formation: the exochelin siderophore is essential in limiting iron conditions for biofilm formation but not for planktonic growth. Mol Microbiol, 2007. 66(2): p. 468-83) was used to assess the inhibition of adhesion/anti-biofilm activity of AB01 & two control AMPs, using a 2 day old biofilm. AB01 was ~100-fold more potent than Model 01; a previously described AMP (Liu, Z., et al., Length effects in antimicrobial peptides of the (RW)n series. Antimicrob Agents Chemother, 2007. 51(2): p. 597-603) (FIG. 6). AB01 uses the technology of U.S. Pat. No. 8,541,545 that results in enhanced in vivo half-life (4-6 hours), oral activity, and blood-brain-barrier transport. In addition, AB01 had an MIC (minimum inhibitory concentration) against Gram-positive bacteria of 5 μM, and 25 μM for *E. coli* (a Gram-negative organism). When incubated with Gram-positive bacteria, AB01 was found in the cytoplasm, because it was released by sonication, concurrent with DNA release. This is similar to the AMPs reported in Table 6.

Figure 5:
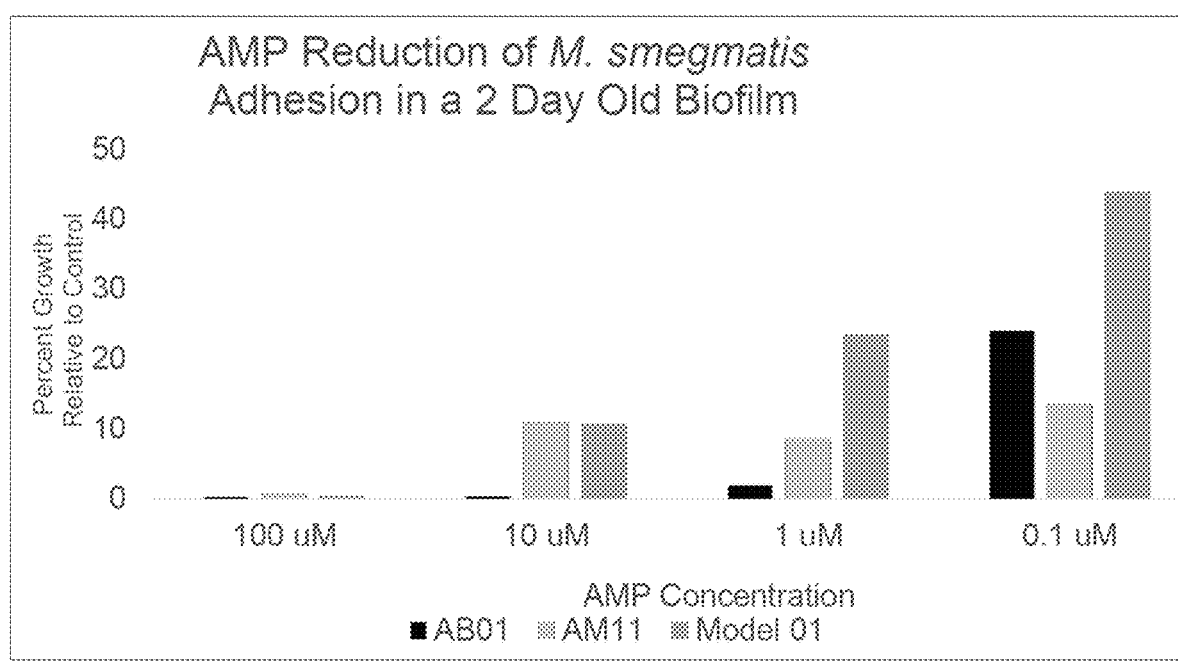
FIG. 5. Graphic representation of AMP reduction of *M. smegmatis* adhesion in a 2-day old biofilm.

The effect of three AMPs on *M. smegmatis* adhesion was measured on day 0 (data not shown) & after 2 days of biofilm growth, counting crystal violet-positive cells (FIG. 5; see O'Toole, G. A., *Microtiter dish biofilm formation assay*. J Vis Exp, 2011(47)). Control bacterial adhesion was designated as 100%, and the effect of an added AMP on the cell count was quantified as a percent of the control. The AMPs included Model 01, an AMP of the $(RW)_n$ series, $(RW)_4$: [17]; AM11, a cyclized analog of the $(RW)_n$ series $_c(RW)_3$; and AB01, a hybrid of a cyclized AMP and a linear anti-biofilm peptide. While 10 μM Model-01 prevented adhesion on day 0, ≥100 μM was needed to prevent adhesion in a 2 day old biofilm. In contrast, AB01 prevented adhesion at 1 μM on day 0 and at 3-5 μM in a 2 day old biofilm.

Example 4

Naturally Occurring Anti-Microbial Pharmacophores

Known naturally occurring anti-microbial pharmacophores that can be artifically modified are show in Table 2 below.

TABLE 2

| Naturally Occurring Anti-microbial Pharmacophores | | |
|---|---|---|
| Melanocortin | His-Phe-Arg-Trp | SEQ ID NO.: 1 |
| Lactoferrin | Arg-Arg-Trp-Gln-Gln-Arg | SEQ ID NO.: 2 |
| Polyphemusin | Arg-Arg-Trp-Cys-Arg | SEQ ID NO.: 3 |
| Tachyplesin | Arg-Trp-Cys-Phe-Arg | SEQ ID NO.: 4 |
| Protegrin | Tyr-Cys-Arg-Arg-Phe | SEQ ID NO.: 5 |
| Defensin | Ala-Cys-Arg-Arg-Arg-Phe | SEQ ID NO.: 6 |
| Other Natural | Arg-Arg-Trp-Trp-Arg | SEQ ID NO.: 7 |

Example 5

Peptides that have Blood Brain Barrier Transport and/or Oral Activity

Known peptides having blood brain barrier transport and/or oral activity are show in Table 3 below.

TABLE 3

| Peptides that have blood brain barrier transport and/or oral activity | | |
|---|---|---|
| Vasopressin | c[Cys-Tr-Phe-Gln-Asn-Cys]-Pro-Arg-Gly-$NH_2$ | SEQ ID NO.: 35 |
| Neurotensin Analog | $N^\alpha Arg^{Me}$-Lys-Pro-Trp-Tle-Leu | SEQ ID NO.: 36 |
| Model Cyclic Peptide | c[Phe(C3)-Gly-Gly-Gly-Gly-Phe]-$NH_2$ | SEQ ID NO.: 37 |
| MC cyclic Analog | c[CO-$(CH_2)_2$-CO-Phe-D-Phe-Arg-Trp-N-$(CH_2)_2$-NH]-$CH_2$CO-$NH_2$ | |
| PG932 | Ac-Nle-c[Asp-Pro-D-Nal2'-Arg-Trp]-Pro-Val-$NH_2$ | |

Example 6

Anti-Biofilm Peptides

Exemplary Anti-biofilm peptide sequences that can be used for preventing or reducing the viability of a microbial biofilm are shown in Table 4 below.

TABLE 4

Anti-biofilm Peptide Sequences

| SEQ NO | Peptide | Peptide Sequence |
|---|---|---|
| SEQ ID NO.: 8 | 1018 | Val-Arg-Leu-Ile-Val-Ala-Val-Arg-Ile-Trp-Arg-Arg |
| SEQ ID NO.: 9 | ATRA1 | Lys-Lys-Phe-Lys-Lys-Phe-Phe-Lys-Lys-Leu-Lys |
| SEQ ID NO.: 10 | ATRA1Arg | Arg-Arg-Phe-Arg-Arg-Phe-Phe-Arg-Arg-Leu-Arg |
| SEQ ID NO.: 11 | ABF1 | Val-Arg-Leu-Ile-Val-Ala-Val-Arg |
| SEQ ID NO.: 12 | ABF2 | Val-Arg-Ile-Trp-Arg-Arg |
| SEQ ID NO.: 13 | ABF3 | Val-Arg-Leu-Ile-Val-Ala |
| SEQ ID NO.: 14 | ABF4 | Lys-Lys-Phe-Lys-Lys-Phe-Phe |
| SEQ ID NO.: 15 | ABF4Arg | Arg-Arg-Phe-Arg-Arg-Phe-Phe |
| SEQ ID NO.: 16 | ABF5 | Phe-Phe-Lys-Lys-Leu-Lys |
| SEQ ID NO.: 17 | ABF5Arg | Phe-Phe-Arg-Arg-Leu-Arg |
| SEQ ID NO.: 18 | ABF6 | Lys-Lys-Phe-Lys-Lys-Phe-Phe-Lys-Lys |
| SEQ ID NO.: 19 | ABF6Arg | Arg-Arg-Phe-Arg-Arg-Phe-Phe-Arg-Arg |
| SEQ ID NO.: 20 | ABF7 | Lys-Lys-Phe-Phe-Lys-Lys-Leu-Lys |
| SEQ ID NO.: 21 | ABF7ARG | Arg-Arg-Phe-Phe-Arg-Arg-Leu-Arg |

Example 7 Exemplary Testing of Antimicrobial Activity Through MIC Determination Bacteria MIC can be determined by using a standard 96 well plate assay with serial dilutions of AMP peptides will be performed as previously described targeting the nosocomial pathogens *Staphylococcus aureus* USA100 and *Klebsiella pneumoniae* KPPR1. Hicks et al., *Bioorganic & Medicinal Chemistry* 21(1): 205-214 (2013). The MIC can be determined using standard methods, using the lowest dilution of peptide without significant growth above the original inoculum. In the case of bacteriostatic effects, the $IC_{50}$ (effective concentration for 50% inhibition of growth) and MIC can be determined. Direct bacteriocidal effects can further be assayed by observation of a loss in $OD_{595}$ from original inoculum readings (P<0.05, t-test).

The determination of the timing of the killing or inhibition of bacteria with AMPs, can be repeated and modified from the above assay with the following modification. Overnight cultures are resuspended in sterile PBS, and seeded into wells with peptides and PBS. In addition, BacLight Live/Dead Viability Staining dyes (Life Technologies) are used as an additional measure of bacterial viability. This kit contains Syto9, a nucleic acid dye that readily penetrates the cells and stains the DNA. Additionally, this kit contains propidium iodide (PI) that will only penetrate disrupted membranes, and will dye the nucleic acids.

Example 8 Exemplary Testing Protocols to Determine the Anti-Microbial Peptide Mode of Action Anti-microbial peptides can have activity through membrane disruption, internally through DNA/RNA synthesis inhibition, septum inhibition, or combinations thereof. Brogden, *Nature Reviews Microbiology* 3(3): 238-250 (2005). To determine preliminary mode of action analysis, *Staphylococcus aureus* USA100 and *Klebsiella pneumoniae* KPPR1 bacteria will be subjected to treatment at different concentrations of anti-microbial peptides, and subjected to the following analyses.

(1) Microscopy. Bacteria can be treated with dilutions of AMPs were directly analyzed via microscopy for membrane disruption phenotypes, including cell agglutination, cell lysis, and cell elongation/septum disruption. Cells can be also monitored for septum inhibition and elongation through use of the membrane dye FM5-95 and DAPI. Additionally the cells can be imaged and stained with the Life Technologies LIVE/DEAD® BacLight™ Bacterial Viability Kit For killing kinetics of the anti-microbial peptides.

(2) Agglutination and Protein Aggregation. Using the antimicrobial 96 well assay described above, imaging of the 96 well plate and can provide a method for the determination of the MAC (minimum agglutination concentration) for the bacteria, as described. Torrent et al., *PLoS Pathogens* 8(11): e1003005 (2012).

(3) Penetration of the AMPs into the cell. Penetration and localization can be determined via biotinylation of the AMPs prior to treatment. Exemplary treatments of the peptides with biotin and treatment is as follows: Cell cultures of *Staphylococcus/Klebsiella* are subjected to biotinylated AMP for 1 hour. After the one hour, the culture is evenly split into two smaller cultures. For the first culture, the cells are washed, and analyzed via a Biotin Quantitative HABA-Avidin Premix Kit (ThermoSci) giving a quantitative analysis of the exposed biotin. For the second tube, the cells are lysed via 2% Sarkosyl and vortexed, and the assay repeated as above to determine total biotin. The ratio of #2 minus #1 is representative of the intracellular concentration of the peptide. The positive control was a known amount of biotin added to a control reaction, the negative controls were cells without AMP added.

(4) Visualization of the penetration of the AMPs. The AMPs can be fluorescein or Alexa Fluor 488 tagged at their N- or C-termini and delivered to the cells and treated with the membrane dye FM5-95. The presence of fluorescein/

Alexa Fluor 488 and localization within the cells is indicative of the internalization of the peptides.

(5) RNA synthesis and Protein synthesis inhibition can be determined with exemplary bacterial lines, such as, *Staphylococcus aureus*, USA100 and *Klebsiella pneumoniae* KPPR1 strains. These strains can be created to constitutively express an unstable GFP variant under a housekeeping gene as previously described. Anderson et al., *Trends in Ecology & Evolution* 13(11): 444-449 (1998); Barysheva et al., *Microbiology* 154(4): 1015-1025 (2008). The expressing cells can be treated for 1 hour with sublethal doses of anti-microbial peptides, and the fluorescence of the cells can be compared to that of an untreated culture via fluorescence microscopy or flow cytometry to determine effects on RNA synthesis or Protein synthesis.

(6) Protein Synthesis. Inducible β-galactosidase expression constructs can be utilized for the quantitation of de novo protein synthesis in *S. aureus*. Rosey et al., *Journal of Bacteriology* 173(19): 5992-5998 (1991); Oskouian et al., *Journal of Bacteriology* 172(7): 3804-3812 (1990). Thus, this model can be utilized to determine protein synthesis inhibition responses to the anti-microbial peptides by detecting the amount of β-galactosidase activity compared to a normalized untreated control (normalized to live cell number).

(7) Hemolysis. Because anti-microbial peptides can act as cell membrane disrupters, a potential "toxic" effect is hemolysis (i.e., a narrow hemolytic therapeutic window). Thus, it is necessary to measure an AMP drug candidate's hemolytic therapeutic index to insure an adequate margin of safety. These assays can be performed in phosphate-buffered saline (PBS) w/wo 10% fetal bovine serum and human RBCs, as previously described for AMP development. Fernandez-Lopez et al., *Nature* 412(6845): 452-455 (2001). Peptide concentrations will be 1-1000 mg. Hemolysis will be assessed with a hemocytometer, using PBS and Triton X-100 as negative and positive controls for zero and 100% hemolysis. An acceptable index for an Anti-microbial peptide should be equivalent to the negative control at a concentration of 5× the proposed in vivo therapeutic dose (therapeutic index=5). In support of the potential safety of cationic-aromatic AMPs, cationic-aromatic peptides (e.g., MCs) have been used clinically, with no evidence of hemolytic activity. Safarinejad, *J. Sex Med.* 5(4): 887-897 (2008).

Example 9

Exemplary non-limiting representations of peptides having anti-microbial, anti-biofilm, or anti-microbial and anti-biofilm activity from the embodiments and aspects described herein are shown in Table 5 below.

TABLE 5

Exemplary Anti-microbial peptides

| SEQ NO: | Peptide | Peptide Sequence |
|---|---|---|
| 22 | TCAM020 | Ac-Nle-c[Asp-Pro-Arg-Arg-Trp-Trp-Arg-Phe-Lys]-D-Val-D-Pro-NH2 |
| 23 | TCAM021 | Ac-Nle-c[Asp-Pro-Arg-Arg-Trp-Trp-Arg-Phe-Lys]-D-Val-D-Phe-NH2 |
| 24 | TCAM022 | Ac-Nle-c[Asp-Pro-Arg-Arg-Trp-Trp-Arg-Phe-Lys]-D-Pro-D-Val-NH2 |
| 25 | TCAM023 | Ac-Nle-c[Asp-Pro-Arg-Arg-Trp-Trp-Arg-Phe-Lys]-D-Phe-D-Val-NH2 |
| 26 | TCAM024 | Ac-Nle-c[Asp-Pro-Arg-Arg-Trp-Trp-Tyr-Phe-Lys]-D-Val-D-Pro-NH2 |
| 27 | TCAM025 | Ac-Nle-c[Asp-Pro-Arg-Arg-Trp-Trp-Tyr-Phe-Lys]-D-Val-D-Phe-NH2 |
| 28 | TCAM026 | Ac-Nle-c[Asp-Pro-Arg-Arg-Trp-Trp-Tyr-Phe-Lys]-D-Pro-D-Val-NH2 |
| 29 | TCAM027 | Ac-Nle-c[Asp-Pro-Arg-Arg-Trp-Trp-Tyr-Phe-Lys]-D-Phe-D-Val-NH2 |
| 30 | TCAM028 | Ac-Nle-c[Asp-Pro-Arg-Arg-Tyr-Tyr-Arg-Phe-Lys]-D-Val-D-Pro-NH2 |
| 31 | TCAM029 | Ac-Nle-c[Asp-Pro-Arg-Arg-Tyr-Tyr-Arg-Phe-Lys]-D-Val-D-Phe-NH2 |
| 32 | TCAM030 | Ac-Nle-c[Asp-Pro-Arg-Arg-Tyr-Tyr-Arg-Phe-Lys]-D-Pro-D-Val-NH2 |
| 33 | TCAM031 | Ac-Nle-c[Asp-Pro-Arg-Arg-Tyr-Tyr-Arg-Phe-Lys]-D-Phe-D-Val-NH2 |
| 34 | TCAM032 | Ac-Nle-c[Asp-Pro-Arg-Arg-Nal-Nal-Arg-Phe-Lys]-D-Val-D-Pro-NH2 |
| 35 | TCAM033 | Ac-Nle-c[Asp-Pro-Arg-Arg-Nal-Nal-Arg-Phe-Lys]-D-Val-D-Phe-NH2 |
| 36 | TCAM034 | Ac-Nle-c[Asp-Pro-Arg-Arg-Nal-Nal-Arg-Phe-Lys]-D-Pro-D-Val-NH2 |
| 37 | TCAM035 | Ac-Nle-c[Asp-Pro-Arg-Arg-Nal-Nal-Arg-Phe-Lys]-D-Phe-D-Val-NH2 |
| 38 | TCAM036 | Ac-Nle-c[Asp-Pro-Arg-Arg-Leu-Trp-Leu-Trp-Lys]-D-Val-D-Pro-NH2 |
| 39 | TCAM037 | Ac-Nle-c[Asp-Pro-Arg-Arg-Leu-Trp-Leu-Trp-Lys]-D-Val-D-Phe-NH2 |
| 40 | TCAM038 | Ac-Nle-c[Asp-Pro-Arg-Arg-Leu-Trp-Leu-Trp-Lys]-D-Pro-D-Val-NH2 |
| 41 | TCAM039 | Ac-Nle-c[Asp-Pro-Arg-Arg-Leu-Trp-Leu-Trp-Lys]-D-Phe-D-Val-NH2 |
| 42 | TCAM040 | Ac-Nle-c[Asp-Pro-Arg-Arg-Leu-Trp-Leu-Trp-Lys]-D-Val-D-Pro-NH2 |

TABLE 5-continued

Exemplary Anti-microbial peptides

| SEQ NO: | Peptide | Peptide Sequence |
|---|---|---|
| 43 | TCAM041 | Ac-Nle-c[Asp-Pro-Arg-Arg-Leu-Trp-Leu-Trp-Lys]-D-Val-D-Phe-NH2 |
| 44 | TCAM042 | Ac-Nle-c[Asp-Pro-Arg-Arg-Leu-Trp-Leu-Trp-Lys]-D-Pro-D-Val-NH2 |
| 45 | TCAM043 | Ac-Nle-c[Asp-Pro-Arg-Arg-Leu-Trp-Leu-Trp-Lys]-D-Phe-D-Val-NH2 |
| 46 | TCAM044 | Ac-Nle-c[Asp-Arg-Arg-Arg-Trp-Leu-Trp-Leu-Trp-Lys]-D-Val-D-Pro-NH2 |
| 47 | TCAM045 | Ac-Nle-c[Asp-Pro-Arg-Arg-Arg-Trp-Leu-Trp-Leu-Trp-Lys]-D-Val-D-Phe-NH2 |
| 48 | TCAM046 | Ac-Nle-c[Asp-Pro-Arg-Arg-Arg-Trp-Leu-Trp-Leu-Trp-Lys]-D-Pro-D-Val-NH2 |
| 49 | TCAM047 | Ac-Nle-c[Asp-Pro-Arg-Arg-Arg-Trp-Leu-Trp-Leu-Trp-Lys]-D-Phe-D-Val-NH2 |
| 50 | TCAM048 | Ac-Nle-c[Asp-Pro-Arg-Gln-Arg-Arg-Trp-Leu-Trp-Leu-Trp-Lys]-D-Val-D-Pro-NH2 |
| 51 | TCAM049 | Ac-Nle-c[Asp-Pro-Arg-Gln-Arg-Arg-Trp-Leu-Trp-Leu-Trp-Lys]-D-Val-D-Phe-NH2 |
| 52 | TCAM050 | Ac-Nle-c[Asp-Pro-Arg-Gln-Arg-Arg-Trp-Leu-Trp-Leu-Trp-Lys]-D-Pro-D-Val-NH2 |
| 53 | TCAM051 | Ac-Nle-c[Asp-Pro-Arg-Gln-Arg-Arg-Trp-Leu-Trp-Leu-Trp-Lys]-D-Phe-D-Val-NH2 |
| 54 | TCAM052 | Ac-Nle-c[Asp-Pro-Trp-Arg-Trp-Trp-Arg-Arg-Lys]-D-Val-D-Phe-NH2 |
| 55 | TCAM053 | Ac-Nle-c[Asp-Pro-Trp-Arg-Trp-Trp-Arg-Arg-Lys]-D-Pro-D-Val-NH2 |
| 56 | TCAM054 | Ac-Nle-c[Asp-Pro-Trp-Arg-Trp-Trp-Arg-Arg-Lys]-D-Phe-D-Val-NH2 |
| 57 | TCAM055 | Ac-Nle-c[Asp-Pro-Trp-Trp-Arg-Arg-Trp-Trp-Arg-Arg-Lys]-D-Val-D-Pro-NH2 |
| 58 | TCAM056 | Ac-Nle-c[Asp-Pro-Trp-Trp-Arg-Arg-Trp-Trp-Arg-Arg-Lys]-D-Val-D-Phe-NH2 |
| 59 | TCAM057 | Ac-Nle-c[Asp-Pro-Trp-Trp-Arg-Arg-Trp-Trp-Arg-Arg-Lys]-D-Pro-D-Val-NH2 |
| 60 | TCAM058 | Ac-Nle-c[Asp-Pro-Trp-Trp-Arg-Arg-Trp-Trp-Arg-Arg-Lys]-D-Phe-D-Val-NH2 |
| 61 | TCAM059 | Ac-Nle-c[Asp-Pro-Trp-Arg-Trp-Arg-Trp-Arg-Lys]-D-Val-D-Pro-NH2 |
| 62 | TCAM060 | Ac-Nle-c[Asp-Pro-Trp-Arg-Trp-Arg-Trp-Arg-Lys]-D-Val-D-Phe-NH2 |
| 63 | TCAM061 | Ac-Nle-c[Asp-Pro-Trp-Arg-Trp-Arg-Trp-Arg-Lys]-D-Pro-D-Val-NH2 |
| 64 | TCAM062 | Ac-Nle-c[Asp-Pro-Trp-Arg-Trp-Arg-Trp-Arg-Lys]-D-Phe-D-Val-NH2 |
| 65 | TCAM063 | Ac-Nle-c[Asp-Pro-Arg-Trp-Arg-Trp-Arg-Trp-Lys]-D-Val-D-Pro-NH2 |
| 66 | TCAM064 | Ac-Nle-c[Asp-Pro-Arg-Trp-Arg-Trp-Arg-Trp-Lys]-D-Val-D-Phe-NH2 |
| 67 | TCAM065 | Ac-Nle-c[Asp-Pro-Arg-Trp-Arg-Trp-Arg-Trp-Lys]-D-Pro-D-Val-NH2 |
| 68 | TCAM066 | Ac-Nle-c[Asp-Pro-Arg-Trp-Arg-Trp-Arg-Trp-Lys]-D-Phe-D-Val-NH2 |
| 69 | TCAM067 | Ac-Nle-c[Asp-Pro-Arg-Trp-Trp-Arg-Arg-Lys]-D-Val-D-Pro-NH2 |
| 70 | TCAM068 | Ac-Nle-c[Asp-Pro-Arg-Trp-Trp-Arg-Arg-Lys]-D-Val-D-Phe-NH2 |
| 71 | TCAM069 | Ac-Nle-c[Asp-Pro-Arg-Trp-Trp-Arg-Arg-Lys]-D-Pro-D-Val-NH2 |
| 72 | TCAM070 | Ac-Nle-c[Asp-Pro-Arg-Trp-Trp-Arg-Arg-Lys]-D-Phe-D-Val-NH2 |
| 73 | TCAM071 | Ac-Nle-c[Asp-Pro-Trp-Trp-Arg-Arg-Trp-Lys]-D-Val-D-Pro-NH2 |
| 74 | TCAM072 | Ac-Nle-c[Asp-Pro-Trp-Trp-Arg-Arg-Trp-Lys]-D-Val-D-Phe-NH2 |
| 75 | TCAM073 | Ac-Nle-c[Asp-Pro-Trp-Trp-Arg-Arg-Trp-Lys]-D-Pro-D-Val-NH2 |
| 76 | TCAM074 | Ac-Nle-c[Asp-Pro-Trp-Trp-Arg-Arg-Trp-Lys]-D-Phe-D-Val-NH2 |
| 77 | TCAM075 | Ac-Nle-c[Asp-Pro-Trp-Arg-Trp-Arg-Trp-Lys]-D-Val-D-Pro-NH2 |
| 78 | TCAM076 | Ac-Nle-c[Asp-Pro-Trp-Arg-Trp-Arg-Trp-Lys]-D-Val-D-Phe-NH2 |
| 79 | TCAM077 | Ac-Nle-c[Asp-Pro-Trp-Arg-Trp-Arg-Trp-Lys]-D-Pro-D-Val-NH2 |
| 80 | TCAM078 | Ac-Nle-c[Asp-Pro-Trp-Arg-Trp-Arg-Trp-Lys]-D-Phe-D-Val-NH2 |

TABLE 5-continued

Exemplary Anti-microbial peptides

| SEQ NO: | Peptide | Peptide Sequence |
|---|---|---|
| 81 | TCAM079 | Ac-Nle-c[Asp-Pro-Arg-Trp-Arg-Trp-Arg-Lys]-D-Val-D-Pro-NH2 |
| 82 | TCAM080 | Ac-Nle-c[Asp-Pro-Arg-Trp-Arg-Trp-Arg-Lys]-D-Val-D-Phe-NH2 |
| 83 | TCAM081 | Ac-Nle-c[Asp-Pro-Arg-Trp-Arg-Trp-Arg-Lys]-D-Pro-D-Val-NH2 |
| 84 | TCAM082 | Ac-Nle-c[Asp-Pro-Arg-Trp-Arg-Trp-Arg-Lys]-D-Phe-D-Val-NH2 |
| 85 | TCAM083 | Ac-Nle-c[Asp-Pro-Trp-Arg-Tyr-Arg-Trp-Lys]-D-Val-D-Pro-NH2 |
| 86 | TCAM084 | Ac-Nle-c[Asp-Pro-Trp-Arg-Tyr-Arg-Trp-Lys]-D-Val-D-Phe-NH2 |
| 87 | TCAM085 | Ac-Nle-c[Asp-Pro-Trp-Arg-Tyr-Arg-Trp-Lys]-D-Pro-D-Val-NH2 |
| 88 | TCAM086 | Ac-Nle-c[Asp-Pro-Trp-Arg-Tyr-Arg-Trp-Lys]-D-Phe-D-Val-NH2 |
| 89 | TCAM087 | Ac-Nle-c[Asp-Pro-Trp-Arg-Trp-Arg-Tyr-Lys]-D-Val-D-Pro-NH2 |
| 90 | TCAM088 | Ac-Nle-c[Asp-Pro-Trp-Arg-Trp-Arg-Tyr-Lys]-D-Val-D-Phe-NH2 |
| 91 | TCAM089 | Ac-Nle-c[Asp-Pro-Trp-Arg-Trp-Arg-Tyr-Lys]-D-Pro-D-Val-NH2 |
| 92 | TCAM090 | Ac-Nle-c[Asp-Pro-Trp-Arg-Trp-Arg-Tyr-Lys]-D-Phe-D-Val-NH2 |
| 93 | TCAM091 | Ac-Nle-c[Asp-Pro-Trp-Arg-Trp-Arg-Lys]-D-Val-D-Pro-NH2 |
| 94 | TCAM092 | Ac-Nle-c[Asp-Pro-Trp-Arg-Trp-Arg-Lys]-D-Val-D-Phe-NH2 |
| 95 | TCAM093 | Ac-Nle-c[Asp-Pro-Trp-Arg-Trp-Arg-Lys]-D-Pro-D-Val-NH2 |
| 96 | TCAM094 | Ac-Nle-c[Asp-Pro-Trp-Arg-Trp-Arg-Lys]-D-Phe-D-Val-NH2 |
| 97 | TCAM095 | Ac-Nle-c[Asp-Pro-Trp-Arg-Arg-Trp-Lys]-D-Val-D-Pro-NH2 |
| 98 | TCAM096 | Ac-Nle-c[Asp-Pro-Trp-Arg-Arg-Trp-Lys]-D-Val-D-Phe-NH2 |
| 99 | TCAM097 | Ac-Nle-c[Asp-Pro-Trp-Arg-Arg-Trp-Lys]-D-Pro-D-Val-NH2 |
| 100 | TCAM098 | Ac-Nle-c[Asp-Pro-Trp-Arg-Arg-Trp-Lys]-D-Phe-D-Val-NH2 |
| 101 | TCAM099 | Ac-Nle-c[Asp-Pro-Arg-Trp-Trp-Arg-Lys]-D-Val-D-Pro-NH2 |
| 102 | TCAM100 | Ac-Nle-c[Asp-Pro-Arg-Trp-Trp-Arg-Lys]-D-Val-D-Phe-NH2 |
| 103 | TCAM101 | Ac-Nle-c[Asp-Pro-Arg-Trp-Trp-Arg-Lys]-D-Pro-D-Val-NH2 |
| 104 | TCAM102 | Ac-Nle-c[Asp-Pro-Arg-Trp-Trp-Arg-Lys]-D-Phe-D-Val-NH2 |
| 105 | TCAM103 | Ac-Nle-c[Asp-Pro-Trp-Arg-Trp-Lys]-D-Val-D-Pro-NH2 |
| 106 | TCAM104 | Ac-Nle-c[Asp-Pro-Trp-Arg-Trp-Lys]-D-Val-D-Phe-NH2 |
| 107 | TCAM105 | Ac-Nle-c[Asp-Pro-Trp-Arg-Trp-Lys]-D-Pro-D-Val-NH2 |
| 108 | TCAM106 | Ac-Nle-c[Asp-Pro-Trp-Arg-Trp-Lys]-D-Phe-D-Val-NH2 |
| 109 | TCAM107 | Ac-Nle-c[Asp-Pro-Arg-Trp-Arg-Lys]-D-Val-D-Pro-NH2 |
| 110 | TCAM108 | Ac-Nle-c[Asp-Pro-Arg-Trp-Arg-Lys]-D-Val-D-Phe-NH2 |
| 111 | TCAM109 | Ac-Nle-c[Asp-Pro-Arg-Trp-Arg-Lys]-D-Pro-D-Val-NH2 |
| 112 | TCAM110 | Ac-Nle-c[Asp-Pro-Arg-Trp-Arg-Lys]-D-Phe-D-Val-NH2 |
| 113 | TCAM111 | Ac-Nle-c[Asp-Arg-Arg-Trp-Trp-Arg-Phe-Lys]-D-Val-D-Pro-NH2 |
| 114 | TCAM112 | Ac-Nle-c[Asp-Arg-Arg-Trp-Trp-Arg-Phe-Lys]-D-Val-D-Phe-NH2 |
| 115 | TCAM113 | Ac-Nle-c[Asp-Arg-Arg-Trp-Trp-Arg-Phe-Lys]-D-Pro-D-Val-NH2 |
| 116 | TCAM114 | Ac-Nle-c[Asp-Arg-Arg-Trp-Trp-Arg-Phe-Lys]-D-Phe-D-Val-NH2 |
| 117 | TCAM115 | Ac-Nle-c[Asp-Arg-Arg-Trp-Trp-Arg-Phe-Lys]-D-Val-D-Pro-NH2 |

TABLE 5-continued

Exemplary Anti-microbial peptides

| SEQ NO: | Peptide | Peptide Sequence |
|---|---|---|
| 118 | TCAM116 | Ac-Nle-c[Asp-Arg-Arg-Trp-Trp-Arg-Phe-Lys]-D-Val-D-Phe-NH2 |
| 119 | TCAM117 | Ac-Nle-c[Asp-Arg-Arg-Trp-Trp-Arg-Phe-Lys]-D-Pro-D-Val-NH2 |
| 120 | TCAM118 | Ac-Nle-c[Asp-Arg-Arg-Trp-Trp-Arg-Phe-Lys]-D-Phe-D-Val-NH2 |
| 121 | TCAM119 | Ac-Nle-c[Asp-Arg-Arg-Tyr-Tyr-Arg-Phe-Lys]-D-Val-D-Pro-NH2 |
| 122 | TCAM120 | Ac-Nle-c[Asp-Arg-Arg-Tyr-Tyr-Arg-Phe-Lys]-D-Val-D-Phe-NH2 |
| 123 | TCAM121 | Ac-Nle-c[Asp-Arg-Arg-Tyr-Tyr-Arg-Phe-Lys]-D-Pro-D-Val-NH2 |
| 124 | TCAM122 | Ac-Nle-c[Asp-Arg-Arg-Tyr-Tyr-Arg-Phe-Lys]-D-Phe-D-Val-NH2 |
| 125 | TCAM123 | Ac-Nle-c[Asp-Arg-Arg-Nal-Nal-Arg-Phe-Lys]-D-Val-D-Pro-NH2 |
| 126 | TCAM124 | Ac-Nle-c[Asp-Arg-Arg-Nal-Nal-Arg-Phe-Lys]-D-Val-D-Phe-NH2 |
| 127 | TCAM125 | Ac-Nle-c[Asp-Arg-Arg-Nal-Nal-Arg-Phe-Lys]-D-Pro-D-Val-NH2 |
| 128 | TCAM126 | Ac-Nle-c[Asp-Arg-Arg-Nal-Nal-Arg-Phe-Lys]-D-Phe-D-Val-NH2 |
| 129 | TCAM127 | Ac-Nle-c[Asp-Arg-Arg-Leu-Trp-Leu-Trp-Lys]-D-Val-D-Pro-NH2 |
| 130 | TCAM128 | Ac-Nle-c[Asp-Arg-Arg-Leu-Trp-Leu-Trp-Lys]-D-Val-D-Phe-NH2 |
| 131 | TCAM129 | Ac-Nle-c[Asp-Arg-Arg-Leu-Trp-Leu-Trp-Lys]-D-Pro-D-Val-NH2 |
| 132 | TCAM130 | Ac-Nle-c[Asp-Arg-Arg-Leu-Trp-Leu-Trp-Lys]-D-Phe-D-Val-NH2 |
| 133 | TCAM131 | Ac-Nle-c[Asp-Arg-Arg-Leu-Trp-Leu-Trp-Lys]-D-Val-D-Pro-NH2 |
| 134 | TCAM132 | Ac-Nle-c[Asp-Arg-Arg-Leu-Trp-Leu-Trp-Lys]-D-Val-D-Phe-NH2 |
| 135 | TCAM133 | Ac-Nle-c[Asp-Arg-Arg-Leu-Trp-Leu-Trp-Lys]-D-Pro-D-Val-NH2 |
| 136 | TCAM134 | Ac-Nle-c[Asp-Arg-Arg-Leu-Trp-Leu-Trp-Lys]-D-Phe-D-Val-NH2 |
| 137 | TCAM135 | Ac-Nle-c[Asp-Arg-Arg-Arg-Trp-Leu-Trp-Leu-Trp-Lys]-D-Val-D-Pro-NH2 |
| 138 | TCAM136 | Ac-Nle-c[Asp-Arg-Arg-Arg-Trp-Leu-Trp-Leu-Trp-Lys]-D-Val-D-Phe-NH2 |
| 139 | TCAM137 | Ac-Nle-c[Asp-Arg-Arg-Arg-Trp-Leu-Trp-Leu-Trp-Lys]-D-Pro-D-Val-NH2 |
| 140 | TCAM138 | Ac-Nle-c[Asp-Arg-Arg-Arg-Trp-Leu-Trp-Leu-Trp-Lys]-D-Phe-D-Val-NH2 |
| 141 | TCAM139 | Ac-Nle-c[Asp-Arg-Gln-Arg-Arg-Trp-Leu-Trp-Leu-Trp-Lys]-D-Val-D-Pro-NH2 |
| 142 | TCAM140 | Ac-Nle-c[Asp-Arg-Gln-Arg-Arg-Trp-Leu-Trp-Leu-Trp-Lys]-D-Val-D-Phe-NH2 |
| 143 | TCAM141 | Ac-Nle-c[Asp-Arg-Gln-Arg-Arg-Trp-Leu-Trp-Leu-Trp-Lys]-D-Pro-D-Val-NH2 |
| 144 | TCAM142 | Ac-Nle-c[Asp-Arg-Gln-Arg-Arg-Trp-Leu-Trp-Leu-Trp-Lys]-D-Phe-D-Val-NH2 |
| 145 | TCAM143 | Ac-Nle-c[Asp-Trp-Arg-Trp-Trp-Arg-Arg-Lys]-D-Val-D-Pro-NH2 |
| 146 | TCAM144 | Ac-Nle-c[Asp-Trp-Arg-Trp-Trp-Arg-Arg-Lys]-D-Val-D-Phe-NH2 |
| 147 | TCAM145 | Ac-Nle-c[Asp-Trp-Arg-Trp-Trp-Arg-Arg-Lys]-D-Pro-D-Val-NH2 |
| 148 | TCAM146 | Ac-Nle-c[Asp-Trp-Arg-Trp-Trp-Arg-Arg-Lys]-D-Phe-D-Val-NH2 |
| 149 | TCAM147 | Ac-Nle-c[Asp-Trp-Trp-Arg-Arg-Trp-Trp-Arg-Arg-Lys]-D-Val-D-Pro-NH2 |
| 150 | TCAM148 | Ac-Nle-c[Asp-Trp-Trp-Arg-Arg-Trp-Trp-Arg-Arg-Lys]-D-Val-D-Phe-NH2 |
| 151 | TCAM149 | Ac-Nle-c[Asp-Trp-Trp-Arg-Arg-Trp-Trp-Arg-Arg-Lys]-D-Pro-D-Val-NH2 |
| 152 | TCAM150 | Ac-Nle-c[Asp-Trp-Trp-Arg-Arg-Trp-Trp-Arg-Arg-Lys]-D-Phe-D-Val-NH2 |
| 153 | TCAM151 | Ac-Nle-c[Asp-Trp-Arg-Trp-Arg-Trp-Arg-Lys]-D-Val-D-Pro-NH2 |
| 154 | TCAM152 | Ac-Nle-c[Asp-Trp-Arg-Trp-Arg-Trp-Arg-Lys]-D-Val-D-Phe-NH2 |
| 155 | TCAM153 | Ac-Nle-c[Asp-Trp-Arg-Trp-Arg-Trp-Arg-Lys]-D-Pro-D-Val-NH2 |

TABLE 5-continued

Exemplary Anti-microbial peptides

| SEQ NO: | Peptide | Peptide Sequence |
|---|---|---|
| 156 | TCAM154 | Ac-Nle-c[Asp-Trp-Arg-Trp-Arg-Trp-Arg-Lys]-D-Phe-D-Val-NH2 |
| 157 | TCAM155 | Ac-Nle-c[Asp-Arg-Trp-Arg-Trp-Arg-Trp-Lys]-D-Val-D-Pro-NH2 |
| 158 | TCAM156 | Ac-Nle-c[Asp-Arg-Trp-Arg-Trp-Arg-Trp-Lys]-D-Val-D-Phe-NH2 |
| 159 | TCAM157 | Ac-Nle-c[Asp-Arg-Trp-Arg-Trp-Arg-Trp-Lys]-D-Pro-D-Val-NH2 |
| 160 | TCAM158 | Ac-Nle-c[Asp-Arg-Trp-Arg-Trp-Arg-Trp-Lys]-D-Phe-D-Val-NH2 |
| 161 | TCAM159 | Ac-Nle-c[Asp-Arg-Trp-Trp-Arg-Arg-Lys]-D-Val-D-Pro-NH2 |
| 162 | TCAM160 | Ac-Nle-c[Asp-Arg-Trp-Trp-Arg-Arg-Lys]-D-Val-D-Phe-NH2 |
| 163 | TCAM161 | Ac-Nle-c[Asp-Arg-Trp-Trp-Arg-Arg-Lys]-D-Pro-D-Val-NH2 |
| 164 | TCAM162 | Ac-Nle-c[Asp-Arg-Trp-Trp-Arg-Arg-Lys]-D-Phe-D-Val-NH2 |
| 165 | TCAM163 | Ac-Nle-c[Asp-Arg-Trp-Arg-Trp-Arg-Lys]-D-Val-D-Pro-NH2 |
| 166 | TCAM164 | Ac-Nle-c[Asp-Arg-Trp-Arg-Trp-Arg-Lys]-D-Val-D-Phe-NH2 |
| 167 | TCAM165 | Ac-Nle-c[Asp-Arg-Trp-Arg-Trp-Arg-Lys]-D-Pro-D-Val-NH2 |
| 168 | TCAM166 | Ac-Nle-c[Asp-Arg-Trp-Arg-Trp-Arg-Lys]-D-Phe-D-Val-NH2 |
| 169 | TCAM167 | Ac-Nle-c[Asp-Trp-Trp-Arg-Arg-Trp-Lys]-D-Val-D-Pro-NH2 |
| 170 | TCAM168 | Ac-Nle-c[Asp-Trp-Trp-Arg-Arg-Trp-Lys]-D-Val-D-Phe-NH2 |
| 171 | TCAM169 | Ac-Nle-c[Asp-Trp-Trp-Arg-Arg-Trp-Lys]-D-Pro-D-Val-NH2 |
| 172 | TCAM170 | Ac-Nle-c[Asp-Trp-Trp-Arg-Arg-Trp-Lys]-D-Phe-D-Val-NH2 |
| 173 | TCAM171 | Ac-Nle-c[Asp-Trp-Arg-Trp-Arg-Trp-Lys]-D-Val-D-Pro-NH2 |
| 174 | TCAM172 | Ac-Nle-c[Asp-Trp-Arg-Trp-Arg-Trp-Lys]-D-Val-D-Phe-NH2 |
| 175 | TCAM173 | Ac-Nle-c[Asp-Trp-Arg-Trp-Arg-Trp-Lys]-D-Pro-D-Val-NH2 |
| 176 | TCAM174 | Ac-Nle-c[Asp-Trp-Arg-Trp-Arg-Trp-Lys]-D-Phe-D-Val-NH2 |
| 177 | TCAM175 | Ac-Nle-c[Asp-Trp-Arg-Tyr-Arg-Trp-Lys]-D-Val-D-Pro-NH2 |
| 178 | TCAM176 | Ac-Nle-c[Asp-Trp-Arg-Tyr-Arg-Trp-Lys]-D-Val-D-Phe-NH2 |
| 179 | TCAM177 | Ac-Nle-c[Asp-Trp-Arg-Tyr-Arg-Trp-Lys]-D-Pro-D-Val-NH2 |
| 180 | TCAM178 | Ac-Nle-c[Asp-Trp-Arg-Tyr-Arg-Trp-Lys]-D-Phe-D-Val-NH2 |
| 181 | TCAM179 | Ac-Nle-c[Asp-Trp-Arg-Trp-Arg-Tyr-Lys]-D-Val-D-Pro-NH2 |
| 182 | TCAM180 | Ac-Nle-c[Asp-Trp-Arg-Trp-Arg-Tyr-Lys]-D-Val-D-Phe-NH2 |
| 183 | TCAM181 | Ac-Nle-c[Asp-Trp-Arg-Trp-Arg-Tyr-Lys]-D-Pro-D-Val-NH2 |
| 184 | TCAM182 | Ac-Nle-c[Asp-Trp-Arg-Trp-Arg-Tyr-Lys]-D-Phe-D-Val-NH2 |
| 185 | TCAM183 | Ac-Nle-c[Asp-Trp-Arg-Trp-Arg-Lys]-D-Val-D-Pro-NH2 |
| 186 | TCAM184 | Ac-Nle-c[Asp-Trp-Arg-Trp-Arg-Lys]-D-Val-D-Phe-NH2 |
| 187 | TCAM185 | Ac-Nle-c[Asp-Trp-Arg-Trp-Arg-Lys]-D-Pro-D-Val-NH2 |
| 188 | TCAM186 | Ac-Nle-c[Asp-Trp-Arg-Trp-Arg-Lys]-D-Phe-D-Val-NH2 |
| 189 | TCAM187 | Ac-Nle-c[Asp-Trp-Arg-Arg-Trp-Lys]-D-Val-D-Pro-NH2 |
| 190 | TCAM188 | Ac-Nle-c[Asp-Trp-Arg-Arg-Trp-Lys]-D-Val-D-Phe-NH2 |
| 191 | TCAM189 | Ac-Nle-c[Asp-Trp-Arg-Arg-Trp-Lys]-D-Pro-D-Val-NH2 |
| 192 | TCAM190 | Ac-Nle-c[Asp-Trp-Arg-Arg-Trp-Lys]-D-Phe-D-Val-NH2 |

TABLE 5-continued

Exemplary Anti-microbial peptides

| SEQ NO: | Peptide | Peptide Sequence |
|---|---|---|
| 193 | TCAM191 | Ac-Nle-c[Asp-Arg-Trp-Trp-Arg-Lys]-D-Val-D-Pro-NH2 |
| 194 | TCAM192 | Ac-Nle-c[Asp-Arg-Trp-Trp-Arg-Lys]-D-Val-D-Phe-NH2 |
| 195 | TCAM193 | Ac-Nle-c[Asp-Arg-Trp-Trp-Arg-Lys]-D-Pro-D-Val-NH2 |
| 196 | TCAM194 | Ac-Nle-c[Asp-Arg-Trp-Trp-Arg-Lys]-D-Phe-D-Val-NH2 |
| 197 | TCAM195 | Ac-Nle-c[Asp-Trp-Arg-Trp-Lys]-D-Val-D-Pro-NH2 |
| 198 | TCAM196 | Ac-Nle-c[Asp-Trp-Arg-Trp-Lys]-D-Val-D-Phe-NH2 |
| 199 | TCAM197 | Ac-Nle-c[Asp-Trp-Arg-Trp-Lys]-D-Pro-D-Val-NH2 |
| 200 | TCAM198 | Ac-Nle-c[Asp-Trp-Arg-Trp-Lys]-D-Phe-D-Val-NH2 |
| 201 | TCAM199 | Ac-Nle-c[Asp-Arg-Trp-Arg-Lys]-D-Val-D-Pro-NH2 |
| 202 | TCAM200 | Ac-Nle-c[Asp-Arg-Trp-Arg-Lys]-D-Val-D-Phe-NH2 |
| 203 | TCAM201 | Ac-Nle-c[Asp-Arg-Trp-Arg-Lys]-D-Pro-D-Val-NH2 |
| 204 | TCAM202 | Ac-Nle-c[Asp-Arg-Trp-Arg-Lys]-D-Phe-D-Val-NH2 |
| 205 | TCAM203 | Ac-Nle-c[Asp-His-D-Nal(2')-Arg-Trp-Lys]-D-Val-D-Pro-NH2 |
| 206 | TCAM204 | Ac-Nle-c[Asp-His-D-Nal(2')-Arg-Trp-Lys]-D-Pro-D-Val-NH2 |
| 207 | TCAM205 | Ac-Nle-c[Asp-His-D-Nal(2')-Arg-Trp-Lys]-D-Val-D-Phe-NH2 |
| 208 | TCAM206 | Ac-Nle-c[Asp-His-D-Nal(2')-Arg-Trp-Lys]-D-Phe-D-Val-NH2 |
| 209 | TCAM207 | Ac-Nle-c[Asp-Pro-D-Nal(2')-Arg-Trp-Lys]-D-Val-D-Pro-NH2 |
| 210 | TCAM208 | Ac-Nle-c[Asp-Pro-D-Nal(2')-Arg-Trp-Lys]-D-Pro-D-Val-NH2 |
| 211 | TCAM209 | Ac-Nle-c[Asp-Pro-D-Nal(2')-Arg-Trp-Lys]-D-Val-D-Phe-NH2 |
| 212 | TCAM210 | Ac-Nle-c[Asp-Pro-D-Nal(2')-Arg-Trp-Lys]-D-Phe-D-Val-NH2 |
| 213 | TCAM211 | Ac-Nle-c[Asp-Arg-Arg-Nal(2')-Arg-Trp-Lys]-D-Val-D-Pro-NH2 |
| 214 | TCAM212 | Ac-Nle-c[Asp-Arg-Arg-Nal(2')-Arg-Trp-Lys]-D-Pro-D-Val-NH2 |
| 215 | TCAM213 | Ac-Nle-c[Asp-Arg-Arg-Nal(2')-Arg-Trp-Lys]-D-Val-D-Phe-NH2 |
| 216 | TCAM214 | Ac-Nle-c[Asp-Arg-Arg-Nal(2')-Arg-Trp-Lys]-D-Phe-D-Val-NH2 |
| 217 | TCAM215 | Ac-Nle-c[Asp-Arg-Arg-Pro-Nal(2')-Arg-Trp-Lys]-D-Val-D-Pro-NH2 |
| 218 | TCAM216 | Ac-Nle-c[Asp-Arg-Arg-Pro-D-Nal(2')-Arg-Trp-Lys]-D-Pro-D-Val-NH2 |
| 219 | TCAM217 | Ac-Nle-c[Asp-Arg-Arg-Pro-D-Nal(2')-Arg-Trp-Lys]-D-Val-D-Phe-NH2 |
| 220 | TCAM218 | Ac-Nle-c[Asp-Arg-Arg-Pro-Nal(2')-Arg-Trp-Lys]-D-Phe-D-Val-NH2 |
| 221 | TCAM219 | Ac-Nle-c[Asp-Arg-D-Nal(2')-Arg-Trp-Lys]-D-Val-D-Pro-NH2 |
| 222 | TCAM220 | Ac-Nle-c[Asp-Arg-D-Nal(2')-Arg-Trp-Lys]-D-Pro-D-Val-NH2 |
| 223 | TCAM221 | Ac-Nle-c[Asp-Arg-D-Nal(2')-Arg-Trp-Lys]-D-Val-D-Phe-NH2 |
| 224 | TCAM222 | Ac-Nle-c[Asp-Arg-D-Nal(2')-Arg-Trp-Lys]-D-Phe-D-Val-NH2 |
| 225 | TCAM223 | Ac-Nle-c[Asp-Arg-Pro-D-Nal(2')-Arg-Trp-Lys]-D-Val-D-Pro-NH2 |
| 226 | TCAM224 | Ac-Nle-c[Asp-Arg-Pro-D-Nal(2')-Arg-Trp-Lys]-D-Pro-D-Val-NH2 |
| 227 | TCAM225 | Ac-Nle-c[Asp-Arg-Pro-D-Nal(2')-Arg-Trp-Lys]-D-Val-D-Phe-NH2 |
| 228 | TCAM226 | Ac-Nle-c[Asp-Arg-Pro-D-Nal(2')-Arg-Trp-Lys]-D-Phe-D-Val-NH2 |
| 229 | TCAM227 | Ac-Nle-Arg-Arg-c[Asp-Pro-D-Nal(2')-Arg-Trp-Lys]-D-Val-D-Pro-NH2 |
| 230 | TCAM228 | Ac-Nle-Arg-Arg-c[Asp-Pro-D-Nal(2')-Arg-Trp-Lys]-D-Pro-D-Val-NH2 |

TABLE 5-continued

Exemplary Anti-microbial peptides

| SEQ NO: | Peptide | Peptide Sequence |
|---|---|---|
| 231 | TCAM229 | Ac-Nle-Arg-Arg-c[Asp-Pro-D-Nal(2')-Arg-Trp-Lys]-D-Val-D-Phe-NH2 |
| 232 | TCAM230 | Ac-Nle-Arg-Arg-c[Asp-Pro-D-Nal(2')-Arg-Trp-Lys]-D-Phe-D-Val-NH2 |
| 233 | TCAM231 | Ac-Nle-Arg-Arg-c[Asp-His-D-Nal(2')-Arg-Trp-Lys]-D-Val-D-Pro-NH2 |
| 234 | TCAM232 | Ac-Nle-Arg-Arg-c[Asp-His-D-Nal(2')-Arg-Trp-Lys]-D-Pro-D-Val-NH2 |
| 235 | TCAM233 | Ac-Nle-Arg-Arg-c[Asp-His-D-Nal(2')-Arg-Trp-Lys]-D-Val-D-Phe-NH2 |
| 236 | TCAM234 | Ac-Nle-Arg-Arg-c[Asp-His-D-Nal(2')-Arg-Trp-Lys]-D-Phe-D-Val-NH2 |
| 237 | TCAM235 | Ac-Nle-c[Asp-Arg-Pro-D-Nal(2')-Arg-Trp-Arg-Lys]-D-Val-D-Pro-NH2 |
| 238 | TCAM236 | Ac-Nle-c[Asp-Arg-Pro-D-Nal(2')-Arg-Trp-Arg-Lys]-D-Pro-D-Val-NH2 |
| 239 | TCAM237 | Ac-Nle-c[Asp-Arg-Pro-D-Nal(2')-Arg-Trp-Arg-Lys]-D-Val-D-Phe-NH2 |
| 240 | TCAM238 | Ac-Nle-c[Asp-Arg-Pro-D-Nal(2')-Arg-Trp-Arg-Lys]-D-Phe-D-Val-NH2 |
| 241 | TCAM239 | Ac-Nle-c[Asp-Arg-His-D-Nal(2')-Arg-Trp-Arg-Lys]-D-Val-D-Pro-NH2 |
| 242 | TCAM240 | Ac-Nle-c[Asp-Arg-His-D-Nal(2')-Arg-Trp-Arg-Lys]-D-Pro-D-Val-NH2 |
| 243 | TCAM241 | Ac-Nle-c[Asp-Arg-His-D-Nal(2')-Arg-Trp-Arg-Lys]-D-Val-D-Phe-NH2 |
| 244 | TCAM242 | Ac-Nle-c[Asp-Arg-His-D-Nal(2')-Arg-Trp-Arg-Lys]-D-Phe-D-Val-NH2 |
| 245 | TCAM243 | Ac-Nle-c[Asp-His-D-Nal(2')-Arg-D-Nal(2')-Lys]-D-Val-D-Phe-NH2 |
| 246 | TCAM244 | Ac-Nle-c[Asp-His-D-Nal(2')-Arg-D-Nal(2')-Lys]-D-Phe-D-Val-NH2 |
| 247 | TCAM245 | Ac-Nle-c[Asp-Pro-D-Nal(2')-Arg-D-Nal(2')-Lys]-D-Val-D-Pro-NH2 |
| 248 | TCAM246 | Ac-Nle-c[Asp-Pro-D-Nal(2')-Arg-D-Nal(2')-Lys]-D-Pro-D-Val-NH2 |
| 249 | TCAM247 | Ac-Nle-c[Asp-Pro-D-Nal(2')-Arg-D-Nal(2')-Lys]-D-Val-D-Phe-NH2 |
| 250 | TCAM248 | Ac-Nle-c[Asp-Pro-D-Nal(2')-Arg-D-Nal(2')-Lys]-D-Phe-D-Val-NH2 |
| 251 | TCAM249 | Ac-Nle-c[Asp-Arg-Arg-D-Nal(2')-Arg-D-Nal(2')-Lys]-D-Val-D-Pro-NH2 |
| 252 | TCAM250 | Ac-Nle-c[Asp-Arg-Arg-D-Nal(2')-Arg-D-Nal(2')-Lys]-D-Pro-D-Val-NH2 |
| 253 | TCAM251 | Ac-Nle-c[Asp-Arg-Arg-D-Nal(2')-Arg-D-Nal(2')-Lys]-D-Val-D-Phe-NH2 |
| 254 | TCAM252 | Ac-Nle-c[Asp-Arg-Arg-D-Nal(2')-Arg-D-Nal(2')-Lys]-D-Phe-D-Val-NH2 |
| 255 | TCAM253 | Ac-Nle-c[Asp-Arg-Arg-Pro-D-Nal(2')-Arg-D-Nal(2')-Lys]-D-Val-D-Pro-NH2 |
| 256 | TCAM254 | Ac-Nle-c[Asp-Arg-Arg-Pro-D-Nal(2')-Arg-D-Nal(2')-Lys]-D-Pro-D-Val-NH2 |
| 257 | TCAM255 | Ac-Nle-c[Asp-Arg-Arg-Pro-D-Nal(2')-Arg-D-Nal(2')-Lys]-D-Val-D-Phe-NH2 |
| 258 | TCAM256 | Ac-Nle-c[Asp-Arg-Arg-Pro-D-Nal(2')-Arg-D-Nal(2')-Lys]-D-Phe-D-Val-NH2 |
| 259 | TCAM257 | Ac-Nle-c[Asp-Arg-D-Nal(2')-Arg-D-Nal(2')-Lys]-D-Val-D-Pro-NH2 |
| 260 | TCAM258 | Ac-Nle-c[Asp-Arg-D-Nal(2')-Arg-D-Nal(2')-Lys]-D-Pro-D-Val-NH2 |
| 261 | TCAM259 | Ac-Nle-c[Asp-Arg-Nal(2')-Arg-D-Nal(2')-Lys]-D-Val-D-Phe-NH2 |
| 262 | TCAM260 | Ac-Nle-c[Asp-Arg-D-Nal(2')-Arg-D-Nal(2')-Lys]-D-Phe-D-Val-NH2 |
| 263 | TCAM261 | Ac-Nle-c[Asp-Arg-Pro-D-Nal(2')-Arg-D-Nal(2')-Lys]-D-Val-D-Pro-NH2 |
| 264 | TCAM262 | Ac-Nle-c[Asp-Arg-Pro-D-Nal(2')-Arg-D-Nal(2')-Lys]-D-Pro-D-Val-NH2 |
| 265 | TCAM263 | Ac-Nle-c[Asp-Arg-Pro-D-Nal(2')-Arg-D-Nal(2')-Lys]-D-Val-D-Phe-NH2 |
| 266 | TCAM264 | Ac-Nle-c[Asp-Arg-Pro-D-Nal(2')-Arg-D-Nal(2')-Lys]-D-Phe-D-Val-NH2 |
| 267 | TCAM265 | Ac-Nle-c[Asp-Arg-His-D-Nal(2')-Arg-D-Nal(2')-Lys]-D-Val-D-Pro-NH2 |

TABLE 5-continued

Exemplary Anti-microbial peptides

| SEQ NO: | Peptide | Peptide Sequence |
|---|---|---|
| 268 | TCAM266 | Ac-Nle-c[Asp-Arg-His-D-Nal(2')-Arg-D-Nal(2')-Lys]-D-Pro-D-Val-NH2 |
| 269 | TCAM267 | Ac-Nle-c[Asp-Arg-His-Nal(2')-Arg-D-Nal(2')-Lys]-D-Val-D-Phe-NH2 |
| 270 | TCAM268 | Ac-Nle-c[Asp-Arg-His-Nal(2')-Arg-D-Nal(2')-Lys]-D-Phe-D-Val-NH2 |
| 271 | TCAM269 | Ac-Nle-c[Asp-Arg-D-D-Nal(2')-Arg-D-Nal(2')-Arg-Lys]-D-Val-D-Pro-NH2 |
| 272 | TCAM270 | Ac-Nle-c[Asp-Arg-D-Nal(2')-Arg-D-Nal(2')-Arg-Lys]-D-Pro-D-Val-NH2 |
| 273 | TCAM271 | Ac-Nle-c[Asp-Arg-D-Nal(2')-Arg-D-Nal(2')-Arg-Lys]-D-Val-D-Phe-NH2 |
| 274 | TCAM272 | Ac-Nle-c[Asp-Arg-D-Nal(2')-Arg-D-Nal(2')-Arg-Lys]-D-Phe-D-Val-NH2 |
| 275 | TCAM273 | Ac-Nle-c[Asp-Arg-Pro-D-Nal(2')-Arg-D-Nal(2')-Arg-Lys]-D-Val-D-Pro-NH2 |
| 276 | TCAM274 | Ac-Nle-c[Asp-Arg-Pro-D-Nal(2')-Arg-D-Nal(2')-Arg-Lys]-D-Pro-D-Val-NH2 |
| 277 | TCAM275 | Ac-Nle-c[Asp-Arg-Pro-D-Nal(2')-Arg-D-Nal(2')-Arg-Lys]-D-Val-D-Phe-NH2 |
| 278 | TCAM276 | Ac-Nle-c[Asp-Arg-Pro-D-Nal(2')-Arg-D-Nal(2')-Arg-Lys]-D-Phe-D-Val-NH2 |
| 279 | TCAM277 | Ac-Nle-c[Asp-Arg-His-D-Nal(2')-Arg-D-Nal(2')-Arg-Lys]-D-Val-D-Pro-NH2 |
| 280 | TCAM278 | Ac-Nle-c[Asp-Arg-His-D-Nal(2')-Arg-D-Nal(2')-Arg-Lys]-D-Pro-D-Val-NH2 |
| 281 | TCAM279 | Ac-Nle-c[Asp-Arg-His-D-Nal(2')-Arg-D-Nal(2')-Arg-Lys]-D-Val-D-Phe-NH2 |
| 282 | TCAM280 | Ac-Nle-c[Asp-Arg-His-D-Nal(2')-Arg-D-Nal(2')-Arg-Lys]-D-Phe-D-Val-NH2 |
| 283 | TCAM281 | Ac-Nle-Arg-Arg-c[Asp-Pro-D-Nal(2')-Arg-D-Nal(2')-Lys]-D-Val-D-Pro-NH2 |
| 284 | TCAM282 | Ac-Nle-Arg-Arg-c[Asp-Pro-D-Nal(2')-Arg-D-Nal(2')-Lys]-D-Pro-D-Val-NH2 |
| 285 | TCAM283 | Ac-Nle-Arg-Arg-c[Asp-Pro-D-Nal(2')-Arg-D-Nal(2')-Lys]-D-Val-D-Phe-NH2 |
| 286 | TCAM284 | Ac-Nle-Arg-Arg-c[Asp-Pro-D-Nal(2')-Arg-D-Nal(2')-Lys]-D-Phe-D-Val-NH2 |
| 287 | TCAM285 | Ac-Nle-Arg-Arg-c[Asp-His-D-Nal(2')-Arg-D-Nal(2')-Lys]-D-Val-D-Pro-NH2 |
| 288 | TCAM286 | Ac-Nle-Arg-Arg-c[Asp-His-D-Nal(2')-Arg-D-Nal(2')-Lys]-D-Pro-D-Val-NH2 |
| 289 | TCAM287 | Ac-Nle-Arg-Arg-c[Asp-His-D-Nal(2')-Arg-D-Nal(2')-Lys]-D-Val-D-Phe-NH2 |
| 290 | TCAM288 | Ac-Nle-Arg-Arg-c[Asp-His-D-Nal(2')-Arg-D-Nal(2')-Lys]-D-Phe-D-Val-NH2 |
| 291 | TCAM289 | Ac-Nle-c[Asp-Arg-Pro-D-Nal(2')-Arg-D-Nal(2')-Arg-Lys]-D-Val-D-Pro-NH2 |
| 292 | TCAM290 | Ac-Nle-c[Asp-Arg-Pro-D-Nal(2')-Arg-D-Nal(2')-Arg-Lys]-D-Pro-D-Val-NH2 |
| 293 | TCAM291 | Ac-Nle-c[Asp-Arg-Pro-D-Nal(2')-Arg-D-Nal(2')-Arg-Lys]-D-Val-D-Phe-NH2 |
| 294 | TCAM292 | Ac-Nle-c[Asp-Arg-Pro-D-Nal(2')-Arg-D-Nal(2')-Arg-Lys]-D-Phe-D-Val-NH2 |
| 295 | TCAM293 | Ac-Nle-c[Asp-Arg-His-D-Nal(2')-Arg-D-Nal(2')-Arg-Lys]-D-Val-D-Pro-NH2 |
| 296 | TCAM294 | Ac-Nle-c[Asp-Arg-His-D-Nal(2')-Arg-D-Nal(2')-Arg-Lys]-D-Pro-D-Val-NH2 |
| 297 | TCAM295 | Ac-Nle-c[Asp-Arg-His-D-Nal(2')-Arg-D-Nal(2')-Arg-Lys]-D-Val-D-Phe-NH2 |
| 298 | TCAM296 | Ac-Nle-c[Asp-Arg-His-D-Nal(2')-Arg-D-Nal(2')-Arg-Lys]-D-Phe-D-Val-NH2 |
| 299 | TCAM296 | Ac-Nle-c[Asp-His-D-Nal(2')-Arg-Trp-Lys]-Arg-Arg-D-Val-D-Pro-NH2 |
| 300 | TCAM297 | Ac-Nle-c[Asp-His-D-Nal(2')-Arg-Trp-Lys]-Arg-Arg-D-Pro-D-Val-NH2 |
| 301 | TCAM298 | Ac-Nle-c[Asp-His-D-Nal(2')-Arg-Trp-Lys]-Arg-Arg-D-Val-D-Phe-NH2 |
| 302 | TCAM299 | Ac-Nle-c[Asp-His-D-Nal(2')-Arg-Trp-Lys]-Arg-Arg-D-Phe-D-Val-NH2 |
| 303 | TCAM300 | Ac-Nle-c[Asp-Pro-D-Nal(2')-Arg-Trp-Lys]-Arg-Arg-D-Val-D-Pro-NH2 |
| 304 | TCAM301 | Ac-Nle-c[Asp-Pro-D-Nal(2')-Arg-Trp-Lys]-Arg-Arg-D-Pro-D-Val-NH2 |
| 305 | TCAM302 | Ac-Nle-c[Asp-Pro-D-Nal(2')-Arg-Trp-Lys]-Arg-Arg-D-Val-D-Phe-NH2 |

TABLE 5-continued

Exemplary Anti-microbial peptides

| SEQ NO: | Peptide | Peptide Sequence |
|---|---|---|
| 306 | TCAM303 | Ac-Nle-c[Asp-Pro-D-Nal(2')-Arg-Trp-Lys]-Arg-Arg-D-Phe-D-Val-NH2 |

Anti-biofilm peptide 1018 linked to ant-microbial peptides

| SEQ NO: | Peptide | Peptide Sequence |
|---|---|---|
| 307 | TCAM304 | Val-Arg-Leu-Ile-Val-Ala-Val-Arg-Ile-Trp-Arg-Arg-c[Asp-Pro-Arg-Arg-Trp-Trp-Arg-Phe-Lys]-D-Val-D-Pro-NH2 |
| 308 | TCAM305 | Val-Arg-Leu-Ile-Val-Ala-Val-Arg-Ile-Trp-Arg-Arg-c[Asp-Pro-Arg-Arg-Trp-Trp-Arg-Phe-Lys]-D-Val-D-Phe-NH2 |
| 309 | TCAM306 | Val-Arg-Leu-Ile-Val-Ala-Val-Arg-Ile-Trp-Arg-Arg-c[Asp-Pro-Arg-Arg-Trp-Trp-Arg-Phe-Lys]-D-Pro-D-Val-NH2 |
| 310 | TCAM307 | Val-Arg-Leu-Ile-Val-Ala-Val-Arg-Ile-Trp-Arg-Arg-c[Asp-Pro-Arg-Arg-Trp-Trp-Arg-Phe-Lys]-D-Phe-D-Val-NH2 |
| 311 | TCAM308 | Val-Arg-Leu-Ile-Val-Ala-Val-Arg-Ile-Trp-Arg-Arg-c[Asp-Pro-Arg-Arg-Trp-Trp-Tyr-Phe-Lys]-D-Val-D-Pro-NH2 |
| 312 | TCAM309 | Val-Arg-Leu-Ile-Val-Ala-Val-Arg-Ile-Trp-Arg-Arg-c[Asp-Pro-Arg-Arg-Trp-Trp-Tyr-Phe-Lys]-D-Val-D-Phe-NH2 |
| 313 | TCAM310 | Val-Arg-Leu-Ile-Val-Ala-Val-Arg-Ile-Trp-Arg-Arg-c[Asp-Pro-Arg-Arg-Trp-Trp-Tyr-Phe-Lys]-D-Pro-D-Val-NH2 |
| 314 | TCAM311 | Val-Arg-Leu-Ile-Val-Ala-Val-Arg-Ile-Trp-Arg-Arg-c[Asp-Pro-Arg-Arg-Trp-Trp-Tyr-Phe-Lys]-D-Phe-D-Val-NH2 |
| 315 | TCAM312 | Val-Arg-Leu-Ile-Val-Ala-Val-Arg-Ile-Trp-Arg-Arg-c[Asp-Pro-Arg-Arg-Tyr-Tyr-Arg-Phe-Lys]-D-Val-D-Pro-NH2 |
| 316 | TCAM313 | Val-Arg-Leu-Ile-Val-Ala-Val-Arg-Ile-Trp-Arg-Arg-c[Asp-Pro-Arg-Arg-Tyr-Tyr-Arg-Phe-Lys]-D-Val-D-Phe-NH2 |
| 317 | TCAM314 | Val-Arg-Leu-Ile-Val-Ala-Val-Arg-Ile-Trp-Arg-Arg-c[Asp-Pro-Arg-Arg-Tyr-Tyr-Arg-Phe-Lys]-D-Pro-D-Val-NH2 |
| 318 | TCAM315 | Val-Arg-Leu-Ile-Val-Ala-Val-Arg-Ile-Trp-Arg-Arg-c[Asp-Pro-Arg-Arg-Tyr-Tyr-Arg-Phe-Lys]-D-Phe-D-Val-NH2 |
| 319 | TCAM316 | Val-Arg-Leu-Ile-Val-Ala-Val-Arg-Ile-Trp-Arg-Arg-c[Asp-Pro-Arg-Arg-Nal-Nal-Arg-Phe-Lys]-D-Val-D-Pro-NH2 |
| 320 | TCAM317 | Val-Arg-Leu-Ile-Val-Ala-Val-Arg-Ile-Trp-Arg-Arg-c[Asp-Pro-Arg-Arg-Nal-Nal-Arg-Phe-Lys]-D-Val-D-Phe-NH2 |
| 321 | TCAM318 | Val-Arg-Leu-Ile-Val-Ala-Val-Arg-Ile-Trp-Arg-Arg-c[Asp-Pro-Arg-Arg-Nal-Nal-Arg-Phe-Lys]-D-Pro-D-Val-NH2 |
| 322 | TCAM319 | Val-Arg-Leu-Ile-Val-Ala-Val-Arg-Ile-Trp-Arg-Arg-c[Asp-Pro-Arg-Arg-Nal-Nal-Arg-Phe-Lys]-D-Phe-D-Val-NH2 |
| 323 | TCAM320 | Val-Arg-Leu-Ile-Val-Ala-Val-Arg-Ile-Trp-Arg-Arg-c[Asp-Pro-Arg-Arg-Leu-Trp-Leu-Trp-Lys]-D-Val-D-Pro-NH2 |
| 324 | TCAM321 | Val-Arg-Leu-Ile-Val-Ala-Val-Arg-Ile-Trp-Arg-Arg-c[Asp-Pro-Arg-Arg-Leu-Trp-Leu-Trp-Lys]-D-Val-D-Phe-NH2 |
| 325 | TCAM322 | Val-Arg-Leu-Ile-Val-Ala-Val-Arg-Ile-Trp-Arg-Arg-c[Asp-Pro-Arg-Arg-Leu-Trp-Leu-Trp-Lys]-D-Pro-D-Val-NH2 |
| 326 | TCAM323 | Val-Arg-Leu-Ile-Val-Ala-Val-Arg-Ile-Trp-Arg-Arg-c[Asp-Pro-Arg-Arg-Leu-Trp-Leu-Trp-Lys]-D-Phe-D-Val-NH2 |
| 327 | TCAM324 | Val-Arg-Leu-Ile-Val-Ala-Val-Arg-Ile-Trp-Arg-Arg-c[Asp-Pro-Arg-Arg-Leu-Trp-Leu-Trp-Lys]-D-Val-D-Pro-NH2 |
| 328 | TCAM325 | Val-Arg-Leu-Ile-Val-Ala-Val-Arg-Ile-Trp-Arg-Arg-c[Asp-Pro-Arg-Arg-Leu-Trp-Leu-Trp-Lys]-D-Val-D-Phe-NH2 |
| 329 | TCAM326 | Val-Arg-Leu-Ile-Val-Ala-Val-Arg-Ile-Trp-Arg-Arg-c[Asp-Pro-Arg-Arg-Leu-Trp-Leu-Trp-Lys]-D-Pro-D-Val-NH2 |

TABLE 5-continued

Exemplary Anti-microbial peptides

| SEQ NO: | Peptide | Peptide Sequence |
|---|---|---|
| 330 | TCAM327 | Val-Arg-Leu-Ile-Val-Ala-Val-Arg-Ile-Trp-Arg-Arg-c[Asp-Pro-Arg-Arg-Leu-Trp-Leu-Trp-Lys]-D-Phe-D-Val-NH2 |
| 331 | TCAM328 | Val-Arg-Leu-Ile-Val-Ala-Val-Arg-Ile-Trp-Arg-Arg-c[Asp-Arg-Arg-Arg-Trp-Leu-Trp-Leu-Trp-Lys]-D-Val-D-Pro-NH2 |
| 332 | TCAM329 | Val-Arg-Leu-Ile-Val-Ala-Val-Arg-Ile-Trp-Arg-Arg-c[Asp-Pro-Arg-Arg-Arg-Trp-Leu-Trp-Leu-Trp-Lys]-D-Val-D-Phe-NH2 |
| 333 | TCAM330 | Val-Arg-Leu-Ile-Val-Ala-Val-Arg-Ile-Trp-Arg-Arg-c[Asp-Pro-Arg-Arg-Arg-Trp-Leu-Trp-Leu-Trp-Lys]-D-Pro-D-Val-NH2 |
| 334 | TCAM331 | Val-Arg-Leu-Ile-Val-Ala-Val-Arg-Ile-Trp-Arg-Arg-c[Asp-Pro-Arg-Arg-Arg-Trp-Leu-Trp-Leu-Trp-Lys]-D-Phe-D-Val-NH2 |
| 335 | TCAM332 | Val-Arg-Leu-Ile-Val-Ala-Val-Arg-Ile-Trp-Arg-Arg-c[Asp-Pro-Arg-Gln-Arg-Arg-Trp-Leu-Trp-Leu-Trp-Lys]-D-Val-D-Pro-NH2 |
| 336 | TCAM333 | Val-Arg-Leu-Ile-Val-Ala-Val-Arg-Ile-Trp-Arg-Arg-c[Asp-Pro-Arg-Gln-Arg-Arg-Trp-Leu-Trp-Leu-Trp-Lys]-D-Val-D-Phe-NH2 |
| 337 | TCAM334 | Val-Arg-Leu-Ile-Val-Ala-Val-Arg-Ile-Trp-Arg-Arg-c[Asp-Pro-Arg-Gln-Arg-Arg-Trp-Leu-Trp-Leu-Trp-Lys]-D-Pro-D-Val-NH2 |
| 338 | TCAM335 | Val-Arg-Leu-Ile-Val-Ala-Val-Arg-Ile-Trp-Arg-Arg-c[Asp-Pro-Arg-Gln-Arg-Arg-Trp-Leu-Trp-Leu-Trp-Lys]-D-Phe-D-Val-NH2 |
| 339 | TCAM336 | Val-Arg-Leu-Ile-Val-Ala-Val-Arg-Ile-Trp-Arg-Arg-c[Asp-Pro-Trp-Arg-Trp-Trp-Arg-Arg-Lys]-D-Val-D-Phe-NH2 |
| 340 | TCAM337 | Val-Arg-Leu-Ile-Val-Ala-Val-Arg-Ile-Trp-Arg-Arg-c[Asp-Pro-Trp-Arg-Trp-Trp-Arg-Arg-Lys]-D-Pro-D-Val-NH2 |
| 341 | TCAM338 | Val-Arg-Leu-Ile-Val-Ala-Val-Arg-Ile-Trp-Arg-Arg-c[Asp-Pro-Trp-Arg-Trp-Trp-Arg-Arg-Lys]-D-Phe-D-Val-NH2 |
| 342 | TCAM339 | Val-Arg-Leu-Ile-Val-Ala-Val-Arg-Ile-Trp-Arg-Arg-c[Asp-Pro-Trp-Trp-Arg-Arg-Trp-Trp-Arg-Arg-Lys]-D-Val-D-Pro-NH2 |
| 343 | TCAM340 | Val-Arg-Leu-Ile-Val-Ala-Val-Arg-Ile-Trp-Arg-Arg-c[Asp-Pro-Trp-Trp-Arg-Arg-Trp-Trp-Arg-Arg-Lys]-D-Val-D-Phe-NH2 |
| 344 | TCAM341 | Val-Arg-Leu-Ile-Val-Ala-Val-Arg-Ile-Trp-Arg-Arg-c[Asp-Pro-Trp-Trp-Arg-Arg-Trp-Trp-Arg-Arg-Lys]-D-Pro-D-Val-NH2 |
| 345 | TCAM342 | Val-Arg-Leu-Ile-Val-Ala-Val-Arg-Ile-Trp-Arg-Arg-c[Asp-Pro-Trp-Trp-Arg-Arg-Trp-Trp-Arg-Arg-Lys]-D-Phe-D-Val-NH2 |
| 346 | TCAM343 | Val-Arg-Leu-Ile-Val-Ala-Val-Arg-Ile-Trp-Arg-Arg-c[Asp-Pro-Trp-Arg-Trp-Arg-Trp-Arg-Lys]-D-Val-D-Pro-NH2 |
| 347 | TCAM344 | Val-Arg-Leu-Ile-Val-Ala-Val-Arg-Ile-Trp-Arg-Arg-c[Asp-Pro-Trp-Arg-Trp-Arg-Trp-Arg-Lys]-D-Val-D-Phe-NH2 |
| 348 | TCAM345 | Val-Arg-Leu-Ile-Val-Ala-Val-Arg-Ile-Trp-Arg-Arg-c[Asp-Pro-Trp-Arg-Trp-Arg-Trp-Arg-Lys]-D-Pro-D-Val-NH2 |
| 349 | TCAM346 | Val-Arg-Leu-Ile-Val-Ala-Val-Arg-Ile-Trp-Arg-Arg-c[Asp-Pro-Trp-Arg-Trp-Arg-Trp-Arg-Lys]-D-Phe-D-Val-NH2 |
| 350 | TCAM347 | Val-Arg-Leu-Ile-Val-Ala-Val-Arg-Ile-Trp-Arg-Arg-c[Asp-Pro-Arg-Trp-Arg-Trp-Arg-Trp-Lys]-D-Val-D-Pro-NH2 |
| 351 | TCAM348 | Val-Arg-Leu-Ile-Val-Ala-Val-Arg-Ile-Trp-Arg-Arg-c[Asp-Pro-Arg-Trp-Arg-Trp-Arg-Trp-Lys]-D-Val-D-Phe-NH2 |
| 352 | TCAM349 | Val-Arg-Leu-Ile-Val-Ala-Val-Arg-Ile-Trp-Arg-Arg-c[Asp-Pro-Arg-Trp-Arg-Trp-Arg-Trp-Lys]-D-Pro-D-Val-NH2 |
| 353 | TCAM350 | Val-Arg-Leu-Ile-Val-Ala-Val-Arg-Ile-Trp-Arg-Arg-c[Asp-Pro-Arg-Trp-Arg-Trp-Arg-Trp-Lys]-D-Phe-D-Val-NH2 |
| 354 | TCAM351 | Val-Arg-Leu-Ile-Val-Ala-Val-Arg-Ile-Trp-Arg-Arg-c[Asp-Pro-Arg-Trp-Trp-Arg-Arg-Lys]-D-Val-D-Pro-NH2 |

TABLE 5-continued

Exemplary Anti-microbial peptides

| SEQ NO: | Peptide | Peptide Sequence |
|---|---|---|
| 355 | TCAM352 | Val-Arg-Leu-Ile-Val-Ala-Val-Arg-Ile-Trp-Arg-Arg-c[Asp-Pro-Arg-Trp-Trp-Arg-Arg-Lys]-D-Val-D-Phe-NH2 |
| 356 | TCAM353 | Val-Arg-Leu-Ile-Val-Ala-Val-Arg-Ile-Trp-Arg-Arg-c[Asp-Pro-Arg-Trp-Trp-Arg-Arg-Lys]-D-Pro-D-Val-NH2 |
| 357 | TCAM354 | Val-Arg-Leu-Ile-Val-Ala-Val-Arg-Ile-Trp-Arg-Arg-c[Asp-Pro-Arg-Trp-Trp-Arg-Arg-Lys]-D-Phe-D-Val-NH2 |
| 358 | TCAM355 | Val-Arg-Leu-Ile-Val-Ala-Val-Arg-Ile-Trp-Arg-Arg-c[Asp-Pro-Trp-Trp-Arg-Arg-Trp-Lys]-D-Val-D-Pro-NH2 |
| 359 | TCAM356 | Val-Arg-Leu-Ile-Val-Ala-Val-Arg-Ile-Trp-Arg-Arg-c[Asp-Pro-Trp-Trp-Arg-Arg-Trp-Lys]-D-Val-D-Phe-NH2 |
| 360 | TCAM357 | Val-Arg-Leu-Ile-Val-Ala-Val-Arg-Ile-Trp-Arg-Arg-c[Asp-Pro-Trp-Trp-Arg-Arg-Trp-Lys]-D-Pro-D-Val-NH2 |
| 361 | TCAM358 | Val-Arg-Leu-Ile-Val-Ala-Val-Arg-Ile-Trp-Arg-Arg-c[Asp-Pro-Trp-Trp-Arg-Arg-Trp-Lys]-D-Phe-D-Val-NH2 |
| 362 | TCAM359 | Val-Arg-Leu-Ile-Val-Ala-Val-Arg-Ile-Trp-Arg-Arg-c[Asp-Pro-Trp-Arg-Trp-Arg-Trp-Lys]-D-Val-D-Pro-NH2 |
| 363 | TCAM360 | Val-Arg-Leu-Ile-Val-Ala-Val-Arg-Ile-Trp-Arg-Arg-c[Asp-Pro-Trp-Arg-Trp-Arg-Trp-Lys]-D-Val-D-Phe-NH2 |
| 364 | TCAM361 | Val-Arg-Leu-Ile-Val-Ala-Val-Arg-Ile-Trp-Arg-Arg-c[Asp-Pro-Trp-Arg-Trp-Arg-Trp-Lys]-D-Pro-D-Val-NH2 |
| 365 | TCAM362 | Val-Arg-Leu-Ile-Val-Ala-Val-Arg-Ile-Trp-Arg-Arg-c[Asp-Pro-Trp-Arg-Trp-Arg-Trp-Lys]-D-Phe-D-Val-NH2 |
| 366 | TCAM363 | Val-Arg-Leu-Ile-Val-Ala-Val-Arg-Ile-Trp-Arg-Arg-c[Asp-Pro-Arg-Trp-Arg-Trp-Arg-Lys]-D-Val-D-Pro-NH2 |
| 367 | TCAM364 | Val-Arg-Leu-Ile-Val-Ala-Val-Arg-Ile-Trp-Arg-Arg-c[Asp-Pro-Arg-Trp-Arg-Trp-Arg-Lys]-D-Val-D-Phe-NH2 |
| 368 | TCAM365 | Val-Arg-Leu-Ile-Val-Ala-Val-Arg-Ile-Trp-Arg-Arg-c[Asp-Pro-Arg-Trp-Arg-Trp-Arg-Lys]-D-Pro-D-Val-NH2 |
| 369 | TCAM366 | Val-Arg-Leu-Ile-Val-Ala-Val-Arg-Ile-Trp-Arg-Arg-c[Asp-Pro-Arg-Trp-Arg-Trp-Arg-Lys]-D-Phe-D-Val-NH2 |
| 370 | TCAM367 | Val-Arg-Leu-Ile-Val-Ala-Val-Arg-Ile-Trp-Arg-Arg-c[Asp-Pro-Trp-Arg-Tyr-Arg-Trp-Lys]-D-Val-D-Pro-NH2 |
| 371 | TCAM368 | Val-Arg-Leu-Ile-Val-Ala-Val-Arg-Ile-Trp-Arg-Arg-c[Asp-Pro-Trp-Arg-Tyr-Arg-Trp-Lys]-D-Val-D-Phe-NH2 |
| 372 | TCAM369 | Val-Arg-Leu-Ile-Val-Ala-Val-Arg-Ile-Trp-Arg-Arg-c[Asp-Pro-Trp-Arg-Tyr-Arg-Trp-Lys]-D-Pro-D-Val-NH2 |
| 373 | TCAM370 | Val-Arg-Leu-Ile-Val-Ala-Val-Arg-Ile-Trp-Arg-Arg-c[Asp-Pro-Trp-Arg-Tyr-Arg-Trp-Lys]-D-Phe-D-Val-NH2 |
| 374 | TCAM371 | Val-Arg-Leu-Ile-Val-Ala-Val-Arg-Ile-Trp-Arg-Arg-c[Asp-Pro-Trp-Arg-Trp-Arg-Tyr-Lys]-D-Val-D-Pro-NH2 |
| 375 | TCAM372 | Val-Arg-Leu-Ile-Val-Ala-Val-Arg-Ile-Trp-Arg-Arg-c[Asp-Pro-Trp-Arg-Trp-Arg-Tyr-Lys]-D-Val-D-Phe-NH2 |
| 376 | TCAM373 | Val-Arg-Leu-Ile-Val-Ala-Val-Arg-Ile-Trp-Arg-Arg-c[Asp-Pro-Trp-Arg-Trp-Arg-Tyr-Lys]-D-Pro-D-Val-NH2 |
| 377 | TCAM374 | Val-Arg-Leu-Ile-Val-Ala-Val-Arg-Ile-Trp-Arg-Arg-c[Asp-Pro-Trp-Arg-Trp-Arg-Tyr-Lys]-D-Phe-D-Val-NH2 |
| 378 | TCAM375 | Val-Arg-Leu-Ile-Val-Ala-Val-Arg-Ile-Trp-Arg-Arg-c[Asp-Pro-Trp-Arg-Trp-Arg-Lys]-D-Val-D-Pro-NH2 |
| 379 | TCAM376 | Val-Arg-Leu-Ile-Val-Ala-Val-Arg-Ile-Trp-Arg-Arg-c[Asp-Pro-Trp-Arg-Trp-Arg-Lys]-D-Val-D-Phe-NH2 |

TABLE 5-continued

Exemplary Anti-microbial peptides

| SEQ NO: | Peptide | Peptide Sequence |
|---|---|---|
| 380 | TCAM377 | Val-Arg-Leu-Ile-Val-Ala-Val-Arg-Ile-Trp-Arg-Arg-c[Asp-Pro-Trp-Arg-Trp-Arg-Lys]-D-Pro-D-Val-NH2 |
| 381 | TCAM378 | Val-Arg-Leu-Ile-Val-Ala-Val-Arg-Ile-Trp-Arg-Arg-c[Asp-Pro-Trp-Arg-Trp-Arg-Lys]-D-Phe-D-Val-NH2 |
| 382 | TCAM379 | Val-Arg-Leu-Ile-Val-Ala-Val-Arg-Ile-Trp-Arg-Arg-c[Asp-Pro-Trp-Arg-Arg-Trp-Lys]-D-Val-D-Pro-NH2 |
| 383 | TCAM380 | Val-Arg-Leu-Ile-Val-Ala-Val-Arg-Ile-Trp-Arg-Arg-c[Asp-Pro-Trp-Arg-Arg-Trp-Lys]-D-Val-D-Phe-NH2 |
| 384 | TCAM381 | Val-Arg-Leu-Ile-Val-Ala-Val-Arg-Ile-Trp-Arg-Arg-c[Asp-Pro-Trp-Arg-Arg-Trp-Lys]-D-Pro-D-Val-NH2 |
| 385 | TCAM382 | Val-Arg-Leu-Ile-Val-Ala-Val-Arg-Ile-Trp-Arg-Arg-c[Asp-Pro-Trp-Arg-Arg-Trp-Lys]-D-Phe-D-Val-NH2 |
| 386 | TCAM383 | Val-Arg-Leu-Ile-Val-Ala-Val-Arg-Ile-Trp-Arg-Arg-c[Asp-Pro-Arg-Trp-Trp-Arg-Lys]-D-Val-D-Pro-NH2 |
| 387 | TCAM384 | Val-Arg-Leu-Ile-Val-Ala-Val-Arg-Ile-Trp-Arg-Arg-c[Asp-Pro-Arg-Trp-Trp-Arg-Lys]-D-Val-D-Phe-NH2 |
| 388 | TCAM385 | Val-Arg-Leu-Ile-Val-Ala-Val-Arg-Ile-Trp-Arg-Arg-c[Asp-Pro-Arg-Trp-Trp-Arg-Lys]-D-Pro-D-Val-NH2 |
| 389 | TCAM386 | Val-Arg-Leu-Ile-Val-Ala-Val-Arg-Ile-Trp-Arg-Arg-c[Asp-Pro-Arg-Trp-Trp-Arg-Lys]-D-Phe-D-Val-NH2 |
| 390 | TCAM387 | Val-Arg-Leu-Ile-Val-Ala-Val-Arg-Ile-Trp-Arg-Arg-c[Asp-Pro-Trp-Arg-Trp-Lys]-D-Val-D-Pro-NH2 |
| 391 | TCAM388 | Val-Arg-Leu-Ile-Val-Ala-Val-Arg-Ile-Trp-Arg-Arg-c[Asp-Pro-Trp-Arg-Trp-Lys]-D-Val-D-Phe-NH2 |
| 392 | TCAM389 | Val-Arg-Leu-Ile-Val-Ala-Val-Arg-Ile-Trp-Arg-Arg-c[Asp-Pro-Trp-Arg-Trp-Lys]-D-Pro-D-Val-NH2 |
| 393 | TCAM390 | Val-Arg-Leu-Ile-Val-Ala-Val-Arg-Ile-Trp-Arg-Arg-c[Asp-Pro-Trp-Arg-Trp-Lys]-D-Phe-D-Val-NH2 |
| 394 | TCAM391 | Val-Arg-Leu-Ile-Val-Ala-Val-Arg-Ile-Trp-Arg-Arg-c[Asp-Pro-Arg-Trp-Arg-Lys]-D-Val-D-Pro-NH2 |
| 395 | TCAM392 | Val-Arg-Leu-Ile-Val-Ala-Val-Arg-Ile-Trp-Arg-Arg-c[Asp-Pro-Arg-Trp-Arg-Lys]-D-Val-D-Phe-NH2 |
| 396 | TCAM393 | Val-Arg-Leu-Ile-Val-Ala-Val-Arg-Ile-Trp-Arg-Arg-c[Asp-Pro-Arg-Trp-Arg-Lys]-D-Pro-D-Val-NH2 |
| 397 | TCAM394 | Val-Arg-Leu-Ile-Val-Ala-Val-Arg-Ile-Trp-Arg-Arg-c[Asp-Pro-Arg-Trp-Arg-Lys]-D-Phe-D-Val-NH2 |
| 398 | TCAM395 | Val-Arg-Leu-Ile-Val-Ala-Val-Arg-Ile-Trp-Arg-Arg-c[Asp-Arg-Arg-Trp-Trp-Arg-Phe-Lys]-D-Val-D-Pro-NH2 |
| 399 | TCAM396 | Val-Arg-Leu-Ile-Val-Ala-Val-Arg-Ile-Trp-Arg-Arg-c[Asp-Arg-Arg-Trp-Trp-Arg-Phe-Lys]-D-Val-D-Phe-NH2 |
| 400 | TCAM397 | Val-Arg-Leu-Ile-Val-Ala-Val-Arg-Ile-Trp-Arg-Arg-c[Asp-Arg-Arg-Trp-Trp-Arg-Phe-Lys]-D-Pro-D-Val-NH2 |
| 401 | TCAM398 | Val-Arg-Leu-Ile-Val-Ala-Val-Arg-Ile-Trp-Arg-Arg-c[Asp-Arg-Arg-Trp-Trp-Arg-Phe-Lys]-D-Phe-D-Val-NH2 |
| 402 | TCAM399 | Val-Arg-Leu-Ile-Val-Ala-Val-Arg-Ile-Trp-Arg-Arg-c[Asp-Arg-Arg-Trp-Trp-Arg-Phe-Lys]-D-Val-D-Pro-NH2 |
| 403 | TCAM400 | Val-Arg-Leu-Ile-Val-Ala-Val-Arg-Ile-Trp-Arg-Arg-c[Asp-Arg-Arg-Trp-Trp-Arg-Phe-Lys]-D-Val-D-Phe-NH2 |
| 404 | TCAM401 | Val-Arg-Leu-Ile-Val-Ala-Val-Arg-Ile-Trp-Arg-Arg-c[Asp-Arg-Arg-Trp-Trp-Arg-Phe-Lys]-D-Pro-D-Val-NH2 |

TABLE 5-continued

Exemplary Anti-microbial peptides

| SEQ NO: | Peptide | Peptide Sequence |
|---|---|---|
| 405 | TCAM402 | Val-Arg-Leu-Ile-Val-Ala-Val-Arg-Ile-Trp-Arg-Arg-c[Asp-Arg-Arg-Trp-Trp-Arg-Phe-Lys]-D-Phe-D-Val-NH2 |
| 406 | TCAM403 | Val-Arg-Leu-Ile-Val-Ala-Val-Arg-Ile-Trp-Arg-Arg-c[Asp-Arg-Arg-Tyr-Tyr-Arg-Phe-Lys]-D-Val-D-Pro-NH2 |
| 407 | TCAM404 | Val-Arg-Leu-Ile-Val-Ala-Val-Arg-Ile-Trp-Arg-Arg-c[Asp-Arg-Arg-Tyr-Tyr-Arg-Phe-Lys]-D-Val-D-Phe-NH2 |
| 408 | TCAM405 | Val-Arg-Leu-Ile-Val-Ala-Val-Arg-Ile-Trp-Arg-Arg-c[Asp-Arg-Arg-Tyr-Tyr-Arg-Phe-Lys]-D-Pro-D-Val-NH2 |
| 409 | TCAM406 | Val-Arg-Leu-Ile-Val-Ala-Val-Arg-Ile-Trp-Arg-Arg-c[Asp-Arg-Arg-Tyr-Tyr-Arg-Phe-Lys]-D-Phe-D-Val-NH2 |
| 410 | TCAM407 | Val-Arg-Leu-Ile-Val-Ala-Val-Arg-Ile-Trp-Arg-Arg-c[Asp-Arg-Arg-Nal-Nal-Arg-Phe-Lys]-D-Val-D-Pro-NH2 |
| 411 | TCAM408 | Val-Arg-Leu-Ile-Val-Ala-Val-Arg-Ile-Trp-Arg-Arg-c[Asp-Arg-Arg-Nal-Nal-Arg-Phe-Lys]-D-Val-D-Phe-NH2 |
| 412 | TCAM409 | Val-Arg-Leu-Ile-Val-Ala-Val-Arg-Ile-Trp-Arg-Arg-c[Asp-Arg-Arg-Nal-Nal-Arg-Phe-Lys]-D-Pro-D-Val-NH2 |
| 413 | TCAM410 | Val-Arg-Leu-Ile-Val-Ala-Val-Arg-Ile-Trp-Arg-Arg-c[Asp-Arg-Arg-Nal-Nal-Arg-Phe-Lys]-D-Phe-D-Val-NH2 |
| 414 | TCAM411 | Val-Arg-Leu-Ile-Val-Ala-Val-Arg-Ile-Trp-Arg-Arg-c[Asp-Arg-Arg-Leu-Trp-Leu-Trp-Lys]-D-Val-D-Pro-NH2 |
| 415 | TCAM412 | Val-Arg-Leu-Ile-Val-Ala-Val-Arg-Ile-Trp-Arg-Arg-c[Asp-Arg-Arg-Leu-Trp-Leu-Trp-Lys]-D-Val-D-Phe-NH2 |
| 416 | TCAM413 | Val-Arg-Leu-Ile-Val-Ala-Val-Arg-Ile-Trp-Arg-Arg-c[Asp-Arg-Arg-Leu-Trp-Leu-Trp-Lys]-D-Pro-D-Val-NH2 |
| 417 | TCAM414 | Val-Arg-Leu-Ile-Val-Ala-Val-Arg-Ile-Trp-Arg-Arg-c[Asp-Arg-Arg-Leu-Trp-Leu-Trp-Lys]-D-Phe-D-Val-NH2 |
| 418 | TCAM415 | Val-Arg-Leu-Ile-Val-Ala-Val-Arg-Ile-Trp-Arg-Arg-c[Asp-Arg-Arg-Leu-Trp-Leu-Trp-Lys]-D-Val-D-Pro-NH2 |
| 419 | TCAM416 | Val-Arg-Leu-Ile-Val-Ala-Val-Arg-Ile-Trp-Arg-Arg-c[Asp-Arg-Arg-Leu-Trp-Leu-Trp-Lys]-D-Val-D-Phe-NH2 |
| 420 | TCAM417 | Val-Arg-Leu-Ile-Val-Ala-Val-Arg-Ile-Trp-Arg-Arg-c[Asp-Arg-Arg-Leu-Trp-Leu-Trp-Lys]-D-Pro-D-Val-NH2 |
| 421 | TCAM418 | Val-Arg-Leu-Ile-Val-Ala-Val-Arg-Ile-Trp-Arg-Arg-c[Asp-Arg-Arg-Leu-Trp-Leu-Trp-Lys]-D-Phe-D-Val-NH2 |
| 422 | TCAM419 | Val-Arg-Leu-Ile-Val-Ala-Val-Arg-Ile-Trp-Arg-Arg-c[Asp-Arg-Arg-Arg-Trp-Leu-Trp-Leu-Trp-Lys]-D-Val-D-Pro-NH2 |
| 423 | TCAM420 | Val-Arg-Leu-Ile-Val-Ala-Val-Arg-Ile-Trp-Arg-Arg-c[Asp-Arg-Arg-Arg-Trp-Leu-Trp-Leu-Trp-Lys]-D-Val-D-Phe-NH2 |
| 424 | TCAM421 | Val-Arg-Leu-Ile-Val-Ala-Val-Arg-Ile-Trp-Arg-Arg-c[Asp-Arg-Arg-Arg-Trp-Leu-Trp-Leu-Trp-Lys]-D-Pro-D-Val-NH2 |
| 425 | TCAM422 | Val-Arg-Leu-Ile-Val-Ala-Val-Arg-Ile-Trp-Arg-Arg-c[Asp-Arg-Arg-Arg-Trp-Leu-Trp-Leu-Trp-Lys]-D-Phe-D-Val-NH2 |
| 426 | TCAM423 | Val-Arg-Leu-Ile-Val-Ala-Val-Arg-Ile-Trp-Arg-Arg-c[Asp-Arg-Gln-Arg-Arg-Trp-Leu-Trp-Leu-Trp-Lys]-D-Val-D-Pro-NH2 |
| 427 | TCAM424 | Val-Arg-Leu-Ile-Val-Ala-Val-Arg-Ile-Trp-Arg-Arg-c[Asp-Arg-Gln-Arg-Arg-Trp-Leu-Trp-Leu-Trp-Lys]-D-Val-D-Phe-NH2 |
| 428 | TCAM425 | Val-Arg-Leu-Ile-Val-Ala-Val-Arg-Ile-Trp-Arg-Arg-c[Asp-Arg-Gln-Arg-Arg-Trp-Leu-Trp-Leu-Trp-Lys]-D-Pro-D-Val-NH2 |
| 429 | TCAM426 | Val-Arg-Leu-Ile-Val-Ala-Val-Arg-Ile-Trp-Arg-Arg-c[Asp-Arg-Gln-Arg-Arg-Trp-Leu-Trp-Leu-Trp-Lys]-D-Phe-D-Val-NH2 |

TABLE 5-continued

Exemplary Anti-microbial peptides

| SEQ NO: | Peptide | Peptide Sequence |
|---|---|---|
| 430 | TCAM427 | Val-Arg-Leu-Ile-Val-Ala-Val-Arg-Ile-Trp-Arg-Arg-c[Asp-Trp-Arg-Trp-Trp-Arg-Arg-Lys]-D-Val-D-Pro-NH2 |
| 431 | TCAM428 | Val-Arg-Leu-Ile-Val-Ala-Val-Arg-Ile-Trp-Arg-Arg-c[Asp-Trp-Arg-Trp-Trp-Arg-Arg-Lys]-D-Val-D-Phe-NH2 |
| 432 | TCAM429 | Val-Arg-Leu-Ile-Val-Ala-Val-Arg-Ile-Trp-Arg-Arg-c[Asp-Trp-Arg-Trp-Trp-Arg-Arg-Lys]-D-Pro-D-Val-NH2 |
| 433 | TCAM430 | Val-Arg-Leu-Ile-Val-Ala-Val-Arg-Ile-Trp-Arg-Arg-c[Asp-Trp-Arg-Trp-Trp-Arg-Arg-Lys]-D-Phe-D-Val-NH2 |
| 434 | TCAM431 | Val-Arg-Leu-Ile-Val-Ala-Val-Arg-Ile-Trp-Arg-Arg-c[Asp-Trp-Trp-Arg-Arg-Trp-Trp-Arg-Arg-Lys]-D-Val-D-Pro-NH2 |
| 435 | TCAM432 | Val-Arg-Leu-Ile-Val-Ala-Val-Arg-Ile-Trp-Arg-Arg-c[Asp-Trp-Trp-Arg-Arg-Trp-Trp-Arg-Arg-Lys]-D-Val-D-Phe-NH2 |
| 436 | TCAM433 | Val-Arg-Leu-Ile-Val-Ala-Val-Arg-Ile-Trp-Arg-Arg-c[Asp-Trp-Trp-Arg-Arg-Trp-Trp-Arg-Arg-Lys]-D-Pro-D-Val-NH2 |
| 437 | TCAM434 | Val-Arg-Leu-Ile-Val-Ala-Val-Arg-Ile-Trp-Arg-Arg-c[Asp-Trp-Trp-Arg-Arg-Trp-Trp-Arg-Arg-Lys]-D-Phe-D-Val-NH2 |
| 438 | TCAM435 | Val-Arg-Leu-Ile-Val-Ala-Val-Arg-Ile-Trp-Arg-Arg-c[Asp-Trp-Arg-Trp-Arg-Trp-Arg-Lys]-D-Val-D-Pro-NH2 |
| 439 | TCAM436 | Val-Arg-Leu-Ile-Val-Ala-Val-Arg-Ile-Trp-Arg-Arg-c[Asp-Trp-Arg-Trp-Arg-Trp-Arg-Lys]-D-Val-D-Phe-NH2 |
| 440 | TCAM437 | Val-Arg-Leu-Ile-Val-Ala-Val-Arg-Ile-Trp-Arg-Arg-c[Asp-Trp-Arg-Trp-Arg-Trp-Arg-Lys]-D-Pro-D-Val-NH2 |
| 441 | TCAM438 | Val-Arg-Leu-Ile-Val-Ala-Val-Arg-Ile-Trp-Arg-Arg-c[Asp-Trp-Arg-Trp-Arg-Trp-Arg-Lys]-D-Phe-D-Val-NH2 |
| 442 | TCAM439 | Val-Arg-Leu-Ile-Val-Ala-Val-Arg-Ile-Trp-Arg-Arg-c[Asp-Arg-Trp-Arg-Trp-Arg-Trp-Lys]-D-Val-D-Pro-NH2 |
| 443 | TCAM440 | Val-Arg-Leu-Ile-Val-Ala-Val-Arg-Ile-Trp-Arg-Arg-c[Asp-Arg-Trp-Arg-Trp-Arg-Trp-Lys]-D-Val-D-Phe-NH2 |
| 444 | TCAM441 | Val-Arg-Leu-Ile-Val-Ala-Val-Arg-Ile-Trp-Arg-Arg-c[Asp-Arg-Trp-Arg-Trp-Arg-Trp-Lys]-D-Pro-D-Val-NH2 |
| 445 | TCAM442 | Val-Arg-Leu-Ile-Val-Ala-Val-Arg-Ile-Trp-Arg-Arg-c[Asp-Arg-Trp-Arg-Trp-Arg-Trp-Lys]-D-Phe-D-Val-NH2 |
| 446 | TCAM443 | Val-Arg-Leu-Ile-Val-Ala-Val-Arg-Ile-Trp-Arg-Arg-c[Asp-Arg-Trp-Trp-Arg-Arg-Lys]-D-Val-D-Pro-NH2 |
| 447 | TCAM444 | Val-Arg-Leu-Ile-Val-Ala-Val-Arg-Ile-Trp-Arg-Arg-c[Asp-Arg-Trp-Trp-Arg-Arg-Lys]-D-Val-D-Phe-NH2 |
| 448 | TCAM445 | Val-Arg-Leu-Ile-Val-Ala-Val-Arg-Ile-Trp-Arg-Arg-c[Asp-Arg-Trp-Trp-Arg-Arg-Lys]-D-Pro-D-Val-NH2 |
| 449 | TCAM446 | Val-Arg-Leu-Ile-Val-Ala-Val-Arg-Ile-Trp-Arg-Arg-c[Asp-Arg-Trp-Trp-Arg-Arg-Lys]-D-Phe-D-Val-NH2 |
| 450 | TCAM447 | Val-Arg-Leu-Ile-Val-Ala-Val-Arg-Ile-Trp-Arg-Arg-c[Asp-Arg-Trp-Arg-Trp-Arg-Lys]-D-Val-D-Pro-NH2 |
| 451 | TCAM448 | Val-Arg-Leu-Ile-Val-Ala-Val-Arg-Ile-Trp-Arg-Arg-c[Asp-Arg-Trp-Arg-Trp-Arg-Lys]-D-Val-D-Phe-NH2 |
| 452 | TCAM449 | Val-Arg-Leu-Ile-Val-Ala-Val-Arg-Ile-Trp-Arg-Arg-c[Asp-Arg-Trp-Arg-Trp-Arg-Lys]-D-Pro-D-Val-NH2 |
| 453 | TCAM450 | Val-Arg-Leu-Ile-Val-Ala-Val-Arg-Ile-Trp-Arg-Arg-c[Asp-Arg-Trp-Arg-Trp-Arg-Lys]-D-Phe-D-Val-NH2 |
| 454 | TCAM451 | Val-Arg-Leu-Ile-Val-Ala-Val-Arg-Ile-Trp-Arg-Arg-c[Asp-Trp-Trp-Arg-Arg-Trp-Lys]-D-Val-D-Pro-NH2 |

TABLE 5-continued

Exemplary Anti-microbial peptides

| SEQ NO: | Peptide | Peptide Sequence |
|---|---|---|
| 455 | TCAM452 | Val-Arg-Leu-Ile-Val-Ala-Val-Arg-Ile-Trp-Arg-Arg-c[Asp-Trp-Trp-Arg-Arg-Trp-Lys]-D-Val-D-Phe-NH2 |
| 456 | TCAM453 | Val-Arg-Leu-Ile-Val-Ala-Val-Arg-Ile-Trp-Arg-Arg-c[Asp-Trp-Trp-Arg-Arg-Trp-Lys]-D-Pro-D-Val-NH2 |
| 457 | TCAM454 | Val-Arg-Leu-Ile-Val-Ala-Val-Arg-Ile-Trp-Arg-Arg-c[Asp-Trp-Trp-Arg-Arg-Trp-Lys]-D-Phe-D-Val-NH2 |
| 458 | TCAM455 | Val-Arg-Leu-Ile-Val-Ala-Val-Arg-Ile-Trp-Arg-Arg-c[Asp-Trp-Arg-Trp-Arg-Trp-Lys]-D-Val-D-Pro-NH2 |
| 459 | TCAM456 | Val-Arg-Leu-Ile-Val-Ala-Val-Arg-Ile-Trp-Arg-Arg-c[Asp-Trp-Arg-Trp-Arg-Trp-Lys]-D-Val-D-Phe-NH2 |
| 460 | TCAM457 | Val-Arg-Leu-Ile-Val-Ala-Val-Arg-Ile-Trp-Arg-Arg-c[Asp-Trp-Arg-Trp-Arg-Trp-Lys]-D-Pro-D-Val-NH2 |
| 461 | TCAM458 | Val-Arg-Leu-Ile-Val-Ala-Val-Arg-Ile-Trp-Arg-Arg-c[Asp-Trp-Arg-Trp-Arg-Trp-Lys]-D-Phe-D-Val-NH2 |
| 462 | TCAM459 | Val-Arg-Leu-Ile-Val-Ala-Val-Arg-Ile-Trp-Arg-Arg-c[Asp-Trp-Arg-Tyr-Arg-Trp-Lys]-D-Val-D-Pro-NH2 |
| 463 | TCAM460 | Val-Arg-Leu-Ile-Val-Ala-Val-Arg-Ile-Trp-Arg-Arg-c[Asp-Trp-Arg-Tyr-Arg-Trp-Lys]-D-Val-D-Phe-NH2 |
| 464 | TCAM461 | Val-Arg-Leu-Ile-Val-Ala-Val-Arg-Ile-Trp-Arg-Arg-c[Asp-Trp-Arg-Tyr-Arg-Trp-Lys]-D-Pro-D-Val-NH2 |
| 465 | TCAM462 | Val-Arg-Leu-Ile-Val-Ala-Val-Arg-Ile-Trp-Arg-Arg-c[Asp-Trp-Arg-Tyr-Arg-Trp-Lys]-D-Phe-D-Val-NH2 |
| 466 | TCAM463 | Val-Arg-Leu-Ile-Val-Ala-Val-Arg-Ile-Trp-Arg-Arg-c[Asp-Trp-Arg-Trp-Arg-Tyr-Lys]-D-Val-D-Pro-NH2 |
| 467 | TCAM464 | Val-Arg-Leu-Ile-Val-Ala-Val-Arg-Ile-Trp-Arg-Arg-c[Asp-Trp-Arg-Trp-Arg-Tyr-Lys]-D-Val-D-Phe-NH2 |
| 468 | TCAM465 | Val-Arg-Leu-Ile-Val-Ala-Val-Arg-Ile-Trp-Arg-Arg-c[Asp-Trp-Arg-Trp-Arg-Tyr-Lys]-D-Pro-D-Val-NH2 |
| 469 | TCAM466 | Val-Arg-Leu-Ile-Val-Ala-Val-Arg-Ile-Trp-Arg-Arg-c[Asp-Trp-Arg-Trp-Arg-Tyr-Lys]-D-Phe-D-Val-NH2 |
| 470 | TCAM467 | Val-Arg-Leu-Ile-Val-Ala-Val-Arg-Ile-Trp-Arg-Arg-c[Asp-Trp-Arg-Trp-Arg-Lys]-D-Val-D-Pro-NH2 |
| 471 | TCAM468 | Val-Arg-Leu-Ile-Val-Ala-Val-Arg-Ile-Trp-Arg-Arg-c[Asp-Trp-Arg-Trp-Arg-Lys]-D-Val-D-Phe-NH2 |
| 472 | TCAM469 | Val-Arg-Leu-Ile-Val-Ala-Val-Arg-Ile-Trp-Arg-Arg-c[Asp-Trp-Arg-Trp-Arg-Lys]-D-Pro-D-Val-NH2 |
| 473 | TCAM470 | Val-Arg-Leu-Ile-Val-Ala-Val-Arg-Ile-Trp-Arg-Arg-c[Asp-Trp-Arg-Trp-Arg-Lys]-D-Phe-D-Val-NH2 |
| 474 | TCAM471 | Val-Arg-Leu-Ile-Val-Ala-Val-Arg-Ile-Trp-Arg-Arg-c[Asp-Trp-Arg-Arg-Trp-Lys]-D-Val-D-Pro-NH2 |
| 475 | TCAM472 | Val-Arg-Leu-Ile-Val-Ala-Val-Arg-Ile-Trp-Arg-Arg-c[Asp-Trp-Arg-Arg-Trp-Lys]-D-Val-D-Phe-NH2 |
| 476 | TCAM473 | Val-Arg-Leu-Ile-Val-Ala-Val-Arg-Ile-Trp-Arg-Arg-c[Asp-Trp-Arg-Arg-Trp-Lys]-D-Pro-D-Val-NH2 |
| 477 | TCAM474 | Val-Arg-Leu-Ile-Val-Ala-Val-Arg-Ile-Trp-Arg-Arg-c[Asp-Trp-Arg-Arg-Trp-Lys]-D-Phe-D-Val-NH2 |
| 478 | TCAM475 | Val-Arg-Leu-Ile-Val-Ala-Val-Arg-Ile-Trp-Arg-Arg-c[Asp-Arg-Trp-Trp-Arg-Lys]-D-Val-D-Pro-NH2 |
| 479 | TCAM476 | Val-Arg-Leu-Ile-Val-Ala-Val-Arg-Ile-Trp-Arg-Arg-c[Asp-Arg-Trp-Trp-Arg-Lys]-D-Val-D-Phe-NH2 |

TABLE 5-continued

Exemplary Anti-microbial peptides

| SEQ NO: | Peptide | Peptide Sequence |
|---|---|---|
| 480 | TCAM477 | Val-Arg-Leu-Ile-Val-Ala-Val-Arg-Ile-Trp-Arg-Arg-c[Asp-Arg-Trp-Trp-Arg-Lys]-D-Pro-D-Val-NH2 |
| 481 | TCAM478 | Val-Arg-Leu-Ile-Val-Ala-Val-Arg-Ile-Trp-Arg-Arg-c[Asp-Arg-Trp-Trp-Arg-Lys]-D-Phe-D-Val-NH2 |
| 482 | TCAM479 | Val-Arg-Leu-Ile-Val-Ala-Val-Arg-Ile-Trp-Arg-Arg-c[Asp-Trp-Arg-Trp-Lys]-D-Val-D-Pro-NH2 |
| 483 | TCAM480 | Val-Arg-Leu-Ile-Val-Ala-Val-Arg-Ile-Trp-Arg-Arg-c[Asp-Trp-Arg-Trp-Lys]-D-Val-D-Phe-NH2 |
| 484 | TCAM481 | Val-Arg-Leu-Ile-Val-Ala-Val-Arg-Ile-Trp-Arg-Arg-c[Asp-Trp-Arg-Trp-Lys]-D-Pro-D-Val-NH2 |
| 485 | TCAM482 | Val-Arg-Leu-Ile-Val-Ala-Val-Arg-Ile-Trp-Arg-Arg-c[Asp-Trp-Arg-Trp-Lys]-D-Phe-D-Val-NH2 |
| 486 | TCAM483 | Val-Arg-Leu-Ile-Val-Ala-Val-Arg-Ile-Trp-Arg-Arg-c[Asp-Arg-Trp-Arg-Lys]-D-Val-D-Pro-NH2 |
| 487 | TCAM484 | Val-Arg-Leu-Ile-Val-Ala-Val-Arg-Ile-Trp-Arg-Arg-c[Asp-Arg-Trp-Arg-Lys]-D-Val-D-Phe-NH2 |
| 488 | TCAM485 | Val-Arg-Leu-Ile-Val-Ala-Val-Arg-Ile-Trp-Arg-Arg-c[Asp-Arg-Trp-Arg-Lys]-D-Pro-D-Val-NH2 |
| 489 | TCAM486 | Val-Arg-Leu-Ile-Val-Ala-Val-Arg-Ile-Trp-Arg-Arg-c[Asp-Arg-Trp-Arg-Lys]-D-Phe-D-Val-NH2 |
| 490 | TCAM487 | Val-Arg-Leu-Ile-Val-Ala-Val-Arg-Ile-Trp-Arg-Arg-c[Asp-His-D-Nal(2')-Arg-Trp-Lys]-D-Val-D-Pro-NH2 |
| 491 | TCAM488 | Val-Arg-Leu-Ile-Val-Ala-Val-Arg-Ile-Trp-Arg-Arg-c[Asp-His-D-Nal(2')-Arg-Trp-Lys]-D-Pro-D-Val-NH2 |
| 492 | TCAM489 | Val-Arg-Leu-Ile-Val-Ala-Val-Arg-Ile-Trp-Arg-Arg-c[Asp-His-D-Nal(2')-Arg-Trp-Lys]-D-Val-D-Phe-NH2 |
| 493 | TCAM490 | Val-Arg-Leu-Ile-Val-Ala-Val-Arg-Ile-Trp-Arg-Arg-c[Asp-His-D-Nal(2')-Arg-Trp-Lys]-D-Phe-D-Val-NH2 |
| 494 | TCAM491 | Val-Arg-Leu-Ile-Val-Ala-Val-Arg-Ile-Trp-Arg-Arg-c[Asp-Pro-D-Nal(2')-Arg-Trp-Lys]-D-Val-D-Pro-NH2 |
| 495 | TCAM492 | Val-Arg-Leu-Ile-Val-Ala-Val-Arg-Ile-Trp-Arg-Arg-c[Asp-Pro-D-Nal(2')-Arg-Trp-Lys]-D-Pro-D-Val-NH2 |
| 496 | TCAM493 | Val-Arg-Leu-Ile-Val-Ala-Val-Arg-Ile-Trp-Arg-Arg-c[Asp-Pro-D-Nal(2')-Arg-Trp-Lys]-D-Val-D-Phe-NH2 |
| 497 | TCAM494 | Val-Arg-Leu-Ile-Val-Ala-Val-Arg-Ile-Trp-Arg-Arg-c[Asp-Pro-D-Nal(2')-Arg-Trp-Lys]-D-Phe-D-Val-NH2 |
| 498 | TCAM495 | Val-Arg-Leu-Ile-Val-Ala-Val-Arg-Ile-Trp-Arg-Arg-c[Asp-Arg-Arg-Nal(2')-Arg-Trp-Lys]-D-Val-D-Pro-NH2 |
| 499 | TCAM496 | Val-Arg-Leu-Ile-Val-Ala-Val-Arg-Ile-Trp-Arg-Arg-c[Asp-Arg-Arg-Nal(2')-Arg-Trp-Lys]-D-Pro-D-Val-NH2 |
| 500 | TCAM497 | Val-Arg-Leu-Ile-Val-Ala-Val-Arg-Ile-Trp-Arg-Arg-c[Asp-Arg-Arg-Nal(2')-Arg-Trp-Lys]-D-Val-D-Phe-NH2 |
| 501 | TCAM498 | Val-Arg-Leu-Ile-Val-Ala-Val-Arg-Ile-Trp-Arg-Arg-c[Asp-Arg-Arg-Nal(2')-Arg-Trp-Lys]-D-Phe-D-Val-NH2 |
| 502 | TCAM499 | Val-Arg-Leu-Ile-Val-Ala-Val-Arg-Ile-Trp-Arg-Arg-c[Asp-Arg-Arg-Pro-Nal(2')-Arg-Trp-Lys]-D-Val-D-Pro-NH2 |
| 503 | TCAM500 | Val-Arg-Leu-Ile-Val-Ala-Val-Arg-Ile-Trp-Arg-Arg-c[Asp-Arg-Arg-Pro-D-Nal(2')-Arg-Trp-Lys]-D-Pro-D-Val-NH2 |
| 504 | TCAM501 | Val-Arg-Leu-Ile-Val-Ala-Val-Arg-Ile-Trp-Arg-Arg-c[Asp-Arg-Arg-Pro-D-Nal(2')-Arg-Trp-Lys]-D-Val-D-Phe-NH2 |

TABLE 5-continued

Exemplary Anti-microbial peptides

| SEQ NO: | Peptide | Peptide Sequence |
|---|---|---|
| 505 | TCAM502 | Val-Arg-Leu-Ile-Val-Ala-Val-Arg-Ile-Trp-Arg-Arg-c[Asp-Arg-Arg-Pro-Nal(2')-Arg-Trp-Lys]-D-Phe-D-Val-NH2 |
| 506 | TCAM503 | Val-Arg-Leu-Ile-Val-Ala-Val-Arg-Ile-Trp-Arg-Arg-c[Asp-Arg-D-Nal(2')-Arg-Trp-Lys]-D-Val-D-Pro-NH2 |
| 507 | TCAM504 | Val-Arg-Leu-Ile-Val-Ala-Val-Arg-Ile-Trp-Arg-Arg-c[Asp-Arg-D-Nal(2')-Arg-Trp-Lys]-D-Pro-D-Val-NH2 |
| 508 | TCAM505 | Val-Arg-Leu-Ile-Val-Ala-Val-Arg-Ile-Trp-Arg-Arg-c[Asp-Arg-D-Nal(2')-Arg-Trp-Lys]-D-Val-D-Phe-NH2 |
| 509 | TCAM506 | Val-Arg-Leu-Ile-Val-Ala-Val-Arg-Ile-Trp-Arg-Arg-c[Asp-Arg-D-Nal(2')-Arg-Trp-Lys]-D-Phe-D-Val-NH2 |
| 510 | TCAM507 | Val-Arg-Leu-Ile-Val-Ala-Val-Arg-Ile-Trp-Arg-Arg-c[Asp-Arg-Pro-D-Nal(2')-Arg-Trp-Lys]-D-Val-D-Pro-NH2 |
| 511 | TCAM508 | Val-Arg-Leu-Ile-Val-Ala-Val-Arg-Ile-Trp-Arg-Arg-c[Asp-Arg-Pro-D-Nal(2')-Arg-Trp-Lys]-D-Pro-D-Val-NH2 |
| 512 | TCAM509 | Val-Arg-Leu-Ile-Val-Ala-Val-Arg-Ile-Trp-Arg-Arg-c[Asp-Arg-Pro-D-Nal(2')-Arg-Trp-Lys]-D-Val-D-Phe-NH2 |
| 513 | TCAM510 | Val-Arg-Leu-Ile-Val-Ala-Val-Arg-Ile-Trp-Arg-Arg-c[Asp-Arg-Pro-D-Nal(2')-Arg-Trp-Lys]-D-Phe-D-Val-NH2 |
| 514 | TCAM511 | Val-Arg-Leu-Ile-Val-Ala-Val-Arg-Ile-Trp-Arg-Arg-Arg-Arg-c[Asp-Pro-D-Nal(2')-Arg-Trp-Lys]-D-Val-D-Pro-NH2 |
| 515 | TCAM512 | Val-Arg-Leu-Ile-Val-Ala-Val-Arg-Ile-Trp-Arg-Arg-Arg-Arg-c[Asp-Pro-D-Nal(2')-Arg-Trp-Lys]-D-Pro-D-Val-NH2 |
| 516 | TCAM513 | Val-Arg-Leu-Ile-Val-Ala-Val-Arg-Ile-Trp-Arg-Arg-Arg-Arg-c[Asp-Pro-D-Nal(2')-Arg-Trp-Lys]-D-Val-D-Phe-NH2 |
| 517 | TCAM514 | Val-Arg-Leu-Ile-Val-Ala-Val-Arg-Ile-Trp-Arg-Arg-Arg-Arg-c[Asp-Pro-D-Nal(2')-Arg-Trp-Lys]-D-Phe-D-Val-NH2 |
| 518 | TCAM515 | Val-Arg-Leu-Ile-Val-Ala-Val-Arg-Ile-Trp-Arg-Arg-Arg-Arg-c[Asp-His-D-Nal(2')-Arg-Trp-Lys]-D-Val-D-Pro-NH2 |
| 519 | TCAM516 | Val-Arg-Leu-Ile-Val-Ala-Val-Arg-Ile-Trp-Arg-Arg-Arg-Arg-c[Asp-His-D-Nal(2')-Arg-Trp-Lys]-D-Pro-D-Val-NH2 |
| 520 | TCAM517 | Val-Arg-Leu-Ile-Val-Ala-Val-Arg-Ile-Trp-Arg-Arg-Arg-Arg-c[Asp-His-D-Nal(2')-Arg-Trp-Lys]-D-Val-D-Phe-NH2 |
| 521 | TCAM518 | Val-Arg-Leu-Ile-Val-Ala-Val-Arg-Ile-Trp-Arg-Arg-Arg-Arg-c[Asp-His-D-Nal(2')-Arg-Trp-Lys]-D-Phe-D-Val-NH2 |
| 522 | TCAM519 | Val-Arg-Leu-Ile-Val-Ala-Val-Arg-Ile-Trp-Arg-Arg-c[Asp-Arg-Pro-D-Nal(2')-Arg-Trp-Arg-Lys]-D-Val-D-Pro-NH2 |
| 523 | TCAM520 | Val-Arg-Leu-Ile-Val-Ala-Val-Arg-Ile-Trp-Arg-Arg-c[Asp-Arg-Pro-D-Nal(2')-Arg-Trp-Arg-Lys]-D-Pro-D-Val-NH2 |
| 524 | TCAM521 | Val-Arg-Leu-Ile-Val-Ala-Val-Arg-Ile-Trp-Arg-Arg-c[Asp-Arg-Pro-D-Nal(2')-Arg-Trp-Arg-Lys]-D-Val-D-Phe-NH2 |
| 525 | TCAM522 | Val-Arg-Leu-Ile-Val-Ala-Val-Arg-Ile-Trp-Arg-Arg-c[Asp-Arg-Pro-D-Nal(2')-Arg-Trp-Arg-Lys]-D-Phe-D-Val-NH2 |
| 526 | TCAM523 | Val-Arg-Leu-Ile-Val-Ala-Val-Arg-Ile-Trp-Arg-Arg-c[Asp-Arg-His-D-Nal(2')-Arg-Trp-Arg-Lys]-D-Val-D-Pro-NH2 |
| 527 | TCAM524 | Val-Arg-Leu-Ile-Val-Ala-Val-Arg-Ile-Trp-Arg-Arg-c[Asp-Arg-His-D-Nal(2')-Arg-Trp-Arg-Lys]-D-Pro-D-Val-NH2 |
| 528 | TCAM525 | Val-Arg-Leu-Ile-Val-Ala-Val-Arg-Ile-Trp-Arg-Arg-c[Asp-Arg-His-D-Nal(2')-Arg-Trp-Arg-Lys]-D-Val-D-Phe-NH2 |
| 529 | TCAM526 | Val-Arg-Leu-Ile-Val-Ala-Val-Arg-Ile-Trp-Arg-Arg-c[Asp-Arg-His-D-Nal(2')-Arg-Trp-Arg-Lys]-D-Phe-D-Val-NH2 |

TABLE 5-continued

Exemplary Anti-microbial peptides

| SEQ NO: | Peptide | Peptide Sequence |
|---|---|---|
| 530 | TCAM527 | Val-Arg-Leu-Ile-Val-Ala-Val-Arg-Ile-Trp-Arg-Arg-c[Asp-His-D-Nal(2')-Arg-D-Nal(2')-Lys]-D-Val-D-Phe-NH2 |
| 531 | TCAM528 | Val-Arg-Leu-Ile-Val-Ala-Val-Arg-Ile-Trp-Arg-Arg-c[Asp-His-D-Nal(2')-Arg-D-Nal(2')-Lys]-D-Phe-D-Val-NH2 |
| 532 | TCAM529 | Val-Arg-Leu-Ile-Val-Ala-Val-Arg-Ile-Trp-Arg-Arg-c[Asp-Pro-D-Nal(2')-Arg-D-Nal(2')-Lys]-D-Val-D-Pro-NH2 |
| 533 | TCAM530 | Val-Arg-Leu-Ile-Val-Ala-Val-Arg-Ile-Trp-Arg-Arg-c[Asp-Pro-D-Nal(2')-Arg-D-Nal(2')-Lys]-D-Pro-D-Val-NH2 |
| 534 | TCAM531 | Val-Arg-Leu-Ile-Val-Ala-Val-Arg-Ile-Trp-Arg-Arg-c[Asp-Pro-D-Nal(2')-Arg-D-Nal(2')-Lys]-D-Val-D-Phe-NH2 |
| 535 | TCAM532 | Val-Arg-Leu-Ile-Val-Ala-Val-Arg-Ile-Trp-Arg-Arg-c[Asp-Pro-D-Nal(2')-Arg-D-Nal(2')-Lys]-D-Phe-D-Val-NH2 |
| 536 | TCAM533 | Val-Arg-Leu-Ile-Val-Ala-Val-Arg-Ile-Trp-Arg-Arg-c[Asp-Arg-Arg-D-Nal(2')-Arg-D-Nal(2')-Lys]-D-Val-D-Pro-NH2 |
| 537 | TCAM534 | Val-Arg-Leu-Ile-Val-Ala-Val-Arg-Ile-Trp-Arg-Arg-c[Asp-Arg-Arg-D-Nal(2')-Arg-D-Nal(2')-Lys]-D-Pro-D-Val-NH2 |
| 538 | TCAM535 | Val-Arg-Leu-Ile-Val-Ala-Val-Arg-Ile-Trp-Arg-Arg-c[Asp-Arg-Arg-D-Nal(2')-Arg-D-Nal(2')-Lys]-D-Val-D-Phe-NH2 |
| 539 | TCAM536 | Val-Arg-Leu-Ile-Val-Ala-Val-Arg-Ile-Trp-Arg-Arg-c[Asp-Arg-Arg-D-Nal(2')-Arg-D-Nal(2')-Lys]-D-Phe-D-Val-NH2 |
| 540 | TCAM537 | Val-Arg-Leu-Ile-Val-Ala-Val-Arg-Ile-Trp-Arg-Arg-c[Asp-Arg-Arg-Pro-D-Nal(2')-Arg-D-Nal(2')-Lys]-D-Val-D-Pro-NH2 |
| 541 | TCAM538 | Val-Arg-Leu-Ile-Val-Ala-Val-Arg-Ile-Trp-Arg-Arg-c[Asp-Arg-Arg-Pro-D-Nal(2')-Arg-D-Nal(2')-Lys]-D-Pro-D-Val-NH2 |
| 542 | TCAM539 | Val-Arg-Leu-Ile-Val-Ala-Val-Arg-Ile-Trp-Arg-Arg-c[Asp-Arg-Arg-Pro-D-Nal(2')-Arg-D-Nal(2')-Lys]-D-Val-D-Phe-NH2 |
| 543 | TCAM540 | Val-Arg-Leu-Ile-Val-Ala-Val-Arg-Ile-Trp-Arg-Arg-c[Asp-Arg-Arg-Pro-D-Nal(2')-Arg-D-Nal(2')-Lys]-D-Phe-D-Val-NH2 |
| 544 | TCAM541 | Val-Arg-Leu-Ile-Val-Ala-Val-Arg-Ile-Trp-Arg-Arg-c[Asp-Arg-D-Nal(2')-Arg-D-Nal(2')-Lys]-D-Val-D-Pro-NH2 |
| 545 | TCAM542 | Val-Arg-Leu-Ile-Val-Ala-Val-Arg-Ile-Trp-Arg-Arg-c[Asp-Arg-D-Nal(2')-Arg-D-Nal(2')-Lys]-D-Pro-D-Val-NH2 |
| 546 | TCAM543 | Val-Arg-Leu-Ile-Val-Ala-Val-Arg-Ile-Trp-Arg-Arg-c[Asp-Arg-Nal(2')-Arg-D-Nal(2')-Lys]-D-Val-D-Phe-NH2 |
| 547 | TCAM544 | Val-Arg-Leu-Ile-Val-Ala-Val-Arg-Ile-Trp-Arg-Arg-c[Asp-Arg-D-Nal(2')-Arg-D-Nal(2')-Lys]-D-Phe-D-Val-NH2 |
| 548 | TCAM545 | Val-Arg-Leu-Ile-Val-Ala-Val-Arg-Ile-Trp-Arg-Arg-c[Asp-Arg-Pro-D-Nal(2')-Arg-D-Nal(2')-Lys]-D-Val-D-Pro-NH2 |
| 549 | TCAM546 | Val-Arg-Leu-Ile-Val-Ala-Val-Arg-Ile-Trp-Arg-Arg-c[Asp-Arg-Pro-D-Nal(2')-Arg-D-Nal(2')-Lys]-D-Pro-D-Val-NH2 |
| 550 | TCAM547 | Val-Arg-Leu-Ile-Val-Ala-Val-Arg-Ile-Trp-Arg-Arg-c[Asp-Arg-Pro-D-Nal(2')-Arg-D-Nal(2')-Lys]-D-Val-D-Phe-NH2 |
| 551 | TCAM548 | Val-Arg-Leu-Ile-Val-Ala-Val-Arg-Ile-Trp-Arg-Arg-c[Asp-Arg-Pro-D-Nal(2')-Arg-D-Nal(2')-Lys]-D-Phe-D-Val-NH2 |
| 552 | TCAM549 | Val-Arg-Leu-Ile-Val-Ala-Val-Arg-Ile-Trp-Arg-Arg-c[Asp-Arg-His-D-Nal(2')-Arg-D-Nal(2')-Lys]-D-Val-D-Pro-NH2 |
| 553 | TCAM550 | Val-Arg-Leu-Ile-Val-Ala-Val-Arg-Ile-Trp-Arg-Arg-c[Asp-Arg-His-D-Nal(2')-Arg-D-Nal(2')-Lys]-D-Pro-D-Val-NH2 |
| 554 | TCAM551 | Val-Arg-Leu-Ile-Val-Ala-Val-Arg-Ile-Trp-Arg-Arg-c[Asp-Arg-His-Nal(2')-Arg-D-Nal(2')-Lys]-D-Val-D-Phe-NH2 |

TABLE 5-continued

Exemplary Anti-microbial peptides

| SEQ NO: | Peptide | Peptide Sequence |
|---|---|---|
| 555 | TCAM552 | Val-Arg-Leu-Ile-Val-Ala-Val-Arg-Ile-Trp-Arg-Arg-c[Asp-Arg-His-Nal(2')-Arg-D-Nal(2')-Lys]-D-Phe-D-Val-NH2 |
| 556 | TCAM553 | Val-Arg-Leu-Ile-Val-Ala-Val-Arg-Ile-Trp-Arg-Arg-c[Asp-Arg-D-D-Nal(2')-Arg-D-Nal(2')-Arg-Lys]-D-Val-D-Pro-NH2 |
| 557 | TCAM554 | Val-Arg-Leu-Ile-Val-Ala-Val-Arg-Ile-Trp-Arg-Arg-c[Asp-Arg-D-Nal(2')-Arg-D-Nal(2')-Arg-Lys]-D-Pro-D-Val-NH2 |
| 558 | TCAM555 | Val-Arg-Leu-Ile-Val-Ala-Val-Arg-Ile-Trp-Arg-Arg-c[Asp-Arg-D-Nal(2')-Arg-D-Nal(2')-Arg-Lys]-D-Val-D-Phe-NH2 |
| 559 | TCAM556 | Val-Arg-Leu-Ile-Val-Ala-Val-Arg-Ile-Trp-Arg-Arg-c[Asp-Arg-D-Nal(2')-Arg-D-Nal(2')-Arg-Lys]-D-Phe-D-Val-NH2 |
| 560 | TCAM557 | Val-Arg-Leu-Ile-Val-Ala-Val-Arg-Ile-Trp-Arg-Arg-c[Asp-Arg-Pro-D-Nal(2')-Arg-D-Nal(2')-Arg-Lys]-D-Val-D-Pro-NH2 |
| 561 | TCAM558 | Val-Arg-Leu-Ile-Val-Ala-Val-Arg-Ile-Trp-Arg-Arg-c[Asp-Arg-Pro-D-Nal(2')-Arg-D-Nal(2')-Arg-Lys]-D-Pro-D-Val-NH2 |
| 562 | TCAM559 | Val-Arg-Leu-Ile-Val-Ala-Val-Arg-Ile-Trp-Arg-Arg-c[Asp-Arg-Pro-D-Nal(2')-Arg-D-Nal(2')-Arg-Lys]-D-Val-D-Phe-NH2 |
| 563 | TCAM560 | Val-Arg-Leu-Ile-Val-Ala-Val-Arg-Ile-Trp-Arg-Arg-c[Asp-Arg-Pro-D-Nal(2')-Arg-D-Nal(2')-Arg-Lys]-D-Phe-D-Val-NH2 |
| 564 | TCAM561 | Val-Arg-Leu-Ile-Val-Ala-Val-Arg-Ile-Trp-Arg-Arg-c[Asp-Arg-His-D-Nal(2')-Arg-D-Nal(2')-Arg-Lys]-D-Val-D-Pro-NH2 |
| 565 | TCAM562 | Val-Arg-Leu-Ile-Val-Ala-Val-Arg-Ile-Trp-Arg-Arg-c[Asp-Arg-His-D-Nal(2')-Arg-D-Nal(2')-Arg-Lys]-D-Pro-D-Val-NH2 |
| 566 | TCAM563 | Val-Arg-Leu-Ile-Val-Ala-Val-Arg-Ile-Trp-Arg-Arg-c[Asp-Arg-His-D-Nal(2')-Arg-D-Nal(2')-Arg-Lys]-D-Val-D-Phe-NH2 |
| 567 | TCAM564 | Val-Arg-Leu-Ile-Val-Ala-Val-Arg-Ile-Trp-Arg-Arg-c[Asp-Arg-His-D-Nal(2')-Arg-D-Nal(2')-Arg-Lys]-D-Phe-D-Val-NH2 |
| 568 | TCAM565 | Val-Arg-Leu-Ile-Val-Ala-Val-Arg-Ile-Trp-Arg-Arg-Arg-Arg-c[Asp-Pro-D-Nal(2')-Arg-D-Nal(2')-Lys]-D-Val-D-Pro-NH2 |
| 569 | TCAM566 | Val-Arg-Leu-Ile-Val-Ala-Val-Arg-Ile-Trp-Arg-Arg-Arg-Arg-c[Asp-Pro-D-Nal(2')-Arg-D-Nal(2')-Lys]-D-Pro-D-Val-NH2 |
| 570 | TCAM567 | Val-Arg-Leu-Ile-Val-Ala-Val-Arg-Ile-Trp-Arg-Arg-Arg-Arg-c[Asp-Pro-D-Nal(2')-Arg-D-Nal(2')-Lys]-D-Val-D-Phe-NH2 |
| 571 | TCAM568 | Val-Arg-Leu-Ile-Val-Ala-Val-Arg-Ile-Trp-Arg-Arg-Arg-Arg-c[Asp-Pro-D-Nal(2')-Arg-D-Nal(2')-Lys]-D-Phe-D-Val-NH2 |
| 572 | TCAM569 | Val-Arg-Leu-Ile-Val-Ala-Val-Arg-Ile-Trp-Arg-Arg-Arg-Arg-c[Asp-His-D-Nal(2')-Arg-D-Nal(2')-Lys]-D-Val-D-Pro-NH2 |
| 573 | TCAM570 | Val-Arg-Leu-Ile-Val-Ala-Val-Arg-Ile-Trp-Arg-Arg-Arg-Arg-c[Asp-His-D-Nal(2')-Arg-D-Nal(2')-Lys]-D-Pro-D-Val-NH2 |
| 574 | TCAM571 | Val-Arg-Leu-Ile-Val-Ala-Val-Arg-Ile-Trp-Arg-Arg-Arg-Arg-c[Asp-His-D-Nal(2')-Arg-D-Nal(2')-Lys]-D-Val-D-Phe-NH2 |
| 575 | TCAM572 | Val-Arg-Leu-Ile-Val-Ala-Val-Arg-Ile-Trp-Arg-Arg-Arg-Arg-c[Asp-His-D-Nal(2')-Arg-D-Nal(2')-Lys]-D-Phe-D-Val-NH2 |
| 576 | TCAM573 | Val-Arg-Leu-Ile-Val-Ala-Val-Arg-Ile-Trp-Arg-Arg-c[Asp-Arg-Pro-D-Nal(2')-Arg-D-Nal(2')-Arg-Lys]-D-Val-D-Pro-NH2 |
| 577 | TCAM574 | Val-Arg-Leu-Ile-Val-Ala-Val-Arg-Ile-Trp-Arg-Arg-c[Asp-Arg-Pro-D-Nal(2')-Arg-D-Nal(2')-Arg-Lys]-D-Pro-D-Val-NH2 |
| 578 | TCAM575 | Val-Arg-Leu-Ile-Val-Ala-Val-Arg-Ile-Trp-Arg-Arg-c[Asp-Arg-Pro-D-Nal(2')-Arg-D-Nal(2')-Arg-Lys]-D-Val-D-Phe-NH2 |
| 579 | TCAM576 | Val-Arg-Leu-Ile-Val-Ala-Val-Arg-Ile-Trp-Arg-Arg-c[Asp-Arg-Pro-D-Nal(2')-Arg-D-Nal(2')-Arg-Lys]-D-Phe-D-Val-NH2 |

TABLE 5-continued

Exemplary Anti-microbial peptides

| SEQ NO: | Peptide | Peptide Sequence |
|---|---|---|
| 580 | TCAM577 | Val-Arg-Leu-Ile-Val-Ala-Val-Arg-Ile-Trp-Arg-Arg-c[Asp-Arg-His-D-Nal(2')-Arg-D-Nal(2')-Arg-Lys]-D-Val-D-Pro-NH2 |
| 581 | TCAM578 | Val-Arg-Leu-Ile-Val-Ala-Val-Arg-Ile-Trp-Arg-Arg-c[Asp-Arg-His-D-Nal(2')-Arg-D-Nal(2')-Arg-Lys]-D-Pro-D-Val-NH2 |
| 582 | TCAM579 | Val-Arg-Leu-Ile-Val-Ala-Val-Arg-Ile-Trp-Arg-Arg-c[Asp-Arg-His-D-Nal(2')-Arg-D-Nal(2')-Arg-Lys]-D-Val-D-Phe-NH2 |
| 583 | TCAM580 | Val-Arg-Leu-Ile-Val-Ala-Val-Arg-Ile-Trp-Arg-Arg-c[Asp-Arg-His-D-Nal(2')-Arg-D-Nal(2')-Arg-Lys]-D-Phe-D-Val-NH2 |
| 584 | TCAM581 | Val-Arg-Leu-Ile-Val-Ala-Val-Arg-Ile-Trp-Arg-Arg-c[Asp-His-D-Nal(2')-Arg-Trp-Lys]-Arg-Arg-D-Val-D-Pro-NH2 |
| 585 | TCAM582 | Val-Arg-Leu-Ile-Val-Ala-Val-Arg-Ile-Trp-Arg-Arg-c[Asp-His-D-Nal(2')-Arg-Trp-Lys]-Arg-Arg-D-Pro-D-Val-NH2 |
| 586 | TCAM583 | Val-Arg-Leu-Ile-Val-Ala-Val-Arg-Ile-Trp-Arg-Arg-c[Asp-His-D-Nal(2')-Arg-Trp-Lys]-Arg-Arg-D-Val-D-Phe-NH2 |
| 587 | TCAM584 | Val-Arg-Leu-Ile-Val-Ala-Val-Arg-Ile-Trp-Arg-Arg-c[Asp-His-D-Nal(2')-Arg-Trp-Lys]-Arg-Arg-D-Phe-D-Val-NH2 |
| 588 | TCAM585 | Val-Arg-Leu-Ile-Val-Ala-Val-Arg-Ile-Trp-Arg-Arg-c[Asp-Pro-D-Nal(2')-Arg-Trp-Lys]-Arg-Arg-D-Val-D-Pro-NH2 |
| 589 | TCAM586 | Val-Arg-Leu-Ile-Val-Ala-Val-Arg-Ile-Trp-Arg-Arg-c[Asp-Pro-D-Nal(2')-Arg-Trp-Lys]-Arg-Arg-D-Pro-D-Val-NH2 |
| 590 | TCAM587 | Val-Arg-Leu-Ile-Val-Ala-Val-Arg-Ile-Trp-Arg-Arg-c[Asp-Pro-D-Nal(2')-Arg-Trp-Lys]-Arg-Arg-D-Val-D-Phe-NH2 |
| 591 | TCAM588 | Val-Arg-Leu-Ile-Val-Ala-Val-Arg-Ile-Trp-Arg-Arg-c[Asp-Pro-D-Nal(2')-Arg-Trp-Lys]-Arg-Arg-D-Phe-D-Val-NH2 |
| Anti-biofilm peptide ATRA1 linked to anti-microbial peptides | | |
| 592 | TCAM589 | Lys-Lys-Phe-Lys-Lys-Phe-Phe-Lys-Lys-Leu-Lys-c[Asp-Pro-Arg-Arg-Trp-Trp-Arg-Phe-Lys]-D-Val-D-Pro-NH2 |
| 593 | TCAM590 | Lys-Lys-Phe-Lys-Lys-Phe-Phe-Lys-Lys-Leu-Lys-c[Asp-Pro-Arg-Arg-Trp-Trp-Arg-Phe-Lys]-D-Val-D-Phe-NH2 |
| 594 | TCAM591 | Lys-Lys-Phe-Lys-Lys-Phe-Phe-Lys-Lys-Leu-Lys-c[Asp-Pro-Arg-Arg-Trp-Trp-Arg-Phe-Lys]-D-Pro-D-Val-NH2 |
| 595 | TCAM592 | Lys-Lys-Phe-Lys-Lys-Phe-Phe-Lys-Lys-Leu-Lys-c[Asp-Pro-Arg-Arg-Trp-Trp-Arg-Phe-Lys]-D-Phe-D-Val-NH2 |
| 596 | TCAM593 | Lys-Lys-Phe-Lys-Lys-Phe-Phe-Lys-Lys-Leu-Lys-c[Asp-Pro-Arg-Arg-Trp-Trp-Tyr-Phe-Lys]-D-Val-D-Pro-NH2 |
| 597 | TCAM594 | Lys-Lys-Phe-Lys-Lys-Phe-Phe-Lys-Lys-Leu-Lys-c[Asp-Pro-Arg-Arg-Trp-Trp-Tyr-Phe-Lys]-D-Val-D-Phe-NH2 |
| 598 | TCAM595 | Lys-Lys-Phe-Lys-Lys-Phe-Phe-Lys-Lys-Leu-Lys-c[Asp-Pro-Arg-Arg-Trp-Trp-Tyr-Phe-Lys]-D-Pro-D-Val-NH2 |
| 599 | TCAM596 | Lys-Lys-Phe-Lys-Lys-Phe-Phe-Lys-Lys-Leu-Lys-c[Asp-Pro-Arg-Arg-Trp-Trp-Tyr-Phe-Lys]-D-Phe-D-Val-NH2 |
| 600 | TCAM597 | Lys-Lys-Phe-Lys-Lys-Phe-Phe-Lys-Lys-Leu-Lys-c[Asp-Pro-Arg-Arg-Tyr-Tyr-Arg-Phe-Lys]-D-Val-D-Pro-NH2 |
| 601 | TCAM598 | Lys-Lys-Phe-Lys-Lys-Phe-Phe-Lys-Lys-Leu-Lys-c[Asp-Pro-Arg-Arg-Tyr-Tyr-Arg-Phe-Lys]-D-Val-D-Phe-NH2 |
| 602 | TCAM599 | Lys-Lys-Phe-Lys-Lys-Phe-Phe-Lys-Lys-Leu-Lys-c[Asp-Pro-Arg-Arg-Tyr-Tyr-Arg-Phe-Lys]-D-Pro-D-Val-NH2 |
| 603 | TCAM600 | Lys-Lys-Phe-Lys-Lys-Phe-Phe-Lys-Lys-Leu-Lys-c[Asp-Pro-Arg-Arg-Tyr-Tyr-Arg-Phe-Lys]-D-Phe-D-Val-NH2 |

TABLE 5-continued

Exemplary Anti-microbial peptides

| SEQ NO: | Peptide | Peptide Sequence |
|---|---|---|
| 604 | TCAM601 | Lys-Lys-Phe-Lys-Lys-Phe-Phe-Lys-Lys-Leu-Lys-c[Asp-Pro-Arg-Arg-Nal-Nal-Arg-Phe-Lys]-D-Val-D-Pro-NH2 |
| 605 | TCAM602 | Lys-Lys-Phe-Lys-Lys-Phe-Phe-Lys-Lys-Leu-Lys-c[Asp-Pro-Arg-Arg-Nal-Nal-Arg-Phe-Lys]-D-Val-D-Phe-NH2 |
| 606 | TCAM603 | Lys-Lys-Phe-Lys-Lys-Phe-Phe-Lys-Lys-Leu-Lys-c[Asp-Pro-Arg-Arg-Nal-Nal-Arg-Phe-Lys]-D-Pro-D-Val-NH2 |
| 607 | TCAM604 | Lys-Lys-Phe-Lys-Lys-Phe-Phe-Lys-Lys-Leu-Lys-c[Asp-Pro-Arg-Arg-Nal-Nal-Arg-Phe-Lys]-D-Phe-D-Val-NH2 |
| 608 | TCAM605 | Lys-Lys-Phe-Lys-Lys-Phe-Phe-Lys-Lys-Leu-Lys-c[Asp-Pro-Arg-Arg-Leu-Trp-Leu-Trp-Lys]-D-Val-D-Pro-NH2 |
| 609 | TCAM606 | Lys-Lys-Phe-Lys-Lys-Phe-Phe-Lys-Lys-Leu-Lys-c[Asp-Pro-Arg-Arg-Leu-Trp-Leu-Trp-Lys]-D-Val-D-Phe-NH2 |
| 610 | TCAM607 | Lys-Lys-Phe-Lys-Lys-Phe-Phe-Lys-Lys-Leu-Lys-c[Asp-Pro-Arg-Arg-Leu-Trp-Leu-Trp-Lys]-D-Pro-D-Val-NH2 |
| 611 | TCAM608 | Lys-Lys-Phe-Lys-Lys-Phe-Phe-Lys-Lys-Leu-Lys-c[Asp-Pro-Arg-Arg-Leu-Trp-Leu-Trp-Lys]-D-Phe-D-Val-NH2 |
| 612 | TCAM609 | Lys-Lys-Phe-Lys-Lys-Phe-Phe-Lys-Lys-Leu-Lys-c[Asp-Pro-Arg-Arg-Leu-Trp-Leu-Trp-Lys]-D-Val-D-Pro-NH2 |
| 613 | TCAM610 | Lys-Lys-Phe-Lys-Lys-Phe-Phe-Lys-Lys-Leu-Lys-c[Asp-Pro-Arg-Arg-Leu-Trp-Leu-Trp-Lys]-D-Val-D-Phe-NH2 |
| 614 | TCAM611 | Lys-Lys-Phe-Lys-Lys-Phe-Phe-Lys-Lys-Leu-Lys-c[Asp-Pro-Arg-Arg-Leu-Trp-Leu-Trp-Lys]-D-Pro-D-Val-NH2 |
| 615 | TCAM612 | Lys-Lys-Phe-Lys-Lys-Phe-Phe-Lys-Lys-Leu-Lys-c[Asp-Pro-Arg-Arg-Leu-Trp-Leu-Trp-Lys]-D-Phe-D-Val-NH2 |
| 616 | TCAM613 | Lys-Lys-Phe-Lys-Lys-Phe-Phe-Lys-Lys-Leu-Lys-c[Asp-Arg-Arg-Arg-Trp-Leu-Trp-Leu-Trp-Lys]-D-Val-D-Pro-NH2 |
| 617 | TCAM614 | Lys-Lys-Phe-Lys-Lys-Phe-Phe-Lys-Lys-Leu-Lys-c[Asp-Pro-Arg-Arg-Arg-Trp-Leu-Trp-Leu-Trp-Lys]-D-Val-D-Phe-NH2 |
| 618 | TCAM615 | Lys-Lys-Phe-Lys-Lys-Phe-Phe-Lys-Lys-Leu-Lys-c[Asp-Pro-Arg-Arg-Arg-Trp-Leu-Trp-Leu-Trp-Lys]-D-Pro-D-Val-NH2 |
| 619 | TCAM616 | Lys-Lys-Phe-Lys-Lys-Phe-Phe-Lys-Lys-Leu-Lys-c[Asp-Pro-Arg-Arg-Arg-Trp-Leu-Trp-Leu-Trp-Lys]-D-Phe-D-Val-NH2 |
| 620 | TCAM617 | Lys-Lys-Phe-Lys-Lys-Phe-Phe-Lys-Lys-Leu-Lys-c[Asp-Pro-Arg-Gln-Arg-Arg-Trp-Leu-Trp-Leu-Trp-Lys]-D-Val-D-Pro-NH2 |
| 621 | TCAM618 | Lys-Lys-Phe-Lys-Lys-Phe-Phe-Lys-Lys-Leu-Lys-c[Asp-Pro-Arg-Gln-Arg-Arg-Trp-Leu-Trp-Leu-Trp-Lys]-D-Val-D-Phe-NH2 |
| 622 | TCAM619 | Lys-Lys-Phe-Lys-Lys-Phe-Phe-Lys-Lys-Leu-Lys-c[Asp-Pro-Arg-Gln-Arg-Arg-Trp-Leu-Trp-Leu-Trp-Lys]-D-Pro-D-Val-NH2 |
| 623 | TCAM620 | Lys-Lys-Phe-Lys-Lys-Phe-Phe-Lys-Lys-Leu-Lys-c[Asp-Pro-Arg-Gln-Arg-Arg-Trp-Leu-Trp-Leu-Trp-Lys]-D-Phe-D-Val-NH2 |
| 624 | TCAM621 | Lys-Lys-Phe-Lys-Lys-Phe-Phe-Lys-Lys-Leu-Lys-c[Asp-Pro-Trp-Arg-Trp-Trp-Arg-Arg-Lys]-D-Val-D-Phe-NH2 |
| 625 | TCAM622 | Lys-Lys-Phe-Lys-Lys-Phe-Phe-Lys-Lys-Leu-Lys-c[Asp-Pro-Trp-Arg-Trp-Trp-Arg-Arg-Lys]-D-Pro-D-Val-NH2 |
| 626 | TCAM623 | Lys-Lys-Phe-Lys-Lys-Phe-Phe-Lys-Lys-Leu-Lys-c[Asp-Pro-Trp-Arg-Trp-Trp-Arg-Arg-Lys]-D-Phe-D-Val-NH2 |
| 627 | TCAM624 | Lys-Lys-Phe-Lys-Lys-Phe-Phe-Lys-Lys-Leu-Lys-c[Asp-Pro-Trp-Trp-Arg-Arg-Trp-Trp-Arg-Arg-Lys]-D-Val-D-Pro-NH2 |
| 628 | TCAM625 | Lys-Lys-Phe-Lys-Lys-Phe-Phe-Lys-Lys-Leu-Lys-c[Asp-Pro-Trp-Trp-Arg-Arg-Trp-Trp-Arg-Arg-Lys]-D-Val-D-Phe-NH2 |

TABLE 5-continued

Exemplary Anti-microbial peptides

| SEQ NO: | Peptide | Peptide Sequence |
|---|---|---|
| 629 | TCAM626 | Lys-Lys-Phe-Lys-Lys-Phe-Phe-Lys-Lys-Leu-Lys-c[Asp-Pro-Trp-Trp-Arg-Arg-Trp-Trp-Arg-Arg-Lys]-D-Pro-D-Val-NH2 |
| 630 | TCAM627 | Lys-Lys-Phe-Lys-Lys-Phe-Phe-Lys-Lys-Leu-Lys-c[Asp-Pro-Trp-Trp-Arg-Arg-Trp-Trp-Arg-Arg-Lys]-D-Phe-D-Val-NH2 |
| 631 | TCAM628 | Lys-Lys-Phe-Lys-Lys-Phe-Phe-Lys-Lys-Leu-Lys-c[Asp-Pro-Trp-Arg-Trp-Arg-Trp-Arg-Lys]-D-Val-D-Pro-NH2 |
| 632 | TCAM629 | Lys-Lys-Phe-Lys-Lys-Phe-Phe-Lys-Lys-Leu-Lys-c[Asp-Pro-Trp-Arg-Trp-Arg-Trp-Arg-Lys]-D-Val-D-Phe-NH2 |
| 633 | TCAM630 | Lys-Lys-Phe-Lys-Lys-Phe-Phe-Lys-Lys-Leu-Lys-c[Asp-Pro-Trp-Arg-Trp-Arg-Trp-Arg-Lys]-D-Pro-D-Val-NH2 |
| 634 | TCAM631 | Lys-Lys-Phe-Lys-Lys-Phe-Phe-Lys-Lys-Leu-Lys-c[Asp-Pro-Trp-Arg-Trp-Arg-Trp-Arg-Lys]-D-Phe-D-Val-NH2 |
| 635 | TCAM632 | Lys-Lys-Phe-Lys-Lys-Phe-Phe-Lys-Lys-Leu-Lys-c[Asp-Pro-Arg-Trp-Arg-Trp-Arg-Trp-Lys]-D-Val-D-Pro-NH2 |
| 636 | TCAM633 | Lys-Lys-Phe-Lys-Lys-Phe-Phe-Lys-Lys-Leu-Lys-c[Asp-Pro-Arg-Trp-Arg-Trp-Arg-Trp-Lys]-D-Val-D-Phe-NH2 |
| 637 | TCAM634 | Lys-Lys-Phe-Lys-Lys-Phe-Phe-Lys-Lys-Leu-Lys-c[Asp-Pro-Arg-Trp-Arg-Trp-Arg-Trp-Lys]-D-Pro-D-Val-NH2 |
| 638 | TCAM635 | Lys-Lys-Phe-Lys-Lys-Phe-Phe-Lys-Lys-Leu-Lys-c[Asp-Pro-Arg-Trp-Arg-Trp-Arg-Trp-Lys]-D-Phe-D-Val-NH2 |
| 639 | TCAM636 | Lys-Lys-Phe-Lys-Lys-Phe-Phe-Lys-Lys-Leu-Lys-c[Asp-Pro-Arg-Trp-Trp-Arg-Arg-Lys]-D-Val-D-Pro-NH2 |
| 640 | TCAM637 | Lys-Lys-Phe-Lys-Lys-Phe-Phe-Lys-Lys-Leu-Lys-c[Asp-Pro-Arg-Trp-Trp-Arg-Arg-Lys]-D-Val-D-Phe-NH2 |
| 641 | TCAM638 | Lys-Lys-Phe-Lys-Lys-Phe-Phe-Lys-Lys-Leu-Lys-c[Asp-Pro-Arg-Trp-Trp-Arg-Arg-Lys]-D-Pro-D-Val-NH2 |
| 642 | TCAM639 | Lys-Lys-Phe-Lys-Lys-Phe-Phe-Lys-Lys-Leu-Lys-c[Asp-Pro-Arg-Trp-Trp-Arg-Arg-Lys]-D-Phe-D-Val-NH2 |
| 643 | TCAM640 | Lys-Lys-Phe-Lys-Lys-Phe-Phe-Lys-Lys-Leu-Lys-c[Asp-Pro-Trp-Trp-Arg-Arg-Trp-Lys]-D-Val-D-Pro-NH2 |
| 644 | TCAM641 | Lys-Lys-Phe-Lys-Lys-Phe-Phe-Lys-Lys-Leu-Lys-c[Asp-Pro-Trp-Trp-Arg-Arg-Trp-Lys]-D-Val-D-Phe-NH2 |
| 645 | TCAM642 | Lys-Lys-Phe-Lys-Lys-Phe-Phe-Lys-Lys-Leu-Lys-c[Asp-Pro-Trp-Trp-Arg-Arg-Trp-Lys]-D-Pro-D-Val-NH2 |
| 646 | TCAM643 | Lys-Lys-Phe-Lys-Lys-Phe-Phe-Lys-Lys-Leu-Lys-c[Asp-Pro-Trp-Trp-Arg-Arg-Trp-Lys]-D-Phe-D-Val-NH2 |
| 647 | TCAM644 | Lys-Lys-Phe-Lys-Lys-Phe-Phe-Lys-Lys-Leu-Lys-c[Asp-Pro-Trp-Arg-Trp-Arg-Trp-Lys]-D-Val-D-Pro-NH2 |
| 648 | TCAM645 | Lys-Lys-Phe-Lys-Lys-Phe-Phe-Lys-Lys-Leu-Lys-c[Asp-Pro-Trp-Arg-Trp-Arg-Trp-Lys]-D-Val-D-Phe-NH2 |
| 649 | TCAM646 | Lys-Lys-Phe-Lys-Lys-Phe-Phe-Lys-Lys-Leu-Lys-c[Asp-Pro-Trp-Arg-Trp-Arg-Trp-Lys]-D-Pro-D-Val-NH2 |
| 650 | TCAM647 | Lys-Lys-Phe-Lys-Lys-Phe-Phe-Lys-Lys-Leu-Lys-c[Asp-Pro-Trp-Arg-Trp-Arg-Trp-Lys]-D-Phe-D-Val-NH2 |
| 651 | TCAM648 | Lys-Lys-Phe-Lys-Lys-Phe-Phe-Lys-Lys-Leu-Lys-c[Asp-Pro-Arg-Trp-Arg-Trp-Arg-Lys]-D-Val-D-Pro-NH2 |
| 652 | TCAM649 | Lys-Lys-Phe-Lys-Lys-Phe-Phe-Lys-Lys-Leu-Lys-c[Asp-Pro-Arg-Trp-Arg-Trp-Arg-Lys]-D-Val-D-Phe-NH2 |
| 653 | TCAM650 | Lys-Lys-Phe-Lys-Lys-Phe-Phe-Lys-Lys-Leu-Lys-c[Asp-Pro-Arg-Trp-Arg-Trp-Arg-Lys]-D-Pro-D-Val-NH2 |

TABLE 5-continued

Exemplary Anti-microbial peptides

| SEQ NO: | Peptide | Peptide Sequence |
|---|---|---|
| 654 | TCAM651 | Lys-Lys-Phe-Lys-Lys-Phe-Phe-Lys-Lys-Leu-Lys-c[Asp-Pro-Arg-Trp-Arg-Trp-Arg-Lys]-D-Phe-D-Val-NH2 |
| 655 | TCAM652 | Lys-Lys-Phe-Lys-Lys-Phe-Phe-Lys-Lys-Leu-Lys-c[Asp-Pro-Trp-Arg-Tyr-Arg-Trp-Lys]-D-Val-D-Pro-NH2 |
| 656 | TCAM653 | Lys-Lys-Phe-Lys-Lys-Phe-Phe-Lys-Lys-Leu-Lys-c[Asp-Pro-Trp-Arg-Tyr-Arg-Trp-Lys]-D-Val-D-Phe-NH2 |
| 657 | TCAM654 | Lys-Lys-Phe-Lys-Lys-Phe-Phe-Lys-Lys-Leu-Lys-c[Asp-Pro-Trp-Arg-Tyr-Arg-Trp-Lys]-D-Pro-D-Val-NH2 |
| 658 | TCAM655 | Lys-Lys-Phe-Lys-Lys-Phe-Phe-Lys-Lys-Leu-Lys-c[Asp-Pro-Trp-Arg-Tyr-Arg-Trp-Lys]-D-Phe-D-Val-NH2 |
| 659 | TCAM656 | Lys-Lys-Phe-Lys-Lys-Phe-Phe-Lys-Lys-Leu-Lys-c[Asp-Pro-Trp-Arg-Trp-Arg-Tyr-Lys]-D-Val-D-Pro-NH2 |
| 660 | TCAM657 | Lys-Lys-Phe-Lys-Lys-Phe-Phe-Lys-Lys-Leu-Lys-c[Asp-Pro-Trp-Arg-Trp-Arg-Tyr-Lys]-D-Val-D-Phe-NH2 |
| 661 | TCAM658 | Lys-Lys-Phe-Lys-Lys-Phe-Phe-Lys-Lys-Leu-Lys-c[Asp-Pro-Trp-Arg-Trp-Arg-Tyr-Lys]-D-Pro-D-Val-NH2 |
| 662 | TCAM659 | Lys-Lys-Phe-Lys-Lys-Phe-Phe-Lys-Lys-Leu-Lys-c[Asp-Pro-Trp-Arg-Trp-Arg-Tyr-Lys]-D-Phe-D-Val-NH2 |
| 663 | TCAM660 | Lys-Lys-Phe-Lys-Lys-Phe-Phe-Lys-Lys-Leu-Lys-c[Asp-Pro-Trp-Arg-Trp-Arg-Lys]-D-Val-D-Pro-NH2 |
| 664 | TCAM661 | Lys-Lys-Phe-Lys-Lys-Phe-Phe-Lys-Lys-Leu-Lys-c[Asp-Pro-Trp-Arg-Trp-Arg-Lys]-D-Val-D-Phe-NH2 |
| 665 | TCAM662 | Lys-Lys-Phe-Lys-Lys-Phe-Phe-Lys-Lys-Leu-Lys-c[Asp-Pro-Trp-Arg-Trp-Arg-Lys]-D-Pro-D-Val-NH2 |
| 666 | TCAM663 | Lys-Lys-Phe-Lys-Lys-Phe-Phe-Lys-Lys-Leu-Lys-c[Asp-Pro-Trp-Arg-Trp-Arg-Lys]-D-Phe-D-Val-NH2 |
| 667 | TCAM664 | Lys-Lys-Phe-Lys-Lys-Phe-Phe-Lys-Lys-Leu-Lys-c[Asp-Pro-Trp-Arg-Arg-Trp-Lys]-D-Val-D-Pro-NH2 |
| 668 | TCAM665 | Lys-Lys-Phe-Lys-Lys-Phe-Phe-Lys-Lys-Leu-Lys-c[Asp-Pro-Trp-Arg-Arg-Trp-Lys]-D-Val-D-Phe-NH2 |
| 669 | TCAM666 | Lys-Lys-Phe-Lys-Lys-Phe-Phe-Lys-Lys-Leu-Lys-c[Asp-Pro-Trp-Arg-Arg-Trp-Lys]-D-Pro-D-Val-NH2 |
| 670 | TCAM667 | Lys-Lys-Phe-Lys-Lys-Phe-Phe-Lys-Lys-Leu-Lys-c[Asp-Pro-Trp-Arg-Arg-Trp-Lys]-D-Phe-D-Val-NH2 |
| 671 | TCAM668 | Lys-Lys-Phe-Lys-Lys-Phe-Phe-Lys-Lys-Leu-Lys-c[Asp-Pro-Arg-Trp-Trp-Arg-Lys]-D-Val-D-Pro-NH2 |
| 672 | TCAM669 | Lys-Lys-Phe-Lys-Lys-Phe-Phe-Lys-Lys-Leu-Lys-c[Asp-Pro-Arg-Trp-Trp-Arg-Lys]-D-Val-D-Phe-NH2 |
| 673 | TCAM670 | Lys-Lys-Phe-Lys-Lys-Phe-Phe-Lys-Lys-Leu-Lys-c[Asp-Pro-Arg-Trp-Trp-Arg-Lys]-D-Pro-D-Val-NH2 |
| 674 | TCAM671 | Lys-Lys-Phe-Lys-Lys-Phe-Phe-Lys-Lys-Leu-Lys-c[Asp-Pro-Arg-Trp-Trp-Arg-Lys]-D-Phe-D-Val-NH2 |
| 675 | TCAM672 | Lys-Lys-Phe-Lys-Lys-Phe-Phe-Lys-Lys-Leu-Lys-c[Asp-Pro-Trp-Arg-Trp-Lys]-D-Val-D-Pro-NH2 |
| 676 | TCAM673 | Lys-Lys-Phe-Lys-Lys-Phe-Phe-Lys-Lys-Leu-Lys-c[Asp-Pro-Trp-Arg-Trp-Lys]-D-Val-D-Phe-NH2 |
| 677 | TCAM674 | Lys-Lys-Phe-Lys-Lys-Phe-Phe-Lys-Lys-Leu-Lys-c[Asp-Pro-Trp-Arg-Trp-Lys]-D-Pro-D-Val-NH2 |
| 678 | TCAM675 | Lys-Lys-Phe-Lys-Lys-Phe-Phe-Lys-Lys-Leu-Lys-c[Asp-Pro-Trp-Arg-Trp-Lys]-D-Phe-D-Val-NH2 |

TABLE 5-continued

Exemplary Anti-microbial peptides

| SEQ NO: | Peptide | Peptide Sequence |
|---|---|---|
| 679 | TCAM676 | Lys-Lys-Phe-Lys-Lys-Phe-Phe-Lys-Lys-Leu-Lys-c[Asp-Pro-Arg-Trp-Arg-Lys]-D-Val-D-Pro-NH2 |
| 680 | TCAM677 | Lys-Lys-Phe-Lys-Lys-Phe-Phe-Lys-Lys-Leu-Lys-c[Asp-Pro-Arg-Trp-Arg-Lys]-D-Val-D-Phe-NH2 |
| 681 | TCAM678 | Lys-Lys-Phe-Lys-Lys-Phe-Phe-Lys-Lys-Leu-Lys-c[Asp-Pro-Arg-Trp-Arg-Lys]-D-Pro-D-Val-NH2 |
| 682 | TCAM679 | Lys-Lys-Phe-Lys-Lys-Phe-Phe-Lys-Lys-Leu-Lys-c[Asp-Pro-Arg-Trp-Arg-Lys]-D-Phe-D-Val-NH2 |
| 683 | TCAM680 | Lys-Lys-Phe-Lys-Lys-Phe-Phe-Lys-Lys-Leu-Lys-c[Asp-Arg-Arg-Trp-Trp-Arg-Phe-Lys]-D-Val-D-Pro-NH2 |
| 684 | TCAM681 | Lys-Lys-Phe-Lys-Lys-Phe-Phe-Lys-Lys-Leu-Lys-c[Asp-Arg-Arg-Trp-Trp-Arg-Phe-Lys]-D-Val-D-Phe-NH2 |
| 685 | TCAM682 | Lys-Lys-Phe-Lys-Lys-Phe-Phe-Lys-Lys-Leu-Lys-c[Asp-Arg-Arg-Trp-Trp-Arg-Phe-Lys]-D-Pro-D-Val-NH2 |
| 686 | TCAM683 | Lys-Lys-Phe-Lys-Lys-Phe-Phe-Lys-Lys-Leu-Lys-c[Asp-Arg-Arg-Trp-Trp-Arg-Phe-Lys]-D-Phe-D-Val-NH2 |
| 687 | TCAM684 | Lys-Lys-Phe-Lys-Lys-Phe-Phe-Lys-Lys-Leu-Lys-c[Asp-Arg-Arg-Trp-Trp-Arg-Phe-Lys]-D-Val-D-Pro-NH2 |
| 688 | TCAM685 | Lys-Lys-Phe-Lys-Lys-Phe-Phe-Lys-Lys-Leu-Lys-c[Asp-Arg-Arg-Trp-Trp-Arg-Phe-Lys]-D-Val-D-Phe-NH2 |
| 689 | TCAM686 | Lys-Lys-Phe-Lys-Lys-Phe-Phe-Lys-Lys-Leu-Lys-c[Asp-Arg-Arg-Trp-Trp-Arg-Phe-Lys]-D-Pro-D-Val-NH2 |
| 690 | TCAM687 | Lys-Lys-Phe-Lys-Lys-Phe-Phe-Lys-Lys-Leu-Lys-c[Asp-Arg-Arg-Trp-Trp-Arg-Phe-Lys]-D-Phe-D-Val-NH2 |
| 691 | TCAM688 | Lys-Lys-Phe-Lys-Lys-Phe-Phe-Lys-Lys-Leu-Lys-c[Asp-Arg-Arg-Tyr-Tyr-Arg-Phe-Lys]-D-Val-D-Pro-NH2 |
| 692 | TCAM689 | Lys-Lys-Phe-Lys-Lys-Phe-Phe-Lys-Lys-Leu-Lys-c[Asp-Arg-Arg-Tyr-Tyr-Arg-Phe-Lys]-D-Val-D-Phe-NH2 |
| 693 | TCAM690 | Lys-Lys-Phe-Lys-Lys-Phe-Phe-Lys-Lys-Leu-Lys-c[Asp-Arg-Arg-Tyr-Tyr-Arg-Phe-Lys]-D-Pro-D-Val-NH2 |
| 694 | TCAM691 | Lys-Lys-Phe-Lys-Lys-Phe-Phe-Lys-Lys-Leu-Lys-c[Asp-Arg-Arg-Tyr-Tyr-Arg-Phe-Lys]-D-Phe-D-Val-NH2 |
| 695 | TCAM692 | Lys-Lys-Phe-Lys-Lys-Phe-Phe-Lys-Lys-Leu-Lys-c[Asp-Arg-Arg-Nal-Nal-Arg-Phe-Lys]-D-Val-D-Pro-NH2 |
| 696 | TCAM693 | Lys-Lys-Phe-Lys-Lys-Phe-Phe-Lys-Lys-Leu-Lys-c[Asp-Arg-Arg-Nal-Nal-Arg-Phe-Lys]-D-Val-D-Phe-NH2 |
| 697 | TCAM694 | Lys-Lys-Phe-Lys-Lys-Phe-Phe-Lys-Lys-Leu-Lys-c[Asp-Arg-Arg-Nal-Nal-Arg-Phe-Lys]-D-Pro-D-Val-NH2 |
| 698 | TCAM695 | Lys-Lys-Phe-Lys-Lys-Phe-Phe-Lys-Lys-Leu-Lys-c[Asp-Arg-Arg-Nal-Nal-Arg-Phe-Lys]-D-Phe-D-Val-NH2 |
| 699 | TCAM696 | Lys-Lys-Phe-Lys-Lys-Phe-Phe-Lys-Lys-Leu-Lys-c[Asp-Arg-Arg-Leu-Trp-Leu-Trp-Lys]-D-Val-D-Pro-NH2 |
| 700 | TCAM697 | Lys-Lys-Phe-Lys-Lys-Phe-Phe-Lys-Lys-Leu-Lys-c[Asp-Arg-Arg-Leu-Trp-Leu-Trp-Lys]-D-Val-D-Phe-NH2 |
| 701 | TCAM698 | Lys-Lys-Phe-Lys-Lys-Phe-Phe-Lys-Lys-Leu-Lys-c[Asp-Arg-Arg-Leu-Trp-Leu-Trp-Lys]-D-Pro-D-Val-NH2 |
| 702 | TCAM699 | Lys-Lys-Phe-Lys-Lys-Phe-Phe-Lys-Lys-Leu-Lys-c[Asp-Arg-Arg-Leu-Trp-Leu-Trp-Lys]-D-Phe-D-Val-NH2 |
| 703 | TCAM700 | Lys-Lys-Phe-Lys-Lys-Phe-Phe-Lys-Lys-Leu-Lys-c[Asp-Arg-Arg-Leu-Trp-Leu-Trp-Lys]-D-Val-D-Pro-NH2 |

TABLE 5-continued

Exemplary Anti-microbial peptides

| SEQ NO: | Peptide | Peptide Sequence |
|---|---|---|
| 704 | TCAM701 | Lys-Lys-Phe-Lys-Lys-Phe-Phe-Lys-Lys-Leu-Lys-c[Asp-Arg-Arg-Leu-Trp-Leu-Trp-Lys]-D-Val-D-Phe-NH2 |
| 705 | TCAM702 | Lys-Lys-Phe-Lys-Lys-Phe-Phe-Lys-Lys-Leu-Lys-c[Asp-Arg-Arg-Leu-Trp-Leu-Trp-Lys]-D-Pro-D-Val-NH2 |
| 706 | TCAM703 | Lys-Lys-Phe-Lys-Lys-Phe-Phe-Lys-Lys-Leu-Lys-c[Asp-Arg-Arg-Leu-Trp-Leu-Trp-Lys]-D-Phe-D-Val-NH2 |
| 707 | TCAM704 | Lys-Lys-Phe-Lys-Lys-Phe-Phe-Lys-Lys-Leu-Lys-c[Asp-Arg-Arg-Arg-Trp-Leu-Trp-Leu-Trp-Lys]-D-Val-D-Pro-NH2 |
| 708 | TCAM705 | Lys-Lys-Phe-Lys-Lys-Phe-Phe-Lys-Lys-Leu-Lys-c[Asp-Arg-Arg-Arg-Trp-Leu-Trp-Leu-Trp-Lys]-D-Val-D-Phe-NH2 |
| 709 | TCAM706 | Lys-Lys-Phe-Lys-Lys-Phe-Phe-Lys-Lys-Leu-Lys-c[Asp-Arg-Arg-Arg-Trp-Leu-Trp-Leu-Trp-Lys]-D-Pro-D-Val-NH2 |
| 710 | TCAM707 | Lys-Lys-Phe-Lys-Lys-Phe-Phe-Lys-Lys-Leu-Lys-c[Asp-Arg-Arg-Arg-Trp-Leu-Trp-Leu-Trp-Lys]-D-Phe-D-Val-NH2 |
| 711 | TCAM708 | Lys-Lys-Phe-Lys-Lys-Phe-Phe-Lys-Lys-Leu-Lys-c[Asp-Arg-Gln-Arg-Arg-Trp-Leu-Trp-Leu-Trp-Lys]-D-Val-D-Pro-NH2 |
| 712 | TCAM709 | Lys-Lys-Phe-Lys-Lys-Phe-Phe-Lys-Lys-Leu-Lys-c[Asp-Arg-Gln-Arg-Arg-Trp-Leu-Trp-Leu-Trp-Lys]-D-Val-D-Phe-NH2 |
| 713 | TCAM710 | Lys-Lys-Phe-Lys-Lys-Phe-Phe-Lys-Lys-Leu-Lys-c[Asp-Arg-Gln-Arg-Arg-Trp-Leu-Trp-Leu-Trp-Lys]-D-Pro-D-Val-NH2 |
| 714 | TCAM711 | Lys-Lys-Phe-Lys-Lys-Phe-Phe-Lys-Lys-Leu-Lys-c[Asp-Arg-Gln-Arg-Arg-Trp-Leu-Trp-Leu-Trp-Lys]-D-Phe-D-Val-NH2 |
| 715 | TCAM712 | Lys-Lys-Phe-Lys-Lys-Phe-Phe-Lys-Lys-Leu-Lys-c[Asp-Trp-Arg-Trp-Trp-Arg-Arg-Lys]-D-Val-D-Pro-NH2 |
| 716 | TCAM713 | Lys-Lys-Phe-Lys-Lys-Phe-Phe-Lys-Lys-Leu-Lys-c[Asp-Trp-Arg-Trp-Trp-Arg-Arg-Lys]-D-Val-D-Phe-NH2 |
| 717 | TCAM714 | Lys-Lys-Phe-Lys-Lys-Phe-Phe-Lys-Lys-Leu-Lys-c[Asp-Trp-Arg-Trp-Trp-Arg-Arg-Lys]-D-Pro-D-Val-NH2 |
| 718 | TCAM715 | Lys-Lys-Phe-Lys-Lys-Phe-Phe-Lys-Lys-Leu-Lys-c[Asp-Trp-Arg-Trp-Trp-Arg-Arg-Lys]-D-Phe-D-Val-NH2 |
| 719 | TCAM716 | Lys-Lys-Phe-Lys-Lys-Phe-Phe-Lys-Lys-Leu-Lys-c[Asp-Trp-Trp-Arg-Arg-Trp-Trp-Arg-Arg-Lys]-D-Val-D-Pro-NH2 |
| 720 | TCAM717 | Lys-Lys-Phe-Lys-Lys-Phe-Phe-Lys-Lys-Leu-Lys-c[Asp-Trp-Trp-Arg-Arg-Trp-Trp-Arg-Arg-Lys]-D-Val-D-Phe-NH2 |
| 721 | TCAM718 | Lys-Lys-Phe-Lys-Lys-Phe-Phe-Lys-Lys-Leu-Lys-c[Asp-Trp-Trp-Arg-Arg-Trp-Trp-Arg-Arg-Lys]-D-Pro-D-Val-NH2 |
| 722 | TCAM719 | Lys-Lys-Phe-Lys-Lys-Phe-Phe-Lys-Lys-Leu-Lys-c[Asp-Trp-Trp-Arg-Arg-Trp-Trp-Arg-Arg-Lys]-D-Phe-D-Val-NH2 |
| 723 | TCAM720 | Lys-Lys-Phe-Lys-Lys-Phe-Phe-Lys-Lys-Leu-Lys-c[Asp-Trp-Arg-Trp-Arg-Trp-Arg-Lys]-D-Val-D-Pro-NH2 |
| 724 | TCAM721 | Lys-Lys-Phe-Lys-Lys-Phe-Phe-Lys-Lys-Leu-Lys-c[Asp-Trp-Arg-Trp-Arg-Trp-Arg-Lys]-D-Val-D-Phe-NH2 |
| 725 | TCAM722 | Lys-Lys-Phe-Lys-Lys-Phe-Phe-Lys-Lys-Leu-Lys-c[Asp-Trp-Arg-Trp-Arg-Trp-Arg-Lys]-D-Pro-D-Val-NH2 |
| 726 | TCAM723 | Lys-Lys-Phe-Lys-Lys-Phe-Phe-Lys-Lys-Leu-Lys-c[Asp-Trp-Arg-Trp-Arg-Trp-Arg-Lys]-D-Phe-D-Val-NH2 |
| 727 | TCAM724 | Lys-Lys-Phe-Lys-Lys-Phe-Phe-Lys-Lys-Leu-Lys-c[Asp-Arg-Trp-Arg-Trp-Arg-Trp-Lys]-D-Val-D-Pro-NH2 |
| 728 | TCAM725 | Lys-Lys-Phe-Lys-Lys-Phe-Phe-Lys-Lys-Leu-Lys-c[Asp-Arg-Trp-Arg-Trp-Arg-Trp-Lys]-D-Val-D-Phe-NH2 |

TABLE 5-continued

Exemplary Anti-microbial peptides

| SEQ NO: | Peptide | Peptide Sequence |
|---|---|---|
| 729 | TCAM726 | Lys-Lys-Phe-Lys-Lys-Phe-Phe-Lys-Lys-Leu-Lys-c[Asp-Arg-Trp-Arg-Trp-Arg-Trp-Lys]-D-Pro-D-Val-NH2 |
| 730 | TCAM727 | Lys-Lys-Phe-Lys-Lys-Phe-Phe-Lys-Lys-Leu-Lys-c[Asp-Arg-Trp-Arg-Trp-Arg-Trp-Lys]-D-Phe-D-Val-NH2 |
| 731 | TCAM728 | Lys-Lys-Phe-Lys-Lys-Phe-Phe-Lys-Lys-Leu-Lys-c[Asp-Arg-Trp-Trp-Arg-Arg-Lys]-D-Val-D-Pro-NH2 |
| 732 | TCAM729 | Lys-Lys-Phe-Lys-Lys-Phe-Phe-Lys-Lys-Leu-Lys-c[Asp-Arg-Trp-Trp-Arg-Arg-Lys]-D-Val-D-Phe-NH2 |
| 733 | TCAM730 | Lys-Lys-Phe-Lys-Lys-Phe-Phe-Lys-Lys-Leu-Lys-c[Asp-Arg-Trp-Trp-Arg-Arg-Lys]-D-Pro-D-Val-NH2 |
| 734 | TCAM731 | Lys-Lys-Phe-Lys-Lys-Phe-Phe-Lys-Lys-Leu-Lys-c[Asp-Arg-Trp-Trp-Arg-Arg-Lys]-D-Phe-D-Val-NH2 |
| 735 | TCAM732 | Lys-Lys-Phe-Lys-Lys-Phe-Phe-Lys-Lys-Leu-Lys-c[Asp-Arg-Trp-Arg-Trp-Arg-Lys]-D-Val-D-Pro-NH2 |
| 736 | TCAM733 | Lys-Lys-Phe-Lys-Lys-Phe-Phe-Lys-Lys-Leu-Lys-c[Asp-Arg-Trp-Arg-Trp-Arg-Lys]-D-Val-D-Phe-NH2 |
| 737 | TCAM734 | Lys-Lys-Phe-Lys-Lys-Phe-Phe-Lys-Lys-Leu-Lys-c[Asp-Arg-Trp-Arg-Trp-Arg-Lys]-D-Pro-D-Val-NH2 |
| 738 | TCAM735 | Lys-Lys-Phe-Lys-Lys-Phe-Phe-Lys-Lys-Leu-Lys-c[Asp-Arg-Trp-Arg-Trp-Arg-Lys]-D-Phe-D-Val-NH2 |
| 739 | TCAM736 | Lys-Lys-Phe-Lys-Lys-Phe-Phe-Lys-Lys-Leu-Lys-c[Asp-Trp-Trp-Arg-Arg-Trp-Lys]-D-Val-D-Pro-NH2 |
| 740 | TCAM737 | Lys-Lys-Phe-Lys-Lys-Phe-Phe-Lys-Lys-Leu-Lys-c[Asp-Trp-Trp-Arg-Arg-Trp-Lys]-D-Val-D-Phe-NH2 |
| 741 | TCAM738 | Lys-Lys-Phe-Lys-Lys-Phe-Phe-Lys-Lys-Leu-Lys-c[Asp-Trp-Trp-Arg-Arg-Trp-Lys]-D-Pro-D-Val-NH2 |
| 742 | TCAM739 | Lys-Lys-Phe-Lys-Lys-Phe-Phe-Lys-Lys-Leu-Lys-c[Asp-Trp-Trp-Arg-Arg-Trp-Lys]-D-Phe-D-Val-NH2 |
| 743 | TCAM740 | Lys-Lys-Phe-Lys-Lys-Phe-Phe-Lys-Lys-Leu-Lys-c[Asp-Trp-Arg-Trp-Arg-Trp-Lys]-D-Val-D-Pro-NH2 |
| 744 | TCAM741 | Lys-Lys-Phe-Lys-Lys-Phe-Phe-Lys-Lys-Leu-Lys-c[Asp-Trp-Arg-Trp-Arg-Trp-Lys]-D-Val-D-Phe-NH2 |
| 745 | TCAM742 | Lys-Lys-Phe-Lys-Lys-Phe-Phe-Lys-Lys-Leu-Lys-c[Asp-Trp-Arg-Trp-Arg-Trp-Lys]-D-Pro-D-Val-NH2 |
| 746 | TCAM743 | Lys-Lys-Phe-Lys-Lys-Phe-Phe-Lys-Lys-Leu-Lys-c[Asp-Trp-Arg-Trp-Arg-Trp-Lys]-D-Phe-D-Val-NH2 |
| 747 | TCAM744 | Lys-Lys-Phe-Lys-Lys-Phe-Phe-Lys-Lys-Leu-Lys-c[Asp-Trp-Arg-Tyr-Arg-Trp-Lys]-D-Val-D-Pro-NH2 |
| 748 | TCAM745 | Lys-Lys-Phe-Lys-Lys-Phe-Phe-Lys-Lys-Leu-Lys-c[Asp-Trp-Arg-Tyr-Arg-Trp-Lys]-D-Val-D-Phe-NH2 |
| 749 | TCAM746 | Lys-Lys-Phe-Lys-Lys-Phe-Phe-Lys-Lys-Leu-Lys-c[Asp-Trp-Arg-Tyr-Arg-Trp-Lys]-D-Pro-D-Val-NH2 |
| 750 | TCAM747 | Lys-Lys-Phe-Lys-Lys-Phe-Phe-Lys-Lys-Leu-Lys-c[Asp-Trp-Arg-Tyr-Arg-Trp-Lys]-D-Phe-D-Val-NH2 |
| 751 | TCAM748 | Lys-Lys-Phe-Lys-Lys-Phe-Phe-Lys-Lys-Leu-Lys-c[Asp-Trp-Arg-Trp-Arg-Tyr-Lys]-D-Val-D-Pro-NH2 |
| 752 | TCAM749 | Lys-Lys-Phe-Lys-Lys-Phe-Phe-Lys-Lys-Leu-Lys-c[Asp-Trp-Arg-Trp-Arg-Tyr-Lys]-D-Val-D-Phe-NH2 |
| 753 | TCAM750 | Lys-Lys-Phe-Lys-Lys-Phe-Phe-Lys-Lys-Leu-Lys-c[Asp-Trp-Arg-Trp-Arg-Tyr-Lys]-D-Pro-D-Val-NH2 |

TABLE 5-continued

Exemplary Anti-microbial peptides

| SEQ NO: | Peptide | Peptide Sequence |
|---|---|---|
| 754 | TCAM751 | Lys-Lys-Phe-Lys-Lys-Phe-Phe-Lys-Lys-Leu-Lys-c[Asp-Trp-Arg-Trp-Arg-Tyr-Lys]-D-Phe-D-Val-NH2 |
| 755 | TCAM752 | Lys-Lys-Phe-Lys-Lys-Phe-Phe-Lys-Lys-Leu-Lys-c[Asp-Trp-Arg-Trp-Arg-Lys]-D-Val-D-Pro-NH2 |
| 756 | TCAM753 | Lys-Lys-Phe-Lys-Lys-Phe-Phe-Lys-Lys-Leu-Lys-c[Asp-Trp-Arg-Trp-Arg-Lys]-D-Val-D-Phe-NH2 |
| 757 | TCAM754 | Lys-Lys-Phe-Lys-Lys-Phe-Phe-Lys-Lys-Leu-Lys-c[Asp-Trp-Arg-Trp-Arg-Lys]-D-Pro-D-Val-NH2 |
| 758 | TCAM755 | Lys-Lys-Phe-Lys-Lys-Phe-Phe-Lys-Lys-Leu-Lys-c[Asp-Trp-Arg-Trp-Arg-Lys]-D-Phe-D-Val-NH2 |
| 759 | TCAM756 | Lys-Lys-Phe-Lys-Lys-Phe-Phe-Lys-Lys-Leu-Lys-c[Asp-Trp-Arg-Arg-Trp-Lys]-D-Val-D-Pro-NH2 |
| 760 | TCAM757 | Lys-Lys-Phe-Lys-Lys-Phe-Phe-Lys-Lys-Leu-Lys-c[Asp-Trp-Arg-Arg-Trp-Lys]-D-Val-D-Phe-NH2 |
| 761 | TCAM758 | Lys-Lys-Phe-Lys-Lys-Phe-Phe-Lys-Lys-Leu-Lys-c[Asp-Trp-Arg-Arg-Trp-Lys]-D-Pro-D-Val-NH2 |
| 762 | TCAM759 | Lys-Lys-Phe-Lys-Lys-Phe-Phe-Lys-Lys-Leu-Lys-c[Asp-Trp-Arg-Arg-Trp-Lys]-D-Phe-D-Val-NH2 |
| 763 | TCAM760 | Lys-Lys-Phe-Lys-Lys-Phe-Phe-Lys-Lys-Leu-Lys-c[Asp-Arg-Trp-Trp-Arg-Lys]-D-Val-D-Pro-NH2 |
| 764 | TCAM761 | Lys-Lys-Phe-Lys-Lys-Phe-Phe-Lys-Lys-Leu-Lys-c[Asp-Arg-Trp-Trp-Arg-Lys]-D-Val-D-Phe-NH2 |
| 765 | TCAM762 | Lys-Lys-Phe-Lys-Lys-Phe-Phe-Lys-Lys-Leu-Lys-c[Asp-Arg-Trp-Trp-Arg-Lys]-D-Pro-D-Val-NH2 |
| 766 | TCAM763 | Lys-Lys-Phe-Lys-Lys-Phe-Phe-Lys-Lys-Leu-Lys-c[Asp-Arg-Trp-Trp-Arg-Lys]-D-Phe-D-Val-NH2 |
| 767 | TCAM764 | Lys-Lys-Phe-Lys-Lys-Phe-Phe-Lys-Lys-Leu-Lys-c[Asp-Trp-Arg-Trp-Lys]-D-Val-D-Pro-NH2 |
| 768 | TCAM765 | Lys-Lys-Phe-Lys-Lys-Phe-Phe-Lys-Lys-Leu-Lys-c[Asp-Trp-Arg-Trp-Lys]-D-Val-D-Phe-NH2 |
| 769 | TCAM766 | Lys-Lys-Phe-Lys-Lys-Phe-Phe-Lys-Lys-Leu-Lys-c[Asp-Trp-Arg-Trp-Lys]-D-Pro-D-Val-NH2 |
| 770 | TCAM767 | Lys-Lys-Phe-Lys-Lys-Phe-Phe-Lys-Lys-Leu-Lys-c[Asp-Trp-Arg-Trp-Lys]-D-Phe-D-Val-NH2 |
| 771 | TCAM768 | Lys-Lys-Phe-Lys-Lys-Phe-Phe-Lys-Lys-Leu-Lys-c[Asp-Arg-Trp-Arg-Lys]-D-Val-D-Pro-NH2 |
| 772 | TCAM769 | Lys-Lys-Phe-Lys-Lys-Phe-Phe-Lys-Lys-Leu-Lys-c[Asp-Arg-Trp-Arg-Lys]-D-Val-D-Phe-NH2 |
| 773 | TCAM770 | Lys-Lys-Phe-Lys-Lys-Phe-Phe-Lys-Lys-Leu-Lys-c[Asp-Arg-Trp-Arg-Lys]-D-Pro-D-Val-NH2 |
| 774 | TCAM771 | Lys-Lys-Phe-Lys-Lys-Phe-Phe-Lys-Lys-Leu-Lys-c[Asp-Arg-Trp-Arg-Lys]-D-Phe-D-Val-NH2 |
| 775 | TCAM772 | Lys-Lys-Phe-Lys-Lys-Phe-Phe-Lys-Lys-Leu-Lys-c[Asp-His-D-Nal(2')-Arg-Trp-Lys]-D-Val-D-Pro-NH2 |
| 776 | TCAM773 | Lys-Lys-Phe-Lys-Lys-Phe-Phe-Lys-Lys-Leu-Lys-c[Asp-His-D-Nal(2')-Arg-Trp-Lys]-D-Pro-D-Val-NH2 |
| 777 | TCAM774 | Lys-Lys-Phe-Lys-Lys-Phe-Phe-Lys-Lys-Leu-Lys-c[Asp-His-D-Nal(2')-Arg-Trp-Lys]-D-Val-D-Phe-NH2 |
| 778 | TCAM775 | Lys-Lys-Phe-Lys-Lys-Phe-Phe-Lys-Lys-Leu-Lys-c[Asp-His-D-Nal(2')-Arg-Trp-Lys]-D-Phe-D-Val-NH2 |

TABLE 5-continued

Exemplary Anti-microbial peptides

| SEQ NO: | Peptide | Peptide Sequence |
|---|---|---|
| 779 | TCAM776 | Lys-Lys-Phe-Lys-Lys-Phe-Phe-Lys-Lys-Leu-Lys-c[Asp-Pro-D-Nal(2')-Arg-Trp-Lys]-D-Val-D-Pro-NH2 |
| 780 | TCAM777 | Lys-Lys-Phe-Lys-Lys-Phe-Phe-Lys-Lys-Leu-Lys-c[Asp-Pro-D-Nal(2')-Arg-Trp-Lys]-D-Pro-D-Val-NH2 |
| 781 | TCAM778 | Lys-Lys-Phe-Lys-Lys-Phe-Phe-Lys-Lys-Leu-Lys-c[Asp-Pro-D-Nal(2')-Arg-Trp-Lys]-D-Val-D-Phe-NH2 |
| 782 | TCAM779 | Lys-Lys-Phe-Lys-Lys-Phe-Phe-Lys-Lys-Leu-Lys-c[Asp-Pro-D-Nal(2')-Arg-Trp-Lys]-D-Phe-D-Val-NH2 |
| 783 | TCAM780 | Lys-Lys-Phe-Lys-Lys-Phe-Phe-Lys-Lys-Leu-Lys-c[Asp-Arg-Arg-Nal(2')-Arg-Trp-Lys]-D-Val-D-Pro-NH2 |
| 784 | TCAM781 | Lys-Lys-Phe-Lys-Lys-Phe-Phe-Lys-Lys-Leu-Lys-c[Asp-Arg-Arg-Nal(2')-Arg-Trp-Lys]-D-Pro-D-Val-NH2 |
| 785 | TCAM782 | Lys-Lys-Phe-Lys-Lys-Phe-Phe-Lys-Lys-Leu-Lys-c[Asp-Arg-Arg-Nal(2')-Arg-Trp-Lys]-D-Val-D-Phe-NH2 |
| 786 | TCAM783 | Lys-Lys-Phe-Lys-Lys-Phe-Phe-Lys-Lys-Leu-Lys-c[Asp-Arg-Arg-Nal(2')-Arg-Trp-Lys]-D-Phe-D-Val-NH2 |
| 787 | TCAM784 | Lys-Lys-Phe-Lys-Lys-Phe-Phe-Lys-Lys-Leu-Lys-c[Asp-Arg-Arg-Pro-Nal(2')-Arg-Trp-Lys]-D-Val-D-Pro-NH2 |
| 788 | TCAM785 | Lys-Lys-Phe-Lys-Lys-Phe-Phe-Lys-Lys-Leu-Lys-c[Asp-Arg-Arg-Pro-D-Nal(2')-Arg-Trp-Lys]-D-Pro-D-Val-NH2 |
| 789 | TCAM786 | Lys-Lys-Phe-Lys-Lys-Phe-Phe-Lys-Lys-Leu-Lys-c[Asp-Arg-Arg-Pro-Nal(2')-Arg-Trp-Lys]-D-Val-D-Phe-NH2 |
| 790 | TCAM787 | Lys-Lys-Phe-Lys-Lys-Phe-Phe-Lys-Lys-Leu-Lys-c[Asp-Arg-Arg-Pro-Nal(2')-Arg-Trp-Lys]-D-Phe-D-Val-NH2 |
| 791 | TCAM788 | Lys-Lys-Phe-Lys-Lys-Phe-Phe-Lys-Lys-Leu-Lys-c[Asp-Arg-D-Nal(2')-Arg-Trp-Lys]-D-Val-D-Pro-NH2 |
| 792 | TCAM789 | Lys-Lys-Phe-Lys-Lys-Phe-Phe-Lys-Lys-Leu-Lys-c[Asp-Arg-D-Nal(2')-Arg-Trp-Lys]-D-Pro-D-Val-NH2 |
| 793 | TCAM790 | Lys-Lys-Phe-Lys-Lys-Phe-Phe-Lys-Lys-Leu-Lys-c[Asp-Arg-D-Nal(2')-Arg-Trp-Lys]-D-Val-D-Phe-NH2 |
| 794 | TCAM791 | Lys-Lys-Phe-Lys-Lys-Phe-Phe-Lys-Lys-Leu-Lys-c[Asp-Arg-D-Nal(2')-Arg-Trp-Lys]-D-Phe-D-Val-NH2 |
| 795 | TCAM792 | Lys-Lys-Phe-Lys-Lys-Phe-Phe-Lys-Lys-Leu-Lys-c[Asp-Arg-Pro-D-Nal(2')-Arg-Trp-Lys]-D-Val-D-Pro-NH2 |
| 796 | TCAM793 | Lys-Lys-Phe-Lys-Lys-Phe-Phe-Lys-Lys-Leu-Lys-c[Asp-Arg-Pro-D-Nal(2')-Arg-Trp-Lys]-D-Pro-D-Val-NH2 |
| 797 | TCAM794 | Lys-Lys-Phe-Lys-Lys-Phe-Phe-Lys-Lys-Leu-Lys-c[Asp-Arg-Pro-D-Nal(2')-Arg-Trp-Lys]-D-Val-D-Phe-NH2 |
| 798 | TCAM795 | Lys-Lys-Phe-Lys-Lys-Phe-Phe-Lys-Lys-Leu-Lys-c[Asp-Arg-Pro-D-Nal(2')-Arg-Trp-Lys]-D-Phe-D-Val-NH2 |
| 799 | TCAM796 | Lys-Lys-Phe-Lys-Lys-Phe-Phe-Lys-Lys-Leu-Lys-Arg-Arg-c[Asp-Pro-D-Nal(2')-Arg-Trp-Lys]-D-Val-D-Pro-NH2 |
| 800 | TCAM797 | Lys-Lys-Phe-Lys-Lys-Phe-Phe-Lys-Lys-Leu-Lys-Arg-Arg-c[Asp-Pro-D-Nal(2')-Arg-Trp-Lys]-D-Pro-D-Val-NH2 |
| 801 | TCAM798 | Lys-Lys-Phe-Lys-Lys-Phe-Phe-Lys-Lys-Leu-Lys-Arg-Arg-c[Asp-Pro-D-Nal(2')-Arg-Trp-Lys]-D-Val-D-Phe-NH2 |
| 802 | TCAM799 | Lys-Lys-Phe-Lys-Lys-Phe-Phe-Lys-Lys-Leu-Lys-Arg-Arg-c[Asp-Pro-D-Nal(2')-Arg-Trp-Lys]-D-Phe-D-Val-NH2 |
| 803 | TCAM800 | Lys-Lys-Phe-Lys-Lys-Phe-Phe-Lys-Lys-Leu-Lys-Arg-Arg-c[Asp-His-D-Nal(2')-Arg-Trp-Lys]-D-Val-D-Pro-NH2 |

TABLE 5-continued

Exemplary Anti-microbial peptides

| SEQ NO: | Peptide | Peptide Sequence |
|---|---|---|
| 804 | TCAM801 | Lys-Lys-Phe-Lys-Lys-Phe-Phe-Lys-Lys-Leu-Lys-Arg-Arg-c[Asp-His-D-Nal(2')-Arg-Trp-Lys]-D-Pro-D-Val-NH2 |
| 805 | TCAM802 | Lys-Lys-Phe-Lys-Lys-Phe-Phe-Lys-Lys-Leu-Lys-Arg-Arg-c[Asp-His-D-Nal(2')-Arg-Trp-Lys]-D-Val-D-Phe-NH2 |
| 806 | TCAM803 | Lys-Lys-Phe-Lys-Lys-Phe-Phe-Lys-Lys-Leu-Lys-Arg-Arg-c[Asp-His-D-Nal(2')-Arg-Trp-Lys]-D-Phe-D-Val-NH2 |
| 807 | TCAM804 | Lys-Lys-Phe-Lys-Lys-Phe-Phe-Lys-Lys-Leu-Lys-c[Asp-Arg-Pro-D-Nal(2')-Arg-Trp-Arg-Lys]-D-Val-D-Pro-NH2 |
| 808 | TCAM805 | Lys-Lys-Phe-Lys-Lys-Phe-Phe-Lys-Lys-Leu-Lys-c[Asp-Arg-Pro-D-Nal(2')-Arg-Trp-Arg-Lys]-D-Pro-D-Val-NH2 |
| 809 | TCAM806 | Lys-Lys-Phe-Lys-Lys-Phe-Phe-Lys-Lys-Leu-Lys-c[Asp-Arg-Pro-D-Nal(2')-Arg-Trp-Arg-Lys]-D-Val-D-Phe-NH2 |
| 810 | TCAM807 | Lys-Lys-Phe-Lys-Lys-Phe-Phe-Lys-Lys-Leu-Lys-c[Asp-Arg-Pro-D-Nal(2')-Arg-Trp-Arg-Lys]-D-Phe-D-Val-NH2 |
| 811 | TCAM808 | Lys-Lys-Phe-Lys-Lys-Phe-Phe-Lys-Lys-Leu-Lys-c[Asp-Arg-His-D-Nal(2')-Arg-Trp-Arg-Lys]-D-Val-D-Pro-NH2 |
| 812 | TCAM809 | Lys-Lys-Phe-Lys-Lys-Phe-Phe-Lys-Lys-Leu-Lys-c[Asp-Arg-His-D-Nal(2')-Arg-Trp-Arg-Lys]-D-Pro-D-Val-NH2 |
| 813 | TCAM810 | Lys-Lys-Phe-Lys-Lys-Phe-Phe-Lys-Lys-Leu-Lys-c[Asp-Arg-His-D-Nal(2')-Arg-Trp-Arg-Lys]-D-Val-D-Phe-NH2 |
| 814 | TCAM811 | Lys-Lys-Phe-Lys-Lys-Phe-Phe-Lys-Lys-Leu-Lys-c[Asp-Arg-His-D-Nal(2')-Arg-Trp-Arg-Lys]-D-Phe-D-Val-NH2 |
| 815 | TCAM812 | Lys-Lys-Phe-Lys-Lys-Phe-Phe-Lys-Lys-Leu-Lys-c[Asp-His-D-Nal(2')-Arg-D-Nal(2')-Lys]-D-Val-D-Phe-NH2 |
| 816 | TCAM813 | Lys-Lys-Phe-Lys-Lys-Phe-Phe-Lys-Lys-Leu-Lys-c[Asp-His-D-Nal(2')-Arg-D-Nal(2')-Lys]-D-Phe-D-Val-NH2 |
| 817 | TCAM814 | Lys-Lys-Phe-Lys-Lys-Phe-Phe-Lys-Lys-Leu-Lys-c[Asp-Pro-D-Nal(2')-Arg-D-Nal(2')-Lys]-D-Val-D-Pro-NH2 |
| 818 | TCAM815 | Lys-Lys-Phe-Lys-Lys-Phe-Phe-Lys-Lys-Leu-Lys-c[Asp-Pro-D-Nal(2')-Arg-D-Nal(2')-Lys]-D-Pro-D-Val-NH2 |
| 819 | TCAM816 | Lys-Lys-Phe-Lys-Lys-Phe-Phe-Lys-Lys-Leu-Lys-c[Asp-Pro-D-Nal(2')-Arg-D-Nal(2')-Lys]-D-Val-D-Phe-NH2 |
| 820 | TCAM817 | Lys-Lys-Phe-Lys-Lys-Phe-Phe-Lys-Lys-Leu-Lys-c[Asp-Pro-D-Nal(2')-Arg-D-Nal(2')-Lys]-D-Phe-D-Val-NH2 |
| 821 | TCAM818 | Lys-Lys-Phe-Lys-Lys-Phe-Phe-Lys-Lys-Leu-Lys-c[Asp-Arg-Arg-D-Nal(2')-Arg-D-Nal(2')-Lys]-D-Val-D-Pro-NH2 |
| 822 | TCAM819 | Lys-Lys-Phe-Lys-Lys-Phe-Phe-Lys-Lys-Leu-Lys-c[Asp-Arg-Arg-D-Nal(2')-Arg-D-Nal(2')-Lys]-D-Pro-D-Val-NH2 |
| 823 | TCAM820 | Lys-Lys-Phe-Lys-Lys-Phe-Phe-Lys-Lys-Leu-Lys-c[Asp-Arg-Arg-D-Nal(2')-Arg-D-Nal(2')-Lys]-D-Val-D-Phe-NH2 |
| 824 | TCAM821 | Lys-Lys-Phe-Lys-Lys-Phe-Phe-Lys-Lys-Leu-Lys-c[Asp-Arg-Arg-D-Nal(2')-Arg-D-Nal(2')-Lys]-D-Phe-D-Val-NH2 |
| 825 | TCAM822 | Lys-Lys-Phe-Lys-Lys-Phe-Phe-Lys-Lys-Leu-Lys-c[Asp-Arg-Arg-Pro-D-Nal(2')-Arg-D-Nal(2')-Lys]-D-Val-D-Pro-NH2 |
| 826 | TCAM823 | Lys-Lys-Phe-Lys-Lys-Phe-Phe-Lys-Lys-Leu-Lys-c[Asp-Arg-Arg-Pro-D-Nal(2')-Arg-D-Nal(2')-Lys]-D-Pro-D-Val-NH2 |
| 827 | TCAM824 | Lys-Lys-Phe-Lys-Lys-Phe-Phe-Lys-Lys-Leu-Lys-c[Asp-Arg-Arg-Pro-D-Nal(2')-Arg-D-Nal(2')-Lys]-D-Val-D-Phe-NH2 |
| 828 | TCAM825 | Lys-Lys-Phe-Lys-Lys-Phe-Phe-Lys-Lys-Leu-Lys-c[Asp-Arg-Arg-Pro-D-Nal(2')-Arg-D-Nal(2')-Lys]-D-Phe-D-Val-NH2 |

TABLE 5-continued

Exemplary Anti-microbial peptides

| SEQ NO: | Peptide | Peptide Sequence |
|---|---|---|
| 829 | TCAM826 | Lys-Lys-Phe-Lys-Lys-Phe-Phe-Lys-Lys-Leu-Lys-c[Asp-Arg-D-Nal(2')-Arg-D-Nal(2')-Lys]-D-Val-D-Pro-NH2 |
| 830 | TCAM827 | Lys-Lys-Phe-Lys-Lys-Phe-Phe-Lys-Lys-Leu-Lys-c[Asp-Arg-D-Nal(2')-Arg-D-Nal(2')-Lys]-D-Pro-D-Val-NH2 |
| 831 | TCAM828 | Lys-Lys-Phe-Lys-Lys-Phe-Phe-Lys-Lys-Leu-Lys-c[Asp-Arg-Nal(2')-Arg-D-Nal(2')-Lys]-D-Val-D-Phe-NH2 |
| 832 | TCAM829 | Lys-Lys-Phe-Lys-Lys-Phe-Phe-Lys-Lys-Leu-Lys-c[Asp-Arg-D-Nal(2')-Arg-D-Nal(2')-Lys]-D-Phe-D-Val-NH2 |
| 833 | TCAM830 | Lys-Lys-Phe-Lys-Lys-Phe-Phe-Lys-Lys-Leu-Lys-c[Asp-Arg-Pro-D-Nal(2')-Arg-D-Nal(2')-Lys]-D-Val-D-Pro-NH2 |
| 834 | TCAM831 | Lys-Lys-Phe-Lys-Lys-Phe-Phe-Lys-Lys-Leu-Lys-c[Asp-Arg-Pro-D-Nal(2')-Arg-D-Nal(2')-Lys]-D-Pro-D-Val-NH2 |
| 835 | TCAM832 | Lys-Lys-Phe-Lys-Lys-Phe-Phe-Lys-Lys-Leu-Lys-c[Asp-Arg-Pro-D-Nal(2')-Arg-D-Nal(2')-Lys]-D-Val-D-Phe-NH2 |
| 836 | TCAM833 | Lys-Lys-Phe-Lys-Lys-Phe-Phe-Lys-Lys-Leu-Lys-c[Asp-Arg-Pro-D-Nal(2')-Arg-D-Nal(2')-Lys]-D-Phe-D-Val-NH2 |
| 837 | TCAM834 | Lys-Lys-Phe-Lys-Lys-Phe-Phe-Lys-Lys-Leu-Lys-c[Asp-Arg-His-D-Nal(2')-Arg-D-Nal(2')-Lys]-D-Val-D-Pro-NH2 |
| 838 | TCAM835 | Lys-Lys-Phe-Lys-Lys-Phe-Phe-Lys-Lys-Leu-Lys-c[Asp-Arg-His-D-Nal(2')-Arg-D-Nal(2')-Lys]-D-Pro-D-Val-NH2 |
| 839 | TCAM836 | Lys-Lys-Phe-Lys-Lys-Phe-Phe-Lys-Lys-Leu-Lys-c[Asp-Arg-His-Nal(2')-Arg-D-Nal(2')-Lys]-D-Val-D-Phe-NH2 |
| 840 | TCAM837 | Lys-Lys-Phe-Lys-Lys-Phe-Phe-Lys-Lys-Leu-Lys-c[Asp-Arg-His-Nal(2')-Arg-D-Nal(2')-Lys]-D-Phe-D-Val-NH2 |
| 841 | TCAM838 | Lys-Lys-Phe-Lys-Lys-Phe-Phe-Lys-Lys-Leu-Lys-c[Asp-Arg-D-Nal(2')-Arg-D-Nal(2')-Arg-Lys]-D-Val-D-Pro-NH2 |
| 842 | TCAM839 | Lys-Lys-Phe-Lys-Lys-Phe-Phe-Lys-Lys-Leu-Lys-c[Asp-Arg-D-Nal(2')-Arg-D-Nal(2')-Arg-Lys]-D-Pro-D-Val-NH2 |
| 843 | TCAM840 | Lys-Lys-Phe-Lys-Lys-Phe-Phe-Lys-Lys-Leu-Lys-c[Asp-Arg-D-Nal(2')-Arg-D-Nal(2')-Arg-Lys]-D-Val-D-Phe-NH2 |
| 844 | TCAM841 | Lys-Lys-Phe-Lys-Lys-Phe-Phe-Lys-Lys-Leu-Lys-c[Asp-Arg-D-Nal(2')-Arg-D-Nal(2')-Arg-Lys]-D-Phe-D-Val-NH2 |
| 845 | TCAM842 | Lys-Lys-Phe-Lys-Lys-Phe-Phe-Lys-Lys-Leu-Lys-c[Asp-Arg-Pro-D-Nal(2')-Arg-D-Nal(2')-Arg-Lys]-D-Val-D-Pro-NH2 |
| 846 | TCAM843 | Lys-Lys-Phe-Lys-Lys-Phe-Phe-Lys-Lys-Leu-Lys-c[Asp-Arg-Pro-D-Nal(2')-Arg-D-Nal(2')-Arg-Lys]-D-Pro-D-Val-NH2 |
| 847 | TCAM844 | Lys-Lys-Phe-Lys-Lys-Phe-Phe-Lys-Lys-Leu-Lys-c[Asp-Arg-Pro-D-Nal(2')-Arg-D-Nal(2')-Arg-Lys]-D-Val-D-Phe-NH2 |
| 848 | TCAM845 | Lys-Lys-Phe-Lys-Lys-Phe-Phe-Lys-Lys-Leu-Lys-c[Asp-Arg-Pro-D-Nal(2')-Arg-D-Nal(2')-Arg-Lys]-D-Phe-D-Val-NH2 |
| 849 | TCAM846 | Lys-Lys-Phe-Lys-Lys-Phe-Phe-Lys-Lys-Leu-Lys-c[Asp-Arg-His-D-Nal(2')-Arg-D-Nal(2')-Arg-Lys]-D-Val-D-Pro-NH2 |
| 850 | TCAM847 | Lys-Lys-Phe-Lys-Lys-Phe-Phe-Lys-Lys-Leu-Lys-c[Asp-Arg-His-D-Nal(2')-Arg-D-Nal(2')-Arg-Lys]-D-Pro-D-Val-NH2 |
| 851 | TCAM848 | Lys-Lys-Phe-Lys-Lys-Phe-Phe-Lys-Lys-Leu-Lys-c[Asp-Arg-His-D-Nal(2')-Arg-D-Nal(2')-Arg-Lys]-D-Val-D-Phe-NH2 |
| 852 | TCAM849 | Lys-Lys-Phe-Lys-Lys-Phe-Phe-Lys-Lys-Leu-Lys-c[Asp-Arg-His-D-Nal(2')-Arg-D-Nal(2')-Arg-Lys]-D-Phe-D-Val-NH2 |
| 853 | TCAM850 | Lys-Lys-Phe-Lys-Lys-Phe-Phe-Lys-Lys-Leu-Lys-Arg-Arg-c[Asp-Pro-D-Nal(2')-Arg-D-Nal(2')-Lys]-D-Val-D-Pro-NH2 |

TABLE 5-continued

Exemplary Anti-microbial peptides

| SEQ NO: | Peptide | Peptide Sequence |
|---|---|---|
| 854 | TCAM851 | Lys-Lys-Phe-Lys-Lys-Phe-Phe-Lys-Lys-Leu-Lys-Arg-Arg-c[Asp-Pro-D-Nal(2')-Arg-D-Nal(2')-Lys]-D-Pro-D-Val-NH2 |
| 855 | TCAM852 | Lys-Lys-Phe-Lys-Lys-Phe-Phe-Lys-Lys-Leu-Lys-Arg-Arg-c[Asp-Pro-D-Nal(2')-Arg-D-Nal(2')-Lys]-D-Val-D-Phe-NH2 |
| 856 | TCAM853 | Lys-Lys-Phe-Lys-Lys-Phe-Phe-Lys-Lys-Leu-Lys-Arg-Arg-c[Asp-Pro-D-Nal(2')-Arg-D-Nal(2')-Lys]-D-Phe-D-Val-NH2 |
| 857 | TCAM854 | Lys-Lys-Phe-Lys-Lys-Phe-Phe-Lys-Lys-Leu-Lys-Arg-Arg-c[Asp-His-D-Nal(2')-Arg-D-Nal(2')-Lys]-D-Val-D-Pro-NH2 |
| 858 | TCAM855 | Lys-Lys-Phe-Lys-Lys-Phe-Phe-Lys-Lys-Leu-Lys-Arg-Arg-c[Asp-His-D-Nal(2')-Arg-D-Nal(2')-Lys]-D-Pro-D-Val-NH2 |
| 859 | TCAM856 | Lys-Lys-Phe-Lys-Lys-Phe-Phe-Lys-Lys-Leu-Lys-Arg-Arg-c[Asp-His-D-Nal(2')-Arg-D-Nal(2')-Lys]-D-Val-D-Phe-NH2 |
| 860 | TCAM857 | Lys-Lys-Phe-Lys-Lys-Phe-Phe-Lys-Lys-Leu-Lys-Arg-Arg-c[Asp-His-D-Nal(2')-Arg-D-Nal(2')-Lys]-D-Phe-D-Val-NH2 |
| 861 | TCAM858 | Lys-Lys-Phe-Lys-Lys-Phe-Phe-Lys-Lys-Leu-Lys-c[Asp-Arg-Pro-D-Nal(2')-Arg-D-Nal(2')-Arg-Lys]-D-Val-D-Pro-NH2 |
| 862 | TCAM859 | Lys-Lys-Phe-Lys-Lys-Phe-Phe-Lys-Lys-Leu-Lys-c[Asp-Arg-Pro-D-Nal(2')-Arg-D-Nal(2')-Arg-Lys]-D-Pro-D-Val-NH2 |
| 863 | TCAM860 | Lys-Lys-Phe-Lys-Lys-Phe-Phe-Lys-Lys-Leu-Lys-c[Asp-Arg-Pro-D-Nal(2')-Arg-D-Nal(2')-Arg-Lys]-D-Val-D-Phe-NH2 |
| 864 | TCAM861 | Lys-Lys-Phe-Lys-Lys-Phe-Phe-Lys-Lys-Leu-Lys-c[Asp-Arg-Pro-D-Nal(2')-Arg-D-Nal(2')-Arg-Lys]-D-Phe-D-Val-NH2 |
| 865 | TCAM862 | Lys-Lys-Phe-Lys-Lys-Phe-Phe-Lys-Lys-Leu-Lys-c[Asp-Arg-His-D-Nal(2')-Arg-D-Nal(2')-Arg-Lys]-D-Val-D-Pro-NH2 |
| 866 | TCAM863 | Lys-Lys-Phe-Lys-Lys-Phe-Phe-Lys-Lys-Leu-Lys-c[Asp-Arg-His-D-Nal(2')-Arg-D-Nal(2')-Arg-Lys]-D-Pro-D-Val-NH2 |
| 867 | TCAM864 | Lys-Lys-Phe-Lys-Lys-Phe-Phe-Lys-Lys-Leu-Lys-c[Asp-Arg-His-D-Nal(2')-Arg-D-Nal(2')-Arg-Lys]-D-Val-D-Phe-NH2 |
| 868 | TCAM865 | Lys-Lys-Phe-Lys-Lys-Phe-Phe-Lys-Lys-Leu-Lys-c[Asp-Arg-His-D-Nal(2')-Arg-D-Nal(2')-Arg-Lys]-D-Phe-D-Val-NH2 |
| 869 | TCAM866 | Lys-Lys-Phe-Lys-Lys-Phe-Phe-Lys-Lys-Leu-Lys-c[Asp-His-D-Nal(2')-Arg-Trp-Lys]-Arg-Arg-D-Val-D-Pro-NH2 |
| 870 | TCAM867 | Lys-Lys-Phe-Lys-Lys-Phe-Phe-Lys-Lys-Leu-Lys-c[Asp-His-D-Nal(2')-Arg-Trp-Lys]-Arg-Arg-D-Pro-D-Val-NH2 |
| 871 | TCAM868 | Lys-Lys-Phe-Lys-Lys-Phe-Phe-Lys-Lys-Leu-Lys-c[Asp-His-D-Nal(2')-Arg-Trp-Lys]-Arg-Arg-D-Val-D-Phe-NH2 |
| 872 | TCAM869 | Lys-Lys-Phe-Lys-Lys-Phe-Phe-Lys-Lys-Leu-Lys-c[Asp-His-D-Nal(2')-Arg-Trp-Lys]-Arg-Arg-D-Phe-D-Val-NH2 |
| 873 | TCAM870 | Lys-Lys-Phe-Lys-Lys-Phe-Phe-Lys-Lys-Leu-Lys-c[Asp-Pro-D-Nal(2')-Arg-Trp-Lys]-Arg-Arg-D-Val-D-Pro-NH2 |
| 874 | TCAM871 | Lys-Lys-Phe-Lys-Lys-Phe-Phe-Lys-Lys-Leu-Lys-c[Asp-Pro-D-Nal(2')-Arg-Trp-Lys]-Arg-Arg-D-Pro-D-Val-NH2 |
| 875 | TCAM872 | Lys-Lys-Phe-Lys-Lys-Phe-Phe-Lys-Lys-Leu-Lys-c[Asp-Pro-D-Nal(2')-Arg-Trp-Lys]-Arg-Arg-D-Val-D-Phe-NH2 |
| 876 | TCAM873 | Lys-Lys-Phe-Lys-Lys-Phe-Phe-Lys-Lys-Leu-Lys-c[Asp-Pro-D-Nal(2')-Arg-Trp-Lys]-Arg-Arg-D-Phe-D-Val-NH2 |

Anti-bioflim peptide ATRA1ARG linked to anti-microbial peptides

| 877 | TCAM874 | Arg-Arg-Phe-Arg-Arg-Phe-Phe-Arg-Arg-Leu-Arg-c[Asp-Pro-Arg-Arg-Trp-Trp-Arg-Phe-Lys]-D-Val-D-Pro-NH2 |

TABLE 5-continued

Exemplary Anti-microbial peptides

| SEQ NO: | Peptide | Peptide Sequence |
|---|---|---|
| 878 | TCAM875 | Arg-Arg-Phe-Arg-Arg-Phe-Phe-Arg-Arg-Leu-Arg-c[Asp-Pro-Arg-Arg-Trp-Trp-Arg-Phe-Lys]-D-Val-D-Phe-NH2 |
| 879 | TCAM876 | Arg-Arg-Phe-Arg-Arg-Phe-Phe-Arg-Arg-Leu-Arg-c[Asp-Pro-Arg-Arg-Trp-Trp-Arg-Phe-Lys]-D-Pro-D-Val-NH2 |
| 880 | TCAM877 | Arg-Arg-Phe-Arg-Arg-Phe-Phe-Arg-Arg-Leu-Arg-c[Asp-Pro-Arg-Arg-Trp-Trp-Arg-Phe-Lys]-D-Phe-D-Val-NH2 |
| 881 | TCAM878 | Arg-Arg-Phe-Arg-Arg-Phe-Phe-Arg-Arg-Leu-Arg-c[Asp-Pro-Arg-Arg-Trp-Trp-Tyr-Phe-Lys]-D-Val-D-Pro-NH2 |
| 882 | TCAM879 | Arg-Arg-Phe-Arg-Arg-Phe-Phe-Arg-Arg-Leu-Arg-c[Asp-Pro-Arg-Arg-Trp-Trp-Tyr-Phe-Lys]-D-Val-D-Phe-NH2 |
| 883 | TCAM880 | Arg-Arg-Phe-Arg-Arg-Phe-Phe-Arg-Arg-Leu-Arg-c[Asp-Pro-Arg-Arg-Trp-Trp-Tyr-Phe-Lys]-D-Pro-D-Val-NH2 |
| 884 | TCAM881 | Arg-Arg-Phe-Arg-Arg-Phe-Phe-Arg-Arg-Leu-Arg-c[Asp-Pro-Arg-Arg-Trp-Trp-Tyr-Phe-Lys]-D-Phe-D-Val-NH2 |
| 885 | TCAM882 | Arg-Arg-Phe-Arg-Arg-Phe-Phe-Arg-Arg-Leu-Arg-c[Asp-Pro-Arg-Arg-Tyr-Tyr-Arg-Phe-Lys]-D-Val-D-Pro-NH2 |
| 886 | TCAM883 | Arg-Arg-Phe-Arg-Arg-Phe-Phe-Arg-Arg-Leu-Arg-c[Asp-Pro-Arg-Arg-Tyr-Tyr-Arg-Phe-Lys]-D-Val-D-Phe-NH2 |
| 887 | TCAM884 | Arg-Arg-Phe-Arg-Arg-Phe-Phe-Arg-Arg-Leu-Arg-c[Asp-Pro-Arg-Arg-Tyr-Tyr-Arg-Phe-Lys]-D-Pro-D-Val-NH2 |
| 888 | TCAM885 | Arg-Arg-Phe-Arg-Arg-Phe-Phe-Arg-Arg-Leu-Arg-c[Asp-Pro-Arg-Arg-Tyr-Tyr-Arg-Phe-Lys]-D-Phe-D-Val-NH2 |
| 889 | TCAM886 | Arg-Arg-Phe-Arg-Arg-Phe-Phe-Arg-Arg-Leu-Arg-c[Asp-Pro-Arg-Arg-Nal-Nal-Arg-Phe-Lys]-D-Val-D-Pro-NH2 |
| 890 | TCAM887 | Arg-Arg-Phe-Arg-Arg-Phe-Phe-Arg-Arg-Leu-Arg-c[Asp-Pro-Arg-Arg-Nal-Nal-Arg-Phe-Lys]-D-Val-D-Phe-NH2 |
| 891 | TCAM888 | Arg-Arg-Phe-Arg-Arg-Phe-Phe-Arg-Arg-Leu-Arg-c[Asp-Pro-Arg-Arg-Nal-Nal-Arg-Phe-Lys]-D-Pro-D-Val-NH2 |
| 892 | TCAM889 | Arg-Arg-Phe-Arg-Arg-Phe-Phe-Arg-Arg-Leu-Arg-c[Asp-Pro-Arg-Arg-Nal-Nal-Arg-Phe-Lys]-D-Phe-D-Val-NH2 |
| 893 | TCAM890 | Arg-Arg-Phe-Arg-Arg-Phe-Phe-Arg-Arg-Leu-Arg-c[Asp-Pro-Arg-Arg-Leu-Trp-Leu-Trp-Lys]-D-Val-D-Pro-NH2 |
| 894 | TCAM891 | Arg-Arg-Phe-Arg-Arg-Phe-Phe-Arg-Arg-Leu-Arg-c[Asp-Pro-Arg-Arg-Leu-Trp-Leu-Trp-Lys]-D-Val-D-Phe-NH2 |
| 895 | TCAM892 | Arg-Arg-Phe-Arg-Arg-Phe-Phe-Arg-Arg-Leu-Arg-c[Asp-Pro-Arg-Arg-Leu-Trp-Leu-Trp-Lys]-D-Pro-D-Val-NH2 |
| 896 | TCAM893 | Arg-Arg-Phe-Arg-Arg-Phe-Phe-Arg-Arg-Leu-Arg-c[Asp-Pro-Arg-Arg-Leu-Trp-Leu-Trp-Lys]-D-Phe-D-Val-NH2 |
| 897 | TCAM894 | Arg-Arg-Phe-Arg-Arg-Phe-Phe-Arg-Arg-Leu-Arg-c[Asp-Pro-Arg-Arg-Leu-Trp-Leu-Trp-Lys]-D-Val-D-Pro-NH2 |
| 898 | TCAM895 | Arg-Arg-Phe-Arg-Arg-Phe-Phe-Arg-Arg-Leu-Arg-c[Asp-Pro-Arg-Arg-Leu-Trp-Leu-Trp-Lys]-D-Val-D-Phe-NH2 |
| 899 | TCAM896 | Arg-Arg-Phe-Arg-Arg-Phe-Phe-Arg-Arg-Leu-Arg-c[Asp-Pro-Arg-Arg-Leu-Trp-Leu-Trp-Lys]-D-Pro-D-Val-NH2 |
| 900 | TCAM897 | Arg-Arg-Phe-Arg-Arg-Phe-Phe-Arg-Arg-Leu-Arg-c[Asp-Pro-Arg-Arg-Leu-Trp-Leu-Trp-Lys]-D-Phe-D-Val-NH2 |
| 901 | TCAM898 | Arg-Arg-Phe-Arg-Arg-Phe-Phe-Arg-Arg-Leu-Arg-c[Asp-Arg-Arg-Arg-Trp-Leu-Trp-Leu-Trp-Lys]-D-Val-D-Pro-NH2 |
| 902 | TCAM899 | Arg-Arg-Phe-Arg-Arg-Phe-Phe-Arg-Arg-Leu-Arg-c[Asp-Pro-Arg-Arg-Arg-Trp-Leu-Trp-Leu-Trp-Lys]-D-Val-D-Phe-NH2 |

TABLE 5-continued

Exemplary Anti-microbial peptides

| SEQ NO: | Peptide | Peptide Sequence |
|---|---|---|
| 903 | TCAM900 | Arg-Arg-Phe-Arg-Arg-Phe-Phe-Arg-Arg-Leu-Arg-c[Asp-Pro-Arg-Arg-Arg-Trp-Leu-Trp-Leu-Trp-Lys]-D-Pro-D-Val-NH2 |
| 904 | TCAM901 | Arg-Arg-Phe-Arg-Arg-Phe-Phe-Arg-Arg-Leu-Arg-c[Asp-Pro-Arg-Arg-Arg-Trp-Leu-Trp-Leu-Trp-Lys]-D-Phe-D-Val-NH2 |
| 905 | TCAM902 | Arg-Arg-Phe-Arg-Arg-Phe-Phe-Arg-Arg-Leu-Arg-c[Asp-Pro-Arg-Gln-Arg-Arg-Trp-Leu-Trp-Leu-Trp-Lys]-D-Val-D-Pro-NH2 |
| 906 | TCAM903 | Arg-Arg-Phe-Arg-Arg-Phe-Phe-Arg-Arg-Leu-Arg-c[Asp-Pro-Arg-Gln-Arg-Arg-Trp-Leu-Trp-Leu-Trp-Lys]-D-Val-D-Phe-NH2 |
| 907 | TCAM904 | Arg-Arg-Phe-Arg-Arg-Phe-Phe-Arg-Arg-Leu-Arg-c[Asp-Pro-Arg-Gln-Arg-Arg-Trp-Leu-Trp-Leu-Trp-Lys]-D-Pro-D-Val-NH2 |
| 908 | TCAM905 | Arg-Arg-Phe-Arg-Arg-Phe-Phe-Arg-Arg-Leu-Arg-c[Asp-Pro-Arg-Gln-Arg-Arg-Trp-Leu-Trp-Leu-Trp-Lys]-D-Phe-D-Val-NH2 |
| 909 | TCAM906 | Arg-Arg-Phe-Arg-Arg-Phe-Phe-Arg-Arg-Leu-Arg-c[Asp-Pro-Trp-Arg-Trp-Trp-Arg-Arg-Lys]-D-Val-D-Phe-NH2 |
| 910 | TCAM907 | Arg-Arg-Phe-Arg-Arg-Phe-Phe-Arg-Arg-Leu-Arg-c[Asp-Pro-Trp-Arg-Trp-Trp-Arg-Arg-Lys]-D-Pro-D-Val-NH2 |
| 911 | TCAM908 | Arg-Arg-Phe-Arg-Arg-Phe-Phe-Arg-Arg-Leu-Arg-c[Asp-Pro-Trp-Arg-Trp-Trp-Arg-Arg-Lys]-D-Phe-D-Val-NH2 |
| 912 | TCAM909 | Arg-Arg-Phe-Arg-Arg-Phe-Phe-Arg-Arg-Leu-Arg-c[Asp-Pro-Trp-Trp-Arg-Arg-Trp-Trp-Arg-Arg-Lys]-D-Val-D-Pro-NH2 |
| 913 | TCAM910 | Arg-Arg-Phe-Arg-Arg-Phe-Phe-Arg-Arg-Leu-Arg-c[Asp-Pro-Trp-Trp-Arg-Arg-Trp-Trp-Arg-Arg-Lys]-D-Val-D-Phe-NH2 |
| 914 | TCAM911 | Arg-Arg-Phe-Arg-Arg-Phe-Phe-Arg-Arg-Leu-Arg-c[Asp-Pro-Trp-Trp-Arg-Arg-Trp-Trp-Arg-Arg-Lys]-D-Pro-D-Val-NH2 |
| 915 | TCAM912 | Arg-Arg-Phe-Arg-Arg-Phe-Phe-Arg-Arg-Leu-Arg-c[Asp-Pro-Trp-Trp-Arg-Arg-Trp-Trp-Arg-Arg-Lys]-D-Phe-D-Val-NH2 |
| 916 | TCAM913 | Arg-Arg-Phe-Arg-Arg-Phe-Phe-Arg-Arg-Leu-Arg-c[Asp-Pro-Trp-Arg-Trp-Arg-Trp-Arg-Lys]-D-Val-D-Pro-NH2 |
| 917 | TCAM914 | Arg-Arg-Phe-Arg-Arg-Phe-Phe-Arg-Arg-Leu-Arg-c[Asp-Pro-Trp-Arg-Trp-Arg-Trp-Arg-Lys]-D-Val-D-Phe-NH2 |
| 918 | TCAM915 | Arg-Arg-Phe-Arg-Arg-Phe-Phe-Arg-Arg-Leu-Arg-c[Asp-Pro-Trp-Arg-Trp-Arg-Trp-Arg-Lys]-D-Pro-D-Val-NH2 |
| 919 | TCAM916 | Arg-Arg-Phe-Arg-Arg-Phe-Phe-Arg-Arg-Leu-Arg-c[Asp-Pro-Trp-Arg-Trp-Arg-Trp-Arg-Lys]-D-Phe-D-Val-NH2 |
| 920 | TCAM917 | Arg-Arg-Phe-Arg-Arg-Phe-Phe-Arg-Arg-Leu-Arg-c[Asp-Pro-Arg-Trp-Arg-Trp-Arg-Trp-Lys]-D-Val-D-Pro-NH2 |
| 921 | TCAM918 | Arg-Arg-Phe-Arg-Arg-Phe-Phe-Arg-Arg-Leu-Arg-c[Asp-Pro-Arg-Trp-Arg-Trp-Arg-Trp-Lys]-D-Val-D-Phe-NH2 |
| 922 | TCAM919 | Arg-Arg-Phe-Arg-Arg-Phe-Phe-Arg-Arg-Leu-Arg-c[Asp-Pro-Arg-Trp-Arg-Trp-Arg-Trp-Lys]-D-Pro-D-Val-NH2 |
| 923 | TCAM920 | Arg-Arg-Phe-Arg-Arg-Phe-Phe-Arg-Arg-Leu-Arg-c[Asp-Pro-Arg-Trp-Arg-Trp-Arg-Trp-Lys]-D-Phe-D-Val-NH2 |
| 924 | TCAM921 | Arg-Arg-Phe-Arg-Arg-Phe-Phe-Arg-Arg-Leu-Arg-c[Asp-Pro-Arg-Trp-Trp-Arg-Arg-Lys]-D-Val-D-Pro-NH2 |
| 925 | TCAM922 | Arg-Arg-Phe-Arg-Arg-Phe-Phe-Arg-Arg-Leu-Arg-c[Asp-Pro-Arg-Trp-Trp-Arg-Arg-Lys]-D-Val-D-Phe-NH2 |
| 926 | TCAM923 | Arg-Arg-Phe-Arg-Arg-Phe-Phe-Arg-Arg-Leu-Arg-c[Asp-Pro-Arg-Trp-Trp-Arg-Arg-Lys]-D-Pro-D-Val-NH2 |
| 927 | TCAM924 | Arg-Arg-Phe-Arg-Arg-Phe-Phe-Arg-Arg-Leu-Arg-c[Asp-Pro-Arg-Trp-Trp-Arg-Arg-Lys]-D-Phe-D-Val-NH2 |

TABLE 5-continued

Exemplary Anti-microbial peptides

| SEQ NO: | Peptide | Peptide Sequence |
|---|---|---|
| 928 | TCAM925 | Arg-Arg-Phe-Arg-Arg-Phe-Phe-Arg-Arg-Leu-Arg-c[Asp-Pro-Trp-Trp-Arg-Arg-Trp-Lys]-D-Val-D-Pro-NH2 |
| 929 | TCAM926 | Arg-Arg-Phe-Arg-Arg-Phe-Phe-Arg-Arg-Leu-Arg-c[Asp-Pro-Trp-Trp-Arg-Arg-Trp-Lys]-D-Val-D-Phe-NH2 |
| 930 | TCAM927 | Arg-Arg-Phe-Arg-Arg-Phe-Phe-Arg-Arg-Leu-Arg-c[Asp-Pro-Trp-Trp-Arg-Arg-Trp-Lys]-D-Pro-D-Val-NH2 |
| 931 | TCAM928 | Arg-Arg-Phe-Arg-Arg-Phe-Phe-Arg-Arg-Leu-Arg-c[Asp-Pro-Trp-Trp-Arg-Arg-Trp-Lys]-D-Phe-D-Val-NH2 |
| 932 | TCAM929 | Arg-Arg-Phe-Arg-Arg-Phe-Phe-Arg-Arg-Leu-Arg-c[Asp-Pro-Trp-Arg-Trp-Arg-Trp-Lys]-D-Val-D-Pro-NH2 |
| 933 | TCAM930 | Arg-Arg-Phe-Arg-Arg-Phe-Phe-Arg-Arg-Leu-Arg-c[Asp-Pro-Trp-Arg-Trp-Arg-Trp-Lys]-D-Val-D-Phe-NH2 |
| 934 | TCAM931 | Arg-Arg-Phe-Arg-Arg-Phe-Phe-Arg-Arg-Leu-Arg-c[Asp-Pro-Trp-Arg-Trp-Arg-Trp-Lys]-D-Pro-D-Val-NH2 |
| 935 | TCAM932 | Arg-Arg-Phe-Arg-Arg-Phe-Phe-Arg-Arg-Leu-Arg-c[Asp-Pro-Trp-Arg-Trp-Arg-Trp-Lys]-D-Phe-D-Val-NH2 |
| 936 | TCAM933 | Arg-Arg-Phe-Arg-Arg-Phe-Phe-Arg-Arg-Leu-Arg-c[Asp-Pro-Arg-Trp-Arg-Trp-Arg-Lys]-D-Val-D-Pro-NH2 |
| 937 | TCAM934 | Arg-Arg-Phe-Arg-Arg-Phe-Phe-Arg-Arg-Leu-Arg-c[Asp-Pro-Arg-Trp-Arg-Trp-Arg-Lys]-D-Val-D-Phe-NH2 |
| 938 | TCAM935 | Arg-Arg-Phe-Arg-Arg-Phe-Phe-Arg-Arg-Leu-Arg-c[Asp-Pro-Arg-Trp-Arg-Trp-Arg-Lys]-D-Pro-D-Val-NH2 |
| 939 | TCAM936 | Arg-Arg-Phe-Arg-Arg-Phe-Phe-Arg-Arg-Leu-Arg-c[Asp-Pro-Arg-Trp-Arg-Trp-Arg-Lys]-D-Phe-D-Val-NH2 |
| 940 | TCAM937 | Arg-Arg-Phe-Arg-Arg-Phe-Phe-Arg-Arg-Leu-Arg-c[Asp-Pro-Trp-Arg-Tyr-Arg-Trp-Lys]-D-Val-D-Pro-NH2 |
| 941 | TCAM938 | Arg-Arg-Phe-Arg-Arg-Phe-Phe-Arg-Arg-Leu-Arg-c[Asp-Pro-Trp-Arg-Tyr-Arg-Trp-Lys]-D-Val-D-Phe-NH2 |
| 942 | TCAM939 | Arg-Arg-Phe-Arg-Arg-Phe-Phe-Arg-Arg-Leu-Arg-c[Asp-Pro-Trp-Arg-Tyr-Arg-Trp-Lys]-D-Pro-D-Val-NH2 |
| 943 | TCAM940 | Arg-Arg-Phe-Arg-Arg-Phe-Phe-Arg-Arg-Leu-Arg-c[Asp-Pro-Trp-Arg-Tyr-Arg-Trp-Lys]-D-Phe-D-Val-NH2 |
| 944 | TCAM941 | Arg-Arg-Phe-Arg-Arg-Phe-Phe-Arg-Arg-Leu-Arg-c[Asp-Pro-Trp-Arg-Trp-Arg-Tyr-Lys]-D-Val-D-Pro-NH2 |
| 945 | TCAM942 | Arg-Arg-Phe-Arg-Arg-Phe-Phe-Arg-Arg-Leu-Arg-c[Asp-Pro-Trp-Arg-Trp-Arg-Tyr-Lys]-D-Val-D-Phe-NH2 |
| 946 | TCAM943 | Arg-Arg-Phe-Arg-Arg-Phe-Phe-Arg-Arg-Leu-Arg-c[Asp-Pro-Trp-Arg-Trp-Arg-Tyr-Lys]-D-Pro-D-Val-NH2 |
| 947 | TCAM944 | Arg-Arg-Phe-Arg-Arg-Phe-Phe-Arg-Arg-Leu-Arg-c[Asp-Pro-Trp-Arg-Trp-Arg-Tyr-Lys]-D-Phe-D-Val-NH2 |
| 948 | TCAM945 | Arg-Arg-Phe-Arg-Arg-Phe-Phe-Arg-Arg-Leu-Arg-c[Asp-Pro-Trp-Arg-Trp-Arg-Lys]-D-Val-D-Pro-NH2 |
| 949 | TCAM946 | Arg-Arg-Phe-Arg-Arg-Phe-Phe-Arg-Arg-Leu-Arg-c[Asp-Pro-Trp-Arg-Trp-Arg-Lys]-D-Val-D-Phe-NH2 |
| 950 | TCAM947 | Arg-Arg-Phe-Arg-Arg-Phe-Phe-Arg-Arg-Leu-Arg-c[Asp-Pro-Trp-Arg-Trp-Arg-Lys]-D-Pro-D-Val-NH2 |
| 951 | TCAM948 | Arg-Arg-Phe-Arg-Arg-Phe-Phe-Arg-Arg-Leu-Arg-c[Asp-Pro-Trp-Arg-Trp-Arg-Lys]-D-Phe-D-Val-NH2 |
| 952 | TCAM949 | Arg-Arg-Phe-Arg-Arg-Phe-Phe-Arg-Arg-Leu-Arg-c[Asp-Pro-Trp-Arg-Arg-Trp-Lys]-D-Val-D-Pro-NH2 |

TABLE 5-continued

Exemplary Anti-microbial peptides

| SEQ NO: | Peptide | Peptide Sequence |
|---|---|---|
| 953 | TCAM950 | Arg-Arg-Phe-Arg-Arg-Phe-Phe-Arg-Arg-Leu-Arg-c[Asp-Pro-Trp-Arg-Arg-Trp-Lys]-D-Val-D-Phe-NH2 |
| 954 | TCAM951 | Arg-Arg-Phe-Arg-Arg-Phe-Phe-Arg-Arg-Leu-Arg-c[Asp-Pro-Trp-Arg-Arg-Trp-Lys]-D-Pro-D-Val-NH2 |
| 955 | TCAM952 | Arg-Arg-Phe-Arg-Arg-Phe-Phe-Arg-Arg-Leu-Arg-c[Asp-Pro-Trp-Arg-Arg-Trp-Lys]-D-Phe-D-Val-NH2 |
| 956 | TCAM953 | Arg-Arg-Phe-Arg-Arg-Phe-Phe-Arg-Arg-Leu-Arg-c[Asp-Pro-Arg-Trp-Trp-Arg-Lys]-D-Val-D-Pro-NH2 |
| 957 | TCAM954 | Arg-Arg-Phe-Arg-Arg-Phe-Phe-Arg-Arg-Leu-Arg-c[Asp-Pro-Arg-Trp-Trp-Arg-Lys]-D-Val-D-Phe-NH2 |
| 958 | TCAM955 | Arg-Arg-Phe-Arg-Arg-Phe-Phe-Arg-Arg-Leu-Arg-c[Asp-Pro-Arg-Trp-Trp-Arg-Lys]-D-Pro-D-Val-NH2 |
| 959 | TCAM956 | Arg-Arg-Phe-Arg-Arg-Phe-Phe-Arg-Arg-Leu-Arg-c[Asp-Pro-Arg-Trp-Trp-Arg-Lys]-D-Phe-D-Val-NH2 |
| 960 | TCAM957 | Arg-Arg-Phe-Arg-Arg-Phe-Phe-Arg-Arg-Leu-Arg-c[Asp-Pro-Trp-Arg-Trp-Lys]-D-Val-D-Pro-NH2 |
| 961 | TCAM958 | Arg-Arg-Phe-Arg-Arg-Phe-Phe-Arg-Arg-Leu-Arg-c[Asp-Pro-Trp-Arg-Trp-Lys]-D-Val-D-Phe-NH2 |
| 962 | TCAM959 | Arg-Arg-Phe-Arg-Arg-Phe-Phe-Arg-Arg-Leu-Arg-c[Asp-Pro-Trp-Arg-Trp-Lys]-D-Pro-D-Val-NH2 |
| 963 | TCAM960 | Arg-Arg-Phe-Arg-Arg-Phe-Phe-Arg-Arg-Leu-Arg-c[Asp-Pro-Trp-Arg-Trp-Lys]-D-Phe-D-Val-NH2 |
| 964 | TCAM961 | Arg-Arg-Phe-Arg-Arg-Phe-Phe-Arg-Arg-Leu-Arg-c[Asp-Pro-Trp-Arg-Arg-Lys]-D-Val-D-Pro-NH2 |
| 965 | TCAM962 | Arg-Arg-Phe-Arg-Arg-Phe-Phe-Arg-Arg-Leu-Arg-c[Asp-Pro-Trp-Arg-Arg-Lys]-D-Val-D-Phe-NH2 |
| 966 | TCAM963 | Arg-Arg-Phe-Arg-Arg-Phe-Phe-Arg-Arg-Leu-Arg-c[Asp-Pro-Trp-Arg-Arg-Lys]-D-Pro-D-Val-NH2 |
| 967 | TCAM964 | Arg-Arg-Phe-Arg-Arg-Phe-Phe-Arg-Arg-Leu-Arg-c[Asp-Pro-Trp-Arg-Arg-Lys]-D-Phe-D-Val-NH2 |
| 968 | TCAM965 | Arg-Arg-Phe-Arg-Arg-Phe-Phe-Arg-Arg-Leu-Arg-c[Asp-Arg-Arg-Trp-Trp-Arg-Phe-Lys]-D-Val-D-Pro-NH2 |
| 969 | TCAM966 | Arg-Arg-Phe-Arg-Arg-Phe-Phe-Arg-Arg-Leu-Arg-c[Asp-Arg-Arg-Trp-Trp-Arg-Phe-Lys]-D-Val-D-Phe-NH2 |
| 970 | TCAM967 | Arg-Arg-Phe-Arg-Arg-Phe-Phe-Arg-Arg-Leu-Arg-c[Asp-Arg-Arg-Trp-Trp-Arg-Phe-Lys]-D-Pro-D-Val-NH2 |
| 971 | TCAM968 | Arg-Arg-Phe-Arg-Arg-Phe-Phe-Arg-Arg-Leu-Arg-c[Asp-Arg-Arg-Trp-Trp-Arg-Phe-Lys]-D-Phe-D-Val-NH2 |
| 972 | TCAM969 | Arg-Arg-Phe-Arg-Arg-Phe-Phe-Arg-Arg-Leu-Arg-c[Asp-Arg-Arg-Trp-Trp-Arg-Phe-Lys]-D-Val-D-Pro-NH2 |
| 973 | TCAM970 | Arg-Arg-Phe-Arg-Arg-Phe-Phe-Arg-Arg-Leu-Arg-c[Asp-Arg-Arg-Trp-Trp-Arg-Phe-Lys]-D-Val-D-Phe-NH2 |
| 974 | TCAM971 | Arg-Arg-Phe-Arg-Arg-Phe-Phe-Arg-Arg-Leu-Arg-c[Asp-Arg-Arg-Trp-Trp-Arg-Phe-Lys]-D-Pro-D-Val-NH2 |
| 975 | TCAM972 | Arg-Arg-Phe-Arg-Arg-Phe-Phe-Arg-Arg-Leu-Arg-c[Asp-Arg-Arg-Trp-Trp-Arg-Phe-Lys]-D-Phe-D-Val-NH2 |
| 976 | TCAM973 | Arg-Arg-Phe-Arg-Arg-Phe-Phe-Arg-Arg-Leu-Arg-c[Asp-Arg-Arg-Tyr-Tyr-Arg-Phe-Lys]-D-Val-D-Pro-NH2 |
| 977 | TCAM974 | Arg-Arg-Phe-Arg-Arg-Phe-Phe-Arg-Arg-Leu-Arg-c[Asp-Arg-Arg-Tyr-Tyr-Arg-Phe-Lys]-D-Val-D-Phe-NH2 |

TABLE 5-continued

Exemplary Anti-microbial peptides

| SEQ NO: | Peptide | Peptide Sequence |
|---|---|---|
| 978 | TCAM975 | Arg-Arg-Phe-Arg-Arg-Phe-Phe-Arg-Arg-Leu-Arg-c[Asp-Arg-Arg-Tyr-Tyr-Arg-Phe-Lys]-D-Pro-D-Val-NH2 |
| 979 | TCAM976 | Arg-Arg-Phe-Arg-Arg-Phe-Phe-Arg-Arg-Leu-Arg-c[Asp-Arg-Arg-Tyr-Tyr-Arg-Phe-Lys]-D-Phe-D-Val-NH2 |
| 980 | TCAM977 | Arg-Arg-Phe-Arg-Arg-Phe-Phe-Arg-Arg-Leu-Arg-c[Asp-Arg-Arg-Nal-Nal-Arg-Phe-Lys]-D-Val-D-Pro-NH2 |
| 981 | TCAM978 | Arg-Arg-Phe-Arg-Arg-Phe-Phe-Arg-Arg-Leu-Arg-c[Asp-Arg-Arg-Nal-Nal-Arg-Phe-Lys]-D-Val-D-Phe-NH2 |
| 982 | TCAM979 | Arg-Arg-Phe-Arg-Arg-Phe-Phe-Arg-Arg-Leu-Arg-c[Asp-Arg-Arg-Nal-Nal-Arg-Phe-Lys]-D-Pro-D-Val-NH2 |
| 983 | TCAM980 | Arg-Arg-Phe-Arg-Arg-Phe-Phe-Arg-Arg-Leu-Arg-c[Asp-Arg-Arg-Nal-Nal-Arg-Phe-Lys]-D-Phe-D-Val-NH2 |
| 984 | TCAM981 | Arg-Arg-Phe-Arg-Arg-Phe-Phe-Arg-Arg-Leu-Arg-c[Asp-Arg-Arg-Leu-Trp-Leu-Trp-Lys]-D-Val-D-Pro-NH2 |
| 985 | TCAM982 | Arg-Arg-Phe-Arg-Arg-Phe-Phe-Arg-Arg-Leu-Arg-c[Asp-Arg-Arg-Leu-Trp-Leu-Trp-Lys]-D-Val-D-Phe-NH2 |
| 986 | TCAM983 | Arg-Arg-Phe-Arg-Arg-Phe-Phe-Arg-Arg-Leu-Arg-c[Asp-Arg-Arg-Leu-Trp-Leu-Trp-Lys]-D-Pro-D-Val-NH2 |
| 987 | TCAM984 | Arg-Arg-Phe-Arg-Arg-Phe-Phe-Arg-Arg-Leu-Arg-c[Asp-Arg-Arg-Leu-Trp-Leu-Trp-Lys]-D-Phe-D-Val-NH2 |
| 988 | TCAM985 | Arg-Arg-Phe-Arg-Arg-Phe-Phe-Arg-Arg-Leu-Arg-c[Asp-Arg-Arg-Leu-Trp-Leu-Trp-Lys]-D-Val-D-Pro-NH2 |
| 989 | TCAM986 | Arg-Arg-Phe-Arg-Arg-Phe-Phe-Arg-Arg-Leu-Arg-c[Asp-Arg-Arg-Leu-Trp-Leu-Trp-Lys]-D-Val-D-Phe-NH2 |
| 990 | TCAM987 | Arg-Arg-Phe-Arg-Arg-Phe-Phe-Arg-Arg-Leu-Arg-c[Asp-Arg-Arg-Leu-Trp-Leu-Trp-Lys]-D-Pro-D-Val-NH2 |
| 991 | TCAM988 | Arg-Arg-Phe-Arg-Arg-Phe-Phe-Arg-Arg-Leu-Arg-c[Asp-Arg-Arg-Leu-Trp-Leu-Trp-Lys]-D-Phe-D-Val-NH2 |
| 992 | TCAM989 | Arg-Arg-Phe-Arg-Arg-Phe-Phe-Arg-Arg-Leu-Arg-c[Asp-Arg-Arg-Arg-Trp-Leu-Trp-Leu-Trp-Lys]-D-Val-D-Pro-NH2 |
| 993 | TCAM990 | Arg-Arg-Phe-Arg-Arg-Phe-Phe-Arg-Arg-Leu-Arg-c[Asp-Arg-Arg-Arg-Trp-Leu-Trp-Leu-Trp-Lys]-D-Val-D-Phe-NH2 |
| 994 | TCAM991 | Arg-Arg-Phe-Arg-Arg-Phe-Phe-Arg-Arg-Leu-Arg-c[Asp-Arg-Arg-Arg-Trp-Leu-Trp-Leu-Trp-Lys]-D-Pro-D-Val-NH2 |
| 995 | TCAM992 | Arg-Arg-Phe-Arg-Arg-Phe-Phe-Arg-Arg-Leu-Arg-c[Asp-Arg-Arg-Arg-Trp-Leu-Trp-Leu-Trp-Lys]-D-Phe-D-Val-NH2 |
| 996 | TCAM993 | Arg-Arg-Phe-Arg-Arg-Phe-Phe-Arg-Arg-Leu-Arg-c[Asp-Arg-Gln-Arg-Arg-Trp-Leu-Trp-Leu-Trp-Lys]-D-Val-D-Pro-NH2 |
| 997 | TCAM994 | Arg-Arg-Phe-Arg-Arg-Phe-Phe-Arg-Arg-Leu-Arg-c[Asp-Arg-Gln-Arg-Arg-Trp-Leu-Trp-Leu-Trp-Lys]-D-Val-D-Phe-NH2 |
| 998 | TCAM995 | Arg-Arg-Phe-Arg-Arg-Phe-Phe-Arg-Arg-Leu-Arg-c[Asp-Arg-Gln-Arg-Arg-Trp-Leu-Trp-Leu-Trp-Lys]-D-Pro-D-Val-NH2 |
| 999 | TCAM996 | Arg-Arg-Phe-Arg-Arg-Phe-Phe-Arg-Arg-Leu-Arg-c[Asp-Arg-Gln-Arg-Arg-Trp-Leu-Trp-Leu-Trp-Lys]-D-Phe-D-Val-NH2 |
| 1000 | TCAM997 | Arg-Arg-Phe-Arg-Arg-Phe-Phe-Arg-Arg-Leu-Arg-c[Asp-Trp-Arg-Trp-Trp-Arg-Arg-Lys]-D-Val-D-Pro-NH2 |
| 1001 | TCAM998 | Arg-Arg-Phe-Arg-Arg-Phe-Phe-Arg-Arg-Leu-Arg-c[Asp-Trp-Arg-Trp-Trp-Arg-Arg-Lys]-D-Val-D-Phe-NH2 |
| 1002 | TCAM999 | Arg-Arg-Phe-Arg-Arg-Phe-Phe-Arg-Arg-Leu-Arg-c[Asp-Trp-Arg-Trp-Trp-Arg-Arg-Lys]-D-Pro-D-Val-NH2 |

TABLE 5-continued

Exemplary Anti-microbial peptides

| SEQ NO: | Peptide | Peptide Sequence |
|---|---|---|
| 1003 | TCAM1000 | Arg-Arg-Phe-Arg-Arg-Phe-Phe-Arg-Arg-Leu-Arg-c[Asp-Trp-Arg-Trp-Trp-Arg-Arg-Lys]-D-Phe-D-Val-NH2 |
| 1004 | TCAM1001 | Arg-Arg-Phe-Arg-Arg-Phe-Phe-Arg-Arg-Leu-Arg-c[Asp-Trp-Trp-Arg-Arg-Trp-Trp-Arg-Arg-Lys]-D-Val-D-Pro-NH2 |
| 1005 | TCAM1002 | Arg-Arg-Phe-Arg-Arg-Phe-Phe-Arg-Arg-Leu-Arg-c[Asp-Trp-Trp-Arg-Arg-Trp-Trp-Arg-Arg-Lys]-D-Val-D-Phe-NH2 |
| 1006 | TCAM1003 | Arg-Arg-Phe-Arg-Arg-Phe-Phe-Arg-Arg-Leu-Arg-c[Asp-Trp-Trp-Arg-Arg-Trp-Trp-Arg-Arg-Lys]-D-Pro-D-Val-NH2 |
| 1007 | TCAM1004 | Arg-Arg-Phe-Arg-Arg-Phe-Phe-Arg-Arg-Leu-Arg-c[Asp-Trp-Trp-Arg-Arg-Trp-Trp-Arg-Arg-Lys]-D-Phe-D-Val-NH2 |
| 1008 | TCAM1005 | Arg-Arg-Phe-Arg-Arg-Phe-Phe-Arg-Arg-Leu-Arg-c[Asp-Trp-Arg-Trp-Arg-Trp-Arg-Lys]-D-Val-D-Pro-NH2 |
| 1009 | TCAM1006 | Arg-Arg-Phe-Arg-Arg-Phe-Phe-Arg-Arg-Leu-Arg-c[Asp-Trp-Arg-Trp-Arg-Trp-Arg-Lys]-D-Val-D-Phe-NH2 |
| 1010 | TCAM1007 | Arg-Arg-Phe-Arg-Arg-Phe-Phe-Arg-Arg-Leu-Arg-c[Asp-Trp-Arg-Trp-Arg-Trp-Arg-Lys]-D-Pro-D-Val-NH2 |
| 1011 | TCAM1008 | Arg-Arg-Phe-Arg-Arg-Phe-Phe-Arg-Arg-Leu-Arg-c[Asp-Trp-Arg-Trp-Arg-Trp-Arg-Lys]-D-Phe-D-Val-NH2 |
| 1012 | TCAM1009 | Arg-Arg-Phe-Arg-Arg-Phe-Phe-Arg-Arg-Leu-Arg-c[Asp-Arg-Trp-Arg-Trp-Arg-Trp-Lys]-D-Val-D-Pro-NH2 |
| 1013 | TCAM1010 | Arg-Arg-Phe-Arg-Arg-Phe-Phe-Arg-Arg-Leu-Arg-c[Asp-Arg-Trp-Arg-Trp-Arg-Trp-Lys]-D-Val-D-Phe-NH2 |
| 1014 | TCAM1011 | Arg-Arg-Phe-Arg-Arg-Phe-Phe-Arg-Arg-Leu-Arg-c[Asp-Arg-Trp-Arg-Trp-Arg-Trp-Lys]-D-Pro-D-Val-NH2 |
| 1015 | TCAM1012 | Arg-Arg-Phe-Arg-Arg-Phe-Phe-Arg-Arg-Leu-Arg-c[Asp-Arg-Trp-Arg-Trp-Arg-Trp-Lys]-D-Phe-D-Val-NH2 |
| 1016 | TCAM1013 | Arg-Arg-Phe-Arg-Arg-Phe-Phe-Arg-Arg-Leu-Arg-c[Asp-Arg-Trp-Trp-Arg-Arg-Lys]-D-Val-D-Pro-NH2 |
| 1017 | TCAM1014 | Arg-Arg-Phe-Arg-Arg-Phe-Phe-Arg-Arg-Leu-Arg-c[Asp-Arg-Trp-Trp-Arg-Arg-Lys]-D-Val-D-Phe-NH2 |
| 1018 | TCAM1015 | Arg-Arg-Phe-Arg-Arg-Phe-Phe-Arg-Arg-Leu-Arg-c[Asp-Arg-Trp-Trp-Arg-Arg-Lys]-D-Pro-D-Val-NH2 |
| 1019 | TCAM1016 | Arg-Arg-Phe-Arg-Arg-Phe-Phe-Arg-Arg-Leu-Arg-c[Asp-Arg-Trp-Trp-Arg-Arg-Lys]-D-Phe-D-Val-NH2 |
| 1020 | TCAM1017 | Arg-Arg-Phe-Arg-Arg-Phe-Phe-Arg-Arg-Leu-Arg-c[Asp-Arg-Trp-Arg-Trp-Arg-Lys]-D-Val-D-Pro-NH2 |
| 1021 | TCAM1018 | Arg-Arg-Phe-Arg-Arg-Phe-Phe-Arg-Arg-Leu-Arg-c[Asp-Arg-Trp-Arg-Trp-Arg-Lys]-D-Val-D-Phe-NH2 |
| 1022 | TCAM1019 | Arg-Arg-Phe-Arg-Arg-Phe-Phe-Arg-Arg-Leu-Arg-c[Asp-Arg-Trp-Arg-Trp-Arg-Lys]-D-Pro-D-Val-NH2 |
| 1023 | TCAM1020 | Arg-Arg-Phe-Arg-Arg-Phe-Phe-Arg-Arg-Leu-Arg-c[Asp-Arg-Trp-Arg-Trp-Arg-Lys]-D-Phe-D-Val-NH2 |
| 1024 | TCAM1021 | Arg-Arg-Phe-Arg-Arg-Phe-Phe-Arg-Arg-Leu-Arg-c[Asp-Trp-Trp-Arg-Arg-Trp-Lys]-D-Val-D-Pro-NH2 |
| 1025 | TCAM1022 | Arg-Arg-Phe-Arg-Arg-Phe-Phe-Arg-Arg-Leu-Arg-c[Asp-Trp-Trp-Arg-Arg-Trp-Lys]-D-Val-D-Phe-NH2 |
| 1026 | TCAM1023 | Arg-Arg-Phe-Arg-Arg-Phe-Phe-Arg-Arg-Leu-Arg-c[Asp-Trp-Trp-Arg-Arg-Trp-Lys]-D-Pro-D-Val-NH2 |
| 1027 | TCAM1024 | Arg-Arg-Phe-Arg-Arg-Phe-Phe-Arg-Arg-Leu-Arg-c[Asp-Trp-Trp-Arg-Arg-Trp-Lys]-D-Phe-D-Val-NH2 |

TABLE 5-continued

Exemplary Anti-microbial peptides

| SEQ NO: | Peptide | Peptide Sequence |
|---|---|---|
| 1028 | TCAM1025 | Arg-Arg-Phe-Arg-Arg-Phe-Phe-Arg-Arg-Leu-Arg-c[Asp-Trp-Arg-Trp-Arg-Trp-Lys]-D-Val-D-Pro-NH2 |
| 1029 | TCAM1026 | Arg-Arg-Phe-Arg-Arg-Phe-Phe-Arg-Arg-Leu-Arg-c[Asp-Trp-Arg-Trp-Arg-Trp-Lys]-D-Val-D-Phe-NH2 |
| 1030 | TCAM1027 | Arg-Arg-Phe-Arg-Arg-Phe-Phe-Arg-Arg-Leu-Arg-c[Asp-Trp-Arg-Trp-Arg-Trp-Lys]-D-Pro-D-Val-NH2 |
| 1031 | TCAM1028 | Arg-Arg-Phe-Arg-Arg-Phe-Phe-Arg-Arg-Leu-Arg-c[Asp-Trp-Arg-Trp-Arg-Trp-Lys]-D-Phe-D-Val-NH2 |
| 1032 | TCAM1029 | Arg-Arg-Phe-Arg-Arg-Phe-Phe-Arg-Arg-Leu-Arg-c[Asp-Trp-Arg-Tyr-Arg-Trp-Lys]-D-Val-D-Pro-NH2 |
| 1033 | TCAM1030 | Arg-Arg-Phe-Arg-Arg-Phe-Phe-Arg-Arg-Leu-Arg-c[Asp-Trp-Arg-Tyr-Arg-Trp-Lys]-D-Val-D-Phe-NH2 |
| 1034 | TCAM1031 | Arg-Arg-Phe-Arg-Arg-Phe-Phe-Arg-Arg-Leu-Arg-c[Asp-Trp-Arg-Tyr-Arg-Trp-Lys]-D-Pro-D-Val-NH2 |
| 1035 | TCAM1032 | Arg-Arg-Phe-Arg-Arg-Phe-Phe-Arg-Arg-Leu-Arg-c[Asp-Trp-Arg-Tyr-Arg-Trp-Lys]-D-Phe-D-Val-NH2 |
| 1036 | TCAM1033 | Arg-Arg-Phe-Arg-Arg-Phe-Phe-Arg-Arg-Leu-Arg-c[Asp-Trp-Arg-Trp-Arg-Tyr-Lys]-D-Val-D-Pro-NH2 |
| 1037 | TCAM1034 | Arg-Arg-Phe-Arg-Arg-Phe-Phe-Arg-Arg-Leu-Arg-c[Asp-Trp-Arg-Trp-Arg-Tyr-Lys]-D-Val-D-Phe-NH2 |
| 1038 | TCAM1035 | Arg-Arg-Phe-Arg-Arg-Phe-Phe-Arg-Arg-Leu-Arg-c[Asp-Trp-Arg-Trp-Arg-Tyr-Lys]-D-Pro-D-Val-NH2 |
| 1039 | TCAM1036 | Arg-Arg-Phe-Arg-Arg-Phe-Phe-Arg-Arg-Leu-Arg-c[Asp-Trp-Arg-Trp-Arg-Tyr-Lys]-D-Phe-D-Val-NH2 |
| 1040 | TCAM1037 | Arg-Arg-Phe-Arg-Arg-Phe-Phe-Arg-Arg-Leu-Arg-c[Asp-Trp-Arg-Trp-Arg-Lys]-D-Val-D-Pro-NH2 |
| 1041 | TCAM1038 | Arg-Arg-Phe-Arg-Arg-Phe-Phe-Arg-Arg-Leu-Arg-c[Asp-Trp-Arg-Trp-Arg-Lys]-D-Val-D-Phe-NH2 |
| 1042 | TCAM1039 | Arg-Arg-Phe-Arg-Arg-Phe-Phe-Arg-Arg-Leu-Arg-c[Asp-Trp-Arg-Trp-Arg-Lys]-D-Pro-D-Val-NH2 |
| 1043 | TCAM1040 | Arg-Arg-Phe-Arg-Arg-Phe-Phe-Arg-Arg-Leu-Arg-c[Asp-Trp-Arg-Trp-Arg-Lys]-D-Phe-D-Val-NH2 |
| 1044 | TCAM1041 | Arg-Arg-Phe-Arg-Arg-Phe-Phe-Arg-Arg-Leu-Arg-c[Asp-Trp-Arg-Arg-Trp-Lys]-D-Val-D-Pro-NH2 |
| 1045 | TCAM1042 | Arg-Arg-Phe-Arg-Arg-Phe-Phe-Arg-Arg-Leu-Arg-c[Asp-Trp-Arg-Arg-Trp-Lys]-D-Val-D-Phe-NH2 |
| 1046 | TCAM1043 | Arg-Arg-Phe-Arg-Arg-Phe-Phe-Arg-Arg-Leu-Arg-c[Asp-Trp-Arg-Arg-Trp-Lys]-D-Pro-D-Val-NH2 |
| 1047 | TCAM1044 | Arg-Arg-Phe-Arg-Arg-Phe-Phe-Arg-Arg-Leu-Arg-c[Asp-Trp-Arg-Arg-Trp-Lys]-D-Phe-D-Val-NH2 |
| 1048 | TCAM1045 | Arg-Arg-Phe-Arg-Arg-Phe-Phe-Arg-Arg-Leu-Arg-c[Asp-Arg-Trp-Trp-Arg-Lys]-D-Val-D-Pro-NH2 |
| 1049 | TCAM1046 | Arg-Arg-Phe-Arg-Arg-Phe-Phe-Arg-Arg-Leu-Arg-c[Asp-Arg-Trp-Trp-Arg-Lys]-D-Val-D-Phe-NH2 |
| 1050 | TCAM1047 | Arg-Arg-Phe-Arg-Arg-Phe-Phe-Arg-Arg-Leu-Arg-c[Asp-Arg-Trp-Trp-Arg-Lys]-D-Pro-D-Val-NH2 |
| 1051 | TCAM1048 | Arg-Arg-Phe-Arg-Arg-Phe-Phe-Arg-Arg-Leu-Arg-c[Asp-Arg-Trp-Trp-Arg-Lys]-D-Phe-D-Val-NH2 |
| 1052 | TCAM1049 | Arg-Arg-Phe-Arg-Arg-Phe-Phe-Arg-Arg-Leu-Arg-c[Asp-Trp-Arg-Trp-Lys]-D-Val-D-Pro-NH2 |

TABLE 5-continued

Exemplary Anti-microbial peptides

| SEQ NO: | Peptide | Peptide Sequence |
|---|---|---|
| 1053 | TCAM1050 | Arg-Arg-Phe-Arg-Arg-Phe-Phe-Arg-Arg-Leu-Arg-c[Asp-Trp-Arg-Trp-Lys]-D-Val-D-Phe-NH2 |
| 1054 | TCAM1051 | Arg-Arg-Phe-Arg-Arg-Phe-Phe-Arg-Arg-Leu-Arg-c[Asp-Trp-Arg-Trp-Lys]-D-Pro-D-Val-NH2 |
| 1055 | TCAM1052 | Arg-Arg-Phe-Arg-Arg-Phe-Phe-Arg-Arg-Leu-Arg-c[Asp-Trp-Arg-Trp-Lys]-D-Phe-D-Val-NH2 |
| 1056 | TCAM1053 | Arg-Arg-Phe-Arg-Arg-Phe-Phe-Arg-Arg-Leu-Arg-c[Asp-Arg-Trp-Arg-Lys]-D-Val-D-Pro-NH2 |
| 1057 | TCAM1054 | Arg-Arg-Phe-Arg-Arg-Phe-Phe-Arg-Arg-Leu-Arg-c[Asp-Arg-Trp-Arg-Lys]-D-Val-D-Phe-NH2 |
| 1058 | TCAM1055 | Arg-Arg-Phe-Arg-Arg-Phe-Phe-Arg-Arg-Leu-Arg-c[Asp-Arg-Trp-Arg-Lys]-D-Pro-D-Val-NH2 |
| 1059 | TCAM1056 | Arg-Arg-Phe-Arg-Arg-Phe-Phe-Arg-Arg-Leu-Arg-c[Asp-Arg-Trp-Arg-Lys]-D-Phe-D-Val-NH2 |
| 1060 | TCAM1057 | Arg-Arg-Phe-Arg-Arg-Phe-Phe-Arg-Arg-Leu-Arg-c[Asp-His-D-Nal(2')-Arg-Trp-Lys]-D-Val-D-Pro-NH2 |
| 1061 | TCAM1058 | Arg-Arg-Phe-Arg-Arg-Phe-Phe-Arg-Arg-Leu-Arg-c[Asp-His-D-Nal(2')-Arg-Trp-Lys]-D-Pro-D-Val-NH2 |
| 1062 | TCAM1059 | Arg-Arg-Phe-Arg-Arg-Phe-Phe-Arg-Arg-Leu-Arg-c[Asp-His-D-Nal(2')-Arg-Trp-Lys]-D-Val-D-Phe-NH2 |
| 1063 | TCAM1060 | Arg-Arg-Phe-Arg-Arg-Phe-Phe-Arg-Arg-Leu-Arg-c[Asp-His-D-Nal(2')-Arg-Trp-Lys]-D-Phe-D-Val-NH2 |
| 1064 | TCAM1061 | Arg-Arg-Phe-Arg-Arg-Phe-Phe-Arg-Arg-Leu-Arg-c[Asp-Pro-D-Nal(2')-Arg-Trp-Lys]-D-Val-D-Pro-NH2 |
| 1065 | TCAM1062 | Arg-Arg-Phe-Arg-Arg-Phe-Phe-Arg-Arg-Leu-Arg-c[Asp-Pro-D-Nal(2')-Arg-Trp-Lys]-D-Pro-D-Val-NH2 |
| 1066 | TCAM1063 | Arg-Arg-Phe-Arg-Arg-Phe-Phe-Arg-Arg-Leu-Arg-c[Asp-Pro-D-Nal(2')-Arg-Trp-Lys]-D-Val-D-Phe-NH2 |
| 1067 | TCAM1064 | Arg-Arg-Phe-Arg-Arg-Phe-Phe-Arg-Arg-Leu-Arg-c[Asp-Pro-D-Nal(2')-Arg-Trp-Lys]-D-Phe-D-Val-NH2 |
| 1068 | TCAM1065 | Arg-Arg-Phe-Arg-Arg-Phe-Phe-Arg-Arg-Leu-Arg-c[Asp-Arg-Arg-Nal(2')-Arg-Trp-Lys]-D-Val-D-Pro-NH2 |
| 1069 | TCAM1066 | Arg-Arg-Phe-Arg-Arg-Phe-Phe-Arg-Arg-Leu-Arg-c[Asp-Arg-Arg-Nal(2')-Arg-Trp-Lys]-D-Pro-D-Val-NH2 |
| 1070 | TCAM1067 | Arg-Arg-Phe-Arg-Arg-Phe-Phe-Arg-Arg-Leu-Arg-c[Asp-Arg-Arg-Nal(2')-Arg-Trp-Lys]-D-Val-D-Phe-NH2 |
| 1071 | TCAM1068 | Arg-Arg-Phe-Arg-Arg-Phe-Phe-Arg-Arg-Leu-Arg-c[Asp-Arg-Arg-Nal(2')-Arg-Trp-Lys]-D-Phe-D-Val-NH2 |
| 1072 | TCAM1069 | Arg-Arg-Phe-Arg-Arg-Phe-Phe-Arg-Arg-Leu-Arg-c[Asp-Arg-Arg-Pro-Nal(2')-Arg-Trp-Lys]-D-Val-D-Pro-NH2 |
| 1073 | TCAM1070 | Arg-Arg-Phe-Arg-Arg-Phe-Phe-Arg-Arg-Leu-Arg-c[Asp-Arg-Arg-Pro-D-Nal(2')-Arg-Trp-Lys]-D-Pro-D-Val-NH2 |
| 1074 | TCAM1071 | Arg-Arg-Phe-Arg-Arg-Phe-Phe-Arg-Arg-Leu-Arg-c[Asp-Arg-Arg-Pro-D-Nal(2')-Arg-Trp-Lys]-D-Val-D-Phe-NH2 |
| 1075 | TCAM1072 | Arg-Arg-Phe-Arg-Arg-Phe-Phe-Arg-Arg-Leu-Arg-c[Asp-Arg-Arg-Pro-Nal(2')-Arg-Trp-Lys]-D-Phe-D-Val-NH2 |
| 1076 | TCAM1073 | Arg-Arg-Phe-Arg-Arg-Phe-Phe-Arg-Arg-Leu-Arg-c[Asp-Arg-D-Nal(2')-Arg-Trp-Lys]-D-Val-D-Pro-NH2 |
| 1077 | TCAM1074 | Arg-Arg-Phe-Arg-Arg-Phe-Phe-Arg-Arg-Leu-Arg-c[Asp-Arg-D-Nal(2')-Arg-Trp-Lys]-D-Pro-D-Val-NH2 |

TABLE 5-continued

Exemplary Anti-microbial peptides

| SEQ NO: | Peptide | Peptide Sequence |
|---|---|---|
| 1078 | TCAM1075 | Arg-Arg-Phe-Arg-Arg-Phe-Phe-Arg-Arg-Leu-Arg-c[Asp-Arg-D-Nal(2')-Arg-Trp-Lys]-D-Val-D-Phe-NH2 |
| 1079 | TCAM1076 | Arg-Arg-Phe-Arg-Arg-Phe-Phe-Arg-Arg-Leu-Arg-c[Asp-Arg-D-Nal(2')-Arg-Trp-Lys]-D-Phe-D-Val-NH2 |
| 1080 | TCAM1077 | Arg-Arg-Phe-Arg-Arg-Phe-Phe-Arg-Arg-Leu-Arg-c[Asp-Arg-Pro-D-Nal(2')-Arg-Trp-Lys]-D-Val-D-Pro-NH2 |
| 1081 | TCAM1078 | Arg-Arg-Phe-Arg-Arg-Phe-Phe-Arg-Arg-Leu-Arg-c[Asp-Arg-Pro-D-Nal(2')-Arg-Trp-Lys]-D-Pro-D-Val-NH2 |
| 1082 | TCAM1079 | Arg-Arg-Phe-Arg-Arg-Phe-Phe-Arg-Arg-Leu-Arg-c[Asp-Arg-Pro-D-Nal(2')-Arg-Trp-Lys]-D-Val-D-Phe-NH2 |
| 1083 | TCAM1080 | Arg-Arg-Phe-Arg-Arg-Phe-Phe-Arg-Arg-Leu-Arg-c[Asp-Arg-Pro-D-Nal(2')-Arg-Trp-Lys]-D-Phe-D-Val-NH2 |
| 1084 | TCAM1081 | Arg-Arg-Phe-Arg-Arg-Phe-Phe-Arg-Arg-Leu-Arg-Arg-Arg-c[Asp-Pro-D-Nal(2')-Arg-Trp-Lys]-D-Val-D-Pro-NH2 |
| 1085 | TCAM1082 | Arg-Arg-Phe-Arg-Arg-Phe-Phe-Arg-Arg-Leu-Arg-Arg-Arg-c[Asp-Pro-D-Nal(2')-Arg-Trp-Lys]-D-Pro-D-Val-NH2 |
| 1086 | TCAM1083 | Arg-Arg-Phe-Arg-Arg-Phe-Phe-Arg-Arg-Leu-Arg-Arg-Arg-c[Asp-Pro-D-Nal(2')-Arg-Trp-Lys]-D-Val-D-Phe-NH2 |
| 1087 | TCAM1084 | Arg-Arg-Phe-Arg-Arg-Phe-Phe-Arg-Arg-Leu-Arg-Arg-Arg-c[Asp-Pro-D-Nal(2')-Arg-Trp-Lys]-D-Phe-D-Val-NH2 |
| 1088 | TCAM1085 | Arg-Arg-Phe-Arg-Arg-Phe-Phe-Arg-Arg-Leu-Arg-Arg-Arg-c[Asp-His-D-Nal(2')-Arg-Trp-Lys]-D-Val-D-Pro-NH2 |
| 1089 | TCAM1086 | Arg-Arg-Phe-Arg-Arg-Phe-Phe-Arg-Arg-Leu-Arg-Arg-Arg-c[Asp-His-D-Nal(2')-Arg-Trp-Lys]-D-Pro-D-Val-NH2 |
| 1090 | TCAM1087 | Arg-Arg-Phe-Arg-Arg-Phe-Phe-Arg-Arg-Leu-Arg-Arg-Arg-c[Asp-His-D-Nal(2')-Arg-Trp-Lys]-D-Val-D-Phe-NH2 |
| 1091 | TCAM1088 | Arg-Arg-Phe-Arg-Arg-Phe-Phe-Arg-Arg-Leu-Arg-Arg-Arg-c[Asp-His-D-Nal(2')-Arg-Trp-Lys]-D-Phe-D-Val-NH2 |
| 1092 | TCAM1089 | Arg-Arg-Phe-Arg-Arg-Phe-Phe-Arg-Arg-Leu-Arg-c[Asp-Arg-Pro-D-Nal(2')-Arg-Trp-Arg-Lys]-D-Val-D-Pro-NH2 |
| 1093 | TCAM1090 | Arg-Arg-Phe-Arg-Arg-Phe-Phe-Arg-Arg-Leu-Arg-c[Asp-Arg-Pro-D-Nal(2')-Arg-Trp-Arg-Lys]-D-Pro-D-Val-NH2 |
| 1094 | TCAM1091 | Arg-Arg-Phe-Arg-Arg-Phe-Phe-Arg-Arg-Leu-Arg-c[Asp-Arg-Pro-D-Nal(2')-Arg-Trp-Arg-Lys]-D-Val-D-Phe-NH2 |
| 1095 | TCAM1092 | Arg-Arg-Phe-Arg-Arg-Phe-Phe-Arg-Arg-Leu-Arg-c[Asp-Arg-Pro-D-Nal(2')-Arg-Trp-Arg-Lys]-D-Phe-D-Val-NH2 |
| 1096 | TCAM1093 | Arg-Arg-Phe-Arg-Arg-Phe-Phe-Arg-Arg-Leu-Arg-c[Asp-Arg-His-D-Nal(2')-Arg-Trp-Arg-Lys]-D-Val-D-Pro-NH2 |
| 1097 | TCAM1094 | Arg-Arg-Phe-Arg-Arg-Phe-Phe-Arg-Arg-Leu-Arg-c[Asp-Arg-His-D-Nal(2')-Arg-Trp-Arg-Lys]-D-Pro-D-Val-NH2 |
| 1098 | TCAM1095 | Arg-Arg-Phe-Arg-Arg-Phe-Phe-Arg-Arg-Leu-Arg-c[Asp-Arg-His-D-Nal(2')-Arg-Trp-Arg-Lys]-D-Val-D-Phe-NH2 |
| 1099 | TCAM1096 | Arg-Arg-Phe-Arg-Arg-Phe-Phe-Arg-Arg-Leu-Arg-c[Asp-Arg-His-D-Nal(2')-Arg-Trp-Arg-Lys]-D-Phe-D-Val-NH2 |
| 1100 | TCAM1097 | Arg-Arg-Phe-Arg-Arg-Phe-Phe-Arg-Arg-Leu-Arg-c[Asp-His-D-Nal(2')-Arg-D-Nal(2')-Lys]-D-Val-D-Phe-NH2 |
| 1101 | TCAM1098 | Arg-Arg-Phe-Arg-Arg-Phe-Phe-Arg-Arg-Leu-Arg-c[Asp-His-D-Nal(2')-Arg-D-Nal(2')-Lys]-D-Phe-D-Val-NH2 |
| 1102 | TCAM1099 | Arg-Arg-Phe-Arg-Arg-Phe-Phe-Arg-Arg-Leu-Arg-c[Asp-Pro-D-Nal(2')-Arg-D-Nal(2')-Lys]-D-Val-D-Pro-NH2 |

TABLE 5-continued

Exemplary Anti-microbial peptides

| SEQ NO: | Peptide | Peptide Sequence |
|---|---|---|
| 1103 | TCAM1100 | Arg-Arg-Phe-Arg-Arg-Phe-Phe-Arg-Arg-Leu-Arg-c[Asp-Pro-D-Nal(2')-Arg-D-Nal(2')-Lys]-D-Pro-D-Val-NH2 |
| 1104 | TCAM1101 | Arg-Arg-Phe-Arg-Arg-Phe-Phe-Arg-Arg-Leu-Arg-c[Asp-Pro-D-Nal(2')-Arg-D-Nal(2')-Lys]-D-Val-D-Phe-NH2 |
| 1105 | TCAM1102 | Arg-Arg-Phe-Arg-Arg-Phe-Phe-Arg-Arg-Leu-Arg-c[Asp-Pro-D-Nal(2')-Arg-D-Nal(2')-Lys]-D-Phe-D-Val-NH2 |
| 1106 | TCAM1103 | Arg-Arg-Phe-Arg-Arg-Phe-Phe-Arg-Arg-Leu-Arg-c[Asp-Arg-Arg-D-Nal(2')-Arg-D-Nal(2')-Lys]-D-Val-D-Pro-NH2 |
| 1107 | TCAM1104 | Arg-Arg-Phe-Arg-Arg-Phe-Phe-Arg-Arg-Leu-Arg-c[Asp-Arg-Arg-D-Nal(2')-Arg-D-Nal(2')-Lys]-D-Pro-D-Val-NH2 |
| 1108 | TCAM1105 | Arg-Arg-Phe-Arg-Arg-Phe-Phe-Arg-Arg-Leu-Arg-c[Asp-Arg-Arg-D-Nal(2')-Arg-D-Nal(2')-Lys]-D-Val-D-Phe-NH2 |
| 1109 | TCAM1106 | Arg-Arg-Phe-Arg-Arg-Phe-Phe-Arg-Arg-Leu-Arg-c[Asp-Arg-Arg-D-Nal(2')-Arg-D-Nal(2')-Lys]-D-Phe-D-Val-NH2 |
| 1110 | TCAM1107 | Arg-Arg-Phe-Arg-Arg-Phe-Phe-Arg-Arg-Leu-Arg-c[Asp-Arg-Arg-Pro-D-Nal(2')-Arg-D-Nal(2')-Lys]-D-Val-D-Pro-NH2 |
| 1111 | TCAM1108 | Arg-Arg-Phe-Arg-Arg-Phe-Phe-Arg-Arg-Leu-Arg-c[Asp-Arg-Arg-Pro-D-Nal(2')-Arg-D-Nal(2')-Lys]-D-Pro-D-Val-NH2 |
| 1112 | TCAM1109 | Arg-Arg-Phe-Arg-Arg-Phe-Phe-Arg-Arg-Leu-Arg-c[Asp-Arg-Arg-Pro-D-Nal(2')-Arg-D-Nal(2')-Lys]-D-Val-D-Phe-NH2 |
| 1113 | TCAM1110 | Arg-Arg-Phe-Arg-Arg-Phe-Phe-Arg-Arg-Leu-Arg-c[Asp-Arg-Arg-Pro-D-Nal(2')-Arg-D-Nal(2')-Lys]-D-Phe-D-Val-NH2 |
| 1114 | TCAM1111 | Arg-Arg-Phe-Arg-Arg-Phe-Phe-Arg-Arg-Leu-Arg-c[Asp-Arg-D-Nal(2')-Arg-D-Nal(2')-Lys]-D-Val-D-Pro-NH2 |
| 1115 | TCAM1112 | Arg-Arg-Phe-Arg-Arg-Phe-Phe-Arg-Arg-Leu-Arg-c[Asp-Arg-D-Nal(2')-Arg-D-Nal(2')-Lys]-D-Pro-D-Val-NH2 |
| 1116 | TCAM1113 | Arg-Arg-Phe-Arg-Arg-Phe-Phe-Arg-Arg-Leu-Arg-c[Asp-Arg-Nal(2')-Arg-D-Nal(2')-Lys]-D-Val-D-Phe-NH2 |
| 1117 | TCAM1114 | Arg-Arg-Phe-Arg-Arg-Phe-Phe-Arg-Arg-Leu-Arg-c[Asp-Arg-D-Nal(2')-Arg-D-Nal(2')-Lys]-D-Phe-D-Val-NH2 |
| 1118 | TCAM1115 | Arg-Arg-Phe-Arg-Arg-Phe-Phe-Arg-Arg-Leu-Arg-c[Asp-Arg-Pro-D-Nal(2')-Arg-D-Nal(2')-Lys]-D-Val-D-Pro-NH2 |
| 1119 | TCAM1116 | Arg-Arg-Phe-Arg-Arg-Phe-Phe-Arg-Arg-Leu-Arg-c[Asp-Arg-Pro-D-Nal(2')-Arg-D-Nal(2')-Lys]-D-Pro-D-Val-NH2 |
| 1120 | TCAM1117 | Arg-Arg-Phe-Arg-Arg-Phe-Phe-Arg-Arg-Leu-Arg-c[Asp-Arg-Pro-D-Nal(2')-Arg-D-Nal(2')-Lys]-D-Val-D-Phe-NH2 |
| 1121 | TCAM1118 | Arg-Arg-Phe-Arg-Arg-Phe-Phe-Arg-Arg-Leu-Arg-c[Asp-Arg-Pro-D-Nal(2')-Arg-D-Nal(2')-Lys]-D-Phe-D-Val-NH2 |
| 1122 | TCAM1119 | Arg-Arg-Phe-Arg-Arg-Phe-Phe-Arg-Arg-Leu-Arg-c[Asp-Arg-His-D-Nal(2')-Arg-D-Nal(2')-Lys]-D-Val-D-Pro-NH2 |
| 1123 | TCAM1120 | Arg-Arg-Phe-Arg-Arg-Phe-Phe-Arg-Arg-Leu-Arg-c[Asp-Arg-His-D-Nal(2')-Arg-D-Nal(2')-Lys]-D-Pro-D-Val-NH2 |
| 1124 | TCAM1121 | Arg-Arg-Phe-Arg-Arg-Phe-Phe-Arg-Arg-Leu-Arg-c[Asp-Arg-His-Nal(2')-Arg-D-Nal(2')-Lys]-D-Val-D-Phe-NH2 |
| 1125 | TCAM1122 | Arg-Arg-Phe-Arg-Arg-Phe-Phe-Arg-Arg-Leu-Arg-c[Asp-Arg-His-Nal(2')-Arg-D-Nal(2')-Lys]-D-Phe-D-Val-NH2 |
| 1126 | TCAM1123 | Arg-Arg-Phe-Arg-Arg-Phe-Phe-Arg-Arg-Leu-Arg-c[Asp-Arg-D-Nal(2')-Arg-D-Nal(2')-Arg-Lys]-D-Val-D-Pro-NH2 |
| 1127 | TCAM1124 | Arg-Arg-Phe-Arg-Arg-Phe-Phe-Arg-Arg-Leu-Arg-c[Asp-Arg-D-Nal(2')-Arg-D-Nal(2')-Arg-Lys]-D-Pro-D-Val-NH2 |

TABLE 5-continued

Exemplary Anti-microbial peptides

| SEQ NO: | Peptide | Peptide Sequence |
|---|---|---|
| 1128 | TCAM1125 | Arg-Arg-Phe-Arg-Arg-Phe-Phe-Arg-Arg-Leu-Arg-c[Asp-Arg-D-Nal(2')-Arg-D-Nal(2')-Arg-Lys]-D-Val-D-Phe-NH2 |
| 1129 | TCAM1126 | Arg-Arg-Phe-Arg-Arg-Phe-Phe-Arg-Arg-Leu-Arg-c[Asp-Arg-D-Nal(2')-Arg-D-Nal(2')-Arg-Lys]-D-Phe-D-Val-NH2 |
| 1130 | TCAM1127 | Arg-Arg-Phe-Arg-Arg-Phe-Phe-Arg-Arg-Leu-Arg-c[Asp-Arg-Pro-D-Nal(2')-Arg-D-Nal(2')-Arg-Lys]-D-Val-D-Pro-NH2 |
| 1131 | TCAM1128 | Arg-Arg-Phe-Arg-Arg-Phe-Phe-Arg-Arg-Leu-Arg-c[Asp-Arg-Pro-D-Nal(2')-Arg-D-Nal(2')-Arg-Lys]-D-Pro-D-Val-NH2 |
| 1132 | TCAM1129 | Arg-Arg-Phe-Arg-Arg-Phe-Phe-Arg-Arg-Leu-Arg-c[Asp-Arg-Pro-D-Nal(2')-Arg-D-Nal(2')-Arg-Lys]-D-Val-D-Phe-NH2 |
| 1133 | TCAM1130 | Arg-Arg-Phe-Arg-Arg-Phe-Phe-Arg-Arg-Leu-Arg-c[Asp-Arg-Pro-D-Nal(2')-Arg-D-Nal(2')-Arg-Lys]-D-Phe-D-Val-NH2 |
| 1134 | TCAM1131 | Arg-Arg-Phe-Arg-Arg-Phe-Phe-Arg-Arg-Leu-Arg-c[Asp-Arg-His-D-Nal(2')-Arg-D-Nal(2')-Arg-Lys]-D-Val-D-Pro-NH2 |
| 1135 | TCAM1132 | Arg-Arg-Phe-Arg-Arg-Phe-Phe-Arg-Arg-Leu-Arg-c[Asp-Arg-His-D-Nal(2')-Arg-D-Nal(2')-Arg-Lys]-D-Pro-D-Val-NH2 |
| 1136 | TCAM1133 | Arg-Arg-Phe-Arg-Arg-Phe-Phe-Arg-Arg-Leu-Arg-c[Asp-Arg-His-D-Nal(2')-Arg-D-Nal(2')-Arg-Lys]-D-Val-D-Phe-NH2 |
| 1137 | TCAM1134 | Arg-Arg-Phe-Arg-Arg-Phe-Phe-Arg-Arg-Leu-Arg-c[Asp-Arg-His-D-Nal(2')-Arg-D-Nal(2')-Arg-Lys]-D-Phe-D-Val-NH2 |
| 1138 | TCAM1135 | Arg-Arg-Phe-Arg-Arg-Phe-Phe-Arg-Arg-Leu-Arg-Arg-Arg-c[Asp-Pro-D-Nal(2')-Arg-D-Nal(2')-Lys]-D-Val-D-Pro-NH2 |
| 1139 | TCAM1136 | Arg-Arg-Phe-Arg-Arg-Phe-Phe-Arg-Arg-Leu-Arg-Arg-Arg-c[Asp-Pro-D-Nal(2')-Arg-D-Nal(2')-Lys]-D-Pro-D-Val-NH2 |
| 1140 | TCAM1137 | Arg-Arg-Phe-Arg-Arg-Phe-Phe-Arg-Arg-Leu-Arg-Arg-Arg-c[Asp-Pro-D-Nal(2')-Arg-D-Nal(2')-Lys]-D-Val-D-Phe-NH2 |
| 1141 | TCAM1138 | Arg-Arg-Phe-Arg-Arg-Phe-Phe-Arg-Arg-Leu-Arg-Arg-Arg-c[Asp-Pro-D-Nal(2')-Arg-D-Nal(2')-Lys]-D-Phe-D-Val-NH2 |
| 1142 | TCAM1139 | Arg-Arg-Phe-Arg-Arg-Phe-Phe-Arg-Arg-Leu-Arg-Arg-Arg-c[Asp-His-D-Nal(2')-Arg-D-Nal(2')-Lys]-D-Val-D-Pro-NH2 |
| 1143 | TCAM1140 | Arg-Arg-Phe-Arg-Arg-Phe-Phe-Arg-Arg-Leu-Arg-Arg-Arg-c[Asp-His-D-Nal(2')-Arg-D-Nal(2')-Lys]-D-Pro-D-Val-NH2 |
| 1144 | TCAM1141 | Arg-Arg-Phe-Arg-Arg-Phe-Phe-Arg-Arg-Leu-Arg-Arg-Arg-c[Asp-His-D-Nal(2')-Arg-D-Nal(2')-Lys]-D-Val-D-Phe-NH2 |
| 1145 | TCAM1142 | Arg-Arg-Phe-Arg-Arg-Phe-Phe-Arg-Arg-Leu-Arg-Arg-Arg-c[Asp-His-D-Nal(2')-Arg-D-Nal(2')-Lys]-D-Phe-D-Val-NH2 |
| 1146 | TCAM1143 | Arg-Arg-Phe-Arg-Arg-Phe-Phe-Arg-Arg-Leu-Arg-c[Asp-Arg-Pro-D-Nal(2')-Arg-D-Nal(2')-Arg-Lys]-D-Val-D-Pro-NH2 |
| 1147 | TCAM1144 | Arg-Arg-Phe-Arg-Arg-Phe-Phe-Arg-Arg-Leu-Arg-c[Asp-Arg-Pro-D-Nal(2')-Arg-D-Nal(2')-Arg-Lys]-D-Pro-D-Val-NH2 |
| 1148 | TCAM1145 | Arg-Arg-Phe-Arg-Arg-Phe-Phe-Arg-Arg-Leu-Arg-c[Asp-Arg-Pro-D-Nal(2')-Arg-D-Nal(2')-Arg-Lys]-D-Val-D-Phe-NH2 |
| 1149 | TCAM1146 | Arg-Arg-Phe-Arg-Arg-Phe-Phe-Arg-Arg-Leu-Arg-c[Asp-Arg-Pro-D-Nal(2')-Arg-D-Nal(2')-Arg-Lys]-D-Phe-D-Val-NH2 |
| 1150 | TCAM1147 | Arg-Arg-Phe-Arg-Arg-Phe-Phe-Arg-Arg-Leu-Arg-c[Asp-Arg-His-D-Nal(2')-Arg-D-Nal(2')-Arg-Lys]-D-Val-D-Pro-NH2 |
| 1151 | TCAM1148 | Arg-Arg-Phe-Arg-Arg-Phe-Phe-Arg-Arg-Leu-Arg-c[Asp-Arg-His-D-Nal(2')-Arg-D-Nal(2')-Arg-Lys]-D-Pro-D-Val-NH2 |
| 1152 | TCAM1149 | Arg-Arg-Phe-Arg-Arg-Phe-Phe-Arg-Arg-Leu-Arg-c[Asp-Arg-His-D-Nal(2')-Arg-D-Nal(2')-Arg-Lys]-D-Val-D-Phe-NH2 |

TABLE 5-continued

Exemplary Anti-microbial peptides

| SEQ NO: | Peptide | Peptide Sequence |
|---|---|---|
| 1153 | TCAM1150 | Arg-Arg-Phe-Arg-Arg-Phe-Phe-Arg-Arg-Leu-Arg-c[Asp-Arg-His-D-Nal(2')-Arg-D-Nal(2')-Arg-Lys]-D-Phe-D-Val-NH2 |
| 1154 | TCAM1151 | Arg-Arg-Phe-Arg-Arg-Phe-Phe-Arg-Arg-Leu-Arg-c[Asp-His-D-Nal(2')-Arg-Trp-Lys]-Arg-Arg-D-Val-D-Pro-NH2 |
| 1155 | TCAM1152 | Arg-Arg-Phe-Arg-Arg-Phe-Phe-Arg-Arg-Leu-Arg-c[Asp-His-D-Nal(2')-Arg-Trp-Lys]-Arg-Arg-D-Pro-D-Val-NH2 |
| 1156 | TCAM1153 | Arg-Arg-Phe-Arg-Arg-Phe-Phe-Arg-Leu-Arg-c[Asp-His-D-Nal(2')-Arg-Trp-Lys]-Arg-Arg-D-Val-D-Phe-NH2 |
| 1157 | TCAM1154 | Arg-Arg-Phe-Arg-Arg-Phe-Phe-Arg-Arg-Leu-Arg-c[Asp-His-D-Nal(2')-Arg-Trp-Lys]-Arg-Arg-D-Phe-D-Val-NH2 |
| 1158 | TCAM1155 | Arg-Arg-Phe-Arg-Arg-Phe-Phe-Arg-Arg-Leu-Arg-c[Asp-Pro-D-Nal(2')-Arg-Trp-Lys]-Arg-Arg-D-Val-D-Pro-NH2 |
| 1159 | TCAM1156 | Arg-Arg-Phe-Arg-Arg-Phe-Phe-Arg-Arg-Leu-Arg-c[Asp-Pro-D-Nal(2')-Arg-Trp-Lys]-Arg-Arg-D-Pro-D-Val-NH2 |
| 1160 | TCAM1157 | Arg-Arg-Phe-Arg-Arg-Phe-Phe-Arg-Arg-Leu-Arg-c[Asp-Pro-D-Nal(2')-Arg-Trp-Lys]-Arg-Arg-D-Val-D-Phe-NH2 |
| 1161 | TCAM1158 | Arg-Arg-Phe-Arg-Arg-Phe-Phe-Arg-Arg-Leu-Arg-c[Asp-Pro-D-Nal(2')-Arg-Trp-Lys]-Arg-Arg-D-Phe-D-Val-NH2 |

Anti-biofilm peptide ABF1 linked to anti-microbial peptides

| SEQ NO: | Peptide | Peptide Sequence |
|---|---|---|
| 1162 | TCAM1159 | Val-Arg-Leu-Ile-Val-Ala-Val-Arg-c[Asp-Pro-Arg-Arg-Trp-Trp-Arg-Phe-Lys]-D-Val-D-Pro-NH2 |
| 1163 | TCAM1160 | Val-Arg-Leu-Ile-Val-Ala-Val-Arg-c[Asp-Pro-Arg-Arg-Trp-Trp-Arg-Phe-Lys]-D-Val-D-Phe-NH2 |
| 1164 | TCAM1161 | Val-Arg-Leu-Ile-Val-Ala-Val-Arg-c[Asp-Pro-Arg-Arg-Trp-Trp-Arg-Phe-Lys]-D-Pro-D-Val-NH2 |
| 1165 | TCAM1162 | Val-Arg-Leu-Ile-Val-Ala-Val-Arg-c[Asp-Pro-Arg-Arg-Trp-Trp-Arg-Phe-Lys]-D-Phe-D-Val-NH2 |
| 1166 | TCAM1163 | Val-Arg-Leu-Ile-Val-Ala-Val-Arg-c[Asp-Pro-Arg-Arg-Trp-Trp-Tyr-Phe-Lys]-D-Val-D-Pro-NH2 |
| 1167 | TCAM1164 | Val-Arg-Leu-Ile-Val-Ala-Val-Arg-c[Asp-Pro-Arg-Arg-Trp-Trp-Tyr-Phe-Lys]-D-Val-D-Phe-NH2 |
| 1168 | TCAM1165 | Val-Arg-Leu-Ile-Val-Ala-Val-Arg-c[Asp-Pro-Arg-Arg-Trp-Trp-Tyr-Phe-Lys]-D-Pro-D-Val-NH2 |
| 1169 | TCAM1166 | Val-Arg-Leu-Ile-Val-Ala-Val-Arg-c[Asp-Pro-Arg-Arg-Trp-Trp-Tyr-Phe-Lys]-D-Phe-D-Val-NH2 |
| 1170 | TCAM1167 | Val-Arg-Leu-Ile-Val-Ala-Val-Arg-c[Asp-Pro-Arg-Arg-Tyr-Tyr-Arg-Phe-Lys]-D-Val-D-Pro-NH2 |
| 1171 | TCAM1168 | Val-Arg-Leu-Ile-Val-Ala-Val-Arg-c[Asp-Pro-Arg-Arg-Tyr-Tyr-Arg-Phe-Lys]-D-Val-D-Phe-NH2 |
| 1172 | TCAM1169 | Val-Arg-Leu-Ile-Val-Ala-Val-Arg-c[Asp-Pro-Arg-Arg-Tyr-Tyr-Arg-Phe-Lys]-D-Pro-D-Val-NH2 |
| 1173 | TCAM1170 | Val-Arg-Leu-Ile-Val-Ala-Val-Arg-c[Asp-Pro-Arg-Arg-Tyr-Tyr-Arg-Phe-Lys]-D-Phe-D-Val-NH2 |
| 1174 | TCAM1171 | Val-Arg-Leu-Ile-Val-Ala-Val-Arg-c[Asp-Pro-Arg-Arg-Nal-Nal-Arg-Phe-Lys]-D-Val-D-Pro-NH2 |
| 1175 | TCAM1172 | Val-Arg-Leu-Ile-Val-Ala-Val-Arg-c[Asp-Pro-Arg-Arg-Nal-Nal-Arg-Phe-Lys]-D-Val-D-Phe-NH2 |
| 1176 | TCAM1173 | Val-Arg-Leu-Ile-Val-Ala-Val-Arg-c[Asp-Pro-Arg-Arg-Nal-Nal-Arg-Phe-Lys]-D-Pro-D-Val-NH2 |

TABLE 5-continued

Exemplary Anti-microbial peptides

| SEQ NO: | Peptide | Peptide Sequence |
|---|---|---|
| 1177 | TCAM1174 | Val-Arg-Leu-Ile-Val-Ala-Val-Arg-c[Asp-Pro-Arg-Arg-Nal-Nal-Arg-Phe-Lys]-D-Phe-D-Val-NH2 |
| 1178 | TCAM1175 | Val-Arg-Leu-Ile-Val-Ala-Val-Arg-c[Asp-Pro-Arg-Arg-Leu-Trp-Leu-Trp-Lys]-D-Val-D-Pro-NH2 |
| 1179 | TCAM1176 | Val-Arg-Leu-Ile-Val-Ala-Val-Arg-c[Asp-Pro-Arg-Arg-Leu-Trp-Leu-Trp-Lys]-D-Val-D-Phe-NH2 |
| 1180 | TCAM1177 | Val-Arg-Leu-Ile-Val-Ala-Val-Arg-c[Asp-Pro-Arg-Arg-Leu-Trp-Leu-Trp-Lys]-D-Pro-D-Val-NH2 |
| 1181 | TCAM1178 | Val-Arg-Leu-Ile-Val-Ala-Val-Arg-c[Asp-Pro-Arg-Arg-Leu-Trp-Leu-Trp-Lys]-D-Phe-D-Val-NH2 |
| 1182 | TCAM1179 | Val-Arg-Leu-Ile-Val-Ala-Val-Arg-c[Asp-Pro-Arg-Arg-Leu-Trp-Leu-Trp-Lys]-D-Val-D-Pro-NH2 |
| 1183 | TCAM1180 | Val-Arg-Leu-Ile-Val-Ala-Val-Arg-c[Asp-Pro-Arg-Arg-Leu-Trp-Leu-Trp-Lys]-D-Val-D-Phe-NH2 |
| 1184 | TCAM1181 | Val-Arg-Leu-Ile-Val-Ala-Val-Arg-c[Asp-Pro-Arg-Arg-Leu-Trp-Leu-Trp-Lys]-D-Pro-D-Val-NH2 |
| 1185 | TCAM1182 | Val-Arg-Leu-Ile-Val-Ala-Val-Arg-c[Asp-Pro-Arg-Arg-Leu-Trp-Leu-Trp-Lys]-D-Phe-D-Val-NH2 |
| 1186 | TCAM1183 | Val-Arg-Leu-Ile-Val-Ala-Val-Arg-c[Asp-Arg-Arg-Arg-Trp-Leu-Trp-Leu-Trp-Lys]-D-Val-D-Pro-NH2 |
| 1187 | TCAM1184 | Val-Arg-Leu-Ile-Val-Ala-Val-Arg-c[Asp-Pro-Arg-Arg-Arg-Trp-Leu-Trp-Leu-Trp-Lys]-D-Val-D-Phe-NH2 |
| 1188 | TCAM1185 | Val-Arg-Leu-Ile-Val-Ala-Val-Arg-c[Asp-Pro-Arg-Arg-Arg-Trp-Leu-Trp-Leu-Trp-Lys]-D-Pro-D-Val-NH2 |
| 1189 | TCAM1186 | Val-Arg-Leu-Ile-Val-Ala-Val-Arg-c[Asp-Pro-Arg-Arg-Arg-Trp-Leu-Trp-Leu-Trp-Lys]-D-Phe-D-Val-NH2 |
| 1190 | TCAM1187 | Val-Arg-Leu-Ile-Val-Ala-Val-Arg-c[Asp-Pro-Arg-Gln-Arg-Arg-Trp-Leu-Trp-Leu-Trp-Lys]-D-Val-D-Pro-NH2 |
| 1191 | TCAM1188 | Val-Arg-Leu-Ile-Val-Ala-Val-Arg-c[Asp-Pro-Arg-Gln-Arg-Arg-Trp-Leu-Trp-Leu-Trp-Lys]-D-Val-D-Phe-NH2 |
| 1192 | TCAM1189 | Val-Arg-Leu-Ile-Val-Ala-Val-Arg-c[Asp-Pro-Arg-Gln-Arg-Arg-Trp-Leu-Trp-Leu-Trp-Lys]-D-Pro-D-Val-NH2 |
| 1193 | TCAM1190 | Val-Arg-Leu-Ile-Val-Ala-Val-Arg-c[Asp-Pro-Arg-Gln-Arg-Arg-Trp-Leu-Trp-Leu-Trp-Lys]-D-Phe-D-Val-NH2 |
| 1194 | TCAM1191 | Val-Arg-Leu-Ile-Val-Ala-Val-Arg-c[Asp-Pro-Trp-Arg-Trp-Trp-Arg-Arg-Lys]-D-Val-D-Phe-NH2 |
| 1195 | TCAM1192 | Val-Arg-Leu-Ile-Val-Ala-Val-Arg-c[Asp-Pro-Trp-Arg-Trp-Trp-Arg-Arg-Lys]-D-Pro-D-Val-NH2 |
| 1196 | TCAM1193 | Val-Arg-Leu-Ile-Val-Ala-Val-Arg-c[Asp-Pro-Trp-Arg-Trp-Trp-Arg-Arg-Lys]-D-Phe-D-Val-NH2 |
| 1197 | TCAM1194 | Val-Arg-Leu-Ile-Val-Ala-Val-Arg-c[Asp-Pro-Trp-Trp-Arg-Arg-Trp-Trp-Arg-Arg-Lys]-D-Val-D-Pro-NH2 |
| 1198 | TCAM1195 | Val-Arg-Leu-Ile-Val-Ala-Val-Arg-c[Asp-Pro-Trp-Trp-Arg-Arg-Trp-Trp-Arg-Arg-Lys]-D-Val-D-Phe-NH2 |
| 1199 | TCAM1196 | Val-Arg-Leu-Ile-Val-Ala-Val-Arg-c[Asp-Pro-Trp-Trp-Arg-Arg-Trp-Trp-Arg-Arg-Lys]-D-Pro-D-Val-NH2 |
| 1200 | TCAM1197 | Val-Arg-Leu-Ile-Val-Ala-Val-Arg-c[Asp-Pro-Trp-Trp-Arg-Arg-Trp-Trp-Arg-Arg-Lys]-D-Phe-D-Val-NH2 |
| 1201 | TCAM1198 | Val-Arg-Leu-Ile-Val-Ala-Val-Arg-c[Asp-Pro-Trp-Arg-Trp-Arg-Trp-Arg-Lys]-D-Val-D-Pro-NH2 |

TABLE 5-continued

Exemplary Anti-microbial peptides

| SEQ NO: | Peptide | Peptide Sequence |
|---|---|---|
| 1202 | TCAM1199 | Val-Arg-Leu-Ile-Val-Ala-Val-Arg-c[Asp-Pro-Trp-Arg-Trp-Arg-Trp-Arg-Lys]-D-Val-D-Phe-NH2 |
| 1203 | TCAM1200 | Val-Arg-Leu-Ile-Val-Ala-Val-Arg-c[Asp-Pro-Trp-Arg-Trp-Arg-Trp-Arg-Lys]-D-Pro-D-Val-NH2 |
| 1204 | TCAM1201 | Val-Arg-Leu-Ile-Val-Ala-Val-Arg-c[Asp-Pro-Trp-Arg-Trp-Arg-Trp-Arg-Lys]-D-Phe-D-Val-NH2 |
| 1205 | TCAM1202 | Val-Arg-Leu-Ile-Val-Ala-Val-Arg-c[Asp-Pro-Arg-Trp-Arg-Trp-Arg-Trp-Lys]-D-Val-D-Pro-NH2 |
| 1206 | TCAM1203 | Val-Arg-Leu-Ile-Val-Ala-Val-Arg-c[Asp-Pro-Arg-Trp-Arg-Trp-Arg-Trp-Lys]-D-Val-D-Phe-NH2 |
| 1207 | TCAM1204 | Val-Arg-Leu-Ile-Val-Ala-Val-Arg-c[Asp-Pro-Arg-Trp-Arg-Trp-Arg-Trp-Lys]-D-Pro-D-Val-NH2 |
| 1208 | TCAM1205 | Val-Arg-Leu-Ile-Val-Ala-Val-Arg-c[Asp-Pro-Arg-Trp-Arg-Trp-Arg-Trp-Lys]-D-Phe-D-Val-NH2 |
| 1209 | TCAM1206 | Val-Arg-Leu-Ile-Val-Ala-Val-Arg-c[Asp-Pro-Arg-Trp-Trp-Arg-Arg-Lys]-D-Val-D-Pro-NH2 |
| 1210 | TCAM1207 | Val-Arg-Leu-Ile-Val-Ala-Val-Arg-c[Asp-Pro-Arg-Trp-Trp-Arg-Arg-Lys]-D-Val-D-Phe-NH2 |
| 1211 | TCAM1208 | Val-Arg-Leu-Ile-Val-Ala-Val-Arg-c[Asp-Pro-Arg-Trp-Trp-Arg-Arg-Lys]-D-Pro-D-Val-NH2 |
| 1212 | TCAM1209 | Val-Arg-Leu-Ile-Val-Ala-Val-Arg-c[Asp-Pro-Arg-Trp-Trp-Arg-Arg-Lys]-D-Phe-D-Val-NH2 |
| 1213 | TCAM1210 | Val-Arg-Leu-Ile-Val-Ala-Val-Arg-c[Asp-Pro-Trp-Trp-Arg-Arg-Trp-Lys]-D-Val-D-Pro-NH2 |
| 1214 | TCAM1211 | Val-Arg-Leu-Ile-Val-Ala-Val-Arg-c[Asp-Pro-Trp-Trp-Arg-Arg-Trp-Lys]-D-Val-D-Phe-NH2 |
| 1215 | TCAM1212 | Val-Arg-Leu-Ile-Val-Ala-Val-Arg-c[Asp-Pro-Trp-Trp-Arg-Arg-Trp-Lys]-D-Pro-D-Val-NH2 |
| 1216 | TCAM1213 | Val-Arg-Leu-Ile-Val-Ala-Val-Arg-c[Asp-Pro-Trp-Trp-Arg-Arg-Trp-Lys]-D-Phe-D-Val-NH2 |
| 1217 | TCAM1214 | Val-Arg-Leu-Ile-Val-Ala-Val-Arg-c[Asp-Pro-Trp-Arg-Trp-Arg-Trp-Lys]-D-Val-D-Pro-NH2 |
| 1218 | TCAM1215 | Val-Arg-Leu-Ile-Val-Ala-Val-Arg-c[Asp-Pro-Trp-Arg-Trp-Arg-Trp-Lys]-D-Val-D-Phe-NH2 |
| 1219 | TCAM1216 | Val-Arg-Leu-Ile-Val-Ala-Val-Arg-c[Asp-Pro-Trp-Arg-Trp-Arg-Trp-Lys]-D-Pro-D-Val-NH2 |
| 1220 | TCAM1217 | Val-Arg-Leu-Ile-Val-Ala-Val-Arg-c[Asp-Pro-Trp-Arg-Trp-Arg-Trp-Lys]-D-Phe-D-Val-NH2 |
| 1221 | TCAM1218 | Val-Arg-Leu-Ile-Val-Ala-Val-Arg-c[Asp-Pro-Arg-Trp-Arg-Trp-Arg-Lys]-D-Val-D-Pro-NH2 |
| 1222 | TCAM1219 | Val-Arg-Leu-Ile-Val-Ala-Val-Arg-c[Asp-Pro-Arg-Trp-Arg-Trp-Arg-Lys]-D-Val-D-Phe-NH2 |
| 1223 | TCAM1220 | Val-Arg-Leu-Ile-Val-Ala-Val-Arg-c[Asp-Pro-Arg-Trp-Arg-Trp-Arg-Lys]-D-Pro-D-Val-NH2 |
| 1224 | TCAM1221 | Val-Arg-Leu-Ile-Val-Ala-Val-Arg-c[Asp-Pro-Arg-Trp-Arg-Trp-Arg-Lys]-D-Phe-D-Val-NH2 |
| 1225 | TCAM1222 | Val-Arg-Leu-IIe-Val-Ala-Val-Arg-c[Asp-Pro-Trp-Arg-Tyr-Arg-Trp-Lys]-D-Val-D-Pro-NH2 |
| 1226 | TCAM1223 | Val-Arg-Leu-IIe-Val-Ala-Val-Arg-c[Asp-Pro-Trp-Arg-Tyr-Arg-Trp-Lys]-D-Val-D-Phe-NH2 |

TABLE 5-continued

Exemplary Anti-microbial peptides

| SEQ NO: | Peptide | Peptide Sequence |
|---|---|---|
| 1227 | TCAM1224 | Val-Arg-Leu-IIe-Val-Ala-Val-Arg-c[Asp-Pro-Trp-Arg-Tyr-Arg-Trp-Lys]-D-Pro-D-Val-NH2 |
| 1228 | TCAM1225 | Val-Arg-Leu-IIe-Val-Ala-Val-Arg-c[Asp-Pro-Trp-Arg-Tyr-Arg-Trp-Lys]-D-Phe-D-Val-NH2 |
| 1229 | TCAM1226 | Val-Arg-Leu-IIe-Val-Ala-Val-Arg-c[Asp-Pro-Trp-Arg-Trp-Arg-Tyr-Lys]-D-Val-D-Pro-NH2 |
| 1230 | TCAM1227 | Val-Arg-Leu-IIe-Val-Ala-Val-Arg-c[Asp-Pro-Trp-Arg-Trp-Arg-Tyr-Lys]-D-Val-D-Phe-NH2 |
| 1231 | TCAM1228 | Val-Arg-Leu-IIe-Val-Ala-Val-Arg-c[Asp-Pro-Trp-Arg-Trp-Arg-Tyr-Lys]-D-Pro-D-Val-NH2 |
| 1232 | TCAM1229 | Val-Arg-Leu-IIe-Val-Ala-Val-Arg-c[Asp-Pro-Trp-Arg-Trp-Arg-Tyr-Lys]-D-Phe-D-Val-NH2 |
| 1233 | TCAM1230 | Val-Arg-Leu-IIe-Val-Ala-Val-Arg-c[Asp-Pro-Trp-Arg-Trp-Arg-Lys]-D-Val-D-Pro-NH2 |
| 1234 | TCAM1231 | Val-Arg-Leu-IIe-Val-Ala-Val-Arg-c[Asp-Pro-Trp-Arg-Trp-Arg-Lys]-D-Val-D-Phe-NH2 |
| 1235 | TCAM1232 | Val-Arg-Leu-IIe-Val-Ala-Val-Arg-c[Asp-Pro-Trp-Arg-Trp-Arg-Lys]-D-Pro-D-Val-NH2 |
| 1236 | TCAM1233 | Val-Arg-Leu-IIe-Val-Ala-Val-Arg-c[Asp-Pro-Trp-Arg-Trp-Arg-Lys]-D-Phe-D-Val-NH2 |
| 1237 | TCAM1234 | Val-Arg-Leu-IIe-Val-Ala-Val-Arg-c[Asp-Pro-Trp-Arg-Arg-Trp-Lys]-D-Val-D-Pro-NH2 |
| 1238 | TCAM1235 | Val-Arg-Leu-IIe-Val-Ala-Val-Arg-c[Asp-Pro-Trp-Arg-Arg-Trp-Lys]-D-Val-D-Phe-NH2 |
| 1239 | TCAM1236 | Val-Arg-Leu-IIe-Val-Ala-Val-Arg-c[Asp-Pro-Trp-Arg-Arg-Trp-Lys]-D-Pro-D-Val-NH2 |
| 1240 | TCAM1237 | Val-Arg-Leu-IIe-Val-Ala-Val-Arg-c[Asp-Pro-Trp-Arg-Arg-Trp-Lys]-D-Phe-D-Val-NH2 |
| 1241 | TCAM1238 | Val-Arg-Leu-IIe-Val-Ala-Val-Arg-c[Asp-Pro-Arg-Trp-Trp-Arg-Lys]-D-Val-D-Pro-NH2 |
| 1242 | TCAM1239 | Val-Arg-Leu-IIe-Val-Ala-Val-Arg-c[Asp-Pro-Arg-Trp-Trp-Arg-Lys]-D-Val-D-Phe-NH2 |
| 1243 | TCAM1240 | Val-Arg-Leu-IIe-Val-Ala-Val-Arg-c[Asp-Pro-Arg-Trp-Trp-Arg-Lys]-D-Pro-D-Val-NH2 |
| 1244 | TCAM1241 | Val-Arg-Leu-IIe-Val-Ala-Val-Arg-c[Asp-Pro-Arg-Trp-Trp-Arg-Lys]-D-Phe-D-Val-NH2 |
| 1245 | TCAM1242 | Val-Arg-Leu-IIe-Val-Ala-Val-Arg-c[Asp-Pro-Trp-Arg-Trp-Lys]-D-Val-D-Pro-NH2 |
| 1246 | TCAM1243 | Val-Arg-Leu-IIe-Val-Ala-Val-Arg-c[Asp-Pro-Trp-Arg-Trp-Lys]-D-Val-D-Phe-NH2 |
| 1247 | TCAM1244 | Val-Arg-Leu-IIe-Val-Ala-Val-Arg-c[Asp-Pro-Trp-Arg-Trp-Lys]-D-Pro-D-Val-NH2 |
| 1248 | TCAM1245 | Val-Arg-Leu-IIe-Val-Ala-Val-Arg-c[Asp-Pro-Trp-Arg-Trp-Lys]-D-Phe-D-Val-NH2 |
| 1249 | TCAM1246 | Val-Arg-Leu-IIe-Val-Ala-Val-Arg-c[Asp-Pro-Arg-Trp-Arg-Lys]-D-Val-D-Pro-NH2 |
| 1250 | TCAM1247 | Val-Arg-Leu-IIe-Val-Ala-Val-Arg-c[Asp-Pro-Arg-Trp-Arg-Lys]-D-Val-D-Phe-NH2 |
| 1251 | TCAM1248 | Val-Arg-Leu-IIe-Val-Ala-Val-Arg-c[Asp-Pro-Arg-Trp-Arg-Lys]-D-Pro-D-Val-NH2 |
| 1252 | TCAM1249 | Val-Arg-Leu-IIe-Val-Ala-Val-Arg-c[Asp-Pro-Arg-Trp-Arg-Lys]-D-Phe-D-Val-NH2 |
| 1253 | TCAM1250 | -Val-Arg-Leu-Ile-Val-Ala-Val-Arg-c[Asp-Arg-Arg-Trp-Trp-Arg-Phe-Lys]-D-Val-D-Pro-NH2 |
| 1254 | TCAM1251 | Val-Arg-Leu-IIe-Val-Ala-Val-Arg-c[Asp-Arg-Arg-Trp-Trp-Arg-Phe-Lys]-D-Val-D-Phe-NH2 |
| 1255 | TCAM1252 | Val-Arg-Leu-IIe-Val-Ala-Val-Arg-c[Asp-Arg-Arg-Trp-Trp-Arg-Phe-Lys]-D-Pro-D-Val-NH2 |
| 1256 | TCAM1253 | Val-Arg-Leu-Ile-Val-Ala-Val-Arg-c[Asp-Arg-Arg-Trp-Trp-Arg-Phe-Lys]-D-Phe-D-Val-NH2 |
| 1257 | TCAM1254 | Val-Arg-Leu-Ile-Val-Ala-Val-Arg-c[Asp-Arg-Arg-Trp-Trp-Arg-Phe-Lys]-D-Val-D-Pro-NH2 |
| 1258 | TCAM1255 | Val-Arg-Leu-Ile-Val-Ala-Val-Arg-c[Asp-Arg-Arg-Trp-Trp-Arg-Phe-Lys]-D-Val-D-Phe-NH2 |

TABLE 5-continued

Exemplary Anti-microbial peptides

| SEQ NO: | Peptide | Peptide Sequence |
|---|---|---|
| 1259 | TCAM1256 | Val-Arg-Leu-Ile-Val-Ala-Val-Arg-c[Asp-Arg-Arg-Trp-Trp-Arg-Phe-Lys]-D-Pro-D-Val-NH2 |
| 1260 | TCAM1257 | Val-Arg-Leu-Ile-Val-Ala-Val-Arg-c[Asp-Arg-Arg-Trp-Trp-Arg-Phe-Lys]-D-Phe-D-Val-NH2 |
| 1261 | TCAM1258 | Val-Arg-Leu-Ile-Val-Ala-Val-Arg-c[Asp-Arg-Arg-Tyr-Tyr-Arg-Phe-Lys]-D-Val-D-Pro-NH2 |
| 1262 | TCAM1259 | Val-Arg-Leu-Ile-Val-Ala-Val-Arg-c[Asp-Arg-Arg-Tyr-Tyr-Arg-Phe-Lys]-D-Val-D-Phe-NH2 |
| 1263 | TCAM1260 | Val-Arg-Leu-Ile-Val-Ala-Val-Arg-c[Asp-Arg-Arg-Tyr-Tyr-Arg-Phe-Lys]-D-Pro-D-Val-NH2 |
| 1264 | TCAM1261 | Val-Arg-Leu-Ile-Val-Ala-Val-Arg-c[Asp-Arg-Arg-Tyr-Tyr-Arg-Phe-Lys]-D-Phe-D-Val-NH2 |
| 1265 | TCAM1262 | Val-Arg-Leu-Ile-Val-Ala-Val-Arg-c[Asp-Arg-Arg-Nal-Nal-Arg-Phe-Lys]-D-Val-D-Pro-NH2 |
| 1266 | TCAM1263 | Val-Arg-Leu-Ile-Val-Ala-Val-Arg-c[Asp-Arg-Arg-Nal-Nal-Arg-Phe-Lys]-D-Val-D-Phe-NH2 |
| 1267 | TCAM1264 | Val-Arg-Leu-Ile-Val-Ala-Val-Arg-c[Asp-Arg-Arg-Nal-Nal-Arg-Phe-Lys]-D-Pro-D-Val-NH2 |
| 1268 | TCAM1265 | Val-Arg-Leu-Ile-Val-Ala-Val-Arg-c[Asp-Arg-Arg-Nal-Nal-Arg-Phe-Lys]-D-Phe-D-Val-NH2 |
| 1269 | TCAM1266 | Val-Arg-Leu-Ile-Val-Ala-Val-Arg-c[Asp-Arg-Arg-Leu-Trp-Leu-Trp-Lys]-D-Val-D-Pro-NH2 |
| 1270 | TCAM1267 | Val-Arg-Leu-Ile-Val-Ala-Val-Arg-c[Asp-Arg-Arg-Leu-Trp-Leu-Trp-Lys]-D-Val-D-Phe-NH2 |
| 1271 | TCAM1268 | Val-Arg-Leu-Ile-Val-Ala-Val-Arg-c[Asp-Arg-Arg-Leu-Trp-Leu-Trp-Lys]-D-Pro-D-Val-NH2 |
| 1272 | TCAM1269 | Val-Arg-Leu-Ile-Val-Ala-Val-Arg-c[Asp-Arg-Arg-Leu-Trp-Leu-Trp-Lys]-D-Phe-D-Val-NH2 |
| 1273 | TCAM1270 | Val-Arg-Leu-Ile-Val-Ala-Val-Arg-c[Asp-Arg-Arg-Leu-Trp-Leu-Trp-Lys]-D-Val-D-Pro-NH2 |
| 1274 | TCAM1271 | Val-Arg-Leu-Ile-Val-Ala-Val-Arg-c[Asp-Arg-Arg-Leu-Trp-Leu-Trp-Lys]-D-Val-D-Phe-NH2 |
| 1275 | TCAM1272 | Val-Arg-Leu-Ile-Val-Ala-Val-Arg-c[Asp-Arg-Arg-Leu-Trp-Leu-Trp-Lys]-D-Pro-D-Val-NH2 |
| 1276 | TCAM1273 | Val-Arg-Leu-Ile-Val-Ala-Val-Arg-c[Asp-Arg-Arg-Leu-Trp-Leu-Trp-Lys]-D-Phe-D-Val-NH2 |
| 1277 | TCAM1274 | Val-Arg-Leu-Ile-Val-Ala-Val-Arg-c[Asp-Arg-Arg-Arg-Trp-Leu-Trp-Leu-Trp-Lys]-D-Val-D-Pro-NH2 |
| 1278 | TCAM1275 | Val-Arg-Leu-Ile-Val-Ala-Val-Arg-c[Asp-Arg-Arg-Arg-Trp-Leu-Trp-Leu-Trp-Lys]-D-Val-D-Phe-NH2 |
| 1279 | TCAM1276 | Val-Arg-Leu-Ile-Val-Ala-Val-Arg-c[Asp-Arg-Arg-Arg-Trp-Leu-Trp-Leu-Trp-Lys]-D-Pro-D-Val-NH2 |
| 1280 | TCAM1277 | Val-Arg-Leu-Ile-Val-Ala-Val-Arg-c[Asp-Arg-Arg-Arg-Trp-Leu-Trp-Leu-Trp-Lys]-D-Phe-D-Val-NH2 |
| 1281 | TCAM1278 | Val-Arg-Leu-Ile-Val-Ala-Val-Arg-c[Asp-Arg-Gln-Arg-Arg-Trp-Leu-Trp-Leu-Trp-Lys]-D-Val-D-Pro-NH2 |
| 1282 | TCAM1279 | Val-Arg-Leu-Ile-Val-Ala-Val-Arg-c[Asp-Arg-Gln-Arg-Arg-Trp-Leu-Trp-Leu-Trp-Lys]-D-Val-D-Phe-NH2 |
| 1283 | TCAM1280 | Val-Arg-Leu-Ile-Val-Ala-Val-Arg-c[Asp-Arg-Gln-Arg-Arg-Trp-Leu-Trp-Leu-Trp-Lys]-D-Pro-D-Val-NH2 |

TABLE 5-continued

Exemplary Anti-microbial peptides

| SEQ NO: | Peptide | Peptide Sequence |
|---|---|---|
| 1284 | TCAM1281 | Val-Arg-Leu-Ile-Val-Ala-Val-Arg-c[Asp-Arg-Gln-Arg-Arg-Trp-Leu-Trp-Leu-Trp-Lys]-D-Phe-D-Val-NH2 |
| 1285 | TCAM1282 | Val-Arg-Leu-Ile-Val-Ala-Val-Arg-c[Asp-Trp-Arg-Trp-Trp-Arg-Arg-Lys]-D-Val-D-Pro-NH2 |
| 1286 | TCAM1283 | Val-Arg-Leu-Ile-Val-Ala-Val-Arg-c[Asp-Trp-Arg-Trp-Trp-Arg-Arg-Lys]-D-Val-D-Phe-NH2 |
| 1287 | TCAM1284 | Val-Arg-Leu-Ile-Val-Ala-Val-Arg-c[Asp-Trp-Arg-Trp-Trp-Arg-Arg-Lys]-D-Pro-D-Val-NH2 |
| 1288 | TCAM1285 | Val-Arg-Leu-Ile-Val-Ala-Val-Arg-c[Asp-Trp-Arg-Trp-Trp-Arg-Arg-Lys]-D-Phe-D-Val-NH2 |
| 1289 | TCAM1286 | Val-Arg-Leu-Ile-Val-Ala-Val-Arg-c[Asp-Trp-Trp-Arg-Arg-Trp-Trp-Arg-Arg-Lys]-D-Val-D-Pro-NH2 |
| 1290 | TCAM1287 | Val-Arg-Leu-Ile-Val-Ala-Val-Arg-c[Asp-Trp-Trp-Arg-Arg-Trp-Trp-Arg-Arg-Lys]-D-Val-D-Phe-NH2 |
| 1291 | TCAM1288 | Val-Arg-Leu-Ile-Val-Ala-Val-Arg-c[Asp-Trp-Trp-Arg-Arg-Trp-Trp-Arg-Arg-Lys]-D-Pro-D-Val-NH2 |
| 1292 | TCAM1289 | Val-Arg-Leu-Ile-Val-Ala-Val-Arg-c[Asp-Trp-Trp-Arg-Arg-Trp-Trp-Arg-Arg-Lys]-D-Phe-D-Val-NH2 |
| 1293 | TCAM1290 | Val-Arg-Leu-Ile-Val-Ala-Val-Arg-c[Asp-Trp-Arg-Trp-Arg-Trp-Arg-Lys]-D-Val-D-Pro-NH2 |
| 1294 | TCAM1291 | Val-Arg-Leu-Ile-Val-Ala-Val-Arg-c[Asp-Trp-Arg-Trp-Arg-Trp-Arg-Lys]-D-Val-D-Phe-NH2 |
| 1295 | TCAM1292 | Val-Arg-Leu-Ile-Val-Ala-Val-Arg-c[Asp-Trp-Arg-Trp-Arg-Trp-Arg-Lys]-D-Pro-D-Val-NH2 |
| 1296 | TCAM1293 | Val-Arg-Leu-Ile-Val-Ala-Val-Arg-c[Asp-Trp-Arg-Trp-Arg-Trp-Arg-Lys]-D-Phe-D-Val-NH2 |
| 1297 | TCAM1294 | Val-Arg-Leu-Ile-Val-Ala-Val-Arg-c[Asp-Arg-Trp-Arg-Trp-Arg-Trp-Lys]-D-Val-D-Pro-NH2 |
| 1298 | TCAM1295 | Val-Arg-Leu-Ile-Val-Ala-Val-Arg-c[Asp-Arg-Trp-Arg-Trp-Arg-Trp-Lys]-D-Val-D-Phe-NH2 |
| 1299 | TCAM1296 | Val-Arg-Leu-Ile-Val-Ala-Val-Arg-c[Asp-Arg-Trp-Arg-Trp-Arg-Trp-Lys]-D-Pro-D-Val-NH2 |
| 1300 | TCAM1297 | Val-Arg-Leu-Ile-Val-Ala-Val-Arg-c[Asp-Arg-Trp-Arg-Trp-Arg-Trp-Lys]-D-Phe-D-Val-NH2 |
| 1301 | TCAM1298 | Val-Arg-Leu-Ile-Val-Ala-Val-Arg-c[Asp-Arg-Trp-Trp-Arg-Arg-Lys]-D-Val-D-Pro-NH2 |
| 1302 | TCAM1299 | Val-Arg-Leu-Ile-Val-Ala-Val-Arg-c[Asp-Arg-Trp-Trp-Arg-Arg-Lys]-D-Val-D-Phe-NH2 |
| 1303 | TCAM1300 | Val-Arg-Leu-Ile-Val-Ala-Val-Arg-c[Asp-Arg-Trp-Trp-Arg-Arg-Lys]-D-Pro-D-Val-NH2 |
| 1304 | TCAM1301 | Val-Arg-Leu-Ile-Val-Ala-Val-Arg-c[Asp-Arg-Trp-Trp-Arg-Arg-Lys]-D-Phe-D-Val-NH2 |
| 1305 | TCAM1302 | Val-Arg-Leu-Ile-Val-Ala-Val-Arg-c[Asp-Arg-Trp-Arg-Trp-Arg-Lys]-D-Val-D-Pro-NH2 |
| 1306 | TCAM1303 | Val-Arg-Leu-Ile-Val-Ala-Val-Arg-c[Asp-Arg-Trp-Arg-Trp-Arg-Lys]-D-Val-D-Phe-NH2 |
| 1307 | TCAM1304 | Val-Arg-Leu-Ile-Val-Ala-Val-Arg-c[Asp-Arg-Trp-Arg-Trp-Arg-Lys]-D-Pro-D-Val-NH2 |
| 1308 | TCAM1305 | Val-Arg-Leu-Ile-Val-Ala-Val-Arg-c[Asp-Arg-Trp-Arg-Trp-Arg-Lys]-D-Phe-D-Val-NH2 |
| 1309 | TCAM1306 | Val-Arg-Leu-Ile-Val-Ala-Val-Arg-c[Asp-Trp-Trp-Arg-Arg-Trp-Lys]-D-Val-D-Pro-NH2 |
| 1310 | TCAM1307 | Val-Arg-Leu-Ile-Val-Ala-Val-Arg-c[Asp-Trp-Trp-Arg-Arg-Trp-Lys]-D-Val-D-Phe-NH2 |
| 1311 | TCAM1308 | Val-Arg-Leu-Ile-Val-Ala-Val-Arg-c[Asp-Trp-Trp-Arg-Arg-Trp-Lys]-D-Pro-D-Val-NH2 |
| 1312 | TCAM1309 | Val-Arg-Leu-Ile-Val-Ala-Val-Arg-c[Asp-Trp-Trp-Arg-Arg-Trp-Lys]-D-Phe-D-Val-NH2 |

TABLE 5-continued

Exemplary Anti-microbial peptides

| SEQ NO: | Peptide | Peptide Sequence |
|---|---|---|
| 1313 | TCAM1310 | Val-Arg-Leu-IIe-Val-Ala-Val-Arg-c[Asp-Trp-Arg-Trp-Arg-Trp-Lys]-D-Val-D-Pro-NH2 |
| 1314 | TCAM1311 | Val-Arg-Leu-IIe-Val-Ala-Val-Arg-c[Asp-Trp-Arg-Trp-Arg-Trp-Lys]-D-Val-D-Phe-NH2 |
| 1315 | TCAM1312 | Val-Arg-Leu-IIe-Val-Ala-Val-Arg-c[Asp-Trp-Arg-Trp-Arg-Trp-Lys]-D-Pro-D-Val-NH2 |
| 1316 | TCAM1313 | Val-Arg-Leu-IIe-Val-Ala-Val-Arg-c[Asp-Trp-Arg-Trp-Arg-Trp-Lys]-D-Phe-D-Val-NH2 |
| 1317 | TCAM1314 | Val-Arg-Leu-IIe-Val-Ala-Val-Arg-c[Asp-Trp-Arg-Tyr-Arg-Trp-Lys]-D-Val-D-Pro-NH2 |
| 1318 | TCAM1315 | Val-Arg-Leu-IIe-Val-Ala-Val-Arg-c[Asp-Trp-Arg-Tyr-Arg-Trp-Lys]-D-Val-D-Phe-NH2 |
| 1319 | TCAM1316 | Val-Arg-Leu-IIe-Val-Ala-Val-Arg-c[Asp-Trp-Arg-Tyr-Arg-Trp-Lys]-D-Pro-D-Val-NH2 |
| 1320 | TCAM1317 | Val-Arg-Leu-IIe-Val-Ala-Val-Arg-c[Asp-Trp-Arg-Tyr-Arg-Trp-Lys]-D-Phe-D-Val-NH2 |
| 1321 | TCAM1318 | Val-Arg-Leu-IIe-Val-Ala-Val-Arg-c[Asp-Trp-Arg-Trp-Arg-Tyr-Lys]-D-Val-D-Pro-NH2 |
| 1322 | TCAM1319 | Val-Arg-Leu-IIe-Val-Ala-Val-Arg-c[Asp-Trp-Arg-Trp-Arg-Tyr-Lys]-D-Val-D-Phe-NH2 |
| 1323 | TCAM1320 | Val-Arg-Leu-IIe-Val-Ala-Val-Arg-c[Asp-Trp-Arg-Trp-Arg-Tyr-Lys]-D-Pro-D-Val-NH2 |
| 1324 | TCAM1321 | Val-Arg-Leu-IIe-Val-Ala-Val-Arg-c[Asp-Trp-Arg-Trp-Arg-Tyr-Lys]-D-Phe-D-Val-NH2 |
| 1325 | TCAM1322 | Val-Arg-Leu-IIe-Val-Ala-Val-Arg-c[Asp-Trp-Arg-Trp-Arg-Lys]-D-Val-D-Pro-NH2 |
| 1326 | TCAM1323 | Val-Arg-Leu-IIe-Val-Ala-Val-Arg-c[Asp-Trp-Arg-Trp-Arg-Lys]-D-Val-D-Phe-NH2 |
| 1327 | TCAM1324 | Val-Arg-Leu-IIe-Val-Ala-Val-Arg-c[Asp-Trp-Arg-Trp-Arg-Lys]-D-Pro-D-Val-NH2 |
| 1328 | TCAM1325 | Val-Arg-Leu-IIe-Val-Ala-Val-Arg-c[Asp-Trp-Arg-Trp-Arg-Lys]-D-Phe-D-Val-NH2 |
| 1329 | TCAM1326 | Val-Arg-Leu-IIe-Val-Ala-Val-Arg-c[Asp-Trp-Arg-Arg-Trp-Lys]-D-Val-D-Pro-NH2 |
| 1330 | TCAM1327 | Val-Arg-Leu-IIe-Val-Ala-Val-Arg-c[Asp-Trp-Arg-Arg-Trp-Lys]-D-Val-D-Phe-NH2 |
| 1331 | TCAM1328 | Val-Arg-Leu-IIe-Val-Ala-Val-Arg-c[Asp-Trp-Arg-Arg-Trp-Lys]-D-Pro-D-Val-NH2 |
| 1332 | TCAM1329 | Val-Arg-Leu-IIe-Val-Ala-Val-Arg-c[Asp-Trp-Arg-Arg-Trp-Lys]-D-Phe-D-Val-NH2 |
| 1333 | TCAM1330 | Val-Arg-Leu-IIe-Val-Ala-Val-Arg-c[Asp-Arg-Trp-Trp-Arg-Lys]-D-Val-D-Pro-NH2 |
| 1334 | TCAM1331 | Val-Arg-Leu-IIe-Val-Ala-Val-Arg-c[Asp-Arg-Trp-Trp-Arg-Lys]-D-Val-D-Phe-NH2 |
| 1335 | TCAM1332 | Val-Arg-Leu-IIe-Val-Ala-Val-Arg-c[Asp-Arg-Trp-Trp-Arg-Lys]-D-Pro-D-Val-NH2 |
| 1336 | TCAM1333 | Val-Arg-Leu-IIe-Val-Ala-Val-Arg-c[Asp-Arg-Trp-Trp-Arg-Lys]-D-Phe-D-Val-NH2 |
| 1337 | TCAM1334 | Val-Arg-Leu-IIe-Val-Ala-Val-Arg-c[Asp-Trp-Arg-Trp-Lys]-D-Val-D-Pro-NH2 |
| 1338 | TCAM1335 | Val-Arg-Leu-IIe-Val-Ala-Val-Arg-c[Asp-Trp-Arg-Trp-Lys]-D-Val-D-Phe-NH2 |
| 1339 | TCAM1336 | Val-Arg-Leu-IIe-Val-Ala-Val-Arg-c[Asp-Trp-Arg-Trp-Lys]-D-Pro-D-Val-NH2 |
| 1340 | TCAM1337 | Val-Arg-Leu-IIe-Val-Ala-Val-Arg-c[Asp-Trp-Arg-Trp-Lys]-D-Phe-D-Val-NH2 |
| 1341 | TCAM1338 | Val-Arg-Leu-IIe-Val-Ala-Val-Arg-c[Asp-Arg-Trp-Arg-Lys]-D-Val-D-Pro-NH2 |
| 1342 | TCAM1339 | Val-Arg-Leu-IIe-Val-Ala-Val-Arg-c[Asp-Arg-Trp-Arg-Lys]-D-Val-D-Phe-NH2 |
| 1343 | TCAM1340 | Val-Arg-Leu-IIe-Val-Ala-Val-Arg-c[Asp-Arg-Trp-Arg-Lys]-D-Pro-D-Val-NH2 |
| 1344 | TCAM1341 | Val-Arg-Leu-IIe-Val-Ala-Val-Arg-c[Asp-Arg-Trp-Arg-Lys]-D-Phe-D-Val-NH2 |
| 1345 | TCAM1342 | Val-Arg-Leu-IIe-Val-Ala-Val-Arg-c[Asp-His-D-Nal(2')-Arg-Trp-Lys]-D-Val-D-Pro-NH2 |
| 1346 | TCAM1343 | Val-Arg-Leu-IIe-Val-Ala-Val-Arg-c[Asp-His-D-Nal(2')-Arg-Trp-Lys]-D-Pro-D-Val-NH2 |
| 1347 | TCAM1344 | Val-Arg-Leu-IIe-Val-Ala-Val-Arg-c[Asp-His-D-Nal(2')-Arg-Trp-Lys]-D-Val-D-Phe-NH2 |
| 1348 | TCAM1345 | Val-Arg-Leu-IIe-Val-Ala-Val-Arg-c[Asp-His-D-Nal(2')-Arg-Trp-Lys]-D-Phe-D-Val-NH2 |
| 1349 | TCAM1346 | Val-Arg-Leu-Ile-Val-Ala-Val-Arg-c[Asp-Pro-D-Nal(2')-Arg-Trp-Lys]-D-Val-D-Pro-NH2 |

TABLE 5-continued

Exemplary Anti-microbial peptides

| SEQ NO: | Peptide | Peptide Sequence |
|---|---|---|
| 1350 | TCAM1347 | Val-Arg-Leu-Ile-Val-Ala-Val-Arg-c[Asp-Pro-D-Nal(2')-Arg-Trp-Lys]-D-Pro-D-Val-NH2 |
| 1351 | TCAM1348 | Val-Arg-Leu-Ile-Val-Ala-Val-Arg-c[Asp-Pro-D-Nal(2')-Arg-Trp-Lys]-D-Val-D-Phe-NH2 |
| 1352 | TCAM1349 | Val-Arg-Leu-Ile-Val-Ala-Val-Arg-c[Asp-Pro-D-Nal(2')-Arg-Trp-Lys]-D-Phe-D-Val-NH2 |
| 1353 | TCAM1350 | Val-Arg-Leu-Ile-Val-Ala-Val-Arg-c[Asp-Arg-Arg-Nal(2')-Arg-Trp-Lys]-D-Val-D-Pro-NH2 |
| 1354 | TCAM1351 | Val-Arg-Leu-Ile-Val-Ala-Val-Arg-c[Asp-Arg-Arg-Nal(2')-Arg-Trp-Lys]-D-Pro-D-Val-NH2 |
| 1355 | TCAM1352 | Val-Arg-Leu-Ile-Val-Ala-Val-Arg-c[Asp-Arg-Arg-Nal(2')-Arg-Trp-Lys]-D-Val-D-Phe-NH2 |
| 1356 | TCAM1353 | Val-Arg-Leu-Ile-Val-Ala-Val-Arg-c[Asp-Arg-Arg-Nal(2')-Arg-Trp-Lys]-D-Phe-D-Val-NH2 |
| 1357 | TCAM1354 | Val-Arg-Leu-Ile-Val-Ala-Val-Arg-c[Asp-Arg-Arg-Pro-Nal(2')-Arg-Trp-Lys]-D-Val-D-Pro-NH2 |
| 1358 | TCAM1355 | Val-Arg-Leu-Ile-Val-Ala-Val-Arg-c[Asp-Arg-Arg-Pro-D-Nal(2')-Arg-Trp-Lys]-D-Pro-D-Val-NH2 |
| 1359 | TCAM1356 | Val-Arg-Leu-Ile-Val-Ala-Val-Arg-c[Asp-Arg-Arg-Pro-D-Nal(2')-Arg-Trp-Lys]-D-Val-D-Phe-NH2 |
| 1360 | TCAM1357 | Val-Arg-Leu-Ile-Val-Ala-Val-Arg-c[Asp-Arg-Arg-Pro-Nal(2')-Arg-Trp-Lys]-D-Phe-D-Val-NH2 |
| 1361 | TCAM1358 | Val-Arg-Leu-Ile-Val-Ala-Val-Arg-c[Asp-Arg-D-Nal(2')-Arg-Trp-Lys]-D-Val-D-Pro-NH2 |
| 1362 | TCAM1359 | Val-Arg-Leu-Ile-Val-Ala-Val-Arg-c[Asp-Arg-D-Nal(2')-Arg-Trp-Lys]-D-Pro-D-Val-NH2 |
| 1363 | TCAM1360 | Val-Arg-Leu-Ile-Val-Ala-Val-Arg-c[Asp-Arg-D-Nal(2')-Arg-Trp-Lys]-D-Val-D-Phe-NH2 |
| 1364 | TCAM1361 | Val-Arg-Leu-Ile-Val-Ala-Val-Arg-c[Asp-Arg-D-Nal(2')-Arg-Trp-Lys]-D-Phe-D-Val-NH2 |
| 1365 | TCAM1362 | Val-Arg-Leu-Ile-Val-Ala-Val-Arg-c[Asp-Arg-Pro-D-Nal(2')-Arg-Trp-Lys]-D-Val-D-Pro-NH2 |
| 1366 | TCAM1363 | Val-Arg-Leu-Ile-Val-Ala-Val-Arg-c[Asp-Arg-Pro-D-Nal(2')-Arg-Trp-Lys]-D-Pro-D-Val-NH2 |
| 1367 | TCAM1364 | Val-Arg-Leu-Ile-Val-Ala-Val-Arg-c[Asp-Arg-Pro-D-Nal(2')-Arg-Trp-Lys]-D-Val-D-Phe-NH2 |
| 1368 | TCAM1365 | Val-Arg-Leu-Ile-Val-Ala-Val-Arg-c[Asp-Arg-Pro-D-Nal(2')-Arg-Trp-Lys]-D-Phe-D-Val-NH2 |
| 1369 | TCAM1366 | Val-Arg-Leu-Ile-Val-Ala-Val-Arg-Arg-Arg-c[Asp-Pro-D-Nal(2')-Arg-Trp-Lys]-D-Val-D-Pro-NH2 |
| 1370 | TCAM1367 | Val-Arg-Leu-Ile-Val-Ala-Val-Arg-Arg-Arg-c[Asp-Pro-D-Nal(2')-Arg-Trp-Lys]-D-Pro-D-Val-NH2 |
| 1371 | TCAM1368 | Val-Arg-Leu-Ile-Val-Ala-Val-Arg-Arg-Arg-c[Asp-Pro-D-Nal(2')-Arg-Trp-Lys]-D-Val-D-Phe-NH2 |
| 1372 | TCAM1369 | Val-Arg-Leu-Ile-Val-Ala-Val-Arg-Arg-Arg-c[Asp-Pro-D-Nal(2')-Arg-Trp-Lys]-D-Phe-D-Val-NH2 |
| 1373 | TCAM1370 | Val-Arg-Leu-Ile-Val-Ala-Val-Arg-Arg-Arg-c[Asp-His-D-Nal(2')-Arg-Trp-Lys]-D-Val-D-Pro-NH2 |
| 1374 | TCAM1371 | Val-Arg-Leu-Ile-Val-Ala-Val-Arg-Arg-Arg-c[Asp-His-D-Nal(2')-Arg-Trp-Lys]-D-Pro-D-Val-NH2 |
| 1375 | TCAM1372 | Val-Arg-Leu-Ile-Val-Ala-Val-Arg-Arg-Arg-c[Asp-His-D-Nal(2')-Arg-Trp-Lys]-D-Val-D-Phe-NH2 |
| 1376 | TCAM1373 | Val-Arg-Leu-Ile-Val-Ala-Val-Arg-Arg-Arg-c[Asp-His-D-Nal(2')-Arg-Trp-Lys]-D-Phe-D-Val-NH2 |
| 1377 | TCAM1374 | Val-Arg-Leu-Ile-Val-Ala-Val-Arg-c[Asp-Arg-Pro-D-Nal(2')-Arg-Trp-Arg-Lys]-D-Val-D-Pro-NH2 |

TABLE 5-continued

Exemplary Anti-microbial peptides

| SEQ NO: | Peptide | Peptide Sequence |
|---|---|---|
| 1378 | TCAM1375 | Val-Arg-Leu-Ile-Val-Ala-Val-Arg-c[Asp-Arg-Pro-D-Nal(2')-Arg-Trp-Arg-Lys]-D-Pro-D-Val-NH2 |
| 1379 | TCAM1376 | Val-Arg-Leu-Ile-Val-Ala-Val-Arg-c[Asp-Arg-Pro-D-Nal(2')-Arg-Trp-Arg-Lys]-D-Val-D-Phe-NH2 |
| 1380 | TCAM1377 | Val-Arg-Leu-Ile-Val-Ala-Val-Arg-c[Asp-Arg-Pro-D-Nal(2')-Arg-Trp-Arg-Lys]-D-Phe-D-Val-NH2 |
| 1381 | TCAM1378 | Val-Arg-Leu-Ile-Val-Ala-Val-Arg-c[Asp-Arg-His-D-Nal(2')-Arg-Trp-Arg-Lys]-D-Val-D-Pro-NH2 |
| 1382 | TCAM1379 | Val-Arg-Leu-Ile-Val-Ala-Val-Arg-c[Asp-Arg-His-D-Nal(2')-Arg-Trp-Arg-Lys]-D-Pro-D-Val-NH2 |
| 1383 | TCAM1380 | Val-Arg-Leu-Ile-Val-Ala-Val-Arg-c[Asp-Arg-His-D-Nal(2')-Arg-Trp-Arg-Lys]-D-Val-D-Phe-NH2 |
| 1384 | TCAM1381 | Val-Arg-Leu-Ile-Val-Ala-Val-Arg-c[Asp-Arg-His-D-Nal(2')-Arg-Trp-Arg-Lys]-D-Phe-D-Val-NH2 |
| 1385 | TCAM1382 | Val-Arg-Leu-Ile-Val-Ala-Val-Arg-c[Asp-His-D-Nal(2')-Arg-D-Nal(2')-Lys]-D-Val-D-Phe-NH2 |
| 1386 | TCAM1383 | Val-Arg-Leu-Ile-Val-Ala-Val-Arg-c[Asp-His-D-Nal(2')-Arg-D-Nal(2')-Lys]-D-Phe-D-Val-NH2 |
| 1387 | TCAM1384 | Val-Arg-Leu-Ile-Val-Ala-Val-Arg-c[Asp-Pro-D-Nal(2')-Arg-D-Nal(2')-Lys]-D-Val-D-Pro-NH2 |
| 1388 | TCAM1385 | Val-Arg-Leu-Ile-Val-Ala-Val-Arg-c[Asp-Pro-D-Nal(2')-Arg-D-Nal(2')-Lys]-D-Pro-D-Val-NH2 |
| 1389 | TCAM1386 | Val-Arg-Leu-Ile-Val-Ala-Val-Arg-c[Asp-Pro-D-Nal(2')-Arg-D-Nal(2')-Lys]-D-Val-D-Phe-NH2 |
| 1390 | TCAM1387 | Val-Arg-Leu-Ile-Val-Ala-Val-Arg-c[Asp-Pro-D-Nal(2')-Arg-D-Nal(2')-Lys]-D-Phe-D-Val-NH2 |
| 1391 | TCAM1388 | Val-Arg-Leu-Ile-Val-Ala-Val-Arg-c[Asp-Arg-Arg-D-Nal(2')-Arg-D-Nal(2')-Lys]-D-Val-D-Pro-NH2 |
| 1392 | TCAM1389 | Val-Arg-Leu-Ile-Val-Ala-Val-Arg-c[Asp-Arg-Arg-D-Nal(2')-Arg-D-Nal(2')-Lys]-D-Pro-D-Val-NH2 |
| 1393 | TCAM1390 | Val-Arg-Leu-Ile-Val-Ala-Val-Arg-c[Asp-Arg-Arg-D-Nal(2')-Arg-D-Nal(2')-Lys]-D-Val-D-Phe-NH2 |
| 1394 | TCAM1391 | Val-Arg-Leu-Ile-Val-Ala-Val-Arg-c[Asp-Arg-Arg-D-Nal(2')-Arg-D-Nal(2')-Lys]-D-Phe-D-Val-NH2 |
| 1395 | TCAM1392 | Val-Arg-Leu-Ile-Val-Ala-Val-Arg-c[Asp-Arg-Arg-Pro-D-Nal(2')-Arg-D-Nal(2')-Lys]-D-Val-D-Pro-NH2 |
| 1396 | TCAM1393 | Val-Arg-Leu-Ile-Val-Ala-Val-Arg-c[Asp-Arg-Arg-Pro-D-Nal(2')-Arg-D-Nal(2')-Lys]-D-Pro-D-Val-NH2 |
| 1397 | TCAM1394 | Val-Arg-Leu-Ile-Val-Ala-Val-Arg-c[Asp-Arg-Arg-Pro-D-Nal(2')-Arg-D-Nal(2')-Lys]-D-Val-D-Phe-NH2 |
| 1398 | TCAM1395 | Val-Arg-Leu-Ile-Val-Ala-Val-Arg-c[Asp-Arg-Arg-Pro-D-Nal(2')-Arg-D-Nal(2')-Lys]-D-Phe-D-Val-NH2 |
| 1399 | TCAM1396 | Val-Arg-Leu-Ile-Val-Ala-Val-Arg-c[Asp-Arg-D-Nal(2')-Arg-D-Nal(2')-Lys]-D-Val-D-Pro-NH2 |
| 1400 | TCAM1397 | Val-Arg-Leu-Ile-Val-Ala-Val-Arg-c[Asp-Arg-D-Nal(2')-Arg-D-Nal(2')-Lys]-D-Pro-D-Val-NH2 |
| 1401 | TCAM1398 | Val-Arg-Leu-Ile-Val-Ala-Val-Arg-c[Asp-Arg-Nal(2')-Arg-D-Nal(2')-Lys]-D-Val-D-Phe-NH2 |
| 1402 | TCAM1399 | Val-Arg-Leu-Ile-Val-Ala-Val-Arg-c[Asp-Arg-D-Nal(2')-Arg-D-Nal(2')-Lys]-D-Phe-D-Val-NH2 |

TABLE 5-continued

Exemplary Anti-microbial peptides

| SEQ NO: | Peptide | Peptide Sequence |
|---|---|---|
| 1403 | TCAM1400 | Val-Arg-Leu-Ile-Val-Ala-Val-Arg-c[Asp-Arg-Pro-D-Nal(2')-Arg-D-Nal(2')-Lys]-D-Val-D-Pro-NH2 |
| 1404 | TCAM1401 | Val-Arg-Leu-Ile-Val-Ala-Val-Arg-c[Asp-Arg-Pro-D-Nal(2')-Arg-D-Nal(2')-Lys]-D-Pro-D-Val-NH2 |
| 1405 | TCAM1402 | Val-Arg-Leu-Ile-Val-Ala-Val-Arg-c[Asp-Arg-Pro-D-Nal(2')-Arg-D-Nal(2')-Lys]-D-Val-D-Phe-NH2 |
| 1406 | TCAM1403 | Val-Arg-Leu-Ile-Val-Ala-Val-Arg-c[Asp-Arg-Pro-D-Nal(2')-Arg-D-Nal(2')-Lys]-D-Phe-D-Val-NH2 |
| 1407 | TCAM1404 | Val-Arg-Leu-Ile-Val-Ala-Val-Arg-c[Asp-Arg-His-D-Nal(2')-Arg-D-Nal(2')-Lys]-D-Val-D-Pro-NH2 |
| 1408 | TCAM1405 | Val-Arg-Leu-Ile-Val-Ala-Val-Arg-c[Asp-Arg-His-D-Nal(2')-Arg-D-Nal(2')-Lys]-D-Pro-D-Val-NH2 |
| 1409 | TCAM1406 | Val-Arg-Leu-Ile-Val-Ala-Val-Arg-c[Asp-Arg-His-Nal(2')-Arg-D-Nal2')-Lys]-D-Val-D-Phe-NH2 |
| 1410 | TCAM1407 | Val-Arg-Leu-Ile-Val-Ala-Val-Arg-c[Asp-Arg-His-Nal(2')-Arg-D-Nal(2')-Lys]-D-Phe-D-Val-NH2 |
| 1411 | TCAM1408 | Val-Arg-Leu-Ile-Val-Ala-Val-Arg-c[Asp-Arg-D-D-Nal(2')-Arg-D-Nal(2')-Arg-Lys]-D-Val-D-Pro-NH2 |
| 1412 | TCAM1409 | Val-Arg-Leu-Ile-Val-Ala-Val-Arg-c[Asp-Arg-D-Nal(2')-Arg-D-Nal(2')-Arg-Lys]-D-Pro-D-Val-NH2 |
| 1413 | TCAM1410 | Val-Arg-Leu-Ile-Val-Ala-Val-Arg-c[Asp-Arg-D-Nal(2')-Arg-D-Nal(2')-Arg-Lys]-D-Val-D-Phe-NH2 |
| 1414 | TCAM1411 | Val-Arg-Leu-Ile-Val-Ala-Val-Arg-c[Asp-Arg-D-Nal(2')-Arg-D-Nal(2')-Arg-Lys]-D-Phe-D-Val-NH2 |
| 1415 | TCAM1412 | Val-Arg-Leu-Ile-Val-Ala-Val-Arg-c[Asp-Arg-Pro-D-Nal(2')-Arg-D-Nal(2')-Arg-Lys]-D-Val-D-Pro-NH2 |
| 1416 | TCAM1413 | Val-Arg-Leu-Ile-Val-Ala-Val-Arg-c[Asp-Arg-Pro-D-Nal(2')-Arg-D-Nal(2')-Arg-Lys]-D-Pro-D-Val-NH2 |
| 1417 | TCAM1414 | Val-Arg-Leu-Ile-Val-Ala-Val-Arg-c[Asp-Arg-Pro-D-Nal(2')-Arg-D-Nal(2')-Arg-Lys]-D-Val-D-Phe-NH2 |
| 1418 | TCAM1415 | Val-Arg-Leu-Ile-Val-Ala-Val-Arg-c[Asp-Arg-Pro-D-Nal(2')-Arg-D-Nal(2')-Arg-Lys]-D-Phe-D-Val-NH2 |
| 1419 | TCAM1416 | Val-Arg-Leu-Ile-Val-Ala-Val-Arg-c[Asp-Arg-His-D-Nal(2')-Arg-D-Nal(2')-Arg-Lys]-D-Val-D-Pro-NH2 |
| 1420 | TCAM1417 | Val-Arg-Leu-Ile-Val-Ala-Val-Arg-c[Asp-Arg-His-D-Nal(2')-Arg-D-Nal(2')-Arg-Lys]-D-Pro-D-Val-NH2 |
| 1421 | TCAM1418 | Val-Arg-Leu-Ile-Val-Ala-Val-Arg-c[Asp-Arg-His-D-Nal(2')-Arg-D-Nal(2')-Arg-Lys]-D-Val-D-Phe-NH2 |
| 1422 | TCAM1419 | Val-Arg-Leu-Ile-Val-Ala-Val-Arg-c[Asp-Arg-His-D-Nal(2')-Arg-D-Nal(2')-Arg-Lys]-D-Phe-D-Val-NH2 |
| 1423 | TCAM1420 | Val-Arg-Leu-Ile-Val-Ala-Val-Arg-Arg-Arg-c[Asp-Pro-D-Nal(2')-Arg-D-Nal(2')-Lys]-D-Val-D-Pro-NH2 |
| 1424 | TCAM1421 | Val-Arg-Leu-Ile-Val-Ala-Val-Arg-Arg-Arg-c[Asp-Pro-D-Nal(2')-Arg-D-Nal(2')-Lys]-D-Pro-D-Val-NH2 |
| 1425 | TCAM1422 | Val-Arg-Leu-Ile-Val-Ala-Val-Arg-Arg-Arg-c[Asp-Pro-D-Nal(2')-Arg-D-Nal(2')-Lys]-D-Val-D-Phe-NH2 |
| 1426 | TCAM1423 | Val-Arg-Leu-Ile-Val-Ala-Val-Arg-Arg-Arg-c[Asp-Pro-D-Nal(2')-Arg-D-Nal(2')-Lys]-D-Phe-D-Val-NH2 |
| 1427 | TCAM1424 | Val-Arg-Leu-Ile-Val-Ala-Val-Arg-Arg-Arg-c[Asp-His-D-Nal(2')-Arg-D-Nal(2')-Lys]-D-Val-D-Pro-NH2 |

TABLE 5-continued

Exemplary Anti-microbial peptides

| SEQ NO: | Peptide | Peptide Sequence |
|---|---|---|
| 1428 | TCAM1425 | Val-Arg-Leu-Ile-Val-Ala-Val-Arg-Arg-Arg-c[Asp-His-D-Nal(2')-Arg-D-Nal(2')-Lys]-D-Pro-D-Val-NH2 |
| 1429 | TCAM1426 | Val-Arg-Leu-Ile-Val-Ala-Val-Arg-Arg-Arg-c[Asp-His-D-Nal(2')-Arg-D-Nal(2')-Lys]-D-Val-D-Phe-NH2 |
| 1430 | TCAM1427 | Val-Arg-Leu-Ile-Val-Ala-Val-Arg-Arg-Arg-c[Asp-His-D-Nal(2')-Arg-D-Nal(2')-Lys]-D-Phe-D-Val-NH2 |
| 1431 | TCAM1428 | Val-Arg-Leu-Ile-Val-Ala-Val-Arg-c[Asp-Arg-Pro-D-Nal(2')-Arg-D-Nal(2')-Arg-Lys]-D-Val-D-Pro-NH2 |
| 1432 | TCAM1429 | Val-Arg-Leu-Ile-Val-Ala-Val-Arg-c[Asp-Arg-Pro-D-Nal(2')-Arg-D-Nal(2')-Arg-Lys]-D-Pro-D-Val-NH2 |
| 1433 | TCAM1430 | Val-Arg-Leu-Ile-Val-Ala-Val-Arg-c[Asp-Arg-Pro-D-Nal(2')-Arg-D-Nal(2')-Arg-Lys]-D-Val-D-Phe-NH2 |
| 1434 | TCAM1431 | Val-Arg-Leu-Ile-Val-Ala-Val-Arg-c[Asp-Arg-Pro-D-Nal(2')-Arg-D-Nal(2')-Arg-Lys]-D-Phe-D-Val-NH2 |
| 1435 | TCAM1432 | Val-Arg-Leu-Ile-Val-Ala-Val-Arg-c[Asp-Arg-His-D-Nal(2')-Arg-D-Nal(2')-Arg-Lys]-D-Val-D-Pro-NH2 |
| 1436 | TCAM1433 | Val-Arg-Leu-Ile-Val-Ala-Val-Arg-c[Asp-Arg-His-D-Nal(2')-Arg-D-Nal(2')-Arg-Lys]-D-Pro-D-Val-NH2 |
| 1437 | TCAM1434 | Val-Arg-Leu-Ile-Val-Ala-Val-Arg-c[Asp-Arg-His-D-Nal(2')-Arg-D-Nal(2')-Arg-Lys]-D-Val-D-Phe-NH2 |
| 1438 | TCAM1435 | Val-Arg-Leu-Ile-Val-Ala-Val-Arg-c[Asp-Arg-His-D-Nal(2')-Arg-D-Nal(2')-Arg-Lys]-D-Phe-D-Val-NH2 |
| 1439 | TCAM1436 | Val-Arg-Leu-Ile-Val-Ala-Val-Arg-c[Asp-His-D-Nal(2')-Arg-Trp-Lys]-Arg-Arg-D-Val-D-Pro-NH2 |
| 1440 | TCAM1437 | Val-Arg-Leu-Ile-Val-Ala-Val-Arg-c[Asp-His-D-Nal(2')-Arg-Trp-Lys]-Arg-Arg-D-Pro-D-Val-NH2 |
| 1441 | TCAM1438 | Val-Arg-Leu-Ile-Val-Ala-Val-Arg-c[Asp-His-D-Nal(2')-Arg-Trp-Lys]-Arg-Arg-D-Val-D-Phe-NH2 |
| 1442 | TCAM1439 | Val-Arg-Leu-Ile-Val-Ala-Val-Arg-c[Asp-His-D-Nal(2')-Arg-Trp-Lys]-Arg-Arg-D-Phe-D-Val-NH2 |
| 1443 | TCAM1440 | Val-Arg-Leu-Ile-Val-Ala-Val-Arg-c[Asp-Pro-D-Nal(2')-Arg-Trp-Lys]-Arg-Arg-D-Val-D-Pro-NH2 |
| 1444 | TCAM1441 | Val-Arg-Leu-Ile-Val-Ala-Val-Arg-c[Asp-Pro-D-Nal(2')-Arg-Trp-Lys]-Arg-Arg-D-Pro-D-Val-NH2 |
| 1445 | TCAM1442 | Val-Arg-Leu-Ile-Val-Ala-Val-Arg-c[Asp-Pro-D-Nal(2')-Arg-Trp-Lys]-Arg-Arg-D-Val-D-Phe-NH2 |
| 1446 | TCAM1443 | Val-Arg-Leu-Ile-Val-Ala-Val-Arg-c[Asp-Pro-D-Nal(2')-Arg-Trp-Lys]-Arg-Arg-D-Phe-D-Val-NH2 |

Anti-biofilm peptide ABF2 linked to ant-microbial peptides

| 1447 | TCAM1444 | Val-Arg-Ile-Trp-Arg-Arg-c[Asp-Pro-Arg-Arg-Trp-Trp-Arg-Phe-Lys]-D-Val-D-Pro-NH2 |
| 1448 | TCAM1445 | Val-Arg-Ile-Trp-Arg-Arg-c[Asp-Pro-Arg-Arg-Trp-Trp-Arg-Phe-Lys]-D-Val-D-Phe-NH2 |
| 1449 | TCAM1446 | Val-Arg-Ile-Trp-Arg-Arg-c[Asp-Pro-Arg-Arg-Trp-Trp-Arg-Phe-Lys]-D-Pro-D-Val-NH2 |
| 1450 | TCAM1447 | Val-Arg-Ile-Trp-Arg-Arg-c[Asp-Pro-Arg-Arg-Trp-Trp-Arg-Phe-Lys]-D-Phe-D-Val-NH2 |
| 1451 | TCAM1448 | Val-Arg-Ile-Trp-Arg-Arg-c[Asp-Pro-Arg-Arg-Trp-Trp-Tyr-Phe-Lys]-D-Val-D-Pro-NH2 |
| 1452 | TCAM1449 | Val-Arg-Ile-Trp-Arg-Arg-c[Asp-Pro-Arg-Arg-Trp-Trp-Tyr-Phe-Lys]-D-Val-D-Phe-NH2 |
| 1453 | TCAM1450 | Val-Arg-Ile-Trp-Arg-Arg-c[Asp-Pro-Arg-Arg-Trp-Trp-Tyr-Phe-Lys]-D-Pro-D-Val-NH2 |
| 1454 | TCAM1451 | Val-Arg-Ile-Trp-Arg-Arg-c[Asp-Pro-Arg-Arg-Trp-Trp-Tyr-Phe-Lys]-D-Phe-D-Val-NH2 |

TABLE 5-continued

Exemplary Anti-microbial peptides

| SEQ NO: | Peptide | Peptide Sequence |
|---|---|---|
| 1455 | TCAM1452 | Val-Arg-Ile-Trp-Arg-Arg-c[Asp-Pro-Arg-Arg-Tyr-Tyr-Arg-Phe-Lys]-D-Val-D-Pro-NH2 |
| 1456 | TCAM1453 | Val-Arg-Ile-Trp-Arg-Arg-c[Asp-Pro-Arg-Arg-Tyr-Tyr-Arg-Phe-Lys]-D-Val-D-Phe-NH2 |
| 1457 | TCAM1454 | Val-Arg-Ile-Trp-Arg-Arg-c[Asp-Pro-Arg-Arg-Tyr-Tyr-Arg-Phe-Lys]-D-Pro-D-Val-NH2 |
| 1458 | TCAM1455 | Val-Arg-Ile-Trp-Arg-Arg-c[Asp-Pro-Arg-Arg-Tyr-Tyr-Arg-Phe-Lys]-D-Phe-D-Val-NH2 |
| 1459 | TCAM1456 | Val-Arg-Ile-Trp-Arg-Arg-c[Asp-Pro-Arg-Arg-Nal-Nal-Arg-Phe-Lys]-D-Val-D-Pro-NH2 |
| 1460 | TCAM1457 | Val-Arg-Ile-Trp-Arg-Arg-c[Asp-Pro-Arg-Arg-Nal-Nal-Arg-Phe-Lys]-D-Val-D-Phe-NH2 |
| 1461 | TCAM1458 | Val-Arg-Ile-Trp-Arg-Arg-c[Asp-Pro-Arg-Arg-Nal-Nal-Arg-Phe-Lys]-D-Pro-D-Val-NH2 |
| 1462 | TCAM1459 | Val-Arg-Ile-Trp-Arg-Arg-c[Asp-Pro-Arg-Arg-Nal-Nal-Arg-Phe-Lys]-D-Phe-D-Val-NH2 |
| 1463 | TCAM1460 | Val-Arg-Ile-Trp-Arg-Arg-c[Asp-Pro-Arg-Arg-Leu-Trp-Leu-Trp-Lys]-D-Val-D-Pro-NH2 |
| 1464 | TCAM1461 | Val-Arg-Ile-Trp-Arg-Arg-c[Asp-Pro-Arg-Arg-Leu-Trp-Leu-Trp-Lys]-D-Val-D-Phe-NH2 |
| 1465 | TCAM1462 | Val-Arg-Ile-Trp-Arg-Arg-c[Asp-Pro-Arg-Arg-Leu-Trp-Leu-Trp-Lys]-D-Pro-D-Val-NH2 |
| 1466 | TCAM1463 | Val-Arg-Ile-Trp-Arg-Arg-c[Asp-Pro-Arg-Arg-Leu-Trp-Leu-Trp-Lys]-D-Phe-D-Val-NH2 |
| 1467 | TCAM1464 | Val-Arg-Ile-Trp-Arg-Arg-c[Asp-Pro-Arg-Arg-Leu-Trp-Leu-Trp-Lys]-D-Val-D-Pro-NH2 |
| 1468 | TCAM1465 | Val-Arg-Ile-Trp-Arg-Arg-c[Asp-Pro-Arg-Arg-Leu-Trp-Leu-Trp-Lys]-D-Val-D-Phe-NH2 |
| 1469 | TCAM1466 | Val-Arg-Ile-Trp-Arg-Arg-c[Asp-Pro-Arg-Arg-Leu-Trp-Leu-Trp-Lys]-D-Pro-D-Val-NH2 |
| 1470 | TCAM1467 | Val-Arg-Ile-Trp-Arg-Arg-c[Asp-Pro-Arg-Arg-Leu-Trp-Leu-Trp-Lys]-D-Phe-D-Val-NH2 |
| 1471 | TCAM1468 | Val-Arg-Ile-Trp-Arg-Arg-c[Asp-Arg-Arg-Arg-Trp-Leu-Trp-Leu-Trp-Lys]-D-Val-D-Pro-NH2 |
| 1472 | TCAM1469 | Val-Arg-Ile-Trp-Arg-Arg-c[Asp-Pro-Arg-Arg-Arg-Trp-Leu-Trp-Leu-Trp-Lys]-D-Val-D-Phe-NH2 |
| 1473 | TCAM1470 | Val-Arg-Ile-Trp-Arg-Arg-c[Asp-Pro-Arg-Arg-Arg-Trp-Leu-Trp-Leu-Trp-Lys]-D-Pro-D-Val-NH2 |
| 1474 | TCAM1471 | Val-Arg-Ile-Trp-Arg-Arg-c[Asp-Pro-Arg-Arg-Arg-Trp-Leu-Trp-Leu-Trp-Lys]-D-Phe-D-Val-NH2 |
| 1475 | TCAM1472 | Val-Arg-Ile-Trp-Arg-Arg-c[Asp-Pro-Arg-Gln-Arg-Arg-Trp-Leu-Trp-Leu-Trp-Lys]-D-Val-D-Pro-NH2 |
| 1476 | TCAM1473 | Val-Arg-Ile-Trp-Arg-Arg-c[Asp-Pro-Arg-Gln-Arg-Arg-Trp-Leu-Trp-Leu-Trp-Lys]-D-Val-D-Phe-NH2 |
| 1477 | TCAM1474 | Val-Arg-Ile-Trp-Arg-Arg-c[Asp-Pro-Arg-Gln-Arg-Arg-Trp-Leu-Trp-Leu-Trp-Lys]-D-Pro-D-Val-NH2 |
| 1478 | TCAM1475 | Val-Arg-Ile-Trp-Arg-Arg-c[Asp-Pro-Arg-Gln-Arg-Arg-Trp-Leu-Trp-Leu-Trp-Lys]-D-Phe-D-Val-NH2 |
| 1479 | TCAM1476 | Val-Arg-Ile-Trp-Arg-Arg-c[Asp-Pro-Trp-Arg-Trp-Trp-Arg-Arg-Lys]-D-Val-D-Phe-NH2 |
| 1480 | TCAM1477 | Val-Arg-Ile-Trp-Arg-Arg-c[Asp-Pro-Trp-Arg-Trp-Trp-Arg-Arg-Lys]-D-Pro-D-Val-NH2 |
| 1481 | TCAM1478 | Val-Arg-Ile-Trp-Arg-Arg-c[Asp-Pro-Trp-Arg-Trp-Trp-Arg-Arg-Lys]-D-Phe-D-Val-NH2 |
| 1482 | TCAM1479 | Val-Arg-Ile-Trp-Arg-Arg-c[Asp-Pro-Trp-Trp-Arg-Arg-Trp-Trp-Arg-Arg-Lys]-D-Val-D-Pro-NH2 |
| 1483 | TCAM1480 | Val-Arg-Ile-Trp-Arg-Arg-c[Asp-Pro-Trp-Trp-Arg-Arg-Trp-Trp-Arg-Arg-Lys]-D-Val-D-Phe-NH2 |
| 1484 | TCAM1481 | Val-Arg-Ile-Trp-Arg-Arg-c[Asp-Pro-Trp-Trp-Arg-Arg-Trp-Trp-Arg-Arg-Lys]-D-Pro-D-Val-NH2 |
| 1485 | TCAM1482 | Val-Arg-Ile-Trp-Arg-Arg-c[Asp-Pro-Trp-Trp-Arg-Arg-Trp-Trp-Arg-Arg-Lys]-D-Phe-D-Val-NH2 |

TABLE 5-continued

Exemplary Anti-microbial peptides

| SEQ NO: | Peptide | Peptide Sequence |
|---|---|---|
| 1486 | TCAM1483 | Val-Arg-Ile-Trp-Arg-Arg-c[Asp-Pro-Trp-Arg-Trp-Arg-Trp-Arg-Lys]-D-Val-D-Pro-NH2 |
| 1487 | TCAM1484 | Val-Arg-Ile-Trp-Arg-Arg-c[Asp-Pro-Trp-Arg-Trp-Arg-Trp-Arg-Lys]-D-Val-D-Phe-NH2 |
| 1488 | TCAM1485 | Val-Arg-Ile-Trp-Arg-Arg-c[Asp-Pro-Trp-Arg-Trp-Arg-Trp-Arg-Lys]-D-Pro-D-Val-NH2 |
| 1489 | TCAM1486 | Val-Arg-Ile-Trp-Arg-Arg-c[Asp-Pro-Trp-Arg-Trp-Arg-Trp-Arg-Lys]-D-Phe-D-Val-NH2 |
| 1490 | TCAM1487 | Val-Arg-Ile-Trp-Arg-Arg-c[Asp-Pro-Arg-Trp-Arg-Trp-Arg-Trp-Lys]-D-Val-D-Pro-NH2 |
| 1491 | TCAM1488 | Val-Arg-Ile-Trp-Arg-Arg-c[Asp-Pro-Arg-Trp-Arg-Trp-Arg-Trp-Lys]-D-Val-D-Phe-NH2 |
| 1492 | TCAM1489 | Val-Arg-Ile-Trp-Arg-Arg-c[Asp-Pro-Arg-Trp-Arg-Trp-Arg-Trp-Lys]-D-Pro-D-Val-NH2 |
| 1493 | TCAM1490 | Val-Arg-Ile-Trp-Arg-Arg-c[Asp-Pro-Arg-Trp-Arg-Trp-Arg-Trp-Lys]-D-Phe-D-Val-NH2 |
| 1494 | TCAM1491 | Val-Arg-Ile-Trp-Arg-Arg-c[Asp-Pro-Arg-Trp-Trp-Arg-Arg-Lys]-D-Val-D-Pro-NH2 |
| 1495 | TCAM1492 | Val-Arg-Ile-Trp-Arg-Arg-c[Asp-Pro-Arg-Trp-Trp-Arg-Arg-Lys]-D-Val-D-Phe-NH2 |
| 1496 | TCAM1493 | Val-Arg-Ile-Trp-Arg-Arg-c[Asp-Pro-Arg-Trp-Trp-Arg-Arg-Lys]-D-Pro-D-Val-NH2 |
| 1497 | TCAM1494 | Val-Arg-Ile-Trp-Arg-Arg-c[Asp-Pro-Arg-Trp-Trp-Arg-Arg-Lys]-D-Phe-D-Val-NH2 |
| 1498 | TCAM1495 | Val-Arg-Ile-Trp-Arg-Arg-c[Asp-Pro-Trp-Trp-Arg-Arg-Trp-Lys]-D-Val-D-Pro-NH2 |
| 1499 | TCAM1496 | Val-Arg-Ile-Trp-Arg-Arg-c[Asp-Pro-Trp-Trp-Arg-Arg-Trp-Lys]-D-Val-D-Phe-NH2 |
| 1500 | TCAM1497 | Val-Arg-Ile-Trp-Arg-Arg-c[Asp-Pro-Trp-Trp-Arg-Arg-Trp-Lys]-D-Pro-D-Val-NH2 |
| 1501 | TCAM1498 | Val-Arg-Ile-Trp-Arg-Arg-c[Asp-Pro-Trp-Trp-Arg-Arg-Trp-Lys]-D-Phe-D-Val-NH2 |
| 1502 | TCAM1499 | Val-Arg-Ile-Trp-Arg-Arg-c[Asp-Pro-Trp-Arg-Trp-Arg-Trp-Lys]-D-Val-D-Pro-NH2 |
| 1503 | TCAM1500 | Val-Arg-Ile-Trp-Arg-Arg-c[Asp-Pro-Trp-Arg-Trp-Arg-Trp-Lys]-D-Val-D-Phe-NH2 |
| 1504 | TCAM1501 | Val-Arg-Ile-Trp-Arg-Arg-c[Asp-Pro-Trp-Arg-Trp-Arg-Trp-Lys]-D-Pro-D-Val-NH2 |
| 1505 | TCAM1502 | Val-Arg-Ile-Trp-Arg-Arg-c[Asp-Pro-Trp-Arg-Trp-Arg-Trp-Lys]-D-Phe-D-Val-NH2 |
| 1506 | TCAM1503 | Val-Arg-Ile-Trp-Arg-Arg-c[Asp-Pro-Arg-Trp-Arg-Trp-Arg-Lys]-D-Val-D-Pro-NH2 |
| 1507 | TCAM1504 | Val-Arg-Ile-Trp-Arg-Arg-c[Asp-Pro-Arg-Trp-Arg-Trp-Arg-Lys]-D-Val-D-Phe-NH2 |
| 1508 | TCAM1505 | Val-Arg-Ile-Trp-Arg-Arg-c[Asp-Pro-Arg-Trp-Arg-Trp-Arg-Lys]-D-Pro-D-Val-NH2 |
| 1509 | TCAM1506 | Val-Arg-Ile-Trp-Arg-Arg-c[Asp-Pro-Arg-Trp-Arg-Trp-Arg-Lys]-D-Phe-D-Val-NH2 |
| 1510 | TCAM1507 | Val-Arg-Ile-Trp-Arg-Arg-c[Asp-Pro-Trp-Arg-Tyr-Arg-Trp-Lys]-D-Val-D-Pro-NH2 |
| 1511 | TCAM1508 | Val-Arg-Ile-Trp-Arg-Arg-c[Asp-Pro-Trp-Arg-Tyr-Arg-Trp-Lys]-D-Val-D-Phe-NH2 |
| 1512 | TCAM1509 | Val-Arg-Ile-Trp-Arg-Arg-c[Asp-Pro-Trp-Arg-Tyr-Arg-Trp-Lys]-D-Pro-D-Val-NH2 |
| 1513 | TCAM1510 | Val-Arg-Ile-Trp-Arg-Arg-c[Asp-Pro-Trp-Arg-Tyr-Arg-Trp-Lys]-D-Phe-D-Val-NH2 |
| 1514 | TCAM1511 | Val-Arg-Ile-Trp-Arg-Arg-c[Asp-Pro-Trp-Arg-Trp-Arg-Tyr-Lys]-D-Val-D-Pro-NH2 |
| 1515 | TCAM1512 | Val-Arg-Ile-Trp-Arg-Arg-c[Asp-Pro-Trp-Arg-Trp-Arg-Tyr-Lys]-D-Val-D-Phe-NH2 |
| 1516 | TCAM1513 | Val-Arg-Ile-Trp-Arg-Arg-c[Asp-Pro-Trp-Arg-Trp-Arg-Tyr-Lys]-D-Pro-D-Val-NH2 |
| 1517 | TCAM1514 | Val-Arg-Ile-Trp-Arg-Arg-c[Asp-Pro-Trp-Arg-Trp-Arg-Tyr-Lys]-D-Phe-D-Val-NH2 |
| 1518 | TCAM1515 | Val-Arg-Ile-Trp-Arg-Arg-c[Asp-Pro-Trp-Arg-Trp-Arg-Lys]-D-Val-D-Pro-NH2 |
| 1519 | TCAM1516 | Val-Arg-Ile-Trp-Arg-Arg-c[Asp-Pro-Trp-Arg-Trp-Arg-Lys]-D-Val-D-Phe-NH2 |
| 1520 | TCAM1517 | Val-Arg-Ile-Trp-Arg-Arg-c[Asp-Pro-Trp-Arg-Trp-Arg-Lys]-D-Pro-D-Val-NH2 |
| 1521 | TCAM1518 | Val-Arg-Ile-Trp-Arg-Arg-c[Asp-Pro-Trp-Arg-Trp-Arg-Lys]-D-Phe-D-Val-NH2 |
| 1522 | TCAM1519 | Val-Arg-Ile-Trp-Arg-Arg-c[Asp-Pro-Trp-Arg-Arg-Trp-Lys]-D-Val-D-Pro-NH2 |

TABLE 5-continued

Exemplary Anti-microbial peptides

| SEQ NO: | Peptide | Peptide Sequence |
|---|---|---|
| 1523 | TCAM1520 | Val-Arg-Ile-Trp-Arg-Arg-c[Asp-Pro-Trp-Arg-Arg-Trp-Lys]-D-Val-D-Phe-NH2 |
| 1524 | TCAM1521 | Val-Arg-Ile-Trp-Arg-Arg-c[Asp-Pro-Trp-Arg-Arg-Trp-Lys]-D-Pro-D-Val-NH2 |
| 1525 | TCAM1522 | Val-Arg-Ile-Trp-Arg-Arg-c[Asp-Pro-Trp-Arg-Arg-Trp-Lys]-D-Phe-D-Val-NH2 |
| 1526 | TCAM1523 | Val-Arg-Ile-Trp-Arg-Arg-c[Asp-Pro-Arg-Trp-Trp-Arg-Lys]-D-Val-D-Pro-NH2 |
| 1527 | TCAM1524 | Val-Arg-Ile-Trp-Arg-Arg-c[Asp-Pro-Arg-Trp-Trp-Arg-Lys]-D-Val-D-Phe-NH2 |
| 1528 | TCAM1525 | Val-Arg-Ile-Trp-Arg-Arg-c[Asp-Pro-Arg-Trp-Trp-Arg-Lys]-D-Pro-D-Val-NH2 |
| 1529 | TCAM1526 | Val-Arg-Ile-Trp-Arg-Arg-c[Asp-Pro-Arg-Trp-Trp-Arg-Lys]-D-Phe-D-Val-NH2 |
| 1530 | TCAM1527 | Val-Arg-Ile-Trp-Arg-Arg-c[Asp-Pro-Trp-Arg-Trp-Lys]-D-Val-D-Pro-NH2 |
| 1531 | TCAM1528 | Val-Arg-Ile-Trp-Arg-Arg-c[Asp-Pro-Trp-Arg-Trp-Lys]-D-Val-D-Phe-NH2 |
| 1532 | TCAM1529 | Val-Arg-Ile-Trp-Arg-Arg-c[Asp-Pro-Trp-Arg-Trp-Lys]-D-Pro-D-Val-NH2 |
| 1533 | TCAM1530 | Val-Arg-Ile-Trp-Arg-Arg-c[Asp-Pro-Trp-Arg-Trp-Lys]-D-Phe-D-Val-NH2 |
| 1534 | TCAM1531 | Val-Arg-Ile-Trp-Arg-Arg-c[Asp-Pro-Arg-Trp-Arg-Lys]-D-Val-D-Pro-NH2 |
| 1535 | TCAM1532 | Val-Arg-Ile-Trp-Arg-Arg-c[Asp-Pro-Arg-Trp-Arg-Lys]-D-Val-D-Phe-NH2 |
| 1536 | TCAM1533 | Val-Arg-Ile-Trp-Arg-Arg-c[Asp-Pro-Arg-Trp-Arg-Lys]-D-Pro-D-Val-NH2 |
| 1537 | TCAM1534 | Val-Arg-Ile-Trp-Arg-Arg-c[Asp-Pro-Arg-Trp-Arg-Lys]-D-Phe-D-Val-NH2 |
| 1538 | TCAM1535 | Val-Arg-Ile-Trp-Arg-Arg-c[Asp-Arg-Arg-Trp-Trp-Arg-Phe-Lys]-D-Val-D-Pro-NH2 |
| 1539 | TCAM1536 | Val-Arg-Ile-Trp-Arg-Arg-c[Asp-Arg-Arg-Trp-Trp-Arg-Phe-Lys]-D-Val-D-Phe-NH2 |
| 1540 | TCAM1537 | Val-Arg-Ile-Trp-Arg-Arg-c[Asp-Arg-Arg-Trp-Trp-Arg-Phe-Lys]-D-Pro-D-Val-NH2 |
| 1541 | TCAM1538 | Val-Arg-Ile-Trp-Arg-Arg-c[Asp-Arg-Arg-Trp-Trp-Arg-Phe-Lys]-D-Phe-D-Val-NH2 |
| 1542 | TCAM1539 | Val-Arg-Ile-Trp-Arg-Arg-c[Asp-Arg-Arg-Trp-Trp-Arg-Phe-Lys]-D-Val-D-Pro-NH2 |
| 1543 | TCAM1540 | Val-Arg-Ile-Trp-Arg-Arg-c[Asp-Arg-Arg-Trp-Trp-Arg-Phe-Lys]-D-Val-D-Phe-NH2 |
| 1544 | TCAM1541 | Val-Arg-Ile-Trp-Arg-Arg-c[Asp-Arg-Arg-Trp-Trp-Arg-Phe-Lys]-D-Pro-D-Val-NH2 |
| 1545 | TCAM1542 | Val-Arg-Ile-Trp-Arg-Arg-c[Asp-Arg-Arg-Trp-Trp-Arg-Phe-Lys]-D-Phe-D-Val-NH2 |
| 1546 | TCAM1543 | Val-Arg-Ile-Trp-Arg-Arg-c[Asp-Arg-Arg-Tyr-Tyr-Arg-Phe-Lys]-D-Val-D-Pro-NH2 |
| 1547 | TCAM1544 | Val-Arg-Ile-Trp-Arg-Arg-c[Asp-Arg-Arg-Tyr-Tyr-Arg-Phe-Lys]-D-Val-D-Phe-NH2 |
| 1548 | TCAM1545 | Val-Arg-Ile-Trp-Arg-Arg-c[Asp-Arg-Arg-Tyr-Tyr-Arg-Phe-Lys]-D-Pro-D-Val-NH2 |
| 1549 | TCAM1546 | Val-Arg-Ile-Trp-Arg-Arg-c[Asp-Arg-Arg-Tyr-Tyr-Arg-Phe-Lys]-D-Phe-D-Val-NH2 |
| 1550 | TCAM1547 | Val-Arg-Ile-Trp-Arg-Arg-c[Asp-Arg-Arg-Nal-Nal-Arg-Phe-Lys]-D-Val-D-Pro-NH2 |
| 1551 | TCAM1548 | Val-Arg-Ile-Trp-Arg-Arg-c[Asp-Arg-Arg-Nal-Nal-Arg-Phe-Lys]-D-Val-D-Phe-NH2 |
| 1552 | TCAM1549 | Val-Arg-Ile-Trp-Arg-Arg-c[Asp-Arg-Arg-Nal-Nal-Arg-Phe-Lys]-D-Pro-D-Val-NH2 |
| 1553 | TCAM1550 | Val-Arg-Ile-Trp-Arg-Arg-c[Asp-Arg-Arg-Nal-Nal-Arg-Phe-Lys]-D-Phe-D-Val-NH2 |
| 1554 | TCAM1551 | Val-Arg-Ile-Trp-Arg-Arg-c[Asp-Arg-Arg-Leu-Trp-Leu-Trp-Lys]-D-Val-D-Pro-NH2 |
| 1555 | TCAM1552 | Val-Arg-Ile-Trp-Arg-Arg-c[Asp-Arg-Arg-Leu-Trp-Leu-Trp-Lys]-D-Val-D-Phe-NH2 |
| 1556 | TCAM1553 | Val-Arg-Ile-Trp-Arg-Arg-c[Asp-Arg-Arg-Leu-Trp-Leu-Trp-Lys]-D-Pro-D-Val-NH2 |
| 1557 | TCAM1554 | Val-Arg-Ile-Trp-Arg-Arg-c[Asp-Arg-Arg-Leu-Trp-Leu-Trp-Lys]-D-Phe-D-Val-NH2 |
| 1558 | TCAM1555 | Val-Arg-Ile-Trp-Arg-Arg-c[Asp-Arg-Arg-Leu-Trp-Leu-Trp-Lys]-D-Val-D-Pro-NH2 |
| 1559 | TCAM1556 | Val-Arg-Ile-Trp-Arg-Arg-c[Asp-Arg-Arg-Leu-Trp-Leu-Trp-Lys]-D-Val-D-Phe-NH2 |
| 1560 | TCAM1557 | Val-Arg-Ile-Trp-Arg-Arg-c[Asp-Arg-Arg-Leu-Trp-Leu-Trp-Lys]-D-Pro-D-Val-NH2 |

TABLE 5-continued

Exemplary Anti-microbial peptides

| SEQ NO: | Peptide | Peptide Sequence |
|---|---|---|
| 1561 | TCAM1558 | Val-Arg-Ile-Trp-Arg-Arg-c[Asp-Arg-Arg-Leu-Trp-Leu-Trp-Lys]-D-Phe-D-Val-NH2 |
| 1562 | TCAM1559 | Val-Arg-Ile-Trp-Arg-Arg-c[Asp-Arg-Arg-Arg-Trp-Leu-Trp-Leu-Trp-Lys]-D-Val-D-Pro-NH2 |
| 1563 | TCAM1560 | Val-Arg-Ile-Trp-Arg-Arg-c[Asp-Arg-Arg-Arg-Trp-Leu-Trp-Leu-Trp-Lys]-D-Val-D-Phe-NH2 |
| 1564 | TCAM1561 | Val-Arg-Ile-Trp-Arg-Arg-c[Asp-Arg-Arg-Arg-Trp-Leu-Trp-Leu-Trp-Lys]-D-Pro-D-Val-NH2 |
| 1565 | TCAM1562 | Val-Arg-Ile-Trp-Arg-Arg-c[Asp-Arg-Arg-Arg-Trp-Leu-Trp-Leu-Trp-Lys]-D-Phe-D-Val-NH2 |
| 1566 | TCAM1563 | Val-Arg-Ile-Trp-Arg-Arg-c[Asp-Arg-Gln-Arg-Arg-Trp-Leu-Trp-Leu-Trp-Lys]-D-Val-D-Pro-NH2 |
| 1567 | TCAM1564 | Val-Arg-Ile-Trp-Arg-Arg-c[Asp-Arg-Gln-Arg-Arg-Trp-Leu-Trp-Leu-Trp-Lys]-D-Val-D-Phe-NH2 |
| 1568 | TCAM1565 | Val-Arg-Ile-Trp-Arg-Arg-c[Asp-Arg-Gln-Arg-Arg-Trp-Leu-Trp-Leu-Trp-Lys]-D-Pro-D-Val-NH2 |
| 1569 | TCAM1566 | Val-Arg-Ile-Trp-Arg-Arg-c[Asp-Arg-Gln-Arg-Arg-Trp-Leu-Trp-Leu-Trp-Lys]-D-Phe-D-Val-NH2 |
| 1570 | TCAM1567 | Val-Arg-Ile-Trp-Arg-Arg-c[Asp-Trp-Arg-Trp-Trp-Arg-Arg-Lys]-D-Val-D-Pro-NH2 |
| 1571 | TCAM1568 | Val-Arg-Ile-Trp-Arg-Arg-c[Asp-Trp-Arg-Trp-Trp-Arg-Arg-Lys]-D-Val-D-Phe-NH2 |
| 1572 | TCAM1569 | Val-Arg-Ile-Trp-Arg-Arg-c[Asp-Trp-Arg-Trp-Trp-Arg-Arg-Lys]-D-Pro-D-Val-NH2 |
| 1573 | TCAM1570 | Val-Arg-Ile-Trp-Arg-Arg-c[Asp-Trp-Arg-Trp-Trp-Arg-Arg-Lys]-D-Phe-D-Val-NH2 |
| 1574 | TCAM1571 | Val-Arg-Ile-Trp-Arg-Arg-c[Asp-Trp-Trp-Arg-Arg-Trp-Trp-Arg-Arg-Lys]-D-Val-D-Pro-NH2 |
| 1575 | TCAM1572 | Val-Arg-Ile-Trp-Arg-Arg-c[Asp-Trp-Trp-Arg-Arg-Trp-Trp-Arg-Arg-Lys]-D-Val-D-Phe-NH2 |
| 1576 | TCAM1573 | Val-Arg-Ile-Trp-Arg-Arg-c[Asp-Trp-Trp-Arg-Arg-Trp-Trp-Arg-Arg-Lys]-D-Pro-D-Val-NH2 |
| 1577 | TCAM1574 | Val-Arg-Ile-Trp-Arg-Arg-c[Asp-Trp-Trp-Arg-Arg-Trp-Trp-Arg-Arg-Lys]-D-Phe-D-Val-NH2 |
| 1578 | TCAM1575 | Val-Arg-Ile-Trp-Arg-Arg-c[Asp-Trp-Arg-Trp-Arg-Trp-Arg-Lys]-D-Val-D-Pro-NH2 |
| 1579 | TCAM1576 | Val-Arg-Ile-Trp-Arg-Arg-c[Asp-Trp-Arg-Trp-Arg-Trp-Arg-Lys]-D-Val-D-Phe-NH2 |
| 1580 | TCAM1577 | Val-Arg-Ile-Trp-Arg-Arg-c[Asp-Trp-Arg-Trp-Arg-Trp-Arg-Lys]-D-Pro-D-Val-NH2 |
| 1581 | TCAM1578 | Val-Arg-Ile-Trp-Arg-Arg-c[Asp-Trp-Arg-Trp-Arg-Trp-Arg-Lys]-D-Phe-D-Val-NH2 |
| 1582 | TCAM1579 | Val-Arg-Ile-Trp-Arg-Arg-c[Asp-Arg-Trp-Arg-Trp-Arg-Trp-Lys]-D-Val-D-Pro-NH2 |
| 1583 | TCAM1580 | Val-Arg-Ile-Trp-Arg-Arg-c[Asp-Arg-Trp-Arg-Trp-Arg-Trp-Lys]-D-Val-D-Phe-NH2 |
| 1584 | TCAM1581 | Val-Arg-Ile-Trp-Arg-Arg-c[Asp-Arg-Trp-Arg-Trp-Arg-Trp-Lys]-D-Pro-D-Val-NH2 |
| 1585 | TCAM1582 | Val-Arg-Ile-Trp-Arg-Arg-c[Asp-Arg-Trp-Arg-Trp-Arg-Trp-Lys]-D-Phe-D-Val-NH2 |
| 1586 | TCAM1583 | Val-Arg-Ile-Trp-Arg-Arg-c[Asp-Arg-Trp-Trp-Arg-Arg-Lys]-D-Val-D-Pro-NH2 |
| 1587 | TCAM1584 | Val-Arg-Ile-Trp-Arg-Arg-c[Asp-Arg-Trp-Trp-Arg-Arg-Lys]-D-Val-D-Phe-NH2 |
| 1588 | TCAM1585 | Val-Arg-Ile-Trp-Arg-Arg-c[Asp-Arg-Trp-Trp-Arg-Arg-Lys]-D-Pro-D-Val-NH2 |
| 1589 | TCAM1586 | Val-Arg-Ile-Trp-Arg-Arg-c[Asp-Arg-Trp-Trp-Arg-Arg-Lys]-D-Phe-D-Val-NH2 |
| 1590 | TCAM1587 | Val-Arg-Ile-Trp-Arg-Arg-c[Asp-Arg-Trp-Arg-Trp-Arg-Lys]-D-Val-D-Pro-NH2 |
| 1591 | TCAM1588 | Val-Arg-Ile-Trp-Arg-Arg-c[Asp-Arg-Trp-Arg-Trp-Arg-Lys]-D-Val-D-Phe-NH2 |

TABLE 5-continued

Exemplary Anti-microbial peptides

| SEQ NO: | Peptide | Peptide Sequence |
|---|---|---|
| 1592 | TCAM1589 | Val-Arg-Ile-Trp-Arg-Arg-c[Asp-Arg-Trp-Arg-Trp-Arg-Lys]-D-Pro-D-Val-NH2 |
| 1593 | TCAM1590 | Val-Arg-Ile-Trp-Arg-Arg-c[Asp-Arg-Trp-Arg-Trp-Arg-Lys]-D-Phe-D-Val-NH2 |
| 1594 | TCAM1591 | Val-Arg-Ile-Trp-Arg-Arg-c[Asp-Trp-Trp-Arg-Arg-Trp-Lys]-D-Val-D-Pro-NH2 |
| 1595 | TCAM1592 | Val-Arg-Ile-Trp-Arg-Arg-c[Asp-Trp-Trp-Arg-Arg-Trp-Lys]-D-Val-D-Phe-NH2 |
| 1596 | TCAM1593 | Val-Arg-Ile-Trp-Arg-Arg-c[Asp-Trp-Trp-Arg-Arg-Trp-Lys]-D-Pro-D-Val-NH2 |
| 1597 | TCAM1594 | Val-Arg-Ile-Trp-Arg-Arg-c[Asp-Trp-Trp-Arg-Arg-Trp-Lys]-D-Phe-D-Val-NH2 |
| 1598 | TCAM1595 | Val-Arg-Ile-Trp-Arg-Arg-c[Asp-Trp-Arg-Trp-Arg-Trp-Lys]-D-Val-D-Pro-NH2 |
| 1599 | TCAM1596 | Val-Arg-Ile-Trp-Arg-Arg-c[Asp-Trp-Arg-Trp-Arg-Trp-Lys]-D-Val-D-Phe-NH2 |
| 1600 | TCAM1597 | Val-Arg-Ile-Trp-Arg-Arg-c[Asp-Trp-Arg-Trp-Arg-Trp-Lys]-D-Pro-D-Val-NH2 |
| 1601 | TCAM1598 | Val-Arg-Ile-Trp-Arg-Arg-c[Asp-Trp-Arg-Trp-Arg-Trp-Lys]-D-Phe-D-Val-NH2 |
| 1602 | TCAM1599 | Val-Arg-Ile-Trp-Arg-Arg-c[Asp-Trp-Arg-Tyr-Arg-Trp-Lys]-D-Val-D-Pro-NH2 |
| 1603 | TCAM1600 | Val-Arg-Ile-Trp-Arg-Arg-c[Asp-Trp-Arg-Tyr-Arg-Trp-Lys]-D-Val-D-Phe-NH2 |
| 1604 | TCAM1601 | Val-Arg-Ile-Trp-Arg-Arg-c[Asp-Trp-Arg-Tyr-Arg-Trp-Lys]-D-Pro-D-Val-NH2 |
| 1605 | TCAM1602 | Val-Arg-Ile-Trp-Arg-Arg-c[Asp-Trp-Arg-Tyr-Arg-Trp-Lys]-D-Phe-D-Val-NH2 |
| 1606 | TCAM1603 | Val-Arg-Ile-Trp-Arg-Arg-c[Asp-Trp-Arg-Trp-Arg-Tyr-Lys]-D-Val-D-Pro-NH2 |
| 1607 | TCAM1604 | Val-Arg-Ile-Trp-Arg-Arg-c[Asp-Trp-Arg-Trp-Arg-Tyr-Lys]-D-Val-D-Phe-NH2 |
| 1608 | TCAM1605 | Val-Arg-Ile-Trp-Arg-Arg-c[Asp-Trp-Arg-Trp-Arg-Tyr-Lys]-D-Pro-D-Val-NH2 |
| 1609 | TCAM1606 | Val-Arg-Ile-Trp-Arg-Arg-c[Asp-Trp-Arg-Trp-Arg-Tyr-Lys]-D-Phe-D-Val-NH2 |
| 1610 | TCAM1607 | Val-Arg-Ile-Trp-Arg-Arg-c[Asp-Trp-Arg-Trp-Arg-Lys]-D-Val-D-Pro-NH2 |
| 1611 | TCAM1608 | Val-Arg-Ile-Trp-Arg-Arg-c[Asp-Trp-Arg-Trp-Arg-Lys]-D-Val-D-Phe-NH2 |
| 1612 | TCAM1609 | Val-Arg-Ile-Trp-Arg-Arg-c[Asp-Trp-Arg-Trp-Arg-Lys]-D-Pro-D-Val-NH2 |
| 1613 | TCAM1610 | Val-Arg-Ile-Trp-Arg-Arg-c[Asp-Trp-Arg-Trp-Arg-Lys]-D-Phe-D-Val-NH2 |
| 1614 | TCAM1611 | Val-Arg-Ile-Trp-Arg-Arg-c[Asp-Trp-Arg-Arg-Trp-Lys]-D-Val-D-Pro-NH2 |
| 1615 | TCAM1612 | Val-Arg-Ile-Trp-Arg-Arg-c[Asp-Trp-Arg-Arg-Trp-Lys]-D-Val-D-Phe-NH2 |
| 1616 | TCAM1613 | Val-Arg-Ile-Trp-Arg-Arg-c[Asp-Trp-Arg-Arg-Trp-Lys]-D-Pro-D-Val-NH2 |
| 1617 | TCAM1614 | Val-Arg-Ile-Trp-Arg-Arg-c[Asp-Trp-Arg-Arg-Trp-Lys]-D-Phe-D-Val-NH2 |
| 1618 | TCAM1615 | Val-Arg-Ile-Trp-Arg-Arg-c[Asp-Arg-Trp-Trp-Arg-Lys]-D-Val-D-Pro-NH2 |
| 1619 | TCAM1616 | Val-Arg-Ile-Trp-Arg-Arg-c[Asp-Arg-Trp-Trp-Arg-Lys]-D-Val-D-Phe-NH2 |
| 1620 | TCAM1617 | Val-Arg-Ile-Trp-Arg-Arg-c[Asp-Arg-Trp-Trp-Arg-Lys]-D-Pro-D-Val-NH2 |
| 1621 | TCAM1618 | Val-Arg-Ile-Trp-Arg-Arg-c[Asp-Arg-Trp-Trp-Arg-Lys]-D-Phe-D-Val-NH2 |
| 1622 | TCAM1619 | Val-Arg-Ile-Trp-Arg-Arg-c[Asp-Trp-Arg-Trp-Lys]-D-Val-D-Pro-NH2 |
| 1623 | TCAM1620 | Val-Arg-Ile-Trp-Arg-Arg-c[Asp-Trp-Arg-Trp-Lys]-D-Val-D-Phe-NH2 |
| 1624 | TCAM1621 | Val-Arg-Ile-Trp-Arg-Arg-c[Asp-Trp-Arg-Trp-Lys]-D-Pro-D-Val-NH2 |
| 1625 | TCAM1622 | Val-Arg-Ile-Trp-Arg-Arg-c[Asp-Trp-Arg-Trp-Lys]-D-Phe-D-Val-NH2 |
| 1626 | TCAM1623 | Val-Arg-Ile-Trp-Arg-Arg-c[Asp-Arg-Trp-Arg-Lys]-D-Val-D-Pro-NH2 |
| 1627 | TCAM1624 | Val-Arg-Ile-Trp-Arg-Arg-c[Asp-Arg-Trp-Arg-Lys]-D-Val-D-Phe-NH2 |
| 1628 | TCAM1625 | Val-Arg-Ile-Trp-Arg-Arg-c[Asp-Arg-Trp-Arg-Lys]-D-Pro-D-Val-NH2 |
| 1629 | TCAM1626 | Val-Arg-Ile-Trp-Arg-Arg-c[Asp-Arg-Trp-Arg-Lys]-D-Phe-D-Val-NH2 |

TABLE 5-continued

Exemplary Anti-microbial peptides

| SEQ NO: | Peptide | Peptide Sequence |
|---|---|---|
| 1630 | TCAM1627 | Val-Arg-Ile-Trp-Arg-Arg-c[Asp-His-D-Nal(2')-Arg-Trp-Lys]-D-Val-D-Pro-NH2 |
| 1631 | TCAM1628 | Val-Arg-Ile-Trp-Arg-Arg-c[Asp-His-D-Nal(2')-Arg-Trp-Lys]-D-Pro-D-Val-NH2 |
| 1632 | TCAM1629 | Val-Arg-Ile-Trp-Arg-Arg-c[Asp-His-D-Nal(2')-Arg-Trp-Lys]-D-Val-D-Phe-NH2 |
| 1633 | TCAM1630 | Val-Arg-Ile-Trp-Arg-Arg-c[Asp-His-D-Nal(2')-Arg-Trp-Lys]-D-Phe-D-Val-NH2 |
| 1634 | TCAM1631 | Val-Arg-Ile-Trp-Arg-Arg-c[Asp-Pro-D-Nal(2')-Arg-Trp-Lys]-D-Val-D-Pro-NH2 |
| 1635 | TCAM1632 | Val-Arg-Ile-Trp-Arg-Arg-c[Asp-Pro-D-Nal(2')-Arg-Trp-Lys]-D-Pro-D-Val-NH2 |
| 1636 | TCAM1633 | Val-Arg-Ile-Trp-Arg-Arg-c[Asp-Pro-D-Nal(2')-Arg-Trp-Lys]-D-Val-D-Phe-NH2 |
| 1637 | TCAM1634 | Val-Arg-Ile-Trp-Arg-Arg-c[Asp-Pro-D-Nal(2')-Arg-Trp-Lys]-D-Phe-D-Val-NH2 |
| 1638 | TCAM1635 | Val-Arg-Ile-Trp-Arg-Arg-c[Asp-Arg-Arg-Nal(2')-Arg-Trp-Lys]-D-Val-D-Pro-NH2 |
| 1639 | TCAM1636 | Val-Arg-Ile-Trp-Arg-Arg-c[Asp-Arg-Arg-Nal(2')-Arg-Trp-Lys]-D-Pro-D-Val-NH2 |
| 1640 | TCAM1637 | Val-Arg-Ile-Trp-Arg-Arg-c[Asp-Arg-Arg-Nal(2')-Arg-Trp-Lys]-D-Val-D-Phe-NH2 |
| 1641 | TCAM1638 | Val-Arg-Ile-Trp-Arg-Arg-c[Asp-Arg-Arg-Nal(2')-Arg-Trp-Lys]-D-Phe-D-Val-NH2 |
| 1642 | TCAM1639 | Val-Arg-Ile-Trp-Arg-Arg-c[Asp-Arg-Arg-Pro-Nal(2')-Arg-Trp-Lys]-D-Val-D-Pro-NH2 |
| 1643 | TCAM1640 | Val-Arg-Ile-Trp-Arg-Arg-c[Asp-Arg-Arg-Pro-D-Nal(2')-Arg-Trp-Lys]-D-Pro-D-Val-NH2 |
| 1644 | TCAM1641 | Val-Arg-Ile-Trp-Arg-Arg-c[Asp-Arg-Arg-Pro-D-Nal(2')-Arg-Trp-Lys]-D-Val-D-Phe-NH2 |
| 1645 | TCAM1642 | Val-Arg-Ile-Trp-Arg-Arg-c[Asp-Arg-Arg-Pro-D-Nal(2')-Arg-Trp-Lys]-D-Phe-D-Val-NH2 |
| 1646 | TCAM1643 | Val-Arg-Ile-Trp-Arg-Arg-c[Asp-Arg-D-Nal(2')-Arg-Trp-Lys]-D-Val-D-Pro-NH2 |
| 1647 | TCAM1644 | Val-Arg-Ile-Trp-Arg-Arg-c[Asp-Arg-D-Nal(2')-Arg-Trp-Lys]-D-Pro-D-Val-NH2 |
| 1648 | TCAM1645 | Val-Arg-Ile-Trp-Arg-Arg-c[Asp-Arg-D-Nal(2')-Arg-Trp-Lys]-D-Val-D-Phe-NH2 |
| 1649 | TCAM1646 | Val-Arg-Ile-Trp-Arg-Arg-c[Asp-Arg-D-Nal(2')-Arg-Trp-Lys]-D-Phe-D-Val-NH2 |
| 1650 | TCAM1647 | Val-Arg-Ile-Trp-Arg-Arg-c[Asp-Arg-Pro-D-Nal(2')-Arg-Trp-Lys]-D-Val-D-Pro-NH2 |
| 1651 | TCAM1648 | Val-Arg-Ile-Trp-Arg-Arg-c[Asp-Arg-Pro-D-Nal(2')-Arg-Trp-Lys]-D-Pro-D-Val-NH2 |
| 1652 | TCAM1649 | Val-Arg-Ile-Trp-Arg-Arg-c[Asp-Arg-Pro-D-Nal(2')-Arg-Trp-Lys]-D-Val-D-Phe-NH2 |
| 1653 | TCAM1650 | Val-Arg-Ile-Trp-Arg-Arg-c[Asp-Arg-Pro-D-Nal(2')-Arg-Trp-Lys]-D-Phe-D-Val-NH2 |
| 1654 | TCAM1651 | Val-Arg-Ile-Trp-Arg-Arg-Arg-Arg-c[Asp-Pro-D-Nal(2')-Arg-Trp-Lys]-D-Val-D-Pro-NH2 |
| 1655 | TCAM1652 | Val-Arg-Ile-Trp-Arg-Arg-Arg-Arg-c[Asp-Pro-D-Nal(2')-Arg-Trp-Lys]-D-Pro-D-Val-NH2 |
| 1656 | TCAM1653 | Val-Arg-Ile-Trp-Arg-Arg-Arg-Arg-c[Asp-Pro-D-Nal(2')-Arg-Trp-Lys]-D-Val-D-Phe-NH2 |
| 1657 | TCAM1654 | Val-Arg-Ile-Trp-Arg-Arg-Arg-Arg-c[Asp-Pro-D-Nal(2')-Arg-Trp-Lys]-D-Phe-D-Val-NH2 |
| 1658 | TCAM1655 | Val-Arg-Ile-Trp-Arg-Arg-Arg-Arg-c[Asp-His-D-Nal(2')-Arg-Trp-Lys]-D-Val-D-Pro-NH2 |
| 1659 | TCAM1656 | Val-Arg-Ile-Trp-Arg-Arg-Arg-Arg-c[Asp-His-D-Nal(2')-Arg-Trp-Lys]-D-Pro-D-Val-NH2 |
| 1660 | TCAM1657 | Val-Arg-Ile-Trp-Arg-Arg-Arg-Arg-c[Asp-His-D-Nal(2')-Arg-Trp-Lys]-D-Val-D-Phe-NH2 |
| 1661 | TCAM1658 | Val-Arg-Ile-Trp-Arg-Arg-Arg-Arg-c[Asp-His-D-Nal(2')-Arg-Trp-Lys]-D-Phe-D-Val-NH2 |
| 1662 | TCAM1659 | Val-Arg-Ile-Trp-Arg-Arg-c[Asp-Arg-Pro-D-Nal(2')-Arg-Trp-Arg-Lys]-D-Val-D-Pro-NH2 |
| 1663 | TCAM1660 | Val-Arg-Ile-Trp-Arg-Arg-c[Asp-Arg-Pro-D-Nal(2')-Arg-Trp-Arg-Lys]-D-Pro-D-Val-NH2 |
| 1664 | TCAM1661 | Val-Arg-Ile-Trp-Arg-Arg-c[Asp-Arg-Pro-D-Nal(2')-Arg-Trp-Arg-Lys]-D-Val-D-Phe-NH2 |
| 1665 | TCAM1662 | Val-Arg-Ile-Trp-Arg-Arg-c[Asp-Arg-Pro-D-Nal(2')-Arg-Trp-Arg-Lys]-D-Phe-D-Val-NH2 |
| 1666 | TCAM1663 | Val-Arg-Ile-Trp-Arg-Arg-c[Asp-Arg-His-D-Nal(2')-Arg-Trp-Arg-Lys]-D-Val-D-Pro-NH2 |

TABLE 5-continued

Exemplary Anti-microbial peptides

| SEQ NO: | Peptide | Peptide Sequence |
|---|---|---|
| 1667 | TCAM1664 | Val-Arg-Ile-Trp-Arg-Arg-c[Asp-Arg-His-D-Nal(2')-Arg-Trp-Arg-Lys]-D-Pro-D-Val-NH2 |
| 1668 | TCAM1665 | Val-Arg-Ile-Trp-Arg-Arg-c[Asp-Arg-His-D-Nal(2')-Arg-Trp-Arg-Lys]-D-Val-D-Phe-NH2 |
| 1669 | TCAM1666 | Val-Arg-Ile-Trp-Arg-Arg-c[Asp-Arg-His-D-Nal(2')-Arg-Trp-Arg-Lys]-D-Phe-D-Val-NH2 |
| 1670 | TCAM1667 | Val-Arg-Ile-Trp-Arg-Arg-c[Asp-His-D-Nal(2')-Arg-D-Nal(2')-Lys]-D-Val-D-Phe-NH2 |
| 1671 | TCAM1668 | Val-Arg-Ile-Trp-Arg-Arg-c[Asp-His-D-Nal(2')-Arg-D-Nal(2')-Lys]-D-Phe-D-Val-NH2 |
| 1672 | TCAM1669 | Val-Arg-Ile-Trp-Arg-Arg-c[Asp-Pro-D-Nal(2')-Arg-D-Nal(2')-Lys]-D-Val-D-Pro-NH2 |
| 1673 | TCAM1670 | Val-Arg-Ile-Trp-Arg-Arg-c[Asp-Pro-D-Nal(2')-Arg-D-Nal(2')-Lys]-D-Pro-D-Val-NH2 |
| 1674 | TCAM1671 | Val-Arg-Ile-Trp-Arg-Arg-c[Asp-Pro-D-Nal(2')-Arg-D-Nal(2')-Lys]-D-Val-D-Phe-NH2 |
| 1675 | TCAM1672 | Val-Arg-Ile-Trp-Arg-Arg-c[Asp-Pro-D-Nal(2')-Arg-D-Nal(2')-Lys]-D-Phe-D-Val-NH2 |
| 1676 | TCAM1673 | Val-Arg-Ile-Trp-Arg-Arg-c[Asp-Arg-Arg-D-Nal(2')-Arg-D-Nal(2')-Lys]-D-Val-D-Pro-NH2 |
| 1677 | TCAM1674 | Val-Arg-Ile-Trp-Arg-Arg-c[Asp-Arg-Arg-D-Nal(2')-Arg-D-Nal(2')-Lys]-D-Pro-D-Val-NH2 |
| 1678 | TCAM1675 | Val-Arg-Ile-Trp-Arg-Arg-c[Asp-Arg-Arg-D-Nal(2')-Arg-D-Nal(2')-Lys]-D-Val-D-Phe-NH2 |
| 1679 | TCAM1676 | Val-Arg-Ile-Trp-Arg-Arg-c[Asp-Arg-Arg-D-Nal(2')-Arg-D-Nal(2')-Lys]-D-Phe-D-Val-NH2 |
| 1680 | TCAM1677 | Val-Arg-Ile-Trp-Arg-Arg-c[Asp-Arg-Arg-Pro-D-Nal(2')-Arg-D-Nal(2')-Lys]-D-Val-D-Pro-NH2 |
| 1681 | TCAM1678 | Val-Arg-Ile-Trp-Arg-Arg-c[Asp-Arg-Arg-Pro-D-Nal(2')-Arg-D-Nal(2')-Lys]-D-Pro-D-Val-NH2 |
| 1682 | TCAM1679 | Val-Arg-Ile-Trp-Arg-Arg-c[Asp-Arg-Arg-Pro-D-Nal(2')-Arg-D-Nal(2')-Lys]-D-Val-D-Phe-NH2 |
| 1683 | TCAM1680 | Val-Arg-Ile-Trp-Arg-Arg-c[Asp-Arg-Arg-Pro-D-Nal(2')-Arg-D-Nal(2')-Lys]-D-Phe-D-Val-NH2 |
| 1684 | TCAM1681 | Val-Arg-Ile-Trp-Arg-Arg-c[Asp-Arg-D-Nal(2')-Arg-D-Nal(2')-Lys]-D-Val-D-Pro-NH2 |
| 1685 | TCAM1682 | Val-Arg-Ile-Trp-Arg-Arg-c[Asp-Arg-D-Nal(2')-Arg-D-Nal(2')-Lys]-D-Pro-D-Val-NH2 |
| 1686 | TCAM1683 | Val-Arg-Ile-Trp-Arg-Arg-c[Asp-Arg-Nal(2')-Arg-D-Nal(2')-Lys]-D-Val-D-Phe-NH2 |
| 1687 | TCAM1684 | Val-Arg-Ile-Trp-Arg-Arg-c[Asp-Arg-D-Nal(2')-Arg-D-Nal(2')-Lys]-D-Phe-D-Val-NH2 |
| 1688 | TCAM1685 | Val-Arg-Ile-Trp-Arg-Arg-c[Asp-Arg-Pro-D-Nal(2')-Arg-D-Nal(2')-Lys]-D-Val-D-Pro-NH2 |
| 1689 | TCAM1686 | Val-Arg-Ile-Trp-Arg-Arg-c[Asp-Arg-Pro-D-Nal(2')-Arg-D-Nal(2')-Lys]-D-Pro-D-Val-NH2 |
| 1690 | TCAM1687 | Val-Arg-Ile-Trp-Arg-Arg-c[Asp-Arg-Pro-D-Nal(2')-Arg-D-Nal(2')-Lys]-D-Val-D-Phe-NH2 |
| 1691 | TCAM1688 | Val-Arg-Ile-Trp-Arg-Arg-c[Asp-Arg-Pro-D-Nal(2')-Arg-D-Nal(2')-Lys]-D-Phe-D-Val-NH2 |
| 1692 | TCAM1689 | Val-Arg-Ile-Trp-Arg-Arg-c[Asp-Arg-His-D-Nal(2')-Arg-D-Nal(2')-Lys]-D-Val-D-Pro-NH2 |
| 1693 | TCAM1690 | Val-Arg-Ile-Trp-Arg-Arg-c[Asp-Arg-His-D-Nal(2')-Arg-D-Nal(2')-Lys]-D-Pro-D-Val-NH2 |
| 1694 | TCAM1691 | Val-Arg-Ile-Trp-Arg-Arg-c[Asp-Arg-His-Nal(2')-Arg-D-Nal(2')-Lys]-D-Val-D-Phe-NH2 |
| 1695 | TCAM1692 | Val-Arg-Ile-Trp-Arg-Arg-c[Asp-Arg-His-Nal(2')-Arg-D-Nal(2')-Lys]-D-Phe-D-Val-NH2 |
| 1696 | TCAM1693 | Val-Arg-Ile-Trp-Arg-Arg-c[Asp-Arg-D-D-Nal(2')-Arg-D-Nal(2')-Arg-Lys]-D-Val-D-Pro-NH2 |
| 1697 | TCAM1694 | Val-Arg-Ile-Trp-Arg-Arg-c[Asp-Arg-D-Nal(2')-Arg-D-Nal(2')-Arg-Lys]-D-Pro-D-Val-NH2 |
| 1698 | TCAM1695 | Val-Arg-Ile-Trp-Arg-Arg-c[Asp-Arg-D-Nal(2')-Arg-D-Nal(2')-Arg-Lys]-D-Val-D-Phe-NH2 |
| 1699 | TCAM1696 | Val-Arg-Ile-Trp-Arg-Arg-c[Asp-Arg-D-Nal(2')-Arg-D-Nal(2')-Arg-Lys]-D-Phe-D-Val-NH2 |
| 1700 | TCAM1697 | Val-Arg-Ile-Trp-Arg-Arg-c[Asp-Arg-Pro-D-Nal(2')-Arg-D-Nal(2')-Arg-Lys]-D-Val-D-Pro-NH2 |

TABLE 5-continued

Exemplary Anti-microbial peptides

| SEQ NO: | Peptide | Peptide Sequence |
|---|---|---|
| 1701 | TCAM1698 | Val-Arg-Ile-Trp-Arg-Arg-c[Asp-Arg-Pro-D-Nal(2')-Arg-D-Nal(2')-Arg-Lys]-D-Pro-D-Val-NH2 |
| 1702 | TCAM1699 | Val-Arg-Ile-Trp-Arg-Arg-c[Asp-Arg-Pro-D-Nal(2')-Arg-D-Nal(2')-Arg-Lys]-D-Val-D-Phe-NH2 |
| 1703 | TCAM1700 | Val-Arg-Ile-Trp-Arg-Arg-c[Asp-Arg-Pro-D-Nal(2')-Arg-D-Nal(2')-Arg-Lys]-D-Phe-D-Val-NH2 |
| 1704 | TCAM1701 | Val-Arg-Ile-Trp-Arg-Arg-c[Asp-Arg-His-D-Nal(2')-Arg-D-Nal(2')-Arg-Lys]-D-Val-D-Pro-NH2 |
| 1705 | TCAM1702 | Val-Arg-Ile-Trp-Arg-Arg-c[Asp-Arg-His-D-Nal(2')-Arg-D-Nal(2')-Arg-Lys]-D-Pro-D-Val-NH2 |
| 1706 | TCAM1703 | Val-Arg-Ile-Trp-Arg-Arg-c[Asp-Arg-His-D-Nal(2')-Arg-D-Nal(2')-Arg-Lys]-D-Val-D-Phe-NH2 |
| 1707 | TCAM1704 | Val-Arg-Ile-Trp-Arg-Arg-c[Asp-Arg-His-D-Nal(2')-Arg-D-Nal(2')-Arg-Lys]-D-Phe-D-Val-NH2 |
| 1708 | TCAM1705 | Val-Arg-Ile-Trp-Arg-Arg-Arg-Arg-c[Asp-Pro-D-Nal(2')-Arg-D-Nal(2')-Lys]-D-Val-D-Pro-NH2 |
| 1709 | TCAM1706 | Val-Arg-Ile-Trp-Arg-Arg-Arg-Arg-c[Asp-Pro-D-Nal(2')-Arg-D-Nal(2')-Lys]-D-Pro-D-Val-NH2 |
| 1710 | TCAM1707 | Val-Arg-Ile-Trp-Arg-Arg-Arg-Arg-c[Asp-Pro-D-Nal(2')-Arg-D-Nal(2')-Lys]-D-Val-D-Phe-NH2 |
| 1711 | TCAM1708 | Val-Arg-Ile-Trp-Arg-Arg-Arg-Arg-c[Asp-Pro-D-Nal(2')-Arg-D-Nal(2')-Lys]-D-Phe-D-Val-NH2 |
| 1712 | TCAM1709 | Val-Arg-Ile-Trp-Arg-Arg-Arg-Arg-c[Asp-His-D-Nal(2')-Arg-D-Nal(2')-Lys]-D-Val-D-Pro-NH2 |
| 1713 | TCAM1710 | Val-Arg-Ile-Trp-Arg-Arg-Arg-Arg-c[Asp-His-D-Nal(2')-Arg-D-Nal(2')-Lys]-D-Pro-D-Val-NH2 |
| 1714 | TCAM1711 | Val-Arg-Ile-Trp-Arg-Arg-Arg-Arg-c[Asp-His-D-Nal(2')-Arg-D-Nal(2')-Lys]-D-Val-D-Phe-NH2 |
| 1715 | TCAM1712 | Val-Arg-Ile-Trp-Arg-Arg-Arg-Arg-c[Asp-His-D-Nal(2')-Arg-D-Nal(2')-Lys]-D-Phe-D-Val-NH2 |
| 1716 | TCAM1713 | Val-Arg-Ile-Trp-Arg-Arg-c[Asp-Arg-Pro-D-Nal(2')-Arg-D-Nal(2')-Arg-Lys]-D-Val-D-Pro-NH2 |
| 1717 | TCAM1714 | Val-Arg-Ile-Trp-Arg-Arg-c[Asp-Arg-Pro-D-Nal(2')-Arg-D-Nal(2')-Arg-Lys]-D-Pro-D-Val-NH2 |
| 1718 | TCAM1715 | Val-Arg-Ile-Trp-Arg-Arg-c[Asp-Arg-Pro-D-Nal(2')-Arg-D-Nal(2')-Arg-Lys]-D-Val-D-Phe-NH2 |
| 1719 | TCAM1716 | Val-Arg-Ile-Trp-Arg-Arg-c[Asp-Arg-Pro-D-Nal(2')-Arg-D-Nal(2')-Arg-Lys]-D-Phe-D-Val-NH2 |
| 1720 | TCAM1717 | Val-Arg-Ile-Trp-Arg-Arg-c[Asp-Arg-His-D-Nal(2')-Arg-D-Nal(2')-Arg-Lys]-D-Val-D-Pro-NH2 |
| 1721 | TCAM1718 | Val-Arg-Ile-Trp-Arg-Arg-c[Asp-Arg-His-D-Nal(2')-Arg-D-Nal(2')-Arg-Lys]-D-Pro-D-Val-NH2 |
| 1722 | TCAM1719 | Val-Arg-Ile-Trp-Arg-Arg-c[Asp-Arg-His-D-Nal(2')-Arg-D-Nal(2')-Arg-Lys]-D-Val-D-Phe-NH2 |
| 1723 | TCAM1720 | Val-Arg-Ile-Trp-Arg-Arg-c[Asp-Arg-His-D-Nal(2')-Arg-D-Nal(2')-Arg-Lys]-D-Phe-D-Val-NH2 |
| 1724 | TCAM1721 | Val-Arg-Ile-Trp-Arg-Arg-c[Asp-His-D-Nal(2')-Arg-Trp-Lys]-Arg-Arg-D-Val-D-Pro-NH2 |
| 1725 | TCAM1722 | Val-Arg-Ile-Trp-Arg-Arg-c[Asp-His-D-Nal(2')-Arg-Trp-Lys]-Arg-Arg-D-Pro-D-Val-NH2 |
| 1726 | TCAM1723 | Val-Arg-Ile-Trp-Arg-Arg-c[Asp-His-D-Nal(2')-Arg-Trp-Lys]-Arg-Arg-D-Val-D-Phe-NH2 |

TABLE 5-continued

Exemplary Anti-microbial peptides

| SEQ NO: | Peptide | Peptide Sequence |
|---|---|---|
| 1727 | TCAM1724 | Val-Arg-Ile-Trp-Arg-Arg-c[Asp-His-D-Nal(2')-Arg-Trp-Lys]-Arg-Arg-D-Phe-D-Val-NH2 |
| 1728 | TCAM1725 | Val-Arg-Ile-Trp-Arg-Arg-c[Asp-Pro-D-Nal(2')-Arg-Trp-Lys]-Arg-Arg-D-Val-D-Pro-NH2 |
| 1729 | TCAM1726 | Val-Arg-Ile-Trp-Arg-Arg-c[Asp-Pro-D-Nal(2')-Arg-Trp-Lys]-Arg-Arg-D-Pro-D-Val-NH2 |
| 1730 | TCAM1727 | Val-Arg-Ile-Trp-Arg-Arg-c[Asp-Pro-D-Nal(2')-Arg-Trp-Lys]-Arg-Arg-D-Val-D-Phe-NH2 |
| 1731 | TCAM1728 | Val-Arg-Ile-Trp-Arg-Arg-c[Asp-Pro-D-Nal(2')-Arg-Trp-Lys]-Arg-Arg-D-Phe-D-Val-NH2 |

Anti-bioflim peptide ABF3 linked to anti-microbial peptides

| SEQ NO: | Peptide | Peptide Sequence |
|---|---|---|
| 1732 | TCAM1729 | Val-Arg-Leu-Ile-Val-Ala-c[Asp-Pro-Arg-Arg-Trp-Trp-Arg-Phe-Lys]-D-Val-D-Pro-NH2 |
| 1733 | TCAM1730 | Val-Arg-Leu-Ile-Val-Ala-c[Asp-Pro-Arg-Arg-Trp-Trp-Arg-Phe-Lys]-D-Val-D-Phe-NH2 |
| 1734 | TCAM1731 | Val-Arg-Leu-Ile-Val-Ala-c[Asp-Pro-Arg-Arg-Trp-Trp-Arg-Phe-Lys]-D-Pro-D-Val-NH2 |
| 1735 | TCAM1732 | Val-Arg-Leu-Ile-Val-Ala-c[Asp-Pro-Arg-Arg-Trp-Trp-Arg-Phe-Lys]-D-Phe-D-Val-NH2 |
| 1736 | TCAM1733 | Val-Arg-Leu-Ile-Val-Ala-c[Asp-Pro-Arg-Arg-Trp-Trp-Tyr-Phe-Lys]-D-Val-D-Pro-NH2 |
| 1737 | TCAM1734 | Val-Arg-Leu-Ile-Val-Ala-c[Asp-Pro-Arg-Arg-Trp-Trp-Tyr-Phe-Lys]-D-Val-D-Phe-NH2 |
| 1738 | TCAM1735 | Val-Arg-Leu-Ile-Val-Ala-c[Asp-Pro-Arg-Arg-Trp-Trp-Tyr-Phe-Lys]-D-Pro-D-Val-NH2 |
| 1739 | TCAM1736 | Val-Arg-Leu-Ile-Val-Ala-c[Asp-Pro-Arg-Arg-Trp-Trp-Tyr-Phe-Lys]-D-Phe-D-Val-NH2 |
| 1740 | TCAM1737 | Val-Arg-Leu-Ile-Val-Ala-c[Asp-Pro-Arg-Arg-Tyr-Tyr-Arg-Phe-Lys]-D-Val-D-Pro-NH2 |
| 1741 | TCAM1738 | Val-Arg-Leu-Ile-Val-Ala-c[Asp-Pro-Arg-Arg-Tyr-Tyr-Arg-Phe-Lys]-D-Val-D-Phe-NH2 |
| 1742 | TCAM1739 | Val-Arg-Leu-Ile-Val-Ala-c[Asp-Pro-Arg-Arg-Tyr-Tyr-Arg-Phe-Lys]-D-Pro-D-Val-NH2 |
| 1743 | TCAM1740 | Val-Arg-Leu-Ile-Val-Ala-c[Asp-Pro-Arg-Arg-Tyr-Tyr-Arg-Phe-Lys]-D-Phe-D-Val-NH2 |
| 1744 | TCAM1741 | Val-Arg-Leu-Ile-Val-Ala-c[Asp-Pro-Arg-Arg-Nal-Nal-Arg-Phe-Lys]-D-Val-D-Pro-NH2 |
| 1745 | TCAM1742 | Val-Arg-Leu-Ile-Val-Ala-c[Asp-Pro-Arg-Arg-Nal-Nal-Arg-Phe-Lys]-D-Val-D-Phe-NH2 |
| 1746 | TCAM1743 | Val-Arg-Leu-Ile-Val-Ala-c[Asp-Pro-Arg-Arg-Nal-Nal-Arg-Phe-Lys]-D-Pro-D-Val-NH2 |
| 1747 | TCAM1744 | Val-Arg-Leu-Ile-Val-Ala-c[Asp-Pro-Arg-Arg-Nal-Nal-Arg-Phe-Lys]-D-Phe-D-Val-NH2 |
| 1748 | TCAM1745 | Val-Arg-Leu-Ile-Val-Ala-c[Asp-Pro-Arg-Arg-Leu-Trp-Leu-Trp-Lys]-D-Val-D-Pro-NH2 |
| 1749 | TCAM1746 | Val-Arg-Leu-Ile-Val-Ala-c[Asp-Pro-Arg-Arg-Leu-Trp-Leu-Trp-Lys]-D-Val-D-Phe-NH2 |
| 1750 | TCAM1747 | Val-Arg-Leu-Ile-Val-Ala-c[Asp-Pro-Arg-Arg-Leu-Trp-Leu-Trp-Lys]-D-Pro-D-Val-NH2 |
| 1751 | TCAM1748 | Val-Arg-Leu-Ile-Val-Ala-c[Asp-Pro-Arg-Arg-Leu-Trp-Leu-Trp-Lys]-D-Phe-D-Val-NH2 |
| 1752 | TCAM1749 | Val-Arg-Leu-Ile-Val-Ala-c[Asp-Pro-Arg-Arg-Leu-Trp-Leu-Trp-Lys]-D-Val-D-Pro-NH2 |
| 1753 | TCAM1750 | Val-Arg-Leu-Ile-Val-Ala-c[Asp-Pro-Arg-Arg-Leu-Trp-Leu-Trp-Lys]-D-Val-D-Phe-NH2 |
| 1754 | TCAM1751 | Val-Arg-Leu-Ile-Val-Ala-c[Asp-Pro-Arg-Arg-Leu-Trp-Leu-Trp-Lys]-D-Pro-D-Val-NH2 |
| 1755 | TCAM1752 | Val-Arg-Leu-Ile-Val-Ala-c[Asp-Pro-Arg-Arg-Leu-Trp-Leu-Trp-Lys]-D-Phe-D-Val-NH2 |
| 1756 | TCAM1753 | Val-Arg-Leu-Ile-Val-Ala-c[Asp-Arg-Arg-Arg-Trp-Leu-Trp-Leu-Trp-Lys]-D-Val-D-Pro-NH2 |
| 1757 | TCAM1754 | Val-Arg-Leu-Ile-Val-Ala-c[Asp-Pro-Arg-Arg-Arg-Trp-Leu-Trp-Leu-Trp-Lys]-D-Val-D-Phe-NH2 |
| 1758 | TCAM1755 | Val-Arg-Leu-Ile-Val-Ala-c[Asp-Pro-Arg-Arg-Arg-Trp-Leu-Trp-Leu-Trp-Lys]-D-Pro-D-Val-NH2 |
| 1759 | TCAM1756 | Val-Arg-Leu-Ile-Val-Ala-c[Asp-Pro-Arg-Arg-Arg-Trp-Leu-Trp-Leu-Trp-Lys]-D-Phe-D-Val-NH2 |
| 1760 | TCAM1757 | Val-Arg-Leu-Ile-Val-Ala-c[Asp-Pro-Arg-Gln-Arg-Arg-Trp-Leu-Trp-Leu-Trp-Lys]-D-Val-D-Pro-NH2 |

TABLE 5-continued

Exemplary Anti-microbial peptides

| SEQ NO: | Peptide | Peptide Sequence |
|---|---|---|
| 1761 | TCAM1758 | Val-Arg-Leu-Ile-Val-Ala-c[Asp-Pro-Arg-Gln-Arg-Arg-Trp-Leu-Trp-Leu-Trp-Lys]-D-Val-D-Phe-NH2 |
| 1762 | TCAM1759 | Val-Arg-Leu-Ile-Val-Ala-c[Asp-Pro-Arg-Gln-Arg-Arg-Trp-Leu-Trp-Leu-Trp-Lys]-D-Pro-D-Val-NH2 |
| 1763 | TCAM1760 | Val-Arg-Leu-Ile-Val-Ala-c[Asp-Pro-Arg-Gln-Arg-Arg-Trp-Leu-Trp-Leu-Trp-Lys]-D-Phe-D-Val-NH2 |
| 1764 | TCAM1761 | Val-Arg-Leu-Ile-Val-Ala-c[Asp-Pro-Trp-Arg-Trp-Trp-Arg-Arg-Lys]-D-Val-D-Phe-NH2 |
| 1765 | TCAM1762 | Val-Arg-Leu-Ile-Val-Ala-c[Asp-Pro-Trp-Arg-Trp-Trp-Arg-Arg-Lys]-D-Pro-D-Val-NH2 |
| 1766 | TCAM1763 | Val-Arg-Leu-Ile-Val-Ala-c[Asp-Pro-Trp-Arg-Trp-Trp-Arg-Arg-Lys]-D-Phe-D-Val-NH2 |
| 1767 | TCAM1764 | Val-Arg-Leu-Ile-Val-Ala-c[Asp-Pro-Trp-Trp-Arg-Arg-Trp-Trp-Arg-Arg-Lys]-D-Val-D-Pro-NH2 |
| 1768 | TCAM1765 | Val-Arg-Leu-Ile-Val-Ala-c[Asp-Pro-Trp-Trp-Arg-Arg-Trp-Trp-Arg-Arg-Lys]-D-Val-D-Phe-NH2 |
| 1769 | TCAM1766 | Val-Arg-Leu-Ile-Val-Ala-c[Asp-Pro-Trp-Trp-Arg-Arg-Trp-Trp-Arg-Arg-Lys]-D-Pro-D-Val-NH2 |
| 1770 | TCAM1767 | Val-Arg-Leu-Ile-Val-Ala-c[Asp-Pro-Trp-Trp-Arg-Arg-Trp-Trp-Arg-Arg-Lys]-D-Phe-D-Val-NH2 |
| 1771 | TCAM1768 | Val-Arg-Leu-Ile-Val-Ala-c[Asp-Pro-Trp-Arg-Trp-Arg-Trp-Arg-Lys]-D-Val-D-Pro-NH2 |
| 1772 | TCAM1769 | Val-Arg-Leu-Ile-Val-Ala-c[Asp-Pro-Trp-Arg-Trp-Arg-Trp-Arg-Lys]-D-Val-D-Phe-NH2 |
| 1773 | TCAM1770 | Val-Arg-Leu-Ile-Val-Ala-c[Asp-Pro-Trp-Arg-Trp-Arg-Trp-Arg-Lys]-D-Pro-D-Val-NH2 |
| 1774 | TCAM1771 | Val-Arg-Leu-Ile-Val-Ala-c[Asp-Pro-Trp-Arg-Trp-Arg-Trp-Arg-Lys]-D-Phe-D-Val-NH2 |
| 1775 | TCAM1772 | Val-Arg-Leu-Ile-Val-Ala-c[Asp-Pro-Arg-Trp-Arg-Trp-Arg-Trp-Lys]-D-Val-D-Pro-NH2 |
| 1776 | TCAM1773 | Val-Arg-Leu-Ile-Val-Ala-c[Asp-Pro-Arg-Trp-Arg-Trp-Arg-Trp-Lys]-D-Val-D-Phe-NH2 |
| 1777 | TCAM1774 | Val-Arg-Leu-Ile-Val-Ala-c[Asp-Pro-Arg-Trp-Arg-Trp-Arg-Trp-Lys]-D-Pro-D-Val-NH2 |
| 1778 | TCAM1775 | Val-Arg-Leu-Ile-Val-Ala-c[Asp-Pro-Arg-Trp-Arg-Trp-Arg-Trp-Lys]-D-Phe-D-Val-NH2 |
| 1779 | TCAM1776 | Val-Arg-Leu-Ile-Val-Ala-c[Asp-Pro-Arg-Trp-Trp-Arg-Arg-Lys]-D-Val-D-Pro-NH2 |
| 1780 | TCAM1777 | Val-Arg-Leu-Ile-Val-Ala-c[Asp-Pro-Arg-Trp-Trp-Arg-Arg-Lys]-D-Val-D-Phe-NH2 |
| 1781 | TCAM1778 | Val-Arg-Leu-Ile-Val-Ala-c[Asp-Pro-Arg-Trp-Trp-Arg-Arg-Lys]-D-Pro-D-Val-NH2 |
| 1782 | TCAM1779 | Val-Arg-Leu-Ile-Val-Ala-c[Asp-Pro-Arg-Trp-Trp-Arg-Arg-Lys]-D-Phe-D-Val-NH2 |
| 1783 | TCAM1780 | Val-Arg-Leu-Ile-Val-Ala-c[Asp-Pro-Trp-Trp-Arg-Arg-Trp-Lys]-D-Val-D-Pro-NH2 |
| 1784 | TCAM1781 | Val-Arg-Leu-Ile-Val-Ala-c[Asp-Pro-Trp-Trp-Arg-Arg-Trp-Lys]-D-Val-D-Phe-NH2 |
| 1785 | TCAM1782 | Val-Arg-Leu-Ile-Val-Ala-c[Asp-Pro-Trp-Trp-Arg-Arg-Trp-Lys]-D-Pro-D-Val-NH2 |
| 1786 | TCAM1783 | Val-Arg-Leu-Ile-Val-Ala-c[Asp-Pro-Trp-Trp-Arg-Arg-Trp-Lys]-D-Phe-D-Val-NH2 |
| 1787 | TCAM1784 | Val-Arg-Leu-Ile-Val-Ala-c[Asp-Pro-Trp-Arg-Trp-Arg-Trp-Lys]-D-Val-D-Pro-NH2 |
| 1788 | TCAM1785 | Val-Arg-Leu-Ile-Val-Ala-c[Asp-Pro-Trp-Arg-Trp-Arg-Trp-Lys]-D-Val-D-Phe-NH2 |
| 1789 | TCAM1786 | Val-Arg-Leu-Ile-Val-Ala-c[Asp-Pro-Trp-Arg-Trp-Arg-Trp-Lys]-D-Pro-D-Val-NH2 |
| 1790 | TCAM1787 | Val-Arg-Leu-Ile-Val-Ala-c[Asp-Pro-Trp-Arg-Trp-Arg-Trp-Lys]-D-Phe-D-Val-NH2 |
| 1791 | TCAM1788 | Val-Arg-Leu-Ile-Val-Ala-c[Asp-Pro-Arg-Trp-Arg-Trp-Arg-Lys]-D-Val-D-Pro-NH2 |
| 1792 | TCAM1789 | Val-Arg-Leu-Ile-Val-Ala-c[Asp-Pro-Arg-Trp-Arg-Trp-Arg-Lys]-D-Val-D-Phe-NH2 |
| 1793 | TCAM1790 | Val-Arg-Leu-Ile-Val-Ala-c[Asp-Pro-Arg-Trp-Arg-Trp-Arg-Lys]-D-Pro-D-Val-NH2 |
| 1794 | TCAM1791 | Val-Arg-Leu-Ile-Val-Ala-c[Asp-Pro-Arg-Trp-Arg-Trp-Arg-Lys]-D-Phe-D-Val-NH2 |

TABLE 5-continued

Exemplary Anti-microbial peptides

| SEQ NO: | Peptide | Peptide Sequence |
|---|---|---|
| 1795 | TCAM1792 | Val-Arg-Leu-Ile-Val-Ala-c[Asp-Pro-Trp-Arg-Tyr-Arg-Trp-Lys]-D-Val-D-Pro-NH2 |
| 1796 | TCAM1793 | Val-Arg-Leu-Ile-Val-Ala-c[Asp-Pro-Trp-Arg-Tyr-Arg-Trp-Lys]-D-Val-D-Phe-NH2 |
| 1797 | TCAM1794 | Val-Arg-Leu-Ile-Val-Ala-c[Asp-Pro-Trp-Arg-Tyr-Arg-Trp-Lys]-D-Pro-D-Val-NH2 |
| 1798 | TCAM1795 | Val-Arg-Leu-Ile-Val-Ala-c[Asp-Pro-Trp-Arg-Tyr-Arg-Trp-Lys]-D-Phe-D-Val-NH2 |
| 1799 | TCAM1796 | Val-Arg-Leu-Ile-Val-Ala-c[Asp-Pro-Trp-Arg-Trp-Arg-Tyr-Lys]-D-Val-D-Pro-NH2 |
| 1800 | TCAM1797 | Val-Arg-Leu-Ile-Val-Ala-c[Asp-Pro-Trp-Arg-Trp-Arg-Tyr-Lys]-D-Val-D-Phe-NH2 |
| 1801 | TCAM1798 | Val-Arg-Leu-Ile-Val-Ala-c[Asp-Pro-Trp-Arg-Trp-Arg-Tyr-Lys]-D-Pro-D-Val-NH2 |
| 1802 | TCAM1799 | Val-Arg-Leu-Ile-Val-Ala-c[Asp-Pro-Trp-Arg-Trp-Arg-Tyr-Lys]-D-Phe-D-Val-NH2 |
| 1803 | TCAM1800 | Val-Arg-Leu-Ile-Val-Ala-c[Asp-Pro-Trp-Arg-Trp-Arg-Lys]-D-Val-D-Pro-NH2 |
| 1804 | TCAM1801 | Val-Arg-Leu-Ile-Val-Ala-c[Asp-Pro-Trp-Arg-Trp-Arg-Lys]-D-Val-D-Phe-NH2 |
| 1805 | TCAM1802 | Val-Arg-Leu-Ile-Val-Ala-c[Asp-Pro-Trp-Arg-Trp-Arg-Lys]-D-Pro-D-Val-NH2 |
| 1806 | TCAM1803 | Val-Arg-Leu-Ile-Val-Ala-c[Asp-Pro-Trp-Arg-Trp-Arg-Lys]-D-Phe-D-Val-NH2 |
| 1807 | TCAM1804 | Val-Arg-Leu-Ile-Val-Ala-c[Asp-Pro-Trp-Arg-Arg-Trp-Lys]-D-Val-D-Pro-NH2 |
| 1808 | TCAM1805 | Val-Arg-Leu-Ile-Val-Ala-c[Asp-Pro-Trp-Arg-Arg-Trp-Lys]-D-Val-D-Phe-NH2 |
| 1809 | TCAM1806 | Val-Arg-Leu-Ile-Val-Ala-c[Asp-Pro-Trp-Arg-Arg-Trp-Lys]-D-Pro-D-Val-NH2 |
| 1810 | TCAM1807 | Val-Arg-Leu-Ile-Val-Ala-c[Asp-Pro-Trp-Arg-Arg-Trp-Lys]-D-Phe-D-Val-NH2 |
| 1811 | TCAM1808 | Val-Arg-Leu-Ile-Val-Ala-c[Asp-Pro-Arg-Trp-Trp-Arg-Lys]-D-Val-D-Pro-NH2 |
| 1812 | TCAM1809 | Val-Arg-Leu-Ile-Val-Ala-c[Asp-Pro-Arg-Trp-Trp-Arg-Lys]-D-Val-D-Phe-NH2 |
| 1813 | TCAM1810 | Val-Arg-Leu-Ile-Val-Ala-c[Asp-Pro-Arg-Trp-Trp-Arg-Lys]-D-Pro-D-Val-NH2 |
| 1814 | TCAM1811 | Val-Arg-Leu-Ile-Val-Ala-c[Asp-Pro-Arg-Trp-Trp-Arg-Lys]-D-Phe-D-Val-NH2 |
| 1815 | TCAM1812 | Val-Arg-Leu-Ile-Val-Ala-c[Asp-Pro-Trp-Arg-Trp-Lys]-D-Val-D-Pro-NH2 |
| 1816 | TCAM1813 | Val-Arg-Leu-Ile-Val-Ala-c[Asp-Pro-Trp-Arg-Trp-Lys]-D-Val-D-Phe-NH2 |
| 1817 | TCAM1814 | Val-Arg-Leu-Ile-Val-Ala-c[Asp-Pro-Trp-Arg-Trp-Lys]-D-Pro-D-Val-NH2 |
| 1818 | TCAM1815 | Val-Arg-Leu-Ile-Val-Ala-c[Asp-Pro-Trp-Arg-Trp-Lys]-D-Phe-D-Val-NH2 |
| 1819 | TCAM1816 | Val-Arg-Leu-Ile-Val-Ala-c[Asp-Pro-Arg-Trp-Arg-Lys]-D-Val-D-Pro-NH2 |
| 1820 | TCAM1817 | Val-Arg-Leu-Ile-Val-Ala-c[Asp-Pro-Arg-Trp-Arg-Lys]-D-Val-D-Phe-NH2 |
| 1821 | TCAM1818 | Val-Arg-Leu-Ile-Val-Ala-c[Asp-Pro-Arg-Trp-Arg-Lys]-D-Pro-D-Val-NH2 |
| 1822 | TCAM1819 | Val-Arg-Leu-Ile-Val-Ala-c[Asp-Pro-Arg-Trp-Arg-Lys]-D-Phe-D-Val-NH2 |
| 1823 | TCAM1820 | -Val-Arg-Leu-Ile-Val-Ala-c[Asp-Arg-Arg-Trp-Trp-Arg-Phe-Lys]-D-Val-D-Pro-NH2 |
| 1824 | TCAM1821 | Val-Arg-Leu-Ile-Val-Ala-c[Asp-Arg-Arg-Trp-Trp-Arg-Phe-Lys]-D-Val-D-Phe-NH2 |
| 1825 | TCAM1822 | Val-Arg-Leu-Ile-Val-Ala-c[Asp-Arg-Arg-Trp-Trp-Arg-Phe-Lys]-D-Pro-D-Val-NH2 |
| 1826 | TCAM1823 | Val-Arg-Leu-Ile-Val-Ala-c[Asp-Arg-Arg-Trp-Trp-Arg-Phe-Lys]-D-Phe-D-Val-NH2 |
| 1827 | TCAM1824 | Val-Arg-Leu-Ile-Val-Ala-c[Asp-Arg-Arg-Trp-Trp-Arg-Phe-Lys]-D-Val-D-Pro-NH2 |
| 1828 | TCAM1825 | Val-Arg-Leu-Ile-Val-Ala-c[Asp-Arg-Arg-Trp-Trp-Arg-Phe-Lys]-D-Val-D-Phe-NH2 |
| 1829 | TCAM1826 | Val-Arg-Leu-Ile-Val-Ala-c[Asp-Arg-Arg-Trp-Trp-Arg-Phe-Lys]-D-Pro-D-Val-NH2 |
| 1830 | TCAM1827 | Val-Arg-Leu-Ile-Val-Ala-c[Asp-Arg-Arg-Trp-Trp-Arg-Phe-Lys]-D-Phe-D-Val-NH2 |
| 1831 | TCAM1828 | Val-Arg-Leu-Ile-Val-Ala-c[Asp-Arg-Arg-Tyr-Tyr-Arg-Phe-Lys]-D-Val-D-Pro-NH2 |

TABLE 5-continued

Exemplary Anti-microbial peptides

| SEQ NO: | Peptide | Peptide Sequence |
|---|---|---|
| 1832 | TCAM1829 | Val-Arg-Leu-Ile-Val-Ala-c[Asp-Arg-Arg-Tyr-Tyr-Arg-Phe-Lys]-D-Val-D-Phe-NH2 |
| 1833 | TCAM1830 | Val-Arg-Leu-Ile-Val-Ala-c[Asp-Arg-Arg-Tyr-Tyr-Arg-Phe-Lys]-D-Pro-D-Val-NH2 |
| 1834 | TCAM1831 | Val-Arg-Leu-Ile-Val-Ala-c[Asp-Arg-Arg-Tyr-Tyr-Arg-Phe-Lys]-D-Phe-D-Val-NH2 |
| 1835 | TCAM1832 | Val-Arg-Leu-Ile-Val-Ala-c[Asp-Arg-Arg-Nal-Nal-Arg-Phe-Lys]-D-Val-D-Pro-NH2 |
| 1836 | TCAM1833 | Val-Arg-Leu-Ile-Val-Ala-c[Asp-Arg-Arg-Nal-Nal-Arg-Phe-Lys]-D-Val-D-Phe-NH2 |
| 1837 | TCAM1834 | Val-Arg-Leu-Ile-Val-Ala-c[Asp-Arg-Arg-Nal-Nal-Arg-Phe-Lys]-D-Pro-D-Val-NH2 |
| 1838 | TCAM1835 | Val-Arg-Leu-Ile-Val-Ala-c[Asp-Arg-Arg-Nal-Nal-Arg-Phe-Lys]-D-Phe-D-Val-NH2 |
| 1839 | TCAM1836 | Val-Arg-Leu-Ile-Val-Ala-c[Asp-Arg-Arg-Leu-Trp-Leu-Trp-Lys]-D-Val-D-Pro-NH2 |
| 1840 | TCAM1837 | Val-Arg-Leu-Ile-Val-Ala-c[Asp-Arg-Arg-Leu-Trp-Leu-Trp-Lys]-D-Val-D-Phe-NH2 |
| 1841 | TCAM1838 | Val-Arg-Leu-Ile-Val-Ala-c[Asp-Arg-Arg-Leu-Trp-Leu-Trp-Lys]-D-Pro-D-Val-NH2 |
| 1842 | TCAM1839 | Val-Arg-Leu-Ile-Val-Ala-c[Asp-Arg-Arg-Leu-Trp-Leu-Trp-Lys]-D-Phe-D-Val-NH2 |
| 1843 | TCAM1840 | Val-Arg-Leu-Ile-Val-Ala-c[Asp-Arg-Arg-Leu-Trp-Leu-Trp-Lys]-D-Val-D-Pro-NH2 |
| 1844 | TCAM1841 | Val-Arg-Leu-Ile-Val-Ala-c[Asp-Arg-Arg-Leu-Trp-Leu-Trp-Lys]-D-Val-D-Phe-NH2 |
| 1845 | TCAM1842 | Val-Arg-Leu-Ile-Val-Ala-c[Asp-Arg-Arg-Leu-Trp-Leu-Trp-Lys]-D-Pro-D-Val-NH2 |
| 1846 | TCAM1843 | Val-Arg-Leu-Ile-Val-Ala-c[Asp-Arg-Arg-Leu-Trp-Leu-Trp-Lys]-D-Phe-D-Val-NH2 |
| 1847 | TCAM1844 | Val-Arg-Leu-Ile-Val-Ala-c[Asp-Arg-Arg-Arg-Trp-Leu-Trp-Leu-Trp-Lys]-D-Val-D-Pro-NH2 |
| 1848 | TCAM1845 | Val-Arg-Leu-Ile-Val-Ala-c[Asp-Arg-Arg-Arg-Trp-Leu-Trp-Leu-Trp-Lys]-D-Val-D-Phe-NH2 |
| 1849 | TCAM1846 | Val-Arg-Leu-Ile-Val-Ala-c[Asp-Arg-Arg-Arg-Trp-Leu-Trp-Leu-Trp-Lys]-D-Pro-D-Val-NH2 |
| 1850 | TCAM1847 | Val-Arg-Leu-Ile-Val-Ala-c[Asp-Arg-Arg-Arg-Trp-Leu-Trp-Leu-Trp-Lys]-D-Phe-D-Val-NH2 |
| 1851 | TCAM1848 | Val-Arg-Leu-Ile-Val-Ala-c[Asp-Arg-Gln-Arg-Arg-Trp-Leu-Trp-Leu-Trp-Lys]-D-Val-D-Pro-NH2 |
| 1852 | TCAM1849 | Val-Arg-Leu-Ile-Val-Ala-c[Asp-Arg-Gln-Arg-Arg-Trp-Leu-Trp-Leu-Trp-Lys]-D-Val-D-Phe-NH2 |
| 1853 | TCAM1850 | Val-Arg-Leu-Ile-Val-Ala-c[Asp-Arg-Gln-Arg-Arg-Trp-Leu-Trp-Leu-Trp-Lys]-D-Pro-D-Val-NH2 |
| 1854 | TCAM1851 | Val-Arg-Leu-Ile-Val-Ala-c[Asp-Arg-Gln-Arg-Arg-Trp-Leu-Trp-Leu-Trp-Lys]-D-Phe-D-Val-NH2 |
| 1855 | TCAM1852 | Val-Arg-Leu-Ile-Val-Ala-c[Asp-Trp-Arg-Trp-Trp-Arg-Arg-Lys]-D-Val-D-Pro-NH2 |
| 1856 | TCAM1853 | Val-Arg-Leu-Ile-Val-Ala-c[Asp-Trp-Arg-Trp-Trp-Arg-Arg-Lys]-D-Val-D-Phe-NH2 |
| 1857 | TCAM1854 | Val-Arg-Leu-Ile-Val-Ala-c[Asp-Trp-Arg-Trp-Trp-Arg-Arg-Lys]-D-Pro-D-Val-NH2 |
| 1858 | TCAM1855 | Val-Arg-Leu-Ile-Val-Ala-c[Asp-Trp-Arg-Trp-Trp-Arg-Arg-Lys]-D-Phe-D-Val-NH2 |
| 1859 | TCAM1856 | Val-Arg-Leu-Ile-Val-Ala-c[Asp-Trp-Trp-Arg-Arg-Trp-Trp-Arg-Arg-Lys]-D-Val-D-Pro-NH2 |
| 1860 | TCAM1857 | Val-Arg-Leu-Ile-Val-Ala-c[Asp-Trp-Trp-Arg-Arg-Trp-Trp-Arg-Arg-Lys]-D-Val-D-Phe-NH2 |
| 1861 | TCAM1858 | Val-Arg-Leu-Ile-Val-Ala-c[Asp-Trp-Trp-Arg-Arg-Trp-Trp-Arg-Arg-Lys]-D-Pro-D-Val-NH2 |
| 1862 | TCAM1859 | Val-Arg-Leu-Ile-Val-Ala-c[Asp-Trp-Trp-Arg-Arg-Trp-Trp-Arg-Arg-Lys]-D-Phe-D-Val-NH2 |

TABLE 5-continued

Exemplary Anti-microbial peptides

| SEQ NO: | Peptide | Peptide Sequence |
|---|---|---|
| 1863 | TCAM1860 | Val-Arg-Leu-Ile-Val-Ala-c[Asp-Trp-Arg-Trp-Arg-Trp-Arg-Lys]-D-Val-D-Pro-NH2 |
| 1864 | TCAM1861 | Val-Arg-Leu-Ile-Val-Ala-c[Asp-Trp-Arg-Trp-Arg-Trp-Arg-Lys]-D-Val-D-Phe-NH2 |
| 1865 | TCAM1862 | Val-Arg-Leu-Ile-Val-Ala-c[Asp-Trp-Arg-Trp-Arg-Trp-Arg-Lys]-D-Pro-D-Val-NH2 |
| 1866 | TCAM1863 | Val-Arg-Leu-Ile-Val-Ala-c[Asp-Trp-Arg-Trp-Arg-Trp-Arg-Lys]-D-Phe-D-Val-NH2 |
| 1867 | TCAM1864 | Val-Arg-Leu-Ile-Val-Ala-c[Asp-Arg-Trp-Arg-Trp-Arg-Trp-Lys]-D-Val-D-Pro-NH2 |
| 1868 | TCAM1865 | Val-Arg-Leu-Ile-Val-Ala-c[Asp-Arg-Trp-Arg-Trp-Arg-Trp-Lys]-D-Val-D-Phe-NH2 |
| 1869 | TCAM1866 | Val-Arg-Leu-Ile-Val-Ala-c[Asp-Arg-Trp-Arg-Trp-Arg-Trp-Lys]-D-Pro-D-Val-NH2 |
| 1870 | TCAM1867 | Val-Arg-Leu-Ile-Val-Ala-c[Asp-Arg-Trp-Arg-Trp-Arg-Trp-Lys]-D-Phe-D-Val-NH2 |
| 1871 | TCAM1868 | Val-Arg-Leu-Ile-Val-Ala-c[Asp-Arg-Trp-Trp-Arg-Arg-Lys]-D-Val-D-Pro-NH2 |
| 1872 | TCAM1869 | Val-Arg-Leu-Ile-Val-Ala-c[Asp-Arg-Trp-Trp-Arg-Arg-Lys]-D-Val-D-Phe-NH2 |
| 1873 | TCAM1870 | Val-Arg-Leu-Ile-Val-Ala-c[Asp-Arg-Trp-Trp-Arg-Arg-Lys]-D-Pro-D-Val-NH2 |
| 1874 | TCAM1871 | Val-Arg-Leu-Ile-Val-Ala-c[Asp-Arg-Trp-Trp-Arg-Arg-Lys]-D-Phe-D-Val-NH2 |
| 1875 | TCAM1872 | Val-Arg-Leu-Ile-Val-Ala-c[Asp-Arg-Trp-Arg-Trp-Arg-Lys]-D-Val-D-Pro-NH2 |
| 1876 | TCAM1873 | Val-Arg-Leu-Ile-Val-Ala-c[Asp-Arg-Trp-Arg-Trp-Arg-Lys]-D-Val-D-Phe-NH2 |
| 1877 | TCAM1874 | Val-Arg-Leu-Ile-Val-Ala-c[Asp-Arg-Trp-Arg-Trp-Arg-Lys]-D-Pro-D-Val-NH2 |
| 1878 | TCAM1875 | Val-Arg-Leu-Ile-Val-Ala-c[Asp-Arg-Trp-Arg-Trp-Arg-Lys]-D-Phe-D-Val-NH2 |
| 1879 | TCAM1876 | Val-Arg-Leu-Ile-Val-Ala-c[Asp-Trp-Trp-Arg-Arg-Trp-Lys]-D-Val-D-Pro-NH2 |
| 1880 | TCAM1877 | Val-Arg-Leu-Ile-Val-Ala-c[Asp-Trp-Trp-Arg-Arg-Trp-Lys]-D-Val-D-Phe-NH2 |
| 1881 | TCAM1878 | Val-Arg-Leu-Ile-Val-Ala-c[Asp-Trp-Trp-Arg-Arg-Trp-Lys]-D-Pro-D-Val-NH2 |
| 1882 | TCAM1879 | Val-Arg-Leu-Ile-Val-Ala-c[Asp-Trp-Trp-Arg-Arg-Trp-Lys]-D-Phe-D-Val-NH2 |
| 1883 | TCAM1880 | Val-Arg-Leu-Ile-Val-Ala-c[Asp-Trp-Arg-Trp-Arg-Trp-Lys]-D-Val-D-Pro-NH2 |
| 1884 | TCAM1881 | Val-Arg-Leu-Ile-Val-Ala-c[Asp-Trp-Arg-Trp-Arg-Trp-Lys]-D-Val-D-Phe-NH2 |
| 1885 | TCAM1882 | Val-Arg-Leu-Ile-Val-Ala-c[Asp-Trp-Arg-Trp-Arg-Trp-Lys]-D-Pro-D-Val-NH2 |
| 1886 | TCAM1883 | Val-Arg-Leu-Ile-Val-Ala-c[Asp-Trp-Arg-Trp-Arg-Trp-Lys]-D-Phe-D-Val-NH2 |
| 1887 | TCAM1884 | Val-Arg-Leu-Ile-Val-Ala-c[Asp-Trp-Arg-Tyr-Arg-Trp-Lys]-D-Val-D-Pro-NH2 |
| 1888 | TCAM1885 | Val-Arg-Leu-Ile-Val-Ala-c[Asp-Trp-Arg-Tyr-Arg-Trp-Lys]-D-Val-D-Phe-NH2 |
| 1889 | TCAM1886 | Val-Arg-Leu-Ile-Val-Ala-c[Asp-Trp-Arg-Tyr-Arg-Trp-Lys]-D-Pro-D-Val-NH2 |
| 1890 | TCAM1887 | Val-Arg-Leu-Ile-Val-Ala-c[Asp-Trp-Arg-Tyr-Arg-Trp-Lys]-D-Phe-D-Val-NH2 |
| 1891 | TCAM1888 | Val-Arg-Leu-Ile-Val-Ala-c[Asp-Trp-Arg-Trp-Arg-Tyr-Lys]-D-Val-D-Pro-NH2 |
| 1892 | TCAM1889 | Val-Arg-Leu-Ile-Val-Ala-c[Asp-Trp-Arg-Trp-Arg-Tyr-Lys]-D-Val-D-Phe-NH2 |
| 1893 | TCAM1890 | Val-Arg-Leu-Ile-Val-Ala-c[Asp-Trp-Arg-Trp-Arg-Tyr-Lys]-D-Pro-D-Val-NH2 |
| 1894 | TCAM1891 | Val-Arg-Leu-Ile-Val-Ala-c[Asp-Trp-Arg-Trp-Arg-Tyr-Lys]-D-Phe-D-Val-NH2 |
| 1895 | TCAM1892 | Val-Arg-Leu-Ile-Val-Ala-c[Asp-Trp-Arg-Trp-Arg-Lys]-D-Val-D-Pro-NH2 |
| 1896 | TCAM1893 | Val-Arg-Leu-Ile-Val-Ala-c[Asp-Trp-Arg-Trp-Arg-Lys]-D-Val-D-Phe-NH2 |
| 1897 | TCAM1894 | Val-Arg-Leu-Ile-Val-Ala-c[Asp-Trp-Arg-Trp-Arg-Lys]-D-Pro-D-Val-NH2 |
| 1898 | TCAM1895 | Val-Arg-Leu-Ile-Val-Ala-c[Asp-Trp-Arg-Trp-Arg-Lys]-D-Phe-D-Val-NH2 |
| 1899 | TCAM1896 | Val-Arg-Leu-Ile-Val-Ala-c[Asp-Trp-Arg-Arg-Trp-Lys]-D-Val-D-Pro-NH2 |

TABLE 5-continued

Exemplary Anti-microbial peptides

| SEQ NO: | Peptide | Peptide Sequence |
|---|---|---|
| 1900 | TCAM1897 | Val-Arg-Leu-Ile-Val-Ala-c[Asp-Trp-Arg-Arg-Trp-Lys]-D-Val-D-Phe-NH2 |
| 1901 | TCAM1898 | Val-Arg-Leu-Ile-Val-Ala-c[Asp-Trp-Arg-Arg-Trp-Lys]-D-Pro-D-Val-NH2 |
| 1902 | TCAM1899 | Val-Arg-Leu-Ile-Val-Ala-c[Asp-Trp-Arg-Arg-Trp-Lys]-D-Phe-D-Val-NH2 |
| 1903 | TCAM1900 | Val-Arg-Leu-Ile-Val-Ala-c[Asp-Arg-Trp-Trp-Arg-Lys]-D-Val-D-Pro-NH2 |
| 1904 | TCAM1901 | Val-Arg-Leu-Ile-Val-Ala-c[Asp-Arg-Trp-Trp-Arg-Lys]-D-Val-D-Phe-NH2 |
| 1905 | TCAM1902 | Val-Arg-Leu-Ile-Val-Ala-c[Asp-Arg-Trp-Trp-Arg-Lys]-D-Pro-D-Val-NH2 |
| 1906 | TCAM1903 | Val-Arg-Leu-Ile-Val-Ala-c[Asp-Arg-Trp-Trp-Arg-Lys]-D-Phe-D-Val-NH2 |
| 1907 | TCAM1904 | Val-Arg-Leu-Ile-Val-Ala-c[Asp-Trp-Arg-Trp-Lys]-D-Val-D-Pro-NH2 |
| 1908 | TCAM1905 | Val-Arg-Leu-Ile-Val-Ala-c[Asp-Trp-Arg-Trp-Lys]-D-Val-D-Phe-NH2 |
| 1909 | TCAM1906 | Val-Arg-Leu-Ile-Val-Ala-c[Asp-Trp-Arg-Trp-Lys]-D-Pro-D-Val-NH2 |
| 1910 | TCAM1907 | Val-Arg-Leu-Ile-Val-Ala-c[Asp-Trp-Arg-Trp-Lys]-D-Phe-D-Val-NH2 |
| 1911 | TCAM1908 | Val-Arg-Leu-Ile-Val-Ala-c[Asp-Arg-Trp-Arg-Lys]-D-Val-D-Pro-NH2 |
| 1912 | TCAM1909 | Val-Arg-Leu-Ile-Val-Ala-c[Asp-Arg-Trp-Arg-Lys]-D-Val-D-Phe-NH2 |
| 1913 | TCAM1910 | Val-Arg-Leu-Ile-Val-Ala-c[Asp-Arg-Trp-Arg-Lys]-D-Pro-D-Val-NH2 |
| 1914 | TCAM1911 | Val-Arg-Leu-Ile-Val-Ala-c[Asp-Arg-Trp-Arg-Lys]-D-Phe-D-Val-NH2 |
| 1915 | TCAM1912 | Val-Arg-Leu-Ile-Val-Ala-c[Asp-His-D-Nal(2')-Arg-Trp-Lys]-D-Val-D-Pro-NH2 |
| 1916 | TCAM1913 | Val-Arg-Leu-Ile-Val-Ala-c[Asp-His-D-Nal(2')-Arg-Trp-Lys]-D-Pro-D-Val-NH2 |
| 1917 | TCAM1914 | Val-Arg-Leu-Ile-Val-Ala-c[Asp-His-D-Nal(2')-Arg-Trp-Lys]-D-Val-D-Phe-NH2 |
| 1918 | TCAM1915 | Val-Arg-Leu-Ile-Val-Ala-c[Asp-His-D-Nal(2')-Arg-Trp-Lys]-D-Phe-D-Val-NH2 |
| 1919 | TCAM1916 | Val-Arg-Leu-Ile-Val-Ala-c[Asp-Pro-D-Nal(2')-Arg-Trp-Lys]-D-Val-D-Pro-NH2 |
| 1920 | TCAM1917 | Val-Arg-Leu-Ile-Val-Ala-c[Asp-Pro-D-Nal(2')-Arg-Trp-Lys]-D-Pro-D-Val-NH2 |
| 1921 | TCAM1918 | Val-Arg-Leu-Ile-Val-Ala-c[Asp-Pro-D-Nal(2')-Arg-Trp-Lys]-D-Val-D-Phe-NH2 |
| 1922 | TCAM1919 | Val-Arg-Leu-Ile-Val-Ala-c[Asp-Pro-D-Nal(2')-Arg-Trp-Lys]-D-Phe-D-Val-NH2 |
| 1923 | TCAM1920 | Val-Arg-Leu-Ile-Val-Ala-c[Asp-Arg-Arg-Nal(2')-Arg-Trp-Lys]-D-Val-D-Pro-NH2 |
| 1924 | TCAM1921 | Val-Arg-Leu-Ile-Val-Ala-c[Asp-Arg-Arg-Nal(2')-Arg-Trp-Lys]-D-Pro-D-Val-NH2 |
| 1925 | TCAM1922 | Val-Arg-Leu-Ile-Val-Ala-c[Asp-Arg-Arg-Nal(2')-Arg-Trp-Lys]-D-Val-D-Phe-NH2 |
| 1926 | TCAM1923 | Val-Arg-Leu-Ile-Val-Ala-c[Asp-Arg-Arg-Nal(2')-Arg-Trp-Lys]-D-Phe-D-Val-NH2 |
| 1927 | TCAM1924 | Val-Arg-Leu-Ile-Val-Ala-c[Asp-Arg-Arg-Pro-Nal(2')-Arg-Trp-Lys]-D-Val-D-Pro-NH2 |
| 1928 | TCAM1925 | Val-Arg-Leu-Ile-Val-Ala-c[Asp-Arg-Arg-Pro-D-Nal(2')-Arg-Trp-Lys]-D-Pro-D-Val-NH2 |
| 1929 | TCAM1926 | Val-Arg-Leu-Ile-Val-Ala-c[Asp-Arg-Arg-Pro-D-Nal(2')-Arg-Trp-Lys]-D-Val-D-Phe-NH2 |
| 1930 | TCAM1927 | Val-Arg-Leu-Ile-Val-Ala-c[Asp-Arg-Arg-Pro-Nal(2')-Arg-Trp-Lys]-D-Phe-D-Val-NH2 |
| 1931 | TCAM1928 | Val-Arg-Leu-Ile-Val-Ala-c[Asp-Arg-D-Nal(2')-Arg-Trp-Lys]-D-Val-D-Pro-NH2 |
| 1932 | TCAM1929 | Val-Arg-Leu-Ile-Val-Ala-c[Asp-Arg-D-Nal(2')-Arg-Trp-Lys]-D-Pro-D-Val-NH2 |
| 1933 | TCAM1930 | Val-Arg-Leu-Ile-Val-Ala-c[Asp-Arg-D-Nal(2')-Arg-Trp-Lys]-D-Val-D-Phe-NH2 |
| 1934 | TCAM1931 | Val-Arg-Leu-Ile-Val-Ala-c[Asp-Arg-D-Nal(2')-Arg-Trp-Lys]-D-Phe-D-Val-NH2 |
| 1935 | TCAM1932 | Val-Arg-Leu-Ile-Val-Ala-c[Asp-Arg-Pro-D-Nal(2')-Arg-Trp-Lys]-D-Val-D-Pro-NH2 |
| 1936 | TCAM1933 | Val-Arg-Leu-Ile-Val-Ala-c[Asp-Arg-Pro-D-Nal(2')-Arg-Trp-Lys]-D-Pro-D-Val-NH2 |
| 1937 | TCAM1934 | Val-Arg-Leu-Ile-Val-Ala-c[Asp-Arg-Pro-D-Nal(2')-Arg-Trp-Lys]-D-Val-D-Phe-NH2 |

TABLE 5-continued

Exemplary Anti-microbial peptides

| SEQ NO: | Peptide | Peptide Sequence |
|---|---|---|
| 1938 | TCAM1935 | Val-Arg-Leu-Ile-Val-Ala-c[Asp-Arg-Pro-D-Nal(2')-Arg-Trp-Lys]-D-Phe-D-Val-NH2 |
| 1939 | TCAM1936 | Val-Arg-Leu-Ile-Val-Ala-Arg-Arg-c[Asp-Pro-D-Nal(2')-Arg-Trp-Lys]-D-Val-D-Pro-NH2 |
| 1940 | TCAM1937 | Val-Arg-Leu-Ile-Val-Ala-Arg-Arg-c[Asp-Pro-D-Nal(2')-Arg-Trp-Lys]-D-Pro-D-Val-NH2 |
| 1941 | TCAM1938 | Val-Arg-Leu-Ile-Val-Ala-Arg-Arg-c[Asp-Pro-D-Nal(2')-Arg-Trp-Lys]-D-Val-D-Phe-NH2 |
| 1942 | TCAM1939 | Val-Arg-Leu-Ile-Val-Ala-Arg-Arg-c[Asp-Pro-D-Nal(2')-Arg-Trp-Lys]-D-Phe-D-Val-NH2 |
| 1943 | TCAM1940 | Val-Arg-Leu-Ile-Val-Ala-Arg-Arg-c[Asp-His-D-Nal(2')-Arg-Trp-Lys]-D-Val-D-Pro-NH2 |
| 1944 | TCAM1941 | Val-Arg-Leu-Ile-Val-Ala-Arg-Arg-c[Asp-His-D-Nal(2')-Arg-Trp-Lys]-D-Pro-D-Val-NH2 |
| 1945 | TCAM1942 | Val-Arg-Leu-Ile-Val-Ala-Arg-Arg-c[Asp-His-D-Nal(2')-Arg-Trp-Lys]-D-Val-D-Phe-NH2 |
| 1946 | TCAM1943 | Val-Arg-Leu-Ile-Val-Ala-Arg-Arg-c[Asp-His-D-Nal(2')-Arg-Trp-Lys]-D-Phe-D-Val-NH2 |
| 1947 | TCAM1944 | Val-Arg-Leu-Ile-Val-Ala-c[Asp-Arg-Pro-D-Nal(2')-Arg-Trp-Arg-Lys]-D-Val-D-Pro-NH2 |
| 1948 | TCAM1945 | Val-Arg-Leu-Ile-Val-Ala-c[Asp-Arg-Pro-D-Nal(2')-Arg-Trp-Arg-Lys]-D-Pro-D-Val-NH2 |
| 1949 | TCAM1946 | Val-Arg-Leu-Ile-Val-Ala-c[Asp-Arg-Pro-D-Nal(2')-Arg-Trp-Arg-Lys]-D-Val-D-Phe-NH2 |
| 1950 | TCAM1947 | Val-Arg-Leu-Ile-Val-Ala-c[Asp-Arg-Pro-D-Nal(2')-Arg-Trp-Arg-Lys]-D-Phe-D-Val-NH2 |
| 1951 | TCAM1948 | Val-Arg-Leu-Ile-Val-Ala-c[Asp-Arg-His-D-Nal(2')-Arg-Trp-Arg-Lys]-D-Val-D-Pro-NH2 |
| 1952 | TCAM1949 | Val-Arg-Leu-Ile-Val-Ala-c[Asp-Arg-His-D-Nal(2')-Arg-Trp-Arg-Lys]-D-Pro-D-Val-NH2 |
| 1953 | TCAM1950 | Val-Arg-Leu-Ile-Val-Ala-c[Asp-Arg-His-D-Nal(2')-Arg-Trp-Arg-Lys]-D-Val-D-Phe-NH2 |
| 1954 | TCAM1951 | Val-Arg-Leu-Ile-Val-Ala-c[Asp-Arg-His-D-Nal(2')-Arg-Trp-Arg-Lys]-D-Phe-D-Val-NH2 |
| 1955 | TCAM1952 | Val-Arg-Leu-Ile-Val-Ala-c[Asp-His-D-Nal(2')-Arg-D-Nal(2')-Lys]-D-Val-D-Phe-NH2 |
| 1956 | TCAM1953 | Val-Arg-Leu-Ile-Val-Ala-c[Asp-His-D-Nal(2')-Arg-D-Nal(2')-Lys]-D-Phe-D-Val-NH2 |
| 1957 | TCAM1954 | Val-Arg-Leu-Ile-Val-Ala-c[Asp-Pro-D-Nal(2')-Arg-D-Nal(2')-Lys]-D-Val-D-Pro-NH2 |
| 1958 | TCAM1955 | Val-Arg-Leu-Ile-Val-Ala-c[Asp-Pro-D-Nal(2')-Arg-D-Nal(2')-Lys]-D-Pro-D-Val-NH2 |
| 1959 | TCAM1956 | Val-Arg-Leu-Ile-Val-Ala-c[Asp-Pro-D-Nal(2')-Arg-D-Nal(2')-Lys]-D-Val-D-Phe-NH2 |
| 1960 | TCAM1957 | Val-Arg-Leu-Ile-Val-Ala-c[Asp-Pro-D-Nal(2')-Arg-D-Nal(2')-Lys]-D-Phe-D-Val-NH2 |
| 1961 | TCAM1958 | Val-Arg-Leu-Ile-Val-Ala-c[Asp-Arg-Arg-D-Nal(2')-Arg-D-Nal(2')-Lys]-D-Val-D-Pro-NH2 |
| 1962 | TCAM1959 | Val-Arg-Leu-Ile-Val-Ala-c[Asp-Arg-Arg-D-Nal(2')-Arg-D-Nal(2')-Lys]-D-Pro-D-Val-NH2 |
| 1963 | TCAM1960 | Val-Arg-Leu-Ile-Val-Ala-c[Asp-Arg-Arg-D-Nal(2')-Arg-D-Nal(2')-Lys]-D-Val-D-Phe-NH2 |
| 1964 | TCAM1961 | Val-Arg-Leu-Ile-Val-Ala-c[Asp-Arg-Arg-D-Nal(2')-Arg-D-Nal(2')-Lys]-D-Phe-D-Val-NH2 |
| 1965 | TCAM1962 | Val-Arg-Leu-Ile-Val-Ala-c[Asp-Arg-Arg-Pro-D-Nal(2')-Arg-D-Nal(2')-Lys]-D-Val-D-Pro-NH2 |
| 1966 | TCAM1963 | Val-Arg-Leu-Ile-Val-Ala-c[Asp-Arg-Arg-Pro-D-Nal(2')-Arg-D-Nal(2')-Lys]-D-Pro-D-Val-NH2 |
| 1967 | TCAM1964 | Val-Arg-Leu-Ile-Val-Ala-c[Asp-Arg-Arg-Pro-D-Nal(2')-Arg-D-Nal(2')-Lys]-D-Val-D-Phe-NH2 |
| 1968 | TCAM1965 | Val-Arg-Leu-Ile-Val-Ala-c[Asp-Arg-Arg-Pro-D-Nal(2')-Arg-D-Nal(2')-Lys]-D-Phe-D-Val-NH2 |
| 1969 | TCAM1966 | Val-Arg-Leu-Ile-Val-Ala-c[Asp-Arg-D-Nal(2')-Arg-D-Nal(2')-Lys]-D-Val-D-Pro-NH2 |
| 1970 | TCAM1967 | Val-Arg-Leu-Ile-Val-Ala-c[Asp-Arg-D-Nal(2')-Arg-D-Nal(2')-Lys]-D-Pro-D-Val-NH2 |
| 1971 | TCAM1968 | Val-Arg-Leu-Ile-Val-Ala-c[Asp-Arg-Nal(2')-Arg-D-Nal(2')-Lys]-D-Val-D-Phe-NH2 |
| 1972 | TCAM1969 | Val-Arg-Leu-Ile-Val-Ala-c[Asp-Arg-D-Nal(2')-Arg-D-Nal(2')-Lys]-D-Phe-D-Val-NH2 |

TABLE 5-continued

Exemplary Anti-microbial peptides

| SEQ NO: | Peptide | Peptide Sequence |
|---|---|---|
| 1973 | TCAM1970 | Val-Arg-Leu-Ile-Val-Ala-c[Asp-Arg-Pro-D-Nal(2')-Arg-D-Nal(2')-Lys]-D-Val-D-Pro-NH2 |
| 1974 | TCAM1971 | Val-Arg-Leu-Ile-Val-Ala-c[Asp-Arg-Pro-D-Nal(2')-Arg-D-Nal(2')-Lys]-D-Pro-D-Val-NH2 |
| 1975 | TCAM1972 | Val-Arg-Leu-Ile-Val-Ala-c[Asp-Arg-Pro-D-Nal(2')-Arg-D-Nal(2')-Lys]-D-Val-D-Phe-NH2 |
| 1976 | TCAM1973 | Val-Arg-Leu-Ile-Val-Ala-c[Asp-Arg-Pro-D-Nal(2')-Arg-D-Nal(2')-Lys]-D-Phe-D-Val-NH2 |
| 1977 | TCAM1974 | Val-Arg-Leu-Ile-Val-Ala-c[Asp-Arg-His-D-Nal(2')-Arg-D-Nal(2')-Lys]-D-Val-D-Pro-NH2 |
| 1978 | TCAM1975 | Val-Arg-Leu-Ile-Val-Ala-c[Asp-Arg-His-D-Nal(2')-Arg-D-Nal(2')-Lys]-D-Pro-D-Val-NH2 |
| 1979 | TCAM1976 | Val-Arg-Leu-Ile-Val-Ala-c[Asp-Arg-His-Nal(2')-Arg-D-Nal(2')-Lys]-D-Val-D-Phe-NH2 |
| 1980 | TCAM1977 | Val-Arg-Leu-Ile-Val-Ala-c[Asp-Arg-His-Nal(2')-Arg-D-Nal(2')-Lys]-D-Phe-D-Val-NH2 |
| 1981 | TCAM1978 | Val-Arg-Leu-Ile-Val-Ala-c[Asp-Arg-D-D-Nal(2')-Arg-D-Nal(2')-Arg-Lys]-D-Val-D-Pro-NH2 |
| 1982 | TCAM1979 | Val-Arg-Leu-Ile-Val-Ala-c[Asp-Arg-D-Nal(2')-Arg-D-Nal(2')-Arg-Lys]-D-Pro-D-Val-NH2 |
| 1983 | TCAM1980 | Val-Arg-Leu-Ile-Val-Ala-c[Asp-Arg-D-Nal(2')-Arg-D-Nal(2')-Arg-Lys]-D-Val-D-Phe-NH2 |
| 1984 | TCAM1981 | Val-Arg-Leu-Ile-Val-Ala-c[Asp-Arg-D-Nal(2')-Arg-D-Nal(2')-Arg-Lys]-D-Phe-D-Val-NH2 |
| 1985 | TCAM1982 | Val-Arg-Leu-Ile-Val-Ala-c[Asp-Arg-Pro-D-Nal(2')-Arg-D-Nal(2')-Arg-Lys]-D-Val-D-Pro-NH2 |
| 1986 | TCAM1983 | Val-Arg-Leu-Ile-Val-Ala-c[Asp-Arg-Pro-D-Nal(2')-Arg-D-Nal(2')-Arg-Lys]-D-Pro-D-Val-NH2 |
| 1987 | TCAM1984 | Val-Arg-Leu-Ile-Val-Ala-c[Asp-Arg-Pro-D-Nal(2')-Arg-D-Nal(2')-Arg-Lys]-D-Val-D-Phe-NH2 |
| 1988 | TCAM1985 | Val-Arg-Leu-Ile-Val-Ala-c[Asp-Arg-Pro-D-Nal(2')-Arg-D-Nal(2')-Arg-Lys]-D-Phe-D-Val-NH2 |
| 1989 | TCAM1986 | Val-Arg-Leu-Ile-Val-Ala-c[Asp-Arg-His-D-Nal(2')-Arg-D-Nal(2')-Arg-Lys]-D-Val-D-Pro-NH2 |
| 1990 | TCAM1987 | Val-Arg-Leu-Ile-Val-Ala-c[Asp-Arg-His-D-Nal(2')-Arg-D-Nal(2')-Arg-Lys]-D-Pro-D-Val-NH2 |
| 1991 | TCAM1988 | Val-Arg-Leu-Ile-Val-Ala-c[Asp-Arg-His-D-Nal(2')-Arg-D-Nal(2')-Arg-Lys]-D-Val-D-Phe-NH2 |
| 1992 | TCAM1989 | Val-Arg-Leu-Ile-Val-Ala-c[Asp-Arg-His-D-Nal(2')-Arg-D-Nal(2')-Arg-Lys]-D-Phe-D-Val-NH2 |
| 1993 | TCAM1990 | Val-Arg-Leu-Ile-Val-Ala-Arg-Arg-c[Asp-Pro-D-Nal(2')-Arg-D-Nal(2')-Lys]-D-Val-D-Pro-NH2 |
| 1994 | TCAM1991 | Val-Arg-Leu-Ile-Val-Ala-Arg-Arg-c[Asp-Pro-D-Nal(2')-Arg-D-Nal(2')-Lys]-D-Pro-D-Val-NH2 |
| 1995 | TCAM1992 | Val-Arg-Leu-Ile-Val-Ala-Arg-Arg-c[Asp-Pro-D-Nal(2')-Arg-D-Nal(2')-Lys]-D-Val-D-Phe-NH2 |
| 1996 | TCAM1993 | Val-Arg-Leu-Ile-Val-Ala-Arg-Arg-c[Asp-Pro-D-Nal(2')-Arg-D-Nal(2')-Lys]-D-Phe-D-Val-NH2 |
| 1997 | TCAM1994 | Val-Arg-Leu-Ile-Val-Ala-Arg-Arg-c[Asp-His-D-Nal(2')-Arg-D-Nal(2')-Lys]-D-Val-D-Pro-NH2 |
| 1998 | TCAM1995 | Val-Arg-Leu-Ile-Val-Ala-Arg-Arg-c[Asp-His-D-Nal(2')-Arg-D-Nal(2')-Lys]-D-Pro-D-Val-NH2 |
| 1999 | TCAM1996 | Val-Arg-Leu-Ile-Val-Ala-Arg-Arg-c[Asp-His-D-Nal(2')-Arg-D-Nal(2')-Lys]-D-Val-D-Phe-NH2 |
| 2000 | TCAM1997 | Val-Arg-Leu-Ile-Val-Ala-Arg-Arg-c[Asp-His-D-Nal(2')-Arg-D-Nal(2')-Lys]-D-Phe-D-Val-NH2 |
| 2001 | TCAM1998 | Val-Arg-Leu-Ile-Val-Ala-c[Asp-Arg-Pro-D-Nal(2')-Arg-D-Nal(2')-Arg-Lys]-D-Val-D-Pro-NH2 |

TABLE 5-continued

Exemplary Anti-microbial peptides

| SEQ NO: | Peptide | Peptide Sequence |
|---|---|---|
| 2002 | TCAM1999 | Val-Arg-Leu-Ile-Val-Ala-c[Asp-Arg-Pro-D-Nal(2')-Arg-D-Nal(2')-Arg-Lys]-D-Pro-D-Val-NH2 |
| 2003 | TCAM2000 | Val-Arg-Leu-Ile-Val-Ala-c[Asp-Arg-Pro-D-Nal(2')-Arg-D-Nal(2')-Arg-Lys]-D-Val-D-Phe-NH2 |
| 2004 | TCAM2001 | Val-Arg-Leu-Ile-Val-Ala-c[Asp-Arg-Pro-D-Nal(2')-Arg-D-Nal(2')-Arg-Lys]-D-Phe-D-Val-NH2 |
| 2005 | TCAM2002 | Val-Arg-Leu-Ile-Val-Ala-c[Asp-Arg-His-D-Nal(2')-Arg-D-Nal(2')-Arg-Lys]-D-Val-D-Pro-NH2 |
| 2006 | TCAM2003 | Val-Arg-Leu-Ile-Val-Ala-c[Asp-Arg-His-D-Nal(2')-Arg-D-Nal(2')-Arg-Lys]-D-Pro-D-Val-NH2 |
| 2007 | TCAM2004 | Val-Arg-Leu-Ile-Val-Ala-c[Asp-Arg-His-D-Nal(2')-Arg-D-Nal(2')-Arg-Lys]-D-Val-D-Phe-NH2 |
| 2008 | TCAM2005 | Val-Arg-Leu-Ile-Val-Ala-c[Asp-Arg-His-D-Nal(2')-Arg-D-Nal(2')-Arg-Lys]-D-Phe-D-Val-NH2 |
| 2009 | TCAM2006 | Val-Arg-Leu-Ile-Val-Ala-c[Asp-His-D-Nal(2')-Arg-Trp-Lys]-Arg-Arg-D-Val-D-Pro-NH2 |
| 2010 | TCAM2007 | Val-Arg-Leu-Ile-Val-Ala-c[Asp-His-D-Nal(2')-Arg-Trp-Lys]-Arg-Arg-D-Pro-D-Val-NH2 |
| 2011 | TCAM2008 | Val-Arg-Leu-Ile-Val-Ala-c[Asp-His-D-Nal(2')-Arg-Trp-Lys]-Arg-Arg-D-Val-D-Phe-NH2 |
| 2012 | TCAM2009 | Val-Arg-Leu-Ile-Val-Ala-c[Asp-His-D-Nal(2')-Arg-Trp-Lys]-Arg-Arg-D-Phe-D-Val-NH2 |
| 2013 | TCAM2010 | Val-Arg-Leu-Ile-Val-Ala-c[Asp-Pro-D-Nal(2')-Arg-Trp-Lys]-Arg-Arg-D-Val-D-Pro-NH2 |
| 2014 | TCAM2011 | Val-Arg-Leu-Ile-Val-Ala-c[Asp-Pro-D-Nal(2')-Arg-Trp-Lys]-Arg-Arg-D-Pro-D-Val-NH2 |
| 2015 | TCAM2012 | Val-Arg-Leu-Ile-Val-Ala-c[Asp-Pro-D-Nal(2')-Arg-Trp-Lys]-Arg-Arg-D-Val-D-Phe-NH2 |
| 2016 | TCAM2013 | Val-Arg-Leu-Ile-Val-Ala-c[Asp-Pro-D-Nal(2')-Arg-Trp-Lys]-Arg-Arg-D-Phe-D-Val-NH2 |

Anti-biofilm peptide ABF4 linked to anti-microbial peptides

| SEQ NO: | Peptide | Peptide Sequence |
|---|---|---|
| 2017 | TCAM2014 | Lys-Lys-Phe-Lys-Lys-Phe-Phe-c[Asp-Pro-Arg-Arg-Trp-Trp-Arg-Phe-Lys]-D-Val-D-Pro-NH2 |
| 2018 | TCAM2015 | Lys-Lys-Phe-Lys-Lys-Phe-Phe-c[Asp-Pro-Arg-Arg-Trp-Trp-Arg-Phe-Lys]-D-Val-D-Phe-NH2 |
| 2019 | TCAM2016 | Lys-Lys-Phe-Lys-Lys-Phe-Phe-c[Asp-Pro-Arg-Arg-Trp-Trp-Arg-Phe-Lys]-D-Pro-D-Val-NH2 |
| 2020 | TCAM2017 | Lys-Lys-Phe-Lys-Lys-Phe-Phe-c[Asp-Pro-Arg-Arg-Trp-Trp-Arg-Phe-Lys]-D-Phe-D-Val-NH2 |
| 2021 | TCAM2018 | Lys-Lys-Phe-Lys-Lys-Phe-Phe-c[Asp-Pro-Arg-Arg-Trp-Trp-Tyr-Phe-Lys]-D-Val-D-Pro-NH2 |
| 2022 | TCAM2019 | Lys-Lys-Phe-Lys-Lys-Phe-Phe-c[Asp-Pro-Arg-Arg-Trp-Trp-Tyr-Phe-Lys]-D-Val-D-Phe-NH2 |
| 2023 | TCAM2020 | Lys-Lys-Phe-Lys-Lys-Phe-Phe-c[Asp-Pro-Arg-Arg-Trp-Trp-Tyr-Phe-Lys]-D-Pro-D-Val-NH2 |
| 2024 | TCAM2021 | Lys-Lys-Phe-Lys-Lys-Phe-Phe-c[Asp-Pro-Arg-Arg-Trp-Trp-Tyr-Phe-Lys]-D-Phe-D-Val-NH2 |
| 2025 | TCAM2022 | Lys-Lys-Phe-Lys-Lys-Phe-Phe-c[Asp-Pro-Arg-Arg-Tyr-Tyr-Arg-Phe-Lys]-D-Val-D-Pro-NH2 |
| 2026 | TCAM2023 | Lys-Lys-Phe-Lys-Lys-Phe-Phe-c[Asp-Pro-Arg-Arg-Tyr-Tyr-Arg-Phe-Lys]-D-Val-D-Phe-NH2 |
| 2027 | TCAM2024 | Lys-Lys-Phe-Lys-Lys-Phe-Phe-c[Asp-Pro-Arg-Arg-Tyr-Tyr-Arg-Phe-Lys]-D-Pro-D-Val-NH2 |
| 2028 | TCAM2025 | Lys-Lys-Phe-Lys-Lys-Phe-Phe-c[Asp-Pro-Arg-Arg-Tyr-Tyr-Arg-Phe-Lys]-D-Phe-D-Val-NH2 |

TABLE 5-continued

Exemplary Anti-microbial peptides

| SEQ NO: | Peptide | Peptide Sequence |
|---|---|---|
| 2029 | TCAM2026 | Lys-Lys-Phe-Lys-Lys-Phe-Phe-c[Asp-Pro-Arg-Arg-Nal-Nal-Arg-Phe-Lys]-D-Val-D-Pro-NH2 |
| 2030 | TCAM2027 | Lys-Lys-Phe-Lys-Lys-Phe-Phe-c[Asp-Pro-Arg-Arg-Nal-Nal-Arg-Phe-Lys]-D-Val-D-Phe-NH2 |
| 2031 | TCAM2028 | Lys-Lys-Phe-Lys-Lys-Phe-Phe-c[Asp-Pro-Arg-Arg-Nal-Nal-Arg-Phe-Lys]-D-Pro-D-Val-NH2 |
| 2032 | TCAM2029 | Lys-Lys-Phe-Lys-Lys-Phe-Phe-c[Asp-Pro-Arg-Arg-Nal-Nal-Arg-Phe-Lys]-D-Phe-D-Val-NH2 |
| 2033 | TCAM2030 | Lys-Lys-Phe-Lys-Lys-Phe-Phe-c[Asp-Pro-Arg-Arg-Leu-Trp-Leu-Trp-Lys]-D-Val-D-Pro-NH2 |
| 2034 | TCAM2031 | Lys-Lys-Phe-Lys-Lys-Phe-Phe-c[Asp-Pro-Arg-Arg-Leu-Trp-Leu-Trp-Lys]-D-Val-D-Phe-NH2 |
| 2035 | TCAM2032 | Lys-Lys-Phe-Lys-Lys-Phe-Phe-c[Asp-Pro-Arg-Arg-Leu-Trp-Leu-Trp-Lys]-D-Pro-D-Val-NH2 |
| 2036 | TCAM2033 | Lys-Lys-Phe-Lys-Lys-Phe-Phe-c[Asp-Pro-Arg-Arg-Leu-Trp-Leu-Trp-Lys]-D-Phe-D-Val-NH2 |
| 2037 | TCAM2034 | Lys-Lys-Phe-Lys-Lys-Phe-Phe-c[Asp-Pro-Arg-Arg-Leu-Trp-Leu-Trp-Lys]-D-Val-D-Pro-NH2 |
| 2038 | TCAM2035 | Lys-Lys-Phe-Lys-Lys-Phe-Phe-c[Asp-Pro-Arg-Arg-Leu-Trp-Leu-Trp-Lys]-D-Val-D-Phe-NH2 |
| 2039 | TCAM2036 | Lys-Lys-Phe-Lys-Lys-Phe-Phe-c[Asp-Pro-Arg-Arg-Leu-Trp-Leu-Trp-Lys]-D-Pro-D-Val-NH2 |
| 2040 | TCAM2037 | Lys-Lys-Phe-Lys-Lys-Phe-Phe-c[Asp-Pro-Arg-Arg-Leu-Trp-Leu-Trp-Lys]-D-Phe-D-Val-NH2 |
| 2041 | TCAM2038 | Lys-Lys-Phe-Lys-Lys-Phe-Phe-c[Asp-Arg-Arg-Arg-Trp-Leu-Trp-Leu-Trp-Lys]-D-Val-D-Pro-NH2 |
| 2042 | TCAM2039 | Lys-Lys-Phe-Lys-Lys-Phe-Phe-c[Asp-Pro-Arg-Arg-Arg-Trp-Leu-Trp-Leu-Trp-Lys]-D-Val-D-Phe-NH2 |
| 2043 | TCAM2040 | Lys-Lys-Phe-Lys-Lys-Phe-Phe-c[Asp-Pro-Arg-Arg-Arg-Trp-Leu-Trp-Leu-Trp-Lys]-D-Pro-D-Val-NH2 |
| 2044 | TCAM2041 | Lys-Lys-Phe-Lys-Lys-Phe-Phe-c[Asp-Pro-Arg-Arg-Arg-Trp-Leu-Trp-Leu-Trp-Lys]-D-Phe-D-Val-NH2 |
| 2045 | TCAM2042 | Lys-Lys-Phe-Lys-Lys-Phe-Phe-c[Asp-Pro-Arg-Gln-Arg-Arg-Trp-Leu-Trp-Leu-Trp-Lys]-D-Val-D-Pro-NH2 |
| 2046 | TCAM2043 | Lys-Lys-Phe-Lys-Lys-Phe-Phe-c[Asp-Pro-Arg-Gln-Arg-Arg-Trp-Leu-Trp-Leu-Trp-Lys]-D-Val-D-Phe-NH2 |
| 2047 | TCAM2044 | Lys-Lys-Phe-Lys-Lys-Phe-Phe-c[Asp-Pro-Arg-Gln-Arg-Arg-Trp-Leu-Trp-Leu-Trp-Lys]-D-Pro-D-Val-NH2 |
| 2048 | TCAM2045 | Lys-Lys-Phe-Lys-Lys-Phe-Phe-c[Asp-Pro-Arg-Gln-Arg-Arg-Trp-Leu-Trp-Leu-Trp-Lys]-D-Phe-D-Val-NH2 |
| 2049 | TCAM2046 | Lys-Lys-Phe-Lys-Lys-Phe-Phe-c[Asp-Pro-Trp-Arg-Trp-Trp-Arg-Arg-Lys]-D-Val-D-Phe-NH2 |
| 2050 | TCAM2047 | Lys-Lys-Phe-Lys-Lys-Phe-Phe-c[Asp-Pro-Trp-Arg-Trp-Trp-Arg-Arg-Lys]-D-Pro-D-Val-NH2 |
| 2051 | TCAM2048 | Lys-Lys-Phe-Lys-Lys-Phe-Phe-c[Asp-Pro-Trp-Arg-Trp-Trp-Arg-Arg-Lys]-D-Phe-D-Val-NH2 |
| 2052 | TCAM2049 | Lys-Lys-Phe-Lys-Lys-Phe-Phe-c[Asp-Pro-Trp-Trp-Arg-Arg-Trp-Trp-Arg-Arg-Lys]-D-Val-D-Pro-NH2 |
| 2053 | TCAM2050 | Lys-Lys-Phe-Lys-Lys-Phe-Phe-c[Asp-Pro-Trp-Trp-Arg-Arg-Trp-Trp-Arg-Arg-Lys]-D-Val-D-Phe-NH2 |

TABLE 5-continued

Exemplary Anti-microbial peptides

| SEQ NO: | Peptide | Peptide Sequence |
|---|---|---|
| 2054 | TCAM2051 | Lys-Lys-Phe-Lys-Lys-Phe-Phe-c[Asp-Pro-Trp-Trp-Arg-Arg-Trp-Trp-Arg-Arg-Lys]-D-Pro-D-Val-NH2 |
| 2055 | TCAM2052 | Lys-Lys-Phe-Lys-Lys-Phe-Phe-c[Asp-Pro-Trp-Trp-Arg-Arg-Trp-Trp-Arg-Arg-Lys]-D-Phe-D-Val-NH2 |
| 2056 | TCAM2053 | Lys-Lys-Phe-Lys-Lys-Phe-Phe-c[Asp-Pro-Trp-Arg-Trp-Arg-Trp-Arg-Lys]-D-Val-D-Pro-NH2 |
| 2057 | TCAM2054 | Lys-Lys-Phe-Lys-Lys-Phe-Phe-c[Asp-Pro-Trp-Arg-Trp-Arg-Trp-Arg-Lys]-D-Val-D-Phe-NH2 |
| 2058 | TCAM2055 | Lys-Lys-Phe-Lys-Lys-Phe-Phe-c[Asp-Pro-Trp-Arg-Trp-Arg-Trp-Arg-Lys]-D-Pro-D-Val-NH2 |
| 2059 | TCAM2056 | Lys-Lys-Phe-Lys-Lys-Phe-Phe-c[Asp-Pro-Trp-Arg-Trp-Arg-Trp-Arg-Lys]-D-Phe-D-Val-NH2 |
| 2060 | TCAM2057 | Lys-Lys-Phe-Lys-Lys-Phe-Phe-c[Asp-Pro-Arg-Trp-Arg-Trp-Arg-Trp-Lys]-D-Val-D-Pro-NH2 |
| 2061 | TCAM2058 | Lys-Lys-Phe-Lys-Lys-Phe-Phe-c[Asp-Pro-Arg-Trp-Arg-Trp-Arg-Trp-Lys]-D-Val-D-Phe-NH2 |
| 2062 | TCAM2059 | Lys-Lys-Phe-Lys-Lys-Phe-Phe-c[Asp-Pro-Arg-Trp-Arg-Trp-Arg-Trp-Lys]-D-Pro-D-Val-NH2 |
| 2063 | TCAM2060 | Lys-Lys-Phe-Lys-Lys-Phe-Phe-c[Asp-Pro-Arg-Trp-Arg-Trp-Arg-Trp-Lys]-D-Phe-D-Val-NH2 |
| 2064 | TCAM2061 | Lys-Lys-Phe-Lys-Lys-Phe-Phe-c[Asp-Pro-Arg-Trp-Trp-Arg-Arg-Lys]-D-Val-D-Pro-NH2 |
| 2065 | TCAM2062 | Lys-Lys-Phe-Lys-Lys-Phe-Phe-c[Asp-Pro-Arg-Trp-Trp-Arg-Arg-Lys]-D-Val-D-Phe-NH2 |
| 2066 | TCAM2063 | Lys-Lys-Phe-Lys-Lys-Phe-Phe-c[Asp-Pro-Arg-Trp-Trp-Arg-Arg-Lys]-D-Pro-D-Val-NH2 |
| 2067 | TCAM2064 | Lys-Lys-Phe-Lys-Lys-Phe-Phe-c[Asp-Pro-Arg-Trp-Trp-Arg-Arg-Lys]-D-Phe-D-Val-NH2 |
| 2068 | TCAM2065 | Lys-Lys-Phe-Lys-Lys-Phe-Phe-c[Asp-Pro-Trp-Trp-Arg-Arg-Trp-Lys]-D-Val-D-Pro-NH2 |
| 2069 | TCAM2066 | Lys-Lys-Phe-Lys-Lys-Phe-Phe-c[Asp-Pro-Trp-Trp-Arg-Arg-Trp-Lys]-D-Val-D-Phe-NH2 |
| 2070 | TCAM2067 | Lys-Lys-Phe-Lys-Lys-Phe-Phe-c[Asp-Pro-Trp-Trp-Arg-Arg-Trp-Lys]-D-Pro-D-Val-NH2 |
| 2071 | TCAM2068 | Lys-Lys-Phe-Lys-Lys-Phe-Phe-c[Asp-Pro-Trp-Trp-Arg-Arg-Trp-Lys]-D-Phe-D-Val-NH2 |
| 2072 | TCAM2069 | Lys-Lys-Phe-Lys-Lys-Phe-Phe-c[Asp-Pro-Trp-Arg-Trp-Arg-Trp-Lys]-D-Val-D-Pro-NH2 |
| 2073 | TCAM2070 | Lys-Lys-Phe-Lys-Lys-Phe-Phe-c[Asp-Pro-Trp-Arg-Trp-Arg-Trp-Lys]-D-Val-D-Phe-NH2 |
| 2074 | TCAM2071 | Lys-Lys-Phe-Lys-Lys-Phe-Phe-c[Asp-Pro-Trp-Arg-Trp-Arg-Trp-Lys]-D-Pro-D-Val-NH2 |
| 2075 | TCAM2072 | Lys-Lys-Phe-Lys-Lys-Phe-Phe-c[Asp-Pro-Trp-Arg-Trp-Arg-Trp-Lys]-D-Phe-D-Val-NH2 |
| 2076 | TCAM2073 | Lys-Lys-Phe-Lys-Lys-Phe-Phe-c[Asp-Pro-Arg-Trp-Arg-Trp-Arg-Lys]-D-Val-D-Pro-NH2 |
| 2077 | TCAM2074 | Lys-Lys-Phe-Lys-Lys-Phe-Phe-c[Asp-Pro-Arg-Trp-Arg-Trp-Arg-Lys]-D-Val-D-Phe-NH2 |
| 2078 | TCAM2075 | Lys-Lys-Phe-Lys-Lys-Phe-Phe-c[Asp-Pro-Arg-Trp-Arg-Trp-Arg-Lys]-D-Pro-D-Val-NH2 |
| 2079 | TCAM2076 | Lys-Lys-Phe-Lys-Lys-Phe-Phe-c[Asp-Pro-Arg-Trp-Arg-Trp-Arg-Lys]-D-Phe-D-Val-NH2 |
| 2080 | TCAM2077 | Lys-Lys-Phe-Lys-Lys-Phe-Phe-c[Asp-Pro-Trp-Arg-Tyr-Arg-Trp-Lys]-D-Val-D-Pro-NH2 |
| 2081 | TCAM2078 | Lys-Lys-Phe-Lys-Lys-Phe-Phe-c[Asp-Pro-Trp-Arg-Tyr-Arg-Trp-Lys]-D-Val-D-Phe-NH2 |
| 2082 | TCAM2079 | Lys-Lys-Phe-Lys-Lys-Phe-Phe-c[Asp-Pro-Trp-Arg-Tyr-Arg-Trp-Lys]-D-Pro-D-Val-NH2 |
| 2083 | TCAM2080 | Lys-Lys-Phe-Lys-Lys-Phe-Phe-c[Asp-Pro-Trp-Arg-Tyr-Arg-Trp-Lys]-D-Phe-D-Val-NH2 |
| 2084 | TCAM2081 | Lys-Lys-Phe-Lys-Lys-Phe-Phe-c[Asp-Pro-Trp-Arg-Trp-Arg-Tyr-Lys]-D-Val-D-Pro-NH2 |
| 2085 | TCAM2082 | Lys-Lys-Phe-Lys-Lys-Phe-Phe-c[Asp-Pro-Trp-Arg-Trp-Arg-Tyr-Lys]-D-Val-D-Phe-NH2 |

TABLE 5-continued

Exemplary Anti-microbial peptides

| SEQ NO: | Peptide | Peptide Sequence |
|---|---|---|
| 2086 | TCAM2083 | Lys-Lys-Phe-Lys-Lys-Phe-Phe-c[Asp-Pro-Trp-Arg-Trp-Arg-Tyr-Lys]-D-Pro-D-Val-NH2 |
| 2087 | TCAM2084 | Lys-Lys-Phe-Lys-Lys-Phe-Phe-c[Asp-Pro-Trp-Arg-Trp-Arg-Tyr-Lys]-D-Phe-D-Val-NH2 |
| 2088 | TCAM2085 | Lys-Lys-Phe-Lys-Lys-Phe-Phe-c[Asp-Pro-Trp-Arg-Trp-Arg-Lys]-D-Val-D-Pro-NH2 |
| 2089 | TCAM2086 | Lys-Lys-Phe-Lys-Lys-Phe-Phe-c[Asp-Pro-Trp-Arg-Trp-Arg-Lys]-D-Val-D-Phe-NH2 |
| 2090 | TCAM2087 | Lys-Lys-Phe-Lys-Lys-Phe-Phe-c[Asp-Pro-Trp-Arg-Trp-Arg-Lys]-D-Pro-D-Val-NH2 |
| 2091 | TCAM2088 | Lys-Lys-Phe-Lys-Lys-Phe-Phe-c[Asp-Pro-Trp-Arg-Trp-Arg-Lys]-D-Phe-D-Val-NH2 |
| 2092 | TCAM2089 | Lys-Lys-Phe-Lys-Lys-Phe-Phe-c[Asp-Pro-Trp-Arg-Arg-Trp-Lys]-D-Val-D-Pro-NH2 |
| 2093 | TCAM2090 | Lys-Lys-Phe-Lys-Lys-Phe-Phe-c[Asp-Pro-Trp-Arg-Arg-Trp-Lys]-D-Val-D-Phe-NH2 |
| 2094 | TCAM2091 | Lys-Lys-Phe-Lys-Lys-Phe-Phe-c[Asp-Pro-Trp-Arg-Arg-Trp-Lys]-D-Pro-D-Val-NH2 |
| 2095 | TCAM2092 | Lys-Lys-Phe-Lys-Lys-Phe-Phe-c[Asp-Pro-Trp-Arg-Arg-Trp-Lys]-D-Phe-D-Val-NH2 |
| 2096 | TCAM2093 | Lys-Lys-Phe-Lys-Lys-Phe-Phe-c[Asp-Pro-Arg-Trp-Trp-Arg-Lys]-D-Val-D-Pro-NH2 |
| 2097 | TCAM2094 | Lys-Lys-Phe-Lys-Lys-Phe-Phe-c[Asp-Pro-Arg-Trp-Trp-Arg-Lys]-D-Val-D-Phe-NH2 |
| 2098 | TCAM2095 | Lys-Lys-Phe-Lys-Lys-Phe-Phe-c[Asp-Pro-Arg-Trp-Trp-Arg-Lys]-D-Pro-D-Val-NH2 |
| 2099 | TCAM2096 | Lys-Lys-Phe-Lys-Lys-Phe-Phe-c[Asp-Pro-Arg-Trp-Trp-Arg-Lys]-D-Phe-D-Val-NH2 |
| 2100 | TCAM2097 | Lys-Lys-Phe-Lys-Lys-Phe-Phe-c[Asp-Pro-Trp-Arg-Trp-Lys]-D-Val-D-Pro-NH2 |
| 2101 | TCAM2098 | Lys-Lys-Phe-Lys-Lys-Phe-Phe-c[Asp-Pro-Trp-Arg-Trp-Lys]-D-Val-D-Phe-NH2 |
| 2102 | TCAM2099 | Lys-Lys-Phe-Lys-Lys-Phe-Phe-c[Asp-Pro-Trp-Arg-Trp-Lys]-D-Pro-D-Val-NH2 |
| 2103 | TCAM2100 | Lys-Lys-Phe-Lys-Lys-Phe-Phe-c[Asp-Pro-Trp-Arg-Trp-Lys]-D-Phe-D-Val-NH2 |
| 2104 | TCAM2101 | Lys-Lys-Phe-Lys-Lys-Phe-Phe-c[Asp-Pro-Arg-Trp-Arg-Lys]-D-Val-D-Pro-NH2 |
| 2105 | TCAM2102 | Lys-Lys-Phe-Lys-Lys-Phe-Phe-c[Asp-Pro-Arg-Trp-Arg-Lys]-D-Val-D-Phe-NH2 |
| 2106 | TCAM2103 | Lys-Lys-Phe-Lys-Lys-Phe-Phe-c[Asp-Pro-Arg-Trp-Arg-Lys]-D-Pro-D-Val-NH2 |
| 2107 | TCAM2104 | Lys-Lys-Phe-Lys-Lys-Phe-Phe-c[Asp-Pro-Arg-Trp-Arg-Lys]-D-Phe-D-Val-NH2 |
| 2108 | TCAM2105 | -Lys-Lys-Phe-Lys-Lys-Phe-Phe-c[Asp-Arg-Arg-Trp-Trp-Arg-Phe-Lys]-D-Val-D-Pro-NH2 |
| 2109 | TCAM2106 | Lys-Lys-Phe-Lys-Lys-Phe-Phe-c[Asp-Arg-Arg-Trp-Trp-Arg-Phe-Lys]-D-Val-D-Phe-NH2 |
| 2110 | TCAM2107 | Lys-Lys-Phe-Lys-Lys-Phe-Phe-c[Asp-Arg-Arg-Trp-Trp-Arg-Phe-Lys]-D-Pro-D-Val-NH2 |
| 2111 | TCAM2108 | Lys-Lys-Phe-Lys-Lys-Phe-Phe-c[Asp-Arg-Arg-Trp-Trp-Arg-Phe-Lys]-D-Phe-D-Val-NH2 |
| 2112 | TCAM2109 | Lys-Lys-Phe-Lys-Lys-Phe-Phe-c[Asp-Arg-Arg-Trp-Trp-Arg-Phe-Lys]-D-Val-D-Pro-NH2 |
| 2113 | TCAM2110 | Lys-Lys-Phe-Lys-Lys-Phe-Phe-c[Asp-Arg-Arg-Trp-Trp-Arg-Phe-Lys]-D-Val-D-Phe-NH2 |
| 2114 | TCAM2111 | Lys-Lys-Phe-Lys-Lys-Phe-Phe-c[Asp-Arg-Arg-Trp-Trp-Arg-Phe-Lys]-D-Pro-D-Val-NH2 |
| 2115 | TCAM2112 | Lys-Lys-Phe-Lys-Lys-Phe-Phe-c[Asp-Arg-Arg-Trp-Trp-Arg-Phe-Lys]-D-Phe-D-Val-NH2 |
| 2116 | TCAM2113 | Lys-Lys-Phe-Lys-Lys-Phe-Phe-c[Asp-Arg-Arg-Tyr-Tyr-Arg-Phe-Lys]-D-Val-D-Pro-NH2 |
| 2117 | TCAM2114 | Lys-Lys-Phe-Lys-Lys-Phe-Phe-c[Asp-Arg-Arg-Tyr-Tyr-Arg-Phe-Lys]-D-Val-D-Phe-NH2 |
| 2118 | TCAM2115 | Lys-Lys-Phe-Lys-Lys-Phe-Phe-c[Asp-Arg-Arg-Tyr-Tyr-Arg-Phe-Lys]-D-Pro-D-Val-NH2 |
| 2119 | TCAM2116 | Lys-Lys-Phe-Lys-Lys-Phe-Phe-c[Asp-Arg-Arg-Tyr-Tyr-Arg-Phe-Lys]-D-Phe-D-Val-NH2 |
| 2120 | TCAM2117 | Lys-Lys-Phe-Lys-Lys-Phe-Phe-c[Asp-Arg-Arg-Nal-Nal-Arg-Phe-Lys]-D-Val-D-Pro-NH2 |
| 2121 | TCAM2118 | Lys-Lys-Phe-Lys-Lys-Phe-Phe-c[Asp-Arg-Arg-Nal-Nal-Arg-Phe-Lys]-D-Val-D-Phe-NH2 |
| 2122 | TCAM2119 | Lys-Lys-Phe-Lys-Lys-Phe-Phe-c[Asp-Arg-Arg-Nal-Nal-Arg-Phe-Lys]-D-Pro-D-Val-NH2 |
| 2123 | TCAM2120 | Lys-Lys-Phe-Lys-Lys-Phe-Phe-c[Asp-Arg-Arg-Nal-Nal-Arg-Phe-Lys]-D-Phe-D-Val-NH2 |

TABLE 5-continued

Exemplary Anti-microbial peptides

| SEQ NO: | Peptide | Peptide Sequence |
|---|---|---|
| 2124 | TCAM2121 | Lys-Lys-Phe-Lys-Lys-Phe-Phe-c[Asp-Arg-Arg-Leu-Trp-Leu-Trp-Lys]-D-Val-D-Pro-NH2 |
| 2125 | TCAM2122 | Lys-Lys-Phe-Lys-Lys-Phe-Phe-c[Asp-Arg-Arg-Leu-Trp-Leu-Trp-Lys]-D-Val-D-Phe-NH2 |
| 2126 | TCAM2123 | Lys-Lys-Phe-Lys-Lys-Phe-Phe-c[Asp-Arg-Arg-Leu-Trp-Leu-Trp-Lys]-D-Pro-D-Val-NH2 |
| 2127 | TCAM2124 | Lys-Lys-Phe-Lys-Lys-Phe-Phe-c[Asp-Arg-Arg-Leu-Trp-Leu-Trp-Lys]-D-Phe-D-Val-NH2 |
| 2128 | TCAM2125 | Lys-Lys-Phe-Lys-Lys-Phe-Phe-c[Asp-Arg-Arg-Leu-Trp-Leu-Trp-Lys]-D-Val-D-Pro-NH2 |
| 2129 | TCAM2126 | Lys-Lys-Phe-Lys-Lys-Phe-Phe-c[Asp-Arg-Arg-Leu-Trp-Leu-Trp-Lys]-D-Val-D-Phe-NH2 |
| 2130 | TCAM2127 | Lys-Lys-Phe-Lys-Lys-Phe-Phe-c[Asp-Arg-Arg-Leu-Trp-Leu-Trp-Lys]-D-Pro-D-Val-NH2 |
| 2131 | TCAM2128 | Lys-Lys-Phe-Lys-Lys-Phe-Phe-c[Asp-Arg-Arg-Leu-Trp-Leu-Trp-Lys]-D-Phe-D-Val-NH2 |
| 2132 | TCAM2129 | Lys-Lys-Phe-Lys-Lys-Phe-Phe-c[Asp-Arg-Arg-Arg-Trp-Leu-Trp-Leu-Trp-Lys]-D-Val-D-Pro-NH2 |
| 2133 | TCAM2130 | Lys-Lys-Phe-Lys-Lys-Phe-Phe-c[Asp-Arg-Arg-Arg-Trp-Leu-Trp-Leu-Trp-Lys]-D-Val-D-Phe-NH2 |
| 2134 | TCAM2131 | Lys-Lys-Phe-Lys-Lys-Phe-Phe-c[Asp-Arg-Arg-Arg-Trp-Leu-Trp-Leu-Trp-Lys]-D-Pro-D-Val-NH2 |
| 2135 | TCAM2132 | Lys-Lys-Phe-Lys-Lys-Phe-Phe-c[Asp-Arg-Arg-Arg-Trp-Leu-Trp-Leu-Trp-Lys]-D-Phe-D-Val-NH2 |
| 2136 | TCAM2133 | Lys-Lys-Phe-Lys-Lys-Phe-Phe-c[Asp-Arg-Gln-Arg-Arg-Trp-Leu-Trp-Leu-Trp-Lys]-D-Val-D-Pro-NH2 |
| 2137 | TCAM2134 | Lys-Lys-Phe-Lys-Lys-Phe-Phe-c[Asp-Arg-Gln-Arg-Arg-Trp-Leu-Trp-Leu-Trp-Lys]-D-Val-D-Phe-NH2 |
| 2138 | TCAM2135 | Lys-Lys-Phe-Lys-Lys-Phe-Phe-c[Asp-Arg-Gln-Arg-Arg-Trp-Leu-Trp-Leu-Trp-Lys]-D-Pro-D-Val-NH2 |
| 2139 | TCAM2136 | Lys-Lys-Phe-Lys-Lys-Phe-Phe-c[Asp-Arg-Gln-Arg-Arg-Trp-Leu-Trp-Leu-Trp-Lys]-D-Phe-D-Val-NH2 |
| 2140 | TCAM2137 | Lys-Lys-Phe-Lys-Lys-Phe-Phe-c[Asp-Trp-Arg-Trp-Trp-Arg-Arg-Lys]-D-Val-D-Pro-NH2 |
| 2141 | TCAM2138 | Lys-Lys-Phe-Lys-Lys-Phe-Phe-c[Asp-Trp-Arg-Trp-Trp-Arg-Arg-Lys]-D-Val-D-Phe-NH2 |
| 2142 | TCAM2139 | Lys-Lys-Phe-Lys-Lys-Phe-Phe-c[Asp-Trp-Arg-Trp-Trp-Arg-Arg-Lys]-D-Pro-D-Val-NH2 |
| 2143 | TCAM2140 | Lys-Lys-Phe-Lys-Lys-Phe-Phe-c[Asp-Trp-Arg-Trp-Trp-Arg-Arg-Lys]-D-Phe-D-Val-NH2 |
| 2144 | TCAM2141 | Lys-Lys-Phe-Lys-Lys-Phe-Phe-c[Asp-Trp-Trp-Arg-Arg-Trp-Trp-Arg-Arg-Lys]-D-Val-D-Pro-NH2 |
| 2145 | TCAM2142 | Lys-Lys-Phe-Lys-Lys-Phe-Phe-c[Asp-Trp-Trp-Arg-Arg-Trp-Trp-Arg-Arg-Lys]-D-Val-D-Phe-NH2 |
| 2146 | TCAM2143 | Lys-Lys-Phe-Lys-Lys-Phe-Phe-c[Asp-Trp-Trp-Arg-Arg-Trp-Trp-Arg-Arg-Lys]-D-Pro-D-Val-NH2 |
| 2147 | TCAM2144 | Lys-Lys-Phe-Lys-Lys-Phe-Phe-c[Asp-Trp-Trp-Arg-Arg-Trp-Trp-Arg-Arg-Lys]-D-Phe-D-Val-NH2 |
| 2148 | TCAM2145 | Lys-Lys-Phe-Lys-Lys-Phe-Phe-c[Asp-Trp-Arg-Trp-Arg-Trp-Arg-Lys]-D-Val-D-Pro-NH2 |
| 2149 | TCAM2146 | Lys-Lys-Phe-Lys-Lys-Phe-Phe-c[Asp-Trp-Arg-Trp-Arg-Trp-Arg-Lys]-D-Val-D-Phe-NH2 |
| 2150 | TCAM2147 | Lys-Lys-Phe-Lys-Lys-Phe-Phe-c[Asp-Trp-Arg-Trp-Arg-Trp-Arg-Lys]-D-Pro-D-Val-NH2 |
| 2151 | TCAM2148 | Lys-Lys-Phe-Lys-Lys-Phe-Phe-c[Asp-Trp-Arg-Trp-Arg-Trp-Arg-Lys]-D-Phe-D-Val-NH2 |
| 2152 | TCAM2149 | Lys-Lys-Phe-Lys-Lys-Phe-Phe-c[Asp-Arg-Trp-Arg-Trp-Arg-Trp-Lys]-D-Val-D-Pro-NH2 |
| 2153 | TCAM2150 | Lys-Lys-Phe-Lys-Lys-Phe-Phe-c[Asp-Arg-Trp-Arg-Trp-Arg-Trp-Lys]-D-Val-D-Phe-NH2 |
| 2154 | TCAM2151 | Lys-Lys-Phe-Lys-Lys-Phe-Phe-c[Asp-Arg-Trp-Arg-Trp-Arg-Trp-Lys]-D-Pro-D-Val-NH2 |

TABLE 5-continued

Exemplary Anti-microbial peptides

| SEQ NO: | Peptide | Peptide Sequence |
|---|---|---|
| 2155 | TCAM2152 | Lys-Lys-Phe-Lys-Lys-Phe-Phe-c[Asp-Arg-Trp-Arg-Trp-Arg-Trp-Lys]-D-Phe-D-Val-NH2 |
| 2156 | TCAM2153 | Lys-Lys-Phe-Lys-Lys-Phe-Phe-c[Asp-Arg-Trp-Trp-Arg-Arg-Lys]-D-Val-D-Pro-NH2 |
| 2157 | TCAM2154 | Lys-Lys-Phe-Lys-Lys-Phe-Phe-c[Asp-Arg-Trp-Trp-Arg-Arg-Lys]-D-Val-D-Phe-NH2 |
| 2158 | TCAM2155 | Lys-Lys-Phe-Lys-Lys-Phe-Phe-c[Asp-Arg-Trp-Trp-Arg-Arg-Lys]-D-Pro-D-Val-NH2 |
| 2159 | TCAM2156 | Lys-Lys-Phe-Lys-Lys-Phe-Phe-c[Asp-Arg-Trp-Trp-Arg-Arg-Lys]-D-Phe-D-Val-NH2 |
| 2160 | TCAM2157 | Lys-Lys-Phe-Lys-Lys-Phe-Phe-c[Asp-Arg-Trp-Arg-Trp-Arg-Lys]-D-Val-D-Pro-NH2 |
| 2161 | TCAM2158 | Lys-Lys-Phe-Lys-Lys-Phe-Phe-c[Asp-Arg-Trp-Arg-Trp-Arg-Lys]-D-Val-D-Phe-NH2 |
| 2162 | TCAM2159 | Lys-Lys-Phe-Lys-Lys-Phe-Phe-c[Asp-Arg-Trp-Arg-Trp-Arg-Lys]-D-Pro-D-Val-NH2 |
| 2163 | TCAM2160 | Lys-Lys-Phe-Lys-Lys-Phe-Phe-c[Asp-Arg-Trp-Arg-Trp-Arg-Lys]-D-Phe-D-Val-NH2 |
| 2164 | TCAM2161 | Lys-Lys-Phe-Lys-Lys-Phe-Phe-c[Asp-Trp-Trp-Arg-Arg-Trp-Lys]-D-Val-D-Pro-NH2 |
| 2165 | TCAM2162 | Lys-Lys-Phe-Lys-Lys-Phe-Phe-c[Asp-Trp-Trp-Arg-Arg-Trp-Lys]-D-Val-D-Phe-NH2 |
| 2166 | TCAM2163 | Lys-Lys-Phe-Lys-Lys-Phe-Phe-c[Asp-Trp-Trp-Arg-Arg-Trp-Lys]-D-Pro-D-Val-NH2 |
| 2167 | TCAM2164 | Lys-Lys-Phe-Lys-Lys-Phe-Phe-c[Asp-Trp-Trp-Arg-Arg-Trp-Lys]-D-Phe-D-Val-NH2 |
| 2168 | TCAM2165 | Lys-Lys-Phe-Lys-Lys-Phe-Phe-c[Asp-Trp-Arg-Trp-Arg-Trp-Lys]-D-Val-D-Pro-NH2 |
| 2169 | TCAM2166 | Lys-Lys-Phe-Lys-Lys-Phe-Phe-c[Asp-Trp-Arg-Trp-Arg-Trp-Lys]-D-Val-D-Phe-NH2 |
| 2170 | TCAM2167 | Lys-Lys-Phe-Lys-Lys-Phe-Phe-c[Asp-Trp-Arg-Trp-Arg-Trp-Lys]-D-Pro-D-Val-NH2 |
| 2171 | TCAM2168 | Lys-Lys-Phe-Lys-Lys-Phe-Phe-c[Asp-Trp-Arg-Trp-Arg-Trp-Lys]-D-Phe-D-Val-NH2 |
| 2172 | TCAM2169 | Lys-Lys-Phe-Lys-Lys-Phe-Phe-c[Asp-Trp-Arg-Tyr-Arg-Trp-Lys]-D-Val-D-Pro-NH2 |
| 2173 | TCAM2170 | Lys-Lys-Phe-Lys-Lys-Phe-Phe-c[Asp-Trp-Arg-Tyr-Arg-Trp-Lys]-D-Val-D-Phe-NH2 |
| 2174 | TCAM2171 | Lys-Lys-Phe-Lys-Lys-Phe-Phe-c[Asp-Trp-Arg-Tyr-Arg-Trp-Lys]-D-Pro-D-Val-NH2 |
| 2175 | TCAM2172 | Lys-Lys-Phe-Lys-Lys-Phe-Phe-c[Asp-Trp-Arg-Tyr-Arg-Trp-Lys]-D-Phe-D-Val-NH2 |
| 2176 | TCAM2173 | Lys-Lys-Phe-Lys-Lys-Phe-Phe-c[Asp-Trp-Arg-Trp-Arg-Tyr-Lys]-D-Val-D-Pro-NH2 |
| 2177 | TCAM2174 | Lys-Lys-Phe-Lys-Lys-Phe-Phe-c[Asp-Trp-Arg-Trp-Arg-Tyr-Lys]-D-Val-D-Phe-NH2 |
| 2178 | TCAM2175 | Lys-Lys-Phe-Lys-Lys-Phe-Phe-c[Asp-Trp-Arg-Trp-Arg-Tyr-Lys]-D-Pro-D-Val-NH2 |
| 2179 | TCAM2176 | Lys-Lys-Phe-Lys-Lys-Phe-Phe-c[Asp-Trp-Arg-Trp-Arg-Tyr-Lys]-D-Phe-D-Val-NH2 |
| 2180 | TCAM2177 | Lys-Lys-Phe-Lys-Lys-Phe-Phe-c[Asp-Trp-Arg-Trp-Arg-Lys]-D-Val-D-Pro-NH2 |
| 2181 | TCAM2178 | Lys-Lys-Phe-Lys-Lys-Phe-Phe-c[Asp-Trp-Arg-Trp-Arg-Lys]-D-Val-D-Phe-NH2 |
| 2182 | TCAM2179 | Lys-Lys-Phe-Lys-Lys-Phe-Phe-c[Asp-Trp-Arg-Trp-Arg-Lys]-D-Pro-D-Val-NH2 |
| 2183 | TCAM2180 | Lys-Lys-Phe-Lys-Lys-Phe-Phe-c[Asp-Trp-Arg-Trp-Arg-Lys]-D-Phe-D-Val-NH2 |
| 2184 | TCAM2181 | Lys-Lys-Phe-Lys-Lys-Phe-Phe-c[Asp-Trp-Arg-Arg-Trp-Lys]-D-Val-D-Pro-NH2 |
| 2185 | TCAM2182 | Lys-Lys-Phe-Lys-Lys-Phe-Phe-c[Asp-Trp-Arg-Arg-Trp-Lys]-D-Val-D-Phe-NH2 |
| 2186 | TCAM2183 | Lys-Lys-Phe-Lys-Lys-Phe-Phe-c[Asp-Trp-Arg-Arg-Trp-Lys]-D-Pro-D-Val-NH2 |
| 2187 | TCAM2184 | Lys-Lys-Phe-Lys-Lys-Phe-Phe-c[Asp-Trp-Arg-Arg-Trp-Lys]-D-Phe-D-Val-NH2 |
| 2188 | TCAM2185 | Lys-Lys-Phe-Lys-Lys-Phe-Phe-c[Asp-Arg-Trp-Trp-Arg-Lys]-D-Val-D-Pro-NH2 |
| 2189 | TCAM2186 | Lys-Lys-Phe-Lys-Lys-Phe-Phe-c[Asp-Arg-Trp-Trp-Arg-Lys]-D-Val-D-Phe-NH2 |
| 2190 | TCAM2187 | Lys-Lys-Phe-Lys-Lys-Phe-Phe-c[Asp-Arg-Trp-Trp-Arg-Lys]-D-Pro-D-Val-NH2 |
| 2191 | TCAM2188 | Lys-Lys-Phe-Lys-Lys-Phe-Phe-c[Asp-Arg-Trp-Trp-Arg-Lys]-D-Phe-D-Val-NH2 |
| 2192 | TCAM2189 | Lys-Lys-Phe-Lys-Lys-Phe-Phe-c[Asp-Trp-Arg-Trp-Lys]-D-Val-D-Pro-NH2 |

TABLE 5-continued

Exemplary Anti-microbial peptides

| SEQ NO: | Peptide | Peptide Sequence |
|---|---|---|
| 2193 | TCAM2190 | Lys-Lys-Phe-Lys-Lys-Phe-Phe-c[Asp-Trp-Arg-Trp-Lys]-D-Val-D-Phe-NH2 |
| 2194 | TCAM2191 | Lys-Lys-Phe-Lys-Lys-Phe-Phe-c[Asp-Trp-Arg-Trp-Lys]-D-Pro-D-Val-NH2 |
| 2195 | TCAM2192 | Lys-Lys-Phe-Lys-Lys-Phe-Phe-c[Asp-Trp-Arg-Trp-Lys]-D-Phe-D-Val-NH2 |
| 2196 | TCAM2193 | Lys-Lys-Phe-Lys-Lys-Phe-Phe-c[Asp-Arg-Trp-Arg-Lys]-D-Val-D-Pro-NH2 |
| 2197 | TCAM2194 | Lys-Lys-Phe-Lys-Lys-Phe-Phe-c[Asp-Arg-Trp-Arg-Lys]-D-Val-D-Phe-NH2 |
| 2198 | TCAM2195 | Lys-Lys-Phe-Lys-Lys-Phe-Phe-c[Asp-Arg-Trp-Arg-Lys]-D-Pro-D-Val-NH2 |
| 2199 | TCAM2196 | Lys-Lys-Phe-Lys-Lys-Phe-Phe-c[Asp-Arg-Trp-Arg-Lys]-D-Phe-D-Val-NH2 |
| 2200 | TCAM2197 | Lys-Lys-Phe-Lys-Lys-Phe-Phe-c[Asp-His-D-Nal(2')-Arg-Trp-Lys]-D-Val-D-Pro-NH2 |
| 2201 | TCAM2198 | Lys-Lys-Phe-Lys-Lys-Phe-Phe-c[Asp-His-D-Nal(2')-Arg-Trp-Lys]-D-Pro-D-Val-NH2 |
| 2202 | TCAM2199 | Lys-Lys-Phe-Lys-Lys-Phe-Phe-c[Asp-His-D-Nal(2')-Arg-Trp-Lys]-D-Val-D-Phe-NH2 |
| 2203 | TCAM2200 | Lys-Lys-Phe-Lys-Lys-Phe-Phe-c[Asp-His-D-Nal(2')-Arg-Trp-Lys]-D-Phe-D-Val-NH2 |
| 2204 | TCAM2201 | Lys-Lys-Phe-Lys-Lys-Phe-Phe-c[Asp-Pro-D-Nal(2')-Arg-Trp-Lys]-D-Val-D-Pro-NH2 |
| 2205 | TCAM2202 | Lys-Lys-Phe-Lys-Lys-Phe-Phe-c[Asp-Pro-D-Nal(2')-Arg-Trp-Lys]-D-Pro-D-Val-NH2 |
| 2206 | TCAM2203 | Lys-Lys-Phe-Lys-Lys-Phe-Phe-c[Asp-Pro-D-Nal(2')-Arg-Trp-Lys]-D-Val-D-Phe-NH2 |
| 2207 | TCAM2204 | Lys-Lys-Phe-Lys-Lys-Phe-Phe-c[Asp-Pro-D-Nal(2')-Arg-Trp-Lys]-D-Phe-D-Val-NH2 |
| 2208 | TCAM2205 | Lys-Lys-Phe-Lys-Lys-Phe-Phe-c[Asp-Arg-Arg-Nal(2')-Arg-Trp-Lys]-D-Val-D-Pro-NH2 |
| 2209 | TCAM2206 | Lys-Lys-Phe-Lys-Lys-Phe-Phe-c[Asp-Arg-Arg-Nal(2')-Arg-Trp-Lys]-D-Pro-D-Val-NH2 |
| 2210 | TCAM2207 | Lys-Lys-Phe-Lys-Lys-Phe-Phe-c[Asp-Arg-Arg-Nal(2')-Arg-Trp-Lys]-D-Val-D-Phe-NH2 |
| 2211 | TCAM2208 | Lys-Lys-Phe-Lys-Lys-Phe-Phe-c[Asp-Arg-Arg-Nal(2')-Arg-Trp-Lys]-D-Phe-D-Val-NH2 |
| 2212 | TCAM2209 | Lys-Lys-Phe-Lys-Lys-Phe-Phe-c[Asp-Arg-Arg-Pro-Nal(2')-Arg-Trp-Lys]-D-Val-D-Pro-NH2 |
| 2213 | TCAM2210 | Lys-Lys-Phe-Lys-Lys-Phe-Phe-c[Asp-Arg-Arg-Pro-D-Nal(2')-Arg-Trp-Lys]-D-Pro-D-Val-NH2 |
| 2214 | TCAM2211 | Lys-Lys-Phe-Lys-Lys-Phe-Phe-c[Asp-Arg-Arg-Pro-D-Nal(2')-Arg-Trp-Lys]-D-Val-D-Phe-NH2 |
| 2215 | TCAM2212 | Lys-Lys-Phe-Lys-Lys-Phe-Phe-c[Asp-Arg-Arg-Pro-Nal(2')-Arg-Trp-Lys]-D-Phe-D-Val-NH2 |
| 2216 | TCAM2213 | Lys-Lys-Phe-Lys-Lys-Phe-Phe-c[Asp-Arg-D-Nal(2')-Arg-Trp-Lys]-D-Val-D-Pro-NH2 |
| 2217 | TCAM2214 | Lys-Lys-Phe-Lys-Lys-Phe-Phe-c[Asp-Arg-D-Nal(2')-Arg-Trp-Lys]-D-Pro-D-Val-NH2 |
| 2218 | TCAM2215 | Lys-Lys-Phe-Lys-Lys-Phe-Phe-c[Asp-Arg-D-Nal(2')-Arg-Trp-Lys]-D-Val-D-Phe-NH2 |
| 2219 | TCAM2216 | Lys-Lys-Phe-Lys-Lys-Phe-Phe-c[Asp-Arg-D-Nal(2')-Arg-Trp-Lys]-D-Phe-D-Val-NH2 |
| 2220 | TCAM2217 | Lys-Lys-Phe-Lys-Lys-Phe-Phe-c[Asp-Arg-Pro-D-Nal(2')-Arg-Trp-Lys]-D-Val-D-Pro-NH2 |
| 2221 | TCAM2218 | Lys-Lys-Phe-Lys-Lys-Phe-Phe-c[Asp-Arg-Pro-D-Nal(2')-Arg-Trp-Lys]-D-Pro-D-Val-NH2 |
| 2222 | TCAM2219 | Lys-Lys-Phe-Lys-Lys-Phe-Phe-c[Asp-Arg-Pro-D-Nal(2')-Arg-Trp-Lys]-D-Val-D-Phe-NH2 |
| 2223 | TCAM2220 | Lys-Lys-Phe-Lys-Lys-Phe-Phe-c[Asp-Arg-Pro-D-Nal(2')-Arg-Trp-Lys]-D-Phe-D-Val-NH2 |
| 2224 | TCAM2221 | Lys-Lys-Phe-Lys-Lys-Phe-Phe-Arg-Arg-c[Asp-Pro-D-Nal(2')-Arg-Trp-Lys]-D-Val-D-Pro-NH2 |
| 2225 | TCAM2222 | Lys-Lys-Phe-Lys-Lys-Phe-Phe-Arg-Arg-c[Asp-Pro-D-Nal(2')-Arg-Trp-Lys]-D-Pro-D-Val-NH2 |
| 2226 | TCAM2223 | Lys-Lys-Phe-Lys-Lys-Phe-Phe-Arg-Arg-c[Asp-Pro-D-Nal(2')-Arg-Trp-Lys]-D-Val-D-Phe-NH2 |

TABLE 5-continued

Exemplary Anti-microbial peptides

| SEQ NO: | Peptide | Peptide Sequence |
|---|---|---|
| 2227 | TCAM2224 | Lys-Lys-Phe-Lys-Lys-Phe-Phe-Arg-Arg-c[Asp-Pro-D-Nal(2')-Arg-Trp-Lys]-D-Phe-D-Val-NH2 |
| 2228 | TCAM2225 | Lys-Lys-Phe-Lys-Lys-Phe-Phe-Arg-Arg-c[Asp-His-D-Nal(2')-Arg-Trp-Lys]-D-Val-D-Pro-NH2 |
| 2229 | TCAM2226 | Lys-Lys-Phe-Lys-Lys-Phe-Phe-Arg-Arg-c[Asp-His-D-Nal(2')-Arg-Trp-Lys]-D-Pro-D-Val-NH2 |
| 2230 | TCAM2227 | Lys-Lys-Phe-Lys-Lys-Phe-Phe-Arg-Arg-c[Asp-His-D-Nal(2')-Arg-Trp-Lys]-D-Val-D-Phe-NH2 |
| 2231 | TCAM2228 | Lys-Lys-Phe-Lys-Lys-Phe-Phe-Arg-Arg-c[Asp-His-D-Nal(2')-Arg-Trp-Lys]-D-Phe-D-Val-NH2 |
| 2232 | TCAM2229 | Lys-Lys-Phe-Lys-Lys-Phe-Phe-c[Asp-Arg-Pro-D-Nal(2')-Arg-Trp-Arg-Lys]-D-Val-D-Pro-NH2 |
| 2233 | TCAM2230 | Lys-Lys-Phe-Lys-Lys-Phe-Phe-c[Asp-Arg-Pro-D-Nal(2')-Arg-Trp-Arg-Lys]-D-Pro-D-Val-NH2 |
| 2234 | TCAM2231 | Lys-Lys-Phe-Lys-Lys-Phe-Phe-c[Asp-Arg-Pro-D-Nal(2')-Arg-Trp-Arg-Lys]-D-Val-D-Phe-NH2 |
| 2235 | TCAM2232 | Lys-Lys-Phe-Lys-Lys-Phe-Phe-c[Asp-Arg-Pro-D-Nal(2')-Arg-Trp-Arg-Lys]-D-Phe-D-Val-NH2 |
| 2236 | TCAM2233 | Lys-Lys-Phe-Lys-Lys-Phe-Phe-c[Asp-Arg-His-D-Nal(2')-Arg-Trp-Arg-Lys]-D-Val-D-Pro-NH2 |
| 2237 | TCAM2234 | Lys-Lys-Phe-Lys-Lys-Phe-Phe-c[Asp-Arg-His-D-Nal(2')-Arg-Trp-Arg-Lys]-D-Pro-D-Val-NH2 |
| 2238 | TCAM2235 | Lys-Lys-Phe-Lys-Lys-Phe-Phe-c[Asp-Arg-His-D-Nal(2')-Arg-Trp-Arg-Lys]-D-Val-D-Phe-NH2 |
| 2239 | TCAM2236 | Lys-Lys-Phe-Lys-Lys-Phe-Phe-c[Asp-Arg-His-D-Nal(2')-Arg-Trp-Arg-Lys]-D-Phe-D-Val-NH2 |
| 2240 | TCAM2237 | Lys-Lys-Phe-Lys-Lys-Phe-Phe-c[Asp-His-D-Nal(2')-Arg-D-Nal(2')-Lys]-D-Val-D-Phe-NH2 |
| 2241 | TCAM2238 | Lys-Lys-Phe-Lys-Lys-Phe-Phe-c[Asp-His-D-Nal(2')-Arg-D-Nal(2')-Lys]-D-Phe-D-Val-NH2 |
| 2242 | TCAM2239 | Lys-Lys-Phe-Lys-Lys-Phe-Phe-c[Asp-Pro-D-Nal(2')-Arg-D-Nal(2')-Lys]-D-Val-D-Pro-NH2 |
| 2243 | TCAM2240 | Lys-Lys-Phe-Lys-Lys-Phe-Phe-c[Asp-Pro-D-Nal(2')-Arg-D-Nal(2')-Lys]-D-Pro-D-Val-NH2 |
| 2244 | TCAM2241 | Lys-Lys-Phe-Lys-Lys-Phe-Phe-c[Asp-Pro-D-Nal(2')-Arg-D-Nal(2')-Lys]-D-Val-D-Phe-NH2 |
| 2245 | TCAM2242 | Lys-Lys-Phe-Lys-Lys-Phe-Phe-c[Asp-Pro-D-Nal(2')-Arg-D-Nal(2')-Lys]-D-Phe-D-Val-NH2 |
| 2246 | TCAM2243 | Lys-Lys-Phe-Lys-Lys-Phe-Phe-c[Asp-Arg-Arg-D-Nal(2')-Arg-D-Nal(2')-Lys]-D-Val-D-Pro-NH2 |
| 2247 | TCAM2244 | Lys-Lys-Phe-Lys-Lys-Phe-Phe-c[Asp-Arg-Arg-D-Nal(2')-Arg-D-Nal(2')-Lys]-D-Pro-D-Val-NH2 |
| 2248 | TCAM2245 | Lys-Lys-Phe-Lys-Lys-Phe-Phe-c[Asp-Arg-Arg-D-Nal(2')-Arg-D-Nal(2')-Lys]-D-Val-D-Phe-NH2 |
| 2249 | TCAM2246 | Lys-Lys-Phe-Lys-Lys-Phe-Phe-c[Asp-Arg-Arg-D-Nal(2')-Arg-D-Nal(2')-Lys]-D-Phe-D-Val-NH2 |
| 2250 | TCAM2247 | Lys-Lys-Phe-Lys-Lys-Phe-Phe-c[Asp-Arg-Arg-Pro-D-Nal(2')-Arg-D-Nal(2')-Lys]-D-Val-D-Pro-NH2 |
| 2251 | TCAM2248 | Lys-Lys-Phe-Lys-Lys-Phe-Phe-c[Asp-Arg-Arg-Pro-D-Nal(2')-Arg-D-Nal(2')-Lys]-D-Pro-D-Val-NH2 |

TABLE 5-continued

Exemplary Anti-microbial peptides

| SEQ NO: | Peptide | Peptide Sequence |
|---|---|---|
| 2252 | TCAM2249 | Lys-Lys-Phe-Lys-Lys-Phe-Phe-c[Asp-Arg-Arg-Pro-D-Nal(2')-Arg-D-Nal(2')-Lys]-D-Val-D-Phe-NH2 |
| 2253 | TCAM2250 | Lys-Lys-Phe-Lys-Lys-Phe-Phe-c[Asp-Arg-Arg-Pro-D-Nal(2')-Arg-D-Nal(2')-Lys]-D-Phe-D-Val-NH2 |
| 2254 | TCAM2251 | Lys-Lys-Phe-Lys-Lys-Phe-Phe-c[Asp-Arg-D-Nal(2')-Arg-D-Nal(2')-Lys]-D-Val-D-Pro-NH2 |
| 2255 | TCAM2252 | Lys-Lys-Phe-Lys-Lys-Phe-Phe-c[Asp-Arg-D-Nal(2')-Arg-D-Nal(2')-Lys]-D-Pro-D-Val-NH2 |
| 2256 | TCAM2253 | Lys-Lys-Phe-Lys-Lys-Phe-Phe-c[Asp-Arg-Nal(2')-Arg-D-Nal(2')-Lys]-D-Val-D-Phe-NH2 |
| 2257 | TCAM2254 | Lys-Lys-Phe-Lys-Lys-Phe-Phe-c[Asp-Arg-D-Nal(2')-Arg-D-Nal(2')-Lys]-D-Phe-D-Val-NH2 |
| 2258 | TCAM2255 | Lys-Lys-Phe-Lys-Lys-Phe-Phe-c[Asp-Arg-Pro-D-Nal(2')-Arg-D-Nal(2')-Lys]-D-Val-D-Pro-NH2 |
| 2259 | TCAM2256 | Lys-Lys-Phe-Lys-Lys-Phe-Phe-c[Asp-Arg-Pro-D-Nal(2')-Arg-D-Nal(2')-Lys]-D-Pro-D-Val-NH2 |
| 2260 | TCAM2257 | Lys-Lys-Phe-Lys-Lys-Phe-Phe-c[Asp-Arg-Pro-D-Nal(2')-Arg-D-Nal(2')-Lys]-D-Val-D-Phe-NH2 |
| 2261 | TCAM2258 | Lys-Lys-Phe-Lys-Lys-Phe-Phe-c[Asp-Arg-Pro-D-Nal(2')-Arg-D-Nal(2')-Lys]-D-Phe-D-Val-NH2 |
| 2262 | TCAM2259 | Lys-Lys-Phe-Lys-Lys-Phe-Phe-c[Asp-Arg-His-D-Nal(2')-Arg-D-Nal(2')-Lys]-D-Val-D-Pro-NH2 |
| 2263 | TCAM2260 | Lys-Lys-Phe-Lys-Lys-Phe-Phe-c[Asp-Arg-His-D-Nal(2')-Arg-D-Nal(2')-Lys]-D-Pro-D-Val-NH2 |
| 2264 | TCAM2261 | Lys-Lys-Phe-Lys-Lys-Phe-Phe-c[Asp-Arg-His-Nal(2')-Arg-D-Nal(2')-Lys]-D-Val-D-Phe-NH2 |
| 2265 | TCAM2262 | Lys-Lys-Phe-Lys-Lys-Phe-Phe-c[Asp-Arg-His-Nal(2')-Arg-D-Nal(2')-Lys]-D-Phe-D-Val-NH2 |
| 2266 | TCAM2263 | Lys-Lys-Phe-Lys-Lys-Phe-Phe-c[Asp-Arg-D-D-Nal(2')-Arg-D-Nal(2')-Arg-Lys]-D-Val-D-Pro-NH2 |
| 2267 | TCAM2264 | Lys-Lys-Phe-Lys-Lys-Phe-Phe-c[Asp-Arg-D-Nal(2')-Arg-D-Nal(2')-Arg-Lys]-D-Pro-D-Val-NH2 |
| 2268 | TCAM2265 | Lys-Lys-Phe-Lys-Lys-Phe-Phe-c[Asp-Arg-D-Nal(2')-Arg-D-Nal(2')-Arg-Lys]-D-Val-D-Phe-NH2 |
| 2269 | TCAM2266 | Lys-Lys-Phe-Lys-Lys-Phe-Phe-c[Asp-Arg-D-Nal(2')-Arg-D-Nal(2')-Arg-Lys]-D-Phe-D-Val-NH2 |
| 2270 | TCAM2267 | Lys-Lys-Phe-Lys-Lys-Phe-Phe-c[Asp-Arg-Pro-D-Nal(2')-Arg-D-Nal(2')-Arg-Lys]-D-Val-D-Pro-NH2 |
| 2271 | TCAM2268 | Lys-Lys-Phe-Lys-Lys-Phe-Phe-c[Asp-Arg-Pro-D-Nal(2')-Arg-D-Nal(2')-Arg-Lys]-D-Pro-D-Val-NH2 |
| 2272 | TCAM2269 | Lys-Lys-Phe-Lys-Lys-Phe-Phe-c[Asp-Arg-Pro-D-Nal(2')-Arg-D-Nal(2')-Arg-Lys]-D-Val-D-Phe-NH2 |
| 2273 | TCAM2270 | Lys-Lys-Phe-Lys-Lys-Phe-Phe-c[Asp-Arg-Pro-D-Nal(2')-Arg-D-Nal(2')-Arg-Lys]-D-Phe-D-Val-NH2 |
| 2274 | TCAM2271 | Lys-Lys-Phe-Lys-Lys-Phe-Phe-c[Asp-Arg-His-D-Nal(2')-Arg-D-Nal(2')-Arg-Lys]-D-Val-D-Pro-NH2 |
| 2275 | TCAM2272 | Lys-Lys-Phe-Lys-Lys-Phe-Phe-c[Asp-Arg-His-D-Nal(2')-Arg-D-Nal(2')-Arg-Lys]-D-Pro-D-Val-NH2 |
| 2276 | TCAM2273 | Lys-Lys-Phe-Lys-Lys-Phe-Phe-c[Asp-Arg-His-D-Nal(2')-Arg-D-Nal(2')-Arg-Lys]-D-Val-D-Phe-NH2 |

TABLE 5-continued

Exemplary Anti-microbial peptides

| SEQ NO: | Peptide | Peptide Sequence |
|---|---|---|
| 2277 | TCAM2274 | Lys-Lys-Phe-Lys-Lys-Phe-Phe-c[Asp-Arg-His-D-Nal(2')-Arg-D-Nal(2')-Arg-Lys]-D-Phe-D-Val-NH2 |
| 2278 | TCAM2275 | Lys-Lys-Phe-Lys-Lys-Phe-Phe-Arg-Arg-c[Asp-Pro-D-Nal(2')-Arg-D-Nal(2')-Lys]-D-Val-D-Pro-NH2 |
| 2279 | TCAM2276 | Lys-Lys-Phe-Lys-Lys-Phe-Phe-Arg-Arg-c[Asp-Pro-D-Nal(2')-Arg-D-Nal(2')-Lys]-D-Pro-D-Val-NH2 |
| 2280 | TCAM2277 | Lys-Lys-Phe-Lys-Lys-Phe-Phe-Arg-Arg-c[Asp-Pro-D-Nal(2')-Arg-D-Nal(2')-Lys]-D-Val-D-Phe-NH2 |
| 2281 | TCAM2278 | Lys-Lys-Phe-Lys-Lys-Phe-Phe-Arg-Arg-c[Asp-Pro-D-Nal(2')-Arg-D-Nal(2')-Lys]-D-Phe-D-Val-NH2 |
| 2282 | TCAM2279 | Lys-Lys-Phe-Lys-Lys-Phe-Phe-Arg-Arg-c[Asp-His-D-Nal(2')-Arg-D-Nal(2')-Lys]-D-Val-D-Pro-NH2 |
| 2283 | TCAM2280 | Lys-Lys-Phe-Lys-Lys-Phe-Phe-Arg-Arg-c[Asp-His-D-Nal(2')-Arg-D-Nal(2')-Lys]-D-Pro-D-Val-NH2 |
| 2284 | TCAM2281 | Lys-Lys-Phe-Lys-Lys-Phe-Phe-Arg-Arg-c[Asp-His-D-Nal(2')-Arg-D-Nal(2')-Lys]-D-Val-D-Phe-NH2 |
| 2285 | TCAM2282 | Lys-Lys-Phe-Lys-Lys-Phe-Phe-Arg-Arg-c[Asp-His-D-Nal(2')-Arg-D-Nal(2')-Lys]-D-Phe-D-Val-NH2 |
| 2286 | TCAM2283 | Lys-Lys-Phe-Lys-Lys-Phe-Phe-c[Asp-Arg-Pro-D-Nal(2')-Arg-D-Nal(2')-Arg-Lys]-D-Val-D-Pro-NH2 |
| 2287 | TCAM2284 | Lys-Lys-Phe-Lys-Lys-Phe-Phe-c[Asp-Arg-Pro-D-Nal(2')-Arg-D-Nal(2')-Arg-Lys]-D-Pro-D-Val-NH2 |
| 2288 | TCAM2285 | Lys-Lys-Phe-Lys-Lys-Phe-Phe-c[Asp-Arg-Pro-D-Nal(2')-Arg-D-Nal(2')-Arg-Lys]-D-Val-D-Phe-NH2 |
| 2289 | TCAM2286 | Lys-Lys-Phe-Lys-Lys-Phe-Phe-c[Asp-Arg-Pro-D-Nal(2')-Arg-D-Nal(2')-Arg-Lys]-D-Phe-D-Val-NH2 |
| 2290 | TCAM2287 | Lys-Lys-Phe-Lys-Lys-Phe-Phe-c[Asp-Arg-His-D-Nal(2')-Arg-D-Nal(2')-Arg-Lys]-D-Val-D-Pro-NH2 |
| 2291 | TCAM2288 | Lys-Lys-Phe-Lys-Lys-Phe-Phe-c[Asp-Arg-His-D-Nal(2')-Arg-D-Nal(2')-Arg-Lys]-D-Pro-D-Val-NH2 |
| 2292 | TCAM2289 | Lys-Lys-Phe-Lys-Lys-Phe-Phe-c[Asp-Arg-His-D-Nal(2')-Arg-D-Nal(2')-Arg-Lys]-D-Val-D-Phe-NH2 |
| 2293 | TCAM2290 | Lys-Lys-Phe-Lys-Lys-Phe-Phe-c[Asp-Arg-His-D-Nal(2')-Arg-D-Nal(2')-Arg-Lys]-D-Phe-D-Val-NH2 |
| 2294 | TCAM2291 | Lys-Lys-Phe-Lys-Lys-Phe-Phe-c[Asp-His-D-Nal(2')-Arg-Trp-Lys]-Arg-Arg-D-Val-D-Pro-NH2 |
| 2295 | TCAM2292 | Lys-Lys-Phe-Lys-Lys-Phe-Phe-c[Asp-His-D-Nal(2')-Arg-Trp-Lys]-Arg-Arg-D-Pro-D-Val-NH2 |
| 2296 | TCAM2293 | Lys-Lys-Phe-Lys-Lys-Phe-Phe-c[Asp-His-D-Nal(2')-Arg-Trp-Lys]-Arg-Arg-D-Val-D-Phe-NH2 |
| 2297 | TCAM2294 | Lys-Lys-Phe-Lys-Lys-Phe-Phe-c[Asp-His-D-Nal(2')-Arg-Trp-Lys]-Arg-Arg-D-Phe-D-Val-NH2 |
| 2298 | TCAM2295 | Lys-Lys-Phe-Lys-Lys-Phe-Phe-c[Asp-Pro-D-Nal(2')-Arg-Trp-Lys]-Arg-Arg-D-Val-D-Pro-NH2 |
| 2299 | TCAM2296 | Lys-Lys-Phe-Lys-Lys-Phe-Phe-c[Asp-Pro-D-Nal(2')-Arg-Trp-Lys]-Arg-Arg-D-Pro-D-Val-NH2 |
| 2300 | TCAM2297 | Lys-Lys-Phe-Lys-Lys-Phe-Phe-c[Asp-Pro-D-Nal(2')-Arg-Trp-Lys]-Arg-Arg-D-Val-D-Phe-NH2 |
| 2301 | TCAM2298 | Lys-Lys-Phe-Lys-Lys-Phe-Phe-c[Asp-Pro-D-Nal(2')-Arg-Trp-Lys]-Arg-Arg-D-Phe-D-Val-NH2 |

TABLE 5-continued

Exemplary Anti-microbial peptides

| SEQ NO: | Peptide | Peptide Sequence |
|---|---|---|
| Anti-biofilm peptide ABF4ARG linked to anti-microbial peptides | | |
| 2302 | TCAM2299 | Arg-Arg-Phe-Arg-Arg-Phe-Phe-c[Asp-Pro-Arg-Arg-Trp-Trp-Arg-Phe-Lys]-D-Val-D-Pro-NH2 |
| 2303 | TCAM2300 | Arg-Arg-Phe-Arg-Arg-Phe-Phe-c[Asp-Pro-Arg-Arg-Trp-Trp-Arg-Phe-Lys]-D-Val-D-Phe-NH2 |
| 2304 | TCAM2301 | Arg-Arg-Phe-Arg-Arg-Phe-Phe-c[Asp-Pro-Arg-Arg-Trp-Trp-Arg-Phe-Lys]-D-Pro-D-Val-NH2 |
| 2305 | TCAM2302 | Arg-Arg-Phe-Arg-Arg-Phe-Phe-c[Asp-Pro-Arg-Arg-Trp-Trp-Arg-Phe-Lys]-D-Phe-D-Val-NH2 |
| 2306 | TCAM2303 | Arg-Arg-Phe-Arg-Arg-Phe-Phe-c[Asp-Pro-Arg-Arg-Trp-Trp-Tyr-Phe-Lys]-D-Val-D-Pro-NH2 |
| 2307 | TCAM2304 | Arg-Arg-Phe-Arg-Arg-Phe-Phe-c[Asp-Pro-Arg-Arg-Trp-Trp-Tyr-Phe-Lys]-D-Val-D-Phe-NH2 |
| 2308 | TCAM2305 | Arg-Arg-Phe-Arg-Arg-Phe-Phe-c[Asp-Pro-Arg-Arg-Trp-Trp-Tyr-Phe-Lys]-D-Pro-D-Val-NH2 |
| 2309 | TCAM2306 | Arg-Arg-Phe-Arg-Arg-Phe-Phe-c[Asp-Pro-Arg-Arg-Trp-Trp-Tyr-Phe-Lys]-D-Phe-D-Val-NH2 |
| 2310 | TCAM2307 | Arg-Arg-Phe-Arg-Arg-Phe-Phe-c[Asp-Pro-Arg-Arg-Tyr-Tyr-Arg-Phe-Lys]-D-Val-D-Pro-NH2 |
| 2311 | TCAM2308 | Arg-Arg-Phe-Arg-Arg-Phe-Phe-c[Asp-Pro-Arg-Arg-Tyr-Tyr-Arg-Phe-Lys]-D-Val-D-Phe-NH2 |
| 2312 | TCAM2309 | Arg-Arg-Phe-Arg-Arg-Phe-Phe-c[Asp-Pro-Arg-Arg-Tyr-Tyr-Arg-Phe-Lys]-D-Pro-D-Val-NH2 |
| 2313 | TCAM2310 | Arg-Arg-Phe-Arg-Arg-Phe-Phe-c[Asp-Pro-Arg-Arg-Tyr-Tyr-Arg-Phe-Lys]-D-Phe-D-Val-NH2 |
| 2314 | TCAM2311 | Arg-Arg-Phe-Arg-Arg-Phe-Phe-c[Asp-Pro-Arg-Arg-Nal-Nal-Arg-Phe-Lys]-D-Val-D-Pro-NH2 |
| 2315 | TCAM2312 | Arg-Arg-Phe-Arg-Arg-Phe-Phe-c[Asp-Pro-Arg-Arg-Nal-Nal-Arg-Phe-Lys]-D-Val-D-Phe-NH2 |
| 2316 | TCAM2313 | Arg-Arg-Phe-Arg-Arg-Phe-Phe-c[Asp-Pro-Arg-Arg-Nal-Nal-Arg-Phe-Lys]-D-Pro-D-Val-NH2 |
| 2317 | TCAM2314 | Arg-Arg-Phe-Arg-Arg-Phe-Phe-c[Asp-Pro-Arg-Arg-Nal-Nal-Arg-Phe-Lys]-D-Phe-D-Val-NH2 |
| 2318 | TCAM2315 | Arg-Arg-Phe-Arg-Arg-Phe-Phe-c[Asp-Pro-Arg-Arg-Leu-Trp-Leu-Trp-Lys]-D-Val-D-Pro-NH2 |
| 2319 | TCAM2316 | Arg-Arg-Phe-Arg-Arg-Phe-Phe-c[Asp-Pro-Arg-Arg-Leu-Trp-Leu-Trp-Lys]-D-Val-D-Phe-NH2 |
| 2320 | TCAM2317 | Arg-Arg-Phe-Arg-Arg-Phe-Phe-c[Asp-Pro-Arg-Arg-Leu-Trp-Leu-Trp-Lys]-D-Pro-D-Val-NH2 |
| 2321 | TCAM2318 | Arg-Arg-Phe-Arg-Arg-Phe-Phe-c[Asp-Pro-Arg-Arg-Leu-Trp-Leu-Trp-Lys]-D-Phe-D-Val-NH2 |
| 2322 | TCAM2319 | Arg-Arg-Phe-Arg-Arg-Phe-Phe-c[Asp-Pro-Arg-Arg-Leu-Trp-Leu-Trp-Lys]-D-Val-D-Pro-NH2 |
| 2323 | TCAM2320 | Arg-Arg-Phe-Arg-Arg-Phe-Phe-c[Asp-Pro-Arg-Arg-Leu-Trp-Leu-Trp-Lys]-D-Val-D-Phe-NH2 |
| 2324 | TCAM2321 | Arg-Arg-Phe-Arg-Arg-Phe-Phe-c[Asp-Pro-Arg-Arg-Leu-Trp-Leu-Trp-Lys]-D-Pro-D-Val-NH2 |
| 2325 | TCAM2322 | Arg-Arg-Phe-Arg-Arg-Phe-Phe-c[Asp-Pro-Arg-Arg-Leu-Trp-Leu-Trp-Lys]-D-Phe-D-Val-NH2 |

TABLE 5-continued

Exemplary Anti-microbial peptides

| SEQ NO: | Peptide | Peptide Sequence |
|---|---|---|
| 2326 | TCAM2323 | Arg-Arg-Phe-Arg-Arg-Phe-Phe-c[Asp-Arg-Arg-Arg-Trp-Leu-Trp-Leu-Trp-Lys]-D-Val-D-Pro-NH2 |
| 2327 | TCAM2324 | Arg-Arg-Phe-Arg-Arg-Phe-Phe-c[Asp-Pro-Arg-Arg-Arg-Trp-Leu-Trp-Leu-Trp-Lys]-D-Val-D-Phe-NH2 |
| 2328 | TCAM2325 | Arg-Arg-Phe-Arg-Arg-Phe-Phe-c[Asp-Pro-Arg-Arg-Arg-Trp-Leu-Trp-Leu-Trp-Lys]-D-Pro-D-Val-NH2 |
| 2329 | TCAM2326 | Arg-Arg-Phe-Arg-Arg-Phe-Phe-c[Asp-Pro-Arg-Arg-Arg-Trp-Leu-Trp-Leu-Trp-Lys]-D-Phe-D-Val-NH2 |
| 2330 | TCAM2327 | Arg-Arg-Phe-Arg-Arg-Phe-Phe-c[Asp-Pro-Arg-Gln-Arg-Arg-Trp-Leu-Trp-Leu-Trp-Lys]-D-Val-D-Pro-NH2 |
| 2331 | TCAM2328 | Arg-Arg-Phe-Arg-Arg-Phe-Phe-c[Asp-Pro-Arg-Gln-Arg-Arg-Trp-Leu-Trp-Leu-Trp-Lys]-D-Val-D-Phe-NH2 |
| 2332 | TCAM2329 | Arg-Arg-Phe-Arg-Arg-Phe-Phe-c[Asp-Pro-Arg-Gln-Arg-Arg-Trp-Leu-Trp-Leu-Trp-Lys]-D-Pro-D-Val-NH2 |
| 2333 | TCAM2330 | Arg-Arg-Phe-Arg-Arg-Phe-Phe-c[Asp-Pro-Arg-Gln-Arg-Arg-Trp-Leu-Trp-Leu-Trp-Lys]-D-Phe-D-Val-NH2 |
| 2334 | TCAM2331 | Arg-Arg-Phe-Arg-Arg-Phe-Phe-c[Asp-Pro-Trp-Arg-Trp-Trp-Arg-Arg-Lys]-D-Val-D-Phe-NH2 |
| 2335 | TCAM2332 | Arg-Arg-Phe-Arg-Arg-Phe-Phe-c[Asp-Pro-Trp-Arg-Trp-Trp-Arg-Arg-Lys]-D-Pro-D-Val-NH2 |
| 2336 | TCAM2333 | Arg-Arg-Phe-Arg-Arg-Phe-Phe-c[Asp-Pro-Trp-Arg-Trp-Trp-Arg-Arg-Lys]-D-Phe-D-Val-NH2 |
| 2337 | TCAM2334 | Arg-Arg-Phe-Arg-Arg-Phe-Phe-c[Asp-Pro-Trp-Trp-Arg-Arg-Trp-Trp-Arg-Arg-Lys]-D-Val-D-Pro-NH2 |
| 2338 | TCAM2335 | Arg-Arg-Phe-Arg-Arg-Phe-Phe-c[Asp-Pro-Trp-Trp-Arg-Arg-Trp-Trp-Arg-Arg-Lys]-D-Val-D-Phe-NH2 |
| 2339 | TCAM2336 | Arg-Arg-Phe-Arg-Arg-Phe-Phe-c[Asp-Pro-Trp-Trp-Arg-Arg-Trp-Trp-Arg-Arg-Lys]-D-Pro-D-Val-NH2 |
| 2340 | TCAM2337 | Arg-Arg-Phe-Arg-Arg-Phe-Phe-c[Asp-Pro-Trp-Trp-Arg-Arg-Trp-Trp-Arg-Arg-Lys]-D-Phe-D-Val-NH2 |
| 2341 | TCAM2338 | Arg-Arg-Phe-Arg-Arg-Phe-Phe-c[Asp-Pro-Trp-Arg-Trp-Arg-Trp-Arg-Lys]-D-Val-D-Pro-NH2 |
| 2342 | TCAM2339 | Arg-Arg-Phe-Arg-Arg-Phe-Phe-c[Asp-Pro-Trp-Arg-Trp-Arg-Trp-Arg-Lys]-D-Val-D-Phe-NH2 |
| 2343 | TCAM2340 | Arg-Arg-Phe-Arg-Arg-Phe-Phe-c[Asp-Pro-Trp-Arg-Trp-Arg-Trp-Arg-Lys]-D-Pro-D-Val-NH2 |
| 2344 | TCAM2341 | Arg-Arg-Phe-Arg-Arg-Phe-Phe-c[Asp-Pro-Trp-Arg-Trp-Arg-Trp-Arg-Lys]-D-Phe-D-Val-NH2 |
| 2345 | TCAM2342 | Arg-Arg-Phe-Arg-Arg-Phe-Phe-c[Asp-Pro-Arg-Trp-Arg-Trp-Arg-Trp-Lys]-D-Val-D-Pro-NH2 |
| 2346 | TCAM2343 | Arg-Arg-Phe-Arg-Arg-Phe-Phe-c[Asp-Pro-Arg-Trp-Arg-Trp-Arg-Trp-Lys]-D-Val-D-Phe-NH2 |
| 2347 | TCAM2344 | Arg-Arg-Phe-Arg-Arg-Phe-Phe-c[Asp-Pro-Arg-Trp-Arg-Trp-Arg-Trp-Lys]-D-Pro-D-Val-NH2 |
| 2348 | TCAM2345 | Arg-Arg-Phe-Arg-Arg-Phe-Phe-c[Asp-Pro-Arg-Trp-Arg-Trp-Arg-Trp-Lys]-D-Phe-D-Val-NH2 |
| 2349 | TCAM2346 | Arg-Arg-Phe-Arg-Arg-Phe-Phe-c[Asp-Pro-Arg-Trp-Trp-Arg-Arg-Lys]-D-Val-D-Pro-NH2 |
| 2350 | TCAM2347 | Arg-Arg-Phe-Arg-Arg-Phe-Phe-c[Asp-Pro-Arg-Trp-Trp-Arg-Arg-Lys]-D-Val-D-Phe-NH2 |

TABLE 5-continued

Exemplary Anti-microbial peptides

| SEQ NO: | Peptide | Peptide Sequence |
|---|---|---|
| 2351 | TCAM2348 | Arg-Arg-Phe-Arg-Arg-Phe-Phe-c[Asp-Pro-Arg-Trp-Trp-Arg-Arg-Lys]-D-Pro-D-Val-NH2 |
| 2352 | TCAM2349 | Arg-Arg-Phe-Arg-Arg-Phe-Phe-c[Asp-Pro-Arg-Trp-Trp-Arg-Arg-Lys]-D-Phe-D-Val-NH2 |
| 2353 | TCAM2350 | Arg-Arg-Phe-Arg-Arg-Phe-Phe-c[Asp-Pro-Trp-Trp-Arg-Arg-Trp-Lys]-D-Val-D-Pro-NH2 |
| 2354 | TCAM2351 | Arg-Arg-Phe-Arg-Arg-Phe-Phe-c[Asp-Pro-Trp-Trp-Arg-Arg-Trp-Lys]-D-Val-D-Phe-NH2 |
| 2355 | TCAM2352 | Arg-Arg-Phe-Arg-Arg-Phe-Phe-c[Asp-Pro-Trp-Trp-Arg-Arg-Trp-Lys]-D-Pro-D-Val-NH2 |
| 2356 | TCAM2353 | Arg-Arg-Phe-Arg-Arg-Phe-Phe-c[Asp-Pro-Trp-Trp-Arg-Arg-Trp-Lys]-D-Phe-D-Val-NH2 |
| 2357 | TCAM2354 | Arg-Arg-Phe-Arg-Arg-Phe-Phe-c[Asp-Pro-Trp-Arg-Trp-Arg-Trp-Lys]-D-Val-D-Pro-NH2 |
| 2358 | TCAM2355 | Arg-Arg-Phe-Arg-Arg-Phe-Phe-c[Asp-Pro-Trp-Arg-Trp-Arg-Trp-Lys]-D-Val-D-Phe-NH2 |
| 2359 | TCAM2356 | Arg-Arg-Phe-Arg-Arg-Phe-Phe-c[Asp-Pro-Trp-Arg-Trp-Arg-Trp-Lys]-D-Pro-D-Val-NH2 |
| 2360 | TCAM2357 | Arg-Arg-Phe-Arg-Arg-Phe-Phe-c[Asp-Pro-Trp-Arg-Trp-Arg-Trp-Lys]-D-Phe-D-Val-NH2 |
| 2361 | TCAM2358 | Arg-Arg-Phe-Arg-Arg-Phe-Phe-c[Asp-Pro-Arg-Trp-Arg-Trp-Arg-Lys]-D-Val-D-Pro-NH2 |
| 2362 | TCAM2359 | Arg-Arg-Phe-Arg-Arg-Phe-Phe-c[Asp-Pro-Arg-Trp-Arg-Trp-Arg-Lys]-D-Val-D-Phe-NH2 |
| 2363 | TCAM2360 | Arg-Arg-Phe-Arg-Arg-Phe-Phe-c[Asp-Pro-Arg-Trp-Arg-Trp-Arg-Lys]-D-Pro-D-Val-NH2 |
| 2364 | TCAM2361 | Arg-Arg-Phe-Arg-Arg-Phe-Phe-c[Asp-Pro-Arg-Trp-Arg-Trp-Arg-Lys]-D-Phe-D-Val-NH2 |
| 2365 | TCAM2362 | Arg-Arg-Phe-Arg-Arg-Phe-Phe-c[Asp-Pro-Trp-Arg-Tyr-Arg-Trp-Lys]-D-Val-D-Pro-NH2 |
| 2366 | TCAM2363 | Arg-Arg-Phe-Arg-Arg-Phe-Phe-c[Asp-Pro-Trp-Arg-Tyr-Arg-Trp-Lys]-D-Val-D-Phe-NH2 |
| 2367 | TCAM2364 | Arg-Arg-Phe-Arg-Arg-Phe-Phe-c[Asp-Pro-Trp-Arg-Tyr-Arg-Trp-Lys]-D-Pro-D-Val-NH2 |
| 2368 | TCAM2365 | Arg-Arg-Phe-Arg-Arg-Phe-Phe-c[Asp-Pro-Trp-Arg-Tyr-Arg-Trp-Lys]-D-Phe-D-Val-NH2 |
| 2369 | TCAM2366 | Arg-Arg-Phe-Arg-Arg-Phe-Phe-c[Asp-Pro-Trp-Arg-Trp-Arg-Tyr-Lys]-D-Val-D-Pro-NH2 |
| 2370 | TCAM2367 | Arg-Arg-Phe-Arg-Arg-Phe-Phe-c[Asp-Pro-Trp-Arg-Trp-Arg-Tyr-Lys]-D-Val-D-Phe-NH2 |
| 2371 | TCAM2368 | Arg-Arg-Phe-Arg-Arg-Phe-Phe-c[Asp-Pro-Trp-Arg-Trp-Arg-Tyr-Lys]-D-Pro-D-Val-NH2 |
| 2372 | TCAM2369 | Arg-Arg-Phe-Arg-Arg-Phe-Phe-c[Asp-Pro-Trp-Arg-Trp-Arg-Tyr-Lys]-D-Phe-D-Val-NH2 |
| 2373 | TCAM2370 | Arg-Arg-Phe-Arg-Arg-Phe-Phe-c[Asp-Pro-Trp-Arg-Trp-Arg-Lys]-D-Val-D-Pro-NH2 |
| 2374 | TCAM2371 | Arg-Arg-Phe-Arg-Arg-Phe-Phe-c[Asp-Pro-Trp-Arg-Trp-Arg-Lys]-D-Val-D-Phe-NH2 |
| 2375 | TCAM2372 | Arg-Arg-Phe-Arg-Arg-Phe-Phe-c[Asp-Pro-Trp-Arg-Trp-Arg-Lys]-D-Pro-D-Val-NH2 |
| 2376 | TCAM2373 | Arg-Arg-Phe-Arg-Arg-Phe-Phe-c[Asp-Pro-Trp-Arg-Trp-Arg-Lys]-D-Phe-D-Val-NH2 |
| 2377 | TCAM2374 | Arg-Arg-Phe-Arg-Arg-Phe-Phe-c[Asp-Pro-Trp-Arg-Arg-Trp-Lys]-D-Val-D-Pro-NH2 |
| 2378 | TCAM2375 | Arg-Arg-Phe-Arg-Arg-Phe-Phe-c[Asp-Pro-Trp-Arg-Arg-Trp-Lys]-D-Val-D-Phe-NH2 |
| 2379 | TCAM2376 | Arg-Arg-Phe-Arg-Arg-Phe-Phe-c[Asp-Pro-Trp-Arg-Arg-Trp-Lys]-D-Pro-D-Val-NH2 |
| 2380 | TCAM2377 | Arg-Arg-Phe-Arg-Arg-Phe-Phe-c[Asp-Pro-Trp-Arg-Arg-Trp-Lys]-D-Phe-D-Val-NH2 |
| 2381 | TCAM2378 | Arg-Arg-Phe-Arg-Arg-Phe-Phe-c[Asp-Pro-Arg-Trp-Trp-Arg-Lys]-D-Val-D-Pro-NH2 |
| 2382 | TCAM2379 | Arg-Arg-Phe-Arg-Arg-Phe-Phe-c[Asp-Pro-Arg-Trp-Trp-Arg-Lys]-D-Val-D-Phe-NH2 |
| 2383 | TCAM2380 | Arg-Arg-Phe-Arg-Arg-Phe-Phe-c[Asp-Pro-Arg-Trp-Trp-Arg-Lys]-D-Pro-D-Val-NH2 |
| 2384 | TCAM2381 | Arg-Arg-Phe-Arg-Arg-Phe-Phe-c[Asp-Pro-Arg-Trp-Trp-Arg-Lys]-D-Phe-D-Val-NH2 |
| 2385 | TCAM2382 | Arg-Arg-Phe-Arg-Arg-Phe-Phe-c[Asp-Pro-Trp-Arg-Trp-Lys]-D-Val-D-Pro-NH2 |
| 2386 | TCAM2383 | Arg-Arg-Phe-Arg-Arg-Phe-Phe-c[Asp-Pro-Trp-Arg-Trp-Lys]-D-Val-D-Phe-NH2 |

TABLE 5-continued

Exemplary Anti-microbial peptides

| SEQ NO: | Peptide | Peptide Sequence |
|---|---|---|
| 2387 | TCAM2384 | Arg-Arg-Phe-Arg-Arg-Phe-Phe-c[Asp-Pro-Trp-Arg-Trp-Lys]-D-Pro-D-Val-NH2 |
| 2388 | TCAM2385 | Arg-Arg-Phe-Arg-Arg-Phe-Phe-c[Asp-Pro-Trp-Arg-Trp-Lys]-D-Phe-D-Val-NH2 |
| 2389 | TCAM2386 | Arg-Arg-Phe-Arg-Arg-Phe-Phe-c[Asp-Pro-Arg-Trp-Arg-Lys]-D-Val-D-Pro-NH2 |
| 2390 | TCAM2387 | Arg-Arg-Phe-Arg-Arg-Phe-Phe-c[Asp-Pro-Arg-Trp-Arg-Lys]-D-Val-D-Phe-NH2 |
| 2391 | TCAM2388 | Arg-Arg-Phe-Arg-Arg-Phe-Phe-c[Asp-Pro-Arg-Trp-Arg-Lys]-D-Pro-D-Val-NH2 |
| 2392 | TCAM2389 | Arg-Arg-Phe-Arg-Arg-Phe-Phe-c[Asp-Pro-Arg-Trp-Arg-Lys]-D-Phe-D-Val-NH2 |
| 2393 | TCAM2390 | -Arg-Arg-Phe-Arg-Arg-Phe-Phe-c[Asp-Arg-Arg-Trp-Trp-Arg-Phe-Lys]-D-Val-D-Pro-NH2 |
| 2394 | TCAM2391 | Arg-Arg-Phe-Arg-Arg-Phe-Phe-c[Asp-Arg-Arg-Trp-Trp-Arg-Phe-Lys]-D-Val-D-Phe-NH2 |
| 2395 | TCAM2392 | Arg-Arg-Phe-Arg-Arg-Phe-Phe-c[Asp-Arg-Arg-Trp-Trp-Arg-Phe-Lys]-D-Pro-D-Val-NH2 |
| 2396 | TCAM2393 | Arg-Arg-Phe-Arg-Arg-Phe-Phe-c[Asp-Arg-Arg-Trp-Trp-Arg-Phe-Lys]-D-Phe-D-Val-NH2 |
| 2397 | TCAM2394 | Arg-Arg-Phe-Arg-Arg-Phe-Phe-c[Asp-Arg-Arg-Trp-Trp-Arg-Phe-Lys]-D-Val-D-Pro-NH2 |
| 2398 | TCAM2395 | Arg-Arg-Phe-Arg-Arg-Phe-Phe-c[Asp-Arg-Arg-Trp-Trp-Arg-Phe-Lys]-D-Val-D-Phe-NH2 |
| 2399 | TCAM2396 | Arg-Arg-Phe-Arg-Arg-Phe-Phe-c[Asp-Arg-Arg-Trp-Trp-Arg-Phe-Lys]-D-Pro-D-Val-NH2 |
| 2400 | TCAM2397 | Arg-Arg-Phe-Arg-Arg-Phe-Phe-c[Asp-Arg-Arg-Trp-Trp-Arg-Phe-Lys]-D-Phe-D-Val-NH2 |
| 2401 | TCAM2398 | Arg-Arg-Phe-Arg-Arg-Phe-Phe-c[Asp-Arg-Arg-Tyr-Tyr-Arg-Phe-Lys]-D-Val-D-Pro-NH2 |
| 2402 | TCAM2399 | Arg-Arg-Phe-Arg-Arg-Phe-Phe-c[Asp-Arg-Arg-Tyr-Tyr-Arg-Phe-Lys]-D-Val-D-Phe-NH2 |
| 2403 | TCAM2400 | Arg-Arg-Phe-Arg-Arg-Phe-Phe-c[Asp-Arg-Arg-Tyr-Tyr-Arg-Phe-Lys]-D-Pro-D-Val-NH2 |
| 2404 | TCAM2401 | Arg-Arg-Phe-Arg-Arg-Phe-Phe-c[Asp-Arg-Arg-Tyr-Tyr-Arg-Phe-Lys]-D-Phe-D-Val-NH2 |
| 2405 | TCAM2402 | Arg-Arg-Phe-Arg-Arg-Phe-Phe-c[Asp-Arg-Arg-Nal-Nal-Arg-Phe-Lys]-D-Val-D-Pro-NH2 |
| 2406 | TCAM2403 | Arg-Arg-Phe-Arg-Arg-Phe-Phe-c[Asp-Arg-Arg-Nal-Nal-Arg-Phe-Lys]-D-Val-D-Phe-NH2 |
| 2407 | TCAM2404 | Arg-Arg-Phe-Arg-Arg-Phe-Phe-c[Asp-Arg-Arg-Nal-Nal-Arg-Phe-Lys]-D-Pro-D-Val-NH2 |
| 2408 | TCAM2405 | Arg-Arg-Phe-Arg-Arg-Phe-Phe-c[Asp-Arg-Arg-Nal-Nal-Arg-Phe-Lys]-D-Phe-D-Val-NH2 |
| 2409 | TCAM2406 | Arg-Arg-Phe-Arg-Arg-Phe-Phe-c[Asp-Arg-Arg-Leu-Trp-Leu-Trp-Lys]-D-Val-D-Pro-NH2 |
| 2410 | TCAM2407 | Arg-Arg-Phe-Arg-Arg-Phe-Phe-c[Asp-Arg-Arg-Leu-Trp-Leu-Trp-Lys]-D-Val-D-Phe-NH2 |
| 2411 | TCAM2408 | Arg-Arg-Phe-Arg-Arg-Phe-Phe-c[Asp-Arg-Arg-Leu-Trp-Leu-Trp-Lys]-D-Pro-D-Val-NH2 |
| 2412 | TCAM2409 | Arg-Arg-Phe-Arg-Arg-Phe-Phe-c[Asp-Arg-Arg-Leu-Trp-Leu-Trp-Lys]-D-Phe-D-Val-NH2 |
| 2413 | TCAM2410 | Arg-Arg-Phe-Arg-Arg-Phe-Phe-c[Asp-Arg-Arg-Leu-Trp-Leu-Trp-Lys]-D-Val-D-Pro-NH2 |
| 2414 | TCAM2411 | Arg-Arg-Phe-Arg-Arg-Phe-Phe-c[Asp-Arg-Arg-Leu-Trp-Leu-Trp-Lys]-D-Val-D-Phe-NH2 |

TABLE 5-continued

Exemplary Anti-microbial peptides

| SEQ NO: | Peptide | Peptide Sequence |
|---|---|---|
| 2415 | TCAM2412 | Arg-Arg-Phe-Arg-Arg-Phe-Phe-c[Asp-Arg-Arg-Leu-Trp-Leu-Trp-Lys]-D-Pro-D-Val-NH2 |
| 2416 | TCAM2413 | Arg-Arg-Phe-Arg-Arg-Phe-Phe-c[Asp-Arg-Arg-Leu-Trp-Leu-Trp-Lys]-D-Phe-D-Val-NH2 |
| 2417 | TCAM2414 | Arg-Arg-Phe-Arg-Arg-Phe-Phe-c[Asp-Arg-Arg-Arg-Trp-Leu-Trp-Leu-Trp-Lys]-D-Val-D-Pro-NH2 |
| 2418 | TCAM2415 | Arg-Arg-Phe-Arg-Arg-Phe-Phe-c[Asp-Arg-Arg-Arg-Trp-Leu-Trp-Leu-Trp-Lys]-D-Val-D-Phe-NH2 |
| 2419 | TCAM2416 | Arg-Arg-Phe-Arg-Arg-Phe-Phe-c[Asp-Arg-Arg-Arg-Trp-Leu-Trp-Leu-Trp-Lys]-D-Pro-D-Val-NH2 |
| 2420 | TCAM2417 | Arg-Arg-Phe-Arg-Arg-Phe-Phe-c[Asp-Arg-Arg-Arg-Trp-Leu-Trp-Leu-Trp-Lys]-D-Phe-D-Val-NH2 |
| 2421 | TCAM2418 | Arg-Arg-Phe-Arg-Arg-Phe-Phe-c[Asp-Arg-Gln-Arg-Arg-Trp-Leu-Trp-Leu-Trp-Lys]-D-Val-D-Pro-NH2 |
| 2422 | TCAM2419 | Arg-Arg-Phe-Arg-Arg-Phe-Phe-c[Asp-Arg-Gln-Arg-Arg-Trp-Leu-Trp-Leu-Trp-Lys]-D-Val-D-Phe-NH2 |
| 2423 | TCAM2420 | Arg-Arg-Phe-Arg-Arg-Phe-Phe-c[Asp-Arg-Gln-Arg-Arg-Trp-Leu-Trp-Leu-Trp-Lys]-D-Pro-D-Val-NH2 |
| 2424 | TCAM2421 | Arg-Arg-Phe-Arg-Arg-Phe-Phe-c[Asp-Arg-Gln-Arg-Arg-Trp-Leu-Trp-Leu-Trp-Lys]-D-Phe-D-Val-NH2 |
| 2425 | TCAM2422 | Arg-Arg-Phe-Arg-Arg-Phe-Phe-c[Asp-Trp-Arg-Trp-Trp-Arg-Arg-Lys]-D-Val-D-Pro-NH2 |
| 2426 | TCAM2423 | Arg-Arg-Phe-Arg-Arg-Phe-Phe-c[Asp-Trp-Arg-Trp-Trp-Arg-Arg-Lys]-D-Val-D-Phe-NH2 |
| 2427 | TCAM2424 | Arg-Arg-Phe-Arg-Arg-Phe-Phe-c[Asp-Trp-Arg-Trp-Trp-Arg-Arg-Lys]-D-Pro-D-Val-NH2 |
| 2428 | TCAM2425 | Arg-Arg-Phe-Arg-Arg-Phe-Phe-c[Asp-Trp-Arg-Trp-Trp-Arg-Arg-Lys]-D-Phe-D-Val-NH2 |
| 2429 | TCAM2426 | Arg-Arg-Phe-Arg-Arg-Phe-Phe-c[Asp-Trp-Trp-Arg-Arg-Trp-Trp-Arg-Arg-Lys]-D-Val-D-Pro-NH2 |
| 2430 | TCAM2427 | Arg-Arg-Phe-Arg-Arg-Phe-Phe-c[Asp-Trp-Trp-Arg-Arg-Trp-Trp-Arg-Arg-Lys]-D-Val-D-Phe-NH2 |
| 2431 | TCAM2428 | Arg-Arg-Phe-Arg-Arg-Phe-Phe-c[Asp-Trp-Trp-Arg-Arg-Trp-Trp-Arg-Arg-Lys]-D-Pro-D-Val-NH2 |
| 2432 | TCAM2429 | Arg-Arg-Phe-Arg-Arg-Phe-Phe-c[Asp-Trp-Trp-Arg-Arg-Trp-Trp-Arg-Arg-Lys]-D-Phe-D-Val-NH2 |
| 2433 | TCAM2430 | Arg-Arg-Phe-Arg-Arg-Phe-Phe-c[Asp-Trp-Arg-Trp-Arg-Trp-Arg-Lys]-D-Val-D-Pro-NH2 |
| 2434 | TCAM2431 | Arg-Arg-Phe-Arg-Arg-Phe-Phe-c[Asp-Trp-Arg-Trp-Arg-Trp-Arg-Lys]-D-Val-D-Phe-NH2 |
| 2435 | TCAM2432 | Arg-Arg-Phe-Arg-Arg-Phe-Phe-c[Asp-Trp-Arg-Trp-Arg-Trp-Arg-Lys]-D-Pro-D-Val-NH2 |
| 2436 | TCAM2433 | Arg-Arg-Phe-Arg-Arg-Phe-Phe-c[Asp-Trp-Arg-Trp-Arg-Trp-Arg-Lys]-D-Phe-D-Val-NH2 |
| 2437 | TCAM2434 | Arg-Arg-Phe-Arg-Arg-Phe-Phe-c[Asp-Arg-Trp-Arg-Trp-Arg-Trp-Lys]-D-Val-D-Pro-NH2 |
| 2438 | TCAM2435 | Arg-Arg-Phe-Arg-Arg-Phe-Phe-c[Asp-Arg-Trp-Arg-Trp-Arg-Trp-Lys]-D-Val-D-Phe-NH2 |
| 2439 | TCAM2436 | Arg-Arg-Phe-Arg-Arg-Phe-Phe-c[Asp-Arg-Trp-Arg-Trp-Arg-Trp-Lys]-D-Pro-D-Val-NH2 |
| 2440 | TCAM2437 | Arg-Arg-Phe-Arg-Arg-Phe-Phe-c[Asp-Arg-Trp-Arg-Trp-Arg-Trp-Lys]-D-Phe-D-Val-NH2 |
| 2441 | TCAM2438 | Arg-Arg-Phe-Arg-Arg-Phe-Phe-c[Asp-Arg-Trp-Trp-Arg-Arg-Lys]-D-Val-D-Pro-NH2 |
| 2442 | TCAM2439 | Arg-Arg-Phe-Arg-Arg-Phe-Phe-c[Asp-Arg-Trp-Trp-Arg-Arg-Lys]-D-Val-D-Phe-NH2 |
| 2443 | TCAM2440 | Arg-Arg-Phe-Arg-Arg-Phe-Phe-c[Asp-Arg-Trp-Trp-Arg-Arg-Lys]-D-Pro-D-Val-NH2 |
| 2444 | TCAM2441 | Arg-Arg-Phe-Arg-Arg-Phe-Phe-c[Asp-Arg-Trp-Trp-Arg-Arg-Lys]-D-Phe-D-Val-NH2 |
| 2445 | TCAM2442 | Arg-Arg-Phe-Arg-Arg-Phe-Phe-c[Asp-Arg-Trp-Arg-Trp-Arg-Lys]-D-Val-D-Pro-NH2 |

TABLE 5-continued

Exemplary Anti-microbial peptides

| SEQ NO: | Peptide | Peptide Sequence |
|---|---|---|
| 2446 | TCAM2443 | Arg-Arg-Phe-Arg-Arg-Phe-Phe-c[Asp-Arg-Trp-Arg-Trp-Arg-Lys]-D-Val-D-Phe-NH2 |
| 2447 | TCAM2444 | Arg-Arg-Phe-Arg-Arg-Phe-Phe-c[Asp-Arg-Trp-Arg-Trp-Arg-Lys]-D-Pro-D-Val-NH2 |
| 2448 | TCAM2445 | Arg-Arg-Phe-Arg-Arg-Phe-Phe-c[Asp-Arg-Trp-Arg-Trp-Arg-Lys]-D-Phe-D-Val-NH2 |
| 2449 | TCAM2446 | Arg-Arg-Phe-Arg-Arg-Phe-Phe-c[Asp-Trp-Trp-Arg-Arg-Trp-Lys]-D-Val-D-Pro-NH2 |
| 2450 | TCAM2447 | Arg-Arg-Phe-Arg-Arg-Phe-Phe-c[Asp-Trp-Trp-Arg-Arg-Trp-Lys]-D-Val-D-Phe-NH2 |
| 2451 | TCAM2448 | Arg-Arg-Phe-Arg-Arg-Phe-Phe-c[Asp-Trp-Trp-Arg-Arg-Trp-Lys]-D-Pro-D-Val-NH2 |
| 2452 | TCAM2449 | Arg-Arg-Phe-Arg-Arg-Phe-Phe-c[Asp-Trp-Trp-Arg-Arg-Trp-Lys]-D-Phe-D-Val-NH2 |
| 2453 | TCAM2450 | Arg-Arg-Phe-Arg-Arg-Phe-Phe-c[Asp-Trp-Arg-Trp-Arg-Trp-Lys]-D-Val-D-Pro-NH2 |
| 2454 | TCAM2451 | Arg-Arg-Phe-Arg-Arg-Phe-Phe-c[Asp-Trp-Arg-Trp-Arg-Trp-Lys]-D-Val-D-Phe-NH2 |
| 2455 | TCAM2452 | Arg-Arg-Phe-Arg-Arg-Phe-Phe-c[Asp-Trp-Arg-Trp-Arg-Trp-Lys]-D-Pro-D-Val-NH2 |
| 2456 | TCAM2453 | Arg-Arg-Phe-Arg-Arg-Phe-Phe-c[Asp-Trp-Arg-Trp-Arg-Trp-Lys]-D-Phe-D-Val-NH2 |
| 2457 | TCAM2454 | Arg-Arg-Phe-Arg-Arg-Phe-Phe-c[Asp-Trp-Arg-Tyr-Arg-Trp-Lys]-D-Val-D-Pro-NH2 |
| 2458 | TCAM2455 | Arg-Arg-Phe-Arg-Arg-Phe-Phe-c[Asp-Trp-Arg-Tyr-Arg-Trp-Lys]-D-Val-D-Phe-NH2 |
| 2459 | TCAM2456 | Arg-Arg-Phe-Arg-Arg-Phe-Phe-c[Asp-Trp-Arg-Tyr-Arg-Trp-Lys]-D-Pro-D-Val-NH2 |
| 2460 | TCAM2457 | Arg-Arg-Phe-Arg-Arg-Phe-Phe-c[Asp-Trp-Arg-Tyr-Arg-Trp-Lys]-D-Phe-D-Val-NH2 |
| 2461 | TCAM2458 | Arg-Arg-Phe-Arg-Arg-Phe-Phe-c[Asp-Trp-Arg-Trp-Arg-Tyr-Lys]-D-Val-D-Pro-NH2 |
| 2462 | TCAM2459 | Arg-Arg-Phe-Arg-Arg-Phe-Phe-c[Asp-Trp-Arg-Trp-Arg-Tyr-Lys]-D-Val-D-Phe-NH2 |
| 2463 | TCAM2460 | Arg-Arg-Phe-Arg-Arg-Phe-Phe-c[Asp-Trp-Arg-Trp-Arg-Tyr-Lys]-D-Pro-D-Val-NH2 |
| 2464 | TCAM2461 | Arg-Arg-Phe-Arg-Arg-Phe-Phe-c[Asp-Trp-Arg-Trp-Arg-Tyr-Lys]-D-Phe-D-Val-NH2 |
| 2465 | TCAM2462 | Arg-Arg-Phe-Arg-Arg-Phe-Phe-c[Asp-Trp-Arg-Trp-Arg-Lys]-D-Val-D-Pro-NH2 |
| 2466 | TCAM2463 | Arg-Arg-Phe-Arg-Arg-Phe-Phe-c[Asp-Trp-Arg-Trp-Arg-Lys]-D-Val-D-Phe-NH2 |
| 2467 | TCAM2464 | Arg-Arg-Phe-Arg-Arg-Phe-Phe-c[Asp-Trp-Arg-Trp-Arg-Lys]-D-Pro-D-Val-NH2 |
| 2468 | TCAM2465 | Arg-Arg-Phe-Arg-Arg-Phe-Phe-c[Asp-Trp-Arg-Trp-Arg-Lys]-D-Phe-D-Val-NH2 |
| 2469 | TCAM2466 | Arg-Arg-Phe-Arg-Arg-Phe-Phe-c[Asp-Trp-Arg-Arg-Trp-Lys]-D-Val-D-Pro-NH2 |
| 2470 | TCAM2467 | Arg-Arg-Phe-Arg-Arg-Phe-Phe-c[Asp-Trp-Arg-Arg-Trp-Lys]-D-Val-D-Phe-NH2 |
| 2471 | TCAM2468 | Arg-Arg-Phe-Arg-Arg-Phe-Phe-c[Asp-Trp-Arg-Arg-Trp-Lys]-D-Pro-D-Val-NH2 |
| 2472 | TCAM2469 | Arg-Arg-Phe-Arg-Arg-Phe-Phe-c[Asp-Trp-Arg-Arg-Trp-Lys]-D-Phe-D-Val-NH2 |
| 2473 | TCAM2470 | Arg-Arg-Phe-Arg-Arg-Phe-Phe-c[Asp-Arg-Trp-Trp-Arg-Lys]-D-Val-D-Pro-NH2 |
| 2474 | TCAM2471 | Arg-Arg-Phe-Arg-Arg-Phe-Phe-c[Asp-Arg-Trp-Trp-Arg-Lys]-D-Val-D-Phe-NH2 |
| 2475 | TCAM2472 | Arg-Arg-Phe-Arg-Arg-Phe-Phe-c[Asp-Arg-Trp-Trp-Arg-Lys]-D-Pro-D-Val-NH2 |
| 2476 | TCAM2473 | Arg-Arg-Phe-Arg-Arg-Phe-Phe-c[Asp-Arg-Trp-Trp-Arg-Lys]-D-Phe-D-Val-NH2 |
| 2477 | TCAM2474 | Arg-Arg-Phe-Arg-Arg-Phe-Phe-c[Asp-Trp-Arg-Trp-Lys]-D-Val-D-Pro-NH2 |
| 2478 | TCAM2475 | Arg-Arg-Phe-Arg-Arg-Phe-Phe-c[Asp-Trp-Arg-Trp-Lys]-D-Val-D-Phe-NH2 |
| 2479 | TCAM2476 | Arg-Arg-Phe-Arg-Arg-Phe-Phe-c[Asp-Trp-Arg-Trp-Lys]-D-Pro-D-Val-NH2 |
| 2480 | TCAM2477 | Arg-Arg-Phe-Arg-Arg-Phe-Phe-c[Asp-Trp-Arg-Trp-Lys]-D-Phe-D-Val-NH2 |
| 2481 | TCAM2478 | Arg-Arg-Phe-Arg-Arg-Phe-Phe-c[Asp-Arg-Trp-Arg-Lys]-D-Val-D-Pro-NH2 |
| 2482 | TCAM2479 | Arg-Arg-Phe-Arg-Arg-Phe-Phe-c[Asp-Arg-Trp-Arg-Lys]-D-Val-D-Phe-NH2 |

TABLE 5-continued

Exemplary Anti-microbial peptides

| SEQ NO: | Peptide | Peptide Sequence |
|---|---|---|
| 2483 | TCAM2480 | Arg-Arg-Phe-Arg-Arg-Phe-Phe-c[Asp-Arg-Trp-Arg-Lys]-D-Pro-D-Val-NH2 |
| 2484 | TCAM2481 | Arg-Arg-Phe-Arg-Arg-Phe-Phe-c[Asp-Arg-Trp-Arg-Lys]-D-Phe-D-Val-NH2 |
| 2485 | TCAM2482 | Arg-Arg-Phe-Arg-Arg-Phe-Phe-c[Asp-His-D-Nal(2')-Arg-Trp-Lys]-D-Val-D-Pro-NH2 |
| 2486 | TCAM2483 | Arg-Arg-Phe-Arg-Arg-Phe-Phe-c[Asp-His-D-Nal(2')-Arg-Trp-Lys]-D-Pro-D-Val-NH2 |
| 2487 | TCAM2484 | Arg-Arg-Phe-Arg-Arg-Phe-Phe-c[Asp-His-D-Nal(2')-Arg-Trp-Lys]-D-Val-D-Phe-NH2 |
| 2488 | TCAM2485 | Arg-Arg-Phe-Arg-Arg-Phe-Phe-c[Asp-His-D-Nal(2')-Arg-Trp-Lys]-D-Phe-D-Val-NH2 |
| 2489 | TCAM2486 | Arg-Arg-Phe-Arg-Arg-Phe-Phe-c[Asp-Pro-D-Nal(2')-Arg-Trp-Lys]-D-Val-D-Pro-NH2 |
| 2490 | TCAM2487 | Arg-Arg-Phe-Arg-Arg-Phe-Phe-c[Asp-Pro-D-Nal(2')-Arg-Trp-Lys]-D-Pro-D-Val-NH2 |
| 2491 | TCAM2488 | Arg-Arg-Phe-Arg-Arg-Phe-Phe-c[Asp-Pro-D-Nal(2')-Arg-Trp-Lys]-D-Val-D-Phe-NH2 |
| 2492 | TCAM2489 | Arg-Arg-Phe-Arg-Arg-Phe-Phe-c[Asp-Pro-D-Nal(2')-Arg-Trp-Lys]-D-Phe-D-Val-NH2 |
| 2493 | TCAM2490 | Arg-Arg-Phe-Arg-Arg-Phe-Phe-c[Asp-Arg-Arg-Nal(2')-Arg-Trp-Lys]-D-Val-D-Pro-NH2 |
| 2494 | TCAM2491 | Arg-Arg-Phe-Arg-Arg-Phe-Phe-c[Asp-Arg-Arg-Nal(2')-Arg-Trp-Lys]-D-Pro-D-Val-NH2 |
| 2495 | TCAM2492 | Arg-Arg-Phe-Arg-Arg-Phe-Phe-c[Asp-Arg-Arg-Nal(2')-Arg-Trp-Lys]-D-Val-D-Phe-NH2 |
| 2496 | TCAM2493 | Arg-Arg-Phe-Arg-Arg-Phe-Phe-c[Asp-Arg-Arg-Nal(2')-Arg-Trp-Lys]-D-Phe-D-Val-NH2 |
| 2497 | TCAM2494 | Arg-Arg-Phe-Arg-Arg-Phe-Phe-c[Asp-Arg-Arg-Pro-Nal(2')-Arg-Trp-Lys]-D-Val-D-Pro-NH2 |
| 2498 | TCAM2495 | Arg-Arg-Phe-Arg-Arg-Phe-Phe-c[Asp-Arg-Arg-Pro-D-Nal(2')-Arg-Trp-Lys]-D-Pro-D-Val-NH2 |
| 2499 | TCAM2496 | Arg-Arg-Phe-Arg-Arg-Phe-Phe-c[Asp-Arg-Arg-Pro-D-Nal(2')-Arg-Trp-Lys]-D-Val-D-Phe-NH2 |
| 2500 | TCAM2497 | Arg-Arg-Phe-Arg-Arg-Phe-Phe-c[Asp-Arg-Arg-Pro-D-Nal(2')-Arg-Trp-Lys]-D-Phe-D-Val-NH2 |
| 2501 | TCAM2498 | Arg-Arg-Phe-Arg-Arg-Phe-Phe-c[Asp-Arg-D-Nal(2')-Arg-Trp-Lys]-D-Val-D-Pro-NH2 |
| 2502 | TCAM2499 | Arg-Arg-Phe-Arg-Arg-Phe-Phe-c[Asp-Arg-D-Nal(2')-Arg-Trp-Lys]-D-Pro-D-Val-NH2 |
| 2503 | TCAM2500 | Arg-Arg-Phe-Arg-Arg-Phe-Phe-c[Asp-Arg-D-Nal(2')-Arg-Trp-Lys]-D-Val-D-Phe-NH2 |
| 2504 | TCAM2501 | Arg-Arg-Phe-Arg-Arg-Phe-Phe-c[Asp-Arg-D-Nal(2')-Arg-Trp-Lys]-D-Phe-D-Val-NH2 |
| 2505 | TCAM2502 | Arg-Arg-Phe-Arg-Arg-Phe-Phe-c[Asp-Arg-Pro-D-Nal(2')-Arg-Trp-Lys]-D-Val-D-Pro-NH2 |
| 2506 | TCAM2503 | Arg-Arg-Phe-Arg-Arg-Phe-Phe-c[Asp-Arg-Pro-D-Nal(2')-Arg-Trp-Lys]-D-Pro-D-Val-NH2 |
| 2507 | TCAM2504 | Arg-Arg-Phe-Arg-Arg-Phe-Phe-c[Asp-Arg-Pro-D-Nal(2')-Arg-Trp-Lys]-D-Val-D-Phe-NH2 |
| 2508 | TCAM2505 | Arg-Arg-Phe-Arg-Arg-Phe-Phe-c[Asp-Arg-Pro-D-Nal(2')-Arg-Trp-Lys]-D-Phe-D-Val-NH2 |
| 2509 | TCAM2506 | Arg-Arg-Phe-Arg-Arg-Phe-Phe-Arg-Arg-c[Asp-Pro-D-Nal(2')-Arg-Trp-Lys]-D-Val-D-Pro-NH2 |
| 2510 | TCAM2507 | Arg-Arg-Phe-Arg-Arg-Phe-Phe-Arg-Arg-c[Asp-Pro-D-Nal(2')-Arg-Trp-Lys]-D-Pro-D-Val-NH2 |
| 2511 | TCAM2508 | Arg-Arg-Phe-Arg-Arg-Phe-Phe-Arg-Arg-c[Asp-Pro-D-Nal(2')-Arg-Trp-Lys]-D-Val-D-Phe-NH2 |
| 2512 | TCAM2509 | Arg-Arg-Phe-Arg-Arg-Phe-Phe-Arg-Arg-c[Asp-Pro-D-Nal(2')-Arg-Trp-Lys]-D-Phe-D-Val-NH2 |
| 2513 | TCAM2510 | Arg-Arg-Phe-Arg-Arg-Phe-Phe-Arg-Arg-c[Asp-His-D-Nal(2')-Arg-Trp-Lys]-D-Val-D-Pro-NH2 |

TABLE 5-continued

Exemplary Anti-microbial peptides

| SEQ NO: | Peptide | Peptide Sequence |
|---|---|---|
| 2514 | TCAM2511 | Arg-Arg-Phe-Arg-Arg-Phe-Phe-Arg-Arg-c[Asp-His-D-Nal(2')-Arg-Trp-Lys]-D-Pro-D-Val-NH2 |
| 2515 | TCAM2512 | Arg-Arg-Phe-Arg-Arg-Phe-Phe-Arg-Arg-c[Asp-His-D-Nal(2')-Arg-Trp-Lys]-D-Val-D-Phe-NH2 |
| 2516 | TCAM2513 | Arg-Arg-Phe-Arg-Arg-Phe-Phe-Arg-Arg-c[Asp-His-D-Nal(2')-Arg-Trp-Lys]-D-Phe-D-Val-NH2 |
| 2517 | TCAM2514 | Arg-Arg-Phe-Arg-Arg-Phe-Phe-c[Asp-Arg-Pro-D-Nal(2')-Arg-Trp-Arg-Lys]-D-Val-D-Pro-NH2 |
| 2518 | TCAM2515 | Arg-Arg-Phe-Arg-Arg-Phe-Phe-c[Asp-Arg-Pro-D-Nal(2')-Arg-Trp-Arg-Lys]-D-Pro-D-Val-NH2 |
| 2519 | TCAM2516 | Arg-Arg-Phe-Arg-Arg-Phe-Phe-c[Asp-Arg-Pro-D-Nal(2')-Arg-Trp-Arg-Lys]-D-Val-D-Phe-NH2 |
| 2520 | TCAM2517 | Arg-Arg-Phe-Arg-Arg-Phe-Phe-c[Asp-Arg-Pro-D-Nal(2')-Arg-Trp-Arg-Lys]-D-Phe-D-Val-NH2 |
| 2521 | TCAM2518 | Arg-Arg-Phe-Arg-Arg-Phe-Phe-c[Asp-Arg-His-D-Nal(2')-Arg-Trp-Arg-Lys]-D-Val-D-Pro-NH2 |
| 2522 | TCAM2519 | Arg-Arg-Phe-Arg-Arg-Phe-Phe-c[Asp-Arg-His-D-Nal(2')-Arg-Trp-Arg-Lys]-D-Pro-D-Val-NH2 |
| 2523 | TCAM2520 | Arg-Arg-Phe-Arg-Arg-Phe-Phe-c[Asp-Arg-His-D-Nal(2')-Arg-Trp-Arg-Lys]-D-Val-D-Phe-NH2 |
| 2524 | TCAM2521 | Arg-Arg-Phe-Arg-Arg-Phe-Phe-c[Asp-Arg-His-D-Nal(2')-Arg-Trp-Arg-Lys]-D-Phe-D-Val-NH2 |
| 2525 | TCAM2522 | Arg-Arg-Phe-Arg-Arg-Phe-Phe-c[Asp-His-D-Nal(2')-Arg-D-Nal(2')-Lys]-D-Val-D-Phe-NH2 |
| 2526 | TCAM2523 | Arg-Arg-Phe-Arg-Arg-Phe-Phe-c[Asp-His-D-Nal(2')-Arg-D-Nal(2')-Lys]-D-Phe-D-Val-NH2 |
| 2527 | TCAM2524 | Arg-Arg-Phe-Arg-Arg-Phe-Phe-c[Asp-Pro-D-Nal(2')-Arg-D-Nal(2')-Lys]-D-Val-D-Pro-NH2 |
| 2528 | TCAM2525 | Arg-Arg-Phe-Arg-Arg-Phe-Phe-c[Asp-Pro-D-Nal(2')-Arg-D-Nal(2')-Lys]-D-Pro-D-Val-NH2 |
| 2529 | TCAM2526 | Arg-Arg-Phe-Arg-Arg-Phe-Phe-c[Asp-Pro-D-Nal(2')-Arg-D-Nal(2')-Lys]-D-Val-D-Phe-NH2 |
| 2530 | TCAM2527 | Arg-Arg-Phe-Arg-Arg-Phe-Phe-c[Asp-Pro-D-Nal(2')-Arg-D-Nal(2')-Lys]-D-Phe-D-Val-NH2 |
| 2531 | TCAM2528 | Arg-Arg-Phe-Arg-Arg-Phe-Phe-c[Asp-Arg-Arg-D-Nal(2')-Arg-D-Nal(2')-Lys]-D-Val-D-Pro-NH2 |
| 2532 | TCAM2529 | Arg-Arg-Phe-Arg-Arg-Phe-Phe-c[Asp-Arg-Arg-D-Nal(2')-Arg-D-Nal(2')-Lys]-D-Pro-D-Val-NH2 |
| 2533 | TCAM2530 | Arg-Arg-Phe-Arg-Arg-Phe-Phe-c[Asp-Arg-Arg-D-Nal(2')-Arg-D-Nal(2')-Lys]-D-Val-D-Phe-NH2 |
| 2534 | TCAM2531 | Arg-Arg-Phe-Arg-Arg-Phe-Phe-c[Asp-Arg-Arg-D-Nal(2')-Arg-D-Nal(2')-Lys]-D-Phe-D-Val-NH2 |
| 2535 | TCAM2532 | Arg-Arg-Phe-Arg-Arg-Phe-Phe-c[Asp-Arg-Arg-Pro-D-Nal(2')-Arg-D-Nal(2')-Lys]-D-Val-D-Pro-NH2 |
| 2536 | TCAM2533 | Arg-Arg-Phe-Arg-Arg-Phe-Phe-c[Asp-Arg-Arg-Pro-D-Nal(2')-Arg-D-Nal(2')-Lys]-D-Pro-D-Val-NH2 |
| 2537 | TCAM2534 | Arg-Arg-Phe-Arg-Arg-Phe-Phe-c[Asp-Arg-Arg-Pro-D-Nal(2')-Arg-D-Nal(2')-Lys]-D-Val-D-Phe-NH2 |
| 2538 | TCAM2535 | Arg-Arg-Phe-Arg-Arg-Phe-Phe-c[Asp-Arg-Arg-Pro-D-Nal(2')-Arg-D-Nal(2')-Lys]-D-Phe-D-Val-NH2 |

TABLE 5-continued

Exemplary Anti-microbial peptides

| SEQ NO: | Peptide | Peptide Sequence |
|---|---|---|
| 2539 | TCAM2536 | Arg-Arg-Phe-Arg-Arg-Phe-Phe-c[Asp-Arg-D-Nal(2')-Arg-D-Nal(2')-Lys]-D-Val-D-Pro-NH2 |
| 2540 | TCAM2537 | Arg-Arg-Phe-Arg-Arg-Phe-Phe-c[Asp-Arg-D-Nal(2')-Arg-D-Nal(2')-Lys]-D-Pro-D-Val-NH2 |
| 2541 | TCAM2538 | Arg-Arg-Phe-Arg-Arg-Phe-Phe-c[Asp-Arg-Nal(2')-Arg-D-Nal(2')-Lys]-D-Val-D-Phe-NH2 |
| 2542 | TCAM2539 | Arg-Arg-Phe-Arg-Arg-Phe-Phe-c[Asp-Arg-D-Nal(2')-Arg-D-Nal(2')-Lys]-D-Phe-D-Val-NH2 |
| 2543 | TCAM2540 | Arg-Arg-Phe-Arg-Arg-Phe-Phe-c[Asp-Arg-Pro-D-Nal(2')-Arg-D-Nal(2')-Lys]-D-Val-D-Pro-NH2 |
| 2544 | TCAM2541 | Arg-Arg-Phe-Arg-Arg-Phe-Phe-c[Asp-Arg-Pro-D-Nal(2')-Arg-D-Nal(2')-Lys]-D-Pro-D-Val-NH2 |
| 2545 | TCAM2542 | Arg-Arg-Phe-Arg-Arg-Phe-Phe-c[Asp-Arg-Pro-D-Nal(2')-Arg-D-Nal(2')-Lys]-D-Val-D-Phe-NH2 |
| 2546 | TCAM2543 | Arg-Arg-Phe-Arg-Arg-Phe-Phe-c[Asp-Arg-Pro-D-Nal(2')-Arg-D-Nal(2')-Lys]-D-Phe-D-Val-NH2 |
| 2547 | TCAM2544 | Arg-Arg-Phe-Arg-Arg-Phe-Phe-c[Asp-Arg-His-D-Nal(2')-Arg-D-Nal(2')-Lys]-D-Val-D-Pro-NH2 |
| 2548 | TCAM2545 | Arg-Arg-Phe-Arg-Arg-Phe-Phe-c[Asp-Arg-His-D-Nal(2')-Arg-D-Nal(2')-Lys]-D-Pro-D-Val-NH2 |
| 2549 | TCAM2546 | Arg-Arg-Phe-Arg-Arg-Phe-Phe-c[Asp-Arg-His-Nal(2')-Arg-D-Nal(2')-Lys]-D-Val-D-Phe-NH2 |
| 2550 | TCAM2547 | Arg-Arg-Phe-Arg-Arg-Phe-Phe-c[Asp-Arg-His-Nal(2')-Arg-D-Nal(2')-Lys]-D-Phe-D-Val-NH2 |
| 2551 | TCAM2548 | Arg-Arg-Phe-Arg-Arg-Phe-Phe-c[Asp-Arg-D-D-Nal(2')-Arg-D-Nal(2')-Arg-Lys]-D-Val-D-Pro-NH2 |
| 2552 | TCAM2549 | Arg-Arg-Phe-Arg-Arg-Phe-Phe-c[Asp-Arg-D-Nal(2')-Arg-D-Nal(2')-Arg-Lys]-D-Pro-D-Val-NH2 |
| 2553 | TCAM2550 | Arg-Arg-Phe-Arg-Arg-Phe-Phe-c[Asp-Arg-D-Nal(2')-Arg-D-Nal(2')-Arg-Lys]-D-Val-D-Phe-NH2 |
| 2554 | TCAM2551 | Arg-Arg-Phe-Arg-Arg-Phe-Phe-c[Asp-Arg-D-Nal(2')-Arg-D-Nal(2')-Arg-Lys]-D-Phe-D-Val-NH2 |
| 2555 | TCAM2552 | Arg-Arg-Phe-Arg-Arg-Phe-Phe-c[Asp-Arg-Pro-D-Nal(2')-Arg-D-Nal(2')-Arg-Lys]-D-Val-D-Pro-NH2 |
| 2556 | TCAM2553 | Arg-Arg-Phe-Arg-Arg-Phe-Phe-c[Asp-Arg-Pro-D-Nal(2')-Arg-D-Nal(2')-Arg-Lys]-D-Pro-D-Val-NH2 |
| 2557 | TCAM2554 | Arg-Arg-Phe-Arg-Arg-Phe-Phe-c[Asp-Arg-Pro-D-Nal(2')-Arg-D-Nal(2')-Arg-Lys]-D-Val-D-Phe-NH2 |
| 2558 | TCAM2555 | Arg-Arg-Phe-Arg-Arg-Phe-Phe-c[Asp-Arg-Pro-D-Nal(2')-Arg-D-Nal(2')-Arg-Lys]-D-Phe-D-Val-NH2 |
| 2559 | TCAM2556 | Arg-Arg-Phe-Arg-Arg-Phe-Phe-c[Asp-Arg-His-D-Nal(2')-Arg-D-Nal(2')-Arg-Lys]-D-Val-D-Pro-NH2 |
| 2560 | TCAM2557 | Arg-Arg-Phe-Arg-Arg-Phe-Phe-c[Asp-Arg-His-D-Nal(2')-Arg-D-Nal(2')-Arg-Lys]-D-Pro-D-Val-NH2 |
| 2561 | TCAM2558 | Arg-Arg-Phe-Arg-Arg-Phe-Phe-c[Asp-Arg-His-D-Nal(2')-Arg-D-Nal(2')-Arg-Lys]-D-Val-D-Phe-NH2 |
| 2562 | TCAM2559 | Arg-Arg-Phe-Arg-Arg-Phe-Phe-c[Asp-Arg-His-D-Nal(2')-Arg-D-Nal(2')-Arg-Lys]-D-Phe-D-Val-NH2 |
| 2563 | TCAM2560 | Arg-Arg-Phe-Arg-Arg-Phe-Phe-Arg-Arg-c[Asp-Pro-D-Nal(2')-Arg-D-Nal(2')-Lys]-D-Val-D-Pro-NH2 |

TABLE 5-continued

Exemplary Anti-microbial peptides

| SEQ NO: | Peptide | Peptide Sequence |
|---|---|---|
| 2564 | TCAM2561 | Arg-Arg-Phe-Arg-Arg-Phe-Phe-Arg-Arg-c[Asp-Pro-D-Nal(2')-Arg-D-Nal(2')-Lys]-D-Pro-D-Val-NH2 |
| 2565 | TCAM2562 | Arg-Arg-Phe-Arg-Arg-Phe-Phe-Arg-Arg-c[Asp-Pro-D-Nal(2')-Arg-D-Nal(2')-Lys]-D-Val-D-Phe-NH2 |
| 2566 | TCAM2563 | Arg-Arg-Phe-Arg-Arg-Phe-Phe-Arg-Arg-c[Asp-Pro-D-Nal(2')-Arg-D-Nal(2')-Lys]-D-Phe-D-Val-NH2 |
| 2567 | TCAM2564 | Arg-Arg-Phe-Arg-Arg-Phe-Phe-Arg-Arg-c[Asp-His-D-Nal(2')-Arg-D-Nal(2')-Lys]-D-Val-D-Pro-NH2 |
| 2568 | TCAM2565 | Arg-Arg-Phe-Arg-Arg-Phe-Phe-Arg-Arg-c[Asp-His-D-Nal(2')-Arg-D-Nal(2')-Lys]-D-Pro-D-Val-NH2 |
| 2569 | TCAM2566 | Arg-Arg-Phe-Arg-Arg-Phe-Phe-Arg-Arg-c[Asp-His-D-Nal(2')-Arg-D-Nal(2')-Lys]-D-Val-D-Phe-NH2 |
| 2570 | TCAM2567 | Arg-Arg-Phe-Arg-Arg-Phe-Phe-Arg-Arg-c[Asp-His-D-Nal(2')-Arg-D-Nal(2')-Lys]-D-Phe-D-Val-NH2 |
| 2571 | TCAM2568 | Arg-Arg-Phe-Arg-Arg-Phe-Phe-c[Asp-Arg-Pro-D-Nal(2')-Arg-D-Nal(2')-Arg-Lys]-D-Val-D-Pro-NH2 |
| 2572 | TCAM2569 | Arg-Arg-Phe-Arg-Arg-Phe-Phe-c[Asp-Arg-Pro-D-Nal(2')-Arg-D-Nal(2')-Arg-Lys]-D-Pro-D-Val-NH2 |
| 2573 | TCAM2570 | Arg-Arg-Phe-Arg-Arg-Phe-Phe-c[Asp-Arg-Pro-D-Nal(2')-Arg-D-Nal(2')-Arg-Lys]-D-Val-D-Phe-NH2 |
| 2574 | TCAM2571 | Arg-Arg-Phe-Arg-Arg-Phe-Phe-c[Asp-Arg-Pro-D-Nal(2')-Arg-D-Nal(2')-Arg-Lys]-D-Phe-D-Val-NH2 |
| 2575 | TCAM2572 | Arg-Arg-Phe-Arg-Arg-Phe-Phe-c[Asp-Arg-His-D-Nal(2')-Arg-D-Nal(2')-Arg-Lys]-D-Val-D-Pro-NH2 |
| 2576 | TCAM2573 | Arg-Arg-Phe-Arg-Arg-Phe-Phe-c[Asp-Arg-His-D-Nal(2')-Arg-D-Nal(2')-Arg-Lys]-D-Pro-D-Val-NH2 |
| 2577 | TCAM2574 | Arg-Arg-Phe-Arg-Arg-Phe-Phe-c[Asp-Arg-His-D-Nal(2')-Arg-D-Nal(2')-Arg-Lys]-D-Val-D-Phe-NH2 |
| 2578 | TCAM2575 | Arg-Arg-Phe-Arg-Arg-Phe-Phe-c[Asp-Arg-His-D-Nal(2')-Arg-D-Nal(2')-Arg-Lys]-D-Phe-D-Val-NH2 |
| 2579 | TCAM2576 | Arg-Arg-Phe-Arg-Arg-Phe-Phe-c[Asp-His-D-Nal(2')-Arg-Trp-Lys]-Arg-Arg-D-Val-D-Pro-NH2 |
| 2580 | TCAM2577 | Arg-Arg-Phe-Arg-Arg-Phe-Phe-c[Asp-His-D-Nal(2')-Arg-Trp-Lys]-Arg-Arg-D-Pro-D-Val-NH2 |
| 2581 | TCAM2578 | Arg-Arg-Phe-Arg-Arg-Phe-Phe-c[Asp-His-D-Nal(2')-Arg-Trp-Lys]-Arg-Arg-D-Val-D-Phe-NH2 |
| 2582 | TCAM2579 | Arg-Arg-Phe-Arg-Arg-Phe-Phe-c[Asp-His-D-Nal(2')-Arg-Trp-Lys]-Arg-Arg-D-Phe-D-Val-NH2 |
| 2583 | TCAM2580 | Arg-Arg-Phe-Arg-Arg-Phe-Phe-c[Asp-Pro-D-Nal(2')-Arg-Trp-Lys]-Arg-Arg-D-Val-D-Pro-NH2 |
| 2584 | TCAM2581 | Arg-Arg-Phe-Arg-Arg-Phe-Phe-c[Asp-Pro-D-Nal(2')-Arg-Trp-Lys]-Arg-Arg-D-Pro-D-Val-NH2 |
| 2585 | TCAM2582 | Arg-Arg-Phe-Arg-Arg-Phe-Phe-c[Asp-Pro-D-Nal(2')-Arg-Trp-Lys]-Arg-Arg-D-Val-D-Phe-NH2 |
| 2586 | TCAM2583 | Arg-Arg-Phe-Arg-Arg-Phe-Phe-c[Asp-Pro-D-Nal(2')-Arg-Trp-Lys]-Arg-Arg-D-Phe-D-Val-NH2 |

Anti-biofilm peptide ABF5 linked to anti-microbial peptides

| | | |
|---|---|---|
| 2587 | TCAM2584 | Phe-Phe-Arg-Arg-Leu-Lys-c[Asp-Pro-Arg-Arg-Trp-Trp-Arg-Phe-Lys]-D-Val-D-Pro-NH2 |
| 2588 | TCAM2585 | Phe-Phe-Arg-Arg-Leu-Lys-c[Asp-Pro-Arg-Arg-Trp-Trp-Arg-Phe-Lys]-D-Val-D-Phe-NH2 |

TABLE 5-continued

Exemplary Anti-microbial peptides

| SEQ NO: | Peptide | Peptide Sequence |
|---|---|---|
| 2589 | TCAM2586 | Phe-Phe-Arg-Arg-Leu-Lys-c[Asp-Pro-Arg-Arg-Trp-Trp-Arg-Phe-Lys]-D-Pro-D-Val-NH2 |
| 2590 | TCAM2587 | Phe-Phe-Arg-Arg-Leu-Lys-c[Asp-Pro-Arg-Arg-Trp-Trp-Arg-Phe-Lys]-D-Phe-D-Val-NH2 |
| 2591 | TCAM2588 | Phe-Phe-Arg-Arg-Leu-Lys-c[Asp-Pro-Arg-Arg-Trp-Trp-Tyr-Phe-Lys]-D-Val-D-Pro-NH2 |
| 2592 | TCAM2589 | Phe-Phe-Arg-Arg-Leu-Lys-c[Asp-Pro-Arg-Arg-Trp-Trp-Tyr-Phe-Lys]-D-Val-D-Phe-NH2 |
| 2593 | TCAM2590 | Phe-Phe-Arg-Arg-Leu-Lys-c[Asp-Pro-Arg-Arg-Trp-Trp-Tyr-Phe-Lys]-D-Pro-D-Val-NH2 |
| 2594 | TCAM2591 | Phe-Phe-Arg-Arg-Leu-Lys-c[Asp-Pro-Arg-Arg-Trp-Trp-Tyr-Phe-Lys]-D-Phe-D-Val-NH2 |
| 2595 | TCAM2592 | Phe-Phe-Arg-Arg-Leu-Lys-c[Asp-Pro-Arg-Arg-Tyr-Tyr-Arg-Phe-Lys]-D-Val-D-Pro-NH2 |
| 2596 | TCAM2593 | Phe-Phe-Arg-Arg-Leu-Lys-c[Asp-Pro-Arg-Arg-Tyr-Tyr-Arg-Phe-Lys]-D-Val-D-Phe-NH2 |
| 2597 | TCAM2594 | Phe-Phe-Arg-Arg-Leu-Lys-c[Asp-Pro-Arg-Arg-Tyr-Tyr-Arg-Phe-Lys]-D-Pro-D-Val-NH2 |
| 2598 | TCAM2595 | Phe-Phe-Arg-Arg-Leu-Lys-c[Asp-Pro-Arg-Arg-Tyr-Tyr-Arg-Phe-Lys]-D-Phe-D-Val-NH2 |
| 2599 | TCAM2596 | Phe-Phe-Arg-Arg-Leu-Lys-c[Asp-Pro-Arg-Arg-Nal-Nal-Arg-Phe-Lys]-D-Val-D-Pro-NH2 |
| 2600 | TCAM2597 | Phe-Phe-Arg-Arg-Leu-Lys-c[Asp-Pro-Arg-Arg-Nal-Nal-Arg-Phe-Lys]-D-Val-D-Phe-NH2 |
| 2601 | TCAM2598 | Phe-Phe-Arg-Arg-Leu-Lys-c[Asp-Pro-Arg-Arg-Nal-Nal-Arg-Phe-Lys]-D-Pro-D-Val-NH2 |
| 2602 | TCAM2599 | Phe-Phe-Arg-Arg-Leu-Lys-c[Asp-Pro-Arg-Arg-Nal-Nal-Arg-Phe-Lys]-D-Phe-D-Val-NH2 |
| 2603 | TCAM2600 | Phe-Phe-Arg-Arg-Leu-Lys-c[Asp-Pro-Arg-Arg-Leu-Trp-Leu-Trp-Lys]-D-Val-D-Pro-NH2 |
| 2604 | TCAM2601 | Phe-Phe-Arg-Arg-Leu-Lys-c[Asp-Pro-Arg-Arg-Leu-Trp-Leu-Trp-Lys]-D-Val-D-Phe-NH2 |
| 2605 | TCAM2602 | Phe-Phe-Arg-Arg-Leu-Lys-c[Asp-Pro-Arg-Arg-Leu-Trp-Leu-Trp-Lys]-D-Pro-D-Val-NH2 |
| 2606 | TCAM2603 | Phe-Phe-Arg-Arg-Leu-Lys-c[Asp-Pro-Arg-Arg-Leu-Trp-Leu-Trp-Lys]-D-Phe-D-Val-NH2 |
| 2607 | TCAM2604 | Phe-Phe-Arg-Arg-Leu-Lys-c[Asp-Pro-Arg-Arg-Leu-Trp-Leu-Trp-Lys]-D-Val-D-Pro-NH2 |
| 2608 | TCAM2605 | Phe-Phe-Arg-Arg-Leu-Lys-c[Asp-Pro-Arg-Arg-Leu-Trp-Leu-Trp-Lys]-D-Val-D-Phe-NH2 |
| 2609 | TCAM2606 | Phe-Phe-Arg-Arg-Leu-Lys-c[Asp-Pro-Arg-Arg-Leu-Trp-Leu-Trp-Lys]-D-Pro-D-Val-NH2 |
| 2610 | TCAM2607 | Phe-Phe-Arg-Arg-Leu-Lys-c[Asp-Pro-Arg-Arg-Leu-Trp-Leu-Trp-Lys]-D-Phe-D-Val-NH2 |
| 2611 | TCAM2608 | Phe-Phe-Arg-Arg-Leu-Lys-c[Asp-Arg-Arg-Arg-Trp-Leu-Trp-Leu-Trp-Lys]-D-Val-D-Pro-NH2 |
| 2612 | TCAM2609 | Phe-Phe-Arg-Arg-Leu-Lys-c[Asp-Pro-Arg-Arg-Arg-Trp-Leu-Trp-Leu-Trp-Lys]-D-Val-D-Phe-NH2 |
| 2613 | TCAM2610 | Phe-Phe-Arg-Arg-Leu-Lys-c[Asp-Pro-Arg-Arg-Arg-Trp-Leu-Trp-Leu-Trp-Lys]-D-Pro-D-Val-NH2 |
| 2614 | TCAM2611 | Phe-Phe-Arg-Arg-Leu-Lys-c[Asp-Pro-Arg-Arg-Arg-Trp-Leu-Trp-Leu-Trp-Lys]-D-Phe-D-Val-NH2 |
| 2615 | TCAM2612 | Phe-Phe-Arg-Arg-Leu-Lys-c[Asp-Pro-Arg-Gln-Arg-Arg-Trp-Leu-Trp-Leu-Trp-Lys]-D-Val-D-Pro-NH2 |
| 2616 | TCAM2613 | Phe-Phe-Arg-Arg-Leu-Lys-c[Asp-Pro-Arg-Gln-Arg-Arg-Trp-Leu-Trp-Leu-Trp-Lys]-D-Val-D-Phe-NH2 |
| 2617 | TCAM2614 | Phe-Phe-Arg-Arg-Leu-Lys-c[Asp-Pro-Arg-Gln-Arg-Arg-Trp-Leu-Trp-Leu-Trp-Lys]-D-Pro-D-Val-NH2 |
| 2618 | TCAM2615 | Phe-Phe-Arg-Arg-Leu-Lys-c[Asp-Pro-Arg-Gln-Arg-Arg-Trp-Leu-Trp-Leu-Trp-Lys]-D-Phe-D-Val-NH2 |
| 2619 | TCAM2616 | Phe-Phe-Arg-Arg-Leu-Lys-c[Asp-Pro-Trp-Arg-Trp-Trp-Arg-Arg-Lys]-D-Val-D-Phe-NH2 |
| 2620 | TCAM2617 | Phe-Phe-Arg-Arg-Leu-Lys-c[Asp-Pro-Trp-Arg-Trp-Trp-Arg-Arg-Lys]-D-Pro-D-Val-NH2 |
| 2621 | TCAM2618 | Phe-Phe-Arg-Arg-Leu-Lys-c[Asp-Pro-Trp-Arg-Trp-Trp-Arg-Arg-Lys]-D-Phe-D-Val-NH2 |

TABLE 5-continued

Exemplary Anti-microbial peptides

| SEQ NO: | Peptide | Peptide Sequence |
|---|---|---|
| 2622 | TCAM2619 | Phe-Phe-Arg-Arg-Leu-Lys-c[Asp-Pro-Trp-Trp-Arg-Arg-Trp-Trp-Arg-Arg-Lys]-D-Val-D-Pro-NH2 |
| 2623 | TCAM2620 | Phe-Phe-Arg-Arg-Leu-Lys-c[Asp-Pro-Trp-Trp-Arg-Arg-Trp-Trp-Arg-Arg-Lys]-D-Val-D-Phe-NH2 |
| 2624 | TCAM2621 | Phe-Phe-Arg-Arg-Leu-Lys-c[Asp-Pro-Trp-Trp-Arg-Arg-Trp-Trp-Arg-Arg-Lys]-D-Pro-D-Val-NH2 |
| 2625 | TCAM2622 | Phe-Phe-Arg-Arg-Leu-Lys-c[Asp-Pro-Trp-Trp-Arg-Arg-Trp-Trp-Arg-Arg-Lys]-D-Phe-D-Val-NH2 |
| 2626 | TCAM2623 | Phe-Phe-Arg-Arg-Leu-Lys-c[Asp-Pro-Trp-Arg-Trp-Arg-Trp-Arg-Lys]-D-Val-D-Pro-NH2 |
| 2627 | TCAM2624 | Phe-Phe-Arg-Arg-Leu-Lys-c[Asp-Pro-Trp-Arg-Trp-Arg-Trp-Arg-Lys]-D-Val-D-Phe-NH2 |
| 2628 | TCAM2625 | Phe-Phe-Arg-Arg-Leu-Lys-c[Asp-Pro-Trp-Arg-Trp-Arg-Trp-Arg-Lys]-D-Pro-D-Val-NH2 |
| 2629 | TCAM2626 | Phe-Phe-Arg-Arg-Leu-Lys-c[Asp-Pro-Trp-Arg-Trp-Arg-Trp-Arg-Lys]-D-Phe-D-Val-NH2 |
| 2630 | TCAM2627 | Phe-Phe-Arg-Arg-Leu-Lys-c[Asp-Pro-Arg-Trp-Arg-Trp-Arg-Trp-Lys]-D-Val-D-Pro-NH2 |
| 2631 | TCAM2628 | Phe-Phe-Arg-Arg-Leu-Lys-c[Asp-Pro-Arg-Trp-Arg-Trp-Arg-Trp-Lys]-D-Val-D-Phe-NH2 |
| 2632 | TCAM2629 | Phe-Phe-Arg-Arg-Leu-Lys-c[Asp-Pro-Arg-Trp-Arg-Trp-Arg-Trp-Lys]-D-Pro-D-Val-NH2 |
| 2633 | TCAM2630 | Phe-Phe-Arg-Arg-Leu-Lys-c[Asp-Pro-Arg-Trp-Arg-Trp-Arg-Trp-Lys]-D-Phe-D-Val-NH2 |
| 2634 | TCAM2631 | Phe-Phe-Arg-Arg-Leu-Lys-c[Asp-Pro-Arg-Trp-Trp-Arg-Arg-Lys]-D-Val-D-Pro-NH2 |
| 2635 | TCAM2632 | Phe-Phe-Arg-Arg-Leu-Lys-c[Asp-Pro-Arg-Trp-Trp-Arg-Arg-Lys]-D-Val-D-Phe-NH2 |
| 2636 | TCAM2633 | Phe-Phe-Arg-Arg-Leu-Lys-c[Asp-Pro-Arg-Trp-Trp-Arg-Arg-Lys]-D-Pro-D-Val-NH2 |
| 2637 | TCAM2634 | Phe-Phe-Arg-Arg-Leu-Lys-c[Asp-Pro-Arg-Trp-Trp-Arg-Arg-Lys]-D-Phe-D-Val-NH2 |
| 2638 | TCAM2635 | Phe-Phe-Arg-Arg-Leu-Lys-c[Asp-Pro-Trp-Trp-Arg-Arg-Trp-Lys]-D-Val-D-Pro-NH2 |
| 2639 | TCAM2636 | Phe-Phe-Arg-Arg-Leu-Lys-c[Asp-Pro-Trp-Trp-Arg-Arg-Trp-Lys]-D-Val-D-Phe-NH2 |
| 2640 | TCAM2637 | Phe-Phe-Arg-Arg-Leu-Lys-c[Asp-Pro-Trp-Trp-Arg-Arg-Trp-Lys]-D-Pro-D-Val-NH2 |
| 2641 | TCAM2638 | Phe-Phe-Arg-Arg-Leu-Lys-c[Asp-Pro-Trp-Trp-Arg-Arg-Trp-Lys]-D-Phe-D-Val-NH2 |
| 2642 | TCAM2639 | Phe-Phe-Arg-Arg-Leu-Lys-c[Asp-Pro-Trp-Arg-Trp-Arg-Trp-Lys]-D-Val-D-Pro-NH2 |
| 2643 | TCAM2640 | Phe-Phe-Arg-Arg-Leu-Lys-c[Asp-Pro-Trp-Arg-Trp-Arg-Trp-Lys]-D-Val-D-Phe-NH2 |
| 2644 | TCAM2641 | Phe-Phe-Arg-Arg-Leu-Lys-c[Asp-Pro-Trp-Arg-Trp-Arg-Trp-Lys]-D-Pro-D-Val-NH2 |
| 2645 | TCAM2642 | Phe-Phe-Arg-Arg-Leu-Lys-c[Asp-Pro-Trp-Arg-Trp-Arg-Trp-Lys]-D-Phe-D-Val-NH2 |
| 2646 | TCAM2643 | Phe-Phe-Arg-Arg-Leu-Lys-c[Asp-Pro-Arg-Trp-Arg-Trp-Arg-Lys]-D-Val-D-Pro-NH2 |
| 2647 | TCAM2644 | Phe-Phe-Arg-Arg-Leu-Lys-c[Asp-Pro-Arg-Trp-Arg-Trp-Arg-Lys]-D-Val-D-Phe-NH2 |
| 2648 | TCAM2645 | Phe-Phe-Arg-Arg-Leu-Lys-c[Asp-Pro-Arg-Trp-Arg-Trp-Arg-Lys]-D-Pro-D-Val-NH2 |
| 2649 | TCAM2646 | Phe-Phe-Arg-Arg-Leu-Lys-c[Asp-Pro-Arg-Trp-Arg-Trp-Arg-Lys]-D-Phe-D-Val-NH2 |
| 2650 | TCAM2647 | Phe-Phe-Arg-Arg-Leu-Lys-c[Asp-Pro-Trp-Arg-Tyr-Arg-Trp-Lys]-D-Val-D-Pro-NH2 |
| 2651 | TCAM2648 | Phe-Phe-Arg-Arg-Leu-Lys-c[Asp-Pro-Trp-Arg-Tyr-Arg-Trp-Lys]-D-Val-D-Phe-NH2 |
| 2652 | TCAM2649 | Phe-Phe-Arg-Arg-Leu-Lys-c[Asp-Pro-Trp-Arg-Tyr-Arg-Trp-Lys]-D-Pro-D-Val-NH2 |
| 2653 | TCAM2650 | Phe-Phe-Arg-Arg-Leu-Lys-c[Asp-Pro-Trp-Arg-Tyr-Arg-Trp-Lys]-D-Phe-D-Val-NH2 |
| 2654 | TCAM2651 | Phe-Phe-Arg-Arg-Leu-Lys-c[Asp-Pro-Trp-Arg-Trp-Arg-Tyr-Lys]-D-Val-D-Pro-NH2 |
| 2655 | TCAM2652 | Phe-Phe-Arg-Arg-Leu-Lys-c[Asp-Pro-Trp-Arg-Trp-Arg-Tyr-Lys]-D-Val-D-Phe-NH2 |
| 2656 | TCAM2653 | Phe-Phe-Arg-Arg-Leu-Lys-c[Asp-Pro-Trp-Arg-Trp-Arg-Tyr-Lys]-D-Pro-D-Val-NH2 |

TABLE 5-continued

Exemplary Anti-microbial peptides

| SEQ NO: | Peptide | Peptide Sequence |
|---|---|---|
| 2657 | TCAM2654 | Phe-Phe-Arg-Arg-Leu-Lys-c[Asp-Pro-Trp-Arg-Trp-Arg-Tyr-Lys]-D-Phe-D-Val-NH2 |
| 2658 | TCAM2655 | Phe-Phe-Arg-Arg-Leu-Lys-c[Asp-Pro-Trp-Arg-Trp-Arg-Lys]-D-Val-D-Pro-NH2 |
| 2659 | TCAM2656 | Phe-Phe-Arg-Arg-Leu-Lys-c[Asp-Pro-Trp-Arg-Trp-Arg-Lys]-D-Val-D-Phe-NH2 |
| 2660 | TCAM2657 | Phe-Phe-Arg-Arg-Leu-Lys-c[Asp-Pro-Trp-Arg-Trp-Arg-Lys]-D-Pro-D-Val-NH2 |
| 2661 | TCAM2658 | Phe-Phe-Arg-Arg-Leu-Lys-c[Asp-Pro-Trp-Arg-Trp-Arg-Lys]-D-Phe-D-Val-NH2 |
| 2662 | TCAM2659 | Phe-Phe-Arg-Arg-Leu-Lys-c[Asp-Pro-Trp-Arg-Arg-Trp-Lys]-D-Val-D-Pro-NH2 |
| 2663 | TCAM2660 | Phe-Phe-Arg-Arg-Leu-Lys-c[Asp-Pro-Trp-Arg-Arg-Trp-Lys]-D-Val-D-Phe-NH2 |
| 2664 | TCAM2661 | Phe-Phe-Arg-Arg-Leu-Lys-c[Asp-Pro-Trp-Arg-Arg-Trp-Lys]-D-Pro-D-Val-NH2 |
| 2665 | TCAM2662 | Phe-Phe-Arg-Arg-Leu-Lys-c[Asp-Pro-Trp-Arg-Arg-Trp-Lys]-D-Phe-D-Val-NH2 |
| 2666 | TCAM2663 | Phe-Phe-Arg-Arg-Leu-Lys-c[Asp-Pro-Arg-Trp-Trp-Arg-Lys]-D-Val-D-Pro-NH2 |
| 2667 | TCAM2664 | Phe-Phe-Arg-Arg-Leu-Lys-c[Asp-Pro-Arg-Trp-Trp-Arg-Lys]-D-Val-D-Phe-NH2 |
| 2668 | TCAM2665 | Phe-Phe-Arg-Arg-Leu-Lys-c[Asp-Pro-Arg-Trp-Trp-Arg-Lys]-D-Pro-D-Val-NH2 |
| 2669 | TCAM2666 | Phe-Phe-Arg-Arg-Leu-Lys-c[Asp-Pro-Arg-Trp-Trp-Arg-Lys]-D-Phe-D-Val-NH2 |
| 2670 | TCAM2667 | Phe-Phe-Arg-Arg-Leu-Lys-c[Asp-Pro-Trp-Arg-Trp-Lys]-D-Val-D-Pro-NH2 |
| 2671 | TCAM2668 | Phe-Phe-Arg-Arg-Leu-Lys-c[Asp-Pro-Trp-Arg-Trp-Lys]-D-Val-D-Phe-NH2 |
| 2672 | TCAM2669 | Phe-Phe-Arg-Arg-Leu-Lys-c[Asp-Pro-Trp-Arg-Trp-Lys]-D-Pro-D-Val-NH2 |
| 2673 | TCAM2670 | Phe-Phe-Arg-Arg-Leu-Lys-c[Asp-Pro-Trp-Arg-Trp-Lys]-D-Phe-D-Val-NH2 |
| 2674 | TCAM2671 | Phe-Phe-Arg-Arg-Leu-Lys-c[Asp-Pro-Arg-Trp-Arg-Lys]-D-Val-D-Pro-NH2 |
| 2675 | TCAM2672 | Phe-Phe-Arg-Arg-Leu-Lys-c[Asp-Pro-Arg-Trp-Arg-Lys]-D-Val-D-Phe-NH2 |
| 2676 | TCAM2673 | Phe-Phe-Arg-Arg-Leu-Lys-c[Asp-Pro-Arg-Trp-Arg-Lys]-D-Pro-D-Val-NH2 |
| 2677 | TCAM2674 | Phe-Phe-Arg-Arg-Leu-Lys-c[Asp-Pro-Arg-Trp-Arg-Lys]-D-Phe-D-Val-NH2 |
| 2678 | TCAM2675 | Phe-Phe-Arg-Arg-Leu-Lys-c[Asp-Arg-Arg-Trp-Trp-Arg-Phe-Lys]-D-Val-D-Pro-NH2 |
| 2679 | TCAM2676 | Phe-Phe-Arg-Arg-Leu-Lys-c[Asp-Arg-Arg-Trp-Trp-Arg-Phe-Lys]-D-Val-D-Phe-NH2 |
| 2680 | TCAM2677 | Phe-Phe-Arg-Arg-Leu-Lys-c[Asp-Arg-Arg-Trp-Trp-Arg-Phe-Lys]-D-Pro-D-Val-NH2 |
| 2681 | TCAM2678 | Phe-Phe-Arg-Arg-Leu-Lys-c[Asp-Arg-Arg-Trp-Trp-Arg-Phe-Lys]-D-Phe-D-Val-NH2 |
| 2682 | TCAM2679 | Phe-Phe-Arg-Arg-Leu-Lys-c[Asp-Arg-Arg-Trp-Trp-Arg-Phe-Lys]-D-Val-D-Pro-NH2 |
| 2683 | TCAM2680 | Phe-Phe-Arg-Arg-Leu-Lys-c[Asp-Arg-Arg-Trp-Trp-Arg-Phe-Lys]-D-Val-D-Phe-NH2 |
| 2684 | TCAM2681 | Phe-Phe-Arg-Arg-Leu-Lys-c[Asp-Arg-Arg-Trp-Trp-Arg-Phe-Lys]-D-Pro-D-Val-NH2 |
| 2685 | TCAM2682 | Phe-Phe-Arg-Arg-Leu-Lys-c[Asp-Arg-Arg-Trp-Trp-Arg-Phe-Lys]-D-Phe-D-Val-NH2 |
| 2686 | TCAM2683 | Phe-Phe-Arg-Arg-Leu-Lys-c[Asp-Arg-Arg-Tyr-Tyr-Arg-Phe-Lys]-D-Val-D-Pro-NH2 |
| 2687 | TCAM2684 | Phe-Phe-Arg-Arg-Leu-Lys-c[Asp-Arg-Arg-Tyr-Tyr-Arg-Phe-Lys]-D-Val-D-Phe-NH2 |
| 2688 | TCAM2685 | Phe-Phe-Arg-Arg-Leu-Lys-c[Asp-Arg-Arg-Tyr-Tyr-Arg-Phe-Lys]-D-Pro-D-Val-NH2 |
| 2689 | TCAM2686 | Phe-Phe-Arg-Arg-Leu-Lys-c[Asp-Arg-Arg-Tyr-Tyr-Arg-Phe-Lys]-D-Phe-D-Val-NH2 |
| 2690 | TCAM2687 | Phe-Phe-Arg-Arg-Leu-Lys-c[Asp-Arg-Arg-Nal-Nal-Arg-Phe-Lys]-D-Val-D-Pro-NH2 |
| 2691 | TCAM2688 | Phe-Phe-Arg-Arg-Leu-Lys-c[Asp-Arg-Arg-Nal-Nal-Arg-Phe-Lys]-D-Val-D-Phe-NH2 |
| 2692 | TCAM2689 | Phe-Phe-Arg-Arg-Leu-Lys-c[Asp-Arg-Arg-Nal-Nal-Arg-Phe-Lys]-D-Pro-D-Val-NH2 |
| 2693 | TCAM2690 | Phe-Phe-Arg-Arg-Leu-Lys-c[Asp-Arg-Arg-Nal-Nal-Arg-Phe-Lys]-D-Phe-D-Val-NH2 |
| 2694 | TCAM2691 | Phe-Phe-Arg-Arg-Leu-Lys-c[Asp-Arg-Arg-Leu-Trp-Leu-Trp-Lys]-D-Val-D-Pro-NH2 |

TABLE 5-continued

Exemplary Anti-microbial peptides

| SEQ NO: | Peptide | Peptide Sequence |
|---|---|---|
| 2695 | TCAM2692 | Phe-Phe-Arg-Arg-Leu-Lys-c[Asp-Arg-Arg-Leu-Trp-Leu-Trp-Lys]-D-Val-D-Phe-NH2 |
| 2696 | TCAM2693 | Phe-Phe-Arg-Arg-Leu-Lys-c[Asp-Arg-Arg-Leu-Trp-Leu-Trp-Lys]-D-Pro-D-Val-NH2 |
| 2697 | TCAM2694 | Phe-Phe-Arg-Arg-Leu-Lys-c[Asp-Arg-Arg-Leu-Trp-Leu-Trp-Lys]-D-Phe-D-Val-NH2 |
| 2698 | TCAM2695 | Phe-Phe-Arg-Arg-Leu-Lys-c[Asp-Arg-Arg-Leu-Trp-Leu-Trp-Lys]-D-Val-D-Pro-NH2 |
| 2699 | TCAM2696 | Phe-Phe-Arg-Arg-Leu-Lys-c[Asp-Arg-Arg-Leu-Trp-Leu-Trp-Lys]-D-Val-D-Phe-NH2 |
| 2700 | TCAM2697 | Phe-Phe-Arg-Arg-Leu-Lys-c[Asp-Arg-Arg-Leu-Trp-Leu-Trp-Lys]-D-Pro-D-Val-NH2 |
| 2701 | TCAM2698 | Phe-Phe-Arg-Arg-Leu-Lys-c[Asp-Arg-Arg-Leu-Trp-Leu-Trp-Lys]-D-Phe-D-Val-NH2 |
| 2702 | TCAM2699 | Phe-Phe-Arg-Arg-Leu-Lys-c[Asp-Arg-Arg-Arg-Trp-Leu-Trp-Leu-Trp-Lys]-D-Val-D-Pro-NH2 |
| 2703 | TCAM2700 | Phe-Phe-Arg-Arg-Leu-Lys-c[Asp-Arg-Arg-Arg-Trp-Leu-Trp-Leu-Trp-Lys]-D-Val-D-Phe-NH2 |
| 2704 | TCAM2701 | Phe-Phe-Arg-Arg-Leu-Lys-c[Asp-Arg-Arg-Arg-Trp-Leu-Trp-Leu-Trp-Lys]-D-Pro-D-Val-NH2 |
| 2705 | TCAM2702 | Phe-Phe-Arg-Arg-Leu-Lys-c[Asp-Arg-Arg-Arg-Trp-Leu-Trp-Leu-Trp-Lys]-D-Phe-D-Val-NH2 |
| 2706 | TCAM2703 | Phe-Phe-Arg-Arg-Leu-Lys-c[Asp-Arg-Gln-Arg-Arg-Trp-Leu-Trp-Leu-Trp-Lys]-D-Val-D-Pro-NH2 |
| 2707 | TCAM2704 | Phe-Phe-Arg-Arg-Leu-Lys-c[Asp-Arg-Gln-Arg-Arg-Trp-Leu-Trp-Leu-Trp-Lys]-D-Val-D-Phe-NH2 |
| 2708 | TCAM2705 | Phe-Phe-Arg-Arg-Leu-Lys-c[Asp-Arg-Gln-Arg-Arg-Trp-Leu-Trp-Leu-Trp-Lys]-D-Pro-D-Val-NH2 |
| 2709 | TCAM2706 | Phe-Phe-Arg-Arg-Leu-Lys-c[Asp-Arg-Gln-Arg-Arg-Trp-Leu-Trp-Leu-Trp-Lys]-D-Phe-D-Val-NH2 |
| 2710 | TCAM2707 | Phe-Phe-Arg-Arg-Leu-Lys-c[Asp-Trp-Arg-Trp-Trp-Arg-Arg-Lys]-D-Val-D-Pro-NH2 |
| 2711 | TCAM2708 | Phe-Phe-Arg-Arg-Leu-Lys-c[Asp-Trp-Arg-Trp-Trp-Arg-Arg-Lys]-D-Val-D-Phe-NH2 |
| 2712 | TCAM2709 | Phe-Phe-Arg-Arg-Leu-Lys-c[Asp-Trp-Arg-Trp-Trp-Arg-Arg-Lys]-D-Pro-D-Val-NH2 |
| 2713 | TCAM2710 | Phe-Phe-Arg-Arg-Leu-Lys-c[Asp-Trp-Arg-Trp-Trp-Arg-Arg-Lys]-D-Phe-D-Val-NH2 |
| 2714 | TCAM2711 | Phe-Phe-Arg-Arg-Leu-Lys-c[Asp-Trp-Trp-Arg-Arg-Trp-Trp-Arg-Arg-Lys]-D-Val-D-Pro-NH2 |
| 2715 | TCAM2712 | Phe-Phe-Arg-Arg-Leu-Lys-c[Asp-Trp-Trp-Arg-Arg-Trp-Trp-Arg-Arg-Lys]-D-Val-D-Phe-NH2 |
| 2716 | TCAM2713 | Phe-Phe-Arg-Arg-Leu-Lys-c[Asp-Trp-Trp-Arg-Arg-Trp-Trp-Arg-Arg-Lys]-D-Pro-D-Val-NH2 |
| 2717 | TCAM2714 | Phe-Phe-Arg-Arg-Leu-Lys-c[Asp-Trp-Trp-Arg-Arg-Trp-Trp-Arg-Arg-Lys]-D-Phe-D-Val-NH2 |
| 2718 | TCAM2715 | Phe-Phe-Arg-Arg-Leu-Lys-c[Asp-Trp-Arg-Trp-Arg-Trp-Arg-Lys]-D-Val-D-Pro-NH2 |
| 2719 | TCAM2716 | Phe-Phe-Arg-Arg-Leu-Lys-c[Asp-Trp-Arg-Trp-Arg-Trp-Arg-Lys]-D-Val-D-Phe-NH2 |
| 2720 | TCAM2717 | Phe-Phe-Arg-Arg-Leu-Lys-c[Asp-Trp-Arg-Trp-Arg-Trp-Arg-Lys]-D-Pro-D-Val-NH2 |
| 2721 | TCAM2718 | Phe-Phe-Arg-Arg-Leu-Lys-c[Asp-Trp-Arg-Trp-Arg-Trp-Arg-Lys]-D-Phe-D-Val-NH2 |
| 2722 | TCAM2719 | Phe-Phe-Arg-Arg-Leu-Lys-c[Asp-Arg-Trp-Arg-Trp-Arg-Trp-Lys]-D-Val-D-Pro-NH2 |
| 2723 | TCAM2720 | Phe-Phe-Arg-Arg-Leu-Lys-c[Asp-Arg-Trp-Arg-Trp-Arg-Trp-Lys]-D-Val-D-Phe-NH2 |
| 2724 | TCAM2721 | Phe-Phe-Arg-Arg-Leu-Lys-c[Asp-Arg-Trp-Arg-Trp-Arg-Trp-Lys]-D-Pro-D-Val-NH2 |
| 2725 | TCAM2722 | Phe-Phe-Arg-Arg-Leu-Lys-c[Asp-Arg-Trp-Arg-Trp-Arg-Trp-Lys]-D-Phe-D-Val-NH2 |

TABLE 5-continued

Exemplary Anti-microbial peptides

| SEQ NO: | Peptide | Peptide Sequence |
|---|---|---|
| 2726 | TCAM2723 | Phe-Phe-Arg-Arg-Leu-Lys-c[Asp-Arg-Trp-Trp-Arg-Arg-Lys]-D-Val-D-Pro-NH2 |
| 2727 | TCAM2724 | Phe-Phe-Arg-Arg-Leu-Lys-c[Asp-Arg-Trp-Trp-Arg-Arg-Lys]-D-Val-D-Phe-NH2 |
| 2728 | TCAM2725 | Phe-Phe-Arg-Arg-Leu-Lys-c[Asp-Arg-Trp-Trp-Arg-Arg-Lys]-D-Pro-D-Val-NH2 |
| 2729 | TCAM2726 | Phe-Phe-Arg-Arg-Leu-Lys-c[Asp-Arg-Trp-Trp-Arg-Arg-Lys]-D-Phe-D-Val-NH2 |
| 2730 | TCAM2727 | Phe-Phe-Arg-Arg-Leu-Lys-c[Asp-Arg-Trp-Arg-Trp-Arg-Lys]-D-Val-D-Pro-NH2 |
| 2731 | TCAM2728 | Phe-Phe-Arg-Arg-Leu-Lys-c[Asp-Arg-Trp-Arg-Trp-Arg-Lys]-D-Val-D-Phe-NH2 |
| 2732 | TCAM2729 | Phe-Phe-Arg-Arg-Leu-Lys-c[Asp-Arg-Trp-Arg-Trp-Arg-Lys]-D-Pro-D-Val-NH2 |
| 2733 | TCAM2730 | Phe-Phe-Arg-Arg-Leu-Lys-c[Asp-Arg-Trp-Arg-Trp-Arg-Lys]-D-Phe-D-Val-NH2 |
| 2734 | TCAM2731 | Phe-Phe-Arg-Arg-Leu-Lys-c[Asp-Trp-Trp-Arg-Arg-Trp-Lys]-D-Val-D-Pro-NH2 |
| 2735 | TCAM2732 | Phe-Phe-Arg-Arg-Leu-Lys-c[Asp-Trp-Trp-Arg-Arg-Trp-Lys]-D-Val-D-Phe-NH2 |
| 2736 | TCAM2733 | Phe-Phe-Arg-Arg-Leu-Lys-c[Asp-Trp-Trp-Arg-Arg-Trp-Lys]-D-Pro-D-Val-NH2 |
| 2737 | TCAM2734 | Phe-Phe-Arg-Arg-Leu-Lys-c[Asp-Trp-Trp-Arg-Arg-Trp-Lys]-D-Phe-D-Val-NH2 |
| 2738 | TCAM2735 | Phe-Phe-Arg-Arg-Leu-Lys-c[Asp-Trp-Arg-Trp-Arg-Trp-Lys]-D-Val-D-Pro-NH2 |
| 2739 | TCAM2736 | Phe-Phe-Arg-Arg-Leu-Lys-c[Asp-Trp-Arg-Trp-Arg-Trp-Lys]-D-Val-D-Phe-NH2 |
| 2740 | TCAM2737 | Phe-Phe-Arg-Arg-Leu-Lys-c[Asp-Trp-Arg-Trp-Arg-Trp-Lys]-D-Pro-D-Val-NH2 |
| 2741 | TCAM2738 | Phe-Phe-Arg-Arg-Leu-Lys-c[Asp-Trp-Arg-Trp-Arg-Trp-Lys]-D-Phe-D-Val-NH2 |
| 2742 | TCAM2739 | Phe-Phe-Arg-Arg-Leu-Lys-c[Asp-Trp-Arg-Tyr-Arg-Trp-Lys]-D-Val-D-Pro-NH2 |
| 2743 | TCAM2740 | Phe-Phe-Arg-Arg-Leu-Lys-c[Asp-Trp-Arg-Tyr-Arg-Trp-Lys]-D-Val-D-Phe-NH2 |
| 2744 | TCAM2741 | Phe-Phe-Arg-Arg-Leu-Lys-c[Asp-Trp-Arg-Tyr-Arg-Trp-Lys]-D-Pro-D-Val-NH2 |
| 2745 | TCAM2742 | Phe-Phe-Arg-Arg-Leu-Lys-c[Asp-Trp-Arg-Tyr-Arg-Trp-Lys]-D-Phe-D-Val-NH2 |
| 2746 | TCAM2743 | Phe-Phe-Arg-Arg-Leu-Lys-c[Asp-Trp-Arg-Trp-Arg-Tyr-Lys]-D-Val-D-Pro-NH2 |
| 2747 | TCAM2744 | Phe-Phe-Arg-Arg-Leu-Lys-c[Asp-Trp-Arg-Trp-Arg-Tyr-Lys]-D-Val-D-Phe-NH2 |
| 2748 | TCAM2745 | Phe-Phe-Arg-Arg-Leu-Lys-c[Asp-Trp-Arg-Trp-Arg-Tyr-Lys]-D-Pro-D-Val-NH2 |
| 2749 | TCAM2746 | Phe-Phe-Arg-Arg-Leu-Lys-c[Asp-Trp-Arg-Trp-Arg-Tyr-Lys]-D-Phe-D-Val-NH2 |
| 2750 | TCAM2747 | Phe-Phe-Arg-Arg-Leu-Lys-c[Asp-Trp-Arg-Trp-Arg-Lys]-D-Val-D-Pro-NH2 |
| 2751 | TCAM2748 | Phe-Phe-Arg-Arg-Leu-Lys-c[Asp-Trp-Arg-Trp-Arg-Lys]-D-Val-D-Phe-NH2 |
| 2752 | TCAM2749 | Phe-Phe-Arg-Arg-Leu-Lys-c[Asp-Trp-Arg-Trp-Arg-Lys]-D-Pro-D-Val-NH2 |
| 2753 | TCAM2750 | Phe-Phe-Arg-Arg-Leu-Lys-c[Asp-Trp-Arg-Trp-Arg-Lys]-D-Phe-D-Val-NH2 |
| 2754 | TCAM2751 | Phe-Phe-Arg-Arg-Leu-Lys-c[Asp-Trp-Arg-Arg-Trp-Lys]-D-Val-D-Pro-NH2 |
| 2755 | TCAM2752 | Phe-Phe-Arg-Arg-Leu-Lys-c[Asp-Trp-Arg-Arg-Trp-Lys]-D-Val-D-Phe-NH2 |
| 2756 | TCAM2753 | Phe-Phe-Arg-Arg-Leu-Lys-c[Asp-Trp-Arg-Arg-Trp-Lys]-D-Pro-D-Val-NH2 |
| 2757 | TCAM2754 | Phe-Phe-Arg-Arg-Leu-Lys-c[Asp-Trp-Arg-Arg-Trp-Lys]-D-Phe-D-Val-NH2 |
| 2758 | TCAM2755 | Phe-Phe-Arg-Arg-Leu-Lys-c[Asp-Arg-Trp-Trp-Arg-Lys]-D-Val-D-Pro-NH2 |
| 2759 | TCAM2756 | Phe-Phe-Arg-Arg-Leu-Lys-c[Asp-Arg-Trp-Trp-Arg-Lys]-D-Val-D-Phe-NH2 |
| 2760 | TCAM2757 | Phe-Phe-Arg-Arg-Leu-Lys-c[Asp-Arg-Trp-Trp-Arg-Lys]-D-Pro-D-Val-NH2 |
| 2761 | TCAM2758 | Phe-Phe-Arg-Arg-Leu-Lys-c[Asp-Arg-Trp-Trp-Arg-Lys]-D-Phe-D-Val-NH2 |
| 2762 | TCAM2759 | Phe-Phe-Arg-Arg-Leu-Lys-c[Asp-Trp-Arg-Trp-Lys]-D-Val-D-Pro-NH2 |
| 2763 | TCAM2760 | Phe-Phe-Arg-Arg-Leu-Lys-c[Asp-Trp-Arg-Trp-Lys]-D-Val-D-Phe-NH2 |

TABLE 5-continued

Exemplary Anti-microbial peptides

| SEQ NO: | Peptide | Peptide Sequence |
|---|---|---|
| 2764 | TCAM2761 | Phe-Phe-Arg-Arg-Leu-Lys-c[Asp-Trp-Arg-Trp-Lys]-D-Pro-D-Val-NH2 |
| 2765 | TCAM2762 | Phe-Phe-Arg-Arg-Leu-Lys-c[Asp-Trp-Arg-Trp-Lys]-D-Phe-D-Val-NH2 |
| 2766 | TCAM2763 | Phe-Phe-Arg-Arg-Leu-Lys-c[Asp-Arg-Trp-Arg-Lys]-D-Val-D-Pro-NH2 |
| 2767 | TCAM2764 | Phe-Phe-Arg-Arg-Leu-Lys-c[Asp-Arg-Trp-Arg-Lys]-D-Val-D-Phe-NH2 |
| 2768 | TCAM2765 | Phe-Phe-Arg-Arg-Leu-Lys-c[Asp-Arg-Trp-Arg-Lys]-D-Pro-D-Val-NH2 |
| 2769 | TCAM2766 | Phe-Phe-Arg-Arg-Leu-Lys-c[Asp-Arg-Trp-Arg-Lys]-D-Phe-D-Val-NH2 |
| 2770 | TCAM2767 | Phe-Phe-Arg-Arg-Leu-Lys-c[Asp-His-D-Nal(2')-Arg-Trp-Lys]-D-Val-D-Pro-NH2 |
| 2771 | TCAM2768 | Phe-Phe-Arg-Arg-Leu-Lys-c[Asp-His-D-Nal(2')-Arg-Trp-Lys]-D-Pro-D-Val-NH2 |
| 2772 | TCAM2769 | Phe-Phe-Arg-Arg-Leu-Lys-c[Asp-His-D-Nal(2')-Arg-Trp-Lys]-D-Val-D-Phe-NH2 |
| 2773 | TCAM2770 | Phe-Phe-Arg-Arg-Leu-Lys-c[Asp-His-D-Nal(2')-Arg-Trp-Lys]-D-Phe-D-Val-NH2 |
| 2774 | TCAM2771 | Phe-Phe-Arg-Arg-Leu-Lys-c[Asp-Pro-D-Nal(2')-Arg-Trp-Lys]-D-Val-D-Pro-NH2 |
| 2775 | TCAM2772 | Phe-Phe-Arg-Arg-Leu-Lys-c[Asp-Pro-D-Nal(2')-Arg-Trp-Lys]-D-Pro-D-Val-NH2 |
| 2776 | TCAM2773 | Phe-Phe-Arg-Arg-Leu-Lys-c[Asp-Pro-D-Nal(2')-Arg-Trp-Lys]-D-Val-D-Phe-NH2 |
| 2777 | TCAM2774 | Phe-Phe-Arg-Arg-Leu-Lys-c[Asp-Pro-D-Nal(2')-Arg-Trp-Lys]-D-Phe-D-Val-NH2 |
| 2778 | TCAM2775 | Phe-Phe-Arg-Arg-Leu-Lys-c[Asp-Arg-Arg-Nal(2')-Arg-Trp-Lys]-D-Val-D-Pro-NH2 |
| 2779 | TCAM2776 | Phe-Phe-Arg-Arg-Leu-Lys-c[Asp-Arg-Arg-Nal(2')-Arg-Trp-Lys]-D-Pro-D-Val-NH2 |
| 2780 | TCAM2777 | Phe-Phe-Arg-Arg-Leu-Lys-c[Asp-Arg-Arg-Nal(2')-Arg-Trp-Lys]-D-Val-D-Phe-NH2 |
| 2781 | TCAM2778 | Phe-Phe-Arg-Arg-Leu-Lys-c[Asp-Arg-Arg-Nal(2')-Arg-Trp-Lys]-D-Phe-D-Val-NH2 |
| 2782 | TCAM2779 | Phe-Phe-Arg-Arg-Leu-Lys-c[Asp-Arg-Arg-Pro-Nal(2')-Arg-Trp-Lys]-D-Val-D-Pro-NH2 |
| 2783 | TCAM2780 | Phe-Phe-Arg-Arg-Leu-Lys-c[Asp-Arg-Arg-Pro-D-Nal(2')-Arg-Trp-Lys]-D-Pro-D-Val-NH2 |
| 2784 | TCAM2781 | Phe-Phe-Arg-Arg-Leu-Lys-c[Asp-Arg-Arg-Pro-D-Nal(2')-Arg-Trp-Lys]-D-Val-D-Phe-NH2 |
| 2785 | TCAM2782 | Phe-Phe-Arg-Arg-Leu-Lys-c[Asp-Arg-Arg-Pro-Nal(2')-Arg-Trp-Lys]-D-Phe-D-Val-NH2 |
| 2786 | TCAM2783 | Phe-Phe-Arg-Arg-Leu-Lys-c[Asp-Arg-D-Nal(2')-Arg-Trp-Lys]-D-Val-D-Pro-NH2 |
| 2787 | TCAM2784 | Phe-Phe-Arg-Arg-Leu-Lys-c[Asp-Arg-D-Nal(2')-Arg-Trp-Lys]-D-Pro-D-Val-NH2 |
| 2788 | TCAM2785 | Phe-Phe-Arg-Arg-Leu-Lys-c[Asp-Arg-D-Nal(2')-Arg-Trp-Lys]-D-Val-D-Phe-NH2 |
| 2789 | TCAM2786 | Phe-Phe-Arg-Arg-Leu-Lys-c[Asp-Arg-D-Nal(2')-Arg-Trp-Lys]-D-Phe-D-Val-NH2 |
| 2790 | TCAM2787 | Phe-Phe-Arg-Arg-Leu-Lys-c[Asp-Arg-Pro-D-Nal(2')-Arg-Trp-Lys]-D-Val-D-Pro-NH2 |
| 2791 | TCAM2788 | Phe-Phe-Arg-Arg-Leu-Lys-c[Asp-Arg-Pro-D-Nal(2')-Arg-Trp-Lys]-D-Pro-D-Val-NH2 |
| 2792 | TCAM2789 | Phe-Phe-Arg-Arg-Leu-Lys-c[Asp-Arg-Pro-D-Nal(2')-Arg-Trp-Lys]-D-Val-D-Phe-NH2 |
| 2793 | TCAM2790 | Phe-Phe-Arg-Arg-Leu-Lys-c[Asp-Arg-Pro-D-Nal(2')-Arg-Trp-Lys]-D-Phe-D-Val-NH2 |
| 2794 | TCAM2791 | Phe-Phe-Arg-Arg-Leu-Lys-Arg-Arg-c[Asp-Pro-D-Nal(2')-Arg-Trp-Lys]-D-Val-D-Pro-NH2 |
| 2795 | TCAM2792 | Phe-Phe-Arg-Arg-Leu-Lys-Arg-Arg-c[Asp-Pro-D-Nal(2')-Arg-Trp-Lys]-D-Pro-D-Val-NH2 |
| 2796 | TCAM2793 | Phe-Phe-Arg-Arg-Leu-Lys-Arg-Arg-c[Asp-Pro-D-Nal(2')-Arg-Trp-Lys]-D-Val-D-Phe-NH2 |
| 2797 | TCAM2794 | Phe-Phe-Arg-Arg-Leu-Lys-Arg-Arg-c[Asp-Pro-D-Nal(2')-Arg-Trp-Lys]-D-Phe-D-Val-NH2 |

TABLE 5-continued

Exemplary Anti-microbial peptides

| SEQ NO: | Peptide | Peptide Sequence |
|---|---|---|
| 2798 | TCAM2795 | Phe-Phe-Arg-Arg-Leu-Lys-Arg-Arg-c[Asp-His-D-Nal(2')-Arg-Trp-Lys]-D-Val-D-Pro-NH2 |
| 2799 | TCAM2796 | Phe-Phe-Arg-Arg-Leu-Lys-Arg-Arg-c[Asp-His-D-Nal(2')-Arg-Trp-Lys]-D-Pro-D-Val-NH2 |
| 2800 | TCAM2797 | Phe-Phe-Arg-Arg-Leu-Lys-Arg-Arg-c[Asp-His-D-Nal(2')-Arg-Trp-Lys]-D-Val-D-Phe-NH2 |
| 2801 | TCAM2798 | Phe-Phe-Arg-Arg-Leu-Lys-Arg-Arg-c[Asp-His-D-Nal(2')-Arg-Trp-Lys]-D-Phe-D-Val-NH2 |
| 2802 | TCAM2799 | Phe-Phe-Arg-Arg-Leu-Lys-c[Asp-Arg-Pro-D-Nal(2')-Arg-Trp-Arg-Lys]-D-Val-D-Pro-NH2 |
| 2803 | TCAM2800 | Phe-Phe-Arg-Arg-Leu-Lys-c[Asp-Arg-Pro-D-Nal(2')-Arg-Trp-Arg-Lys]-D-Pro-D-Val-NH2 |
| 2804 | TCAM2801 | Phe-Phe-Arg-Arg-Leu-Lys-c[Asp-Arg-Pro-D-Nal(2')-Arg-Trp-Arg-Lys]-D-Val-D-Phe-NH2 |
| 2805 | TCAM2802 | Phe-Phe-Arg-Arg-Leu-Lys-c[Asp-Arg-Pro-D-Nal(2')-Arg-Trp-Arg-Lys]-D-Phe-D-Val-NH2 |
| 2806 | TCAM2803 | Phe-Phe-Arg-Arg-Leu-Lys-c[Asp-Arg-His-D-Nal(2')-Arg-Trp-Arg-Lys]-D-Val-D-Pro-NH2 |
| 2807 | TCAM2804 | Phe-Phe-Arg-Arg-Leu-Lys-c[Asp-Arg-His-D-Nal(2')-Arg-Trp-Arg-Lys]-D-Pro-D-Val-NH2 |
| 2808 | TCAM2805 | Phe-Phe-Arg-Arg-Leu-Lys-c[Asp-Arg-His-D-Nal(2')-Arg-Trp-Arg-Lys]-D-Val-D-Phe-NH2 |
| 2809 | TCAM2806 | Phe-Phe-Arg-Arg-Leu-Lys-c[Asp-Arg-His-D-Nal(2')-Arg-Trp-Arg-Lys]-D-Phe-D-Val-NH2 |
| 2810 | TCAM2807 | Phe-Phe-Arg-Arg-Leu-Lys-c[Asp-His-D-Nal(2')-Arg-D-Nal(2')-Lys]-D-Val-D-Phe-NH2 |
| 2811 | TCAM2808 | Phe-Phe-Arg-Arg-Leu-Lys-c[Asp-His-D-Nal(2')-Arg-D-Nal(2')-Lys]-D-Phe-D-Val-NH2 |
| 2812 | TCAM2809 | Phe-Phe-Arg-Arg-Leu-Lys-c[Asp-Pro-D-Nal(2')-Arg-D-Nal(2')-Lys]-D-Val-D-Pro-NH2 |
| 2813 | TCAM2810 | Phe-Phe-Arg-Arg-Leu-Lys-c[Asp-Pro-D-Nal(2')-Arg-D-Nal(2')-Lys]-D-Pro-D-Val-NH2 |
| 2814 | TCAM2811 | Phe-Phe-Arg-Arg-Leu-Lys-c[Asp-Pro-D-Nal(2')-Arg-D-Nal(2')-Lys]-D-Val-D-Phe-NH2 |
| 2815 | TCAM2812 | Phe-Phe-Arg-Arg-Leu-Lys-c[Asp-Pro-D-Nal(2')-Arg-D-Nal(2')-Lys]-D-Phe-D-Val-NH2 |
| 2816 | TCAM2813 | Phe-Phe-Arg-Arg-Leu-Lys-c[Asp-Arg-Arg-D-Nal(2')-Arg-D-Nal(2')-Lys]-D-Val-D-Pro-NH2 |
| 2817 | TCAM2814 | Phe-Phe-Arg-Arg-Leu-Lys-c[Asp-Arg-Arg-D-Nal(2')-Arg-D-Nal(2')-Lys]-D-Pro-D-Val-NH2 |
| 2818 | TCAM2815 | Phe-Phe-Arg-Arg-Leu-Lys-c[Asp-Arg-Arg-D-Nal(2')-Arg-D-Nal(2')-Lys]-D-Val-D-Phe-NH2 |
| 2819 | TCAM2816 | Phe-Phe-Arg-Arg-Leu-Lys-c[Asp-Arg-Arg-D-Nal(2')-Arg-D-Nal(2')-Lys]-D-Phe-D-Val-NH2 |
| 2820 | TCAM2817 | Phe-Phe-Arg-Arg-Leu-Lys-c[Asp-Arg-Arg-Pro-D-Nal(2')-Arg-D-Nal(2')-Lys]-D-Val-D-Pro-NH2 |
| 2821 | TCAM2818 | Phe-Phe-Arg-Arg-Leu-Lys-c[Asp-Arg-Arg-Pro-D-Nal(2')-Arg-D-Nal(2')-Lys]-D-Pro-D-Val-NH2 |
| 2822 | TCAM2819 | Phe-Phe-Arg-Arg-Leu-Lys-c[Asp-Arg-Arg-Pro-D-Nal(2')-Arg-D-Nal(2')-Lys]-D-Val-D-Phe-NH2 |
| 2823 | TCAM2820 | Phe-Phe-Arg-Arg-Leu-Lys-c[Asp-Arg-Arg-Pro-D-Nal(2')-Arg-D-Nal(2')-Lys]-D-Phe-D-Val-NH2 |
| 2824 | TCAM2821 | Phe-Phe-Arg-Arg-Leu-Lys-c[Asp-Arg-D-Nal(2')-Arg-D-Nal(2')-Lys]-D-Val-D-Pro-NH2 |
| 2825 | TCAM2822 | Phe-Phe-Arg-Arg-Leu-Lys-c[Asp-Arg-D-Nal(2')-Arg-D-Nal(2')-Lys]-D-Pro-D-Val-NH2 |
| 2826 | TCAM2823 | Phe-Phe-Arg-Arg-Leu-Lys-c[Asp-Arg-Nal(2')-Arg-D-Nal(2')-Lys]-D-Val-D-Phe-NH2 |
| 2827 | TCAM2824 | Phe-Phe-Arg-Arg-Leu-Lys-c[Asp-Arg-D-Nal(2')-Arg-D-Nal(2')-Lys]-D-Phe-D-Val-NH2 |

TABLE 5-continued

Exemplary Anti-microbial peptides

| SEQ NO: | Peptide | Peptide Sequence |
|---|---|---|
| 2828 | TCAM2825 | Phe-Phe-Arg-Arg-Leu-Lys-c[Asp-Arg-Pro-D-Nal(2')-Arg-D-Nal(2')-Lys]-D-Val-D-Pro-NH2 |
| 2829 | TCAM2826 | Phe-Phe-Arg-Arg-Leu-Lys-c[Asp-Arg-Pro-D-Nal(2')-Arg-D-Nal(2')-Lys]-D-Pro-D-Val-NH2 |
| 2830 | TCAM2827 | Phe-Phe-Arg-Arg-Leu-Lys-c[Asp-Arg-Pro-D-Nal(2')-Arg-D-Nal(2')-Lys]-D-Val-D-Phe-NH2 |
| 2831 | TCAM2828 | Phe-Phe-Arg-Arg-Leu-Lys-c[Asp-Arg-Pro-D-Nal(2')-Arg-D-Nal(2')-Lys]-D-Phe-D-Val-NH2 |
| 2832 | TCAM2829 | Phe-Phe-Arg-Arg-Leu-Lys-c[Asp-Arg-His-D-Nal(2')-Arg-D-Nal(2')-Lys]-D-Val-D-Pro-NH2 |
| 2833 | TCAM2830 | Phe-Phe-Arg-Arg-Leu-Lys-c[Asp-Arg-His-D-Nal(2')-Arg-D-Nal(2')-Lys]-D-Pro-D-Val-NH2 |
| 2834 | TCAM2831 | Phe-Phe-Arg-Arg-Leu-Lys-c[Asp-Arg-His-Nal(2')-Arg-D-Nal(2')-Lys]-D-Val-D-Phe-NH2 |
| 2835 | TCAM2832 | Phe-Phe-Arg-Arg-Leu-Lys-c[Asp-Arg-His-Nal(2')-Arg-D-Nal(2')-Lys]-D-Phe-D-Val-NH2 |
| 2836 | TCAM2833 | Phe-Phe-Arg-Arg-Leu-Lys-c[Asp-Arg-D-D-Nal(2')-Arg-D-Nal(2')-Arg-Lys]-D-Val-D-Pro-NH2 |
| 2837 | TCAM2834 | Phe-Phe-Arg-Arg-Leu-Lys-c[Asp-Arg-D-Nal(2')-Arg-D-Nal(2')-Arg-Lys]-D-Pro-D-Val-NH2 |
| 2838 | TCAM2835 | Phe-Phe-Arg-Arg-Leu-Lys-c[Asp-Arg-D-Nal(2')-Arg-D-Nal(2')-Arg-Lys]-D-Val-D-Phe-NH2 |
| 2839 | TCAM2836 | Phe-Phe-Arg-Arg-Leu-Lys-c[Asp-Arg-D-Nal(2')-Arg-D-Nal(2')-Arg-Lys]-D-Phe-D-Val-NH2 |
| 2840 | TCAM2837 | Phe-Phe-Arg-Arg-Leu-Lys-c[Asp-Arg-Pro-D-Nal(2')-Arg-D-Nal(2')-Arg-Lys]-D-Val-D-Pro-NH2 |
| 2841 | TCAM2838 | Phe-Phe-Arg-Arg-Leu-Lys-c[Asp-Arg-Pro-D-Nal(2')-Arg-D-Nal(2')-Arg-Lys]-D-Pro-D-Val-NH2 |
| 2842 | TCAM2839 | Phe-Phe-Arg-Arg-Leu-Lys-c[Asp-Arg-Pro-D-Nal(2')-Arg-D-Nal(2')-Arg-Lys]-D-Val-D-Phe-NH2 |
| 2843 | TCAM2840 | Phe-Phe-Arg-Arg-Leu-Lys-c[Asp-Arg-Pro-D-Nal(2')-Arg-D-Nal(2')-Arg-Lys]-D-Phe-D-Val-NH2 |
| 2844 | TCAM2841 | Phe-Phe-Arg-Arg-Leu-Lys-c[Asp-Arg-His-D-Nal(2')-Arg-D-Nal(2')-Arg-Lys]-D-Val-D-Pro-NH2 |
| 2845 | TCAM2842 | Phe-Phe-Arg-Arg-Leu-Lys-c[Asp-Arg-His-D-Nal(2')-Arg-D-Nal(2')-Arg-Lys]-D-Pro-D-Val-NH2 |
| 2846 | TCAM2843 | Phe-Phe-Arg-Arg-Leu-Lys-c[Asp-Arg-His-D-Nal(2')-Arg-D-Nal(2')-Arg-Lys]-D-Val-D-Phe-NH2 |
| 2847 | TCAM2844 | Phe-Phe-Arg-Arg-Leu-Lys-c[Asp-Arg-His-D-Nal(2')-Arg-D-Nal(2')-Arg-Lys]-D-Phe-D-Val-NH2 |
| 2848 | TCAM2845 | Phe-Phe-Arg-Arg-Leu-Lys-Arg-Arg-c[Asp-Pro-D-Nal(2')-Arg-D-Nal(2')-Lys]-D-Val-D-Pro-NH2 |
| 2849 | TCAM2846 | Phe-Phe-Arg-Arg-Leu-Lys-Arg-Arg-c[Asp-Pro-D-Nal(2')-Arg-D-Nal(2')-Lys]-D-Pro-D-Val-NH2 |
| 2850 | TCAM2847 | Phe-Phe-Arg-Arg-Leu-Lys-Arg-Arg-c[Asp-Pro-D-Nal(2')-Arg-D-Nal(2')-Lys]-D-Val-D-Phe-NH2 |
| 2851 | TCAM2848 | Phe-Phe-Arg-Arg-Leu-Lys-Arg-Arg-c[Asp-Pro-D-Nal(2')-Arg-D-Nal(2')-Lys]-D-Phe-D-Val-NH2 |
| 2852 | TCAM2849 | Phe-Phe-Arg-Arg-Leu-Lys-Arg-Arg-c[Asp-His-D-Nal(2')-Arg-D-Nal(2')-Lys]-D-Val-D-Pro-NH2 |

TABLE 5-continued

Exemplary Anti-microbial peptides

| SEQ NO: | Peptide | Peptide Sequence |
|---|---|---|
| 2853 | TCAM2850 | Phe-Phe-Arg-Arg-Leu-Lys-Arg-Arg-c[Asp-His-D-Nal(2')-Arg-D-Nal(2')-Lys]-D-Pro-D-Val-NH2 |
| 2854 | TCAM2851 | Phe-Phe-Arg-Arg-Leu-Lys-Arg-Arg-c[Asp-His-D-Nal(2')-Arg-D-Nal(2')-Lys]-D-Val-D-Phe-NH2 |
| 2855 | TCAM2852 | Phe-Phe-Arg-Arg-Leu-Lys-Arg-Arg-c[Asp-His-D-Nal(2')-Arg-D-Nal(2')-Lys]-D-Phe-D-Val-NH2 |
| 2856 | TCAM2853 | Phe-Phe-Arg-Arg-Leu-Lys-c[Asp-Arg-Pro-D-Nal(2')-Arg-D-Nal(2')-Arg-Lys]-D-Val-D-Pro-NH2 |
| 2857 | TCAM2854 | Phe-Phe-Arg-Arg-Leu-Lys-c[Asp-Arg-Pro-D-Nal(2')-Arg-D-Nal(2')-Arg-Lys]-D-Pro-D-Val-NH2 |
| 2858 | TCAM2855 | Phe-Phe-Arg-Arg-Leu-Lys-c[Asp-Arg-Pro-D-Nal(2')-Arg-D-Nal(2')-Arg-Lys]-D-Val-D-Phe-NH2 |
| 2859 | TCAM2856 | Phe-Phe-Arg-Arg-Leu-Lys-c[Asp-Arg-Pro-D-Nal(2')-Arg-D-Nal(2')-Arg-Lys]-D-Phe-D-Val-NH2 |
| 2860 | TCAM2857 | Phe-Phe-Arg-Arg-Leu-Lys-c[Asp-Arg-His-D-Nal(2')-Arg-D-Nal(2')-Arg-Lys]-D-Val-D-Pro-NH2 |
| 2861 | TCAM2858 | Phe-Phe-Arg-Arg-Leu-Lys-c[Asp-Arg-His-D-Nal(2')-Arg-D-Nal(2')-Arg-Lys]-D-Pro-D-Val-NH2 |
| 2862 | TCAM2859 | Phe-Phe-Arg-Arg-Leu-Lys-c[Asp-Arg-His-D-Nal(2')-Arg-D-Nal(2')-Arg-Lys]-D-Val-D-Phe-NH2 |
| 2863 | TCAM2860 | Phe-Phe-Arg-Arg-Leu-Lys-c[Asp-Arg-His-D-Nal(2')-Arg-D-Nal(2')-Arg-Lys]-D-Phe-D-Val-NH2 |
| 2864 | TCAM2861 | Phe-Phe-Arg-Arg-Leu-Lys-c[Asp-His-D-Nal(2')-Arg-Trp-Lys]-Arg-Arg-D-Val-D-Pro-NH2 |
| 2865 | TCAM2862 | Phe-Phe-Arg-Arg-Leu-Lys-c[Asp-His-D-Nal(2')-Arg-Trp-Lys]-Arg-Arg-D-Pro-D-Val-NH2 |
| 2866 | TCAM2863 | Phe-Phe-Arg-Arg-Leu-Lys-c[Asp-His-D-Nal(2')-Arg-Trp-Lys]-Arg-Arg-D-Val-D-Phe-NH2 |
| 2867 | TCAM2864 | Phe-Phe-Arg-Arg-Leu-Lys-c[Asp-His-D-Nal(2')-Arg-Trp-Lys]-Arg-Arg-D-Phe-D-Val-NH2 |
| 2868 | TCAM2865 | Phe-Phe-Arg-Arg-Leu-Lys-c[Asp-Pro-D-Nal(2')-Arg-Trp-Lys]-Arg-Arg-D-Val-D-Pro-NH2 |
| 2869 | TCAM2866 | Phe-Phe-Arg-Arg-Leu-Lys-c[Asp-Pro-D-Nal(2')-Arg-Trp-Lys]-Arg-Arg-D-Pro-D-Val-NH2 |
| 2870 | TCAM2867 | Phe-Phe-Arg-Arg-Leu-Lys-c[Asp-Pro-D-Nal(2')-Arg-Trp-Lys]-Arg-Arg-D-Val-D-Phe-NH2 |
| 2871 | TCAM2868 | Phe-Phe-Arg-Arg-Leu-Lys-c[Asp-Pro-D-Nal(2')-Arg-Trp-Lys]-Arg-Arg-D-Phe-D-Val-NH2 |
| Anti-biofilm peptide ABF5ARG linked to anti-microbial peptides | | |
| 2872 | TCAM2869 | Phe-Phe-Arg-Arg-Leu-Arg-c[Asp-Pro-Arg-Arg-Trp-Trp-Arg-Phe-Lys]-D-Val-D-Pro-NH2 |
| 2873 | TCAM2870 | Phe-Phe-Arg-Arg-Leu-Arg-c[Asp-Pro-Arg-Arg-Trp-Trp-Arg-Phe-Lys]-D-Val-D-Phe-NH2 |
| 2874 | TCAM2871 | Phe-Phe-Arg-Arg-Leu-Arg-c[Asp-Pro-Arg-Arg-Trp-Trp-Arg-Phe-Lys]-D-Pro-D-Val-NH2 |
| 2875 | TCAM2872 | Phe-Phe-Arg-Arg-Leu-Arg-c[Asp-Pro-Arg-Arg-Trp-Trp-Arg-Phe-Lys]-D-Phe-D-Val-NH2 |
| 2876 | TCAM2873 | Phe-Phe-Arg-Arg-Leu-Arg-c[Asp-Pro-Arg-Arg-Trp-Trp-Tyr-Phe-Lys]-D-Val-D-Pro-NH2 |
| 2877 | TCAM2874 | Phe-Phe-Arg-Arg-Leu-Arg-c[Asp-Pro-Arg-Arg-Trp-Trp-Tyr-Phe-Lys]-D-Val-D-Phe-NH2 |
| 2878 | TCAM2875 | Phe-Phe-Arg-Arg-Leu-Arg-c[Asp-Pro-Arg-Arg-Trp-Trp-Tyr-Phe-Lys]-D-Pro-D-Val-NH2 |
| 2879 | TCAM2876 | Phe-Phe-Arg-Arg-Leu-Arg-c[Asp-Pro-Arg-Arg-Trp-Trp-Tyr-Phe-Lys]-D-Phe-D-Val-NH2 |

TABLE 5-continued

Exemplary Anti-microbial peptides

| SEQ NO: | Peptide | Peptide Sequence |
|---|---|---|
| 2880 | TCAM2877 | Phe-Phe-Arg-Arg-Leu-Arg-c[Asp-Pro-Arg-Arg-Tyr-Tyr-Arg-Phe-Lys]-D-Val-D-Pro-NH2 |
| 2881 | TCAM2878 | Phe-Phe-Arg-Arg-Leu-Arg-c[Asp-Pro-Arg-Arg-Tyr-Tyr-Arg-Phe-Lys]-D-Val-D-Phe-NH2 |
| 2882 | TCAM2879 | Phe-Phe-Arg-Arg-Leu-Arg-c[Asp-Pro-Arg-Arg-Tyr-Tyr-Arg-Phe-Lys]-D-Pro-D-Val-NH2 |
| 2883 | TCAM2880 | Phe-Phe-Arg-Arg-Leu-Arg-c[Asp-Pro-Arg-Arg-Tyr-Tyr-Arg-Phe-Lys]-D-Phe-D-Val-NH2 |
| 2884 | TCAM2881 | Phe-Phe-Arg-Arg-Leu-Arg-c[Asp-Pro-Arg-Arg-Nal-Nal-Arg-Phe-Lys]-D-Val-D-Pro-NH2 |
| 2885 | TCAM2882 | Phe-Phe-Arg-Arg-Leu-Arg-c[Asp-Pro-Arg-Arg-Nal-Nal-Arg-Phe-Lys]-D-Val-D-Phe-NH2 |
| 2886 | TCAM2883 | Phe-Phe-Arg-Arg-Leu-Arg-c[Asp-Pro-Arg-Arg-Nal-Nal-Arg-Phe-Lys]-D-Pro-D-Val-NH2 |
| 2887 | TCAM2884 | Phe-Phe-Arg-Arg-Leu-Arg-c[Asp-Pro-Arg-Arg-Nal-Nal-Arg-Phe-Lys]-D-Phe-D-Val-NH2 |
| 2888 | TCAM2885 | Phe-Phe-Arg-Arg-Leu-Arg-c[Asp-Pro-Arg-Arg-Leu-Trp-Leu-Trp-Lys]-D-Val-D-Pro-NH2 |
| 2889 | TCAM2886 | Phe-Phe-Arg-Arg-Leu-Arg-c[Asp-Pro-Arg-Arg-Leu-Trp-Leu-Trp-Lys]-D-Val-D-Phe-NH2 |
| 2890 | TCAM2887 | Phe-Phe-Arg-Arg-Leu-Arg-c[Asp-Pro-Arg-Arg-Leu-Trp-Leu-Trp-Lys]-D-Pro-D-Val-NH2 |
| 2891 | TCAM2888 | Phe-Phe-Arg-Arg-Leu-Arg-c[Asp-Pro-Arg-Arg-Leu-Trp-Leu-Trp-Lys]-D-Phe-D-Val-NH2 |
| 2892 | TCAM2889 | Phe-Phe-Arg-Arg-Leu-Arg-c[Asp-Pro-Arg-Arg-Leu-Trp-Leu-Trp-Lys]-D-Val-D-Pro-NH2 |
| 2893 | TCAM2890 | Phe-Phe-Arg-Arg-Leu-Arg-c[Asp-Pro-Arg-Arg-Leu-Trp-Leu-Trp-Lys]-D-Val-D-Phe-NH2 |
| 2894 | TCAM2891 | Phe-Phe-Arg-Arg-Leu-Arg-c[Asp-Pro-Arg-Arg-Leu-Trp-Leu-Trp-Lys]-D-Pro-D-Val-NH2 |
| 2895 | TCAM2892 | Phe-Phe-Arg-Arg-Leu-Arg-c[Asp-Pro-Arg-Arg-Leu-Trp-Leu-Trp-Lys]-D-Phe-D-Val-NH2 |
| 2896 | TCAM2893 | Phe-Phe-Arg-Arg-Leu-Arg-c[Asp-Arg-Arg-Arg-Trp-Leu-Trp-Leu-Trp-Lys]-D-Val-D-Pro-NH2 |
| 2897 | TCAM2894 | Phe-Phe-Arg-Arg-Leu-Arg-c[Asp-Pro-Arg-Arg-Arg-Trp-Leu-Trp-Leu-Trp-Lys]-D-Val-D-Phe-NH2 |
| 2898 | TCAM2895 | Phe-Phe-Arg-Arg-Leu-Arg-c[Asp-Pro-Arg-Arg-Arg-Trp-Leu-Trp-Leu-Trp-Lys]-D-Pro-D-Val-NH2 |
| 2899 | TCAM2896 | Phe-Phe-Arg-Arg-Leu-Arg-c[Asp-Pro-Arg-Arg-Arg-Trp-Leu-Trp-Leu-Trp-Lys]-D-Phe-D-Val-NH2 |
| 2900 | TCAM2897 | Phe-Phe-Arg-Arg-Leu-Arg-c[Asp-Pro-Arg-Gln-Arg-Arg-Trp-Leu-Trp-Leu-Trp-Lys]-D-Val-D-Pro-NH2 |
| 2901 | TCAM2898 | Phe-Phe-Arg-Arg-Leu-Arg-c[Asp-Pro-Arg-Gln-Arg-Arg-Trp-Leu-Trp-Leu-Trp-Lys]-D-Val-D-Phe-NH2 |
| 2902 | TCAM2899 | Phe-Phe-Arg-Arg-Leu-Arg-c[Asp-Pro-Arg-Gln-Arg-Arg-Trp-Leu-Trp-Leu-Trp-Lys]-D-Pro-D-Val-NH2 |
| 2903 | TCAM2900 | Phe-Phe-Arg-Arg-Leu-Arg-c[Asp-Pro-Arg-Gln-Arg-Arg-Trp-Leu-Trp-Leu-Trp-Lys]-D-Phe-D-Val-NH2 |
| 2904 | TCAM2901 | Phe-Phe-Arg-Arg-Leu-Arg-c[Asp-Pro-Trp-Arg-Trp-Trp-Arg-Arg-Lys]-D-Val-D-Phe-NH2 |
| 2905 | TCAM2902 | Phe-Phe-Arg-Arg-Leu-Arg-c[Asp-Pro-Trp-Arg-Trp-Trp-Arg-Arg-Lys]-D-Pro-D-Val-NH2 |
| 2906 | TCAM2903 | Phe-Phe-Arg-Arg-Leu-Arg-c[Asp-Pro-Trp-Arg-Trp-Trp-Arg-Arg-Lys]-D-Phe-D-Val-NH2 |
| 2907 | TCAM2904 | Phe-Phe-Arg-Arg-Leu-Arg-c[Asp-Pro-Trp-Trp-Arg-Arg-Trp-Trp-Arg-Arg-Lys]-D-Val-D-Pro-NH2 |
| 2908 | TCAM2905 | Phe-Phe-Arg-Arg-Leu-Arg-c[Asp-Pro-Trp-Trp-Arg-Arg-Trp-Trp-Arg-Arg-Lys]-D-Val-D-Phe-NH2 |

TABLE 5-continued

Exemplary Anti-microbial peptides

| SEQ NO: | Peptide | Peptide Sequence |
|---|---|---|
| 2909 | TCAM2906 | Phe-Phe-Arg-Arg-Leu-Arg-c[Asp-Pro-Trp-Trp-Arg-Arg-Trp-Trp-Arg-Arg-Lys]-D-Pro-D-Val-NH2 |
| 2910 | TCAM2907 | Phe-Phe-Arg-Arg-Leu-Arg-c[Asp-Pro-Trp-Trp-Arg-Arg-Trp-Trp-Arg-Arg-Lys]-D-Phe-D-Val-NH2 |
| 2911 | TCAM2908 | Phe-Phe-Arg-Arg-Leu-Arg-c[Asp-Pro-Trp-Arg-Trp-Arg-Trp-Arg-Lys]-D-Val-D-Pro-NH2 |
| 2912 | TCAM2909 | Phe-Phe-Arg-Arg-Leu-Arg-c[Asp-Pro-Trp-Arg-Trp-Arg-Trp-Arg-Lys]-D-Val-D-Phe-NH2 |
| 2913 | TCAM2910 | Phe-Phe-Arg-Arg-Leu-Arg-c[Asp-Pro-Trp-Arg-Trp-Arg-Trp-Arg-Lys]-D-Pro-D-Val-NH2 |
| 2914 | TCAM2911 | Phe-Phe-Arg-Arg-Leu-Arg-c[Asp-Pro-Trp-Arg-Trp-Arg-Trp-Arg-Lys]-D-Phe-D-Val-NH2 |
| 2915 | TCAM2912 | Phe-Phe-Arg-Arg-Leu-Arg-c[Asp-Pro-Arg-Trp-Arg-Trp-Arg-Trp-Lys]-D-Val-D-Pro-NH2 |
| 2916 | TCAM2913 | Phe-Phe-Arg-Arg-Leu-Arg-c[Asp-Pro-Arg-Trp-Arg-Trp-Arg-Trp-Lys]-D-Val-D-Phe-NH2 |
| 2917 | TCAM2914 | Phe-Phe-Arg-Arg-Leu-Arg-c[Asp-Pro-Arg-Trp-Arg-Trp-Arg-Trp-Lys]-D-Pro-D-Val-NH2 |
| 2918 | TCAM2915 | Phe-Phe-Arg-Arg-Leu-Arg-c[Asp-Pro-Arg-Trp-Arg-Trp-Arg-Trp-Lys]-D-Phe-D-Val-NH2 |
| 2919 | TCAM2916 | Phe-Phe-Arg-Arg-Leu-Arg-c[Asp-Pro-Arg-Trp-Trp-Arg-Arg-Lys]-D-Val-D-Pro-NH2 |
| 2920 | TCAM2917 | Phe-Phe-Arg-Arg-Leu-Arg-c[Asp-Pro-Arg-Trp-Trp-Arg-Arg-Lys]-D-Val-D-Phe-NH2 |
| 2921 | TCAM2918 | Phe-Phe-Arg-Arg-Leu-Arg-c[Asp-Pro-Arg-Trp-Trp-Arg-Arg-Lys]-D-Pro-D-Val-NH2 |
| 2922 | TCAM2919 | Phe-Phe-Arg-Arg-Leu-Arg-c[Asp-Pro-Arg-Trp-Trp-Arg-Arg-Lys]-D-Phe-D-Val-NH2 |
| 2923 | TCAM2920 | Phe-Phe-Arg-Arg-Leu-Arg-c[Asp-Pro-Trp-Trp-Arg-Arg-Trp-Lys]-D-Val-D-Pro-NH2 |
| 2924 | TCAM2921 | Phe-Phe-Arg-Arg-Leu-Arg-c[Asp-Pro-Trp-Trp-Arg-Arg-Trp-Lys]-D-Val-D-Phe-NH2 |
| 2925 | TCAM2922 | Phe-Phe-Arg-Arg-Leu-Arg-c[Asp-Pro-Trp-Trp-Arg-Arg-Trp-Lys]-D-Pro-D-Val-NH2 |
| 2926 | TCAM2923 | Phe-Phe-Arg-Arg-Leu-Arg-c[Asp-Pro-Trp-Trp-Arg-Arg-Trp-Lys]-D-Phe-D-Val-NH2 |
| 2927 | TCAM2924 | Phe-Phe-Arg-Arg-Leu-Arg-c[Asp-Pro-Trp-Arg-Trp-Arg-Trp-Lys]-D-Val-D-Pro-NH2 |
| 2928 | TCAM2925 | Phe-Phe-Arg-Arg-Leu-Arg-c[Asp-Pro-Trp-Arg-Trp-Arg-Trp-Lys]-D-Val-D-Phe-NH2 |
| 2929 | TCAM2926 | Phe-Phe-Arg-Arg-Leu-Arg-c[Asp-Pro-Trp-Arg-Trp-Arg-Trp-Lys]-D-Pro-D-Val-NH2 |
| 2930 | TCAM2927 | Phe-Phe-Arg-Arg-Leu-Arg-c[Asp-Pro-Trp-Arg-Trp-Arg-Trp-Lys]-D-Phe-D-Val-NH2 |
| 2931 | TCAM2928 | Phe-Phe-Arg-Arg-Leu-Arg-c[Asp-Pro-Arg-Trp-Arg-Trp-Arg-Lys]-D-Val-D-Pro-NH2 |
| 2932 | TCAM2929 | Phe-Phe-Arg-Arg-Leu-Arg-c[Asp-Pro-Arg-Trp-Arg-Trp-Arg-Lys]-D-Val-D-Phe-NH2 |
| 2933 | TCAM2930 | Phe-Phe-Arg-Arg-Leu-Arg-c[Asp-Pro-Arg-Trp-Arg-Trp-Arg-Lys]-D-Pro-D-Val-NH2 |
| 2934 | TCAM2931 | Phe-Phe-Arg-Arg-Leu-Arg-c[Asp-Pro-Arg-Trp-Arg-Trp-Arg-Lys]-D-Phe-D-Val-NH2 |
| 2935 | TCAM2932 | Phe-Phe-Arg-Arg-Leu-Arg-c[Asp-Pro-Trp-Arg-Tyr-Arg-Trp-Lys]-D-Val-D-Pro-NH2 |
| 2936 | TCAM2933 | Phe-Phe-Arg-Arg-Leu-Arg-c[Asp-Pro-Trp-Arg-Tyr-Arg-Trp-Lys]-D-Val-D-Phe-NH2 |
| 2937 | TCAM2934 | Phe-Phe-Arg-Arg-Leu-Arg-c[Asp-Pro-Trp-Arg-Tyr-Arg-Trp-Lys]-D-Pro-D-Val-NH2 |
| 2938 | TCAM2935 | Phe-Phe-Arg-Arg-Leu-Arg-c[Asp-Pro-Trp-Arg-Tyr-Arg-Trp-Lys]-D-Phe-D-Val-NH2 |
| 2939 | TCAM2936 | Phe-Phe-Arg-Arg-Leu-Arg-c[Asp-Pro-Trp-Arg-Trp-Arg-Tyr-Lys]-D-Val-D-Pro-NH2 |
| 2940 | TCAM2937 | Phe-Phe-Arg-Arg-Leu-Arg-c[Asp-Pro-Trp-Arg-Trp-Arg-Tyr-Lys]-D-Val-D-Phe-NH2 |
| 2941 | TCAM2938 | Phe-Phe-Arg-Arg-Leu-Arg-c[Asp-Pro-Trp-Arg-Trp-Arg-Tyr-Lys]-D-Pro-D-Val-NH2 |
| 2942 | TCAM2939 | Phe-Phe-Arg-Arg-Leu-Arg-c[Asp-Pro-Trp-Arg-Trp-Arg-Tyr-Lys]-D-Phe-D-Val-NH2 |
| 2943 | TCAM2940 | Phe-Phe-Arg-Arg-Leu-Arg-c[Asp-Pro-Trp-Arg-Trp-Arg-Lys]-D-Val-D-Pro-NH2 |
| 2944 | TCAM2941 | Phe-Phe-Arg-Arg-Leu-Arg-c[Asp-Pro-Trp-Arg-Trp-Arg-Lys]-D-Val-D-Phe-NH2 |
| 2945 | TCAM2942 | Phe-Phe-Arg-Arg-Leu-Arg-c[Asp-Pro-Trp-Arg-Trp-Arg-Lys]-D-Pro-D-Val-NH2 |

TABLE 5-continued

Exemplary Anti-microbial peptides

| SEQ NO: | Peptide | Peptide Sequence |
|---|---|---|
| 2946 | TCAM2943 | Phe-Phe-Arg-Arg-Leu-Arg-c[Asp-Pro-Trp-Arg-Trp-Arg-Lys]-D-Phe-D-Val-NH2 |
| 2947 | TCAM2944 | Phe-Phe-Arg-Arg-Leu-Arg-c[Asp-Pro-Trp-Arg-Arg-Trp-Lys]-D-Val-D-Pro-NH2 |
| 2948 | TCAM2945 | Phe-Phe-Arg-Arg-Leu-Arg-c[Asp-Pro-Trp-Arg-Arg-Trp-Lys]-D-Val-D-Phe-NH2 |
| 2949 | TCAM2946 | Phe-Phe-Arg-Arg-Leu-Arg-c[Asp-Pro-Trp-Arg-Arg-Trp-Lys]-D-Pro-D-Val-NH2 |
| 2950 | TCAM2947 | Phe-Phe-Arg-Arg-Leu-Arg-c[Asp-Pro-Trp-Arg-Arg-Trp-Lys]-D-Phe-D-Val-NH2 |
| 2951 | TCAM2948 | Phe-Phe-Arg-Arg-Leu-Arg-c[Asp-Pro-Arg-Trp-Trp-Arg-Lys]-D-Val-D-Pro-NH2 |
| 2952 | TCAM2949 | Phe-Phe-Arg-Arg-Leu-Arg-c[Asp-Pro-Arg-Trp-Trp-Arg-Lys]-D-Val-D-Phe-NH2 |
| 2953 | TCAM2950 | Phe-Phe-Arg-Arg-Leu-Arg-c[Asp-Pro-Arg-Trp-Trp-Arg-Lys]-D-Pro-D-Val-NH2 |
| 2954 | TCAM2951 | Phe-Phe-Arg-Arg-Leu-Arg-c[Asp-Pro-Arg-Trp-Trp-Arg-Lys]-D-Phe-D-Val-NH2 |
| 2955 | TCAM2952 | Phe-Phe-Arg-Arg-Leu-Arg-c[Asp-Pro-Trp-Arg-Trp-Lys]-D-Val-D-Pro-NH2 |
| 2956 | TCAM2953 | Phe-Phe-Arg-Arg-Leu-Arg-c[Asp-Pro-Trp-Arg-Trp-Lys]-D-Val-D-Phe-NH2 |
| 2957 | TCAM2954 | Phe-Phe-Arg-Arg-Leu-Arg-c[Asp-Pro-Trp-Arg-Trp-Lys]-D-Pro-D-Val-NH2 |
| 2958 | TCAM2955 | Phe-Phe-Arg-Arg-Leu-Arg-c[Asp-Pro-Trp-Arg-Trp-Lys]-D-Phe-D-Val-NH2 |
| 2959 | TCAM2956 | Phe-Phe-Arg-Arg-Leu-Arg-c[Asp-Pro-Arg-Trp-Arg-Lys]-D-Val-D-Pro-NH2 |
| 2960 | TCAM2957 | Phe-Phe-Arg-Arg-Leu-Arg-c[Asp-Pro-Arg-Trp-Arg-Lys]-D-Val-D-Phe-NH2 |
| 2961 | TCAM2958 | Phe-Phe-Arg-Arg-Leu-Arg-c[Asp-Pro-Arg-Trp-Arg-Lys]-D-Pro-D-Val-NH2 |
| 2962 | TCAM2959 | Phe-Phe-Arg-Arg-Leu-Arg-c[Asp-Pro-Arg-Trp-Arg-Lys]-D-Phe-D-Val-NH2 |
| 2963 | TCAM2960 | Phe-Phe-Arg-Arg-Leu-Arg-c[Asp-Arg-Arg-Trp-Trp-Arg-Phe-Lys]-D-Val-D-Pro-NH2 |
| 2964 | TCAM2961 | Phe-Phe-Arg-Arg-Leu-Arg-c[Asp-Arg-Arg-Trp-Trp-Arg-Phe-Lys]-D-Val-D-Phe-NH2 |
| 2965 | TCAM2962 | Phe-Phe-Arg-Arg-Leu-Arg-c[Asp-Arg-Arg-Trp-Trp-Arg-Phe-Lys]-D-Pro-D-Val-NH2 |
| 2966 | TCAM2963 | Phe-Phe-Arg-Arg-Leu-Arg-c[Asp-Arg-Arg-Trp-Trp-Arg-Phe-Lys]-D-Phe-D-Val-NH2 |
| 2967 | TCAM2964 | Phe-Phe-Arg-Arg-Leu-Arg-c[Asp-Arg-Arg-Trp-Trp-Arg-Phe-Lys]-D-Val-D-Pro-NH2 |
| 2968 | TCAM2965 | Phe-Phe-Arg-Arg-Leu-Arg-c[Asp-Arg-Arg-Trp-Trp-Arg-Phe-Lys]-D-Val-D-Phe-NH2 |
| 2969 | TCAM2966 | Phe-Phe-Arg-Arg-Leu-Arg-c[Asp-Arg-Arg-Trp-Trp-Arg-Phe-Lys]-D-Pro-D-Val-NH2 |
| 2970 | TCAM2967 | Phe-Phe-Arg-Arg-Leu-Arg-c[Asp-Arg-Arg-Trp-Trp-Arg-Phe-Lys]-D-Phe-D-Val-NH2 |
| 2971 | TCAM2968 | Phe-Phe-Arg-Arg-Leu-Arg-c[Asp-Arg-Arg-Tyr-Tyr-Arg-Phe-Lys]-D-Val-D-Pro-NH2 |
| 2972 | TCAM2969 | Phe-Phe-Arg-Arg-Leu-Arg-c[Asp-Arg-Arg-Tyr-Tyr-Arg-Phe-Lys]-D-Val-D-Phe-NH2 |
| 2973 | TCAM2970 | Phe-Phe-Arg-Arg-Leu-Arg-c[Asp-Arg-Arg-Tyr-Tyr-Arg-Phe-Lys]-D-Pro-D-Val-NH2 |
| 2974 | TCAM2971 | Phe-Phe-Arg-Arg-Leu-Arg-c[Asp-Arg-Arg-Tyr-Tyr-Arg-Phe-Lys]-D-Phe-D-Val-NH2 |
| 2975 | TCAM2972 | Phe-Phe-Arg-Arg-Leu-Arg-c[Asp-Arg-Arg-Nal-Nal-Arg-Phe-Lys]-D-Val-D-Pro-NH2 |
| 2976 | TCAM2973 | Phe-Phe-Arg-Arg-Leu-Arg-c[Asp-Arg-Arg-Nal-Nal-Arg-Phe-Lys]-D-Val-D-Phe-NH2 |
| 2977 | TCAM2974 | Phe-Phe-Arg-Arg-Leu-Arg-c[Asp-Arg-Arg-Nal-Nal-Arg-Phe-Lys]-D-Pro-D-Val-NH2 |
| 2978 | TCAM2975 | Phe-Phe-Arg-Arg-Leu-Arg-c[Asp-Arg-Arg-Nal-Nal-Arg-Phe-Lys]-D-Phe-D-Val-NH2 |
| 2979 | TCAM2976 | Phe-Phe-Arg-Arg-Leu-Arg-c[Asp-Arg-Arg-Leu-Trp-Leu-Trp-Lys]-D-Val-D-Pro-NH2 |
| 2980 | TCAM2977 | Phe-Phe-Arg-Arg-Leu-Arg-c[Asp-Arg-Arg-Leu-Trp-Leu-Trp-Lys]-D-Val-D-Phe-NH2 |
| 2981 | TCAM2978 | Phe-Phe-Arg-Arg-Leu-Arg-c[Asp-Arg-Arg-Leu-Trp-Leu-Trp-Lys]-D-Pro-D-Val-NH2 |
| 2982 | TCAM2979 | Phe-Phe-Arg-Arg-Leu-Arg-c[Asp-Arg-Arg-Leu-Trp-Leu-Trp-Lys]-D-Phe-D-Val-NH2 |

TABLE 5-continued

Exemplary Anti-microbial peptides

| SEQ NO: | Peptide | Peptide Sequence |
|---|---|---|
| 2983 | TCAM2980 | Phe-Phe-Arg-Arg-Leu-Arg-c[Asp-Arg-Arg-Leu-Trp-Leu-Trp-Lys]-D-Val-D-Pro-NH2 |
| 2984 | TCAM2981 | Phe-Phe-Arg-Arg-Leu-Arg-c[Asp-Arg-Arg-Leu-Trp-Leu-Trp-Lys]-D-Val-D-Phe-NH2 |
| 2985 | TCAM2982 | Phe-Phe-Arg-Arg-Leu-Arg-c[Asp-Arg-Arg-Leu-Trp-Leu-Trp-Lys]-D-Pro-D-Val-NH2 |
| 2986 | TCAM2983 | Phe-Phe-Arg-Arg-Leu-Arg-c[Asp-Arg-Arg-Leu-Trp-Leu-Trp-Lys]-D-Phe-D-Val-NH2 |
| 2987 | TCAM2984 | Phe-Phe-Arg-Arg-Leu-Arg-c[Asp-Arg-Arg-Arg-Trp-Leu-Trp-Leu-Trp-Lys]-D-Val-D-Pro-NH2 |
| 2988 | TCAM2985 | Phe-Phe-Arg-Arg-Leu-Arg-c[Asp-Arg-Arg-Arg-Trp-Leu-Trp-Leu-Trp-Lys]-D-Val-D-Phe-NH2 |
| 2989 | TCAM2986 | Phe-Phe-Arg-Arg-Leu-Arg-c[Asp-Arg-Arg-Arg-Trp-Leu-Trp-Leu-Trp-Lys]-D-Pro-D-Val-NH2 |
| 2990 | TCAM2987 | Phe-Phe-Arg-Arg-Leu-Arg-c[Asp-Arg-Arg-Arg-Trp-Leu-Trp-Leu-Trp-Lys]-D-Phe-D-Val-NH2 |
| 2991 | TCAM2988 | Phe-Phe-Arg-Arg-Leu-Arg-c[Asp-Arg-Gln-Arg-Arg-Trp-Leu-Trp-Leu-Trp-Lys]-D-Val-D-Pro-NH2 |
| 2992 | TCAM2989 | Phe-Phe-Arg-Arg-Leu-Arg-c[Asp-Arg-Gln-Arg-Arg-Trp-Leu-Trp-Leu-Trp-Lys]-D-Val-D-Phe-NH2 |
| 2993 | TCAM2990 | Phe-Phe-Arg-Arg-Leu-Arg-c[Asp-Arg-Gln-Arg-Arg-Trp-Leu-Trp-Leu-Trp-Lys]-D-Pro-D-Val-NH2 |
| 2994 | TCAM2991 | Phe-Phe-Arg-Arg-Leu-Arg-c[Asp-Arg-Gln-Arg-Arg-Trp-Leu-Trp-Leu-Trp-Lys]-D-Phe-D-Val-NH2 |
| 2995 | TCAM2992 | Phe-Phe-Arg-Arg-Leu-Arg-c[Asp-Trp-Arg-Trp-Trp-Arg-Arg-Lys]-D-Val-D-Pro-NH2 |
| 2996 | TCAM2993 | Phe-Phe-Arg-Arg-Leu-Arg-c[Asp-Trp-Arg-Trp-Trp-Arg-Arg-Lys]-D-Val-D-Phe-NH2 |
| 2997 | TCAM2994 | Phe-Phe-Arg-Arg-Leu-Arg-c[Asp-Trp-Arg-Trp-Trp-Arg-Arg-Lys]-D-Pro-D-Val-NH2 |
| 2998 | TCAM2995 | Phe-Phe-Arg-Arg-Leu-Arg-c[Asp-Trp-Arg-Trp-Trp-Arg-Arg-Lys]-D-Phe-D-Val-NH2 |
| 2999 | TCAM2996 | Phe-Phe-Arg-Arg-Leu-Arg-c[Asp-Trp-Trp-Arg-Arg-Trp-Trp-Arg-Arg-Lys]-D-Val-D-Pro-NH2 |
| 3000 | TCAM2997 | Phe-Phe-Arg-Arg-Leu-Arg-c[Asp-Trp-Trp-Arg-Arg-Trp-Trp-Arg-Arg-Lys]-D-Val-D-Phe-NH2 |
| 3001 | TCAM2998 | Phe-Phe-Arg-Arg-Leu-Arg-c[Asp-Trp-Trp-Arg-Arg-Trp-Trp-Arg-Arg-Lys]-D-Pro-D-Val-NH2 |
| 3002 | TCAM2999 | Phe-Phe-Arg-Arg-Leu-Arg-c[Asp-Trp-Trp-Arg-Arg-Trp-Trp-Arg-Arg-Lys]-D-Phe-D-Val-NH2 |
| 3003 | TCAM3000 | Phe-Phe-Arg-Arg-Leu-Arg-c[Asp-Trp-Arg-Trp-Arg-Trp-Arg-Lys]-D-Val-D-Pro-NH2 |
| 3004 | TCAM3001 | Phe-Phe-Arg-Arg-Leu-Arg-c[Asp-Trp-Arg-Trp-Arg-Trp-Arg-Lys]-D-Val-D-Phe-NH2 |
| 3005 | TCAM3002 | Phe-Phe-Arg-Arg-Leu-Arg-c[Asp-Trp-Arg-Trp-Arg-Trp-Arg-Lys]-D-Pro-D-Val-NH2 |
| 3006 | TCAM3003 | Phe-Phe-Arg-Arg-Leu-Arg-c[Asp-Trp-Arg-Trp-Arg-Trp-Arg-Lys]-D-Phe-D-Val-NH2 |
| 3007 | TCAM3004 | Phe-Phe-Arg-Arg-Leu-Arg-c[Asp-Arg-Trp-Arg-Trp-Arg-Trp-Lys]-D-Val-D-Pro-NH2 |
| 3008 | TCAM3005 | Phe-Phe-Arg-Arg-Leu-Arg-c[Asp-Arg-Trp-Arg-Trp-Arg-Trp-Lys]-D-Val-D-Phe-NH2 |
| 3009 | TCAM3006 | Phe-Phe-Arg-Arg-Leu-Arg-c[Asp-Arg-Trp-Arg-Trp-Arg-Trp-Lys]-D-Pro-D-Val-NH2 |
| 3010 | TCAM3007 | Phe-Phe-Arg-Arg-Leu-Arg-c[Asp-Arg-Trp-Arg-Trp-Arg-Trp-Lys]-D-Phe-D-Val-NH2 |
| 3011 | TCAM3008 | Phe-Phe-Arg-Arg-Leu-Arg-c[Asp-Arg-Trp-Trp-Arg-Arg-Lys]-D-Val-D-Pro-NH2 |
| 3012 | TCAM3009 | Phe-Phe-Arg-Arg-Leu-Arg-c[Asp-Arg-Trp-Trp-Arg-Arg-Lys]-D-Val-D-Phe-NH2 |
| 3013 | TCAM3010 | Phe-Phe-Arg-Arg-Leu-Arg-c[Asp-Arg-Trp-Trp-Arg-Arg-Lys]-D-Pro-D-Val-NH2 |
| 3014 | TCAM3011 | Phe-Phe-Arg-Arg-Leu-Arg-c[Asp-Arg-Trp-Trp-Arg-Arg-Lys]-D-Phe-D-Val-NH2 |

TABLE 5-continued

Exemplary Anti-microbial peptides

| SEQ NO: | Peptide | Peptide Sequence |
|---|---|---|
| 3015 | TCAM3012 | Phe-Phe-Arg-Arg-Leu-Arg-c[Asp-Arg-Trp-Arg-Trp-Arg-Lys]-D-Val-D-Pro-NH2 |
| 3016 | TCAM3013 | Phe-Phe-Arg-Arg-Leu-Arg-c[Asp-Arg-Trp-Arg-Trp-Arg-Lys]-D-Val-D-Phe-NH2 |
| 3017 | TCAM3014 | Phe-Phe-Arg-Arg-Leu-Arg-c[Asp-Arg-Trp-Arg-Trp-Arg-Lys]-D-Pro-D-Val-NH2 |
| 3018 | TCAM3015 | Phe-Phe-Arg-Arg-Leu-Arg-c[Asp-Arg-Trp-Arg-Trp-Arg-Lys]-D-Phe-D-Val-NH2 |
| 3019 | TCAM3016 | Phe-Phe-Arg-Arg-Leu-Arg-c[Asp-Trp-Trp-Arg-Arg-Trp-Lys]-D-Val-D-Pro-NH2 |
| 3020 | TCAM3017 | Phe-Phe-Arg-Arg-Leu-Arg-c[Asp-Trp-Trp-Arg-Arg-Trp-Lys]-D-Val-D-Phe-NH2 |
| 3021 | TCAM3018 | Phe-Phe-Arg-Arg-Leu-Arg-c[Asp-Trp-Trp-Arg-Arg-Trp-Lys]-D-Pro-D-Val-NH2 |
| 3022 | TCAM3019 | Phe-Phe-Arg-Arg-Leu-Arg-c[Asp-Trp-Trp-Arg-Arg-Trp-Lys]-D-Phe-D-Val-NH2 |
| 3023 | TCAM3020 | Phe-Phe-Arg-Arg-Leu-Arg-c[Asp-Trp-Arg-Trp-Arg-Trp-Lys]-D-Val-D-Pro-NH2 |
| 3024 | TCAM3021 | Phe-Phe-Arg-Arg-Leu-Arg-c[Asp-Trp-Arg-Trp-Arg-Trp-Lys]-D-Val-D-Phe-NH2 |
| 3025 | TCAM3022 | Phe-Phe-Arg-Arg-Leu-Arg-c[Asp-Trp-Arg-Trp-Arg-Trp-Lys]-D-Pro-D-Val-NH2 |
| 3026 | TCAM3023 | Phe-Phe-Arg-Arg-Leu-Arg-c[Asp-Trp-Arg-Trp-Arg-Trp-Lys]-D-Phe-D-Val-NH2 |
| 3027 | TCAM3024 | Phe-Phe-Arg-Arg-Leu-Arg-c[Asp-Trp-Arg-Tyr-Arg-Trp-Lys]-D-Val-D-Pro-NH2 |
| 3028 | TCAM3025 | Phe-Phe-Arg-Arg-Leu-Arg-c[Asp-Trp-Arg-Tyr-Arg-Trp-Lys]-D-Val-D-Phe-NH2 |
| 3029 | TCAM3026 | Phe-Phe-Arg-Arg-Leu-Arg-c[Asp-Trp-Arg-Tyr-Arg-Trp-Lys]-D-Pro-D-Val-NH2 |
| 3030 | TCAM3027 | Phe-Phe-Arg-Arg-Leu-Arg-c[Asp-Trp-Arg-Tyr-Arg-Trp-Lys]-D-Phe-D-Val-NH2 |
| 3031 | TCAM3028 | Phe-Phe-Arg-Arg-Leu-Arg-c[Asp-Trp-Arg-Trp-Arg-Tyr-Lys]-D-Val-D-Pro-NH2 |
| 3032 | TCAM3029 | Phe-Phe-Arg-Arg-Leu-Arg-c[Asp-Trp-Arg-Trp-Arg-Tyr-Lys]-D-Val-D-Phe-NH2 |
| 3033 | TCAM3030 | Phe-Phe-Arg-Arg-Leu-Arg-c[Asp-Trp-Arg-Trp-Arg-Tyr-Lys]-D-Pro-D-Val-NH2 |
| 3034 | TCAM3031 | Phe-Phe-Arg-Arg-Leu-Arg-c[Asp-Trp-Arg-Trp-Arg-Tyr-Lys]-D-Phe-D-Val-NH2 |
| 3035 | TCAM3032 | Phe-Phe-Arg-Arg-Leu-Arg-c[Asp-Trp-Arg-Trp-Arg-Lys]-D-Val-D-Pro-NH2 |
| 3036 | TCAM3033 | Phe-Phe-Arg-Arg-Leu-Arg-c[Asp-Trp-Arg-Trp-Arg-Lys]-D-Val-D-Phe-NH2 |
| 3037 | TCAM3034 | Phe-Phe-Arg-Arg-Leu-Arg-c[Asp-Trp-Arg-Trp-Arg-Lys]-D-Pro-D-Val-NH2 |
| 3038 | TCAM3035 | Phe-Phe-Arg-Arg-Leu-Arg-c[Asp-Trp-Arg-Trp-Arg-Lys]-D-Phe-D-Val-NH2 |
| 3039 | TCAM3036 | Phe-Phe-Arg-Arg-Leu-Arg-c[Asp-Trp-Arg-Arg-Trp-Lys]-D-Val-D-Pro-NH2 |
| 3040 | TCAM3037 | Phe-Phe-Arg-Arg-Leu-Arg-c[Asp-Trp-Arg-Arg-Trp-Lys]-D-Val-D-Phe-NH2 |
| 3041 | TCAM3038 | Phe-Phe-Arg-Arg-Leu-Arg-c[Asp-Trp-Arg-Arg-Trp-Lys]-D-Pro-D-Val-NH2 |
| 3042 | TCAM3039 | Phe-Phe-Arg-Arg-Leu-Arg-c[Asp-Trp-Arg-Arg-Trp-Lys]-D-Phe-D-Val-NH2 |
| 3043 | TCAM3040 | Phe-Phe-Arg-Arg-Leu-Arg-c[Asp-Arg-Trp-Trp-Arg-Lys]-D-Val-D-Pro-NH2 |
| 3044 | TCAM3041 | Phe-Phe-Arg-Arg-Leu-Arg-c[Asp-Arg-Trp-Trp-Arg-Lys]-D-Val-D-Phe-NH2 |
| 3045 | TCAM3042 | Phe-Phe-Arg-Arg-Leu-Arg-c[Asp-Arg-Trp-Trp-Arg-Lys]-D-Pro-D-Val-NH2 |
| 3046 | TCAM3043 | Phe-Phe-Arg-Arg-Leu-Arg-c[Asp-Arg-Trp-Trp-Arg-Lys]-D-Phe-D-Val-NH2 |
| 3047 | TCAM3044 | Phe-Phe-Arg-Arg-Leu-Arg-c[Asp-Trp-Arg-Trp-Lys]-D-Val-D-Pro-NH2 |
| 3048 | TCAM3045 | Phe-Phe-Arg-Arg-Leu-Arg-c[Asp-Trp-Arg-Trp-Lys]-D-Val-D-Phe-NH2 |
| 3049 | TCAM3046 | Phe-Phe-Arg-Arg-Leu-Arg-c[Asp-Trp-Arg-Trp-Lys]-D-Pro-D-Val-NH2 |
| 3050 | TCAM3047 | Phe-Phe-Arg-Arg-Leu-Arg-c[Asp-Trp-Arg-Trp-Lys]-D-Phe-D-Val-NH2 |
| 3051 | TCAM3048 | Phe-Phe-Arg-Arg-Leu-Arg-c[Asp-Arg-Trp-Arg-Lys]-D-Val-D-Pro-NH2 |

TABLE 5-continued

Exemplary Anti-microbial peptides

| SEQ NO: | Peptide | Peptide Sequence |
|---|---|---|
| 3052 | TCAM3049 | Phe-Phe-Arg-Arg-Leu-Arg-c[Asp-Arg-Trp-Arg-Lys]-D-Val-D-Phe-NH2 |
| 3053 | TCAM3050 | Phe-Phe-Arg-Arg-Leu-Arg-c[Asp-Arg-Trp-Arg-Lys]-D-Pro-D-Val-NH2 |
| 3054 | TCAM3051 | Phe-Phe-Arg-Arg-Leu-Arg-c[Asp-Arg-Trp-Arg-Lys]-D-Phe-D-Val-NH2 |
| 3055 | TCAM3052 | Phe-Phe-Arg-Arg-Leu-Arg-c[Asp-His-D-Nal(2')-Arg-Trp-Lys]-D-Val-D-Pro-NH2 |
| 3056 | TCAM3053 | Phe-Phe-Arg-Arg-Leu-Arg-c[Asp-His-D-Nal(2')-Arg-Trp-Lys]-D-Pro-D-Val-NH2 |
| 3057 | TCAM3054 | Phe-Phe-Arg-Arg-Leu-Arg-c[Asp-His-D-Nal(2')-Arg-Trp-Lys]-D-Val-D-Phe-NH2 |
| 3058 | TCAM3055 | Phe-Phe-Arg-Arg-Leu-Arg-c[Asp-His-D-Nal(2')-Arg-Trp-Lys]-D-Phe-D-Val-NH2 |
| 3059 | TCAM3056 | Phe-Phe-Arg-Arg-Leu-Arg-c[Asp-Pro-D-Nal(2')-Arg-Trp-Lys]-D-Val-D-Pro-NH2 |
| 3060 | TCAM3057 | Phe-Phe-Arg-Arg-Leu-Arg-c[Asp-Pro-D-Nal(2')-Arg-Trp-Lys]-D-Pro-D-Val-NH2 |
| 3061 | TCAM3058 | Phe-Phe-Arg-Arg-Leu-Arg-c[Asp-Pro-D-Nal(2')-Arg-Trp-Lys]-D-Val-D-Phe-NH2 |
| 3062 | TCAM3059 | Phe-Phe-Arg-Arg-Leu-Arg-c[Asp-Pro-D-Nal(2')-Arg-Trp-Lys]-D-Phe-D-Val-NH2 |
| 3063 | TCAM3060 | Phe-Phe-Arg-Arg-Leu-Arg-c[Asp-Arg-Arg-Nal(2')-Arg-Trp-Lys]-D-Val-D-Pro-NH2 |
| 3064 | TCAM3061 | Phe-Phe-Arg-Arg-Leu-Arg-c[Asp-Arg-Arg-Nal(2')-Arg-Trp-Lys]-D-Pro-D-Val-NH2 |
| 3065 | TCAM3062 | Phe-Phe-Arg-Arg-Leu-Arg-c[Asp-Arg-Arg-Nal(2')-Arg-Trp-Lys]-D-Val-D-Phe-NH2 |
| 3066 | TCAM3063 | Phe-Phe-Arg-Arg-Leu-Arg-c[Asp-Arg-Arg-Nal(2')-Arg-Trp-Lys]-D-Phe-D-Val-NH2 |
| 3067 | TCAM3064 | Phe-Phe-Arg-Arg-Leu-Arg-c[Asp-Arg-Arg-Pro-Nal(2')-Arg-Trp-Lys]-D-Val-D-Pro-NH2 |
| 3068 | TCAM3065 | Phe-Phe-Arg-Arg-Leu-Arg-c[Asp-Arg-Arg-Pro-D-Nal(2')-Arg-Trp-Lys]-D-Pro-D-Val-NH2 |
| 3069 | TCAM3066 | Phe-Phe-Arg-Arg-Leu-Arg-c[Asp-Arg-Arg-Pro-D-Nal(2')-Arg-Trp-Lys]-D-Val-D-Phe-NH2 |
| 3070 | TCAM3067 | Phe-Phe-Arg-Arg-Leu-Arg-c[Asp-Arg-Arg-Pro-Nal(2')-Arg-Trp-Lys]-D-Phe-D-Val-NH2 |
| 3071 | TCAM3068 | Phe-Phe-Arg-Arg-Leu-Arg-c[Asp-Arg-D-Nal(2')-Arg-Trp-Lys]-D-Val-D-Pro-NH2 |
| 3072 | TCAM3069 | Phe-Phe-Arg-Arg-Leu-Arg-c[Asp-Arg-D-Nal(2')-Arg-Trp-Lys]-D-Pro-D-Val-NH2 |
| 3073 | TCAM3070 | Phe-Phe-Arg-Arg-Leu-Arg-c[Asp-Arg-D-Nal(2')-Arg-Trp-Lys]-D-Val-D-Phe-NH2 |
| 3074 | TCAM3071 | Phe-Phe-Arg-Arg-Leu-Arg-c[Asp-Arg-D-Nal(2')-Arg-Trp-Lys]-D-Phe-D-Val-NH2 |
| 3075 | TCAM3072 | Phe-Phe-Arg-Arg-Leu-Arg-c[Asp-Arg-Pro-D-Nal(2')-Arg-Trp-Lys]-D-Val-D-Pro-NH2 |
| 3076 | TCAM3073 | Phe-Phe-Arg-Arg-Leu-Arg-c[Asp-Arg-Pro-D-Nal(2')-Arg-Trp-Lys]-D-Pro-D-Val-NH2 |
| 3077 | TCAM3074 | Phe-Phe-Arg-Arg-Leu-Arg-c[Asp-Arg-Pro-D-Nal(2')-Arg-Trp-Lys]-D-Val-D-Phe-NH2 |
| 3078 | TCAM3075 | Phe-Phe-Arg-Arg-Leu-Arg-c[Asp-Arg-Pro-D-Nal(2')-Arg-Trp-Lys]-D-Phe-D-Val-NH2 |
| 3079 | TCAM3076 | Phe-Phe-Arg-Arg-Leu-Arg-Arg-Arg-c[Asp-Pro-D-Nal(2')-Arg-Trp-Lys]-D-Val-D-Pro-NH2 |
| 3080 | TCAM3077 | Phe-Phe-Arg-Arg-Leu-Arg-Arg-Arg-c[Asp-Pro-D-Nal(2')-Arg-Trp-Lys]-D-Pro-D-Val-NH2 |
| 3081 | TCAM3078 | Phe-Phe-Arg-Arg-Leu-Arg-Arg-Arg-c[Asp-Pro-D-Nal(2')-Arg-Trp-Lys]-D-Val-D-Phe-NH2 |
| 3082 | TCAM3079 | Phe-Phe-Arg-Arg-Leu-Arg-Arg-Arg-c[Asp-Pro-D-Nal(2')-Arg-Trp-Lys]-D-Phe-D-Val-NH2 |
| 3083 | TCAM3080 | Phe-Phe-Arg-Arg-Leu-Arg-Arg-Arg-c[Asp-His-D-Nal(2')-Arg-Trp-Lys]-D-Val-D-Pro-NH2 |
| 3084 | TCAM3081 | Phe-Phe-Arg-Arg-Leu-Arg-Arg-Arg-c[Asp-His-D-Nal(2')-Arg-Trp-Lys]-D-Pro-D-Val-NH2 |

TABLE 5-continued

Exemplary Anti-microbial peptides

| SEQ NO: | Peptide | Peptide Sequence |
|---|---|---|
| 3085 | TCAM3082 | Phe-Phe-Arg-Arg-Leu-Arg-Arg-Arg-c[Asp-His-D-Nal(2')-Arg-Trp-Lys]-D-Val-D-Phe-NH2 |
| 3086 | TCAM3083 | Phe-Phe-Arg-Arg-Leu-Arg-Arg-Arg-c[Asp-His-D-Nal(2')-Arg-Trp-Lys]-D-Phe-D-Val-NH2 |
| 3087 | TCAM3084 | Phe-Phe-Arg-Arg-Leu-Arg-c[Asp-Arg-Pro-D-Nal(2')-Arg-Trp-Arg-Lys]-D-Val-D-Pro-NH2 |
| 3088 | TCAM3085 | Phe-Phe-Arg-Arg-Leu-Arg-c[Asp-Arg-Pro-D-Nal(2')-Arg-Trp-Arg-Lys]-D-Pro-D-Val-NH2 |
| 3089 | TCAM3086 | Phe-Phe-Arg-Arg-Leu-Arg-c[Asp-Arg-Pro-D-Nal(2')-Arg-Trp-Arg-Lys]-D-Val-D-Phe-NH2 |
| 3090 | TCAM3087 | Phe-Phe-Arg-Arg-Leu-Arg-c[Asp-Arg-Pro-D-Nal(2')-Arg-Trp-Arg-Lys]-D-Phe-D-Val-NH2 |
| 3091 | TCAM3088 | Phe-Phe-Arg-Arg-Leu-Arg-c[Asp-Arg-His-D-Nal(2')-Arg-Trp-Arg-Lys]-D-Val-D-Pro-NH2 |
| 3092 | TCAM3089 | Phe-Phe-Arg-Arg-Leu-Arg-c[Asp-Arg-His-D-Nal(2')-Arg-Trp-Arg-Lys]-D-Pro-D-Val-NH2 |
| 3093 | TCAM3090 | Phe-Phe-Arg-Arg-Leu-Arg-c[Asp-Arg-His-D-Nal(2')-Arg-Trp-Arg-Lys]-D-Val-D-Phe-NH2 |
| 3094 | TCAM3091 | Phe-Phe-Arg-Arg-Leu-Arg-c[Asp-Arg-His-D-Nal(2')-Arg-Trp-Arg-Lys]-D-Phe-D-Val-NH2 |
| 3095 | TCAM3092 | Phe-Phe-Arg-Arg-Leu-Arg-c[Asp-His-D-Nal(2')-Arg-D-Nal(2')-Lys]-D-Val-D-Phe-NH2 |
| 3096 | TCAM3093 | Phe-Phe-Arg-Arg-Leu-Arg-c[Asp-His-D-Nal(2')-Arg-D-Nal(2')-Lys]-D-Phe-D-Val-NH2 |
| 3097 | TCAM3094 | Phe-Phe-Arg-Arg-Leu-Arg-c[Asp-Pro-D-Nal(2')-Arg-D-Nal(2')-Lys]-D-Val-D-Pro-NH2 |
| 3098 | TCAM3095 | Phe-Phe-Arg-Arg-Leu-Arg-c[Asp-Pro-D-Nal(2')-Arg-D-Nal(2')-Lys]-D-Pro-D-Val-NH2 |
| 3099 | TCAM3096 | Phe-Phe-Arg-Arg-Leu-Arg-c[Asp-Pro-D-Nal(2')-Arg-D-Nal(2')-Lys]-D-Val-D-Phe-NH2 |
| 3100 | TCAM3097 | Phe-Phe-Arg-Arg-Leu-Arg-c[Asp-Pro-D-Nal(2')-Arg-D-Nal(2')-Lys]-D-Phe-D-Val-NH2 |
| 3101 | TCAM3098 | Phe-Phe-Arg-Arg-Leu-Arg-c[Asp-Arg-Arg-D-Nal(2')-Arg-D-Nal(2')-Lys]-D-Val-D-Pro-NH2 |
| 3102 | TCAM3099 | Phe-Phe-Arg-Arg-Leu-Arg-c[Asp-Arg-Arg-D-Nal(2')-Arg-D-Nal(2')-Lys]-D-Pro-D-Val-NH2 |
| 3103 | TCAM3100 | Phe-Phe-Arg-Arg-Leu-Arg-c[Asp-Arg-Arg-D-Nal(2')-Arg-D-Nal(2')-Lys]-D-Val-D-Phe-NH2 |
| 3104 | TCAM3101 | Phe-Phe-Arg-Arg-Leu-Arg-c[Asp-Arg-Arg-D-Nal(2')-Arg-D-Nal(2')-Lys]-D-Phe-D-Val-NH2 |
| 3105 | TCAM3102 | Phe-Phe-Arg-Arg-Leu-Arg-c[Asp-Arg-Arg-Pro-D-Nal(2')-Arg-D-Nal(2')-Lys]-D-Val-D-Pro-NH2 |
| 3106 | TCAM3103 | Phe-Phe-Arg-Arg-Leu-Arg-c[Asp-Arg-Arg-Pro-D-Nal(2')-Arg-D-Nal(2')-Lys]-D-Pro-D-Val-NH2 |
| 3107 | TCAM3104 | Phe-Phe-Arg-Arg-Leu-Arg-c[Asp-Arg-Arg-Pro-D-Nal(2')-Arg-D-Nal(2')-Lys]-D-Val-D-Phe-NH2 |
| 3108 | TCAM3105 | Phe-Phe-Arg-Arg-Leu-Arg-c[Asp-Arg-Arg-Pro-D-Nal(2')-Arg-D-Nal(2')-Lys]-D-Phe-D-Val-NH2 |
| 3109 | TCAM3106 | Phe-Phe-Arg-Arg-Leu-Arg-c[Asp-Arg-D-Nal(2')-Arg-D-Nal(2')-Lys]-D-Val-D-Pro-NH2 |
| 3110 | TCAM3107 | Phe-Phe-Arg-Arg-Leu-Arg-c[Asp-Arg-D-Nal(2')-Arg-D-Nal(2')-Lys]-D-Pro-D-Val-NH2 |
| 3111 | TCAM3108 | Phe-Phe-Arg-Arg-Leu-Arg-c[Asp-Arg-Nal(2')-Arg-D-Nal(2')-Lys]-D-Val-D-Phe-NH2 |
| 3112 | TCAM3109 | Phe-Phe-Arg-Arg-Leu-Arg-c[Asp-Arg-D-Nal(2')-Arg-D-Nal(2')-Lys]-D-Phe-D-Val-NH2 |

TABLE 5-continued

Exemplary Anti-microbial peptides

| SEQ NO: | Peptide | Peptide Sequence |
|---|---|---|
| 3113 | TCAM3110 | Phe-Phe-Arg-Arg-Leu-Arg-c[Asp-Arg-Pro-D-Nal(2')-Arg-D-Nal(2')-Lys]-D-Val-D-Pro-NH2 |
| 3114 | TCAM3111 | Phe-Phe-Arg-Arg-Leu-Arg-c[Asp-Arg-Pro-D-Nal(2')-Arg-D-Nal(2')-Lys]-D-Pro-D-Val-NH2 |
| 3115 | TCAM3112 | Phe-Phe-Arg-Arg-Leu-Arg-c[Asp-Arg-Pro-D-Nal(2')-Arg-D-Nal(2')-Lys]-D-Val-D-Phe-NH2 |
| 3116 | TCAM3113 | Phe-Phe-Arg-Arg-Leu-Arg-c[Asp-Arg-Pro-D-Nal(2')-Arg-D-Nal(2')-Lys]-D-Phe-D-Val-NH2 |
| 3117 | TCAM3114 | Phe-Phe-Arg-Arg-Leu-Arg-c[Asp-Arg-His-D-Nal(2')-Arg-D-Nal(2')-Lys]-D-Val-D-Pro-NH2 |
| 3118 | TCAM3115 | Phe-Phe-Arg-Arg-Leu-Arg-c[Asp-Arg-His-D-Nal(2')-Arg-D-Nal(2')-Lys]-D-Pro-D-Val-NH2 |
| 3119 | TCAM3116 | Phe-Phe-Arg-Arg-Leu-Arg-c[Asp-Arg-His-Nal(2')-Arg-D-Nal(2')-Lys]-D-Val-D-Phe-NH2 |
| 3120 | TCAM3117 | Phe-Phe-Arg-Arg-Leu-Arg-c[Asp-Arg-His-Nal(2')-Arg-D-Nal(2')-Lys]-D-Phe-D-Val-NH2 |
| 3121 | TCAM3118 | Phe-Phe-Arg-Arg-Leu-Arg-c[Asp-Arg-D-D-Nal(2')-Arg-D-Nal(2')-Arg-Lys]-D-Val-D-Pro-NH2 |
| 3122 | TCAM3119 | Phe-Phe-Arg-Arg-Leu-Arg-c[Asp-Arg-D-Nal(2')-Arg-D-Nal(2')-Arg-Lys]-D-Pro-D-Val-NH2 |
| 3123 | TCAM3120 | Phe-Phe-Arg-Arg-Leu-Arg-c[Asp-Arg-D-Nal(2')-Arg-D-Nal(2')-Arg-Lys]-D-Val-D-Phe-NH2 |
| 3124 | TCAM3121 | Phe-Phe-Arg-Arg-Leu-Arg-c[Asp-Arg-D-Nal(2')-Arg-D-Nal(2')-Arg-Lys]-D-Phe-D-Val-NH2 |
| 3125 | TCAM3122 | Phe-Phe-Arg-Arg-Leu-Arg-c[Asp-Arg-Pro-D-Nal(2')-Arg-D-Nal(2')-Arg-Lys]-D-Val-D-Pro-NH2 |
| 3126 | TCAM3123 | Phe-Phe-Arg-Arg-Leu-Arg-c[Asp-Arg-Pro-D-Nal(2')-Arg-D-Nal(2')-Arg-Lys]-D-Pro-D-Val-NH2 |
| 3127 | TCAM3124 | Phe-Phe-Arg-Arg-Leu-Arg-c[Asp-Arg-Pro-D-Nal(2')-Arg-D-Nal(2')-Arg-Lys]-D-Val-D-Phe-NH2 |
| 3128 | TCAM3125 | Phe-Phe-Arg-Arg-Leu-Arg-c[Asp-Arg-Pro-D-Nal(2')-Arg-D-Nal(2')-Arg-Lys]-D-Phe-D-Val-NH2 |
| 3129 | TCAM3126 | Phe-Phe-Arg-Arg-Leu-Arg-c[Asp-Arg-His-D-Nal(2')-Arg-D-Nal(2')-Arg-Lys]-D-Val-D-Pro-NH2 |
| 3130 | TCAM3127 | Phe-Phe-Arg-Arg-Leu-Arg-c[Asp-Arg-His-D-Nal(2')-Arg-D-Nal(2')-Arg-Lys]-D-Pro-D-Val-NH2 |
| 3131 | TCAM3128 | Phe-Phe-Arg-Arg-Leu-Arg-c[Asp-Arg-His-D-Nal(2')-Arg-D-Nal(2')-Arg-Lys]-D-Val-D-Phe-NH2 |
| 3132 | TCAM3129 | Phe-Phe-Arg-Arg-Leu-Arg-c[Asp-Arg-His-D-Nal(2')-Arg-D-Nal(2')-Arg-Lys]-D-Phe-D-Val-NH2 |
| 3133 | TCAM3130 | Phe-Phe-Arg-Arg-Leu-Arg-Arg-Arg-c[Asp-Pro-D-Nal(2')-Arg-D-Nal(2')-Lys]-D-Val-D-Pro-NH2 |
| 3134 | TCAM3131 | Phe-Phe-Arg-Arg-Leu-Arg-Arg-Arg-c[Asp-Pro-D-Nal(2')-Arg-D-Nal(2')-Lys]-D-Pro-D-Val-NH2 |
| 3135 | TCAM3132 | Phe-Phe-Arg-Arg-Leu-Arg-Arg-Arg-c[Asp-Pro-D-Nal(2')-Arg-D-Nal(2')-Lys]-D-Val-D-Phe-NH2 |
| 3136 | TCAM3133 | Phe-Phe-Arg-Arg-Leu-Arg-Arg-Arg-c[Asp-Pro-D-Nal(2')-Arg-D-Nal(2')-Lys]-D-Phe-D-Val-NH2 |
| 3137 | TCAM3134 | Phe-Phe-Arg-Arg-Leu-Arg-Arg-Arg-c[Asp-His-D-Nal(2')-Arg-D-Nal(2')-Lys]-D-Val-D-Pro-NH2 |
| 3138 | TCAM3135 | Phe-Phe-Arg-Arg-Leu-Arg-Arg-Arg-c[Asp-His-D-Nal(2')-Arg-D-Nal(2')-Lys]-D-Pro-D-Val-NH2 |

TABLE 5-continued

Exemplary Anti-microbial peptides

| SEQ NO: | Peptide | Peptide Sequence |
|---|---|---|
| 3139 | TCAM3136 | Phe-Phe-Arg-Arg-Leu-Arg-Arg-Arg-c[Asp-His-D-Nal(2')-Arg-D-Nal(2')-Lys]-D-Val-D-Phe-NH2 |
| 3140 | TCAM3137 | Phe-Phe-Arg-Arg-Leu-Arg-Arg-Arg-c[Asp-His-D-Nal(2')-Arg-D-Nal(2')-Lys]-D-Phe-D-Val-NH2 |
| 3141 | TCAM3138 | Phe-Phe-Arg-Arg-Leu-Arg-c[Asp-Arg-Pro-D-Nal(2')-Arg-D-Nal(2')-Arg-Lys]-D-Val-D-Pro-NH2 |
| 3142 | TCAM3139 | Phe-Phe-Arg-Arg-Leu-Arg-c[Asp-Arg-Pro-D-Nal(2')-Arg-D-Nal(2')-Arg-Lys]-D-Pro-D-Val-NH2 |
| 3143 | TCAM3140 | Phe-Phe-Arg-Arg-Leu-Arg-c[Asp-Arg-Pro-D-Nal(2')-Arg-D-Nal(2')-Arg-Lys]-D-Val-D-Phe-NH2 |
| 3144 | TCAM3141 | Phe-Phe-Arg-Arg-Leu-Arg-c[Asp-Arg-Pro-D-Nal(2')-Arg-D-Nal(2')-Arg-Lys]-D-Phe-D-Val-NH2 |
| 3145 | TCAM3142 | Phe-Phe-Arg-Arg-Leu-Arg-c[Asp-Arg-His-D-Nal(2')-Arg-D-Nal(2')-Arg-Lys]-D-Val-D-Pro-NH2 |
| 3146 | TCAM3143 | Phe-Phe-Arg-Arg-Leu-Arg-c[Asp-Arg-His-D-Nal(2')-Arg-D-Nal(2')-Arg-Lys]-D-Pro-D-Val-NH2 |
| 3147 | TCAM3144 | Phe-Phe-Arg-Arg-Leu-Arg-c[Asp-Arg-His-D-Nal(2')-Arg-D-Nal(2')-Arg-Lys]-D-Val-D-Phe-NH2 |
| 3148 | TCAM3145 | Phe-Phe-Arg-Arg-Leu-Arg-c[Asp-Arg-His-D-Nal(2')-Arg-D-Nal(2')-Arg-Lys]-D-Phe-D-Val-NH2 |
| 3149 | TCAM3146 | Phe-Phe-Arg-Arg-Leu-Arg-c[Asp-His-D-Nal(2')-Arg-Trp-Lys]-Arg-Arg-D-Val-D-Pro-NH2 |
| 3150 | TCAM3147 | Phe-Phe-Arg-Arg-Leu-Arg-c[Asp-His-D-Nal(2')-Arg-Trp-Lys]-Arg-Arg-D-Pro-D-Val-NH2 |
| 3151 | TCAM3148 | Phe-Phe-Arg-Arg-Leu-Arg-c[Asp-His-D-Nal(2')-Arg-Trp-Lys]-Arg-Arg-D-Val-D-Phe-NH2 |
| 3152 | TCAM3149 | Phe-Phe-Arg-Arg-Leu-Arg-c[Asp-His-D-Nal(2')-Arg-Trp-Lys]-Arg-Arg-D-Phe-D-Val-NH2 |
| 3153 | TCAM3150 | Phe-Phe-Arg-Arg-Leu-Arg-c[Asp-Pro-D-Nal(2')-Arg-Trp-Lys]-Arg-Arg-D-Val-D-Pro-NH2 |
| 3154 | TCAM3151 | Phe-Phe-Arg-Arg-Leu-Arg-c[Asp-Pro-D-Nal(2')-Arg-Trp-Lys]-Arg-Arg-D-Pro-D-Val-NH2 |
| 3155 | TCAM3152 | Phe-Phe-Arg-Arg-Leu-Arg-c[Asp-Pro-D-Nal(2')-Arg-Trp-Lys]-Arg-Arg-D-Val-D-Phe-NH2 |
| 3156 | TCAM3153 | Phe-Phe-Arg-Arg-Leu-Arg-c[Asp-Pro-D-Nal(2')-Arg-Trp-Lys]-Arg-Arg-D-Phe-D-Val-NH2 |
| Anti-biofilm peptide ABF6 linked to anti-microbial peptides | | |
| 3157 | TCAM3154 | Lys-Lys-Phe-Lys-Lys-Phe-Phe-Lys-Lys-c[Asp-Pro-Arg-Arg-Trp-Trp-Arg-Phe-Lys]-D-Val-D-Pro-NH2 |
| 3158 | TCAM3155 | Lys-Lys-Phe-Lys-Lys-Phe-Phe-Lys-Lys-c[Asp-Pro-Arg-Arg-Trp-Trp-Arg-Phe-Lys]-D-Val-D-Phe-NH2 |
| 3159 | TCAM3156 | Lys-Lys-Phe-Lys-Lys-Phe-Phe-Lys-Lys-c[Asp-Pro-Arg-Arg-Trp-Trp-Arg-Phe-Lys]-D-Pro-D-Val-NH2 |
| 3160 | TCAM3157 | Lys-Lys-Phe-Lys-Lys-Phe-Phe-Lys-Lys-c[Asp-Pro-Arg-Arg-Trp-Trp-Arg-Phe-Lys]-D-Phe-D-Val-NH2 |
| 3161 | TCAM3158 | Lys-Lys-Phe-Lys-Lys-Phe-Phe-Lys-Lys-c[Asp-Pro-Arg-Arg-Trp-Trp-Tyr-Phe-Lys]-D-Val-D-Pro-NH2 |
| 3162 | TCAM3159 | Lys-Lys-Phe-Lys-Lys-Phe-Phe-Lys-Lys-c[Asp-Pro-Arg-Arg-Trp-Trp-Tyr-Phe-Lys]-D-Val-D-Phe-NH2 |

TABLE 5-continued

Exemplary Anti-microbial peptides

| SEQ NO: | Peptide | Peptide Sequence |
|---|---|---|
| 3163 | TCAM3160 | Lys-Lys-Phe-Lys-Lys-Phe-Phe-Lys-Lys-c[Asp-Pro-Arg-Arg-Trp-Trp-Tyr-Phe-Lys]-D-Pro-D-Val-NH2 |
| 3164 | TCAM3161 | Lys-Lys-Phe-Lys-Lys-Phe-Phe-Lys-Lys-c[Asp-Pro-Arg-Arg-Trp-Trp-Tyr-Phe-Lys]-D-Phe-D-Val-NH2 |
| 3165 | TCAM3162 | Lys-Lys-Phe-Lys-Lys-Phe-Phe-Lys-Lys-c[Asp-Pro-Arg-Arg-Tyr-Tyr-Arg-Phe-Lys]-D-Val-D-Pro-NH2 |
| 3166 | TCAM3163 | Lys-Lys-Phe-Lys-Lys-Phe-Phe-Lys-Lys-c[Asp-Pro-Arg-Arg-Tyr-Tyr-Arg-Phe-Lys]-D-Val-D-Phe-NH2 |
| 3167 | TCAM3164 | Lys-Lys-Phe-Lys-Lys-Phe-Phe-Lys-Lys-c[Asp-Pro-Arg-Arg-Tyr-Tyr-Arg-Phe-Lys]-D-Pro-D-Val-NH2 |
| 3168 | TCAM3165 | Lys-Lys-Phe-Lys-Lys-Phe-Phe-Lys-Lys-c[Asp-Pro-Arg-Arg-Tyr-Tyr-Arg-Phe-Lys]-D-Phe-D-Val-NH2 |
| 3169 | TCAM3166 | Lys-Lys-Phe-Lys-Lys-Phe-Phe-Lys-Lys-c[Asp-Pro-Arg-Arg-Nal-Nal-Arg-Phe-Lys]-D-Val-D-Pro-NH2 |
| 3170 | TCAM3167 | Lys-Lys-Phe-Lys-Lys-Phe-Phe-Lys-Lys-c[Asp-Pro-Arg-Arg-Nal-Nal-Arg-Phe-Lys]-D-Val-D-Phe-NH2 |
| 3171 | TCAM3168 | Lys-Lys-Phe-Lys-Lys-Phe-Phe-Lys-Lys-c[Asp-Pro-Arg-Arg-Nal-Nal-Arg-Phe-Lys]-D-Pro-D-Val-NH2 |
| 3172 | TCAM3169 | Lys-Lys-Phe-Lys-Lys-Phe-Phe-Lys-Lys-c[Asp-Pro-Arg-Arg-Nal-Nal-Arg-Phe-Lys]-D-Phe-D-Val-NH2 |
| 3173 | TCAM3170 | Lys-Lys-Phe-Lys-Lys-Phe-Phe-Lys-Lys-c[Asp-Pro-Arg-Arg-Leu-Trp-Leu-Trp-Lys]-D-Val-D-Pro-NH2 |
| 3174 | TCAM3171 | Lys-Lys-Phe-Lys-Lys-Phe-Phe-Lys-Lys-c[Asp-Pro-Arg-Arg-Leu-Trp-Leu-Trp-Lys]-D-Val-D-Phe-NH2 |
| 3175 | TCAM3172 | Lys-Lys-Phe-Lys-Lys-Phe-Phe-Lys-Lys-c[Asp-Pro-Arg-Arg-Leu-Trp-Leu-Trp-Lys]-D-Pro-D-Val-NH2 |
| 3176 | TCAM3173 | Lys-Lys-Phe-Lys-Lys-Phe-Phe-Lys-Lys-c[Asp-Pro-Arg-Arg-Leu-Trp-Leu-Trp-Lys]-D-Phe-D-Val-NH2 |
| 3177 | TCAM3174 | Lys-Lys-Phe-Lys-Lys-Phe-Phe-Lys-Lys-c[Asp-Pro-Arg-Arg-Leu-Trp-Leu-Trp-Lys]-D-Val-D-Pro-NH2 |
| 3178 | TCAM3175 | Lys-Lys-Phe-Lys-Lys-Phe-Phe-Lys-Lys-c[Asp-Pro-Arg-Arg-Leu-Trp-Leu-Trp-Lys]-D-Val-D-Phe-NH2 |
| 3179 | TCAM3176 | Lys-Lys-Phe-Lys-Lys-Phe-Phe-Lys-Lys-c[Asp-Pro-Arg-Arg-Leu-Trp-Leu-Trp-Lys]-D-Pro-D-Val-NH2 |
| 3180 | TCAM3177 | Lys-Lys-Phe-Lys-Lys-Phe-Phe-Lys-Lys-c[Asp-Pro-Arg-Arg-Leu-Trp-Leu-Trp-Lys]-D-Phe-D-Val-NH2 |
| 3181 | TCAM3178 | Lys-Lys-Phe-Lys-Lys-Phe-Phe-Lys-Lys-c[Asp-Arg-Arg-Arg-Trp-Leu-Trp-Leu-Trp-Lys]-D-Val-D-Pro-NH2 |
| 3182 | TCAM3179 | Lys-Lys-Phe-Lys-Lys-Phe-Phe-Lys-Lys-c[Asp-Pro-Arg-Arg-Arg-Trp-Leu-Trp-Leu-Trp-Lys]-D-Val-D-Phe-NH2 |
| 3183 | TCAM3180 | Lys-Lys-Phe-Lys-Lys-Phe-Phe-Lys-Lys-c[Asp-Pro-Arg-Arg-Arg-Trp-Leu-Trp-Leu-Trp-Lys]-D-Pro-D-Val-NH2 |
| 3184 | TCAM3181 | Lys-Lys-Phe-Lys-Lys-Phe-Phe-Lys-Lys-c[Asp-Pro-Arg-Arg-Arg-Trp-Leu-Trp-Leu-Trp-Lys]-D-Phe-D-Val-NH2 |
| 3185 | TCAM3182 | Lys-Lys-Phe-Lys-Lys-Phe-Phe-Lys-Lys-c[Asp-Pro-Arg-Gln-Arg-Arg-Trp-Leu-Trp-Leu-Trp-Lys]-D-Val-D-Pro-NH2 |
| 3186 | TCAM3183 | Lys-Lys-Phe-Lys-Lys-Phe-Phe-Lys-Lys-c[Asp-Pro-Arg-Gln-Arg-Arg-Trp-Leu-Trp-Leu-Trp-Lys]-D-Val-D-Phe-NH2 |
| 3187 | TCAM3184 | Lys-Lys-Phe-Lys-Lys-Phe-Phe-Lys-Lys-c[Asp-Pro-Arg-Gln-Arg-Arg-Trp-Leu-Trp-Leu-Trp-Lys]-D-Pro-D-Val-NH2 |

TABLE 5-continued

Exemplary Anti-microbial peptides

| SEQ NO: | Peptide | Peptide Sequence |
|---|---|---|
| 3188 | TCAM3185 | Lys-Lys-Phe-Lys-Lys-Phe-Phe-Lys-Lys-c[Asp-Pro-Arg-Gln-Arg-Arg-Trp-Leu-Trp-Leu-Trp-Lys]-D-Phe-D-Val-NH2 |
| 3189 | TCAM3186 | Lys-Lys-Phe-Lys-Lys-Phe-Phe-Lys-Lys-c[Asp-Pro-Trp-Arg-Trp-Trp-Arg-Arg-Lys]-D-Val-D-Phe-NH2 |
| 3190 | TCAM3187 | Lys-Lys-Phe-Lys-Lys-Phe-Phe-Lys-Lys-c[Asp-Pro-Trp-Arg-Trp-Trp-Arg-Arg-Lys]-D-Pro-D-Val-NH2 |
| 3191 | TCAM3188 | Lys-Lys-Phe-Lys-Lys-Phe-Phe-Lys-Lys-c[Asp-Pro-Trp-Arg-Trp-Trp-Arg-Arg-Lys]-D-Phe-D-Val-NH2 |
| 3192 | TCAM3189 | Lys-Lys-Phe-Lys-Lys-Phe-Phe-Lys-Lys-c[Asp-Pro-Trp-Trp-Arg-Arg-Trp-Trp-Arg-Arg-Lys]-D-Val-D-Pro-NH2 |
| 3193 | TCAM3190 | Lys-Lys-Phe-Lys-Lys-Phe-Phe-Lys-Lys-c[Asp-Pro-Trp-Trp-Arg-Arg-Trp-Trp-Arg-Arg-Lys]-D-Val-D-Phe-NH2 |
| 3194 | TCAM3191 | Lys-Lys-Phe-Lys-Lys-Phe-Phe-Lys-Lys-c[Asp-Pro-Trp-Trp-Arg-Arg-Trp-Trp-Arg-Arg-Lys]-D-Pro-D-Val-NH2 |
| 3195 | TCAM3192 | Lys-Lys-Phe-Lys-Lys-Phe-Phe-Lys-Lys-c[Asp-Pro-Trp-Trp-Arg-Arg-Trp-Trp-Arg-Arg-Lys]-D-Phe-D-Val-NH2 |
| 3196 | TCAM3193 | Lys-Lys-Phe-Lys-Lys-Phe-Phe-Lys-Lys-c[Asp-Pro-Trp-Arg-Trp-Arg-Trp-Arg-Lys]-D-Val-D-Pro-NH2 |
| 3197 | TCAM3194 | Lys-Lys-Phe-Lys-Lys-Phe-Phe-Lys-Lys-c[Asp-Pro-Trp-Arg-Trp-Arg-Trp-Arg-Lys]-D-Val-D-Phe-NH2 |
| 3198 | TCAM3195 | Lys-Lys-Phe-Lys-Lys-Phe-Phe-Lys-Lys-c[Asp-Pro-Trp-Arg-Trp-Arg-Trp-Arg-Lys]-D-Pro-D-Val-NH2 |
| 3199 | TCAM3196 | Lys-Lys-Phe-Lys-Lys-Phe-Phe-Lys-Lys-c[Asp-Pro-Trp-Arg-Trp-Arg-Trp-Arg-Lys]-D-Phe-D-Val-NH2 |
| 3200 | TCAM3197 | Lys-Lys-Phe-Lys-Lys-Phe-Phe-Lys-Lys-c[Asp-Pro-Arg-Trp-Arg-Trp-Arg-Trp-Lys]-D-Val-D-Pro-NH2 |
| 3201 | TCAM3198 | Lys-Lys-Phe-Lys-Lys-Phe-Phe-Lys-Lys-c[Asp-Pro-Arg-Trp-Arg-Trp-Arg-Trp-Lys]-D-Val-D-Phe-NH2 |
| 3202 | TCAM3199 | Lys-Lys-Phe-Lys-Lys-Phe-Phe-Lys-Lys-c[Asp-Pro-Arg-Trp-Arg-Trp-Arg-Trp-Lys]-D-Pro-D-Val-NH2 |
| 3203 | TCAM3200 | Lys-Lys-Phe-Lys-Lys-Phe-Phe-Lys-Lys-c[Asp-Pro-Arg-Trp-Arg-Trp-Arg-Trp-Lys]-D-Phe-D-Val-NH2 |
| 3204 | TCAM3201 | Lys-Lys-Phe-Lys-Lys-Phe-Phe-Lys-Lys-c[Asp-Pro-Arg-Trp-Trp-Arg-Arg-Lys]-D-Val-D-Pro-NH2 |
| 3205 | TCAM3202 | Lys-Lys-Phe-Lys-Lys-Phe-Phe-Lys-Lys-c[Asp-Pro-Arg-Trp-Trp-Arg-Arg-Lys]-D-Val-D-Phe-NH2 |
| 3206 | TCAM3203 | Lys-Lys-Phe-Lys-Lys-Phe-Phe-Lys-Lys-c[Asp-Pro-Arg-Trp-Trp-Arg-Arg-Lys]-D-Pro-D-Val-NH2 |
| 3207 | TCAM3204 | Lys-Lys-Phe-Lys-Lys-Phe-Phe-Lys-Lys-c[Asp-Pro-Arg-Trp-Trp-Arg-Arg-Lys]-D-Phe-D-Val-NH2 |
| 3208 | TCAM3205 | Lys-Lys-Phe-Lys-Lys-Phe-Phe-Lys-Lys-c[Asp-Pro-Trp-Trp-Arg-Arg-Trp-Lys]-D-Val-D-Pro-NH2 |
| 3209 | TCAM3206 | Lys-Lys-Phe-Lys-Lys-Phe-Phe-Lys-Lys-c[Asp-Pro-Trp-Trp-Arg-Arg-Trp-Lys]-D-Val-D-Phe-NH2 |
| 3210 | TCAM3207 | Lys-Lys-Phe-Lys-Lys-Phe-Phe-Lys-Lys-c[Asp-Pro-Trp-Trp-Arg-Arg-Trp-Lys]-D-Pro-D-Val-NH2 |
| 3211 | TCAM3208 | Lys-Lys-Phe-Lys-Lys-Phe-Phe-Lys-Lys-c[Asp-Pro-Trp-Trp-Arg-Arg-Trp-Lys]-D-Phe-D-Val-NH2 |
| 3212 | TCAM3209 | Lys-Lys-Phe-Lys-Lys-Phe-Phe-Lys-Lys-c[Asp-Pro-Trp-Arg-Trp-Arg-Trp-Lys]-D-Val-D-Pro-NH2 |

TABLE 5-continued

Exemplary Anti-microbial peptides

| SEQ NO: | Peptide | Peptide Sequence |
|---|---|---|
| 3213 | TCAM3210 | Lys-Lys-Phe-Lys-Lys-Phe-Phe-Lys-Lys-c[Asp-Pro-Trp-Arg-Trp-Arg-Trp-Lys]-D-Val-D-Phe-NH2 |
| 3214 | TCAM3211 | Lys-Lys-Phe-Lys-Lys-Phe-Phe-Lys-Lys-c[Asp-Pro-Trp-Arg-Trp-Arg-Trp-Lys]-D-Pro-D-Val-NH2 |
| 3215 | TCAM3212 | Lys-Lys-Phe-Lys-Lys-Phe-Phe-Lys-Lys-c[Asp-Pro-Trp-Arg-Trp-Arg-Trp-Lys]-D-Phe-D-Val-NH2 |
| 3216 | TCAM3213 | Lys-Lys-Phe-Lys-Lys-Phe-Phe-Lys-Lys-c[Asp-Pro-Arg-Trp-Arg-Trp-Arg-Lys]-D-Val-D-Pro-NH2 |
| 3217 | TCAM3214 | Lys-Lys-Phe-Lys-Lys-Phe-Phe-Lys-Lys-c[Asp-Pro-Arg-Trp-Arg-Trp-Arg-Lys]-D-Val-D-Phe-NH2 |
| 3218 | TCAM3215 | Lys-Lys-Phe-Lys-Lys-Phe-Phe-Lys-Lys-c[Asp-Pro-Arg-Trp-Arg-Trp-Arg-Lys]-D-Pro-D-Val-NH2 |
| 3219 | TCAM3216 | Lys-Lys-Phe-Lys-Lys-Phe-Phe-Lys-Lys-c[Asp-Pro-Arg-Trp-Arg-Trp-Arg-Lys]-D-Phe-D-Val-NH2 |
| 3220 | TCAM3217 | Lys-Lys-Phe-Lys-Lys-Phe-Phe-Lys-Lys-c[Asp-Pro-Trp-Arg-Tyr-Arg-Trp-Lys]-D-Val-D-Pro-NH2 |
| 3221 | TCAM3218 | Lys-Lys-Phe-Lys-Lys-Phe-Phe-Lys-Lys-c[Asp-Pro-Trp-Arg-Tyr-Arg-Trp-Lys]-D-Val-D-Phe-NH2 |
| 3222 | TCAM3219 | Lys-Lys-Phe-Lys-Lys-Phe-Phe-Lys-Lys-c[Asp-Pro-Trp-Arg-Tyr-Arg-Trp-Lys]-D-Pro-D-Val-NH2 |
| 3223 | TCAM3220 | Lys-Lys-Phe-Lys-Lys-Phe-Phe-Lys-Lys-c[Asp-Pro-Trp-Arg-Tyr-Arg-Trp-Lys]-D-Phe-D-Val-NH2 |
| 3224 | TCAM3221 | Lys-Lys-Phe-Lys-Lys-Phe-Phe-Lys-Lys-c[Asp-Pro-Trp-Arg-Trp-Arg-Tyr-Lys]-D-Val-D-Pro-NH2 |
| 3225 | TCAM3222 | Lys-Lys-Phe-Lys-Lys-Phe-Phe-Lys-Lys-c[Asp-Pro-Trp-Arg-Trp-Arg-Tyr-Lys]-D-Val-D-Phe-NH2 |
| 3226 | TCAM3223 | Lys-Lys-Phe-Lys-Lys-Phe-Phe-Lys-Lys-c[Asp-Pro-Trp-Arg-Trp-Arg-Tyr-Lys]-D-Pro-D-Val-NH2 |
| 3227 | TCAM3224 | Lys-Lys-Phe-Lys-Lys-Phe-Phe-Lys-Lys-c[Asp-Pro-Trp-Arg-Trp-Arg-Tyr-Lys]-D-Phe-D-Val-NH2 |
| 3228 | TCAM3225 | Lys-Lys-Phe-Lys-Lys-Phe-Phe-Lys-Lys-c[Asp-Pro-Trp-Arg-Trp-Arg-Lys]-D-Val-D-Pro-NH2 |
| 3229 | TCAM3226 | Lys-Lys-Phe-Lys-Lys-Phe-Phe-Lys-Lys-c[Asp-Pro-Trp-Arg-Trp-Arg-Lys]-D-Val-D-Phe-NH2 |
| 3230 | TCAM3227 | Lys-Lys-Phe-Lys-Lys-Phe-Phe-Lys-Lys-c[Asp-Pro-Trp-Arg-Trp-Arg-Lys]-D-Pro-D-Val-NH2 |
| 3231 | TCAM3228 | Lys-Lys-Phe-Lys-Lys-Phe-Phe-Lys-Lys-c[Asp-Pro-Trp-Arg-Trp-Arg-Lys]-D-Phe-D-Val-NH2 |
| 3232 | TCAM3229 | Lys-Lys-Phe-Lys-Lys-Phe-Phe-Lys-Lys-c[Asp-Pro-Trp-Arg-Arg-Trp-Lys]-D-Val-D-Pro-NH2 |
| 3233 | TCAM3230 | Lys-Lys-Phe-Lys-Lys-Phe-Phe-Lys-Lys-c[Asp-Pro-Trp-Arg-Arg-Trp-Lys]-D-Val-D-Phe-NH2 |
| 3234 | TCAM3231 | Lys-Lys-Phe-Lys-Lys-Phe-Phe-Lys-Lys-c[Asp-Pro-Trp-Arg-Arg-Trp-Lys]-D-Pro-D-Val-NH2 |
| 3235 | TCAM3232 | Lys-Lys-Phe-Lys-Lys-Phe-Phe-Lys-Lys-c[Asp-Pro-Trp-Arg-Arg-Trp-Lys]-D-Phe-D-Val-NH2 |
| 3236 | TCAM3233 | Lys-Lys-Phe-Lys-Lys-Phe-Phe-Lys-Lys-c[Asp-Pro-Arg-Trp-Trp-Arg-Lys]-D-Val-D-Pro-NH2 |
| 3237 | TCAM3234 | Lys-Lys-Phe-Lys-Lys-Phe-Phe-Lys-Lys-c[Asp-Pro-Arg-Trp-Trp-Arg-Lys]-D-Val-D-Phe-NH2 |

TABLE 5-continued

Exemplary Anti-microbial peptides

| SEQ NO: | Peptide | Peptide Sequence |
|---|---|---|
| 3238 | TCAM3235 | Lys-Lys-Phe-Lys-Lys-Phe-Phe-Lys-Lys-c[Asp-Pro-Arg-Trp-Trp-Arg-Lys]-D-Pro-D-Val-NH2 |
| 3239 | TCAM3236 | Lys-Lys-Phe-Lys-Lys-Phe-Phe-Lys-Lys-c[Asp-Pro-Arg-Trp-Trp-Arg-Lys]-D-Phe-D-Val-NH2 |
| 3240 | TCAM3237 | Lys-Lys-Phe-Lys-Lys-Phe-Phe-Lys-Lys-c[Asp-Pro-Trp-Arg-Trp-Lys]-D-Val-D-Pro-NH2 |
| 3241 | TCAM3238 | Lys-Lys-Phe-Lys-Lys-Phe-Phe-Lys-Lys-c[Asp-Pro-Trp-Arg-Trp-Lys]-D-Val-D-Phe-NH2 |
| 3242 | TCAM3239 | Lys-Lys-Phe-Lys-Lys-Phe-Phe-Lys-Lys-c[Asp-Pro-Trp-Arg-Trp-Lys]-D-Pro-D-Val-NH2 |
| 3243 | TCAM3240 | Lys-Lys-Phe-Lys-Lys-Phe-Phe-Lys-Lys-c[Asp-Pro-Trp-Arg-Trp-Lys]-D-Phe-D-Val-NH2 |
| 3244 | TCAM3241 | Lys-Lys-Phe-Lys-Lys-Phe-Phe-Lys-Lys-c[Asp-Pro-Arg-Trp-Arg-Lys]-D-Val-D-Pro-NH2 |
| 3245 | TCAM3242 | Lys-Lys-Phe-Lys-Lys-Phe-Phe-Lys-Lys-c[Asp-Pro-Arg-Trp-Arg-Lys]-D-Val-D-Phe-NH2 |
| 3246 | TCAM3243 | Lys-Lys-Phe-Lys-Lys-Phe-Phe-Lys-Lys-c[Asp-Pro-Arg-Trp-Arg-Lys]-D-Pro-D-Val-NH2 |
| 3247 | TCAM3244 | Lys-Lys-Phe-Lys-Lys-Phe-Phe-Lys-Lys-c[Asp-Pro-Arg-Trp-Arg-Lys]-D-Phe-D-Val-NH2 |
| 3248 | TCAM3245 | Lys-Lys-Phe-Lys-Lys-Phe-Phe-Lys-Lys-c[Asp-Arg-Arg-Trp-Trp-Arg-Phe-Lys]-D-Val-D-Pro-NH2 |
| 3249 | TCAM3246 | Lys-Lys-Phe-Lys-Lys-Phe-Phe-Lys-Lys-c[Asp-Arg-Arg-Trp-Trp-Arg-Phe-Lys]-D-Val-D-Phe-NH2 |
| 3250 | TCAM3247 | Lys-Lys-Phe-Lys-Lys-Phe-Phe-Lys-Lys-c[Asp-Arg-Arg-Trp-Trp-Arg-Phe-Lys]-D-Pro-D-Val-NH2 |
| 3251 | TCAM3248 | Lys-Lys-Phe-Lys-Lys-Phe-Phe-Lys-Lys-c[Asp-Arg-Arg-Trp-Trp-Arg-Phe-Lys]-D-Phe-D-Val-NH2 |
| 3252 | TCAM3249 | Lys-Lys-Phe-Lys-Lys-Phe-Phe-Lys-Lys-c[Asp-Arg-Arg-Trp-Trp-Arg-Phe-Lys]-D-Val-D-Pro-NH2 |
| 3253 | TCAM3250 | Lys-Lys-Phe-Lys-Lys-Phe-Phe-Lys-Lys-c[Asp-Arg-Arg-Trp-Trp-Arg-Phe-Lys]-D-Val-D-Phe-NH2 |
| 3254 | TCAM3251 | Lys-Lys-Phe-Lys-Lys-Phe-Phe-Lys-Lys-c[Asp-Arg-Arg-Trp-Trp-Arg-Phe-Lys]-D-Pro-D-Val-NH2 |
| 3255 | TCAM3252 | Lys-Lys-Phe-Lys-Lys-Phe-Phe-Lys-Lys-c[Asp-Arg-Arg-Trp-Trp-Arg-Phe-Lys]-D-Phe-D-Val-NH2 |
| 3256 | TCAM3253 | Lys-Lys-Phe-Lys-Lys-Phe-Phe-Lys-Lys-c[Asp-Arg-Arg-Tyr-Tyr-Arg-Phe-Lys]-D-Val-D-Pro-NH2 |
| 3257 | TCAM3254 | Lys-Lys-Phe-Lys-Lys-Phe-Phe-Lys-Lys-c[Asp-Arg-Arg-Tyr-Tyr-Arg-Phe-Lys]-D-Val-D-Phe-NH2 |
| 3258 | TCAM3255 | Lys-Lys-Phe-Lys-Lys-Phe-Phe-Lys-Lys-c[Asp-Arg-Arg-Tyr-Tyr-Arg-Phe-Lys]-D-Pro-D-Val-NH2 |
| 3259 | TCAM3256 | Lys-Lys-Phe-Lys-Lys-Phe-Phe-Lys-Lys-c[Asp-Arg-Arg-Tyr-Tyr-Arg-Phe-Lys]-D-Phe-D-Val-NH2 |
| 3260 | TCAM3257 | Lys-Lys-Phe-Lys-Lys-Phe-Phe-Lys-Lys-c[Asp-Arg-Arg-Nal-Nal-Arg-Phe-Lys]-D-Val-D-Pro-NH2 |
| 3261 | TCAM3258 | Lys-Lys-Phe-Lys-Lys-Phe-Phe-Lys-Lys-c[Asp-Arg-Arg-Nal-Nal-Arg-Phe-Lys]-D-Val-D-Phe-NH2 |
| 3262 | TCAM3259 | Lys-Lys-Phe-Lys-Lys-Phe-Phe-Lys-Lys-c[Asp-Arg-Arg-Nal-Nal-Arg-Phe-Lys]-D-Pro-D-Val-NH2 |
| 3263 | TCAM3260 | Lys-Lys-Phe-Lys-Lys-Phe-Phe-Lys-Lys-c[Asp-Arg-Arg-Nal-Nal-Arg-Phe-Lys]-D-Phe-D-Val-NH2 |
| 3264 | TCAM3261 | Lys-Lys-Phe-Lys-Lys-Phe-Phe-Lys-Lys-c[Asp-Arg-Arg-Leu-Trp-Leu-Trp-Lys]-D-Val-D-Pro-NH2 |
| 3265 | TCAM3262 | Lys-Lys-Phe-Lys-Lys-Phe-Phe-Lys-Lys-c[Asp-Arg-Arg-Leu-Trp-Leu-Trp-Lys]-D-Val-D-Phe-NH2 |

TABLE 5-continued

Exemplary Anti-microbial peptides

| SEQ NO: | Peptide | Peptide Sequence |
|---|---|---|
| 3266 | TCAM3263 | Lys-Lys-Phe-Lys-Lys-Phe-Phe-Lys-Lys-c[Asp-Arg-Arg-Leu-Trp-Leu-Trp-Lys]-D-Pro-D-Val-NH2 |
| 3267 | TCAM3264 | Lys-Lys-Phe-Lys-Lys-Phe-Phe-Lys-Lys-c[Asp-Arg-Arg-Leu-Trp-Leu-Trp-Lys]-D-Phe-D-Val-NH2 |
| 3268 | TCAM3265 | Lys-Lys-Phe-Lys-Lys-Phe-Phe-Lys-Lys-c[Asp-Arg-Arg-Leu-Trp-Leu-Trp-Lys]-D-Val-D-Pro-NH2 |
| 3269 | TCAM3266 | Lys-Lys-Phe-Lys-Lys-Phe-Phe-Lys-Lys-c[Asp-Arg-Arg-Leu-Trp-Leu-Trp-Lys]-D-Val-D-Phe-NH2 |
| 3270 | TCAM3267 | Lys-Lys-Phe-Lys-Lys-Phe-Phe-Lys-Lys-c[Asp-Arg-Arg-Leu-Trp-Leu-Trp-Lys]-D-Pro-D-Val-NH2 |
| 3271 | TCAM3268 | Lys-Lys-Phe-Lys-Lys-Phe-Phe-Lys-Lys-c[Asp-Arg-Arg-Leu-Trp-Leu-Trp-Lys]-D-Phe-D-Val-NH2 |
| 3272 | TCAM3269 | Lys-Lys-Phe-Lys-Lys-Phe-Phe-Lys-Lys-c[Asp-Arg-Arg-Arg-Trp-Leu-Trp-Leu-Trp-Lys]-D-Val-D-Pro-NH2 |
| 3273 | TCAM3270 | Lys-Lys-Phe-Lys-Lys-Phe-Phe-Lys-Lys-c[Asp-Arg-Arg-Arg-Trp-Leu-Trp-Leu-Trp-Lys]-D-Val-D-Phe-NH2 |
| 3274 | TCAM3271 | Lys-Lys-Phe-Lys-Lys-Phe-Phe-Lys-Lys-c[Asp-Arg-Arg-Arg-Trp-Leu-Trp-Leu-Trp-Lys]-D-Pro-D-Val-NH2 |
| 3275 | TCAM3272 | Lys-Lys-Phe-Lys-Lys-Phe-Phe-Lys-Lys-c[Asp-Arg-Arg-Arg-Trp-Leu-Trp-Leu-Trp-Lys]-D-Phe-D-Val-NH2 |
| 3276 | TCAM3273 | Lys-Lys-Phe-Lys-Lys-Phe-Phe-Lys-Lys-c[Asp-Arg-Gln-Arg-Arg-Trp-Leu-Trp-Leu-Trp-Lys]-D-Val-D-Pro-NH2 |
| 3277 | TCAM3274 | Lys-Lys-Phe-Lys-Lys-Phe-Phe-Lys-Lys-c[Asp-Arg-Gln-Arg-Arg-Trp-Leu-Trp-Leu-Trp-Lys]-D-Val-D-Phe-NH2 |
| 3278 | TCAM3275 | Lys-Lys-Phe-Lys-Lys-Phe-Phe-Lys-Lys-c[Asp-Arg-Gln-Arg-Arg-Trp-Leu-Trp-Leu-Trp-Lys]-D-Pro-D-Val-NH2 |
| 3279 | TCAM3276 | Lys-Lys-Phe-Lys-Lys-Phe-Phe-Lys-Lys-c[Asp-Arg-Gln-Arg-Arg-Trp-Leu-Trp-Leu-Trp-Lys]-D-Phe-D-Val-NH2 |
| 3280 | TCAM3277 | Lys-Lys-Phe-Lys-Lys-Phe-Phe-Lys-Lys-c[Asp-Trp-Arg-Trp-Trp-Arg-Arg-Lys]-D-Val-D-Pro-NH2 |
| 3281 | TCAM3278 | Lys-Lys-Phe-Lys-Lys-Phe-Phe-Lys-Lys-c[Asp-Trp-Arg-Trp-Trp-Arg-Arg-Lys]-D-Val-D-Phe-NH2 |
| 3282 | TCAM3279 | Lys-Lys-Phe-Lys-Lys-Phe-Phe-Lys-Lys-c[Asp-Trp-Arg-Trp-Trp-Arg-Arg-Lys]-D-Pro-D-Val-NH2 |
| 3283 | TCAM3280 | Lys-Lys-Phe-Lys-Lys-Phe-Phe-Lys-Lys-c[Asp-Trp-Arg-Trp-Trp-Arg-Arg-Lys]-D-Phe-D-Val-NH2 |
| 3284 | TCAM3281 | Lys-Lys-Phe-Lys-Lys-Phe-Phe-Lys-Lys-c[Asp-Trp-Trp-Arg-Arg-Trp-Trp-Arg-Arg-Lys]-D-Val-D-Pro-NH2 |
| 3285 | TCAM3282 | Lys-Lys-Phe-Lys-Lys-Phe-Phe-Lys-Lys-c[Asp-Trp-Trp-Arg-Arg-Trp-Trp-Arg-Arg-Lys]-D-Val-D-Phe-NH2 |
| 3286 | TCAM3283 | Lys-Lys-Phe-Lys-Lys-Phe-Phe-Lys-Lys-c[Asp-Trp-Trp-Arg-Arg-Trp-Trp-Arg-Arg-Lys]-D-Pro-D-Val-NH2 |
| 3287 | TCAM3284 | Lys-Lys-Phe-Lys-Lys-Phe-Phe-Lys-Lys-c[Asp-Trp-Trp-Arg-Arg-Trp-Trp-Arg-Arg-Lys]-D-Phe-D-Val-NH2 |
| 3288 | TCAM3285 | Lys-Lys-Phe-Lys-Lys-Phe-Phe-Lys-Lys-c[Asp-Trp-Arg-Trp-Arg-Trp-Arg-Lys]-D-Val-D-Pro-NH2 |
| 3289 | TCAM3286 | Lys-Lys-Phe-Lys-Lys-Phe-Phe-Lys-Lys-c[Asp-Trp-Arg-Trp-Arg-Trp-Arg-Lys]-D-Val-D-Phe-NH2 |
| 3290 | TCAM3287 | Lys-Lys-Phe-Lys-Lys-Phe-Phe-Lys-Lys-c[Asp-Trp-Arg-Trp-Arg-Trp-Arg-Lys]-D-Pro-D-Val-NH2 |

TABLE 5-continued

Exemplary Anti-microbial peptides

| SEQ NO: | Peptide | Peptide Sequence |
|---|---|---|
| 3291 | TCAM3288 | Lys-Lys-Phe-Lys-Lys-Phe-Phe-Lys-Lys-c[Asp-Trp-Arg-Trp-Arg-Trp-Arg-Lys]-D-Phe-D-Val-NH2 |
| 3292 | TCAM3289 | Lys-Lys-Phe-Lys-Lys-Phe-Phe-Lys-Lys-c[Asp-Arg-Trp-Arg-Trp-Arg-Trp-Lys]-D-Val-D-Pro-NH2 |
| 3293 | TCAM3290 | Lys-Lys-Phe-Lys-Lys-Phe-Phe-Lys-Lys-c[Asp-Arg-Trp-Arg-Trp-Arg-Trp-Lys]-D-Val-D-Phe-NH2 |
| 3294 | TCAM3291 | Lys-Lys-Phe-Lys-Lys-Phe-Phe-Lys-Lys-c[Asp-Arg-Trp-Arg-Trp-Arg-Trp-Lys]-D-Pro-D-Val-NH2 |
| 3295 | TCAM3292 | Lys-Lys-Phe-Lys-Lys-Phe-Phe-Lys-Lys-c[Asp-Arg-Trp-Arg-Trp-Arg-Trp-Lys]-D-Phe-D-Val-NH2 |
| 3296 | TCAM3293 | Lys-Lys-Phe-Lys-Lys-Phe-Phe-Lys-Lys-c[Asp-Arg-Trp-Trp-Arg-Arg-Lys]-D-Val-D-Pro-NH2 |
| 3297 | TCAM3294 | Lys-Lys-Phe-Lys-Lys-Phe-Phe-Lys-Lys-c[Asp-Arg-Trp-Trp-Arg-Arg-Lys]-D-Val-D-Phe-NH2 |
| 3298 | TCAM3295 | Lys-Lys-Phe-Lys-Lys-Phe-Phe-Lys-Lys-c[Asp-Arg-Trp-Trp-Arg-Arg-Lys]-D-Pro-D-Val-NH2 |
| 3299 | TCAM3296 | Lys-Lys-Phe-Lys-Lys-Phe-Phe-Lys-Lys-c[Asp-Arg-Trp-Trp-Arg-Arg-Lys]-D-Phe-D-Val-NH2 |
| 3300 | TCAM3297 | Lys-Lys-Phe-Lys-Lys-Phe-Phe-Lys-Lys-c[Asp-Arg-Trp-Arg-Trp-Arg-Lys]-D-Val-D-Pro-NH2 |
| 3301 | TCAM3298 | Lys-Lys-Phe-Lys-Lys-Phe-Phe-Lys-Lys-c[Asp-Arg-Trp-Arg-Trp-Arg-Lys]-D-Val-D-Phe-NH2 |
| 3302 | TCAM3299 | Lys-Lys-Phe-Lys-Lys-Phe-Phe-Lys-Lys-c[Asp-Arg-Trp-Arg-Trp-Arg-Lys]-D-Pro-D-Val-NH2 |
| 3303 | TCAM3300 | Lys-Lys-Phe-Lys-Lys-Phe-Phe-Lys-Lys-c[Asp-Arg-Trp-Arg-Trp-Arg-Lys]-D-Phe-D-Val-NH2 |
| 3304 | TCAM3301 | Lys-Lys-Phe-Lys-Lys-Phe-Phe-Lys-Lys-c[Asp-Trp-Trp-Arg-Trp-Lys]-D-Val-D-Pro-NH2 |
| 3305 | TCAM3302 | Lys-Lys-Phe-Lys-Lys-Phe-Phe-Lys-Lys-c[Asp-Trp-Trp-Arg-Trp-Lys]-D-Val-D-Phe-NH2 |
| 3306 | TCAM3303 | Lys-Lys-Phe-Lys-Lys-Phe-Phe-Lys-Lys-c[Asp-Trp-Trp-Arg-Trp-Lys]-D-Pro-D-Val-NH2 |
| 3307 | TCAM3304 | Lys-Lys-Phe-Lys-Lys-Phe-Phe-Lys-Lys-c[Asp-Trp-Trp-Arg-Trp-Lys]-D-Phe-D-Val-NH2 |
| 3308 | TCAM3305 | Lys-Lys-Phe-Lys-Lys-Phe-Phe-Lys-Lys-c[Asp-Trp-Arg-Trp-Arg-Trp-Lys]-D-Val-D-Pro-NH2 |
| 3309 | TCAM3306 | Lys-Lys-Phe-Lys-Lys-Phe-Phe-Lys-Lys-c[Asp-Trp-Arg-Trp-Arg-Trp-Lys]-D-Val-D-Phe-NH2 |
| 3310 | TCAM3307 | Lys-Lys-Phe-Lys-Lys-Phe-Phe-Lys-Lys-c[Asp-Trp-Arg-Trp-Arg-Trp-Lys]-D-Pro-D-Val-NH2 |
| 3311 | TCAM3308 | Lys-Lys-Phe-Lys-Lys-Phe-Phe-Lys-Lys-c[Asp-Trp-Arg-Trp-Arg-Trp-Lys]-D-Phe-D-Val-NH2 |
| 3312 | TCAM3309 | Lys-Lys-Phe-Lys-Lys-Phe-Phe-Lys-Lys-c[Asp-Trp-Arg-Tyr-Arg-Trp-Lys]-D-Val-D-Pro-NH2 |
| 3313 | TCAM3310 | Lys-Lys-Phe-Lys-Lys-Phe-Phe-Lys-Lys-c[Asp-Trp-Arg-Tyr-Arg-Trp-Lys]-D-Val-D-Phe-NH2 |
| 3314 | TCAM3311 | Lys-Lys-Phe-Lys-Lys-Phe-Phe-Lys-Lys-c[Asp-Trp-Arg-Tyr-Arg-Trp-Lys]-D-Pro-D-Val-NH2 |
| 3315 | TCAM3312 | Lys-Lys-Phe-Lys-Lys-Phe-Phe-Lys-Lys-c[Asp-Trp-Arg-Tyr-Arg-Trp-Lys]-D-Phe-D-Val-NH2 |

TABLE 5-continued

Exemplary Anti-microbial peptides

| SEQ NO: | Peptide | Peptide Sequence |
|---|---|---|
| 3316 | TCAM3313 | Lys-Lys-Phe-Lys-Lys-Phe-Phe-Lys-Lys-c[Asp-Trp-Arg-Trp-Arg-Tyr-Lys]-D-Val-D-Pro-NH2 |
| 3317 | TCAM3314 | Lys-Lys-Phe-Lys-Lys-Phe-Phe-Lys-Lys-c[Asp-Trp-Arg-Trp-Arg-Tyr-Lys]-D-Val-D-Phe-NH2 |
| 3318 | TCAM3315 | Lys-Lys-Phe-Lys-Lys-Phe-Phe-Lys-Lys-c[Asp-Trp-Arg-Trp-Arg-Tyr-Lys]-D-Pro-D-Val-NH2 |
| 3319 | TCAM3316 | Lys-Lys-Phe-Lys-Lys-Phe-Phe-Lys-Lys-c[Asp-Trp-Arg-Trp-Arg-Tyr-Lys]-D-Phe-D-Val-NH2 |
| 3320 | TCAM3317 | Lys-Lys-Phe-Lys-Lys-Phe-Phe-Lys-Lys-c[Asp-Trp-Arg-Trp-Arg-Lys]-D-Val-D-Pro-NH2 |
| 3321 | TCAM3318 | Lys-Lys-Phe-Lys-Lys-Phe-Phe-Lys-Lys-c[Asp-Trp-Arg-Trp-Arg-Lys]-D-Val-D-Phe-NH2 |
| 3322 | TCAM3319 | Lys-Lys-Phe-Lys-Lys-Phe-Phe-Lys-Lys-c[Asp-Trp-Arg-Trp-Arg-Lys]-D-Pro-D-Val-NH2 |
| 3323 | TCAM3320 | Lys-Lys-Phe-Lys-Lys-Phe-Phe-Lys-Lys-c[Asp-Trp-Arg-Trp-Arg-Lys]-D-Phe-D-Val-NH2 |
| 3324 | TCAM3321 | Lys-Lys-Phe-Lys-Lys-Phe-Phe-Lys-Lys-c[Asp-Trp-Arg-Arg-Trp-Lys]-D-Val-D-Pro-NH2 |
| 3325 | TCAM3322 | Lys-Lys-Phe-Lys-Lys-Phe-Phe-Lys-Lys-c[Asp-Trp-Arg-Arg-Trp-Lys]-D-Val-D-Phe-NH2 |
| 3326 | TCAM3323 | Lys-Lys-Phe-Lys-Lys-Phe-Phe-Lys-Lys-c[Asp-Trp-Arg-Arg-Trp-Lys]-D-Pro-D-Val-NH2 |
| 3327 | TCAM3324 | Lys-Lys-Phe-Lys-Lys-Phe-Phe-Lys-Lys-c[Asp-Trp-Arg-Arg-Trp-Lys]-D-Phe-D-Val-NH2 |
| 3328 | TCAM3325 | Lys-Lys-Phe-Lys-Lys-Phe-Phe-Lys-Lys-c[Asp-Arg-Trp-Trp-Arg-Lys]-D-Val-D-Pro-NH2 |
| 3329 | TCAM3326 | Lys-Lys-Phe-Lys-Lys-Phe-Phe-Lys-Lys-c[Asp-Arg-Trp-Trp-Arg-Lys]-D-Val-D-Phe-NH2 |
| 3330 | TCAM3327 | Lys-Lys-Phe-Lys-Lys-Phe-Phe-Lys-Lys-c[Asp-Arg-Trp-Trp-Arg-Lys]-D-Pro-D-Val-NH2 |
| 3331 | TCAM3328 | Lys-Lys-Phe-Lys-Lys-Phe-Phe-Lys-Lys-c[Asp-Arg-Trp-Trp-Arg-Lys]-D-Phe-D-Val-NH2 |
| 3332 | TCAM3329 | Lys-Lys-Phe-Lys-Lys-Phe-Phe-Lys-Lys-c[Asp-Trp-Arg-Trp-Lys]-D-Val-D-Pro-NH2 |
| 3333 | TCAM3330 | Lys-Lys-Phe-Lys-Lys-Phe-Phe-Lys-Lys-c[Asp-Trp-Arg-Trp-Lys]-D-Val-D-Phe-NH2 |
| 3334 | TCAM3331 | Lys-Lys-Phe-Lys-Lys-Phe-Phe-Lys-Lys-c[Asp-Trp-Arg-Trp-Lys]-D-Pro-D-Val-NH2 |
| 3335 | TCAM3332 | Lys-Lys-Phe-Lys-Lys-Phe-Phe-Lys-Lys-c[Asp-Trp-Arg-Trp-Lys]-D-Phe-D-Val-NH2 |
| 3336 | TCAM3333 | Lys-Lys-Phe-Lys-Lys-Phe-Phe-Lys-Lys-c[Asp-Arg-Trp-Arg-Lys]-D-Val-D-Pro-NH2 |
| 3337 | TCAM3334 | Lys-Lys-Phe-Lys-Lys-Phe-Phe-Lys-Lys-c[Asp-Arg-Trp-Arg-Lys]-D-Val-D-Phe-NH2 |
| 3338 | TCAM3335 | Lys-Lys-Phe-Lys-Lys-Phe-Phe-Lys-Lys-c[Asp-Arg-Trp-Arg-Lys]-D-Pro-D-Val-NH2 |
| 3339 | TCAM3336 | Lys-Lys-Phe-Lys-Lys-Phe-Phe-Lys-Lys-c[Asp-Arg-Trp-Arg-Lys]-D-Phe-D-Val-NH2 |
| 3340 | TCAM3337 | Lys-Lys-Phe-Lys-Lys-Phe-Phe-Lys-Lys-c[Asp-His-D-Nal(2')-Arg-Trp-Lys]-D-Val-D-Pro-NH2 |
| 3341 | TCAM3338 | Lys-Lys-Phe-Lys-Lys-Phe-Phe-Lys-Lys-c[Asp-His-D-Nal(2')-Arg-Trp-Lys]-D-Pro-D-Val-NH2 |
| 3342 | TCAM3339 | Lys-Lys-Phe-Lys-Lys-Phe-Phe-Lys-Lys-c[Asp-His-D-Nal(2')-Arg-Trp-Lys]-D-Val-D-Phe-NH2 |
| 3343 | TCAM3340 | Lys-Lys-Phe-Lys-Lys-Phe-Phe-Lys-Lys-c[Asp-His-D-Nal(2')-Arg-Trp-Lys]-D-Phe-D-Val-NH2 |
| 3344 | TCAM3341 | Lys-Lys-Phe-Lys-Lys-Phe-Phe-Lys-Lys-c[Asp-Pro-D-Nal(2')-Arg-Trp-Lys]-D-Val-D-Pro-NH2 |
| 3345 | TCAM3342 | Lys-Lys-Phe-Lys-Lys-Phe-Phe-Lys-Lys-c[Asp-Pro-D-Nal(2')-Arg-Trp-Lys]-D-Pro-D-Val-NH2 |
| 3346 | TCAM3343 | Lys-Lys-Phe-Lys-Lys-Phe-Phe-Lys-Lys-c[Asp-Pro-D-Nal(2')-Arg-Trp-Lys]-D-Val-D-Phe-NH2 |

TABLE 5-continued

Exemplary Anti-microbial peptides

| SEQ NO: | Peptide | Peptide Sequence |
|---|---|---|
| 3347 | TCAM3344 | Lys-Lys-Phe-Lys-Lys-Phe-Phe-Lys-Lys-c[Asp-Pro-D-Nal(2')-Arg-Trp-Lys]-D-Phe-D-Val-NH2 |
| 3348 | TCAM3345 | Lys-Lys-Phe-Lys-Lys-Phe-Phe-Lys-Lys-c[Asp-Arg-Arg-Nal(2')-Arg-Trp-Lys]-D-Val-D-Pro-NH2 |
| 3349 | TCAM3346 | Lys-Lys-Phe-Lys-Lys-Phe-Phe-Lys-Lys-c[Asp-Arg-Arg-Nal(2')-Arg-Trp-Lys]-D-Pro-D-Val-NH2 |
| 3350 | TCAM3347 | Lys-Lys-Phe-Lys-Lys-Phe-Phe-Lys-Lys-c[Asp-Arg-Arg-Nal(2')-Arg-Trp-Lys]-D-Val-D-Phe-NH2 |
| 3351 | TCAM3348 | Lys-Lys-Phe-Lys-Lys-Phe-Phe-Lys-Lys-c[Asp-Arg-Arg-Nal(2')-Arg-Trp-Lys]-D-Phe-D-Val-NH2 |
| 3352 | TCAM3349 | Lys-Lys-Phe-Lys-Lys-Phe-Phe-Lys-Lys-c[Asp-Arg-Arg-Pro-Nal(2')-Arg-Trp-Lys]-D-Val-D-Pro-NH2 |
| 3353 | TCAM3350 | Lys-Lys-Phe-Lys-Lys-Phe-Phe-Lys-Lys-c[Asp-Arg-Arg-Pro-D-Nal(2')-Arg-Trp-Lys]-D-Pro-D-Val-NH2 |
| 3354 | TCAM3351 | Lys-Lys-Phe-Lys-Lys-Phe-Phe-Lys-Lys-c[Asp-Arg-Arg-Pro-D-Nal(2')-Arg-Trp-Lys]-D-Val-D-Phe-NH2 |
| 3355 | TCAM3352 | Lys-Lys-Phe-Lys-Lys-Phe-Phe-Lys-Lys-c[Asp-Arg-Arg-Pro-Nal(2')-Arg-Trp-Lys]-D-Phe-D-Val-NH2 |
| 3356 | TCAM3353 | Lys-Lys-Phe-Lys-Lys-Phe-Phe-Lys-Lys-c[Asp-Arg-D-Nal(2')-Arg-Trp-Lys]-D-Val-D-Pro-NH2 |
| 3357 | TCAM3354 | Lys-Lys-Phe-Lys-Lys-Phe-Phe-Lys-Lys-c[Asp-Arg-D-Nal(2')-Arg-Trp-Lys]-D-Pro-D-Val-NH2 |
| 3358 | TCAM3355 | Lys-Lys-Phe-Lys-Lys-Phe-Phe-Lys-Lys-c[Asp-Arg-D-Nal(2')-Arg-Trp-Lys]-D-Val-D-Phe-NH2 |
| 3359 | TCAM3356 | Lys-Lys-Phe-Lys-Lys-Phe-Phe-Lys-Lys-c[Asp-Arg-D-Nal(2')-Arg-Trp-Lys]-D-Phe-D-Val-NH2 |
| 3360 | TCAM3357 | Lys-Lys-Phe-Lys-Lys-Phe-Phe-Lys-Lys-c[Asp-Arg-Pro-D-Nal(2')-Arg-Trp-Lys]-D-Val-D-Pro-NH2 |
| 3361 | TCAM3358 | Lys-Lys-Phe-Lys-Lys-Phe-Phe-Lys-Lys-c[Asp-Arg-Pro-D-Nal(2')-Arg-Trp-Lys]-D-Pro-D-Val-NH2 |
| 3362 | TCAM3359 | Lys-Lys-Phe-Lys-Lys-Phe-Phe-Lys-Lys-c[Asp-Arg-Pro-D-Nal(2')-Arg-Trp-Lys]-D-Val-D-Phe-NH2 |
| 3363 | TCAM3360 | Lys-Lys-Phe-Lys-Lys-Phe-Phe-Lys-Lys-c[Asp-Arg-Pro-D-Nal(2')-Arg-Trp-Lys]-D-Phe-D-Val-NH2 |
| 3364 | TCAM3361 | Lys-Lys-Phe-Lys-Lys-Phe-Phe-Lys-Lys-Arg-Arg-c[Asp-Pro-D-Nal(2')-Arg-Trp-Lys]-D-Val-D-Pro-NH2 |
| 3365 | TCAM3362 | Lys-Lys-Phe-Lys-Lys-Phe-Phe-Lys-Lys-Arg-Arg-c[Asp-Pro-D-Nal(2')-Arg-Trp-Lys]-D-Pro-D-Val-NH2 |
| 3366 | TCAM3363 | Lys-Lys-Phe-Lys-Lys-Phe-Phe-Lys-Lys-Arg-Arg-c[Asp-Pro-D-Nal(2')-Arg-Trp-Lys]-D-Val-D-Phe-NH2 |
| 3367 | TCAM3364 | Lys-Lys-Phe-Lys-Lys-Phe-Phe-Lys-Lys-Arg-Arg-c[Asp-Pro-D-Nal(2')-Arg-Trp-Lys]-D-Phe-D-Val-NH2 |
| 3368 | TCAM3365 | Lys-Lys-Phe-Lys-Lys-Phe-Phe-Lys-Lys-Arg-Arg-c[Asp-His-D-Nal(2')-Arg-Trp-Lys]-D-Val-D-Pro-NH2 |
| 3369 | TCAM3366 | Lys-Lys-Phe-Lys-Lys-Phe-Phe-Lys-Lys-Arg-Arg-c[Asp-His-D-Nal(2')-Arg-Trp-Lys]-D-Pro-D-Val-NH2 |
| 3370 | TCAM3367 | Lys-Lys-Phe-Lys-Lys-Phe-Phe-Lys-Lys-Arg-Arg-c[Asp-His-D-Nal(2')-Arg-Trp-Lys]-D-Val-D-Phe-NH2 |
| 3371 | TCAM3368 | Lys-Lys-Phe-Lys-Lys-Phe-Phe-Lys-Lys-Arg-Arg-c[Asp-His-D-Nal(2')-Arg-Trp-Lys]-D-Phe-D-Val-NH2 |

TABLE 5-continued

Exemplary Anti-microbial peptides

| SEQ NO: | Peptide | Peptide Sequence |
|---|---|---|
| 3372 | TCAM3369 | Lys-Lys-Phe-Lys-Lys-Phe-Phe-Lys-Lys-c[Asp-Arg-Pro-D-Nal(2')-Arg-Trp-Arg-Lys]-D-Val-D-Pro-NH2 |
| 3373 | TCAM3370 | Lys-Lys-Phe-Lys-Lys-Phe-Phe-Lys-Lys-c[Asp-Arg-Pro-D-Nal(2')-Arg-Trp-Arg-Lys]-D-Pro-D-Val-NH2 |
| 3374 | TCAM3371 | Lys-Lys-Phe-Lys-Lys-Phe-Phe-Lys-Lys-c[Asp-Arg-Pro-D-Nal(2')-Arg-Trp-Arg-Lys]-D-Val-D-Phe-NH2 |
| 3375 | TCAM3372 | Lys-Lys-Phe-Lys-Lys-Phe-Phe-Lys-Lys-c[Asp-Arg-Pro-D-Nal(2')-Arg-Trp-Arg-Lys]-D-Phe-D-Val-NH2 |
| 3376 | TCAM3373 | Lys-Lys-Phe-Lys-Lys-Phe-Phe-Lys-Lys-c[Asp-Arg-His-D-Nal(2')-Arg-Trp-Arg-Lys]-D-Val-D-Pro-NH2 |
| 3377 | TCAM3374 | Lys-Lys-Phe-Lys-Lys-Phe-Phe-Lys-Lys-c[Asp-Arg-His-D-Nal(2')-Arg-Trp-Arg-Lys]-D-Pro-D-Val-NH2 |
| 3378 | TCAM3375 | Lys-Lys-Phe-Lys-Lys-Phe-Phe-Lys-Lys-c[Asp-Arg-His-D-Nal(2')-Arg-Trp-Arg-Lys]-D-Val-D-Phe-NH2 |
| 3379 | TCAM3376 | Lys-Lys-Phe-Lys-Lys-Phe-Phe-Lys-Lys-c[Asp-Arg-His-D-Nal(2')-Arg-Trp-Arg-Lys]-D-Phe-D-Val-NH2 |
| 3380 | TCAM3377 | Lys-Lys-Phe-Lys-Lys-Phe-Phe-Lys-Lys-c[Asp-His-D-Nal(2')-Arg-D-Nal(2')-Lys]-D-Val-D-Phe-NH2 |
| 3381 | TCAM3378 | Lys-Lys-Phe-Lys-Lys-Phe-Phe-Lys-Lys-c[Asp-His-D-Nal(2')-Arg-D-Nal(2')-Lys]-D-Phe-D-Val-NH2 |
| 3382 | TCAM3379 | Lys-Lys-Phe-Lys-Lys-Phe-Phe-Lys-Lys-c[Asp-Pro-D-Nal(2')-Arg-D-Nal(2')-Lys]-D-Val-D-Pro-NH2 |
| 3383 | TCAM3380 | Lys-Lys-Phe-Lys-Lys-Phe-Phe-Lys-Lys-c[Asp-Pro-D-Nal(2')-Arg-D-Nal(2')-Lys]-D-Pro-D-Val-NH2 |
| 3384 | TCAM3381 | Lys-Lys-Phe-Lys-Lys-Phe-Phe-Lys-Lys-c[Asp-Pro-D-Nal(2')-Arg-D-Nal(2')-Lys]-D-Val-D-Phe-NH2 |
| 3385 | TCAM3382 | Lys-Lys-Phe-Lys-Lys-Phe-Phe-Lys-Lys-c[Asp-Pro-D-Nal(2')-Arg-D-Nal(2')-Lys]-D-Phe-D-Val-NH2 |
| 3386 | TCAM3383 | Lys-Lys-Phe-Lys-Lys-Phe-Phe-Lys-Lys-c[Asp-Arg-Arg-D-Nal(2')-Arg-D-Nal(2')-Lys]-D-Val-D-Pro-NH2 |
| 3387 | TCAM3384 | Lys-Lys-Phe-Lys-Lys-Phe-Phe-Lys-Lys-c[Asp-Arg-Arg-D-Nal(2')-Arg-D-Nal(2')-Lys]-D-Pro-D-Val-NH2 |
| 3388 | TCAM3385 | Lys-Lys-Phe-Lys-Lys-Phe-Phe-Lys-Lys-c[Asp-Arg-Arg-D-Nal(2')-Arg-D-Nal(2')-Lys]-D-Val-D-Phe-NH2 |
| 3389 | TCAM3386 | Lys-Lys-Phe-Lys-Lys-Phe-Phe-Lys-Lys-c[Asp-Arg-Arg-D-Nal(2')-Arg-D-Nal(2')-Lys]-D-Phe-D-Val-NH2 |
| 3390 | TCAM3387 | Lys-Lys-Phe-Lys-Lys-Phe-Phe-Lys-Lys-c[Asp-Arg-Arg-Pro-D-Nal(2')-Arg-D-Nal(2')-Lys]-D-Val-D-Pro-NH2 |
| 3391 | TCAM3388 | Lys-Lys-Phe-Lys-Lys-Phe-Phe-Lys-Lys-c[Asp-Arg-Arg-Pro-D-Nal(2')-Arg-D-Nal(2')-Lys]-D-Pro-D-Val-NH2 |
| 3392 | TCAM3389 | Lys-Lys-Phe-Lys-Lys-Phe-Phe-Lys-Lys-c[Asp-Arg-Arg-Pro-D-Nal(2')-Arg-D-Nal(2')-Lys]-D-Val-D-Phe-NH2 |
| 3393 | TCAM3390 | Lys-Lys-Phe-Lys-Lys-Phe-Phe-Lys-Lys-c[Asp-Arg-Arg-Pro-D-Nal(2')-Arg-D-Nal(2')-Lys]-D-Phe-D-Val-NH2 |
| 3394 | TCAM3391 | Lys-Lys-Phe-Lys-Lys-Phe-Phe-Lys-Lys-c[Asp-Arg-D-Nal(2')-Arg-D-Nal(2')-Lys]-D-Val-D-Pro-NH2 |
| 3395 | TCAM3392 | Lys-Lys-Phe-Lys-Lys-Phe-Phe-Lys-Lys-c[Asp-Arg-D-Nal(2')-Arg-D-Nal(2')-Lys]-D-Pro-D-Val-NH2 |
| 3396 | TCAM3393 | Lys-Lys-Phe-Lys-Lys-Phe-Phe-Lys-Lys-c[Asp-Arg-Nal(2')-Arg-D-Nal(2')-Lys]-D-Val-D-Phe-NH2 |

TABLE 5-continued

Exemplary Anti-microbial peptides

| SEQ NO: | Peptide | Peptide Sequence |
|---|---|---|
| 3397 | TCAM3394 | Lys-Lys-Phe-Lys-Lys-Phe-Phe-Lys-Lys-c[Asp-Arg-D-Nal(2')-Arg-D-Nal(2')-Lys]-D-Phe-D-Val-NH2 |
| 3398 | TCAM3395 | Lys-Lys-Phe-Lys-Lys-Phe-Phe-Lys-Lys-c[Asp-Arg-Pro-D-Nal(2')-Arg-D-Nal(2')-Lys]-D-Val-D-Pro-NH2 |
| 3399 | TCAM3396 | Lys-Lys-Phe-Lys-Lys-Phe-Phe-Lys-Lys-c[Asp-Arg-Pro-D-Nal(2')-Arg-D-Nal(2')-Lys]-D-Pro-D-Val-NH2 |
| 3400 | TCAM3397 | Lys-Lys-Phe-Lys-Lys-Phe-Phe-Lys-Lys-c[Asp-Arg-Pro-D-Nal(2')-Arg-D-Nal(2')-Lys]-D-Val-D-Phe-NH2 |
| 3401 | TCAM3398 | Lys-Lys-Phe-Lys-Lys-Phe-Phe-Lys-Lys-c[Asp-Arg-Pro-D-Nal(2')-Arg-D-Nal(2')-Lys]-D-Phe-D-Val-NH2 |
| 3402 | TCAM3399 | Lys-Lys-Phe-Lys-Lys-Phe-Phe-Lys-Lys-c[Asp-Arg-His-D-Nal(2')-Arg-D-Nal(2')-Lys]-D-Val-D-Pro-NH2 |
| 3403 | TCAM3400 | Lys-Lys-Phe-Lys-Lys-Phe-Phe-Lys-Lys-c[Asp-Arg-His-D-Nal(2')-Arg-D-Nal(2')-Lys]-D-Pro-D-Val-NH2 |
| 3404 | TCAM3401 | Lys-Lys-Phe-Lys-Lys-Phe-Phe-Lys-Lys-c[Asp-Arg-His-Nal(2')-Arg-D-Nal(2')-Lys]-D-Val-D-Phe-NH2 |
| 3405 | TCAM3402 | Lys-Lys-Phe-Lys-Lys-Phe-Phe-Lys-Lys-c[Asp-Arg-His-Nal(2')-Arg-D-Nal(2')-Lys]-D-Phe-D-Val-NH2 |
| 3406 | TCAM3403 | Lys-Lys-Phe-Lys-Lys-Phe-Phe-Lys-Lys-c[Asp-Arg-D-D-Nal(2')-Arg-D-Nal(2')-Arg-Lys]-D-Val-D-Pro-NH2 |
| 3407 | TCAM3404 | Lys-Lys-Phe-Lys-Lys-Phe-Phe-Lys-Lys-c[Asp-Arg-D-Nal(2')-Arg-D-Nal(2')-Arg-Lys]-D-Pro-D-Val-NH2 |
| 3408 | TCAM3405 | Lys-Lys-Phe-Lys-Lys-Phe-Phe-Lys-Lys-c[Asp-Arg-D-Nal(2')-Arg-D-Nal(2')-Arg-Lys]-D-Val-D-Phe-NH2 |
| 3409 | TCAM3406 | Lys-Lys-Phe-Lys-Lys-Phe-Phe-Lys-Lys-c[Asp-Arg-D-Nal(2')-Arg-D-Nal(2')-Arg-Lys]-D-Phe-D-Val-NH2 |
| 3410 | TCAM3407 | Lys-Lys-Phe-Lys-Lys-Phe-Phe-Lys-Lys-c[Asp-Arg-Pro-D-Nal(2')-Arg-D-Nal(2')-Arg-Lys]-D-Val-D-Pro-NH2 |
| 3411 | TCAM3408 | Lys-Lys-Phe-Lys-Lys-Phe-Phe-Lys-Lys-c[Asp-Arg-Pro-D-Nal(2')-Arg-D-Nal(2')-Arg-Lys]-D-Pro-D-Val-NH2 |
| 3412 | TCAM3409 | Lys-Lys-Phe-Lys-Lys-Phe-Phe-Lys-Lys-c[Asp-Arg-Pro-D-Nal(2')-Arg-D-Nal(2')-Arg-Lys]-D-Val-D-Phe-NH2 |
| 3413 | TCAM3410 | Lys-Lys-Phe-Lys-Lys-Phe-Phe-Lys-Lys-c[Asp-Arg-Pro-D-Nal(2')-Arg-D-Nal(2')-Arg-Lys]-D-Phe-D-Val-NH2 |
| 3414 | TCAM3411 | Lys-Lys-Phe-Lys-Lys-Phe-Phe-Lys-Lys-c[Asp-Arg-His-D-Nal(2')-Arg-D-Nal(2')-Arg-Lys]-D-Val-D-Pro-NH2 |
| 3415 | TCAM3412 | Lys-Lys-Phe-Lys-Lys-Phe-Phe-Lys-Lys-c[Asp-Arg-His-D-Nal(2')-Arg-D-Nal(2')-Arg-Lys]-D-Pro-D-Val-NH2 |
| 3416 | TCAM3413 | Lys-Lys-Phe-Lys-Lys-Phe-Phe-Lys-Lys-c[Asp-Arg-His-D-Nal(2')-Arg-D-Nal(2')-Arg-Lys]-D-Val-D-Phe-NH2 |
| 3417 | TCAM3414 | Lys-Lys-Phe-Lys-Lys-Phe-Phe-Lys-Lys-c[Asp-Arg-His-D-Nal(2')-Arg-D-Nal(2')-Arg-Lys]-D-Phe-D-Val-NH2 |
| 3418 | TCAM3415 | Lys-Lys-Phe-Lys-Lys-Phe-Phe-Lys-Lys-Arg-Arg-c[Asp-Pro-D-Nal(2')-Arg-D-Nal(2')-Lys]-D-Val-D-Pro-NH2 |
| 3419 | TCAM3416 | Lys-Lys-Phe-Lys-Lys-Phe-Phe-Lys-Lys-Arg-Arg-c[Asp-Pro-D-Nal(2')-Arg-D-Nal(2')-Lys]-D-Pro-D-Val-NH2 |
| 3420 | TCAM3417 | Lys-Lys-Phe-Lys-Lys-Phe-Phe-Lys-Lys-Arg-Arg-c[Asp-Pro-D-Nal(2')-Arg-D-Nal(2')-Lys]-D-Val-D-Phe-NH2 |
| 3421 | TCAM3418 | Lys-Lys-Phe-Lys-Lys-Phe-Phe-Lys-Lys-Arg-Arg-c[Asp-Pro-D-Nal(2')-Arg-D-Nal(2')-Lys]-D-Phe-D-Val-NH2 |

TABLE 5-continued

Exemplary Anti-microbial peptides

| SEQ NO: | Peptide | Peptide Sequence |
|---|---|---|
| 3422 | TCAM3419 | Lys-Lys-Phe-Lys-Lys-Phe-Phe-Lys-Lys-Arg-Arg-c[Asp-His-D-Nal(2')-Arg-D-Nal(2')-Lys]-D-Val-D-Pro-NH2 |
| 3423 | TCAM3420 | Lys-Lys-Phe-Lys-Lys-Phe-Phe-Lys-Lys-Arg-Arg-c[Asp-His-D-Nal(2')-Arg-D-Nal(2')-Lys]-D-Pro-D-Val-NH2 |
| 3424 | TCAM3421 | Lys-Lys-Phe-Lys-Lys-Phe-Phe-Lys-Lys-Arg-Arg-c[Asp-His-D-Nal(2')-Arg-D-Nal(2')-Lys]-D-Val-D-Phe-NH2 |
| 3425 | TCAM3422 | Lys-Lys-Phe-Lys-Lys-Phe-Phe-Lys-Lys-Arg-Arg-c[Asp-His-D-Nal(2')-Arg-D-Nal(2')-Lys]-D-Phe-D-Val-NH2 |
| 3426 | TCAM3423 | Lys-Lys-Phe-Lys-Lys-Phe-Phe-Lys-Lys-c[Asp-Arg-Pro-D-Nal(2')-Arg-D-Nal(2')-Arg-Lys]-D-Val-D-Pro-NH2 |
| 3427 | TCAM3424 | Lys-Lys-Phe-Lys-Lys-Phe-Phe-Lys-Lys-c[Asp-Arg-Pro-D-Nal(2')-Arg-D-Nal(2')-Arg-Lys]-D-Pro-D-Val-NH2 |
| 3428 | TCAM3425 | Lys-Lys-Phe-Lys-Lys-Phe-Phe-Lys-Lys-c[Asp-Arg-Pro-D-Nal(2')-Arg-D-Nal(2')-Arg-Lys]-D-Val-D-Phe-NH2 |
| 3429 | TCAM3426 | Lys-Lys-Phe-Lys-Lys-Phe-Phe-Lys-Lys-c[Asp-Arg-Pro-D-Nal(2')-Arg-D-Nal(2')-Arg-Lys]-D-Phe-D-Val-NH2 |
| 3430 | TCAM3427 | Lys-Lys-Phe-Lys-Lys-Phe-Phe-Lys-Lys-c[Asp-Arg-His-D-Nal(2')-Arg-D-Nal(2')-Arg-Lys]-D-Val-D-Pro-NH2 |
| 3431 | TCAM3428 | Lys-Lys-Phe-Lys-Lys-Phe-Phe-Lys-Lys-c[Asp-Arg-His-D-Nal(2')-Arg-D-Nal(2')-Arg-Lys]-D-Pro-D-Val-NH2 |
| 3432 | TCAM3429 | Lys-Lys-Phe-Lys-Lys-Phe-Phe-Lys-Lys-c[Asp-Arg-His-D-Nal(2')-Arg-D-Nal(2')-Arg-Lys]-D-Val-D-Phe-NH2 |
| 3433 | TCAM3430 | Lys-Lys-Phe-Lys-Lys-Phe-Phe-Lys-Lys-c[Asp-Arg-His-D-Nal(2')-Arg-D-Nal(2')-Arg-Lys]-D-Phe-D-Val-NH2 |
| 3434 | TCAM3431 | Lys-Lys-Phe-Lys-Lys-Phe-Phe-Lys-Lys-c[Asp-His-D-Nal(2')-Arg-Trp-Lys]-Arg-Arg-D-Val-D-Pro-NH2 |
| 3435 | TCAM3432 | Lys-Lys-Phe-Lys-Lys-Phe-Phe-Lys-Lys-c[Asp-His-D-Nal(2')-Arg-Trp-Lys]-Arg-Arg-D-Pro-D-Val-NH2 |
| 3436 | TCAM3433 | Lys-Lys-Phe-Lys-Lys-Phe-Phe-Lys-Lys-c[Asp-His-D-Nal(2')-Arg-Trp-Lys]-Arg-Arg-D-Val-D-Phe-NH2 |
| 3437 | TCAM3434 | Lys-Lys-Phe-Lys-Lys-Phe-Phe-Lys-Lys-c[Asp-His-D-Nal(2')-Arg-Trp-Lys]-Arg-Arg-D-Phe-D-Val-NH2 |
| 3438 | TCAM3435 | Lys-Lys-Phe-Lys-Lys-Phe-Phe-Lys-Lys-c[Asp-Pro-D-Nal(2')-Arg-Trp-Lys]-Arg-Arg-D-Val-D-Pro-NH2 |
| 3439 | TCAM3436 | Lys-Lys-Phe-Lys-Lys-Phe-Phe-Lys-Lys-c[Asp-Pro-D-Nal(2')-Arg-Trp-Lys]-Arg-Arg-D-Pro-D-Val-NH2 |
| 3440 | TCAM3437 | Lys-Lys-Phe-Lys-Lys-Phe-Phe-Lys-Lys-c[Asp-Pro-D-Nal(2')-Arg-Trp-Lys]-Arg-Arg-D-Val-D-Phe-NH2 |
| 3441 | TCAM3438 | Lys-Lys-Phe-Lys-Lys-Phe-Phe-Lys-Lys-c[Asp-Pro-D-Nal(2')-Arg-Trp-Lys]-Arg-Arg-D-Phe-D-Val-NH2 |
| | Anti-biofilm peptide ABF6ARG linked to anti-microbial peptides | |
| 3442 | TCAM3439 | Arg-Arg-Phe-Arg-Arg-Phe-Phe-Arg-Arg-c[Asp-Pro-Arg-Arg-Trp-Trp-Arg-Phe-Lys]-D-Val-D-Pro-NH2 |
| 3443 | TCAM3440 | Arg-Arg-Phe-Arg-Arg-Phe-Phe-Arg-Arg-c[Asp-Pro-Arg-Arg-Trp-Trp-Arg-Phe-Lys]-D-Val-D-Phe-NH2 |
| 3444 | TCAM3441 | Arg-Arg-Phe-Arg-Arg-Phe-Phe-Arg-Arg-c[Asp-Pro-Arg-Arg-Trp-Trp-Arg-Phe-Lys]-D-Pro-D-Val-NH2 |
| 3445 | TCAM3442 | Arg-Arg-Phe-Arg-Arg-Phe-Phe-Arg-Arg-c[Asp-Pro-Arg-Arg-Trp-Trp-Arg-Phe-Lys]-D-Phe-D-Val-NH2 |

TABLE 5-continued

Exemplary Anti-microbial peptides

| SEQ NO: | Peptide | Peptide Sequence |
|---|---|---|
| 3446 | TCAM3443 | Arg-Arg-Phe-Arg-Arg-Phe-Phe-Arg-Arg-c[Asp-Pro-Arg-Arg-Trp-Trp-Tyr-Phe-Lys]-D-Val-D-Pro-NH2 |
| 3447 | TCAM3444 | Arg-Arg-Phe-Arg-Arg-Phe-Phe-Arg-Arg-c[Asp-Pro-Arg-Arg-Trp-Trp-Tyr-Phe-Lys]-D-Val-D-Phe-NH2 |
| 3448 | TCAM3445 | Arg-Arg-Phe-Arg-Arg-Phe-Phe-Arg-Arg-c[Asp-Pro-Arg-Arg-Trp-Trp-Tyr-Phe-Lys]-D-Pro-D-Val-NH2 |
| 3449 | TCAM3446 | Arg-Arg-Phe-Arg-Arg-Phe-Phe-Arg-Arg-c[Asp-Pro-Arg-Arg-Trp-Trp-Tyr-Phe-Lys]-D-Phe-D-Val-NH2 |
| 3450 | TCAM3447 | Arg-Arg-Phe-Arg-Arg-Phe-Phe-Arg-Arg-c[Asp-Pro-Arg-Arg-Tyr-Tyr-Arg-Phe-Lys]-D-Val-D-Pro-NH2 |
| 3451 | TCAM3448 | Arg-Arg-Phe-Arg-Arg-Phe-Phe-Arg-Arg-c[Asp-Pro-Arg-Arg-Tyr-Tyr-Arg-Phe-Lys]-D-Val-D-Phe-NH2 |
| 3452 | TCAM3449 | Arg-Arg-Phe-Arg-Arg-Phe-Phe-Arg-Arg-c[Asp-Pro-Arg-Arg-Tyr-Tyr-Arg-Phe-Lys]-D-Pro-D-Val-NH2 |
| 3453 | TCAM3450 | Arg-Arg-Phe-Arg-Arg-Phe-Phe-Arg-Arg-c[Asp-Pro-Arg-Arg-Tyr-Tyr-Arg-Phe-Lys]-D-Phe-D-Val-NH2 |
| 3454 | TCAM3451 | Arg-Arg-Phe-Arg-Arg-Phe-Phe-Arg-Arg-c[Asp-Pro-Arg-Arg-Nal-Nal-Arg-Phe-Lys]-D-Val-D-Pro-NH2 |
| 3455 | TCAM3452 | Arg-Arg-Phe-Arg-Arg-Phe-Phe-Arg-Arg-c[Asp-Pro-Arg-Arg-Nal-Nal-Arg-Phe-Lys]-D-Val-D-Phe-NH2 |
| 3456 | TCAM3453 | Arg-Arg-Phe-Arg-Arg-Phe-Phe-Arg-Arg-c[Asp-Pro-Arg-Arg-Nal-Nal-Arg-Phe-Lys]-D-Pro-D-Val-NH2 |
| 3457 | TCAM3454 | Arg-Arg-Phe-Arg-Arg-Phe-Phe-Arg-Arg-c[Asp-Pro-Arg-Arg-Nal-Nal-Arg-Phe-Lys]-D-Phe-D-Val-NH2 |
| 3458 | TCAM3455 | Arg-Arg-Phe-Arg-Arg-Phe-Phe-Arg-Arg-c[Asp-Pro-Arg-Arg-Leu-Trp-Leu-Trp-Lys]-D-Val-D-Pro-NH2 |
| 3459 | TCAM3456 | Arg-Arg-Phe-Arg-Arg-Phe-Phe-Arg-Arg-c[Asp-Pro-Arg-Arg-Leu-Trp-Leu-Trp-Lys]-D-Val-D-Phe-NH2 |
| 3460 | TCAM3457 | Arg-Arg-Phe-Arg-Arg-Phe-Phe-Arg-Arg-c[Asp-Pro-Arg-Arg-Leu-Trp-Leu-Trp-Lys]-D-Pro-D-Val-NH2 |
| 3461 | TCAM3458 | Arg-Arg-Phe-Arg-Arg-Phe-Phe-Arg-Arg-c[Asp-Pro-Arg-Arg-Leu-Trp-Leu-Trp-Lys]-D-Phe-D-Val-NH2 |
| 3462 | TCAM3459 | Arg-Arg-Phe-Arg-Arg-Phe-Phe-Arg-Arg-c[Asp-Pro-Arg-Arg-Leu-Trp-Leu-Trp-Lys]-D-Val-D-Pro-NH2 |
| 3463 | TCAM3460 | Arg-Arg-Phe-Arg-Arg-Phe-Phe-Arg-Arg-c[Asp-Pro-Arg-Arg-Leu-Trp-Leu-Trp-Lys]-D-Val-D-Phe-NH2 |
| 3464 | TCAM3461 | Arg-Arg-Phe-Arg-Arg-Phe-Phe-Arg-Arg-c[Asp-Pro-Arg-Arg-Leu-Trp-Leu-Trp-Lys]-D-Pro-D-Val-NH2 |
| 3465 | TCAM3462 | Arg-Arg-Phe-Arg-Arg-Phe-Phe-Arg-Arg-c[Asp-Pro-Arg-Arg-Leu-Trp-Leu-Trp-Lys]-D-Phe-D-Val-NH2 |
| 3466 | TCAM3463 | Arg-Arg-Phe-Arg-Arg-Phe-Phe-Arg-Arg-c[Asp-Arg-Arg-Arg-Trp-Leu-Trp-Leu-Trp-Lys]-D-Val-D-Pro-NH2 |
| 3467 | TCAM3464 | Arg-Arg-Phe-Arg-Arg-Phe-Phe-Arg-Arg-c[Asp-Pro-Arg-Arg-Arg-Trp-Leu-Trp-Leu-Trp-Lys]-D-Val-D-Phe-NH2 |
| 3468 | TCAM3465 | Arg-Arg-Phe-Arg-Arg-Phe-Phe-Arg-Arg-c[Asp-Pro-Arg-Arg-Arg-Trp-Leu-Trp-Leu-Trp-Lys]-D-Pro-D-Val-NH2 |
| 3469 | TCAM3466 | Arg-Arg-Phe-Arg-Arg-Phe-Phe-Arg-Arg-c[Asp-Pro-Arg-Arg-Arg-Trp-Leu-Trp-Leu-Trp-Lys]-D-Phe-D-Val-NH2 |
| 3470 | TCAM3467 | Arg-Arg-Phe-Arg-Arg-Phe-Phe-Arg-Arg-c[Asp-Pro-Arg-Gln-Arg-Arg-Trp-Leu-Trp-Leu-Trp-Lys]-D-Val-D-Pro-NH2 |

TABLE 5-continued

Exemplary Anti-microbial peptides

| SEQ NO: | Peptide | Peptide Sequence |
|---|---|---|
| 3471 | TCAM3468 | Arg-Arg-Phe-Arg-Arg-Phe-Phe-Arg-Arg-c[Asp-Pro-Arg-Gln-Arg-Arg-Trp-Leu-Trp-Leu-Trp-Lys]-D-Val-D-Phe-NH2 |
| 3472 | TCAM3469 | Arg-Arg-Phe-Arg-Arg-Phe-Phe-Arg-Arg-c[Asp-Pro-Arg-Gln-Arg-Arg-Trp-Leu-Trp-Leu-Trp-Lys]-D-Pro-D-Val-NH2 |
| 3473 | TCAM3470 | Arg-Arg-Phe-Arg-Arg-Phe-Phe-Arg-Arg-c[Asp-Pro-Arg-Gln-Arg-Arg-Trp-Leu-Trp-Leu-Trp-Lys]-D-Phe-D-Val-NH2 |
| 3474 | TCAM3471 | Arg-Arg-Phe-Arg-Arg-Phe-Phe-Arg-Arg-c[Asp-Pro-Trp-Arg-Trp-Trp-Arg-Arg-Lys]-D-Val-D-Phe-NH2 |
| 3475 | TCAM3472 | Arg-Arg-Phe-Arg-Arg-Phe-Phe-Arg-Arg-c[Asp-Pro-Trp-Arg-Trp-Trp-Arg-Arg-Lys]-D-Pro-D-Val-NH2 |
| 3476 | TCAM3473 | Arg-Arg-Phe-Arg-Arg-Phe-Phe-Arg-Arg-c[Asp-Pro-Trp-Arg-Trp-Trp-Arg-Arg-Lys]-D-Phe-D-Val-NH2 |
| 3477 | TCAM3474 | Arg-Arg-Phe-Arg-Arg-Phe-Phe-Arg-Arg-c[Asp-Pro-Trp-Trp-Arg-Arg-Trp-Trp-Arg-Arg-Lys]-D-Val-D-Pro-NH2 |
| 3478 | TCAM3475 | Arg-Arg-Phe-Arg-Arg-Phe-Phe-Arg-Arg-c[Asp-Pro-Trp-Trp-Arg-Arg-Trp-Trp-Arg-Arg-Lys]-D-Val-D-Phe-NH2 |
| 3479 | TCAM3476 | Arg-Arg-Phe-Arg-Arg-Phe-Phe-Arg-Arg-c[Asp-Pro-Trp-Trp-Arg-Arg-Trp-Trp-Arg-Arg-Lys]-D-Pro-D-Val-NH2 |
| 3480 | TCAM3477 | Arg-Arg-Phe-Arg-Arg-Phe-Phe-Arg-Arg-c[Asp-Pro-Trp-Trp-Arg-Arg-Trp-Trp-Arg-Arg-Lys]-D-Phe-D-Val-NH2 |
| 3481 | TCAM3478 | Arg-Arg-Phe-Arg-Arg-Phe-Phe-Arg-Arg-c[Asp-Pro-Trp-Arg-Trp-Arg-Trp-Arg-Lys]-D-Val-D-Pro-NH2 |
| 3482 | TCAM3479 | Arg-Arg-Phe-Arg-Arg-Phe-Phe-Arg-Arg-c[Asp-Pro-Trp-Arg-Trp-Arg-Trp-Arg-Lys]-D-Val-D-Phe-NH2 |
| 3483 | TCAM3480 | Arg-Arg-Phe-Arg-Arg-Phe-Phe-Arg-Arg-c[Asp-Pro-Trp-Arg-Trp-Arg-Trp-Arg-Lys]-D-Pro-D-Val-NH2 |
| 3484 | TCAM3481 | Arg-Arg-Phe-Arg-Arg-Phe-Phe-Arg-Arg-c[Asp-Pro-Trp-Arg-Trp-Arg-Trp-Arg-Lys]-D-Phe-D-Val-NH2 |
| 3485 | TCAM3482 | Arg-Arg-Phe-Arg-Arg-Phe-Phe-Arg-Arg-c[Asp-Pro-Arg-Trp-Arg-Trp-Arg-Trp-Lys]-D-Val-D-Pro-NH2 |
| 3486 | TCAM3483 | Arg-Arg-Phe-Arg-Arg-Phe-Phe-Arg-Arg-c[Asp-Pro-Arg-Trp-Arg-Trp-Arg-Trp-Lys]-D-Val-D-Phe-NH2 |
| 3487 | TCAM3484 | Arg-Arg-Phe-Arg-Arg-Phe-Phe-Arg-Arg-c[Asp-Pro-Arg-Trp-Arg-Trp-Arg-Trp-Lys]-D-Pro-D-Val-NH2 |
| 3488 | TCAM3485 | Arg-Arg-Phe-Arg-Arg-Phe-Phe-Arg-Arg-c[Asp-Pro-Arg-Trp-Arg-Trp-Arg-Trp-Lys]-D-Phe-D-Val-NH2 |
| 3489 | TCAM3486 | Arg-Arg-Phe-Arg-Arg-Phe-Phe-Arg-Arg-c[Asp-Pro-Arg-Trp-Trp-Arg-Arg-Lys]-D-Val-D-Pro-NH2 |
| 3490 | TCAM3487 | Arg-Arg-Phe-Arg-Arg-Phe-Phe-Arg-Arg-c[Asp-Pro-Arg-Trp-Trp-Arg-Arg-Lys]-D-Val-D-Phe-NH2 |
| 3491 | TCAM3488 | Arg-Arg-Phe-Arg-Arg-Phe-Phe-Arg-Arg-c[Asp-Pro-Arg-Trp-Trp-Arg-Arg-Lys]-D-Pro-D-Val-NH2 |
| 3492 | TCAM3489 | Arg-Arg-Phe-Arg-Arg-Phe-Phe-Arg-Arg-c[Asp-Pro-Arg-Trp-Trp-Arg-Arg-Lys]-D-Phe-D-Val-NH2 |
| 3493 | TCAM3490 | Arg-Arg-Phe-Arg-Arg-Phe-Phe-Arg-Arg-c[Asp-Pro-Trp-Trp-Arg-Arg-Trp-Lys]-D-Val-D-Pro-NH2 |
| 3494 | TCAM3491 | Arg-Arg-Phe-Arg-Arg-Phe-Phe-Arg-Arg-c[Asp-Pro-Trp-Trp-Arg-Arg-Trp-Lys]-D-Val-D-Phe-NH2 |
| 3495 | TCAM3492 | Arg-Arg-Phe-Arg-Arg-Phe-Phe-Arg-Arg-c[Asp-Pro-Trp-Trp-Arg-Arg-Trp-Lys]-D-Pro-D-Val-NH2 |

TABLE 5-continued

Exemplary Anti-microbial peptides

| SEQ NO: | Peptide | Peptide Sequence |
|---|---|---|
| 3496 | TCAM3493 | Arg-Arg-Phe-Arg-Arg-Phe-Phe-Arg-Arg-c[Asp-Pro-Trp-Trp-Arg-Arg-Trp-Lys]-D-Phe-D-Val-NH2 |
| 3497 | TCAM3494 | Arg-Arg-Phe-Arg-Arg-Phe-Phe-Arg-Arg-c[Asp-Pro-Trp-Arg-Trp-Arg-Trp-Lys]-D-Val-D-Pro-NH2 |
| 3498 | TCAM3495 | Arg-Arg-Phe-Arg-Arg-Phe-Phe-Arg-Arg-c[Asp-Pro-Trp-Arg-Trp-Arg-Trp-Lys]-D-Val-D-Phe-NH2 |
| 3499 | TCAM3496 | Arg-Arg-Phe-Arg-Arg-Phe-Phe-Arg-Arg-c[Asp-Pro-Trp-Arg-Trp-Arg-Trp-Lys]-D-Pro-D-Val-NH2 |
| 3500 | TCAM3497 | Arg-Arg-Phe-Arg-Arg-Phe-Phe-Arg-Arg-c[Asp-Pro-Trp-Arg-Trp-Arg-Trp-Lys]-D-Phe-D-Val-NH2 |
| 3501 | TCAM3498 | Arg-Arg-Phe-Arg-Arg-Phe-Phe-Arg-Arg-c[Asp-Pro-Arg-Trp-Arg-Trp-Arg-Lys]-D-Val-D-Pro-NH2 |
| 3502 | TCAM3499 | Arg-Arg-Phe-Arg-Arg-Phe-Phe-Arg-Arg-c[Asp-Pro-Arg-Trp-Arg-Trp-Arg-Lys]-D-Val-D-Phe-NH2 |
| 3503 | TCAM3500 | Arg-Arg-Phe-Arg-Arg-Phe-Phe-Arg-Arg-c[Asp-Pro-Arg-Trp-Arg-Trp-Arg-Lys]-D-Pro-D-Val-NH2 |
| 3504 | TCAM3501 | Arg-Arg-Phe-Arg-Arg-Phe-Phe-Arg-Arg-c[Asp-Pro-Arg-Trp-Arg-Trp-Arg-Lys]-D-Phe-D-Val-NH2 |
| 3505 | TCAM3502 | Arg-Arg-Phe-Arg-Arg-Phe-Phe-Arg-Arg-c[Asp-Pro-Trp-Arg-Tyr-Arg-Trp-Lys]-D-Val-D-Pro-NH2 |
| 3506 | TCAM3503 | Arg-Arg-Phe-Arg-Arg-Phe-Phe-Arg-Arg-c[Asp-Pro-Trp-Arg-Tyr-Arg-Trp-Lys]-D-Val-D-Phe-NH2 |
| 3507 | TCAM3504 | Arg-Arg-Phe-Arg-Arg-Phe-Phe-Arg-Arg-c[Asp-Pro-Trp-Arg-Tyr-Arg-Trp-Lys]-D-Pro-D-Val-NH2 |
| 3508 | TCAM3505 | Arg-Arg-Phe-Arg-Arg-Phe-Phe-Arg-Arg-c[Asp-Pro-Trp-Arg-Tyr-Arg-Trp-Lys]-D-Phe-D-Val-NH2 |
| 3509 | TCAM3506 | Arg-Arg-Phe-Arg-Arg-Phe-Phe-Arg-Arg-c[Asp-Pro-Trp-Arg-Trp-Arg-Tyr-Lys]-D-Val-D-Pro-NH2 |
| 3510 | TCAM3507 | Arg-Arg-Phe-Arg-Arg-Phe-Phe-Arg-Arg-c[Asp-Pro-Trp-Arg-Trp-Arg-Tyr-Lys]-D-Val-D-Phe-NH2 |
| 3511 | TCAM3508 | Arg-Arg-Phe-Arg-Arg-Phe-Phe-Arg-Arg-c[Asp-Pro-Trp-Arg-Trp-Arg-Tyr-Lys]-D-Pro-D-Val-NH2 |
| 3512 | TCAM3509 | Arg-Arg-Phe-Arg-Arg-Phe-Phe-Arg-Arg-c[Asp-Pro-Trp-Arg-Trp-Arg-Tyr-Lys]-D-Phe-D-Val-NH2 |
| 3513 | TCAM3510 | Arg-Arg-Phe-Arg-Arg-Phe-Phe-Arg-Arg-c[Asp-Pro-Trp-Arg-Trp-Arg-Lys]-D-Val-D-Pro-NH2 |
| 3514 | TCAM3511 | Arg-Arg-Phe-Arg-Arg-Phe-Phe-Arg-Arg-c[Asp-Pro-Trp-Arg-Trp-Arg-Lys]-D-Val-D-Phe-NH2 |
| 3515 | TCAM3512 | Arg-Arg-Phe-Arg-Arg-Phe-Phe-Arg-Arg-c[Asp-Pro-Trp-Arg-Trp-Arg-Lys]-D-Pro-D-Val-NH2 |
| 3516 | TCAM3513 | Arg-Arg-Phe-Arg-Arg-Phe-Phe-Arg-Arg-c[Asp-Pro-Trp-Arg-Trp-Arg-Lys]-D-Phe-D-Val-NH2 |
| 3517 | TCAM3514 | Arg-Arg-Phe-Arg-Arg-Phe-Phe-Arg-Arg-c[Asp-Pro-Trp-Arg-Arg-Trp-Lys]-D-Val-D-Pro-NH2 |
| 3518 | TCAM3515 | Arg-Arg-Phe-Arg-Arg-Phe-Phe-Arg-Arg-c[Asp-Pro-Trp-Arg-Arg-Trp-Lys]-D-Val-D-Phe-NH2 |
| 3519 | TCAM3516 | Arg-Arg-Phe-Arg-Arg-Phe-Phe-Arg-Arg-c[Asp-Pro-Trp-Arg-Arg-Trp-Lys]-D-Pro-D-Val-NH2 |
| 3520 | TCAM3517 | Arg-Arg-Phe-Arg-Arg-Phe-Phe-Arg-Arg-c[Asp-Pro-Trp-Arg-Arg-Trp-Lys]-D-Phe-D-Val-NH2 |

TABLE 5-continued

Exemplary Anti-microbial peptides

| SEQ NO: | Peptide | Peptide Sequence |
|---|---|---|
| 3521 | TCAM3518 | Arg-Arg-Phe-Arg-Arg-Phe-Phe-Arg-Arg-c[Asp-Pro-Arg-Trp-Trp-Arg-Lys]-D-Val-D-Pro-NH2 |
| 3522 | TCAM3519 | Arg-Arg-Phe-Arg-Arg-Phe-Phe-Arg-Arg-c[Asp-Pro-Arg-Trp-Trp-Arg-Lys]-D-Val-D-Phe-NH2 |
| 3523 | TCAM3520 | Arg-Arg-Phe-Arg-Arg-Phe-Phe-Arg-Arg-c[Asp-Pro-Arg-Trp-Trp-Arg-Lys]-D-Pro-D-Val-NH2 |
| 3524 | TCAM3521 | Arg-Arg-Phe-Arg-Arg-Phe-Phe-Arg-Arg-c[Asp-Pro-Arg-Trp-Trp-Arg-Lys]-D-Phe-D-Val-NH2 |
| 3525 | TCAM3522 | Arg-Arg-Phe-Arg-Arg-Phe-Phe-Arg-Arg-c[Asp-Pro-Trp-Arg-Trp-Lys]-D-Val-D-Pro-NH2 |
| 3526 | TCAM3523 | Arg-Arg-Phe-Arg-Arg-Phe-Phe-Arg-Arg-c[Asp-Pro-Trp-Arg-Trp-Lys]-D-Val-D-Phe-NH2 |
| 3527 | TCAM3524 | Arg-Arg-Phe-Arg-Arg-Phe-Phe-Arg-Arg-c[Asp-Pro-Trp-Arg-Trp-Lys]-D-Pro-D-Val-NH2 |
| 3528 | TCAM3525 | Arg-Arg-Phe-Arg-Arg-Phe-Phe-Arg-Arg-c[Asp-Pro-Trp-Arg-Trp-Lys]-D-Phe-D-Val-NH2 |
| 3529 | TCAM3526 | Arg-Arg-Phe-Arg-Arg-Phe-Phe-Arg-Arg-c[Asp-Pro-Trp-Arg-Lys]-D-Val-D-Pro-NH2 |
| 3530 | TCAM3527 | Arg-Arg-Phe-Arg-Arg-Phe-Phe-Arg-Arg-c[Asp-Pro-Trp-Arg-Lys]-D-Val-D-Phe-NH2 |
| 3531 | TCAM3528 | Arg-Arg-Phe-Arg-Arg-Phe-Phe-Arg-Arg-c[Asp-Pro-Trp-Arg-Lys]-D-Pro-D-Val-NH2 |
| 3532 | TCAM3529 | Arg-Arg-Phe-Arg-Arg-Phe-Phe-Arg-Arg-c[Asp-Pro-Trp-Arg-Lys]-D-Phe-D-Val-NH2 |
| 3533 | TCAM3530 | -Arg-Arg-Phe-Arg-Arg-Phe-Phe-Arg-Arg-c[Asp-Arg-Arg-Trp-Trp-Arg-Phe-Lys]-D-Val-D-Pro-NH2 |
| 3534 | TCAM3531 | Arg-Arg-Phe-Arg-Arg-Phe-Phe-Arg-Arg-c[Asp-Arg-Arg-Trp-Trp-Arg-Phe-Lys]-D-Val-D-Phe-NH2 |
| 3535 | TCAM3532 | Arg-Arg-Phe-Arg-Arg-Phe-Phe-Arg-Arg-c[Asp-Arg-Arg-Trp-Trp-Arg-Phe-Lys]-D-Pro-D-Val-NH2 |
| 3536 | TCAM3533 | Arg-Arg-Phe-Arg-Arg-Phe-Phe-Arg-Arg-c[Asp-Arg-Arg-Trp-Trp-Arg-Phe-Lys]-D-Phe-D-Val-NH2 |
| 3537 | TCAM3534 | Arg-Arg-Phe-Arg-Arg-Phe-Phe-Arg-Arg-c[Asp-Arg-Arg-Trp-Trp-Arg-Phe-Lys]-D-Val-D-Pro-NH2 |
| 3538 | TCAM3535 | Arg-Arg-Phe-Arg-Arg-Phe-Phe-Arg-Arg-c[Asp-Arg-Arg-Trp-Trp-Arg-Phe-Lys]-D-Val-D-Phe-NH2 |
| 3539 | TCAM3536 | Arg-Arg-Phe-Arg-Arg-Phe-Phe-Arg-Arg-c[Asp-Arg-Arg-Trp-Trp-Arg-Phe-Lys]-D-Pro-D-Val-NH2 |
| 3540 | TCAM3537 | Arg-Arg-Phe-Arg-Arg-Phe-Phe-Arg-Arg-c[Asp-Arg-Arg-Trp-Trp-Arg-Phe-Lys]-D-Phe-D-Val-NH2 |
| 3541 | TCAM3538 | Arg-Arg-Phe-Arg-Arg-Phe-Phe-Arg-Arg-c[Asp-Arg-Arg-Tyr-Tyr-Arg-Phe-Lys]-D-Val-D-Pro-NH2 |
| 3542 | TCAM3539 | Arg-Arg-Phe-Arg-Arg-Phe-Phe-Arg-Arg-c[Asp-Arg-Arg-Tyr-Tyr-Arg-Phe-Lys]-D-Val-D-Phe-NH2 |
| 3543 | TCAM3540 | Arg-Arg-Phe-Arg-Arg-Phe-Phe-Arg-Arg-c[Asp-Arg-Arg-Tyr-Tyr-Arg-Phe-Lys]-D-Pro-D-Val-NH2 |
| 3544 | TCAM3541 | Arg-Arg-Phe-Arg-Arg-Phe-Phe-Arg-Arg-c[Asp-Arg-Arg-Tyr-Tyr-Arg-Phe-Lys]-D-Phe-D-Val-NH2 |
| 3545 | TCAM3542 | Arg-Arg-Phe-Arg-Arg-Phe-Phe-Arg-Arg-c[Asp-Arg-Arg-Nal-Nal-Arg-Phe-Lys]-D-Val-D-Pro-NH2 |
| 3546 | TCAM3543 | Arg-Arg-Phe-Arg-Arg-Phe-Phe-Arg-Arg-c[Asp-Arg-Arg-Nal-Nal-Arg-Phe-Lys]-D-Val-D-Phe-NH2 |

TABLE 5-continued

Exemplary Anti-microbial peptides

| SEQ NO: | Peptide | Peptide Sequence |
|---|---|---|
| 3547 | TCAM3544 | Arg-Arg-Phe-Arg-Arg-Phe-Phe-Arg-Arg-c[Asp-Arg-Arg-Nal-Nal-Arg-Phe-Lys]-D-Pro-D-Val-NH2 |
| 3548 | TCAM3545 | Arg-Arg-Phe-Arg-Arg-Phe-Phe-Arg-Arg-c[Asp-Arg-Arg-Nal-Nal-Arg-Phe-Lys]-D-Phe-D-Val-NH2 |
| 3549 | TCAM3546 | Arg-Arg-Phe-Arg-Arg-Phe-Phe-Arg-Arg-c[Asp-Arg-Arg-Leu-Trp-Leu-Trp-Lys]-D-Val-D-Pro-NH2 |
| 3550 | TCAM3547 | Arg-Arg-Phe-Arg-Arg-Phe-Phe-Arg-Arg-c[Asp-Arg-Arg-Leu-Trp-Leu-Trp-Lys]-D-Val-D-Phe-NH2 |
| 3551 | TCAM3548 | Arg-Arg-Phe-Arg-Arg-Phe-Phe-Arg-Arg-c[Asp-Arg-Arg-Leu-Trp-Leu-Trp-Lys]-D-Pro-D-Val-NH2 |
| 3552 | TCAM3549 | Arg-Arg-Phe-Arg-Arg-Phe-Phe-Arg-Arg-c[Asp-Arg-Arg-Leu-Trp-Leu-Trp-Lys]-D-Phe-D-Val-NH2 |
| 3553 | TCAM3550 | Arg-Arg-Phe-Arg-Arg-Phe-Phe-Arg-Arg-c[Asp-Arg-Arg-Leu-Trp-Leu-Trp-Lys]-D-Val-D-Pro-NH2 |
| 3554 | TCAM3551 | Arg-Arg-Phe-Arg-Arg-Phe-Phe-Arg-Arg-c[Asp-Arg-Arg-Leu-Trp-Leu-Trp-Lys]-D-Val-D-Phe-NH2 |
| 3555 | TCAM3552 | Arg-Arg-Phe-Arg-Arg-Phe-Phe-Arg-Arg-c[Asp-Arg-Arg-Leu-Trp-Leu-Trp-Lys]-D-Pro-D-Val-NH2 |
| 3556 | TCAM3553 | Arg-Arg-Phe-Arg-Arg-Phe-Phe-Arg-Arg-c[Asp-Arg-Arg-Leu-Trp-Leu-Trp-Lys]-D-Phe-D-Val-NH2 |
| 3557 | TCAM3554 | Arg-Arg-Phe-Arg-Arg-Phe-Phe-Arg-Arg-c[Asp-Arg-Arg-Arg-Trp-Leu-Trp-Leu-Trp-Lys]-D-Val-D-Pro-NH2 |
| 3558 | TCAM3555 | Arg-Arg-Phe-Arg-Arg-Phe-Phe-Arg-Arg-c[Asp-Arg-Arg-Arg-Trp-Leu-Trp-Leu-Trp-Lys]-D-Val-D-Phe-NH2 |
| 3559 | TCAM3556 | Arg-Arg-Phe-Arg-Arg-Phe-Phe-Arg-Arg-c[Asp-Arg-Arg-Arg-Trp-Leu-Trp-Leu-Trp-Lys]-D-Pro-D-Val-NH2 |
| 3560 | TCAM3557 | Arg-Arg-Phe-Arg-Arg-Phe-Phe-Arg-Arg-c[Asp-Arg-Arg-Arg-Trp-Leu-Trp-Leu-Trp-Lys]-D-Phe-D-Val-NH2 |
| 3561 | TCAM3558 | Arg-Arg-Phe-Arg-Arg-Phe-Phe-Arg-Arg-c[Asp-Arg-Gln-Arg-Arg-Trp-Leu-Trp-Leu-Trp-Lys]-D-Val-D-Pro-NH2 |
| 3562 | TCAM3559 | Arg-Arg-Phe-Arg-Arg-Phe-Phe-Arg-Arg-c[Asp-Arg-Gln-Arg-Arg-Trp-Leu-Trp-Leu-Trp-Lys]-D-Val-D-Phe-NH2 |
| 3563 | TCAM3560 | Arg-Arg-Phe-Arg-Arg-Phe-Phe-Arg-Arg-c[Asp-Arg-Gln-Arg-Arg-Trp-Leu-Trp-Leu-Trp-Lys]-D-Pro-D-Val-NH2 |
| 3564 | TCAM3561 | Arg-Arg-Phe-Arg-Arg-Phe-Phe-Arg-Arg-c[Asp-Arg-Gln-Arg-Arg-Trp-Leu-Trp-Leu-Trp-Lys]-D-Phe-D-Val-NH2 |
| 3565 | TCAM3562 | Arg-Arg-Phe-Arg-Arg-Phe-Phe-Arg-Arg-c[Asp-Trp-Arg-Trp-Trp-Arg-Arg-Lys]-D-Val-D-Pro-NH2 |
| 3566 | TCAM3563 | Arg-Arg-Phe-Arg-Arg-Phe-Phe-Arg-Arg-c[Asp-Trp-Arg-Trp-Trp-Arg-Arg-Lys]-D-Val-D-Phe-NH2 |
| 3567 | TCAM3564 | Arg-Arg-Phe-Arg-Arg-Phe-Phe-Arg-Arg-c[Asp-Trp-Arg-Trp-Trp-Arg-Arg-Lys]-D-Pro-D-Val-NH2 |
| 3568 | TCAM3565 | Arg-Arg-Phe-Arg-Arg-Phe-Phe-Arg-Arg-c[Asp-Trp-Arg-Trp-Trp-Arg-Arg-Lys]-D-Phe-D-Val-NH2 |
| 3569 | TCAM3566 | Arg-Arg-Phe-Arg-Arg-Phe-Phe-Arg-Arg-c[Asp-Trp-Trp-Arg-Arg-Trp-Trp-Arg-Arg-Lys]-D-Val-D-Pro-NH2 |
| 3570 | TCAM3567 | Arg-Arg-Phe-Arg-Arg-Phe-Phe-Arg-Arg-c[Asp-Trp-Trp-Arg-Arg-Trp-Trp-Arg-Arg-Lys]-D-Val-D-Phe-NH2 |
| 3571 | TCAM3568 | Arg-Arg-Phe-Arg-Arg-Phe-Phe-Arg-Arg-c[Asp-Trp-Trp-Arg-Arg-Trp-Trp-Arg-Arg-Lys]-D-Pro-D-Val-NH2 |

TABLE 5-continued

Exemplary Anti-microbial peptides

| SEQ NO: | Peptide | Peptide Sequence |
|---|---|---|
| 3572 | TCAM3569 | Arg-Arg-Phe-Arg-Arg-Phe-Phe-Arg-Arg-c[Asp-Trp-Trp-Arg-Arg-Trp-Trp-Arg-Arg-Lys]-D-Phe-D-Val-NH2 |
| 3573 | TCAM3570 | Arg-Arg-Phe-Arg-Arg-Phe-Phe-Arg-Arg-c[Asp-Trp-Arg-Trp-Arg-Trp-Arg-Lys]-D-Val-D-Pro-NH2 |
| 3574 | TCAM3571 | Arg-Arg-Phe-Arg-Arg-Phe-Phe-Arg-Arg-c[Asp-Trp-Arg-Trp-Arg-Trp-Arg-Lys]-D-Val-D-Phe-NH2 |
| 3575 | TCAM3572 | Arg-Arg-Phe-Arg-Arg-Phe-Phe-Arg-Arg-c[Asp-Trp-Arg-Trp-Arg-Trp-Arg-Lys]-D-Pro-D-Val-NH2 |
| 3576 | TCAM3573 | Arg-Arg-Phe-Arg-Arg-Phe-Phe-Arg-Arg-c[Asp-Trp-Arg-Trp-Arg-Trp-Arg-Lys]-D-Phe-D-Val-NH2 |
| 3577 | TCAM3574 | Arg-Arg-Phe-Arg-Arg-Phe-Phe-Arg-Arg-c[Asp-Arg-Trp-Arg-Trp-Arg-Trp-Lys]-D-Val-D-Pro-NH2 |
| 3578 | TCAM3575 | Arg-Arg-Phe-Arg-Arg-Phe-Phe-Arg-Arg-c[Asp-Arg-Trp-Arg-Trp-Arg-Trp-Lys]-D-Val-D-Phe-NH2 |
| 3579 | TCAM3576 | Arg-Arg-Phe-Arg-Arg-Phe-Phe-Arg-Arg-c[Asp-Arg-Trp-Arg-Trp-Arg-Trp-Lys]-D-Pro-D-Val-NH2 |
| 3580 | TCAM3577 | Arg-Arg-Phe-Arg-Arg-Phe-Phe-Arg-Arg-c[Asp-Arg-Trp-Arg-Trp-Arg-Trp-Lys]-D-Phe-D-Val-NH2 |
| 3581 | TCAM3578 | Arg-Arg-Phe-Arg-Arg-Phe-Phe-Arg-Arg-c[Asp-Arg-Trp-Trp-Arg-Arg-Lys]-D-Val-D-Pro-NH2 |
| 3582 | TCAM3579 | Arg-Arg-Phe-Arg-Arg-Phe-Phe-Arg-Arg-c[Asp-Arg-Trp-Trp-Arg-Arg-Lys]-D-Val-D-Phe-NH2 |
| 3583 | TCAM3580 | Arg-Arg-Phe-Arg-Arg-Phe-Phe-Arg-Arg-c[Asp-Arg-Trp-Trp-Arg-Arg-Lys]-D-Pro-D-Val-NH2 |
| 3584 | TCAM3581 | Arg-Arg-Phe-Arg-Arg-Phe-Phe-Arg-Arg-c[Asp-Arg-Trp-Trp-Arg-Arg-Lys]-D-Phe-D-Val-NH2 |
| 3585 | TCAM3582 | Arg-Arg-Phe-Arg-Arg-Phe-Phe-Arg-Arg-c[Asp-Arg-Trp-Arg-Trp-Arg-Lys]-D-Val-D-Pro-NH2 |
| 3586 | TCAM3583 | Arg-Arg-Phe-Arg-Arg-Phe-Phe-Arg-Arg-c[Asp-Arg-Trp-Arg-Trp-Arg-Lys]-D-Val-D-Phe-NH2 |
| 3587 | TCAM3584 | Arg-Arg-Phe-Arg-Arg-Phe-Phe-Arg-Arg-c[Asp-Arg-Trp-Arg-Trp-Arg-Lys]-D-Pro-D-Val-NH2 |
| 3588 | TCAM3585 | Arg-Arg-Phe-Arg-Arg-Phe-Phe-Arg-Arg-c[Asp-Arg-Trp-Arg-Trp-Arg-Lys]-D-Phe-D-Val-NH2 |
| 3589 | TCAM3586 | Arg-Arg-Phe-Arg-Arg-Phe-Phe-Arg-Arg-c[Asp-Trp-Trp-Arg-Arg-Trp-Lys]-D-Val-D-Pro-NH2 |
| 3590 | TCAM3587 | Arg-Arg-Phe-Arg-Arg-Phe-Phe-Arg-Arg-c[Asp-Trp-Trp-Arg-Arg-Trp-Lys]-D-Val-D-Phe-NH2 |
| 3591 | TCAM3588 | Arg-Arg-Phe-Arg-Arg-Phe-Phe-Arg-Arg-c[Asp-Trp-Trp-Arg-Arg-Trp-Lys]-D-Pro-D-Val-NH2 |
| 3592 | TCAM3589 | Arg-Arg-Phe-Arg-Arg-Phe-Phe-Arg-Arg-c[Asp-Trp-Trp-Arg-Arg-Trp-Lys]-D-Phe-D-Val-NH2 |
| 3593 | TCAM3590 | Arg-Arg-Phe-Arg-Arg-Phe-Phe-Arg-Arg-c[Asp-Trp-Arg-Trp-Arg-Trp-Lys]-D-Val-D-Pro-NH2 |
| 3594 | TCAM3591 | Arg-Arg-Phe-Arg-Arg-Phe-Phe-Arg-Arg-c[Asp-Trp-Arg-Trp-Arg-Trp-Lys]-D-Val-D-Phe-NH2 |
| 3595 | TCAM3592 | Arg-Arg-Phe-Arg-Arg-Phe-Phe-Arg-Arg-c[Asp-Trp-Arg-Trp-Arg-Trp-Lys]-D-Pro-D-Val-NH2 |
| 3596 | TCAM3593 | Arg-Arg-Phe-Arg-Arg-Phe-Phe-Arg-Arg-c[Asp-Trp-Arg-Trp-Arg-Trp-Lys]-D-Phe-D-Val-NH2 |

TABLE 5-continued

Exemplary Anti-microbial peptides

| SEQ NO: | Peptide | Peptide Sequence |
|---|---|---|
| 3597 | TCAM3594 | Arg-Arg-Phe-Arg-Arg-Phe-Phe-Arg-Arg-c[Asp-Trp-Arg-Tyr-Arg-Trp-Lys]-D-Val-D-Pro-NH2 |
| 3598 | TCAM3595 | Arg-Arg-Phe-Arg-Arg-Phe-Phe-Arg-Arg-c[Asp-Trp-Arg-Tyr-Arg-Trp-Lys]-D-Val-D-Phe-NH2 |
| 3599 | TCAM3596 | Arg-Arg-Phe-Arg-Arg-Phe-Phe-Arg-Arg-c[Asp-Trp-Arg-Tyr-Arg-Trp-Lys]-D-Pro-D-Val-NH2 |
| 3600 | TCAM3597 | Arg-Arg-Phe-Arg-Arg-Phe-Phe-Arg-Arg-c[Asp-Trp-Arg-Tyr-Arg-Trp-Lys]-D-Phe-D-Val-NH2 |
| 3601 | TCAM3598 | Arg-Arg-Phe-Arg-Arg-Phe-Phe-Arg-Arg-c[Asp-Trp-Arg-Trp-Arg-Tyr-Lys]-D-Val-D-Pro-NH2 |
| 3602 | TCAM3599 | Arg-Arg-Phe-Arg-Arg-Phe-Phe-Arg-Arg-c[Asp-Trp-Arg-Trp-Arg-Tyr-Lys]-D-Val-D-Phe-NH2 |
| 3603 | TCAM3600 | Arg-Arg-Phe-Arg-Arg-Phe-Phe-Arg-Arg-c[Asp-Trp-Arg-Trp-Arg-Tyr-Lys]-D-Pro-D-Val-NH2 |
| 3604 | TCAM3601 | Arg-Arg-Phe-Arg-Arg-Phe-Phe-Arg-Arg-c[Asp-Trp-Arg-Trp-Arg-Tyr-Lys]-D-Phe-D-Val-NH2 |
| 3605 | TCAM3602 | Arg-Arg-Phe-Arg-Arg-Phe-Phe-Arg-Arg-c[Asp-Trp-Arg-Trp-Arg-Lys]-D-Val-D-Pro-NH2 |
| 3606 | TCAM3603 | Arg-Arg-Phe-Arg-Arg-Phe-Phe-Arg-Arg-c[Asp-Trp-Arg-Trp-Arg-Lys]-D-Val-D-Phe-NH2 |
| 3607 | TCAM3604 | Arg-Arg-Phe-Arg-Arg-Phe-Phe-Arg-Arg-c[Asp-Trp-Arg-Trp-Arg-Lys]-D-Pro-D-Val-NH2 |
| 3608 | TCAM3605 | Arg-Arg-Phe-Arg-Arg-Phe-Phe-Arg-Arg-c[Asp-Trp-Arg-Trp-Arg-Lys]-D-Phe-D-Val-NH2 |
| 3609 | TCAM3606 | Arg-Arg-Phe-Arg-Arg-Phe-Phe-Arg-Arg-c[Asp-Trp-Arg-Arg-Trp-Lys]-D-Val-D-Pro-NH2 |
| 3610 | TCAM3607 | Arg-Arg-Phe-Arg-Arg-Phe-Phe-Arg-Arg-c[Asp-Trp-Arg-Arg-Trp-Lys]-D-Val-D-Phe-NH2 |
| 3611 | TCAM3608 | Arg-Arg-Phe-Arg-Arg-Phe-Phe-Arg-Arg-c[Asp-Trp-Arg-Arg-Trp-Lys]-D-Pro-D-Val-NH2 |
| 3612 | TCAM3609 | Arg-Arg-Phe-Arg-Arg-Phe-Phe-Arg-Arg-c[Asp-Trp-Arg-Arg-Trp-Lys]-D-Phe-D-Val-NH2 |
| 3613 | TCAM3610 | Arg-Arg-Phe-Arg-Arg-Phe-Phe-Arg-Arg-c[Asp-Arg-Trp-Trp-Arg-Lys]-D-Val-D-Pro-NH2 |
| 3614 | TCAM3611 | Arg-Arg-Phe-Arg-Arg-Phe-Phe-Arg-Arg-c[Asp-Arg-Trp-Trp-Arg-Lys]-D-Val-D-Phe-NH2 |
| 3615 | TCAM3612 | Arg-Arg-Phe-Arg-Arg-Phe-Phe-Arg-Arg-c[Asp-Arg-Trp-Trp-Arg-Lys]-D-Pro-D-Val-NH2 |
| 3616 | TCAM3613 | Arg-Arg-Phe-Arg-Arg-Phe-Phe-Arg-Arg-c[Asp-Arg-Trp-Trp-Arg-Lys]-D-Phe-D-Val-NH2 |
| 3617 | TCAM3614 | Arg-Arg-Phe-Arg-Arg-Phe-Phe-Arg-Arg-c[Asp-Trp-Arg-Trp-Lys]-D-Val-D-Pro-NH2 |
| 3618 | TCAM3615 | Arg-Arg-Phe-Arg-Arg-Phe-Phe-Arg-Arg-c[Asp-Trp-Arg-Trp-Lys]-D-Val-D-Phe-NH2 |
| 3619 | TCAM3616 | Arg-Arg-Phe-Arg-Arg-Phe-Phe-Arg-Arg-c[Asp-Trp-Arg-Trp-Lys]-D-Pro-D-Val-NH2 |
| 3620 | TCAM3617 | Arg-Arg-Phe-Arg-Arg-Phe-Phe-Arg-Arg-c[Asp-Trp-Arg-Trp-Lys]-D-Phe-D-Val-NH2 |
| 3621 | TCAM3618 | Arg-Arg-Phe-Arg-Arg-Phe-Phe-Arg-Arg-c[Asp-Arg-Trp-Arg-Lys]-D-Val-D-Pro-NH2 |
| 3622 | TCAM3619 | Arg-Arg-Phe-Arg-Arg-Phe-Phe-Arg-Arg-c[Asp-Arg-Trp-Arg-Lys]-D-Val-D-Phe-NH2 |
| 3623 | TCAM3620 | Arg-Arg-Phe-Arg-Arg-Phe-Phe-Arg-Arg-c[Asp-Arg-Trp-Arg-Lys]-D-Pro-D-Val-NH2 |
| 3624 | TCAM3621 | Arg-Arg-Phe-Arg-Arg-Phe-Phe-Arg-Arg-c[Asp-Arg-Trp-Arg-Lys]-D-Phe-D-Val-NH2 |
| 3625 | TCAM3622 | Arg-Arg-Phe-Arg-Arg-Phe-Phe-Arg-Arg-c[Asp-His-D-Nal(2')-Arg-Trp-Lys]-D-Val-D-Pro-NH2 |

TABLE 5-continued

Exemplary Anti-microbial peptides

| SEQ NO: | Peptide | Peptide Sequence |
|---|---|---|
| 3626 | TCAM3623 | Arg-Arg-Phe-Arg-Arg-Phe-Phe-Arg-Arg-c[Asp-His-D-Nal(2')-Arg-Trp-Lys]-D-Pro-D-Val-NH2 |
| 3627 | TCAM3624 | Arg-Arg-Phe-Arg-Arg-Phe-Phe-Arg-Arg-c[Asp-His-D-Nal(2')-Arg-Trp-Lys]-D-Val-D-Phe-NH2 |
| 3628 | TCAM3625 | Arg-Arg-Phe-Arg-Arg-Phe-Phe-Arg-Arg-c[Asp-His-D-Nal(2')-Arg-Trp-Lys]-D-Phe-D-Val-NH2 |
| 3629 | TCAM3626 | Arg-Arg-Phe-Arg-Arg-Phe-Phe-Arg-Arg-c[Asp-Pro-D-Nal(2')-Arg-Trp-Lys]-D-Val-D-Pro-NH2 |
| 3630 | TCAM3627 | Arg-Arg-Phe-Arg-Arg-Phe-Phe-Arg-Arg-c[Asp-Pro-D-Nal(2')-Arg-Trp-Lys]-D-Pro-D-Val-NH2 |
| 3631 | TCAM3628 | Arg-Arg-Phe-Arg-Arg-Phe-Phe-Arg-Arg-c[Asp-Pro-D-Nal(2')-Arg-Trp-Lys]-D-Val-D-Phe-NH2 |
| 3632 | TCAM3629 | Arg-Arg-Phe-Arg-Arg-Phe-Phe-Arg-Arg-c[Asp-Pro-D-Nal(2')-Arg-Trp-Lys]-D-Phe-D-Val-NH2 |
| 3633 | TCAM3630 | Arg-Arg-Phe-Arg-Arg-Phe-Phe-Arg-Arg-c[Asp-Arg-Arg-Nal(2')-Arg-Trp-Lys]-D-Val-D-Pro-NH2 |
| 3634 | TCAM3631 | Arg-Arg-Phe-Arg-Arg-Phe-Phe-Arg-Arg-c[Asp-Arg-Arg-Nal(2')-Arg-Trp-Lys]-D-Pro-D-Val-NH2 |
| 3635 | TCAM3632 | Arg-Arg-Phe-Arg-Arg-Phe-Phe-Arg-Arg-c[Asp-Arg-Arg-Nal(2')-Arg-Trp-Lys]-D-Val-D-Phe-NH2 |
| 3636 | TCAM3633 | Arg-Arg-Phe-Arg-Arg-Phe-Phe-Arg-Arg-c[Asp-Arg-Arg-Nal(2')-Arg-Trp-Lys]-D-Phe-D-Val-NH2 |
| 3637 | TCAM3634 | Arg-Arg-Phe-Arg-Arg-Phe-Phe-Arg-Arg-c[Asp-Arg-Arg-Pro-Nal(2')-Arg-Trp-Lys]-D-Val-D-Pro-NH2 |
| 3638 | TCAM3635 | Arg-Arg-Phe-Arg-Arg-Phe-Phe-Arg-Arg-c[Asp-Arg-Arg-Pro-D-Nal(2')-Arg-Trp-Lys]-D-Pro-D-Val-NH2 |
| 3639 | TCAM3636 | Arg-Arg-Phe-Arg-Arg-Phe-Phe-Arg-Arg-c[Asp-Arg-Arg-Pro-D-Nal(2')-Arg-Trp-Lys]-D-Val-D-Phe-NH2 |
| 3640 | TCAM3637 | Arg-Arg-Phe-Arg-Arg-Phe-Phe-Arg-Arg-c[Asp-Arg-Arg-Pro-Nal(2')-Arg-Trp-Lys]-D-Phe-D-Val-NH2 |
| 3641 | TCAM3638 | Arg-Arg-Phe-Arg-Arg-Phe-Phe-Arg-Arg-c[Asp-Arg-D-Nal(2')-Arg-Trp-Lys]-D-Val-D-Pro-NH2 |
| 3642 | TCAM3639 | Arg-Arg-Phe-Arg-Arg-Phe-Phe-Arg-Arg-c[Asp-Arg-D-Nal(2')-Arg-Trp-Lys]-D-Pro-D-Val-NH2 |
| 3643 | TCAM3640 | Arg-Arg-Phe-Arg-Arg-Phe-Phe-Arg-Arg-c[Asp-Arg-D-Nal(2')-Arg-Trp-Lys]-D-Val-D-Phe-NH2 |
| 3644 | TCAM3641 | Arg-Arg-Phe-Arg-Arg-Phe-Phe-Arg-Arg-c[Asp-Arg-D-Nal(2')-Arg-Trp-Lys]-D-Phe-D-Val-NH2 |
| 3645 | TCAM3642 | Arg-Arg-Phe-Arg-Arg-Phe-Phe-Arg-Arg-c[Asp-Arg-Pro-D-Nal(2')-Arg-Trp-Lys]-D-Val-D-Pro-NH2 |
| 3646 | TCAM3643 | Arg-Arg-Phe-Arg-Arg-Phe-Phe-Arg-Arg-c[Asp-Arg-Pro-D-Nal(2')-Arg-Trp-Lys]-D-Pro-D-Val-NH2 |
| 3647 | TCAM3644 | Arg-Arg-Phe-Arg-Arg-Phe-Phe-Arg-Arg-c[Asp-Arg-Pro-D-Nal(2')-Arg-Trp-Lys]-D-Val-D-Phe-NH2 |
| 3648 | TCAM3645 | Arg-Arg-Phe-Arg-Arg-Phe-Phe-Arg-Arg-c[Asp-Arg-Pro-D-Nal(2')-Arg-Trp-Lys]-D-Phe-D-Val-NH2 |
| 3649 | TCAM3646 | Arg-Arg-Phe-Arg-Arg-Phe-Phe-Arg-Arg-Arg-Arg-c[Asp-Pro-D-Nal(2')-Arg-Trp-Lys]-D-Val-D-Pro-NH2 |
| 3650 | TCAM3647 | Arg-Arg-Phe-Arg-Arg-Phe-Phe-Arg-Arg-Arg-Arg-c[Asp-Pro-D-Nal(2')-Arg-Trp-Lys]-D-Pro-D-Val-NH2 |

TABLE 5-continued

Exemplary Anti-microbial peptides

| SEQ NO: | Peptide | Peptide Sequence |
|---|---|---|
| 3651 | TCAM3648 | Arg-Arg-Phe-Arg-Arg-Phe-Phe-Arg-Arg-Arg-Arg-c[Asp-Pro-D-Nal(2')-Arg-Trp-Lys]-D-Val-D-Phe-NH2 |
| 3652 | TCAM3649 | Arg-Arg-Phe-Arg-Arg-Phe-Phe-Arg-Arg-Arg-Arg-c[Asp-Pro-D-Nal(2')-Arg-Trp-Lys]-D-Phe-D-Val-NH2 |
| 3653 | TCAM3650 | Arg-Arg-Phe-Arg-Arg-Phe-Phe-Arg-Arg-Arg-Arg-c[Asp-His-D-Nal(2')-Arg-Trp-Lys]-D-Val-D-Pro-NH2 |
| 3654 | TCAM3651 | Arg-Arg-Phe-Arg-Arg-Phe-Phe-Arg-Arg-Arg-Arg-c[Asp-His-D-Nal(2')-Arg-Trp-Lys]-D-Pro-D-Val-NH2 |
| 3655 | TCAM3652 | Arg-Arg-Phe-Arg-Arg-Phe-Phe-Arg-Arg-Arg-Arg-c[Asp-His-D-Nal(2')-Arg-Trp-Lys]-D-Val-D-Phe-NH2 |
| 3656 | TCAM3653 | Arg-Arg-Phe-Arg-Arg-Phe-Phe-Arg-Arg-Arg-Arg-c[Asp-His-D-Nal(2')-Arg-Trp-Lys]-D-Phe-D-Val-NH2 |
| 3657 | TCAM3654 | Arg-Arg-Phe-Arg-Arg-Phe-Phe-Arg-Arg-c[Asp-Arg-Pro-D-Nal(2')-Arg-Trp-Arg-Lys]-D-Val-D-Pro-NH2 |
| 3658 | TCAM3655 | Arg-Arg-Phe-Arg-Arg-Phe-Phe-Arg-Arg-c[Asp-Arg-Pro-D-Nal(2')-Arg-Trp-Arg-Lys]-D-Pro-D-Val-NH2 |
| 3659 | TCAM3656 | Arg-Arg-Phe-Arg-Arg-Phe-Phe-Arg-Arg-c[Asp-Arg-Pro-D-Nal(2')-Arg-Trp-Arg-Lys]-D-Val-D-Phe-NH2 |
| 3660 | TCAM3657 | Arg-Arg-Phe-Arg-Arg-Phe-Phe-Arg-Arg-c[Asp-Arg-Pro-D-Nal(2')-Arg-Trp-Arg-Lys]-D-Phe-D-Val-NH2 |
| 3661 | TCAM3658 | Arg-Arg-Phe-Arg-Arg-Phe-Phe-Arg-Arg-c[Asp-Arg-His-D-Nal(2')-Arg-Trp-Arg-Lys]-D-Val-D-Pro-NH2 |
| 3662 | TCAM3659 | Arg-Arg-Phe-Arg-Arg-Phe-Phe-Arg-Arg-c[Asp-Arg-His-D-Nal(2')-Arg-Trp-Arg-Lys]-D-Pro-D-Val-NH2 |
| 3663 | TCAM3660 | Arg-Arg-Phe-Arg-Arg-Phe-Phe-Arg-Arg-c[Asp-Arg-His-D-Nal(2')-Arg-Trp-Arg-Lys]-D-Val-D-Phe-NH2 |
| 3664 | TCAM3661 | Arg-Arg-Phe-Arg-Arg-Phe-Phe-Arg-Arg-c[Asp-Arg-His-D-Nal(2')-Arg-Trp-Arg-Lys]-D-Phe-D-Val-NH2 |
| 3665 | TCAM3662 | Arg-Arg-Phe-Arg-Arg-Phe-Phe-Arg-Arg-c[Asp-His-D-Nal(2')-Arg-D-Nal(2')-Lys]-D-Val-D-Phe-NH2 |
| 3666 | TCAM3663 | Arg-Arg-Phe-Arg-Arg-Phe-Phe-Arg-Arg-c[Asp-His-D-Nal(2')-Arg-D-Nal(2')-Lys]-D-Phe-D-Val-NH2 |
| 3667 | TCAM3664 | Arg-Arg-Phe-Arg-Arg-Phe-Phe-Arg-Arg-c[Asp-Pro-D-Nal(2')-Arg-D-Nal(2')-Lys]-D-Val-D-Pro-NH2 |
| 3668 | TCAM3665 | Arg-Arg-Phe-Arg-Arg-Phe-Phe-Arg-Arg-c[Asp-Pro-D-Nal(2')-Arg-D-Nal(2')-Lys]-D-Pro-D-Val-NH2 |
| 3669 | TCAM3666 | Arg-Arg-Phe-Arg-Arg-Phe-Phe-Arg-Arg-c[Asp-Pro-D-Nal(2')-Arg-D-Nal(2')-Lys]-D-Val-D-Phe-NH2 |
| 3670 | TCAM3667 | Arg-Arg-Phe-Arg-Arg-Phe-Phe-Arg-Arg-c[Asp-Pro-D-Nal(2')-Arg-D-Nal(2')-Lys]-D-Phe-D-Val-NH2 |
| 3671 | TCAM3668 | Arg-Arg-Phe-Arg-Arg-Phe-Phe-Arg-Arg-c[Asp-Arg-Arg-D-Nal(2')-Arg-D-Nal(2')-Lys]-D-Val-D-Pro-NH2 |
| 3672 | TCAM3669 | Arg-Arg-Phe-Arg-Arg-Phe-Phe-Arg-Arg-c[Asp-Arg-Arg-D-Nal(2')-Arg-D-Nal(2')-Lys]-D-Pro-D-Val-NH2 |
| 3673 | TCAM3670 | Arg-Arg-Phe-Arg-Arg-Phe-Phe-Arg-Arg-c[Asp-Arg-Arg-D-Nal(2')-Arg-D-Nal(2')-Lys]-D-Val-D-Phe-NH2 |
| 3674 | TCAM3671 | Arg-Arg-Phe-Arg-Arg-Phe-Phe-Arg-Arg-c[Asp-Arg-Arg-D-Nal(2')-Arg-D-Nal(2')-Lys]-D-Phe-D-Val-NH2 |
| 3675 | TCAM3672 | Arg-Arg-Phe-Arg-Arg-Phe-Phe-Arg-Arg-c[Asp-Arg-Arg-Pro-D-Nal(2')-Arg-D-Nal(2')-Lys]-D-Val-D-Pro-NH2 |

TABLE 5-continued

Exemplary Anti-microbial peptides

| SEQ NO: | Peptide | Peptide Sequence |
|---|---|---|
| 3676 | TCAM3673 | Arg-Arg-Phe-Arg-Arg-Phe-Phe-Arg-Arg-c[Asp-Arg-Arg-Pro-D-Nal(2')-Arg-D-Nal(2')-Lys]-D-Pro-D-Val-NH2 |
| 3677 | TCAM3674 | Arg-Arg-Phe-Arg-Arg-Phe-Phe-Arg-Arg-c[Asp-Arg-Arg-Pro-D-Nal(2')-Arg-D-Nal(2')-Lys]-D-Val-D-Phe-NH2 |
| 3678 | TCAM3675 | Arg-Arg-Phe-Arg-Arg-Phe-Phe-Arg-Arg-c[Asp-Arg-Arg-Pro-D-Nal(2')-Arg-D-Nal(2')-Lys]-D-Phe-D-Val-NH2 |
| 3679 | TCAM3676 | Arg-Arg-Phe-Arg-Arg-Phe-Phe-Arg-Arg-c[Asp-Arg-D-Nal(2')-Arg-D-Nal(2')-Lys]-D-Val-D-Pro-NH2 |
| 3680 | TCAM3677 | Arg-Arg-Phe-Arg-Arg-Phe-Phe-Arg-Arg-c[Asp-Arg-D-Nal(2')-Arg-D-Nal(2')-Lys]-D-Pro-D-Val-NH2 |
| 3681 | TCAM3678 | Arg-Arg-Phe-Arg-Arg-Phe-Phe-Arg-Arg-c[Asp-Arg-Nal(2')-Arg-D-Nal(2')-Lys]-D-Val-D-Phe-NH2 |
| 3682 | TCAM3679 | Arg-Arg-Phe-Arg-Arg-Phe-Phe-Arg-Arg-c[Asp-Arg-D-Nal(2')-Arg-D-Nal(2')-Lys]-D-Phe-D-Val-NH2 |
| 3683 | TCAM3680 | Arg-Arg-Phe-Arg-Arg-Phe-Phe-Arg-Arg-c[Asp-Arg-Pro-D-Nal(2')-Arg-D-Nal(2')-Lys]-D-Val-D-Pro-NH2 |
| 3684 | TCAM3681 | Arg-Arg-Phe-Arg-Arg-Phe-Phe-Arg-Arg-c[Asp-Arg-Pro-D-Nal(2')-Arg-D-Nal(2')-Lys]-D-Pro-D-Val-NH2 |
| 3685 | TCAM3682 | Arg-Arg-Phe-Arg-Arg-Phe-Phe-Arg-Arg-c[Asp-Arg-Pro-D-Nal(2')-Arg-D-Nal(2')-Lys]-D-Val-D-Phe-NH2 |
| 3686 | TCAM3683 | Arg-Arg-Phe-Arg-Arg-Phe-Phe-Arg-Arg-c[Asp-Arg-Pro-D-Nal(2')-Arg-D-Nal(2')-Lys]-D-Phe-D-Val-NH2 |
| 3687 | TCAM3684 | Arg-Arg-Phe-Arg-Arg-Phe-Phe-Arg-Arg-c[Asp-Arg-His-D-Nal(2')-Arg-D-Nal(2')-Lys]-D-Val-D-Pro-NH2 |
| 3688 | TCAM3685 | Arg-Arg-Phe-Arg-Arg-Phe-Phe-Arg-Arg-c[Asp-Arg-His-D-Nal(2')-Arg-D-Nal(2')-Lys]-D-Pro-D-Val-NH2 |
| 3689 | TCAM3686 | Arg-Arg-Phe-Arg-Arg-Phe-Phe-Arg-Arg-c[Asp-Arg-His-Nal(2')-Arg-D-Nal(2')-Lys]-D-Val-D-Phe-NH2 |
| 3690 | TCAM3687 | Arg-Arg-Phe-Arg-Arg-Phe-Phe-Arg-Arg-c[Asp-Arg-His-Nal(2')-Arg-D-Nal(2')-Lys]-D-Phe-D-Val-NH2 |
| 3691 | TCAM3688 | Arg-Arg-Phe-Arg-Arg-Phe-Phe-Arg-Arg-c[Asp-Arg-D-D-Nal(2')-Arg-D-Nal(2')-Arg-Lys]-D-Val-D-Pro-NH2 |
| 3692 | TCAM3689 | Arg-Arg-Phe-Arg-Arg-Phe-Phe-Arg-Arg-c[Asp-Arg-D-Nal(2')-Arg-D-Nal(2')-Arg-Lys]-D-Pro-D-Val-NH2 |
| 3693 | TCAM3690 | Arg-Arg-Phe-Arg-Arg-Phe-Phe-Arg-Arg-c[Asp-Arg-D-Nal(2')-Arg-D-Nal(2')-Arg-Lys]-D-Val-D-Phe-NH2 |
| 3694 | TCAM3691 | Arg-Arg-Phe-Arg-Arg-Phe-Phe-Arg-Arg-c[Asp-Arg-D-Nal(2')-Arg-D-Nal(2')-Arg-Lys]-D-Phe-D-Val-NH2 |
| 3695 | TCAM3692 | Arg-Arg-Phe-Arg-Arg-Phe-Phe-Arg-Arg-c[Asp-Arg-Pro-D-Nal(2')-Arg-D-Nal(2')-Arg-Lys]-D-Val-D-Pro-NH2 |
| 3696 | TCAM3693 | Arg-Arg-Phe-Arg-Arg-Phe-Phe-Arg-Arg-c[Asp-Arg-Pro-D-Nal(2')-Arg-D-Nal(2')-Arg-Lys]-D-Pro-D-Val-NH2 |
| 3697 | TCAM3694 | Arg-Arg-Phe-Arg-Arg-Phe-Phe-Arg-Arg-c[Asp-Arg-Pro-D-Nal(2')-Arg-D-Nal(2')-Arg-Lys]-D-Val-D-Phe-NH2 |
| 3698 | TCAM3695 | Arg-Arg-Phe-Arg-Arg-Phe-Phe-Arg-Arg-c[Asp-Arg-Pro-D-Nal(2')-Arg-D-Nal(2')-Arg-Lys]-D-Phe-D-Val-NH2 |
| 3699 | TCAM3696 | Arg-Arg-Phe-Arg-Arg-Phe-Phe-Arg-Arg-c[Asp-Arg-His-D-Nal(2')-Arg-D-Nal(2')-Arg-Lys]-D-Val-D-Pro-NH2 |
| 3700 | TCAM3697 | Arg-Arg-Phe-Arg-Arg-Phe-Phe-Arg-Arg-c[Asp-Arg-His-D-Nal(2')-Arg-D-Nal(2')-Arg-Lys]-D-Pro-D-Val-NH2 |

TABLE 5-continued

Exemplary Anti-microbial peptides

| SEQ NO: | Peptide | Peptide Sequence |
|---|---|---|
| 3701 | TCAM3698 | Arg-Arg-Phe-Arg-Arg-Phe-Phe-Arg-Arg-c[Asp-Arg-His-D-Nal(2')-Arg-D-Nal(2')-Arg-Lys]-D-Val-D-Phe-NH2 |
| 3702 | TCAM3699 | Arg-Arg-Phe-Arg-Arg-Phe-Phe-Arg-Arg-c[Asp-Arg-His-D-Nal(2')-Arg-D-Nal(2')-Arg-Lys]-D-Phe-D-Val-NH2 |
| 3703 | TCAM3700 | Arg-Arg-Phe-Arg-Arg-Phe-Phe-Arg-Arg-Arg-Arg-c[Asp-Pro-D-Nal(2')-Arg-D-Nal(2')-Lys]-D-Val-D-Pro-NH2 |
| 3704 | TCAM3701 | Arg-Arg-Phe-Arg-Arg-Phe-Phe-Arg-Arg-Arg-Arg-c[Asp-Pro-D-Nal(2')-Arg-D-Nal(2')-Lys]-D-Pro-D-Val-NH2 |
| 3705 | TCAM3702 | Arg-Arg-Phe-Arg-Arg-Phe-Phe-Arg-Arg-Arg-c[Asp-Pro-D-Nal(2')-Arg-D-Nal(2')-Lys]-D-Val-D-Phe-NH2 |
| 3706 | TCAM3703 | Arg-Arg-Phe-Arg-Arg-Phe-Phe-Arg-Arg-Arg-c[Asp-Pro-D-Nal(2')-Arg-D-Nal(2')-Lys]-D-Phe-D-Val-NH2 |
| 3707 | TCAM3704 | Arg-Arg-Phe-Arg-Arg-Phe-Phe-Arg-Arg-Arg-c[Asp-His-D-Nal(2')-Arg-D-Nal(2')-Lys]-D-Val-D-Pro-NH2 |
| 3708 | TCAM3705 | Arg-Arg-Phe-Arg-Arg-Phe-Phe-Arg-Arg-Arg-c[Asp-His-D-Nal(2')-Arg-D-Nal(2')-Lys]-D-Pro-D-Val-NH2 |
| 3709 | TCAM3706 | Arg-Arg-Phe-Arg-Arg-Phe-Phe-Arg-Arg-Arg-c[Asp-His-D-Nal(2')-Arg-D-Nal(2')-Lys]-D-Val-D-Phe-NH2 |
| 3710 | TCAM3707 | Arg-Arg-Phe-Arg-Arg-Phe-Phe-Arg-Arg-Arg-c[Asp-His-D-Nal(2')-Arg-D-Nal(2')-Lys]-D-Phe-D-Val-NH2 |
| 3711 | TCAM3708 | Arg-Arg-Phe-Arg-Arg-Phe-Phe-Arg-Arg-c[Asp-Arg-Pro-D-Nal(2')-Arg-D-Nal(2')-Arg-Lys]-D-Val-D-Pro-NH2 |
| 3712 | TCAM3709 | Arg-Arg-Phe-Arg-Arg-Phe-Phe-Arg-Arg-c[Asp-Arg-Pro-D-Nal(2')-Arg-D-Nal(2')-Arg-Lys]-D-Pro-D-Val-NH2 |
| 3713 | TCAM3710 | Arg-Arg-Phe-Arg-Arg-Phe-Phe-Arg-Arg-c[Asp-Arg-Pro-D-Nal(2')-Arg-D-Nal(2')-Arg-Lys]-D-Val-D-Phe-NH2 |
| 3714 | TCAM3711 | Arg-Arg-Phe-Arg-Arg-Phe-Phe-Arg-Arg-c[Asp-Arg-Pro-D-Nal(2')-Arg-D-Nal(2')-Arg-Lys]-D-Phe-D-Val-NH2 |
| 3715 | TCAM3712 | Arg-Arg-Phe-Arg-Arg-Phe-Phe-Arg-Arg-c[Asp-Arg-His-D-Nal(2')-Arg-D-Nal(2')-Arg-Lys]-D-Val-D-Pro-NH2 |
| 3716 | TCAM3713 | Arg-Arg-Phe-Arg-Arg-Phe-Phe-Arg-Arg-c[Asp-Arg-His-D-Nal(2')-Arg-D-Nal(2')-Arg-Lys]-D-Pro-D-Val-NH2 |
| 3717 | TCAM3714 | Arg-Arg-Phe-Arg-Arg-Phe-Phe-Arg-Arg-c[Asp-Arg-His-D-Nal(2')-Arg-D-Nal(2')-Arg-Lys]-D-Val-D-Phe-NH2 |
| 3718 | TCAM3715 | Arg-Arg-Phe-Arg-Arg-Phe-Phe-Arg-Arg-c[Asp-Arg-His-D-Nal(2')-Arg-D-Nal(2')-Arg-Lys]-D-Phe-D-Val-NH2 |
| 3719 | TCAM3716 | Arg-Arg-Phe-Arg-Arg-Phe-Phe-Arg-Arg-c[Asp-His-D-Nal(2')-Arg-Trp-Lys]-Arg-Arg-D-Val-D-Pro-NH2 |
| 3720 | TCAM3717 | Arg-Arg-Phe-Arg-Arg-Phe-Phe-Arg-Arg-c[Asp-His-D-Nal(2')-Arg-Trp-Lys]-Arg-Arg-D-Pro-D-Val-NH2 |
| 3721 | TCAM3718 | Arg-Arg-Phe-Arg-Arg-Phe-Phe-Arg-Arg-c[Asp-His-D-Nal(2')-Arg-Trp-Lys]-Arg-Arg-D-Val-D-Phe-NH2 |
| 3722 | TCAM3719 | Arg-Arg-Phe-Arg-Arg-Phe-Phe-Arg-Arg-c[Asp-His-D-Nal(2')-Arg-Trp-Lys]-Arg-Arg-D-Phe-D-Val-NH2 |
| 3723 | TCAM3720 | Arg-Arg-Phe-Arg-Arg-Phe-Phe-Arg-Arg-c[Asp-Pro-D-Nal(2')-Arg-Trp-Lys]-Arg-Arg-D-Val-D-Pro-NH2 |
| 3724 | TCAM3721 | Arg-Arg-Phe-Arg-Arg-Phe-Phe-Arg-Arg-c[Asp-Pro-D-Nal(2')-Arg-Trp-Lys]-Arg-Arg-D-Pro-D-Val-NH2 |
| 3725 | TCAM3722 | Arg-Arg-Phe-Arg-Arg-Phe-Phe-Arg-Arg-c[Asp-Pro-D-Nal(2')-Arg-Trp-Lys]-Arg-Arg-D-Val-D-Phe-NH2 |

TABLE 5-continued

Exemplary Anti-microbial peptides

| SEQ NO: | Peptide | Peptide Sequence |
|---|---|---|
| 3726 | TCAM3723 | Arg-Arg-Phe-Arg-Arg-Phe-Phe-Arg-Arg-c[Asp-Pro-D-Nal(2')-Arg-Trp-Lys]-Arg-Arg-D-Phe-D-Val-NH2 |

Anti-biofilm peptide ABF7 linked to anti-microbial peptides

| SEQ NO: | Peptide | Peptide Sequence |
|---|---|---|
| 3727 | TCAM3724 | Lys-Lys-Phe-Phe-Lys-Lys-Leu-Lys-c[Asp-Pro-Arg-Arg-Trp-Trp-Arg-Phe-Lys]-D-Val-D-Pro-NH2 |
| 3728 | TCAM3725 | Lys-Lys-Phe-Phe-Lys-Lys-Leu-Lys-c[Asp-Pro-Arg-Arg-Trp-Trp-Arg-Phe-Lys]-D-Val-D-Phe-NH2 |
| 3729 | TCAM3726 | Lys-Lys-Phe-Phe-Lys-Lys-Leu-Lys-c[Asp-Pro-Arg-Arg-Trp-Trp-Arg-Phe-Lys]-D-Pro-D-Val-NH2 |
| 3730 | TCAM3727 | Lys-Lys-Phe-Phe-Lys-Lys-Leu-Lys-c[Asp-Pro-Arg-Arg-Trp-Trp-Arg-Phe-Lys]-D-Phe-D-Val-NH2 |
| 3731 | TCAM3728 | Lys-Lys-Phe-Phe-Lys-Lys-Leu-Lys-c[Asp-Pro-Arg-Arg-Trp-Trp-Tyr-Phe-Lys]-D-Val-D-Pro-NH2 |
| 3732 | TCAM3729 | Lys-Lys-Phe-Phe-Lys-Lys-Leu-Lys-c[Asp-Pro-Arg-Arg-Trp-Trp-Tyr-Phe-Lys]-D-Val-D-Phe-NH2 |
| 3733 | TCAM3730 | Lys-Lys-Phe-Phe-Lys-Lys-Leu-Lys-c[Asp-Pro-Arg-Arg-Trp-Trp-Tyr-Phe-Lys]-D-Pro-D-Val-NH2 |
| 3734 | TCAM3731 | Lys-Lys-Phe-Phe-Lys-Lys-Leu-Lys-c[Asp-Pro-Arg-Arg-Trp-Trp-Tyr-Phe-Lys]-D-Phe-D-Val-NH2 |
| 3735 | TCAM3732 | Lys-Lys-Phe-Phe-Lys-Lys-Leu-Lys-c[Asp-Pro-Arg-Arg-Tyr-Tyr-Arg-Phe-Lys]-D-Val-D-Pro-NH2 |
| 3736 | TCAM3733 | Lys-Lys-Phe-Phe-Lys-Lys-Leu-Lys-c[Asp-Pro-Arg-Arg-Tyr-Tyr-Arg-Phe-Lys]-D-Val-D-Phe-NH2 |
| 3737 | TCAM3734 | Lys-Lys-Phe-Phe-Lys-Lys-Leu-Lys-c[Asp-Pro-Arg-Arg-Tyr-Tyr-Arg-Phe-Lys]-D-Pro-D-Val-NH2 |
| 3738 | TCAM3735 | Lys-Lys-Phe-Phe-Lys-Lys-Leu-Lys-c[Asp-Pro-Arg-Arg-Tyr-Tyr-Arg-Phe-Lys]-D-Phe-D-Val-NH2 |
| 3739 | TCAM3736 | Lys-Lys-Phe-Phe-Lys-Lys-Leu-Lys-c[Asp-Pro-Arg-Arg-Nal-Nal-Arg-Phe-Lys]-D-Val-D-Pro-NH2 |
| 3740 | TCAM3737 | Lys-Lys-Phe-Phe-Lys-Lys-Leu-Lys-c[Asp-Pro-Arg-Arg-Nal-Nal-Arg-Phe-Lys]-D-Val-D-Phe-NH2 |
| 3741 | TCAM3738 | Lys-Lys-Phe-Phe-Lys-Lys-Leu-Lys-c[Asp-Pro-Arg-Arg-Nal-Nal-Arg-Phe-Lys]-D-Pro-D-Val-NH2 |
| 3742 | TCAM3739 | Lys-Lys-Phe-Phe-Lys-Lys-Leu-Lys-c[Asp-Pro-Arg-Arg-Nal-Nal-Arg-Phe-Lys]-D-Phe-D-Val-NH2 |
| 3743 | TCAM3740 | Lys-Lys-Phe-Phe-Lys-Lys-Leu-Lys-c[Asp-Pro-Arg-Arg-Leu-Trp-Leu-Trp-Lys]-D-Val-D-Pro-NH2 |
| 3744 | TCAM3741 | Lys-Lys-Phe-Phe-Lys-Lys-Leu-Lys-c[Asp-Pro-Arg-Arg-Leu-Trp-Leu-Trp-Lys]-D-Val-D-Phe-NH2 |
| 3745 | TCAM3742 | Lys-Lys-Phe-Phe-Lys-Lys-Leu-Lys-c[Asp-Pro-Arg-Arg-Leu-Trp-Leu-Trp-Lys]-D-Pro-D-Val-NH2 |
| 3746 | TCAM3743 | Lys-Lys-Phe-Phe-Lys-Lys-Leu-Lys-c[Asp-Pro-Arg-Arg-Leu-Trp-Leu-Trp-Lys]-D-Phe-D-Val-NH2 |
| 3747 | TCAM3744 | Lys-Lys-Phe-Phe-Lys-Lys-Leu-Lys-c[Asp-Pro-Arg-Arg-Leu-Trp-Leu-Trp-Lys]-D-Val-D-Pro-NH2 |
| 3748 | TCAM3745 | Lys-Lys-Phe-Phe-Lys-Lys-Leu-Lys-c[Asp-Pro-Arg-Arg-Leu-Trp-Leu-Trp-Lys]-D-Val-D-Phe-NH2 |
| 3749 | TCAM3746 | Lys-Lys-Phe-Phe-Lys-Lys-Leu-Lys-c[Asp-Pro-Arg-Arg-Leu-Trp-Leu-Trp-Lys]-D-Pro-D-Val-NH2 |

TABLE 5-continued

Exemplary Anti-microbial peptides

| SEQ NO: | Peptide | Peptide Sequence |
|---|---|---|
| 3750 | TCAM3747 | Lys-Lys-Phe-Phe-Lys-Lys-Leu-Lys-c[Asp-Pro-Arg-Arg-Leu-Trp-Leu-Trp-Lys]-D-Phe-D-Val-NH2 |
| 3751 | TCAM3748 | Lys-Lys-Phe-Phe-Lys-Lys-Leu-Lys-c[Asp-Arg-Arg-Arg-Trp-Leu-Trp-Leu-Trp-Lys]-D-Val-D-Pro-NH2 |
| 3752 | TCAM3749 | Lys-Lys-Phe-Phe-Lys-Lys-Leu-Lys-c[Asp-Pro-Arg-Arg-Arg-Trp-Leu-Trp-Leu-Trp-Lys]-D-Val-D-Phe-NH2 |
| 3753 | TCAM3750 | Lys-Lys-Phe-Phe-Lys-Lys-Leu-Lys-c[Asp-Pro-Arg-Arg-Arg-Trp-Leu-Trp-Leu-Trp-Lys]-D-Pro-D-Val-NH2 |
| 3754 | TCAM3751 | Lys-Lys-Phe-Phe-Lys-Lys-Leu-Lys-c[Asp-Pro-Arg-Arg-Arg-Trp-Leu-Trp-Leu-Trp-Lys]-D-Phe-D-Val-NH2 |
| 3755 | TCAM3752 | Lys-Lys-Phe-Phe-Lys-Lys-Leu-Lys-c[Asp-Pro-Arg-Gln-Arg-Arg-Trp-Leu-Trp-Leu-Trp-Lys]-D-Val-D-Pro-NH2 |
| 3756 | TCAM3753 | Lys-Lys-Phe-Phe-Lys-Lys-Leu-Lys-c[Asp-Pro-Arg-Gln-Arg-Arg-Trp-Leu-Trp-Leu-Trp-Lys]-D-Val-D-Phe-NH2 |
| 3757 | TCAM3754 | Lys-Lys-Phe-Phe-Lys-Lys-Leu-Lys-c[Asp-Pro-Arg-Gln-Arg-Arg-Trp-Leu-Trp-Leu-Trp-Lys]-D-Pro-D-Val-NH2 |
| 3758 | TCAM3755 | Lys-Lys-Phe-Phe-Lys-Lys-Leu-Lys-c[Asp-Pro-Arg-Gln-Arg-Arg-Trp-Leu-Trp-Leu-Trp-Lys]-D-Phe-D-Val-NH2 |
| 3759 | TCAM3756 | Lys-Lys-Phe-Phe-Lys-Lys-Leu-Lys-c[Asp-Pro-Trp-Arg-Trp-Trp-Arg-Arg-Lys]-D-Val-D-Phe-NH2 |
| 3760 | TCAM3757 | Lys-Lys-Phe-Phe-Lys-Lys-Leu-Lys-c[Asp-Pro-Trp-Arg-Trp-Trp-Arg-Arg-Lys]-D-Pro-D-Val-NH2 |
| 3761 | TCAM3758 | Lys-Lys-Phe-Phe-Lys-Lys-Leu-Lys-c[Asp-Pro-Trp-Arg-Trp-Trp-Arg-Arg-Lys]-D-Phe-D-Val-NH2 |
| 3762 | TCAM3759 | Lys-Lys-Phe-Phe-Lys-Lys-Leu-Lys-c[Asp-Pro-Trp-Trp-Arg-Arg-Trp-Trp-Arg-Arg-Lys]-D-Val-D-Pro-NH2 |
| 3763 | TCAM3760 | Lys-Lys-Phe-Phe-Lys-Lys-Leu-Lys-c[Asp-Pro-Trp-Trp-Arg-Arg-Trp-Trp-Arg-Arg-Lys]-D-Val-D-Phe-NH2 |
| 3764 | TCAM3761 | Lys-Lys-Phe-Phe-Lys-Lys-Leu-Lys-c[Asp-Pro-Trp-Trp-Arg-Arg-Trp-Trp-Arg-Arg-Lys]-D-Pro-D-Val-NH2 |
| 3765 | TCAM3762 | Lys-Lys-Phe-Phe-Lys-Lys-Leu-Lys-c[Asp-Pro-Trp-Trp-Arg-Arg-Trp-Trp-Arg-Arg-Lys]-D-Phe-D-Val-NH2 |
| 3766 | TCAM3763 | Lys-Lys-Phe-Phe-Lys-Lys-Leu-Lys-c[Asp-Pro-Trp-Arg-Trp-Arg-Trp-Arg-Lys]-D-Val-D-Pro-NH2 |
| 3767 | TCAM3764 | Lys-Lys-Phe-Phe-Lys-Lys-Leu-Lys-c[Asp-Pro-Trp-Arg-Trp-Arg-Trp-Arg-Lys]-D-Val-D-Phe-NH2 |
| 3768 | TCAM3765 | Lys-Lys-Phe-Phe-Lys-Lys-Leu-Lys-c[Asp-Pro-Trp-Arg-Trp-Arg-Trp-Arg-Lys]-D-Pro-D-Val-NH2 |
| 3769 | TCAM3766 | Lys-Lys-Phe-Phe-Lys-Lys-Leu-Lys-c[Asp-Pro-Trp-Arg-Trp-Arg-Trp-Arg-Lys]-D-Phe-D-Val-NH2 |
| 3770 | TCAM3767 | Lys-Lys-Phe-Phe-Lys-Lys-Leu-Lys-c[Asp-Pro-Arg-Trp-Arg-Trp-Arg-Trp-Lys]-D-Val-D-Pro-NH2 |
| 3771 | TCAM3768 | Lys-Lys-Phe-Phe-Lys-Lys-Leu-Lys-c[Asp-Pro-Arg-Trp-Arg-Trp-Arg-Trp-Lys]-D-Val-D-Phe-NH2 |
| 3772 | TCAM3769 | Lys-Lys-Phe-Phe-Lys-Lys-Leu-Lys-c[Asp-Pro-Arg-Trp-Arg-Trp-Arg-Trp-Lys]-D-Pro-D-Val-NH2 |
| 3773 | TCAM3770 | Lys-Lys-Phe-Phe-Lys-Lys-Leu-Lys-c[Asp-Pro-Arg-Trp-Arg-Trp-Arg-Trp-Lys]-D-Phe-D-Val-NH2 |
| 3774 | TCAM3771 | Lys-Lys-Phe-Phe-Lys-Lys-Leu-Lys-c[Asp-Pro-Arg-Trp-Trp-Arg-Arg-Lys]-D-Val-D-Pro-NH2 |

TABLE 5-continued

Exemplary Anti-microbial peptides

| SEQ NO: | Peptide | Peptide Sequence |
|---|---|---|
| 3775 | TCAM3772 | Lys-Lys-Phe-Phe-Lys-Lys-Leu-Lys-c[Asp-Pro-Arg-Trp-Trp-Arg-Arg-Lys]-D-Val-D-Phe-NH2 |
| 3776 | TCAM3773 | Lys-Lys-Phe-Phe-Lys-Lys-Leu-Lys-c[Asp-Pro-Arg-Trp-Trp-Arg-Arg-Lys]-D-Pro-D-Val-NH2 |
| 3777 | TCAM3774 | Lys-Lys-Phe-Phe-Lys-Lys-Leu-Lys-c[Asp-Pro-Arg-Trp-Trp-Arg-Arg-Lys]-D-Phe-D-Val-NH2 |
| 3778 | TCAM3775 | Lys-Lys-Phe-Phe-Lys-Lys-Leu-Lys-c[Asp-Pro-Trp-Trp-Arg-Arg-Trp-Lys]-D-Val-D-Pro-NH2 |
| 3779 | TCAM3776 | Lys-Lys-Phe-Phe-Lys-Lys-Leu-Lys-c[Asp-Pro-Trp-Trp-Arg-Arg-Trp-Lys]-D-Val-D-Phe-NH2 |
| 3780 | TCAM3777 | Lys-Lys-Phe-Phe-Lys-Lys-Leu-Lys-c[Asp-Pro-Trp-Trp-Arg-Arg-Trp-Lys]-D-Pro-D-Val-NH2 |
| 3781 | TCAM3778 | Lys-Lys-Phe-Phe-Lys-Lys-Leu-Lys-c[Asp-Pro-Trp-Trp-Arg-Arg-Trp-Lys]-D-Phe-D-Val-NH2 |
| 3782 | TCAM3779 | Lys-Lys-Phe-Phe-Lys-Lys-Leu-Lys-c[Asp-Pro-Trp-Arg-Trp-Arg-Trp-Lys]-D-Val-D-Pro-NH2 |
| 3783 | TCAM3780 | Lys-Lys-Phe-Phe-Lys-Lys-Leu-Lys-c[Asp-Pro-Trp-Arg-Trp-Arg-Trp-Lys]-D-Val-D-Phe-NH2 |
| 3784 | TCAM3781 | Lys-Lys-Phe-Phe-Lys-Lys-Leu-Lys-c[Asp-Pro-Trp-Arg-Trp-Arg-Trp-Lys]-D-Pro-D-Val-NH2 |
| 3785 | TCAM3782 | Lys-Lys-Phe-Phe-Lys-Lys-Leu-Lys-c[Asp-Pro-Trp-Arg-Trp-Arg-Trp-Lys]-D-Phe-D-Val-NH2 |
| 3786 | TCAM3783 | Lys-Lys-Phe-Phe-Lys-Lys-Leu-Lys-c[Asp-Pro-Arg-Trp-Arg-Trp-Arg-Lys]-D-Val-D-Pro-NH2 |
| 3787 | TCAM3784 | Lys-Lys-Phe-Phe-Lys-Lys-Leu-Lys-c[Asp-Pro-Arg-Trp-Arg-Trp-Arg-Lys]-D-Val-D-Phe-NH2 |
| 3788 | TCAM3785 | Lys-Lys-Phe-Phe-Lys-Lys-Leu-Lys-c[Asp-Pro-Arg-Trp-Arg-Trp-Arg-Lys]-D-Pro-D-Val-NH2 |
| 3789 | TCAM3786 | Lys-Lys-Phe-Phe-Lys-Lys-Leu-Lys-c[Asp-Pro-Arg-Trp-Arg-Trp-Arg-Lys]-D-Phe-D-Val-NH2 |
| 3790 | TCAM3787 | Lys-Lys-Phe-Phe-Lys-Lys-Leu-Lys-c[Asp-Pro-Trp-Arg-Tyr-Arg-Trp-Lys]-D-Val-D-Pro-NH2 |
| 3791 | TCAM3788 | Lys-Lys-Phe-Phe-Lys-Lys-Leu-Lys-c[Asp-Pro-Trp-Arg-Tyr-Arg-Trp-Lys]-D-Val-D-Phe-NH2 |
| 3792 | TCAM3789 | Lys-Lys-Phe-Phe-Lys-Lys-Leu-Lys-c[Asp-Pro-Trp-Arg-Tyr-Arg-Trp-Lys]-D-Pro-D-Val-NH2 |
| 3793 | TCAM3790 | Lys-Lys-Phe-Phe-Lys-Lys-Leu-Lys-c[Asp-Pro-Trp-Arg-Tyr-Arg-Trp-Lys]-D-Phe-D-Val-NH2 |
| 3794 | TCAM3791 | Lys-Lys-Phe-Phe-Lys-Lys-Leu-Lys-c[Asp-Pro-Trp-Arg-Trp-Arg-Tyr-Lys]-D-Val-D-Pro-NH2 |
| 3795 | TCAM3792 | Lys-Lys-Phe-Phe-Lys-Lys-Leu-Lys-c[Asp-Pro-Trp-Arg-Trp-Arg-Tyr-Lys]-D-Val-D-Phe-NH2 |
| 3796 | TCAM3793 | Lys-Lys-Phe-Phe-Lys-Lys-Leu-Lys-c[Asp-Pro-Trp-Arg-Trp-Arg-Tyr-Lys]-D-Pro-D-Val-NH2 |
| 3797 | TCAM3794 | Lys-Lys-Phe-Phe-Lys-Lys-Leu-Lys-c[Asp-Pro-Trp-Arg-Trp-Arg-Tyr-Lys]-D-Phe-D-Val-NH2 |
| 3798 | TCAM3795 | Lys-Lys-Phe-Phe-Lys-Lys-Leu-Lys-c[Asp-Pro-Trp-Arg-Trp-Arg-Lys]-D-Val-D-Pro-NH2 |
| 3799 | TCAM3796 | Lys-Lys-Phe-Phe-Lys-Lys-Leu-Lys-c[Asp-Pro-Trp-Arg-Trp-Arg-Lys]-D-Val-D-Phe-NH2 |
| 3800 | TCAM3797 | Lys-Lys-Phe-Phe-Lys-Lys-Leu-Lys-c[Asp-Pro-Trp-Arg-Trp-Arg-Lys]-D-Pro-D-Val-NH2 |

TABLE 5-continued

Exemplary Anti-microbial peptides

| SEQ NO: | Peptide | Peptide Sequence |
|---|---|---|
| 3801 | TCAM3798 | Lys-Lys-Phe-Phe-Lys-Lys-Leu-Lys-c[Asp-Pro-Trp-Arg-Trp-Arg-Lys]-D-Phe-D-Val-NH2 |
| 3802 | TCAM3799 | Lys-Lys-Phe-Phe-Lys-Lys-Leu-Lys-c[Asp-Pro-Trp-Arg-Arg-Trp-Lys]-D-Val-D-Pro-NH2 |
| 3803 | TCAM3800 | Lys-Lys-Phe-Phe-Lys-Lys-Leu-Lys-c[Asp-Pro-Trp-Arg-Arg-Trp-Lys]-D-Val-D-Phe-NH2 |
| 3804 | TCAM3801 | Lys-Lys-Phe-Phe-Lys-Lys-Leu-Lys-c[Asp-Pro-Trp-Arg-Arg-Trp-Lys]-D-Pro-D-Val-NH2 |
| 3805 | TCAM3802 | Lys-Lys-Phe-Phe-Lys-Lys-Leu-Lys-c[Asp-Pro-Trp-Arg-Arg-Trp-Lys]-D-Phe-D-Val-NH2 |
| 3806 | TCAM3803 | Lys-Lys-Phe-Phe-Lys-Lys-Leu-Lys-c[Asp-Pro-Arg-Trp-Trp-Arg-Lys]-D-Val-D-Pro-NH2 |
| 3807 | TCAM3804 | Lys-Lys-Phe-Phe-Lys-Lys-Leu-Lys-c[Asp-Pro-Arg-Trp-Trp-Arg-Lys]-D-Val-D-Phe-NH2 |
| 3808 | TCAM3805 | Lys-Lys-Phe-Phe-Lys-Lys-Leu-Lys-c[Asp-Pro-Arg-Trp-Trp-Arg-Lys]-D-Pro-D-Val-NH2 |
| 3809 | TCAM3806 | Lys-Lys-Phe-Phe-Lys-Lys-Leu-Lys-c[Asp-Pro-Arg-Trp-Trp-Arg-Lys]-D-Phe-D-Val-NH2 |
| 3810 | TCAM3807 | Lys-Lys-Phe-Phe-Lys-Lys-Leu-Lys-c[Asp-Pro-Trp-Arg-Trp-Lys]-D-Val-D-Pro-NH2 |
| 3811 | TCAM3808 | Lys-Lys-Phe-Phe-Lys-Lys-Leu-Lys-c[Asp-Pro-Trp-Arg-Trp-Lys]-D-Val-D-Phe-NH2 |
| 3812 | TCAM3809 | Lys-Lys-Phe-Phe-Lys-Lys-Leu-Lys-c[Asp-Pro-Trp-Arg-Trp-Lys]-D-Pro-D-Val-NH2 |
| 3813 | TCAM3810 | Lys-Lys-Phe-Phe-Lys-Lys-Leu-Lys-c[Asp-Pro-Trp-Arg-Trp-Lys]-D-Phe-D-Val-NH2 |
| 3814 | TCAM3811 | Lys-Lys-Phe-Phe-Lys-Lys-Leu-Lys-c[Asp-Pro-Arg-Trp-Arg-Lys]-D-Val-D-Pro-NH2 |
| 3815 | TCAM3812 | Lys-Lys-Phe-Phe-Lys-Lys-Leu-Lys-c[Asp-Pro-Arg-Trp-Arg-Lys]-D-Val-D-Phe-NH2 |
| 3816 | TCAM3813 | Lys-Lys-Phe-Phe-Lys-Lys-Leu-Lys-c[Asp-Pro-Arg-Trp-Arg-Lys]-D-Pro-D-Val-NH2 |
| 3817 | TCAM3814 | Lys-Lys-Phe-Phe-Lys-Lys-Leu-Lys-c[Asp-Pro-Arg-Trp-Arg-Lys]-D-Phe-D-Val-NH2 |
| 3818 | TCAM3815 | -Lys-Lys-Phe-Phe-Lys-Lys-Leu-Lys-c[Asp-Arg-Arg-Trp-Trp-Arg-Phe-Lys]-D-Val-D-Pro-NH2 |
| 3819 | TCAM3816 | Lys-Lys-Phe-Phe-Lys-Lys-Leu-Lys-c[Asp-Arg-Arg-Trp-Trp-Arg-Phe-Lys]-D-Val-D-Phe-NH2 |
| 3820 | TCAM3817 | Lys-Lys-Phe-Phe-Lys-Lys-Leu-Lys-c[Asp-Arg-Arg-Trp-Trp-Arg-Phe-Lys]-D-Pro-D-Val-NH2 |
| 3821 | TCAM3818 | Lys-Lys-Phe-Phe-Lys-Lys-Leu-Lys-c[Asp-Arg-Arg-Trp-Trp-Arg-Phe-Lys]-D-Phe-D-Val-NH2 |
| 3822 | TCAM3819 | Lys-Lys-Phe-Phe-Lys-Lys-Leu-Lys-c[Asp-Arg-Arg-Trp-Trp-Arg-Phe-Lys]-D-Val-D-Pro-NH2 |
| 3823 | TCAM3820 | Lys-Lys-Phe-Phe-Lys-Lys-Leu-Lys-c[Asp-Arg-Arg-Trp-Trp-Arg-Phe-Lys]-D-Val-D-Phe-NH2 |
| 3824 | TCAM3821 | Lys-Lys-Phe-Phe-Lys-Lys-Leu-Lys-c[Asp-Arg-Arg-Trp-Trp-Arg-Phe-Lys]-D-Pro-D-Val-NH2 |
| 3825 | TCAM3822 | Lys-Lys-Phe-Phe-Lys-Lys-Leu-Lys-c[Asp-Arg-Arg-Trp-Trp-Arg-Phe-Lys]-D-Phe-D-Val-NH2 |
| 3826 | TCAM3823 | Lys-Lys-Phe-Phe-Lys-Lys-Leu-Lys-c[Asp-Arg-Arg-Tyr-Tyr-Arg-Phe-Lys]-D-Val-D-Pro-NH2 |
| 3827 | TCAM3824 | Lys-Lys-Phe-Phe-Lys-Lys-Leu-Lys-c[Asp-Arg-Arg-Tyr-Tyr-Arg-Phe-Lys]-D-Val-D-Phe-NH2 |
| 3828 | TCAM3825 | Lys-Lys-Phe-Phe-Lys-Lys-Leu-Lys-c[Asp-Arg-Arg-Tyr-Tyr-Arg-Phe-Lys]-D-Pro-D-Val-NH2 |
| 3829 | TCAM3826 | Lys-Lys-Phe-Phe-Lys-Lys-Leu-Lys-c[Asp-Arg-Arg-Tyr-Tyr-Arg-Phe-Lys]-D-Phe-D-Val-NH2 |
| 3830 | TCAM3827 | Lys-Lys-Phe-Phe-Lys-Lys-Leu-Lys-c[Asp-Arg-Arg-Nal-Nal-Arg-Phe-Lys]-D-Val-D-Pro-NH2 |
| 3831 | TCAM3828 | Lys-Lys-Phe-Phe-Lys-Lys-Leu-Lys-c[Asp-Arg-Arg-Nal-Nal-Arg-Phe-Lys]-D-Val-D-Phe-NH2 |

TABLE 5-continued

Exemplary Anti-microbial peptides

| SEQ NO: | Peptide | Peptide Sequence |
|---|---|---|
| 3832 | TCAM3829 | Lys-Lys-Phe-Phe-Lys-Lys-Leu-Lys-c[Asp-Arg-Arg-Nal-Nal-Arg-Phe-Lys]-D-Pro-D-Val-NH2 |
| 3833 | TCAM3830 | Lys-Lys-Phe-Phe-Lys-Lys-Leu-Lys-c[Asp-Arg-Arg-Nal-Nal-Arg-Phe-Lys]-D-Phe-D-Val-NH2 |
| 3834 | TCAM3831 | Lys-Lys-Phe-Phe-Lys-Lys-Leu-Lys-c[Asp-Arg-Arg-Leu-Trp-Leu-Trp-Lys]-D-Val-D-Pro-NH2 |
| 3835 | TCAM3832 | Lys-Lys-Phe-Phe-Lys-Lys-Leu-Lys-c[Asp-Arg-Arg-Leu-Trp-Leu-Trp-Lys]-D-Val-D-Phe-NH2 |
| 3836 | TCAM3833 | Lys-Lys-Phe-Phe-Lys-Lys-Leu-Lys-c[Asp-Arg-Arg-Leu-Trp-Leu-Trp-Lys]-D-Pro-D-Val-NH2 |
| 3837 | TCAM3834 | Lys-Lys-Phe-Phe-Lys-Lys-Leu-Lys-c[Asp-Arg-Arg-Leu-Trp-Leu-Trp-Lys]-D-Phe-D-Val-NH2 |
| 3838 | TCAM3835 | Lys-Lys-Phe-Phe-Lys-Lys-Leu-Lys-c[Asp-Arg-Arg-Leu-Trp-Leu-Trp-Lys]-D-Val-D-Pro-NH2 |
| 3839 | TCAM3836 | Lys-Lys-Phe-Phe-Lys-Lys-Leu-Lys-c[Asp-Arg-Arg-Leu-Trp-Leu-Trp-Lys]-D-Val-D-Phe-NH2 |
| 3840 | TCAM3837 | Lys-Lys-Phe-Phe-Lys-Lys-Leu-Lys-c[Asp-Arg-Arg-Leu-Trp-Leu-Trp-Lys]-D-Pro-D-Val-NH2 |
| 3841 | TCAM3838 | Lys-Lys-Phe-Phe-Lys-Lys-Leu-Lys-c[Asp-Arg-Arg-Leu-Trp-Leu-Trp-Lys]-D-Phe-D-Val-NH2 |
| 3842 | TCAM3839 | Lys-Lys-Phe-Phe-Lys-Lys-Leu-Lys-c[Asp-Arg-Arg-Arg-Trp-Leu-Trp-Leu-Trp-Lys]-D-Val-D-Pro-NH2 |
| 3843 | TCAM3840 | Lys-Lys-Phe-Phe-Lys-Lys-Leu-Lys-c[Asp-Arg-Arg-Arg-Trp-Leu-Trp-Leu-Trp-Lys]-D-Val-D-Phe-NH2 |
| 3844 | TCAM3841 | Lys-Lys-Phe-Phe-Lys-Lys-Leu-Lys-c[Asp-Arg-Arg-Arg-Trp-Leu-Trp-Leu-Trp-Lys]-D-Pro-D-Val-NH2 |
| 3845 | TCAM3842 | Lys-Lys-Phe-Phe-Lys-Lys-Leu-Lys-c[Asp-Arg-Arg-Arg-Trp-Leu-Trp-Leu-Trp-Lys]-D-Phe-D-Val-NH2 |
| 3846 | TCAM3843 | Lys-Lys-Phe-Phe-Lys-Lys-Leu-Lys-c[Asp-Arg-Gln-Arg-Arg-Trp-Leu-Trp-Leu-Trp-Lys]-D-Val-D-Pro-NH2 |
| 3847 | TCAM3844 | Lys-Lys-Phe-Phe-Lys-Lys-Leu-Lys-c[Asp-Arg-Gln-Arg-Arg-Trp-Leu-Trp-Leu-Trp-Lys]-D-Val-D-Phe-NH2 |
| 3848 | TCAM3845 | Lys-Lys-Phe-Phe-Lys-Lys-Leu-Lys-c[Asp-Arg-Gln-Arg-Arg-Trp-Leu-Trp-Leu-Trp-Lys]-D-Pro-D-Val-NH2 |
| 3849 | TCAM3846 | Lys-Lys-Phe-Phe-Lys-Lys-Leu-Lys-c[Asp-Arg-Gln-Arg-Arg-Trp-Leu-Trp-Leu-Trp-Lys]-D-Phe-D-Val-NH2 |
| 3850 | TCAM3847 | Lys-Lys-Phe-Phe-Lys-Lys-Leu-Lys-c[Asp-Trp-Arg-Trp-Trp-Arg-Arg-Lys]-D-Val-D-Pro-NH2 |
| 3851 | TCAM3848 | Lys-Lys-Phe-Phe-Lys-Lys-Leu-Lys-c[Asp-Trp-Arg-Trp-Trp-Arg-Arg-Lys]-D-Val-D-Phe-NH2 |
| 3852 | TCAM3849 | Lys-Lys-Phe-Phe-Lys-Lys-Leu-Lys-c[Asp-Trp-Arg-Trp-Trp-Arg-Arg-Lys]-D-Pro-D-Val-NH2 |
| 3853 | TCAM3850 | Lys-Lys-Phe-Phe-Lys-Lys-Leu-Lys-c[Asp-Trp-Arg-Trp-Trp-Arg-Arg-Lys]-D-Phe-D-Val-NH2 |
| 3854 | TCAM3851 | Lys-Lys-Phe-Phe-Lys-Lys-Leu-Lys-c[Asp-Trp-Trp-Arg-Arg-Trp-Trp-Arg-Arg-Lys]-D-Val-D-Pro-NH2 |
| 3855 | TCAM3852 | Lys-Lys-Phe-Phe-Lys-Lys-Leu-Lys-c[Asp-Trp-Trp-Arg-Arg-Trp-Trp-Arg-Arg-Lys]-D-Val-D-Phe-NH2 |
| 3856 | TCAM3853 | Lys-Lys-Phe-Phe-Lys-Lys-Leu-Lys-c[Asp-Trp-Trp-Arg-Arg-Trp-Trp-Arg-Arg-Lys]-D-Pro-D-Val-NH2 |

TABLE 5-continued

Exemplary Anti-microbial peptides

| SEQ NO: | Peptide | Peptide Sequence |
|---|---|---|
| 3857 | TCAM3854 | Lys-Lys-Phe-Phe-Lys-Lys-Leu-Lys-c[Asp-Trp-Trp-Arg-Arg-Trp-Trp-Arg-Arg-Lys]-D-Phe-D-Val-NH2 |
| 3858 | TCAM3855 | Lys-Lys-Phe-Phe-Lys-Lys-Leu-Lys-c[Asp-Trp-Arg-Trp-Arg-Trp-Arg-Lys]-D-Val-D-Pro-NH2 |
| 3859 | TCAM3856 | Lys-Lys-Phe-Phe-Lys-Lys-Leu-Lys-c[Asp-Trp-Arg-Trp-Arg-Trp-Arg-Lys]-D-Val-D-Phe-NH2 |
| 3860 | TCAM3857 | Lys-Lys-Phe-Phe-Lys-Lys-Leu-Lys-c[Asp-Trp-Arg-Trp-Arg-Trp-Arg-Lys]-D-Pro-D-Val-NH2 |
| 3861 | TCAM3858 | Lys-Lys-Phe-Phe-Lys-Lys-Leu-Lys-c[Asp-Trp-Arg-Trp-Arg-Trp-Arg-Lys]-D-Phe-D-Val-NH2 |
| 3862 | TCAM3859 | Lys-Lys-Phe-Phe-Lys-Lys-Leu-Lys-c[Asp-Arg-Trp-Arg-Trp-Arg-Trp-Lys]-D-Val-D-Pro-NH2 |
| 3863 | TCAM3860 | Lys-Lys-Phe-Phe-Lys-Lys-Leu-Lys-c[Asp-Arg-Trp-Arg-Trp-Arg-Trp-Lys]-D-Val-D-Phe-NH2 |
| 3864 | TCAM3861 | Lys-Lys-Phe-Phe-Lys-Lys-Leu-Lys-c[Asp-Arg-Trp-Arg-Trp-Arg-Trp-Lys]-D-Pro-D-Val-NH2 |
| 3865 | TCAM3862 | Lys-Lys-Phe-Phe-Lys-Lys-Leu-Lys-c[Asp-Arg-Trp-Arg-Trp-Arg-Trp-Lys]-D-Phe-D-Val-NH2 |
| 3866 | TCAM3863 | Lys-Lys-Phe-Phe-Lys-Lys-Leu-Lys-c[Asp-Arg-Trp-Trp-Arg-Arg-Lys]-D-Val-D-Pro-NH2 |
| 3867 | TCAM3864 | Lys-Lys-Phe-Phe-Lys-Lys-Leu-Lys-c[Asp-Arg-Trp-Trp-Arg-Arg-Lys]-D-Val-D-Phe-NH2 |
| 3868 | TCAM3865 | Lys-Lys-Phe-Phe-Lys-Lys-Leu-Lys-c[Asp-Arg-Trp-Trp-Arg-Arg-Lys]-D-Pro-D-Val-NH2 |
| 3869 | TCAM3866 | Lys-Lys-Phe-Phe-Lys-Lys-Leu-Lys-c[Asp-Arg-Trp-Trp-Arg-Arg-Lys]-D-Phe-D-Val-NH2 |
| 3870 | TCAM3867 | Lys-Lys-Phe-Phe-Lys-Lys-Leu-Lys-c[Asp-Arg-Trp-Arg-Trp-Arg-Lys]-D-Val-D-Pro-NH2 |
| 3871 | TCAM3868 | Lys-Lys-Phe-Phe-Lys-Lys-Leu-Lys-c[Asp-Arg-Trp-Arg-Trp-Arg-Lys]-D-Val-D-Phe-NH2 |
| 3872 | TCAM3869 | Lys-Lys-Phe-Phe-Lys-Lys-Leu-Lys-c[Asp-Arg-Trp-Arg-Trp-Arg-Lys]-D-Pro-D-Val-NH2 |
| 3873 | TCAM3870 | Lys-Lys-Phe-Phe-Lys-Lys-Leu-Lys-c[Asp-Arg-Trp-Arg-Trp-Arg-Lys]-D-Phe-D-Val-NH2 |
| 3874 | TCAM3871 | Lys-Lys-Phe-Phe-Lys-Lys-Leu-Lys-c[Asp-Trp-Trp-Arg-Arg-Trp-Lys]-D-Val-D-Pro-NH2 |
| 3875 | TCAM3872 | Lys-Lys-Phe-Phe-Lys-Lys-Leu-Lys-c[Asp-Trp-Trp-Arg-Arg-Trp-Lys]-D-Val-D-Phe-NH2 |
| 3876 | TCAM3873 | Lys-Lys-Phe-Phe-Lys-Lys-Leu-Lys-c[Asp-Trp-Trp-Arg-Arg-Trp-Lys]-D-Pro-D-Val-NH2 |
| 3877 | TCAM3874 | Lys-Lys-Phe-Phe-Lys-Lys-Leu-Lys-c[Asp-Trp-Trp-Arg-Arg-Trp-Lys]-D-Phe-D-Val-NH2 |
| 3878 | TCAM3875 | Lys-Lys-Phe-Phe-Lys-Lys-Leu-Lys-c[Asp-Trp-Arg-Trp-Arg-Trp-Lys]-D-Val-D-Pro-NH2 |
| 3879 | TCAM3876 | Lys-Lys-Phe-Phe-Lys-Lys-Leu-Lys-c[Asp-Trp-Arg-Trp-Arg-Trp-Lys]-D-Val-D-Phe-NH2 |
| 3880 | TCAM3877 | Lys-Lys-Phe-Phe-Lys-Lys-Leu-Lys-c[Asp-Trp-Arg-Trp-Arg-Trp-Lys]-D-Pro-D-Val-NH2 |
| 3881 | TCAM3878 | Lys-Lys-Phe-Phe-Lys-Lys-Leu-Lys-c[Asp-Trp-Arg-Trp-Arg-Trp-Lys]-D-Phe-D-Val-NH2 |
| 3882 | TCAM3879 | Lys-Lys-Phe-Phe-Lys-Lys-Leu-Lys-c[Asp-Trp-Arg-Tyr-Arg-Trp-Lys]-D-Val-D-Pro-NH2 |
| 3883 | TCAM3880 | Lys-Lys-Phe-Phe-Lys-Lys-Leu-Lys-c[Asp-Trp-Arg-Tyr-Arg-Trp-Lys]-D-Val-D-Phe-NH2 |
| 3884 | TCAM3881 | Lys-Lys-Phe-Phe-Lys-Lys-Leu-Lys-c[Asp-Trp-Arg-Tyr-Arg-Trp-Lys]-D-Pro-D-Val-NH2 |
| 3885 | TCAM3882 | Lys-Lys-Phe-Phe-Lys-Lys-Leu-Lys-c[Asp-Trp-Arg-Tyr-Arg-Trp-Lys]-D-Phe-D-Val-NH2 |
| 3886 | TCAM3883 | Lys-Lys-Phe-Phe-Lys-Lys-Leu-Lys-c[Asp-Trp-Arg-Trp-Arg-Tyr-Lys]-D-Val-D-Pro-NH2 |
| 3887 | TCAM3884 | Lys-Lys-Phe-Phe-Lys-Lys-Leu-Lys-c[Asp-Trp-Arg-Trp-Arg-Tyr-Lys]-D-Val-D-Phe-NH2 |
| 3888 | TCAM3885 | Lys-Lys-Phe-Phe-Lys-Lys-Leu-Lys-c[Asp-Trp-Arg-Trp-Arg-Tyr-Lys]-D-Pro-D-Val-NH2 |
| 3889 | TCAM3886 | Lys-Lys-Phe-Phe-Lys-Lys-Leu-Lys-c[Asp-Trp-Arg-Trp-Arg-Tyr-Lys]-D-Phe-D-Val-NH2 |

TABLE 5-continued

Exemplary Anti-microbial peptides

| SEQ NO: | Peptide | Peptide Sequence |
|---|---|---|
| 3890 | TCAM3887 | Lys-Lys-Phe-Phe-Lys-Lys-Leu-Lys-c[Asp-Trp-Arg-Trp-Arg-Lys]-D-Val-D-Pro-NH2 |
| 3891 | TCAM3888 | Lys-Lys-Phe-Phe-Lys-Lys-Leu-Lys-c[Asp-Trp-Arg-Trp-Arg-Lys]-D-Val-D-Phe-NH2 |
| 3892 | TCAM3889 | Lys-Lys-Phe-Phe-Lys-Lys-Leu-Lys-c[Asp-Trp-Arg-Trp-Arg-Lys]-D-Pro-D-Val-NH2 |
| 3893 | TCAM3890 | Lys-Lys-Phe-Phe-Lys-Lys-Leu-Lys-c[Asp-Trp-Arg-Trp-Arg-Lys]-D-Phe-D-Val-NH2 |
| 3894 | TCAM3891 | Lys-Lys-Phe-Phe-Lys-Lys-Leu-Lys-c[Asp-Trp-Arg-Arg-Trp-Lys]-D-Val-D-Pro-NH2 |
| 3895 | TCAM3892 | Lys-Lys-Phe-Phe-Lys-Lys-Leu-Lys-c[Asp-Trp-Arg-Arg-Trp-Lys]-D-Val-D-Phe-NH2 |
| 3896 | TCAM3893 | Lys-Lys-Phe-Phe-Lys-Lys-Leu-Lys-c[Asp-Trp-Arg-Arg-Trp-Lys]-D-Pro-D-Val-NH2 |
| 3897 | TCAM3894 | Lys-Lys-Phe-Phe-Lys-Lys-Leu-Lys-c[Asp-Trp-Arg-Arg-Trp-Lys]-D-Phe-D-Val-NH2 |
| 3898 | TCAM3895 | Lys-Lys-Phe-Phe-Lys-Lys-Leu-Lys-c[Asp-Arg-Trp-Trp-Arg-Lys]-D-Val-D-Pro-NH2 |
| 3899 | TCAM3896 | Lys-Lys-Phe-Phe-Lys-Lys-Leu-Lys-c[Asp-Arg-Trp-Trp-Arg-Lys]-D-Val-D-Phe-NH2 |
| 3900 | TCAM3897 | Lys-Lys-Phe-Phe-Lys-Lys-Leu-Lys-c[Asp-Arg-Trp-Trp-Arg-Lys]-D-Pro-D-Val-NH2 |
| 3901 | TCAM3898 | Lys-Lys-Phe-Phe-Lys-Lys-Leu-Lys-c[Asp-Arg-Trp-Trp-Arg-Lys]-D-Phe-D-Val-NH2 |
| 3902 | TCAM3899 | Lys-Lys-Phe-Phe-Lys-Lys-Leu-Lys-c[Asp-Trp-Arg-Trp-Lys]-D-Val-D-Pro-NH2 |
| 3903 | TCAM3900 | Lys-Lys-Phe-Phe-Lys-Lys-Leu-Lys-c[Asp-Trp-Arg-Trp-Lys]-D-Val-D-Phe-NH2 |
| 3904 | TCAM3901 | Lys-Lys-Phe-Phe-Lys-Lys-Leu-Lys-c[Asp-Trp-Arg-Trp-Lys]-D-Pro-D-Val-NH2 |
| 3905 | TCAM3902 | Lys-Lys-Phe-Phe-Lys-Lys-Leu-Lys-c[Asp-Trp-Arg-Trp-Lys]-D-Phe-D-Val-NH2 |
| 3906 | TCAM3903 | Lys-Lys-Phe-Phe-Lys-Lys-Leu-Lys-c[Asp-Arg-Trp-Arg-Lys]-D-Val-D-Pro-NH2 |
| 3907 | TCAM3904 | Lys-Lys-Phe-Phe-Lys-Lys-Leu-Lys-c[Asp-Arg-Trp-Arg-Lys]-D-Val-D-Phe-NH2 |
| 3908 | TCAM3905 | Lys-Lys-Phe-Phe-Lys-Lys-Leu-Lys-c[Asp-Arg-Trp-Arg-Lys]-D-Pro-D-Val-NH2 |
| 3909 | TCAM3906 | Lys-Lys-Phe-Phe-Lys-Lys-Leu-Lys-c[Asp-Arg-Trp-Arg-Lys]-D-Phe-D-Val-NH2 |
| 3910 | TCAM3907 | Lys-Lys-Phe-Phe-Lys-Lys-Leu-Lys-c[Asp-His-D-Nal(2')-Arg-Trp-Lys]-D-Val-D-Pro-NH2 |
| 3911 | TCAM3908 | Lys-Lys-Phe-Phe-Lys-Lys-Leu-Lys-c[Asp-His-D-Nal(2')-Arg-Trp-Lys]-D-Pro-D-Val-NH2 |
| 3912 | TCAM3909 | Lys-Lys-Phe-Phe-Lys-Lys-Leu-Lys-c[Asp-His-D-Nal(2')-Arg-Trp-Lys]-D-Val-D-Phe-NH2 |
| 3913 | TCAM3910 | Lys-Lys-Phe-Phe-Lys-Lys-Leu-Lys-c[Asp-His-D-Nal(2')-Arg-Trp-Lys]-D-Phe-D-Val-NH2 |
| 3914 | TCAM3911 | Lys-Lys-Phe-Phe-Lys-Lys-Leu-Lys-c[Asp-Pro-D-Nal(2')-Arg-Trp-Lys]-D-Val-D-Pro-NH2 |
| 3915 | TCAM3912 | Lys-Lys-Phe-Phe-Lys-Lys-Leu-Lys-c[Asp-Pro-D-Nal(2')-Arg-Trp-Lys]-D-Pro-D-Val-NH2 |
| 3916 | TCAM3913 | Lys-Lys-Phe-Phe-Lys-Lys-Leu-Lys-c[Asp-Pro-D-Nal(2')-Arg-Trp-Lys]-D-Val-D-Phe-NH2 |
| 3917 | TCAM3914 | Lys-Lys-Phe-Phe-Lys-Lys-Leu-Lys-c[Asp-Pro-D-Nal(2')-Arg-Trp-Lys]-D-Phe-D-Val-NH2 |
| 3918 | TCAM3915 | Lys-Lys-Phe-Phe-Lys-Lys-Leu-Lys-c[Asp-Arg-Arg-Nal(2')-Arg-Trp-Lys]-D-Val-D-Pro-NH2 |
| 3919 | TCAM3916 | Lys-Lys-Phe-Phe-Lys-Lys-Leu-Lys-c[Asp-Arg-Arg-Nal(2')-Arg-Trp-Lys]-D-Pro-D-Val-NH2 |
| 3920 | TCAM3917 | Lys-Lys-Phe-Phe-Lys-Lys-Leu-Lys-c[Asp-Arg-Arg-Nal(2')-Arg-Trp-Lys]-D-Val-D-Phe-NH2 |
| 3921 | TCAM3918 | Lys-Lys-Phe-Phe-Lys-Lys-Leu-Lys-c[Asp-Arg-Arg-Nal(2')-Arg-Trp-Lys]-D-Phe-D-Val-NH2 |
| 3922 | TCAM3919 | Lys-Lys-Phe-Phe-Lys-Lys-Leu-Lys-c[Asp-Arg-Arg-Pro-Nal(2')-Arg-Trp-Lys]-D-Val-D-Pro-NH2 |
| 3923 | TCAM3920 | Lys-Lys-Phe-Phe-Lys-Lys-Leu-Lys-c[Asp-Arg-Arg-Pro-D-Nal(2')-Arg-Trp-Lys]-D-Pro-D-Val-NH2 |

TABLE 5-continued

Exemplary Anti-microbial peptides

| SEQ NO: | Peptide | Peptide Sequence |
|---|---|---|
| 3924 | TCAM3921 | Lys-Lys-Phe-Phe-Lys-Lys-Leu-Lys-c[Asp-Arg-Arg-Pro-D-Nal(2')-Arg-Trp-Lys]-D-Val-D-Phe-NH2 |
| 3925 | TCAM3922 | Lys-Lys-Phe-Phe-Lys-Lys-Leu-Lys-c[Asp-Arg-Arg-Pro-Nal(2')-Arg-Trp-Lys]-D-Phe-D-Val-NH2 |
| 3926 | TCAM3923 | Lys-Lys-Phe-Phe-Lys-Lys-Leu-Lys-c[Asp-Arg-D-Nal(2')-Arg-Trp-Lys]-D-Val-D-Pro-NH2 |
| 3927 | TCAM3924 | Lys-Lys-Phe-Phe-Lys-Lys-Leu-Lys-c[Asp-Arg-D-Nal(2')-Arg-Trp-Lys]-D-Pro-D-Val-NH2 |
| 3928 | TCAM3925 | Lys-Lys-Phe-Phe-Lys-Lys-Leu-Lys-c[Asp-Arg-D-Nal(2')-Arg-Trp-Lys]-D-Val-D-Phe-NH2 |
| 3929 | TCAM3926 | Lys-Lys-Phe-Phe-Lys-Lys-Leu-Lys-c[Asp-Arg-D-Nal(2')-Arg-Trp-Lys]-D-Phe-D-Val-NH2 |
| 3930 | TCAM3927 | Lys-Lys-Phe-Phe-Lys-Lys-Leu-Lys-c[Asp-Arg-Pro-D-Nal(2')-Arg-Trp-Lys]-D-Val-D-Pro-NH2 |
| 3931 | TCAM3928 | Lys-Lys-Phe-Phe-Lys-Lys-Leu-Lys-c[Asp-Arg-Pro-D-Nal(2')-Arg-Trp-Lys]-D-Pro-D-Val-NH2 |
| 3932 | TCAM3929 | Lys-Lys-Phe-Phe-Lys-Lys-Leu-Lys-c[Asp-Arg-Pro-D-Nal(2')-Arg-Trp-Lys]-D-Val-D-Phe-NH2 |
| 3933 | TCAM3930 | Lys-Lys-Phe-Phe-Lys-Lys-Leu-Lys-c[Asp-Arg-Pro-D-Nal(2')-Arg-Trp-Lys]-D-Phe-D-Val-NH2 |
| 3934 | TCAM3931 | Lys-Lys-Phe-Phe-Lys-Lys-Leu-Lys-Arg-Arg-c[Asp-Pro-D-Nal(2')-Arg-Trp-Lys]-D-Val-D-Pro-NH2 |
| 3935 | TCAM3932 | Lys-Lys-Phe-Phe-Lys-Lys-Leu-Lys-Arg-Arg-c[Asp-Pro-D-Nal(2')-Arg-Trp-Lys]-D-Pro-D-Val-NH2 |
| 3936 | TCAM3933 | Lys-Lys-Phe-Phe-Lys-Lys-Leu-Lys-Arg-Arg-c[Asp-Pro-D-Nal(2')-Arg-Trp-Lys]-D-Val-D-Phe-NH2 |
| 3937 | TCAM3934 | Lys-Lys-Phe-Phe-Lys-Lys-Leu-Lys-Arg-Arg-c[Asp-Pro-D-Nal(2')-Arg-Trp-Lys]-D-Phe-D-Val-NH2 |
| 3938 | TCAM3935 | Lys-Lys-Phe-Phe-Lys-Lys-Leu-Lys-Arg-Arg-c[Asp-His-D-Nal(2')-Arg-Trp-Lys]-D-Val-D-Pro-NH2 |
| 3939 | TCAM3936 | Lys-Lys-Phe-Phe-Lys-Lys-Leu-Lys-Arg-Arg-c[Asp-His-D-Nal(2')-Arg-Trp-Lys]-D-Pro-D-Val-NH2 |
| 3940 | TCAM3937 | Lys-Lys-Phe-Phe-Lys-Lys-Leu-Lys-Arg-Arg-c[Asp-His-D-Nal(2')-Arg-Trp-Lys]-D-Val-D-Phe-NH2 |
| 3941 | TCAM3938 | Lys-Lys-Phe-Phe-Lys-Lys-Leu-Lys-Arg-Arg-c[Asp-His-D-Nal(2')-Arg-Trp-Lys]-D-Phe-D-Val-NH2 |
| 3942 | TCAM3939 | Lys-Lys-Phe-Phe-Lys-Lys-Leu-Lys-c[Asp-Arg-Pro-D-Nal(2')-Arg-Trp-Arg-Lys]-D-Val-D-Pro-NH2 |
| 3943 | TCAM3940 | Lys-Lys-Phe-Phe-Lys-Lys-Leu-Lys-c[Asp-Arg-Pro-D-Nal(2')-Arg-Trp-Arg-Lys]-D-Pro-D-Val-NH2 |
| 3944 | TCAM3941 | Lys-Lys-Phe-Phe-Lys-Lys-Leu-Lys-c[Asp-Arg-Pro-D-Nal(2')-Arg-Trp-Arg-Lys]-D-Val-D-Phe-NH2 |
| 3945 | TCAM3942 | Lys-Lys-Phe-Phe-Lys-Lys-Leu-Lys-c[Asp-Arg-Pro-D-Nal(2')-Arg-Trp-Arg-Lys]-D-Phe-D-Val-NH2 |
| 3946 | TCAM3943 | Lys-Lys-Phe-Phe-Lys-Lys-Leu-Lys-c[Asp-Arg-His-D-Nal(2')-Arg-Trp-Arg-Lys]-D-Val-D-Pro-NH2 |
| 3947 | TCAM3944 | Lys-Lys-Phe-Phe-Lys-Lys-Leu-Lys-c[Asp-Arg-His-D-Nal(2')-Arg-Trp-Arg-Lys]-D-Pro-D-Val-NH2 |
| 3948 | TCAM3945 | Lys-Lys-Phe-Phe-Lys-Lys-Leu-Lys-c[Asp-Arg-His-D-Nal(2')-Arg-Trp-Arg-Lys]-D-Val-D-Phe-NH2 |
| 3949 | TCAM3946 | Lys-Lys-Phe-Phe-Lys-Lys-Leu-Lys-c[Asp-Arg-His-D-Nal(2')-Arg-Trp-Arg-Lys]-D-Phe-D-Val-NH2 |

TABLE 5-continued

Exemplary Anti-microbial peptides

| SEQ NO: | Peptide | Peptide Sequence |
|---|---|---|
| 3950 | TCAM3947 | Lys-Lys-Phe-Phe-Lys-Lys-Leu-Lys-c[Asp-His-D-Nal(2')-Arg-D-Nal(2')-Lys]-D-Val-D-Phe-NH2 |
| 3951 | TCAM3948 | Lys-Lys-Phe-Phe-Lys-Lys-Leu-Lys-c[Asp-His-D-Nal(2')-Arg-D-Nal(2')-Lys]-D-Phe-D-Val-NH2 |
| 3952 | TCAM3949 | Lys-Lys-Phe-Phe-Lys-Lys-Leu-Lys-c[Asp-Pro-D-Nal(2')-Arg-D-Nal(2')-Lys]-D-Val-D-Pro-NH2 |
| 3953 | TCAM3950 | Lys-Lys-Phe-Phe-Lys-Lys-Leu-Lys-c[Asp-Pro-D-Nal(2')-Arg-D-Nal(2')-Lys]-D-Pro-D-Val-NH2 |
| 3954 | TCAM3951 | Lys-Lys-Phe-Phe-Lys-Lys-Leu-Lys-c[Asp-Pro-D-Nal(2')-Arg-D-Nal(2')-Lys]-D-Val-D-Phe-NH2 |
| 3955 | TCAM3952 | Lys-Lys-Phe-Phe-Lys-Lys-Leu-Lys-c[Asp-Pro-D-Nal(2')-Arg-D-Nal(2')-Lys]-D-Phe-D-Val-NH2 |
| 3956 | TCAM3953 | Lys-Lys-Phe-Phe-Lys-Lys-Leu-Lys-c[Asp-Arg-Arg-D-Nal(2')-Arg-D-Nal(2')-Lys]-D-Val-D-Pro-NH2 |
| 3957 | TCAM3954 | Lys-Lys-Phe-Phe-Lys-Lys-Leu-Lys-c[Asp-Arg-Arg-D-Nal(2')-Arg-D-Nal(2')-Lys]-D-Pro-D-Val-NH2 |
| 3958 | TCAM3955 | Lys-Lys-Phe-Phe-Lys-Lys-Leu-Lys-c[Asp-Arg-Arg-D-Nal(2')-Arg-D-Nal(2')-Lys]-D-Val-D-Phe-NH2 |
| 3959 | TCAM3956 | Lys-Lys-Phe-Phe-Lys-Lys-Leu-Lys-c[Asp-Arg-Arg-D-Nal(2')-Arg-D-Nal(2')-Lys]-D-Phe-D-Val-NH2 |
| 3960 | TCAM3957 | Lys-Lys-Phe-Phe-Lys-Lys-Leu-Lys-c[Asp-Arg-Arg-Pro-D-Nal(2')-Arg-D-Nal(2')-Lys]-D-Val-D-Pro-NH2 |
| 3961 | TCAM3958 | Lys-Lys-Phe-Phe-Lys-Lys-Leu-Lys-c[Asp-Arg-Arg-Pro-D-Nal(2')-Arg-D-Nal(2')-Lys]-D-Pro-D-Val-NH2 |
| 3962 | TCAM3959 | Lys-Lys-Phe-Phe-Lys-Lys-Leu-Lys-c[Asp-Arg-Arg-Pro-D-Nal(2')-Arg-D-Nal(2')-Lys]-D-Val-D-Phe-NH2 |
| 3963 | TCAM3960 | Lys-Lys-Phe-Phe-Lys-Lys-Leu-Lys-c[Asp-Arg-Arg-Pro-D-Nal(2')-Arg-D-Nal(2')-Lys]-D-Phe-D-Val-NH2 |
| 3964 | TCAM3961 | Lys-Lys-Phe-Phe-Lys-Lys-Leu-Lys-c[Asp-Arg-D-Nal(2')-Arg-D-Nal(2')-Lys]-D-Val-D-Pro-NH2 |
| 3965 | TCAM3962 | Lys-Lys-Phe-Phe-Lys-Lys-Leu-Lys-c[Asp-Arg-D-Nal(2')-Arg-D-Nal(2')-Lys]-D-Pro-D-Val-NH2 |
| 3966 | TCAM3963 | Lys-Lys-Phe-Phe-Lys-Lys-Leu-Lys-c[Asp-Arg-Nal(2')-Arg-D-Nal(2')-Lys]-D-Val-D-Phe-NH2 |
| 3967 | TCAM3964 | Lys-Lys-Phe-Phe-Lys-Lys-Leu-Lys-c[Asp-Arg-D-Nal(2')-Arg-D-Nal(2')-Lys]-D-Phe-D-Val-NH2 |
| 3968 | TCAM3965 | Lys-Lys-Phe-Phe-Lys-Lys-Leu-Lys-c[Asp-Arg-Pro-D-Nal(2')-Arg-D-Nal(2')-Lys]-D-Val-D-Pro-NH2 |
| 3969 | TCAM3966 | Lys-Lys-Phe-Phe-Lys-Lys-Leu-Lys-c[Asp-Arg-Pro-D-Nal(2')-Arg-D-Nal(2')-Lys]-D-Pro-D-Val-NH2 |
| 3970 | TCAM3967 | Lys-Lys-Phe-Phe-Lys-Lys-Leu-Lys-c[Asp-Arg-Pro-D-Nal(2')-Arg-D-Nal(2')-Lys]-D-Val-D-Phe-NH2 |
| 3971 | TCAM3968 | Lys-Lys-Phe-Phe-Lys-Lys-Leu-Lys-c[Asp-Arg-Pro-D-Nal(2')-Arg-D-Nal(2')-Lys]-D-Phe-D-Val-NH2 |
| 3972 | TCAM3969 | Lys-Lys-Phe-Phe-Lys-Lys-Leu-Lys-c[Asp-Arg-His-D-Nal(2')-Arg-D-Nal(2')-Lys]-D-Val-D-Pro-NH2 |
| 3973 | TCAM3970 | Lys-Lys-Phe-Phe-Lys-Lys-Leu-Lys-c[Asp-Arg-His-D-Nal(2')-Arg-D-Nal(2')-Lys]-D-Pro-D-Val-NH2 |
| 3974 | TCAM3971 | Lys-Lys-Phe-Phe-Lys-Lys-Leu-Lys-c[Asp-Arg-His-Nal(2')-Arg-D-Nal(2')-Lys]-D-Val-D-Phe-NH2 |

TABLE 5-continued

Exemplary Anti-microbial peptides

| SEQ NO: | Peptide | Peptide Sequence |
|---|---|---|
| 3975 | TCAM3972 | Lys-Lys-Phe-Phe-Lys-Lys-Leu-Lys-c[Asp-Arg-His-Nal(2')-Arg-D-Nal(2')-Lys]-D-Phe-D-Val-NH2 |
| 3976 | TCAM3973 | Lys-Lys-Phe-Phe-Lys-Lys-Leu-Lys-c[Asp-Arg-D-D-Nal(2')-Arg-D-Nal(2')-Arg-Lys]-D-Val-D-Pro-NH2 |
| 3977 | TCAM3974 | Lys-Lys-Phe-Phe-Lys-Lys-Leu-Lys-c[Asp-Arg-D-Nal(2')-Arg-D-Nal(2')-Arg-Lys]-D-Pro-D-Val-NH2 |
| 3978 | TCAM3975 | Lys-Lys-Phe-Phe-Lys-Lys-Leu-Lys-c[Asp-Arg-D-Nal(2')-Arg-D-Nal(2')-Arg-Lys]-D-Val-D-Phe-NH2 |
| 3979 | TCAM3976 | Lys-Lys-Phe-Phe-Lys-Lys-Leu-Lys-c[Asp-Arg-D-Nal(2')-Arg-D-Nal(2')-Arg-Lys]-D-Phe-D-Val-NH2 |
| 3980 | TCAM3977 | Lys-Lys-Phe-Phe-Lys-Lys-Leu-Lys-c[Asp-Arg-Pro-D-Nal(2')-Arg-D-Nal(2')-Arg-Lys]-D-Val-D-Pro-NH2 |
| 3981 | TCAM3978 | Lys-Lys-Phe-Phe-Lys-Lys-Leu-Lys-c[Asp-Arg-Pro-D-Nal(2')-Arg-D-Nal(2')-Arg-Lys]-D-Pro-D-Val-NH2 |
| 3982 | TCAM3979 | Lys-Lys-Phe-Phe-Lys-Lys-Leu-Lys-c[Asp-Arg-Pro-D-Nal(2')-Arg-D-Nal(2')-Arg-Lys]-D-Val-D-Phe-NH2 |
| 3983 | TCAM3980 | Lys-Lys-Phe-Phe-Lys-Lys-Leu-Lys-c[Asp-Arg-Pro-D-Nal(2')-Arg-D-Nal(2')-Arg-Lys]-D-Phe-D-Val-NH2 |
| 3984 | TCAM3981 | Lys-Lys-Phe-Phe-Lys-Lys-Leu-Lys-c[Asp-Arg-His-D-Nal(2')-Arg-D-Nal(2')-Arg-Lys]-D-Val-D-Pro-NH2 |
| 3985 | TCAM3982 | Lys-Lys-Phe-Phe-Lys-Lys-Leu-Lys-c[Asp-Arg-His-D-Nal(2')-Arg-D-Nal(2')-Arg-Lys]-D-Pro-D-Val-NH2 |
| 3986 | TCAM3983 | Lys-Lys-Phe-Phe-Lys-Lys-Leu-Lys-c[Asp-Arg-His-D-Nal(2')-Arg-D-Nal(2')-Arg-Lys]-D-Val-D-Phe-NH2 |
| 3987 | TCAM3984 | Lys-Lys-Phe-Phe-Lys-Lys-Leu-Lys-c[Asp-Arg-His-D-Nal(2')-Arg-D-Nal(2')-Arg-Lys]-D-Phe-D-Val-NH2 |
| 3988 | TCAM3985 | Lys-Lys-Phe-Phe-Lys-Lys-Leu-Lys-Arg-Arg-c[Asp-Pro-D-Nal(2')-Arg-D-Nal(2')-Lys]-D-Val-D-Pro-NH2 |
| 3989 | TCAM3986 | Lys-Lys-Phe-Phe-Lys-Lys-Leu-Lys-Arg-Arg-c[Asp-Pro-D-Nal(2')-Arg-D-Nal(2')-Lys]-D-Pro-D-Val-NH2 |
| 3990 | TCAM3987 | Lys-Lys-Phe-Phe-Lys-Lys-Leu-Lys-Arg-Arg-c[Asp-Pro-D-Nal(2')-Arg-D-Nal(2')-Lys]-D-Val-D-Phe-NH2 |
| 3991 | TCAM3988 | Lys-Lys-Phe-Phe-Lys-Lys-Leu-Lys-Arg-Arg-c[Asp-Pro-D-Nal(2')-Arg-D-Nal(2')-Lys]-D-Phe-D-Val-NH2 |
| 3992 | TCAM3989 | Lys-Lys-Phe-Phe-Lys-Lys-Leu-Lys-Arg-Arg-c[Asp-His-D-Nal(2')-Arg-D-Nal(2')-Lys]-D-Val-D-Pro-NH2 |
| 3993 | TCAM3990 | Lys-Lys-Phe-Phe-Lys-Lys-Leu-Lys-Arg-Arg-c[Asp-His-D-Nal(2')-Arg-D-Nal(2')-Lys]-D-Pro-D-Val-NH2 |
| 3994 | TCAM3991 | Lys-Lys-Phe-Phe-Lys-Lys-Leu-Lys-Arg-Arg-c[Asp-His-D-Nal(2')-Arg-D-Nal(2')-Lys]-D-Val-D-Phe-NH2 |
| 3995 | TCAM3992 | Lys-Lys-Phe-Phe-Lys-Lys-Leu-Lys-Arg-Arg-c[Asp-His-D-Nal(2')-Arg-D-Nal(2')-Lys]-D-Phe-D-Val-NH2 |
| 3996 | TCAM3993 | Lys-Lys-Phe-Phe-Lys-Lys-Leu-Lys-c[Asp-Arg-Pro-D-Nal(2')-Arg-D-Nal(2')-Arg-Lys]-D-Val-D-Pro-NH2 |
| 3997 | TCAM3994 | Lys-Lys-Phe-Phe-Lys-Lys-Leu-Lys-c[Asp-Arg-Pro-D-Nal(2')-Arg-D-Nal(2')-Arg-Lys]-D-Pro-D-Val-NH2 |
| 3998 | TCAM3995 | Lys-Lys-Phe-Phe-Lys-Lys-Leu-Lys-c[Asp-Arg-Pro-D-Nal(2')-Arg-D-Nal(2')-Arg-Lys]-D-Val-D-Phe-NH2 |
| 3999 | TCAM3996 | Lys-Lys-Phe-Phe-Lys-Lys-Leu-Lys-c[Asp-Arg-Pro-D-Nal(2')-Arg-D-Nal(2')-Arg-Lys]-D-Phe-D-Val-NH2 |

TABLE 5-continued

Exemplary Anti-microbial peptides

| SEQ NO: | Peptide | Peptide Sequence |
|---|---|---|
| 4000 | TCAM3997 | Lys-Lys-Phe-Phe-Lys-Lys-Leu-Lys-c[Asp-Arg-His-D-Nal(2')-Arg-D-Nal(2')-Arg-Lys]-D-Val-D-Pro-NH2 |
| 4001 | TCAM3998 | Lys-Lys-Phe-Phe-Lys-Lys-Leu-Lys-c[Asp-Arg-His-D-Nal(2')-Arg-D-Nal(2')-Arg-Lys]-D-Pro-D-Val-NH2 |
| 4002 | TCAM3999 | Lys-Lys-Phe-Phe-Lys-Lys-Leu-Lys-c[Asp-Arg-His-D-Nal(2')-Arg-D-Nal(2')-Arg-Lys]-D-Val-D-Phe-NH2 |
| 4003 | TCAM4000 | Lys-Lys-Phe-Phe-Lys-Lys-Leu-Lys-c[Asp-Arg-His-D-Nal(2')-Arg-D-Nal(2')-Arg-Lys]-D-Phe-D-Val-NH2 |
| 4004 | TCAM4001 | Lys-Lys-Phe-Phe-Lys-Lys-Leu-Lys-c[Asp-His-D-Nal(2')-Arg-Trp-Lys]-Arg-Arg-D-Val-D-Pro-NH2 |
| 4005 | TCAM4002 | Lys-Lys-Phe-Phe-Lys-Lys-Leu-Lys-c[Asp-His-D-Nal(2')-Arg-Trp-Lys]-Arg-Arg-D-Pro-D-Val-NH2 |
| 4006 | TCAM4003 | Lys-Lys-Phe-Phe-Lys-Lys-Leu-Lys-c[Asp-His-D-Nal(2')-Arg-Trp-Lys]-Arg-Arg-D-Val-D-Phe-NH2 |
| 4007 | TCAM4004 | Lys-Lys-Phe-Phe-Lys-Lys-Leu-Lys-c[Asp-His-D-Nal(2')-Arg-Trp-Lys]-Arg-Arg-D-Phe-D-Val-NH2 |
| 4008 | TCAM4005 | Lys-Lys-Phe-Phe-Lys-Lys-Leu-Lys-c[Asp-Pro-D-Nal(2')-Arg-Trp-Lys]-Arg-Arg-D-Val-D-Pro-NH2 |
| 4009 | TCAM4006 | Lys-Lys-Phe-Phe-Lys-Lys-Leu-Lys-c[Asp-Pro-D-Nal(2')-Arg-Trp-Lys]-Arg-Arg-D-Pro-D-Val-NH2 |
| 4010 | TCAM4007 | Lys-Lys-Phe-Phe-Lys-Lys-Leu-Lys-c[Asp-Pro-D-Nal(2')-Arg-Trp-Lys]-Arg-Arg-D-Val-D-Phe-NH2 |
| 4011 | TCAM4008 | Lys-Lys-Phe-Phe-Lys-Lys-Leu-Lys-c[Asp-Pro-D-Nal(2')-Arg-Trp-Lys]-Arg-Arg-D-Phe-D-Val-NH2 |

Anti-biofilm peptide ABF7ARG linked to anti-microbial peptides

| 4012 | TCAM4009 | Arg-Arg-Phe-Phe-Arg-Arg-Leu-Arg-c[Asp-Pro-Arg-Arg-Trp-Trp-Arg-Phe-Lys]-D-Val-D-Pro-NH2 |
| 4013 | TCAM4010 | Arg-Arg-Phe-Phe-Arg-Arg-Leu-Arg-c[Asp-Pro-Arg-Arg-Trp-Trp-Arg-Phe-Lys]-D-Val-D-Phe-NH2 |
| 4014 | TCAM4011 | Arg-Arg-Phe-Phe-Arg-Arg-Leu-Arg-c[Asp-Pro-Arg-Arg-Trp-Trp-Arg-Phe-Lys]-D-Pro-D-Val-NH2 |
| 4015 | TCAM4012 | Arg-Arg-Phe-Phe-Arg-Arg-Leu-Arg-c[Asp-Pro-Arg-Arg-Trp-Trp-Arg-Phe-Lys]-D-Phe-D-Val-NH2 |
| 4016 | TCAM4013 | Arg-Arg-Phe-Phe-Arg-Arg-Leu-Arg-c[Asp-Pro-Arg-Arg-Trp-Trp-Tyr-Phe-Lys]-D-Val-D-Pro-NH2 |
| 4017 | TCAM4014 | Arg-Arg-Phe-Phe-Arg-Arg-Leu-Arg-c[Asp-Pro-Arg-Arg-Trp-Trp-Tyr-Phe-Lys]-D-Val-D-Phe-NH2 |
| 4018 | TCAM4015 | Arg-Arg-Phe-Phe-Arg-Arg-Leu-Arg-c[Asp-Pro-Arg-Arg-Trp-Trp-Tyr-Phe-Lys]-D-Pro-D-Val-NH2 |
| 4019 | TCAM4016 | Arg-Arg-Phe-Phe-Arg-Arg-Leu-Arg-c[Asp-Pro-Arg-Arg-Trp-Trp-Tyr-Phe-Lys]-D-Phe-D-Val-NH2 |
| 4020 | TCAM4017 | Arg-Arg-Phe-Phe-Arg-Arg-Leu-Arg-c[Asp-Pro-Arg-Arg-Tyr-Tyr-Arg-Phe-Lys]-D-Val-D-Pro-NH2 |
| 4021 | TCAM4018 | Arg-Arg-Phe-Phe-Arg-Arg-Leu-Arg-c[Asp-Pro-Arg-Arg-Tyr-Tyr-Arg-Phe-Lys]-D-Val-D-Phe-NH2 |
| 4022 | TCAM4019 | Arg-Arg-Phe-Phe-Arg-Arg-Leu-Arg-c[Asp-Pro-Arg-Arg-Tyr-Tyr-Arg-Phe-Lys]-D-Pro-D-Val-NH2 |
| 4023 | TCAM4020 | Arg-Arg-Phe-Phe-Arg-Arg-Leu-Arg-c[Asp-Pro-Arg-Arg-Tyr-Tyr-Arg-Phe-Lys]-D-Phe-D-Val-NH2 |

TABLE 5-continued

Exemplary Anti-microbial peptides

| SEQ NO: | Peptide | Peptide Sequence |
|---|---|---|
| 4024 | TCAM4021 | Arg-Arg-Phe-Phe-Arg-Arg-Leu-Arg-c[Asp-Pro-Arg-Arg-Nal-Nal-Arg-Phe-Lys]-D-Val-D-Pro-NH2 |
| 4025 | TCAM4022 | Arg-Arg-Phe-Phe-Arg-Arg-Leu-Arg-c[Asp-Pro-Arg-Arg-Nal-Nal-Arg-Phe-Lys]-D-Val-D-Phe-NH2 |
| 4026 | TCAM4023 | Arg-Arg-Phe-Phe-Arg-Arg-Leu-Arg-c[Asp-Pro-Arg-Arg-Nal-Nal-Arg-Phe-Lys]-D-Pro-D-Val-NH2 |
| 4027 | TCAM4024 | Arg-Arg-Phe-Phe-Arg-Arg-Leu-Arg-c[Asp-Pro-Arg-Arg-Nal-Nal-Arg-Phe-Lys]-D-Phe-D-Val-NH2 |
| 4028 | TCAM4025 | Arg-Arg-Phe-Phe-Arg-Arg-Leu-Arg-c[Asp-Pro-Arg-Arg-Leu-Trp-Leu-Trp-Lys]-D-Val-D-Pro-NH2 |
| 4029 | TCAM4026 | Arg-Arg-Phe-Phe-Arg-Arg-Leu-Arg-c[Asp-Pro-Arg-Arg-Leu-Trp-Leu-Trp-Lys]-D-Val-D-Phe-NH2 |
| 4030 | TCAM4027 | Arg-Arg-Phe-Phe-Arg-Arg-Leu-Arg-c[Asp-Pro-Arg-Arg-Leu-Trp-Leu-Trp-Lys]-D-Pro-D-Val-NH2 |
| 4031 | TCAM4028 | Arg-Arg-Phe-Phe-Arg-Arg-Leu-Arg-c[Asp-Pro-Arg-Arg-Leu-Trp-Leu-Trp-Lys]-D-Phe-D-Val-NH2 |
| 4032 | TCAM4029 | Arg-Arg-Phe-Phe-Arg-Arg-Leu-Arg-c[Asp-Pro-Arg-Arg-Leu-Trp-Leu-Trp-Lys]-D-Val-D-Pro-NH2 |
| 4033 | TCAM4030 | Arg-Arg-Phe-Phe-Arg-Arg-Leu-Arg-c[Asp-Pro-Arg-Arg-Leu-Trp-Leu-Trp-Lys]-D-Val-D-Phe-NH2 |
| 4034 | TCAM4031 | Arg-Arg-Phe-Phe-Arg-Arg-Leu-Arg-c[Asp-Pro-Arg-Arg-Leu-Trp-Leu-Trp-Lys]-D-Pro-D-Val-NH2 |
| 4035 | TCAM4032 | Arg-Arg-Phe-Phe-Arg-Arg-Leu-Arg-c[Asp-Pro-Arg-Arg-Leu-Trp-Leu-Trp-Lys]-D-Phe-D-Val-NH2 |
| 4036 | TCAM4033 | Arg-Arg-Phe-Phe-Arg-Arg-Leu-Arg-c[Asp-Arg-Arg-Arg-Trp-Leu-Trp-Leu-Trp-Lys]-D-Val-D-Pro-NH2 |
| 4037 | TCAM4034 | Arg-Arg-Phe-Phe-Arg-Arg-Leu-Arg-c[Asp-Pro-Arg-Arg-Arg-Trp-Leu-Trp-Leu-Trp-Lys]-D-Val-D-Phe-NH2 |
| 4038 | TCAM4035 | Arg-Arg-Phe-Phe-Arg-Arg-Leu-Arg-c[Asp-Pro-Arg-Arg-Arg-Trp-Leu-Trp-Leu-Trp-Lys]-D-Pro-D-Val-NH2 |
| 4039 | TCAM4036 | Arg-Arg-Phe-Phe-Arg-Arg-Leu-Arg-c[Asp-Pro-Arg-Arg-Arg-Trp-Leu-Trp-Leu-Trp-Lys]-D-Phe-D-Val-NH2 |
| 4040 | TCAM4037 | Arg-Arg-Phe-Phe-Arg-Arg-Leu-Arg-c[Asp-Pro-Arg-Gln-Arg-Arg-Trp-Leu-Trp-Leu-Trp-Lys]-D-Val-D-Pro-NH2 |
| 4041 | TCAM4038 | Arg-Arg-Phe-Phe-Arg-Arg-Leu-Arg-c[Asp-Pro-Arg-Gln-Arg-Arg-Trp-Leu-Trp-Leu-Trp-Lys]-D-Val-D-Phe-NH2 |
| 4042 | TCAM4039 | Arg-Arg-Phe-Phe-Arg-Arg-Leu-Arg-c[Asp-Pro-Arg-Gln-Arg-Arg-Trp-Leu-Trp-Leu-Trp-Lys]-D-Pro-D-Val-NH2 |
| 4043 | TCAM4040 | Arg-Arg-Phe-Phe-Arg-Arg-Leu-Arg-c[Asp-Pro-Arg-Gln-Arg-Arg-Trp-Leu-Trp-Leu-Trp-Lys]-D-Phe-D-Val-NH2 |
| 4044 | TCAM4041 | Arg-Arg-Phe-Phe-Arg-Arg-Leu-Arg-c[Asp-Pro-Trp-Arg-Trp-Trp-Arg-Arg-Lys]-D-Val-D-Phe-NH2 |
| 4045 | TCAM4042 | Arg-Arg-Phe-Phe-Arg-Arg-Leu-Arg-c[Asp-Pro-Trp-Arg-Trp-Trp-Arg-Arg-Lys]-D-Pro-D-Val-NH2 |
| 4046 | TCAM4043 | Arg-Arg-Phe-Phe-Arg-Arg-Leu-Arg-c[Asp-Pro-Trp-Arg-Trp-Trp-Arg-Arg-Lys]-D-Phe-D-Val-NH2 |
| 4047 | TCAM4044 | Arg-Arg-Phe-Phe-Arg-Arg-Leu-Arg-c[Asp-Pro-Trp-Trp-Arg-Arg-Trp-Trp-Arg-Arg-Lys]-D-Val-D-Pro-NH2 |
| 4048 | TCAM4045 | Arg-Arg-Phe-Phe-Arg-Arg-Leu-Arg-c[Asp-Pro-Trp-Trp-Arg-Arg-Trp-Trp-Arg-Arg-Lys]-D-Val-D-Phe-NH2 |

TABLE 5-continued

Exemplary Anti-microbial peptides

| SEQ NO: | Peptide | Peptide Sequence |
|---|---|---|
| 4049 | TCAM4046 | Arg-Arg-Phe-Phe-Arg-Arg-Leu-Arg-c[Asp-Pro-Trp-Trp-Arg-Trp-Trp-Arg-Arg-Lys]-D-Pro-D-Val-NH2 |
| 4050 | TCAM4047 | Arg-Arg-Phe-Phe-Arg-Arg-Leu-Arg-c[Asp-Pro-Trp-Trp-Arg-Trp-Trp-Arg-Arg-Lys]-D-Phe-D-Val-NH2 |
| 4051 | TCAM4048 | Arg-Arg-Phe-Phe-Arg-Arg-Leu-Arg-c[Asp-Pro-Trp-Arg-Trp-Arg-Trp-Arg-Lys]-D-Val-D-Pro-NH2 |
| 4052 | TCAM4049 | Arg-Arg-Phe-Phe-Arg-Arg-Leu-Arg-c[Asp-Pro-Trp-Arg-Trp-Arg-Trp-Arg-Lys]-D-Val-D-Phe-NH2 |
| 4053 | TCAM4050 | Arg-Arg-Phe-Phe-Arg-Arg-Leu-Arg-c[Asp-Pro-Trp-Arg-Trp-Arg-Trp-Arg-Lys]-D-Pro-D-Val-NH2 |
| 4054 | TCAM4051 | Arg-Arg-Phe-Phe-Arg-Arg-Leu-Arg-c[Asp-Pro-Trp-Arg-Trp-Arg-Trp-Arg-Lys]-D-Phe-D-Val-NH2 |
| 4055 | TCAM4052 | Arg-Arg-Phe-Phe-Arg-Arg-Leu-Arg-c[Asp-Pro-Arg-Trp-Arg-Trp-Arg-Trp-Lys]-D-Val-D-Pro-NH2 |
| 4056 | TCAM4053 | Arg-Arg-Phe-Phe-Arg-Arg-Leu-Arg-c[Asp-Pro-Arg-Trp-Arg-Trp-Arg-Trp-Lys]-D-Val-D-Phe-NH2 |
| 4057 | TCAM4054 | Arg-Arg-Phe-Phe-Arg-Arg-Leu-Arg-c[Asp-Pro-Arg-Trp-Arg-Trp-Arg-Trp-Lys]-D-Pro-D-Val-NH2 |
| 4058 | TCAM4055 | Arg-Arg-Phe-Phe-Arg-Arg-Leu-Arg-c[Asp-Pro-Arg-Trp-Arg-Trp-Arg-Trp-Lys]-D-Phe-D-Val-NH2 |
| 4059 | TCAM4056 | Arg-Arg-Phe-Phe-Arg-Arg-Leu-Arg-c[Asp-Pro-Arg-Trp-Trp-Arg-Arg-Lys]-D-Val-D-Pro-NH2 |
| 4060 | TCAM4057 | Arg-Arg-Phe-Phe-Arg-Arg-Leu-Arg-c[Asp-Pro-Arg-Trp-Trp-Arg-Arg-Lys]-D-Val-D-Phe-NH2 |
| 4061 | TCAM4058 | Arg-Arg-Phe-Phe-Arg-Arg-Leu-Arg-c[Asp-Pro-Arg-Trp-Trp-Arg-Arg-Lys]-D-Pro-D-Val-NH2 |
| 4062 | TCAM4059 | Arg-Arg-Phe-Phe-Arg-Arg-Leu-Arg-c[Asp-Pro-Arg-Trp-Trp-Arg-Arg-Lys]-D-Phe-D-Val-NH2 |
| 4063 | TCAM4060 | Arg-Arg-Phe-Phe-Arg-Arg-Leu-Arg-c[Asp-Pro-Trp-Trp-Arg-Arg-Trp-Lys]-D-Val-D-Pro-NH2 |
| 4064 | TCAM4061 | Arg-Arg-Phe-Phe-Arg-Arg-Leu-Arg-c[Asp-Pro-Trp-Trp-Arg-Arg-Trp-Lys]-D-Val-D-Phe-NH2 |
| 4065 | TCAM4062 | Arg-Arg-Phe-Phe-Arg-Arg-Leu-Arg-c[Asp-Pro-Trp-Trp-Arg-Arg-Trp-Lys]-D-Pro-D-Val-NH2 |
| 4066 | TCAM4063 | Arg-Arg-Phe-Phe-Arg-Arg-Leu-Arg-c[Asp-Pro-Trp-Trp-Arg-Arg-Trp-Lys]-D-Phe-D-Val-NH2 |
| 4067 | TCAM4064 | Arg-Arg-Phe-Phe-Arg-Arg-Leu-Arg-c[Asp-Pro-Trp-Arg-Trp-Arg-Trp-Lys]-D-Val-D-Pro-NH2 |
| 4068 | TCAM4065 | Arg-Arg-Phe-Phe-Arg-Arg-Leu-Arg-c[Asp-Pro-Trp-Arg-Trp-Arg-Trp-Lys]-D-Val-D-Phe-NH2 |
| 4069 | TCAM4066 | Arg-Arg-Phe-Phe-Arg-Arg-Leu-Arg-c[Asp-Pro-Trp-Arg-Trp-Arg-Trp-Lys]-D-Pro-D-Val-NH2 |
| 4070 | TCAM4067 | Arg-Arg-Phe-Phe-Arg-Arg-Leu-Arg-c[Asp-Pro-Trp-Arg-Trp-Arg-Trp-Lys]-D-Phe-D-Val-NH2 |
| 4071 | TCAM4068 | Arg-Arg-Phe-Phe-Arg-Arg-Leu-Arg-c[Asp-Pro-Arg-Trp-Arg-Trp-Arg-Lys]-D-Val-D-Pro-NH2 |
| 4072 | TCAM4069 | Arg-Arg-Phe-Phe-Arg-Arg-Leu-Arg-c[Asp-Pro-Arg-Trp-Arg-Trp-Arg-Lys]-D-Val-D-Phe-NH2 |
| 4073 | TCAM4070 | Arg-Arg-Phe-Phe-Arg-Arg-Leu-Arg-c[Asp-Pro-Arg-Trp-Arg-Trp-Arg-Lys]-D-Pro-D-Val-NH2 |

TABLE 5-continued

Exemplary Anti-microbial peptides

| SEQ NO: | Peptide | Peptide Sequence |
|---|---|---|
| 4074 | TCAM4071 | Arg-Arg-Phe-Phe-Arg-Arg-Leu-Arg-c[Asp-Pro-Arg-Trp-Arg-Trp-Arg-Lys]-D-Phe-D-Val-NH2 |
| 4075 | TCAM4072 | Arg-Arg-Phe-Phe-Arg-Arg-Leu-Arg-c[Asp-Pro-Trp-Arg-Tyr-Arg-Trp-Lys]-D-Val-D-Pro-NH2 |
| 4076 | TCAM4073 | Arg-Arg-Phe-Phe-Arg-Arg-Leu-Arg-c[Asp-Pro-Trp-Arg-Tyr-Arg-Trp-Lys]-D-Val-D-Phe-NH2 |
| 4077 | TCAM4074 | Arg-Arg-Phe-Phe-Arg-Arg-Leu-Arg-c[Asp-Pro-Trp-Arg-Tyr-Arg-Trp-Lys]-D-Pro-D-Val-NH2 |
| 4078 | TCAM4075 | Arg-Arg-Phe-Phe-Arg-Arg-Leu-Arg-c[Asp-Pro-Trp-Arg-Tyr-Arg-Trp-Lys]-D-Phe-D-Val-NH2 |
| 4079 | TCAM4076 | Arg-Arg-Phe-Phe-Arg-Arg-Leu-Arg-c[Asp-Pro-Trp-Arg-Trp-Arg-Tyr-Lys]-D-Val-D-Pro-NH2 |
| 4080 | TCAM4077 | Arg-Arg-Phe-Phe-Arg-Arg-Leu-Arg-c[Asp-Pro-Trp-Arg-Trp-Arg-Tyr-Lys]-D-Val-D-Phe-NH2 |
| 4081 | TCAM4078 | Arg-Arg-Phe-Phe-Arg-Arg-Leu-Arg-c[Asp-Pro-Trp-Arg-Trp-Arg-Tyr-Lys]-D-Pro-D-Val-NH2 |
| 4082 | TCAM4079 | Arg-Arg-Phe-Phe-Arg-Arg-Leu-Arg-c[Asp-Pro-Trp-Arg-Trp-Arg-Tyr-Lys]-D-Phe-D-Val-NH2 |
| 4083 | TCAM4080 | Arg-Arg-Phe-Phe-Arg-Arg-Leu-Arg-c[Asp-Pro-Trp-Arg-Trp-Arg-Lys]-D-Val-D-Pro-NH2 |
| 4084 | TCAM4081 | Arg-Arg-Phe-Phe-Arg-Arg-Leu-Arg-c[Asp-Pro-Trp-Arg-Trp-Arg-Lys]-D-Val-D-Phe-NH2 |
| 4085 | TCAM4082 | Arg-Arg-Phe-Phe-Arg-Arg-Leu-Arg-c[Asp-Pro-Trp-Arg-Trp-Arg-Lys]-D-Pro-D-Val-NH2 |
| 4086 | TCAM4083 | Arg-Arg-Phe-Phe-Arg-Arg-Leu-Arg-c[Asp-Pro-Trp-Arg-Trp-Arg-Lys]-D-Phe-D-Val-NH2 |
| 4087 | TCAM4084 | Arg-Arg-Phe-Phe-Arg-Arg-Leu-Arg-c[Asp-Pro-Trp-Arg-Arg-Trp-Lys]-D-Val-D-Pro-NH2 |
| 4088 | TCAM4085 | Arg-Arg-Phe-Phe-Arg-Arg-Leu-Arg-c[Asp-Pro-Trp-Arg-Arg-Trp-Lys]-D-Val-D-Phe-NH2 |
| 4089 | TCAM4086 | Arg-Arg-Phe-Phe-Arg-Arg-Leu-Arg-c[Asp-Pro-Trp-Arg-Arg-Trp-Lys]-D-Pro-D-Val-NH2 |
| 4090 | TCAM4087 | Arg-Arg-Phe-Phe-Arg-Arg-Leu-Arg-c[Asp-Pro-Trp-Arg-Arg-Trp-Lys]-D-Phe-D-Val-NH2 |
| 4091 | TCAM4088 | Arg-Arg-Phe-Phe-Arg-Arg-Leu-Arg-c[Asp-Pro-Arg-Trp-Trp-Arg-Lys]-D-Val-D-Pro-NH2 |
| 4092 | TCAM4089 | Arg-Arg-Phe-Phe-Arg-Arg-Leu-Arg-c[Asp-Pro-Arg-Trp-Trp-Arg-Lys]-D-Val-D-Phe-NH2 |
| 4093 | TCAM4090 | Arg-Arg-Phe-Phe-Arg-Arg-Leu-Arg-c[Asp-Pro-Arg-Trp-Trp-Arg-Lys]-D-Pro-D-Val-NH2 |
| 4094 | TCAM4091 | Arg-Arg-Phe-Phe-Arg-Arg-Leu-Arg-c[Asp-Pro-Arg-Trp-Trp-Arg-Lys]-D-Phe-D-Val-NH2 |
| 4095 | TCAM4092 | Arg-Arg-Phe-Phe-Arg-Arg-Leu-Arg-c[Asp-Pro-Trp-Arg-Trp-Lys]-D-Val-D-Pro-NH2 |
| 4096 | TCAM4093 | Arg-Arg-Phe-Phe-Arg-Arg-Leu-Arg-c[Asp-Pro-Trp-Arg-Trp-Lys]-D-Val-D-Phe-NH2 |
| 4097 | TCAM4094 | Arg-Arg-Phe-Phe-Arg-Arg-Leu-Arg-c[Asp-Pro-Trp-Arg-Trp-Lys]-D-Pro-D-Val-NH2 |
| 4098 | TCAM4095 | Arg-Arg-Phe-Phe-Arg-Arg-Leu-Arg-c[Asp-Pro-Trp-Arg-Trp-Lys]-D-Phe-D-Val-NH2 |
| 4099 | TCAM4096 | Arg-Arg-Phe-Phe-Arg-Arg-Leu-Arg-c[Asp-Pro-Arg-Trp-Arg-Lys]-D-Val-D-Pro-NH2 |
| 4100 | TCAM4097 | Arg-Arg-Phe-Phe-Arg-Arg-Leu-Arg-c[Asp-Pro-Arg-Trp-Arg-Lys]-D-Val-D-Phe-NH2 |
| 4101 | TCAM4098 | Arg-Arg-Phe-Phe-Arg-Arg-Leu-Arg-c[Asp-Pro-Arg-Trp-Arg-Lys]-D-Pro-D-Val-NH2 |
| 4102 | TCAM4099 | Arg-Arg-Phe-Phe-Arg-Arg-Leu-Arg-c[Asp-Pro-Arg-Trp-Arg-Lys]-D-Phe-D-Val-NH2 |
| 4103 | TCAM4100 | -Arg-Arg-Phe-Phe-Arg-Arg-Leu-Arg-c[Asp-Arg-Arg-Trp-Trp-Arg-Phe-Lys]-D-Val-D-Pro-NH2 |
| 4104 | TCAM4101 | Arg-Arg-Phe-Phe-Arg-Arg-Leu-Arg-c[Asp-Arg-Arg-Trp-Trp-Arg-Phe-Lys]-D-Val-D-Phe-NH2 |
| 4105 | TCAM4102 | Arg-Arg-Phe-Phe-Arg-Arg-Leu-Arg-c[Asp-Arg-Arg-Trp-Trp-Arg-Phe-Lys]-D-Pro-D-Val-NH2 |

TABLE 5-continued

Exemplary Anti-microbial peptides

| SEQ NO: | Peptide | Peptide Sequence |
|---|---|---|
| 4106 | TCAM4103 | Arg-Arg-Phe-Phe-Arg-Arg-Leu-Arg-c[Asp-Arg-Arg-Trp-Trp-Arg-Phe-Lys]-D-Phe-D-Val-NH2 |
| 4107 | TCAM4104 | Arg-Arg-Phe-Phe-Arg-Arg-Leu-Arg-c[Asp-Arg-Arg-Trp-Trp-Arg-Phe-Lys]-D-Val-D-Pro-NH2 |
| 4108 | TCAM4105 | Arg-Arg-Phe-Phe-Arg-Arg-Leu-Arg-c[Asp-Arg-Arg-Trp-Trp-Arg-Phe-Lys]-D-Val-D-Phe-NH2 |
| 4109 | TCAM4106 | Arg-Arg-Phe-Phe-Arg-Arg-Leu-Arg-c[Asp-Arg-Arg-Trp-Trp-Arg-Phe-Lys]-D-Pro-D-Val-NH2 |
| 4110 | TCAM4107 | Arg-Arg-Phe-Phe-Arg-Arg-Leu-Arg-c[Asp-Arg-Arg-Trp-Trp-Arg-Phe-Lys]-D-Phe-D-Val-NH2 |
| 4111 | TCAM4108 | Arg-Arg-Phe-Phe-Arg-Arg-Leu-Arg-c[Asp-Arg-Arg-Tyr-Tyr-Arg-Phe-Lys]-D-Val-D-Pro-NH2 |
| 4112 | TCAM4109 | Arg-Arg-Phe-Phe-Arg-Arg-Leu-Arg-c[Asp-Arg-Arg-Tyr-Tyr-Arg-Phe-Lys]-D-Val-D-Phe-NH2 |
| 4113 | TCAM4110 | Arg-Arg-Phe-Phe-Arg-Arg-Leu-Arg-c[Asp-Arg-Arg-Tyr-Tyr-Arg-Phe-Lys]-D-Pro-D-Val-NH2 |
| 4114 | TCAM4111 | Arg-Arg-Phe-Phe-Arg-Arg-Leu-Arg-c[Asp-Arg-Arg-Tyr-Tyr-Arg-Phe-Lys]-D-Phe-D-Val-NH2 |
| 4115 | TCAM4112 | Arg-Arg-Phe-Phe-Arg-Arg-Leu-Arg-c[Asp-Arg-Arg-Nal-Nal-Arg-Phe-Lys]-D-Val-D-Pro-NH2 |
| 4116 | TCAM4113 | Arg-Arg-Phe-Phe-Arg-Arg-Leu-Arg-c[Asp-Arg-Arg-Nal-Nal-Arg-Phe-Lys]-D-Val-D-Phe-NH2 |
| 4117 | TCAM4114 | Arg-Arg-Phe-Phe-Arg-Arg-Leu-Arg-c[Asp-Arg-Arg-Nal-Nal-Arg-Phe-Lys]-D-Pro-D-Val-NH2 |
| 4118 | TCAM4115 | Arg-Arg-Phe-Phe-Arg-Arg-Leu-Arg-c[Asp-Arg-Arg-Nal-Nal-Arg-Phe-Lys]-D-Phe-D-Val-NH2 |
| 4119 | TCAM4116 | Arg-Arg-Phe-Phe-Arg-Arg-Leu-Arg-c[Asp-Arg-Arg-Leu-Trp-Leu-Trp-Lys]-D-Val-D-Pro-NH2 |
| 4120 | TCAM4117 | Arg-Arg-Phe-Phe-Arg-Arg-Leu-Arg-c[Asp-Arg-Arg-Leu-Trp-Leu-Trp-Lys]-D-Val-D-Phe-NH2 |
| 4121 | TCAM4118 | Arg-Arg-Phe-Phe-Arg-Arg-Leu-Arg-c[Asp-Arg-Arg-Leu-Trp-Leu-Trp-Lys]-D-Pro-D-Val-NH2 |
| 4122 | TCAM4119 | Arg-Arg-Phe-Phe-Arg-Arg-Leu-Arg-c[Asp-Arg-Arg-Leu-Trp-Leu-Trp-Lys]-D-Phe-D-Val-NH2 |
| 4123 | TCAM4120 | Arg-Arg-Phe-Phe-Arg-Arg-Leu-Arg-c[Asp-Arg-Arg-Leu-Trp-Leu-Trp-Lys]-D-Val-D-Pro-NH2 |
| 4124 | TCAM4121 | Arg-Arg-Phe-Phe-Arg-Arg-Leu-Arg-c[Asp-Arg-Arg-Leu-Trp-Leu-Trp-Lys]-D-Val-D-Phe-NH2 |
| 4125 | TCAM4122 | Arg-Arg-Phe-Phe-Arg-Arg-Leu-Arg-c[Asp-Arg-Arg-Leu-Trp-Leu-Trp-Lys]-D-Pro-D-Val-NH2 |
| 4126 | TCAM4123 | Arg-Arg-Phe-Phe-Arg-Arg-Leu-Arg-c[Asp-Arg-Arg-Leu-Trp-Leu-Trp-Lys]-D-Phe-D-Val-NH2 |
| 4127 | TCAM4124 | Arg-Arg-Phe-Phe-Arg-Arg-Leu-Arg-c[Asp-Arg-Arg-Arg-Trp-Leu-Trp-Leu-Trp-Lys]-D-Val-D-Pro-NH2 |
| 4128 | TCAM4125 | Arg-Arg-Phe-Phe-Arg-Arg-Leu-Arg-c[Asp-Arg-Arg-Arg-Trp-Leu-Trp-Leu-Trp-Lys]-D-Val-D-Phe-NH2 |
| 4129 | TCAM4126 | Arg-Arg-Phe-Phe-Arg-Arg-Leu-Arg-c[Asp-Arg-Arg-Arg-Trp-Leu-Trp-Leu-Trp-Lys]-D-Pro-D-Val-NH2 |
| 4130 | TCAM4127 | Arg-Arg-Phe-Phe-Arg-Arg-Leu-Arg-c[Asp-Arg-Arg-Arg-Trp-Leu-Trp-Leu-Trp-Lys]-D-Phe-D-Val-NH2 |

TABLE 5-continued

Exemplary Anti-microbial peptides

| SEQ NO: | Peptide | Peptide Sequence |
|---|---|---|
| 4131 | TCAM4128 | Arg-Arg-Phe-Phe-Arg-Arg-Leu-Arg-c[Asp-Arg-Gln-Arg-Arg-Trp-Leu-Trp-Leu-Trp-Lys]-D-Val-D-Pro-NH2 |
| 4132 | TCAM4129 | Arg-Arg-Phe-Phe-Arg-Arg-Leu-Arg-c[Asp-Arg-Gln-Arg-Arg-Trp-Leu-Trp-Leu-Trp-Lys]-D-Val-D-Phe-NH2 |
| 4133 | TCAM4130 | Arg-Arg-Phe-Phe-Arg-Arg-Leu-Arg-c[Asp-Arg-Gln-Arg-Arg-Trp-Leu-Trp-Leu-Trp-Lys]-D-Pro-D-Val-NH2 |
| 4134 | TCAM4131 | Arg-Arg-Phe-Phe-Arg-Arg-Leu-Arg-c[Asp-Arg-Gln-Arg-Arg-Trp-Leu-Trp-Leu-Trp-Lys]-D-Phe-D-Val-NH2 |
| 4135 | TCAM4132 | Arg-Arg-Phe-Phe-Arg-Arg-Leu-Arg-c[Asp-Trp-Arg-Trp-Trp-Arg-Arg-Lys]-D-Val-D-Pro-NH2 |
| 4136 | TCAM4133 | Arg-Arg-Phe-Phe-Arg-Arg-Leu-Arg-c[Asp-Trp-Arg-Trp-Trp-Arg-Arg-Lys]-D-Val-D-Phe-NH2 |
| 4137 | TCAM4134 | Arg-Arg-Phe-Phe-Arg-Arg-Leu-Arg-c[Asp-Trp-Arg-Trp-Trp-Arg-Arg-Lys]-D-Pro-D-Val-NH2 |
| 4138 | TCAM4135 | Arg-Arg-Phe-Phe-Arg-Arg-Leu-Arg-c[Asp-Trp-Arg-Trp-Trp-Arg-Arg-Lys]-D-Phe-D-Val-NH2 |
| 4139 | TCAM4136 | Arg-Arg-Phe-Phe-Arg-Arg-Leu-Arg-c[Asp-Trp-Trp-Arg-Arg-Trp-Trp-Arg-Arg-Lys]-D-Val-D-Pro-NH2 |
| 4140 | TCAM4137 | Arg-Arg-Phe-Phe-Arg-Arg-Leu-Arg-c[Asp-Trp-Trp-Arg-Arg-Trp-Trp-Arg-Arg-Lys]-D-Val-D-Phe-NH2 |
| 4141 | TCAM4138 | Arg-Arg-Phe-Phe-Arg-Arg-Leu-Arg-c[Asp-Trp-Trp-Arg-Arg-Trp-Trp-Arg-Arg-Lys]-D-Pro-D-Val-NH2 |
| 4142 | TCAM4139 | Arg-Arg-Phe-Phe-Arg-Arg-Leu-Arg-c[Asp-Trp-Trp-Arg-Arg-Trp-Trp-Arg-Arg-Lys]-D-Phe-D-Val-NH2 |
| 4143 | TCAM4140 | Arg-Arg-Phe-Phe-Arg-Arg-Leu-Arg-c[Asp-Trp-Arg-Trp-Arg-Trp-Arg-Lys]-D-Val-D-Pro-NH2 |
| 4144 | TCAM4141 | Arg-Arg-Phe-Phe-Arg-Arg-Leu-Arg-c[Asp-Trp-Arg-Trp-Arg-Trp-Arg-Lys]-D-Val-D-Phe-NH2 |
| 4145 | TCAM4142 | Arg-Arg-Phe-Phe-Arg-Arg-Leu-Arg-c[Asp-Trp-Arg-Trp-Arg-Trp-Arg-Lys]-D-Pro-D-Val-NH2 |
| 4146 | TCAM4143 | Arg-Arg-Phe-Phe-Arg-Arg-Leu-Arg-c[Asp-Trp-Arg-Trp-Arg-Trp-Arg-Lys]-D-Phe-D-Val-NH2 |
| 4147 | TCAM4144 | Arg-Arg-Phe-Phe-Arg-Arg-Leu-Arg-c[Asp-Arg-Trp-Arg-Trp-Arg-Trp-Lys]-D-Val-D-Pro-NH2 |
| 4148 | TCAM4145 | Arg-Arg-Phe-Phe-Arg-Arg-Leu-Arg-c[Asp-Arg-Trp-Arg-Trp-Arg-Trp-Lys]-D-Val-D-Phe-NH2 |
| 4149 | TCAM4146 | Arg-Arg-Phe-Phe-Arg-Arg-Leu-Arg-c[Asp-Arg-Trp-Arg-Trp-Arg-Trp-Lys]-D-Pro-D-Val-NH2 |
| 4150 | TCAM4147 | Arg-Arg-Phe-Phe-Arg-Arg-Leu-Arg-c[Asp-Arg-Trp-Arg-Trp-Arg-Trp-Lys]-D-Phe-D-Val-NH2 |
| 4151 | TCAM4148 | Arg-Arg-Phe-Phe-Arg-Arg-Leu-Arg-c[Asp-Arg-Trp-Trp-Arg-Arg-Lys]-D-Val-D-Pro-NH2 |
| 4152 | TCAM4149 | Arg-Arg-Phe-Phe-Arg-Arg-Leu-Arg-c[Asp-Arg-Trp-Trp-Arg-Arg-Lys]-D-Val-D-Phe-NH2 |
| 4153 | TCAM4150 | Arg-Arg-Phe-Phe-Arg-Arg-Leu-Arg-c[Asp-Arg-Trp-Trp-Arg-Arg-Lys]-D-Pro-D-Val-NH2 |
| 4154 | TCAM4151 | Arg-Arg-Phe-Phe-Arg-Arg-Leu-Arg-c[Asp-Arg-Trp-Trp-Arg-Arg-Lys]-D-Phe-D-Val-NH2 |
| 4155 | TCAM4152 | Arg-Arg-Phe-Phe-Arg-Arg-Leu-Arg-c[Asp-Arg-Trp-Arg-Trp-Arg-Lys]-D-Val-D-Pro-NH2 |
| 4156 | TCAM4153 | Arg-Arg-Phe-Phe-Arg-Arg-Leu-Arg-c[Asp-Arg-Trp-Arg-Trp-Arg-Lys]-D-Val-D-Phe-NH2 |
| 4157 | TCAM4154 | Arg-Arg-Phe-Phe-Arg-Arg-Leu-Arg-c[Asp-Arg-Trp-Arg-Trp-Arg-Lys]-D-Pro-D-Val-NH2 |

TABLE 5-continued

Exemplary Anti-microbial peptides

| SEQ NO: | Peptide | Peptide Sequence |
|---|---|---|
| 4158 | TCAM4155 | Arg-Arg-Phe-Phe-Arg-Arg-Leu-Arg-c[Asp-Arg-Trp-Arg-Trp-Arg-Lys]-D-Phe-D-Val-NH2 |
| 4159 | TCAM4156 | Arg-Arg-Phe-Phe-Arg-Arg-Leu-Arg-c[Asp-Trp-Trp-Arg-Arg-Trp-Lys]-D-Val-D-Pro-NH2 |
| 4160 | TCAM4157 | Arg-Arg-Phe-Phe-Arg-Arg-Leu-Arg-c[Asp-Trp-Trp-Arg-Arg-Trp-Lys]-D-Val-D-Phe-NH2 |
| 4161 | TCAM4158 | Arg-Arg-Phe-Phe-Arg-Arg-Leu-Arg-c[Asp-Trp-Trp-Arg-Arg-Trp-Lys]-D-Pro-D-Val-NH2 |
| 4162 | TCAM4159 | Arg-Arg-Phe-Phe-Arg-Arg-Leu-Arg-c[Asp-Trp-Trp-Arg-Arg-Trp-Lys]-D-Phe-D-Val-NH2 |
| 4163 | TCAM4160 | Arg-Arg-Phe-Phe-Arg-Arg-Leu-Arg-c[Asp-Trp-Arg-Trp-Arg-Trp-Lys]-D-Val-D-Pro-NH2 |
| 4164 | TCAM4161 | Arg-Arg-Phe-Phe-Arg-Arg-Leu-Arg-c[Asp-Trp-Arg-Trp-Arg-Trp-Lys]-D-Val-D-Phe-NH2 |
| 4165 | TCAM4162 | Arg-Arg-Phe-Phe-Arg-Arg-Leu-Arg-c[Asp-Trp-Arg-Trp-Arg-Trp-Lys]-D-Pro-D-Val-NH2 |
| 4166 | TCAM4163 | Arg-Arg-Phe-Phe-Arg-Arg-Leu-Arg-c[Asp-Trp-Arg-Trp-Arg-Trp-Lys]-D-Phe-D-Val-NH2 |
| 4167 | TCAM4164 | Arg-Arg-Phe-Phe-Arg-Arg-Leu-Arg-c[Asp-Trp-Arg-Tyr-Arg-Trp-Lys]-D-Val-D-Pro-NH2 |
| 4168 | TCAM4165 | Arg-Arg-Phe-Phe-Arg-Arg-Leu-Arg-c[Asp-Trp-Arg-Tyr-Arg-Trp-Lys]-D-Val-D-Phe-NH2 |
| 4169 | TCAM4166 | Arg-Arg-Phe-Phe-Arg-Arg-Leu-Arg-c[Asp-Trp-Arg-Tyr-Arg-Trp-Lys]-D-Pro-D-Val-NH2 |
| 4170 | TCAM4167 | Arg-Arg-Phe-Phe-Arg-Arg-Leu-Arg-c[Asp-Trp-Arg-Tyr-Arg-Trp-Lys]-D-Phe-D-Val-NH2 |
| 4171 | TCAM4168 | Arg-Arg-Phe-Phe-Arg-Arg-Leu-Arg-c[Asp-Trp-Arg-Trp-Arg-Tyr-Lys]-D-Val-D-Pro-NH2 |
| 4172 | TCAM4169 | Arg-Arg-Phe-Phe-Arg-Arg-Leu-Arg-c[Asp-Trp-Arg-Trp-Arg-Tyr-Lys]-D-Val-D-Phe-NH2 |
| 4173 | TCAM4170 | Arg-Arg-Phe-Phe-Arg-Arg-Leu-Arg-c[Asp-Trp-Arg-Trp-Arg-Tyr-Lys]-D-Pro-D-Val-NH2 |
| 4174 | TCAM4171 | Arg-Arg-Phe-Phe-Arg-Arg-Leu-Arg-c[Asp-Trp-Arg-Trp-Arg-Tyr-Lys]-D-Phe-D-Val-NH2 |
| 4175 | TCAM4172 | Arg-Arg-Phe-Phe-Arg-Arg-Leu-Arg-c[Asp-Trp-Arg-Trp-Arg-Lys]-D-Val-D-Pro-NH2 |
| 4176 | TCAM4173 | Arg-Arg-Phe-Phe-Arg-Arg-Leu-Arg-c[Asp-Trp-Arg-Trp-Arg-Lys]-D-Val-D-Phe-NH2 |
| 4177 | TCAM4174 | Arg-Arg-Phe-Phe-Arg-Arg-Leu-Arg-c[Asp-Trp-Arg-Trp-Arg-Lys]-D-Pro-D-Val-NH2 |
| 4178 | TCAM4175 | Arg-Arg-Phe-Phe-Arg-Arg-Leu-Arg-c[Asp-Trp-Arg-Trp-Arg-Lys]-D-Phe-D-Val-NH2 |
| 4179 | TCAM4176 | Arg-Arg-Phe-Phe-Arg-Arg-Leu-Arg-c[Asp-Trp-Arg-Arg-Trp-Lys]-D-Val-D-Pro-NH2 |
| 4180 | TCAM4177 | Arg-Arg-Phe-Phe-Arg-Arg-Leu-Arg-c[Asp-Trp-Arg-Arg-Trp-Lys]-D-Val-D-Phe-NH2 |
| 4181 | TCAM4178 | Arg-Arg-Phe-Phe-Arg-Arg-Leu-Arg-c[Asp-Trp-Arg-Arg-Trp-Lys]-D-Pro-D-Val-NH2 |
| 4182 | TCAM4179 | Arg-Arg-Phe-Phe-Arg-Arg-Leu-Arg-c[Asp-Trp-Arg-Arg-Trp-Lys]-D-Phe-D-Val-NH2 |
| 4183 | TCAM4180 | Arg-Arg-Phe-Phe-Arg-Arg-Leu-Arg-c[Asp-Arg-Trp-Trp-Arg-Lys]-D-Val-D-Pro-NH2 |
| 4184 | TCAM4181 | Arg-Arg-Phe-Phe-Arg-Arg-Leu-Arg-c[Asp-Arg-Trp-Trp-Arg-Lys]-D-Val-D-Phe-NH2 |
| 4185 | TCAM4182 | Arg-Arg-Phe-Phe-Arg-Arg-Leu-Arg-c[Asp-Arg-Trp-Trp-Arg-Lys]-D-Pro-D-Val-NH2 |
| 4186 | TCAM4183 | Arg-Arg-Phe-Phe-Arg-Arg-Leu-Arg-c[Asp-Arg-Trp-Trp-Arg-Lys]-D-Phe-D-Val-NH2 |
| 4187 | TCAM4184 | Arg-Arg-Phe-Phe-Arg-Arg-Leu-Arg-c[Asp-Trp-Arg-Trp-Lys]-D-Val-D-Pro-NH2 |
| 4188 | TCAM4185 | Arg-Arg-Phe-Phe-Arg-Arg-Leu-Arg-c[Asp-Trp-Arg-Trp-Lys]-D-Val-D-Phe-NH2 |
| 4189 | TCAM4186 | Arg-Arg-Phe-Phe-Arg-Arg-Leu-Arg-c[Asp-Trp-Arg-Trp-Lys]-D-Pro-D-Val-NH2 |
| 4190 | TCAM4187 | Arg-Arg-Phe-Phe-Arg-Arg-Leu-Arg-c[Asp-Trp-Arg-Trp-Lys]-D-Phe-D-Val-NH2 |
| 4191 | TCAM4188 | Arg-Arg-Phe-Phe-Arg-Arg-Leu-Arg-c[Asp-Arg-Trp-Arg-Lys]-D-Val-D-Pro-NH2 |
| 4192 | TCAM4189 | Arg-Arg-Phe-Phe-Arg-Arg-Leu-Arg-c[Asp-Arg-Trp-Arg-Lys]-D-Val-D-Phe-NH2 |
| 4193 | TCAM4190 | Arg-Arg-Phe-Phe-Arg-Arg-Leu-Arg-c[Asp-Arg-Trp-Arg-Lys]-D-Pro-D-Val-NH2 |
| 4194 | TCAM4191 | Arg-Arg-Phe-Phe-Arg-Arg-Leu-Arg-c[Asp-Arg-Trp-Arg-Lys]-D-Phe-D-Val-NH2 |

TABLE 5-continued

Exemplary Anti-microbial peptides

| SEQ NO: | Peptide | Peptide Sequence |
|---|---|---|
| 4195 | TCAM4192 | Arg-Arg-Phe-Phe-Arg-Arg-Leu-Arg-c[Asp-His-D-Nal(2')-Arg-Trp-Lys]-D-Val-D-Pro-NH2 |
| 4196 | TCAM4193 | Arg-Arg-Phe-Phe-Arg-Arg-Leu-Arg-c[Asp-His-D-Nal(2')-Arg-Trp-Lys]-D-Pro-D-Val-NH2 |
| 4197 | TCAM4194 | Arg-Arg-Phe-Phe-Arg-Arg-Leu-Arg-c[Asp-His-D-Nal(2')-Arg-Trp-Lys]-D-Val-D-Phe-NH2 |
| 4198 | TCAM4195 | Arg-Arg-Phe-Phe-Arg-Arg-Leu-Arg-c[Asp-His-D-Nal(2')-Arg-Trp-Lys]-D-Phe-D-Val-NH2 |
| 4199 | TCAM4196 | Arg-Arg-Phe-Phe-Arg-Arg-Leu-Arg-c[Asp-Pro-D-Nal(2')-Arg-Trp-Lys]-D-Val-D-Pro-NH2 |
| 4200 | TCAM4197 | Arg-Arg-Phe-Phe-Arg-Arg-Leu-Arg-c[Asp-Pro-D-Nal(2')-Arg-Trp-Lys]-D-Pro-D-Val-NH2 |
| 4201 | TCAM4198 | Arg-Arg-Phe-Phe-Arg-Arg-Leu-Arg-c[Asp-Pro-D-Nal(2')-Arg-Trp-Lys]-D-Val-D-Phe-NH2 |
| 4202 | TCAM4199 | Arg-Arg-Phe-Phe-Arg-Arg-Leu-Arg-c[Asp-Pro-D-Nal(2')-Arg-Trp-Lys]-D-Phe-D-Val-NH2 |
| 4203 | TCAM4200 | Arg-Arg-Phe-Phe-Arg-Arg-Leu-Arg-c[Asp-Arg-Arg-Nal(2')-Arg-Trp-Lys]-D-Val-D-Pro-NH2 |
| 4204 | TCAM4201 | Arg-Arg-Phe-Phe-Arg-Arg-Leu-Arg-c[Asp-Arg-Arg-Nal(2')-Arg-Trp-Lys]-D-Pro-D-Val-NH2 |
| 4205 | TCAM4202 | Arg-Arg-Phe-Phe-Arg-Arg-Leu-Arg-c[Asp-Arg-Arg-Nal(2')-Arg-Trp-Lys]-D-Val-D-Phe-NH2 |
| 4206 | TCAM4203 | Arg-Arg-Phe-Phe-Arg-Arg-Leu-Arg-c[Asp-Arg-Arg-Nal(2')-Arg-Trp-Lys]-D-Phe-D-Val-NH2 |
| 4207 | TCAM4204 | Arg-Arg-Phe-Phe-Arg-Arg-Leu-Arg-c[Asp-Arg-Arg-Pro-Nal(2')-Arg-Trp-Lys]-D-Val-D-Pro-NH2 |
| 4208 | TCAM4205 | Arg-Arg-Phe-Phe-Arg-Arg-Leu-Arg-c[Asp-Arg-Arg-Pro-D-Nal(2')-Arg-Trp-Lys]-D-Pro-D-Val-NH2 |
| 4209 | TCAM4206 | Arg-Arg-Phe-Phe-Arg-Arg-Leu-Arg-c[Asp-Arg-Arg-Pro-D-Nal(2')-Arg-Trp-Lys]-D-Val-D-Phe-NH2 |
| 4210 | TCAM4207 | Arg-Arg-Phe-Phe-Arg-Arg-Leu-Arg-c[Asp-Arg-Arg-Pro-Nal(2')-Arg-Trp-Lys]-D-Phe-D-Val-NH2 |
| 4211 | TCAM4208 | Arg-Arg-Phe-Phe-Arg-Arg-Leu-Arg-c[Asp-Arg-D-Nal(2')-Arg-Trp-Lys]-D-Val-D-Pro-NH2 |
| 4212 | TCAM4209 | Arg-Arg-Phe-Phe-Arg-Arg-Leu-Arg-c[Asp-Arg-D-Nal(2')-Arg-Trp-Lys]-D-Pro-D-Val-NH2 |
| 4213 | TCAM4210 | Arg-Arg-Phe-Phe-Arg-Arg-Leu-Arg-c[Asp-Arg-D-Nal(2')-Arg-Trp-Lys]-D-Val-D-Phe-NH2 |
| 4214 | TCAM4211 | Arg-Arg-Phe-Phe-Arg-Arg-Leu-Arg-c[Asp-Arg-D-Nal(2')-Arg-Trp-Lys]-D-Phe-D-Val-NH2 |
| 4215 | TCAM4212 | Arg-Arg-Phe-Phe-Arg-Arg-Leu-Arg-c[Asp-Arg-Pro-D-Nal(2')-Arg-Trp-Lys]-D-Val-D-Pro-NH2 |
| 4216 | TCAM4213 | Arg-Arg-Phe-Phe-Arg-Arg-Leu-Arg-c[Asp-Arg-Pro-D-Nal(2')-Arg-Trp-Lys]-D-Pro-D-Val-NH2 |
| 4217 | TCAM4214 | Arg-Arg-Phe-Phe-Arg-Arg-Leu-Arg-c[Asp-Arg-Pro-D-Nal(2')-Arg-Trp-Lys]-D-Val-D-Phe-NH2 |
| 4218 | TCAM4215 | Arg-Arg-Phe-Phe-Arg-Arg-Leu-Arg-c[Asp-Arg-Pro-D-Nal(2')-Arg-Trp-Lys]-D-Phe-D-Val-NH2 |
| 4219 | TCAM4216 | Arg-Arg-Phe-Phe-Arg-Arg-Leu-Arg-Arg-Arg-c[Asp-Pro-D-Nal(2')-Arg-Trp-Lys]-D-Val-D-Pro-NH2 |

TABLE 5-continued

Exemplary Anti-microbial peptides

| SEQ NO: | Peptide | Peptide Sequence |
|---|---|---|
| 4220 | TCAM4217 | Arg-Arg-Phe-Phe-Arg-Arg-Leu-Arg-Arg-Arg-c[Asp-Pro-D-Nal(2')-Arg-Trp-Lys]-D-Pro-D-Val-NH2 |
| 4221 | TCAM4218 | Arg-Arg-Phe-Phe-Arg-Arg-Leu-Arg-Arg-Arg-c[Asp-Pro-D-Nal(2')-Arg-Trp-Lys]-D-Val-D-Phe-NH2 |
| 4222 | TCAM4219 | Arg-Arg-Phe-Phe-Arg-Arg-Leu-Arg-Arg-Arg-c[Asp-Pro-D-Nal(2')-Arg-Trp-Lys]-D-Phe-D-Val-NH2 |
| 4223 | TCAM4220 | Arg-Arg-Phe-Phe-Arg-Arg-Leu-Arg-Arg-Arg-c[Asp-His-D-Nal(2')-Arg-Trp-Lys]-D-Val-D-Pro-NH2 |
| 4224 | TCAM4221 | Arg-Arg-Phe-Phe-Arg-Arg-Leu-Arg-Arg-Arg-c[Asp-His-D-Nal(2')-Arg-Trp-Lys]-D-Pro-D-Val-NH2 |
| 4225 | TCAM4222 | Arg-Arg-Phe-Phe-Arg-Arg-Leu-Arg-Arg-Arg-c[Asp-His-D-Nal(2')-Arg-Trp-Lys]-D-Val-D-Phe-NH2 |
| 4226 | TCAM4223 | Arg-Arg-Phe-Phe-Arg-Arg-Leu-Arg-Arg-Arg-c[Asp-His-D-Nal(2')-Arg-Trp-Lys]-D-Phe-D-Val-NH2 |
| 4227 | TCAM4224 | Arg-Arg-Phe-Phe-Arg-Arg-Leu-Arg-c[Asp-Arg-Pro-D-Nal(2')-Arg-Trp-Arg-Lys]-D-Val-D-Pro-NH2 |
| 4228 | TCAM4225 | Arg-Arg-Phe-Phe-Arg-Arg-Leu-Arg-c[Asp-Arg-Pro-D-Nal(2')-Arg-Trp-Arg-Lys]-D-Pro-D-Val-NH2 |
| 4229 | TCAM4226 | Arg-Arg-Phe-Phe-Arg-Arg-Leu-Arg-c[Asp-Arg-Pro-D-Nal(2')-Arg-Trp-Arg-Lys]-D-Val-D-Phe-NH2 |
| 4230 | TCAM4227 | Arg-Arg-Phe-Phe-Arg-Arg-Leu-Arg-c[Asp-Arg-Pro-D-Nal(2')-Arg-Trp-Arg-Lys]-D-Phe-D-Val-NH2 |
| 4231 | TCAM4228 | Arg-Arg-Phe-Phe-Arg-Arg-Leu-Arg-c[Asp-Arg-His-D-Nal(2')-Arg-Trp-Arg-Lys]-D-Val-D-Pro-NH2 |
| 4232 | TCAM4229 | Arg-Arg-Phe-Phe-Arg-Arg-Leu-Arg-c[Asp-Arg-His-D-Nal(2')-Arg-Trp-Arg-Lys]-D-Pro-D-Val-NH2 |
| 4233 | TCAM4230 | Arg-Arg-Phe-Phe-Arg-Arg-Leu-Arg-c[Asp-Arg-His-D-Nal(2')-Arg-Trp-Arg-Lys]-D-Val-D-Phe-NH2 |
| 4234 | TCAM4231 | Arg-Arg-Phe-Phe-Arg-Arg-Leu-Arg-c[Asp-Arg-His-D-Nal(2')-Arg-Trp-Arg-Lys]-D-Phe-D-Val-NH2 |
| 4235 | TCAM4232 | Arg-Arg-Phe-Phe-Arg-Arg-Leu-Arg-c[Asp-His-D-Nal(2')-Arg-D-Nal(2')-Lys]-D-Val-D-Phe-NH2 |
| 4236 | TCAM4233 | Arg-Arg-Phe-Phe-Arg-Arg-Leu-Arg-c[Asp-His-D-Nal(2')-Arg-D-Nal(2')-Lys]-D-Phe-D-Val-NH2 |
| 4237 | TCAM4234 | Arg-Arg-Phe-Phe-Arg-Arg-Leu-Arg-c[Asp-Pro-D-Nal(2')-Arg-D-Nal(2')-Lys]-D-Val-D-Pro-NH2 |
| 4238 | TCAM4235 | Arg-Arg-Phe-Phe-Arg-Arg-Leu-Arg-c[Asp-Pro-D-Nal(2')-Arg-D-Nal(2')-Lys]-D-Pro-D-Val-NH2 |
| 4239 | TCAM4236 | Arg-Arg-Phe-Phe-Arg-Arg-Leu-Arg-c[Asp-Pro-D-Nal(2')-Arg-D-Nal(2')-Lys]-D-Val-D-Phe-NH2 |
| 4240 | TCAM4237 | Arg-Arg-Phe-Phe-Arg-Arg-Leu-Arg-c[Asp-Pro-D-Nal(2')-Arg-D-Nal(2')-Lys]-D-Phe-D-Val-NH2 |
| 4241 | TCAM4238 | Arg-Arg-Phe-Phe-Arg-Arg-Leu-Arg-c[Asp-Arg-Arg-D-Nal(2')-Arg-D-Nal(2')-Lys]-D-Val-D-Pro-NH2 |
| 4242 | TCAM4239 | Arg-Arg-Phe-Phe-Arg-Arg-Leu-Arg-c[Asp-Arg-Arg-D-Nal(2')-Arg-D-Nal(2')-Lys]-D-Pro-D-Val-NH2 |
| 4243 | TCAM4240 | Arg-Arg-Phe-Phe-Arg-Arg-Leu-Arg-c[Asp-Arg-Arg-D-Nal(2')-Arg-D-Nal(2')-Lys]-D-Val-D-Phe-NH2 |
| 4244 | TCAM4241 | Arg-Arg-Phe-Phe-Arg-Arg-Leu-Arg-c[Asp-Arg-Arg-D-Nal(2')-Arg-D-Nal(2')-Lys]-D-Phe-D-Val-NH2 |

TABLE 5-continued

Exemplary Anti-microbial peptides

| SEQ NO: | Peptide | Peptide Sequence |
|---|---|---|
| 4245 | TCAM4242 | Arg-Arg-Phe-Phe-Arg-Arg-Leu-Arg-c[Asp-Arg-Arg-Pro-D-Nal(2')-Arg-D-Nal(2')-Lys]-D-Val-D-Pro-NH2 |
| 4246 | TCAM4243 | Arg-Arg-Phe-Phe-Arg-Arg-Leu-Arg-c[Asp-Arg-Arg-Pro-D-Nal(2')-Arg-D-Nal(2')-Lys]-D-Pro-D-Val-NH2 |
| 4247 | TCAM4244 | Arg-Arg-Phe-Phe-Arg-Arg-Leu-Arg-c[Asp-Arg-Arg-Pro-D-Nal(2')-Arg-D-Nal(2')-Lys]-D-Val-D-Phe-NH2 |
| 4248 | TCAM4245 | Arg-Arg-Phe-Phe-Arg-Arg-Leu-Arg-c[Asp-Arg-Arg-Pro-D-Nal(2')-Arg-D-Nal(2')-Lys]-D-Phe-D-Val-NH2 |
| 4249 | TCAM4246 | Arg-Arg-Phe-Phe-Arg-Arg-Leu-Arg-c[Asp-Arg-D-Nal(2')-Arg-D-Nal(2')-Lys]-D-Val-D-Pro-NH2 |
| 4250 | TCAM4247 | Arg-Arg-Phe-Phe-Arg-Arg-Leu-Arg-c[Asp-Arg-D-Nal(2')-Arg-D-Nal(2')-Lys]-D-Pro-D-Val-NH2 |
| 4251 | TCAM4248 | Arg-Arg-Phe-Phe-Arg-Arg-Leu-Arg-c[Asp-Arg-Nal(2')-Arg-D-Nal(2')-Lys]-D-Val-D-Phe-NH2 |
| 4252 | TCAM4249 | Arg-Arg-Phe-Phe-Arg-Arg-Leu-Arg-c[Asp-Arg-D-Nal(2')-Arg-D-Nal(2')-Lys]-D-Phe-D-Val-NH2 |
| 4253 | TCAM4250 | Arg-Arg-Phe-Phe-Arg-Arg-Leu-Arg-c[Asp-Arg-Pro-D-Nal(2')-Arg-D-Nal(2')-Lys]-D-Val-D-Pro-NH2 |
| 4254 | TCAM4251 | Arg-Arg-Phe-Phe-Arg-Arg-Leu-Arg-c[Asp-Arg-Pro-D-Nal(2')-Arg-D-Nal(2')-Lys]-D-Pro-D-Val-NH2 |
| 4255 | TCAM4252 | Arg-Arg-Phe-Phe-Arg-Arg-Leu-Arg-c[Asp-Arg-Pro-D-Nal(2')-Arg-D-Nal(2')-Lys]-D-Val-D-Phe-NH2 |
| 4256 | TCAM4253 | Arg-Arg-Phe-Phe-Arg-Arg-Leu-Arg-c[Asp-Arg-Pro-D-Nal(2')-Arg-D-Nal(2')-Lys]-D-Phe-D-Val-NH2 |
| 4257 | TCAM4254 | Arg-Arg-Phe-Phe-Arg-Arg-Leu-Arg-c[Asp-Arg-His-D-Nal(2')-Arg-D-Nal(2')-Lys]-D-Val-D-Pro-NH2 |
| 4258 | TCAM4255 | Arg-Arg-Phe-Phe-Arg-Arg-Leu-Arg-c[Asp-Arg-His-D-Nal(2')-Arg-D-Nal(2')-Lys]-D-Pro-D-Val-NH2 |
| 4259 | TCAM4256 | Arg-Arg-Phe-Phe-Arg-Arg-Leu-Arg-c[Asp-Arg-His-Nal(2')-Arg-D-Nal(2')-Lys]-D-Val-D-Phe-NH2 |
| 4260 | TCAM4257 | Arg-Arg-Phe-Phe-Arg-Arg-Leu-Arg-c[Asp-Arg-His-Nal(2')-Arg-D-Nal(2')-Lys]-D-Phe-D-Val-NH2 |
| 4261 | TCAM4258 | Arg-Arg-Phe-Phe-Arg-Arg-Leu-Arg-c[Asp-Arg-D-D-Nal(2')-Arg-D-Nal(2')-Arg-Lys]-D-Val-D-Pro-NH2 |
| 4262 | TCAM4259 | Arg-Arg-Phe-Phe-Arg-Arg-Leu-Arg-c[Asp-Arg-D-Nal(2')-Arg-D-Nal(2')-Arg-Lys]-D-Pro-D-Val-NH2 |
| 4263 | TCAM4260 | Arg-Arg-Phe-Phe-Arg-Arg-Leu-Arg-c[Asp-Arg-D-Nal(2')-Arg-D-Nal(2')-Arg-Lys]-D-Val-D-Phe-NH2 |
| 4264 | TCAM4261 | Arg-Arg-Phe-Phe-Arg-Arg-Leu-Arg-c[Asp-Arg-D-Nal(2')-Arg-D-Nal(2')-Arg-Lys]-D-Phe-D-Val-NH2 |
| 4265 | TCAM4262 | Arg-Arg-Phe-Phe-Arg-Arg-Leu-Arg-c[Asp-Arg-Pro-D-Nal(2')-Arg-D-Nal(2')-Arg-Lys]-D-Val-D-Pro-NH2 |
| 4266 | TCAM4263 | Arg-Arg-Phe-Phe-Arg-Arg-Leu-Arg-c[Asp-Arg-Pro-D-Nal(2')-Arg-D-Nal(2')-Arg-Lys]-D-Pro-D-Val-NH2 |
| 4267 | TCAM4264 | Arg-Arg-Phe-Phe-Arg-Arg-Leu-Arg-c[Asp-Arg-Pro-D-Nal(2')-Arg-D-Nal(2')-Arg-Lys]-D-Val-D-Phe-NH2 |
| 4268 | TCAM4265 | Arg-Arg-Phe-Phe-Arg-Arg-Leu-Arg-c[Asp-Arg-Pro-D-Nal(2')-Arg-D-Nal(2')-Arg-Lys]-D-Phe-D-Val-NH2 |
| 4269 | TCAM4266 | Arg-Arg-Phe-Phe-Arg-Arg-Leu-Arg-c[Asp-Arg-His-D-Nal(2')-Arg-D-Nal(2')-Arg-Lys]-D-Val-D-Pro-NH2 |

TABLE 5-continued

Exemplary Anti-microbial peptides

| SEQ NO: | Peptide | Peptide Sequence |
|---|---|---|
| 4270 | TCAM4267 | Arg-Arg-Phe-Phe-Arg-Arg-Leu-Arg-c[Asp-Arg-His-D-Nal(2')-Arg-D-Nal(2')-Arg-Lys]-D-Pro-D-Val-NH2 |
| 4271 | TCAM4268 | Arg-Arg-Phe-Phe-Arg-Arg-Leu-Arg-c[Asp-Arg-His-D-Nal(2')-Arg-D-Nal(2')-Arg-Lys]-D-Val-D-Phe-NH2 |
| 4272 | TCAM4269 | Arg-Arg-Phe-Phe-Arg-Arg-Leu-Arg-c[Asp-Arg-His-D-Nal(2')-Arg-D-Nal(2')-Arg-Lys]-D-Phe-D-Val-NH2 |
| 4273 | TCAM4270 | Arg-Arg-Phe-Phe-Arg-Arg-Leu-Arg-Arg-Arg-c[Asp-Pro-D-Nal(2')-Arg-D-Nal(2')-Lys]-D-Val-D-Pro-NH2 |
| 4274 | TCAM4271 | Arg-Arg-Phe-Phe-Arg-Arg-Leu-Arg-Arg-Arg-c[Asp-Pro-D-Nal(2')-Arg-D-Nal(2')-Lys]-D-Pro-D-Val-NH2 |
| 4275 | TCAM4272 | Arg-Arg-Phe-Phe-Arg-Arg-Leu-Arg-Arg-Arg-c[Asp-Pro-D-Nal(2')-Arg-D-Nal(2')-Lys]-D-Val-D-Phe-NH2 |
| 4276 | TCAM4273 | Arg-Arg-Phe-Phe-Arg-Arg-Leu-Arg-Arg-Arg-c[Asp-Pro-D-Nal(2')-Arg-D-Nal(2')-Lys]-D-Phe-D-Val-NH2 |
| 4277 | TCAM4274 | Arg-Arg-Phe-Phe-Arg-Arg-Leu-Arg-Arg-Arg-c[Asp-His-D-Nal(2')-Arg-D-Nal(2')-Lys]-D-Val-D-Pro-NH2 |
| 4278 | TCAM4275 | Arg-Arg-Phe-Phe-Arg-Arg-Leu-Arg-Arg-Arg-c[Asp-His-D-Nal(2')-Arg-D-Nal(2')-Lys]-D-Pro-D-Val-NH2 |
| 4279 | TCAM4276 | Arg-Arg-Phe-Phe-Arg-Arg-Leu-Arg-Arg-Arg-c[Asp-His-D-Nal(2')-Arg-D-Nal(2')-Lys]-D-Val-D-Phe-NH2 |
| 4280 | TCAM4277 | Arg-Arg-Phe-Phe-Arg-Arg-Leu-Arg-Arg-c[Asp-His-D-Nal(2')-Arg-D-Nal(2')-Lys]-D-Phe-D-Val-NH2 |
| 4281 | TCAM4278 | Arg-Arg-Phe-Phe-Arg-Arg-Leu-Arg-c[Asp-Arg-Pro-D-Nal(2')-Arg-D-Nal(2')-Arg-Lys]-D-Val-D-Pro-NH2 |
| 4282 | TCAM4279 | Arg-Arg-Phe-Phe-Arg-Arg-Leu-Arg-c[Asp-Arg-Pro-D-Nal(2')-Arg-D-Nal(2')-Arg-Lys]-D-Pro-D-Val-NH2 |
| 4283 | TCAM4280 | Arg-Arg-Phe-Phe-Arg-Arg-Leu-Arg-c[Asp-Arg-Pro-D-Nal(2')-Arg-D-Nal(2')-Arg-Lys]-D-Val-D-Phe-NH2 |
| 4284 | TCAM4281 | Arg-Arg-Phe-Phe-Arg-Arg-Leu-Arg-c[Asp-Arg-Pro-D-Nal(2')-Arg-D-Nal(2')-Arg-Lys]-D-Phe-D-Val-NH2 |
| 4285 | TCAM4282 | Arg-Arg-Phe-Phe-Arg-Arg-Leu-Arg-c[Asp-Arg-His-D-Nal(2')-Arg-D-Nal(2')-Arg-Lys]-D-Val-D-Pro-NH2 |
| 4286 | TCAM4283 | Arg-Arg-Phe-Phe-Arg-Arg-Leu-Arg-c[Asp-Arg-His-D-Nal(2')-Arg-D-Nal(2')-Arg-Lys]-D-Pro-D-Val-NH2 |
| 4287 | TCAM4284 | Arg-Arg-Phe-Phe-Arg-Arg-Leu-Arg-c[Asp-Arg-His-D-Nal(2')-Arg-D-Nal(2')-Arg-Lys]-D-Val-D-Phe-NH2 |
| 4288 | TCAM4285 | Arg-Arg-Phe-Phe-Arg-Arg-Leu-Arg-c[Asp-Arg-His-D-Nal(2')-Arg-D-Nal(2')-Arg-Lys]-D-Phe-D-Val-NH2 |
| 4289 | TCAM4286 | Arg-Arg-Phe-Phe-Arg-Arg-Leu-Arg-c[Asp-His-D-Nal(2')-Arg-Trp-Lys]-Arg-Arg-D-Val-D-Pro-NH2 |
| 4290 | TCAM4287 | Arg-Arg-Phe-Phe-Arg-Arg-Leu-Arg-c[Asp-His-D-Nal(2')-Arg-Trp-Lys]-Arg-Arg-D-Pro-D-Val-NH2 |
| 4291 | TCAM4288 | Arg-Arg-Phe-Phe-Arg-Arg-Leu-Arg-c[Asp-His-D-Nal(2')-Arg-Trp-Lys]-Arg-Arg-D-Val-D-Phe-NH2 |
| 4292 | TCAM4289 | Arg-Arg-Phe-Phe-Arg-Arg-Leu-Arg-c[Asp-His-D-Nal(2')-Arg-Trp-Lys]-Arg-Arg-D-Phe-D-Val-NH2 |
| 4293 | TCAM4290 | Arg-Arg-Phe-Phe-Arg-Arg-Leu-Arg-c[Asp-Pro-D-Nal(2')-Arg-Trp-Lys]-Arg-Arg-D-Val-D-Pro-NH2 |
| 4294 | TCAM4291 | Arg-Arg-Phe-Phe-Arg-Arg-Leu-Arg-c[Asp-Pro-D-Nal(2')-Arg-Trp-Lys]-Arg-Arg-D-Pro-D-Val-NH2 |

TABLE 5-continued

Exemplary Anti-microbial peptides

| SEQ NO: | Peptide | Peptide Sequence |
|---|---|---|
| 4295 | TCAM4292 | Arg-Arg-Phe-Phe-Arg-Arg-Leu-Arg-c[Asp-Pro-D-Nal(2')-Arg-Trp-Lys]-Arg-Arg-D-Val-D-Phe-NH2 |
| 4296 | TCAM4293 | Arg-Arg-Phe-Phe-Arg-Arg-Leu-Arg-c[Asp-Pro-D-Nal(2')-Arg-Trp-Lys]-Arg-Arg-D-Phe-D-Val-NH2 |

What is claimed is:

1. A non-naturally occurring anti-microbial peptide comprising between 5 and 15 natural, synthetic, or chemically modified residues, the peptide comprising the sequence according to Formula I: $X^1$-$X^2$-$X^3$-$R^1$-$R^2$-[$R^3$-$R^4$-$R^5$-$R^6$-$R^7$-$R^8$-$R^9$-$R^{10}$-$R^{11}$-$R^{12}$-$R^{13}$-$R^{14}$-$R^{15}$-$R^{16}$-$R^{17}$]-$Y^1$-$Y^2$-$Y^3$,
wherein:
$X^1$, $X^2$, and $X^3$ are absent;
$R^1$ to $R^{17}$ represent residues of the anti-microbial peptide, wherein:
$R^1$ is absent;
$R^2$ is absent;
$R^3$ is aspartic acid;
$R^4$ is Arg or Trp;
$R^5$ is Arg, Trp, Gln, D-Nal2', Pro, or His;
$R^6$ is Arg, Gln, Trp, Tyr, Leu, Nal, D-Nal2', or Pro;
$R^7$ is Lys, Trp, Tyr, Leu, Arg, Phe, Nal, or D-Nal2';
$R^8$ is absent or is Lys, Trp, Tyr, Leu, Arg, Nal, or D-Nal2';
$R^9$ is absent or is Lys, Arg, Tyr, Trp, Leu, or Phe;
$R^{10}$ is absent or is Lys, Phe, Trp, Leu, or Arg;
$R^{11}$ is absent or is Lys, Leu, Trp, or Arg;
$R^{12}$ is absent or is Lys or Trp;
$R^{13}$ is absent or is Lys or Trp;
$R^{14}$ is absent or is Lys;
$R^{15}$-$R^{1-7}$ are absent;

wherein at least one of $R^7$ to $R^{14}$ is Lys, and wherein the peptide is cyclized through a side chain lactam between $R^3$ and one of the said at least one Lys;
$Y^1$, $Y^2$, and $Y^3$ represent optional degradation-resistant C-terminal stabilizing residues; and
wherein an anti-biofilm peptide is covalently linked to the N-terminus of the antimicrobial peptide, the anti-biofilm peptide having the sequence Phe-Arg-Ile-Arg-Val-Arg-Val.

2. The non-naturally occurring anti-microbial peptide of claim 1, wherein
$R^3$ is aspartic acid;
$R^4$ is Arg;
$R^5$ is Arg;
$R^6$ is D-Nal2';
$R^7$ is Phe;
$R^8$ is Trp;
$R^9$ is Arg;
$R^{10}$ is Lys; and
$R^{11}$-$R^{17}$ are absent.

3. The non-naturally occurring anti-microbial peptide of claim 1, wherein the anti-biofilm peptide is acylated at the N-terminus.

4. The non-naturally occurring anti-microbial peptide of claim 1, wherein:

$Y^1$ and $Y^2$ are independently selected for each occasion from the group consisting of D-threonine, L-threonine, D-proline, L-proline, β-homo proline, D-alanine, L-alanine, D-valine, L-valine, β-valine, 3-methyl-β-valine, D-leucine, L-leucine, β-leucine, D-norleucine, L-norleucine, D-isoleucine, L-isoleucine, β-isoleucine, D-phenylalanine, L-phenylalanine, or a piperazin-2-one ring; and $Y^3$ is absent.

5. The non-naturally occurring anti-microbial peptide of claim 4, wherein:

$Y^1$ is D-Val; and $Y^2$ is D-Pro.

6. The non-naturally occurring anti-microbial peptide of claim 5, wherein the C-terminus is amidated.

7. The non-naturally occurring anti-microbial peptide of claim 1, having the sequence: Ac-Phe-Arg-Ile-Arg-Val-Arg-Val-c[Asp-Arg-Arg-D-Nal(2')-Phe-Trp-Arg-Lys]-D-Val-D-Pro-CONH$_2$.

* * * * *

SEQUENCE LISTING

<160> NUMBER OF SEQ ID NOS: 37

<210> SEQ ID NO 1
<211> LENGTH: 4
<212> TYPE: PRT
<213> ORGANISM: Artificial Sequence
<220> FEATURE:
<223> OTHER INFORMATION: synthetic melanocortin pharmacophore

<400> SEQUENCE: 1

His Phe Arg Trp
1

<210> SEQ ID NO 2
<211> LENGTH: 6
<212> TYPE: PRT
<213> ORGANISM: Artificial Sequence
<220> FEATURE:
<223> OTHER INFORMATION: Lactoferrin Pharmacophore

<400> SEQUENCE: 2

Arg Arg Trp Gln Gln Arg
1               5

<210> SEQ ID NO 3
<211> LENGTH: 5
<212> TYPE: PRT
<213> ORGANISM: Artificial Sequence
<220> FEATURE:
<223> OTHER INFORMATION: polyphemusin pharmacophore

<400> SEQUENCE: 3

Arg Arg Trp Cys Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Tachyplesin pharmacophore

<400> SEQUENCE: 4

Arg Trp Cys Phe Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Protegrin pharmacophore

```
<400> SEQUENCE: 5

Tyr Cys Arg Arg Phe
1               5

<210> SEQ ID NO 6
<211> LENGTH: 6
<212> TYPE: PRT
<213> ORGANISM: Artificial Sequence
<220> FEATURE:
<223> OTHER INFORMATION: Defensin pharmacophore

<400> SEQUENCE: 6

Ala Cys Arg Arg Arg Phe
1               5

<210> SEQ ID NO 7
<211> LENGTH: 5
<212> TYPE: PRT
<213> ORGANISM: Artificial Sequence
<220> FEATURE:
<223> OTHER INFORMATION: Other Natural pharmacophore

<400> SEQUENCE: 7

Arg Arg Trp Trp Arg
1               5

<210> SEQ ID NO 8
<211> LENGTH: 12
<212> TYPE: PRT
<213> ORGANISM: Artificial Sequence
<220> FEATURE:
<223> OTHER INFORMATION: synthetic peptide

<400> SEQUENCE: 8

Val Arg Leu Ile Val Ala Val Arg Ile Trp Arg Arg
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 9

Lys Lys Phe Lys Lys Phe Phe Lys Lys Leu Lys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 10

Arg Arg Phe Arg Arg Phe Phe Arg Arg Leu Arg
1               5                   10

<210> SEQ ID NO 11
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 11
```

Val Arg Leu Ile Val Ala Val Arg
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 12

Val Arg Ile Trp Arg Arg
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 13

Val Arg Leu Ile Val Ala
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 14

Lys Lys Phe Lys Lys Phe Phe
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 15

Arg Arg Phe Arg Arg Phe Phe
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 16

Phe Phe Lys Lys Leu Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 17

Phe Phe Arg Arg Leu Arg
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 18

Lys Lys Phe Lys Lys Phe Phe Lys Lys
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 19

Arg Arg Phe Arg Arg Phe Phe Arg Arg
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 20

Lys Lys Phe Phe Lys Lys Leu Lys
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 21

Arg Arg Phe Phe Arg Arg Leu Arg
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Gly Gly Ser Gly Gly Ser
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide

<400> SEQUENCE: 23

Pro Ser Pro Ser Pro

```
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide

<400> SEQUENCE: 24

Ala Ser Ala Ser Ala
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide

<400> SEQUENCE: 25

Pro Ser Pro Ser Pro
1               5

<210> SEQ ID NO 26
<211> LENGTH: 4
<212> TYPE: PRT
<213> ORGANISM: Artificial Sequence
<220> FEATURE:
<223> OTHER INFORMATION: Synthetic peptide

<400> SEQUENCE: 26

Lys Lys Lys Lys
1

<210> SEQ ID NO 27
<211> LENGTH: 4
<212> TYPE: PRT
<213> ORGANISM: Artificial Sequence
<220> FEATURE:
<223> OTHER INFORMATION: Synthetic peptide

<400> SEQUENCE: 27

Arg Arg Arg Arg
1

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide

<400> SEQUENCE: 28

Gly Gly Gly Gly Ser Gly Gly Gly Ser Gly Gly Gly Ser
1               5                   10                  15

<210> SEQ ID NO 29
<211> LENGTH: 4
<212> TYPE: PRT
<213> ORGANISM: Artificial Sequence
<220> FEATURE:
<223> OTHER INFORMATION: Synthetic peptide

<400> SEQUENCE: 29

Gly Gly Gly Gly
1
```

<210> SEQ ID NO 30
<211> LENGTH: 5
<212> TYPE: PRT
<213> ORGANISM: Artificial Sequence
<220> FEATURE:
<223> OTHER INFORMATION: Synthetic peptide

<400> SEQUENCE: 30

Gly Gly Gly Gly Ser
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic peptide

<400> SEQUENCE: 31

Gly Gly Gly Gly Ser Gly Gly Gly Gly Ser
1               5                   10

<210> SEQ ID NO 32
<211> LENGTH: 20
<212> TYPE: PRT
<213> ORGANISM: Artificial Sequence
<220> FEATURE:
<223> OTHER INFORMATION: Synthetic peptide

<400> SEQUENCE: 32

Gly Gly Gly Gly Ser Gly Gly Gly Gly Ser Gly Gly Gly Gly Ser Gly
1               5                   10                  15

Gly Gly Gly Ser
        20

<210> SEQ ID NO 33
<211> LENGTH: 25
<212> TYPE: PRT
<213> ORGANISM: Artificial Sequence
<220> FEATURE:
<223> OTHER INFORMATION: Synthetic peptide

<400> SEQUENCE: 33

Gly Gly Gly Gly Ser Gly Gly Gly Gly Ser Gly Gly Gly Gly Ser Gly
1               5                   10                  15

Gly Gly Gly Ser Gly Gly Gly Gly Ser
        20                  25

<210> SEQ ID NO 34
<211> LENGTH: 30
<212> TYPE: PRT
<213> ORGANISM: Artificial Sequence
<220> FEATURE:
<223> OTHER INFORMATION: Synthetic peptide

<400> SEQUENCE: 34

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
        20                  25                  30

<210> SEQ ID NO 35
<211> LENGTH: 9
<212> TYPE: PRT

```
<213> ORGANISM: Homo sapiens
<220> FEATURE:
<221> NAME/KEY: DISULFID
<222> LOCATION: (1)..(6)
<220> FEATURE:
<221> NAME/KEY: MOD_RES
<222> LOCATION: (9)..(9)
<223> OTHER INFORMATION: AMIDATION

<400> SEQUENCE: 35

Cys Tyr Phe Gln Asn Cys Pro Arg Gly
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic analog of neurotensin
<220> FEATURE:
<221> NAME/KEY: MOD_RES
<222> LOCATION: (1)..(1)
<223> OTHER INFORMATION: METHYLATION

<400> SEQUENCE: 36

Arg Lys Pro Trp Ile Leu
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 37

Phe Gly Gly Gly Gly Phe
1               5
```